(12) United States Patent
Boxer et al.

(10) Patent No.: US 10,703,746 B2
(45) Date of Patent: Jul. 7, 2020

(54) MUTANT IDH1 INHIBITORS USEFUL FOR TREATING CANCER

(71) Applicants: THE UNITED STATES OF AMERICA, AS REPRESENTED BY THE SECRETARY, DEPARTMENT OF HEALTH AND HUMAN SERVICE, Bethesda, MD (US); THE UNIVERSITY OF NORTH CAROLINA AT CHAPEL HILL, Chapel Hill, NC (US)

(72) Inventors: Matthew Brian Boxer, New Market, MD (US); Jason Matthew Rohde, Poolesville, MD (US); Rajan Pragani, Gaithersburg, MD (US); Li Liu, Germantown, MD (US); Mindy Irene Emily Davis, Rockville, MD (US); Kyle Ryan Brimacombe, Bethesda, MD (US); Min Shen, Boyds, MD (US); Anton Simeonov, Bethesda, MD (US); Surendra Karavadhi, Gaithersburg, MD (US); Daniel Jason Urban, Rockville, MD (US); Ajit Jadhav, Chantilly, VA (US); Xiaodong Wang, Chapel Hill, NC (US); Andrew Louis McIver, Durham, NC (US)

(73) Assignees: THE UNITED STATES OF AMERICA, AS REPRESENTED BY THE SECRETARY, DEPARTMENT OF HEALTH AND HUMAN SERVICES, Bethesda, MD (US); THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 134 days.

(21) Appl. No.: 15/538,570

(22) PCT Filed: Dec. 22, 2015

(86) PCT No.: PCT/US2015/067406
§ 371 (c)(1),
(2) Date: Jun. 21, 2017

(87) PCT Pub. No.: WO2016/106331
PCT Pub. Date: Jun. 30, 2016

(65) Prior Publication Data
US 2019/0071434 A1    Mar. 7, 2019

Related U.S. Application Data

(60) Provisional application No. 62/095,322, filed on Dec. 22, 2014.

(51) Int. Cl.
*C07D 417/04*    (2006.01)
*A61K 31/4709*    (2006.01)
(Continued)

(52) U.S. Cl.
CPC .......... *C07D 417/04* (2013.01); *A61K 31/435* (2013.01); *A61K 31/437* (2013.01);
(Continued)

(58) Field of Classification Search
None
See application file for complete search history.

(56) References Cited

U.S. PATENT DOCUMENTS 5,294,620 A       3/1994   Ratcliffe et al.
8,063,055 B2 *   11/2011   Hu ........................ C07D 471/04
                                                                  514/266.4
(Continued)

FOREIGN PATENT DOCUMENTS

WO    2004060890 A1    7/2004
WO    2011050210 A1    4/2011
(Continued)

OTHER PUBLICATIONS

Cairns et al. "Oncogenic Isocitrate Dehydrogenase Mutations: Mechanisms, Models, and Clinical Opportunities" Cancer Discovery Jul. 2013 (pp. 730-741)
(Continued)

*Primary Examiner* — Po-Chih Chen
(74) *Attorney, Agent, or Firm* — Cantor Colburn LLP

(57) ABSTRACT

Compounds of Formula I and Formula II and the pharmaceutically acceptable salts thereof are disclosed The variables A, B, Y, Z, $X^1$, $X^2$, $R^{1-4}$ and $R^{13-18}$ are disclosed herein. The compounds are useful for treating cancer disorders, especially those involving mutant IDH1 enzymes. Pharmaceutical compositions containing compounds of Formula I or Formula II and methods of treatment comprising administering compounds of Formula I and Formula II are also disclosed.

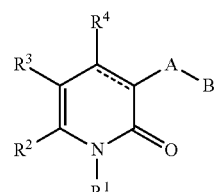

Formula I

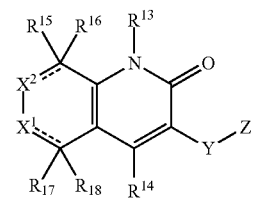

Formula II (Continued)

12 Claims, No Drawings

(51) Int. Cl.
| | |
|---|---|
| A61K 31/496 | (2006.01) |
| A61K 31/4439 | (2006.01) |
| C07D 417/14 | (2006.01) |
| A61K 31/4375 | (2006.01) |
| C07D 471/04 | (2006.01) |
| A61K 31/435 | (2006.01) |
| A61K 31/4545 | (2006.01) |
| A61K 31/551 | (2006.01) |
| A61K 31/437 | (2006.01) |
| A61K 31/5377 | (2006.01) |
| A61K 31/4704 | (2006.01) |
| C07D 215/54 | (2006.01) |
| C07D 401/04 | (2006.01) |
| A61K 31/506 | (2006.01) |
| C07D 215/227 | (2006.01) |
| C07D 491/048 | (2006.01) |
| C07D 213/82 | (2006.01) |
| C07D 487/10 | (2006.01) |
| C07D 451/02 | (2006.01) |
| A61K 31/46 | (2006.01) |
| A61K 31/499 | (2006.01) |
| C07D 413/14 | (2006.01) |
| C07D 215/22 | (2006.01) |
| C07D 491/052 | (2006.01) |
| C07D 401/14 | (2006.01) |
| C07D 491/107 | (2006.01) |
| C07D 487/08 | (2006.01) |
| C07D 413/04 | (2006.01) |
| C07D 471/14 | (2006.01) |
| A61P 35/00 | (2006.01) |

(52) U.S. Cl.
CPC ...... *A61K 31/4375* (2013.01); *A61K 31/4439* (2013.01); *A61K 31/4545* (2013.01); *A61K 31/46* (2013.01); *A61K 31/4704* (2013.01); *A61K 31/4709* (2013.01); *A61K 31/496* (2013.01); *A61K 31/499* (2013.01); *A61K 31/506* (2013.01); *A61K 31/5377* (2013.01); *A61K 31/551* (2013.01); *A61P 35/00* (2018.01); *C07D 213/82* (2013.01); *C07D 215/22* (2013.01); *C07D 215/227* (2013.01); *C07D 215/54* (2013.01); *C07D 401/04* (2013.01); *C07D 401/14* (2013.01); *C07D 413/04* (2013.01); *C07D 413/14* (2013.01); *C07D 417/14* (2013.01); *C07D 451/02* (2013.01); *C07D 471/04* (2013.01); *C07D 471/14* (2013.01); *C07D 487/08* (2013.01); *C07D 487/10* (2013.01); *C07D 491/048* (2013.01); *C07D 491/052* (2013.01); *C07D 491/107* (2013.01)

(56) References Cited

U.S. PATENT DOCUMENTS

| 8,188,113 | B2 | 5/2012 | Flynn et al. |
| 8,440,674 | B2 | 5/2013 | De Morin et al. |
| 8,957,068 | B2 | 2/2015 | Caferro et al. |
| 9,434,979 | B2 | 9/2016 | Su et al. |
| 9,856,279 | B2 | 1/2018 | Cao et al. |
| 2006/0270709 | A1 | 11/2006 | Gray et al. |
| 2008/0161340 | A1 | 7/2008 | Gustafson et al. |
| 2009/0312321 | A1 | 12/2009 | Ren et al. |
| 2010/0029578 | A1 | 2/2010 | Olgin et al. |
| 2010/0256191 | A1 | 10/2010 | Hanada et al. |
| 2013/0035329 | A1 | 2/2013 | Saunders et al. |
| 2013/0184222 | A1 | 7/2013 | Popovici-Muller et al. |

FOREIGN PATENT DOCUMENTS

| WO | 2011050211 A2 | 4/2011 |
| WO | 2011072174 A1 | 6/2011 |
| WO | 2012009678 A1 | 1/2012 |
| WO | 2012106472 A1 | 8/2012 |
| WO | 2012171337 A1 | 12/2012 |
| WO | 2013046136 A1 | 4/2013 |
| WO | 2013130855 A1 | 9/2013 |
| WO | 2016044789 A1 | 3/2016 |

OTHER PUBLICATIONS

Cui et al. "Structure and Properties of N-Heterocycle-Containing Benzotriazoles as UV Absorbers," Journal of Molecular Structure 1054-1055, (2013); pp. 94-99.
Dang et al. "Cancer-associated IDH1 mutations produce 2-hydroxyglutarate" Nature, vol. 462, 2009, pp. 739-746.
Database Registry, Chemical Abstracts Service, Columbus, OH; XP002755021, (Mar. 12, 2014); 2 pages.
Database Registry, Chemical Abstracts Service, Columbus, OH; XP002755022, (Dec. 18, 2013); 2 pages.
Database Registry, Chemical Abstracts Service, Columbus, OH; XP002755023, (Jun. 5, 2013); 1 page.
Dzhavakhishvili et al. Synthesis of Novel 3-(1,3-thiazol-2-yl)-7, 8-Dihydroquinoline-2, 5 (1H,6H)-Diones; Russian Chemical Bulletin, International Edition, vol. 57, No. 2, pp. 422-427, Feb. 2008; 6 pages.
International Search Report dated Jun. 9, 2016; International Application No. PCT/US2015/067406; International Filing Date Dec. 22, 2015 (9 pages).
Losman, et al., "(R)-2-Hydroxygulutarate Is Sufficient to Promote Leukemogenesis and Its Effects Are Reversible", Science, 339, 1621 (2013) pp. 1621-1625.
Paulekuhn; "Trends in Active Pharmaceutical Ingredient Salt Selection based on Analysis of the Orange Book Database" Journal of Medicinal Chemistry 2007, 50, 6665-6672.
Prostakov, "Synthesis of Substituted 2-Pyridones and 4-aza-3 Fluorenones," Database Caplus, Chemical Abstract Service, Columbus, OH; XP002755020, (1986), 2 pages.
Rohle et al. "An Inhibitor of Mutant IDH1 Delays Growth and Promotes Differentiation of Glioma Cells", Science 340, 626 (2013), pp. 626-630.
Sasaki et al. "IDH1(R132H) mutation increases murine haematopoietic progenitors and alters epigenetics" Nature, vol. 488, Aug. 2012, pp. 656-662).
Stahl et al. List of Pharmaceutical salts(2002), Handbook of Pharmaceutical salts: Wiley-VCH-VHCA (1 page).
Zheng et al. "Crystallographic Investigation and Selective Inhibition of Mutant Isocitrate Dehydrogenase," ACS Publications, (2013) No. 4; American Chemical Society, pp. 542-546.
Hengmiao Cheng et al., "Structure-based design, SAR analysis and antitumor activity of PI3K/mTOR dual inhibitors from 4-methylpyridopryimidinone series" Bioorganic & Medicinal Chemistry Letters, vol. 23, 2013 pp. 2787-2792.
Database Registry (STN) RN 931343-02-1, [online], Apr. 20, 2007, [Retrieved on Sep. 17, 2019].
Database Registry (STN) RN 931343-06-5, [online], Apr. 20, 2007, [Retrieved on Sep. 17, 2019].
Database Registry (STN) RN 931366-53-9, [online], Apr. 20, 2007, [Retrieved on Sep. 17, 2019].
Database Registry (STN) RN 1069766-29-5, [online], Nov. 2, 2008, [Retrieved on Sep. 17, 2019].
Database Registry (STN) RN 1070252-05-9, [online], Nov. 3, 2008, [Retrieved on Sep. 17, 2019].
Database Registry (STN) RN 1112278-91-7, [online], Feb. 26, 2009, [Retrieved on Sep. 17, 2019].

(56) References Cited

OTHER PUBLICATIONS

Database Registry (STN) RN 1112278-92-8, [online], Feb. 26, 2009, [Retrieved on Sep. 17, 2019].
Database Registry (STN) RN 1112278-93-9, [online], Feb. 26, 2009, [Retrieved on Sep. 17, 2019].
Database Registry (STN) RN 1112278-94-0, [online], Feb. 26, 2009, [Retrieved on Sep. 17, 2019].
Database Registry (STN) RN 1112357-68-2, [online], Feb. 26, 2009, [Retrieved on Sep. 17, 2019].
Database Registry (STN) RN 1112384-56-1, [online], Feb. 26, 2009, [Retrieved on Sep. 17, 2019].
Database Registry (STN) RN 1112384-57-2, [online], Feb. 26, 2009, [Retrieved on Sep. 17, 2019].
Database Registry (STN) RN 1112384-58-3, [online], Feb. 26, 2009, [Retrieved on Sep. 17, 2019].
Database Registry (STN) RN 1112445-37-0, [online], Feb. 26, 2009, [Retrieved on Sep. 17, 2019].
Database Registry (STN) RN 1112445-39-2, [online], Feb. 26, 2009, [Retrieved on Sep. 17, 2019].
Database Registry (STN) RN 1113111-91-3, [online], Mar. 1, 2009, [Retrieved on Sep. 17, 2019].
Database Registry (STN) RN 1113111-95-7, [online], Mar. 1, 2009, [Retrieved on Sep. 17, 2019].
Database Registry (STN) RN 1114860-85-3, [online], Mar. 3, 2009, [Retrieved on Sep. 17, 2019].
Database Registry (STN) RN 1609799-10-1, [online], Jun. 6, 2014, [Retrieved on Sep. 17, 2019].
Database Registry (STN) RN 931343-10-1, [online], Apr. 20, 2007, [Retrieved on Sep. 17, 2019].
Database Registry (STN) RN 931343-14-5, [online], Apr. 20, 2007, [Retrieved on Sep. 17, 2019].
Database Registry (STN) RN 931366-47-1, [online], Apr. 20, 2007, [Retrieved on Sep. 17, 2019].
Database Registry (STN) RN 931366-50-6, [online], Apr. 20, 2007, [Retrieved on Sep. 17, 2019].
Database Registry (STN) RN 931366-62-0, [online], Apr. 20, 2007, [Retrieved on Sep. 17, 2019].
Database Registry (STN) RN 931729-42-9, [online], Apr. 22, 2007, [Retrieved on Sep. 17, 2019].
Database Registry (STN) RN 931729-48-5, [online], Apr. 22, 2007, [Retrieved on Sep. 17, 2019].
Database Registry (STN) RN 931945-64-1, [online], Apr. 23, 2007, [Retrieved on Sep. 17, 2019].
Database Registry (STN) RN 931945-66-3, [online], Apr. 23, 2007, [Retrieved on Sep. 17, 2019].
Database Registry (STN) RN 931945-68-5, [online], Apr. 23, 2007, [Retrieved on Sep. 17, 2019].

* cited by examiner

MUTANT IDH1 INHIBITORS USEFUL FOR TREATING CANCER

CROSS REFERENCE TO RELATED APPLICATIONS

This application is a U.S. National Stage Application of PCT/US2015/067406 filed Dec. 22, 2015, which claims priority to U.S. Provisional Application No. 62/095,322, filed 22 Dec. 2014, both of which are hereby incorporated by reference in their entirety

STATEMENT OF GOVERNMENT SUPPORT

This invention was made with government support under Grant Number HHSN261200800001E awarded by the National Institutes of Health. The government has certain rights in this invention.

BACKGROUND

Isocitrate dehydrogenase 1 (IDH1, protein accession number NP_005887.2) is an enzyme whose normal function is to convert isocitrate to α-ketoglutarate. Mutated forms of this enzyme, most commonly IDH1(R132H) in which arginine 132 is mutated to histidine, are common in a variety of cancers including glioma, cholangiocarcinoma, chondrosarcoma, and AML. The IDH1(R132H, R132C, R132S) mutation and similar IDH1 mutations are gain-of-function mutations which result in the enzyme gaining the ability to catalyze the NADPH-dependent reduction of α-ketoglutarate to R-2-hydroxyglutarate (2HG). Elevated levels of 2HG have been shown to lead to an elevated risk of brain tumors in humans. 2HG is described as an oncometabolite, and a proposed mode of action is that it leads to hypermethylation of histones and causing inhibited cell differentiation and the development of cancerous cells.

Mutant IDH1 is an attractive target for anti-cancer therapeutics. Inhibition of mutant IDH1 reduces levels of 2HG. It is expected that lower 2HG levels will result in fewer undifferentiated cancer cells. Furthermore, inhibition of mutant IDH1 is expected to have little effect on non-cancerous cells, as these cells do not express the IDH1 mutation resulting in lower toxicity than typical cytotoxic anticancer agents.

For these reasons mutant IDH1 inhibitors are needed as anti-cancer therapeutics. This disclosure provides mutant IDH1 inhibitors and possesses additional advantages which are set forth in the following descriptions

SUMMARY

Described herein are mutant IDH1 inhibitors, their methods of manufacture, compositions containing the described compounds, and methods of using the described compounds. In a first aspect, a compound of Formula I and the pharmaceutically acceptable salts of a compound of Formula I is provided.

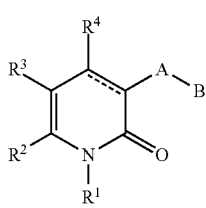

Formula I

Within Formula I the following conditions are met.

Each bond shown as a solid line and a dashed line together, ===, can be a single or double bond.

$R^1$ is $C_1$-$C_6$alkyl, $C_1$-$C_6$haloalkyl, —($C_0$-$C_6$alkyl)cycloalkyl, —($C_0$-$C_6$alkyl)phenyl, or a monocyclic or bicyclic heterocycle of 4 to 10 ring atoms having 1, 2, or 3 ring atoms independently chosen from N, S and O, where $R^1$ is substituted by 0-3 substituents independently chosen from hydroxyl, halogen, cyano, nitro, oxo, —($C_0$-$C_6$alkyl)phenyl, —O—($C_0$-$C_6$alkyl)phenyl, $C_1$-$C_6$alkyl, $C_2$-$C_6$alkenyl, $C_2$-$C_6$alkynyl, $C_1$-$C_6$alkylthio, $C_1$-$C_6$alkoxy, $C_1$-$C_6$haloalkyl, $C_1$-$C_6$haloalkoxy, —($C_0$-$C_6$alkyl)cycloalkyl, —O—($C_0$-$C_6$alkyl)cycloalkyl, —($C_0$-$C_6$alkyl)$CO_2R^5$, —($C_0$-$C_6$alkyl)C(O)$NR^5R^6$, —($C_1$-$C_6$alkyl)$OR^5$, —($C_0$-$C_6$alkyl)$NR^5R^6$, —($C_0$-$C_6$alkyl)$NR^5C(O)R^6$, and monocyclic heterocycle of 4 to 6 ring atoms having 1, 2, or 3 ring atoms independently chosen from N, O, and S, which monocyclic heterocycle of 4 to 6 ring atoms is optionally substituted with one or more substituents independently chosen from halogen, cyano, —$CO_2H$, $C_1$-$C_6$alkyl, $C_1$-$C_6$alkoxy, $C_1$-$C_6$haloalkyl, and $C_1$-$C_6$haloalkoxy.

$R^2$ is hydrogen, halogen, hydroxyl, cyano, —$CO_2H$, $C_1$-$C_6$alkyl, $C_2$-$C_6$alkenyl, $C_2$-$C_6$alkynyl, $C_1$-$C_6$alkoxy, —($C_0$-$C_6$alkyl)cycloalkyl, or phenyl, each of which $R^2$ other than halogen, cyano, and —$CO_2H$ can have one or more methylenes replaced with O, S, or N($R^5$), and can have one or more methines replaced by N, or $R^2$ is a monocyclic heteroaryl of 5 ring atoms having 1 to 4 ring atoms independently chosen from N, O, and S, and each of which $R^2$ other than halogen, cyano, and —$CO_2H$ is optionally substituted with one or more substituents chosen from halogen, hydroxyl, $C_1$-$C_6$alkyl, —$OR^5$, —$SR^5$, $NR_5R_6$, $C_1$-$C_6$haloalkyl, phenyl, and $C_1$-$C_6$haloalkoxy.

$R^3$ is $C_1$-$C_6$alkyl, cyano, —$CO_2R^7$, —C(O)$C_1$-$C_6$alkyl, —C(O)$NR^7R^8$, or ($C_0$-$C_6$alkyl)$NR^7R^8$.

$R^4$ is hydrogen, hydroxyl, halogen, cyano, —$CO_2H$, $C_1$-$C_6$alkyl, $C_2$-$C_6$alkenyl, $C_2$-$C_6$alkynyl, $C_1$-$C_6$alkoxy, or $C_1$-$C_6$haloalkyl.

A is a phenyl or a monocyclic heteroaryl of 5 or 6 ring atoms having 1 to 4 ring atoms independently chosen from N, O, and S, wherein A is substituted with 0-2 substituents chosen from halogen, cyano, $C_1$-$C_6$alkyl, $C_1$-$C_6$alkoxy, $C_1$-$C_6$haloalkyl, $C_1$-$C_6$haloalkoxy, and —($C_0$-$C_6$alkyl)cycloalkyl, —O($C_0$-$C_6$alkyl)cycloalkyl, —($C_0$-$C_6$alkyl)$CO_2R^5$, and —($C_0$-$C_6$alkyl)C(O)$NR^5R^6$.

B is a phenyl, —($C_1$-$C_6$alkyl)phenyl, —($C_2$-$C_6$alkenyl)phenyl, —($C_2$-$C_6$alkynyl)phenyl, $C_3$-$C_7$cycloalkyl, or a monocyclic heterocycle of 5 or 6 ring atoms having 1, 2, or 3 ring atoms independently chosen from N, O, and S, wherein B is substituted with 0-3 substituents independently chosen from hydroxyl, halogen, cyano, $C_1$-$C_6$alkyl, $C_2$-$C_6$alkenyl, $C_2$-$C_6$alkynyl, $C_1$-$C_6$alkoxy, —$C_0$-$C_2$alkyl$NR^5R^6$, $C_1$-$C_6$haloalkyl, $C_1$-$C_6$haloalkoxy, —($C_0$-$C_6$alkyl)cycloalkyl, —($C_0$-$C_6$alkyl)phenyl, —O—($C_0$-$C_6$alkyl)phenyl, —($C_0$-$C_6$alkyl)cycloalkyl, —O($C_0$-$C_6$alkyl)cycloalkyl, —($C_0$-$C_6$alkyl)$CO_2R^9$, —($C_0$-$C_6$alkyl)C(O)$NR^9R^{10}$, —($C_0$-$C_6$alkyl)$NR^9R^{10}$, and —($C_1$-$C_6$alkyl)$OR^9$.

A and B can be taken together to be a bicyclic heteroaryl of 8 to 10 ring atoms, having 1, 2, or 3 ring atoms independently chosen from N, O, and S, wherein the bicyclic heteroaryl is substituted with 0-2 substituents independently chosen from halogen, cyano, $C_1$-$C_6$alkyl, $C_1$-$C_6$alkoxy, $C_1$-$C_6$haloalkyl, and $C_1$-$C_6$haloalkoxy.

$R^5$, $R^6$, $R^7$, $R^9$, and $R^{10}$ are each independently chosen at each occurrence from hydrogen, $C_1$-$C_6$ alkyl, and —($C_0$-$C_6$alkyl)cycloalkyl.

$R^8$ is hydrogen, $C_1$-$C_6$ alkyl, —($C_0$-$C_6$alkyl)cycloalkyl, —($C_0$-$C_6$alkyl)phenyl, or a 4- to 7-membered heterocycloalkyl ring having 1, 2, or 3 ring atoms independently chosen from N, O, and S, where each $R^8$ is substituted with 0-3 substituents independently chosen from hydroxyl, halogen, oxo, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)phenyl, —($C_0$-$C_6$alkyl)$CO_2R^{11}$, —($C_0$-$C_6$alkyl)C(O)$NR^{11}R^{12}$, —($C_0$-$C_6$alkyl)$NR^{11}$C(O)$R^{12}$, —($C_1$-$C_6$alkyl)$OR^{11}$, and —($C_0$-$C_6$alkyl)$NR^{11}R^{12}$.

Any $R^5$ and $R^6$, or $R^7$ and $R^8$, bound to the same nitrogen atom may be taken together to form a 4- to 7-membered monocyclic heterocycloalkyl ring or 6- to 11-membered bridged bicyclic heterocycloalkyl ring, which heterocycloalkyl ring contains 0, 1, or 2 additional heteroatoms chosen from N, O, and S, which heterocycloalkyl ring is optionally substituted at any carbon ring atom with halogen, hydroxyl, cyano, oxo, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)phenyl, —($C_0$-$C_6$alkyl)$CO_2R^{11}$, —($C_0$-$C_6$alkyl)C(O)$NR^{11}R^{12}$, —($C_1$-$C_6$alkyl)$OR^{11}$, or —($C_0$-$C_6$alkyl)$NR^{11}R^{12}$, a Spiro fused cycloalkyl ring of 3 to 7 carbons, or a spiro fused heterocycloalkyl ring of 3 to 7 ring atoms with 1 to 3 ring atoms chosen from O, S, and N, the N atoms of said Spiro fused heterocycloalkyl ring of 3 to 7 ring atoms are optionally substituted with $C_1$-$C_6$ alkyl, and optionally substituted at any nitrogen ring atom available for substitution with $C_1$-$C_6$ alkyl or —($C_0$-$C_4$alkyl)cycloalkyl.

Any $R^9$ and $R^{10}$ bound to the same nitrogen atom may be taken together to form a 4 to 7-membered heterocycloalkyl ring, which heterocycloalkyl ring contains 0, 1, or 2 additional heteroatoms chosen from N, O, and S, which heterocycloalkyl ring is optionally substituted at any carbon ring atom with halogen, hydroxyl, oxo, $C_1$-$C_6$alkoxy, $C_1$-$C_6$haloalkyl, $C_1$-$C_6$haloalkoxy, or —($C_0$-$C_6$alkyl)cycloalkyl, and optionally substituted at any nitrogen ring atom available for substitution by $C_1$-$C_6$ alkyl or —($C_0$-$C_4$alkyl)cycloalkyl.

$R^{11}$ and $R^{12}$ are each independently chosen at each occurrence from hydrogen, $C_1$-$C_6$ alkyl, and —($C_0$-$C_6$alkyl)cycloalkyl.

In a second aspect, a compound of Formula II and the pharmaceutically acceptable salts of a compound of Formula II is provided.

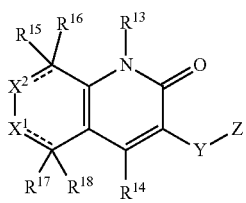

Formula II

Each bond shown as a solid line and a dashed line together, ═══, can be a single bond, double, or aromatic bond.

$X^1$ is $CR^{19}R^{20}$, $NR^{19}$ or O.

$X^2$ is $CR^{21}R^{22}$, $NR^{21}$ or absent.

$R^{13}$ is $C_1$-$C_6$alkyl, $C_1$-$C_6$haloalkyl, —($C_0$-$C_6$alkyl)cycloalkyl, —($C_0$-$C_6$alkyl)phenyl, naphthyl, tetrahydronaphthyl, or a monocyclic or bicyclic heterocycle of 4 to 10 ring atoms having 1, 2, or 3 ring atoms independently chosen from N, S, and O, wherein $R^{13}$ is substituted by 0-3 substituents independently chosen from hydroxyl, halogen, cyano, nitro, oxo, —($C_0$-$C_6$alkyl)phenyl, —O—($C_0$-$C_6$alkyl)phenyl, $C_1$-$C_6$alkyl, $C_2$-$C_6$alkenyl, $C_2$-$C_6$alkynyl, $C_1$-$C_6$alkylthio, $C_1$-$C_6$alkoxy, $C_1$-$C_6$haloalkyl, $C_1$-$C_6$haloalkoxy, —($C_0$-$C_6$alkyl)cycloalkyl, —O—($C_0$-$C_6$alkyl)cycloalkyl, —($C_0$-$C_6$alkyl)$CO_2R^{23}$, —($C_0$-$C_6$alkyl)C(O)$NR^{23}R^{24}$, —($C_0$-$C_6$alkyl)$NR^{23}$C(O)$R^{24}$, —($C_1$-$C_6$alkyl)$OR^{23}$, —($C_0$-$C_6$alkyl)$NR^{23}R^{24}$, and a monocyclic heterocycle of 4 to 6 ring atoms having 1, 2, or 3 ring atoms independently chosen from N, O, and S, which monocyclic heterocycle of 4 to 6 ring atoms is optionally substituted with one or more substituents independently chosen from halogen, cyano, —$CO_2H$, $C_1$-$C_6$alkyl, $C_1$-$C_6$alkoxy, $C_1$-$C_6$haloalkyl, and $C_1$-$C_6$haloalkoxy.

$R^{14}$ is hydrogen, hydroxyl, halogen, cyano, —$CO_2H$, $C_1$-$C_6$alkyl, $C_2$-$C_6$alkenyl, $C_2$-$C_6$alkynyl, $C_1$-$C_6$alkoxy, or $C_1$-$C_6$haloalkyl.

Y is a phenyl or a monocyclic heteroaryl of 5 or 6 ring atoms having 1 to 4 ring atoms independently chosen from N, O, and S, wherein Y is substituted with 0-2 substituents chosen from halogen, hydroxyl, cyano, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —O($C_0$-$C_6$alkyl)cycloalkyl, —($C_0$-$C_6$alkyl)$CO_2R^{23}$, and —($C_0$-$C_6$alkyl)C(O)$NR^{23}R^{24}$.

Z is phenyl, —($C_1$-$C_6$alkyl)phenyl, —($C_2$-$C_6$alkenyl)phenyl, —($C_2$-$C_6$alkynyl)phenyl, $C_3$-$C_7$cycloalkyl, or a monocyclic heterocycle of 5 or 6 ring atoms having 1, 2, or 3 ring atoms independently chosen from N, O, and S, wherein Z is substituted with 0-3 substituents independently chosen from hydroxyl, halogen, cyano, $C_1$-$C_6$alkyl, $C_2$-$C_6$alkenyl, $C_2$-$C_6$alkynyl, $C_1$-$C_6$alkoxy, —$C_0$-$C_2$alkyl$NR^{25}R^{26}$, $C_1$-$C_6$haloalkyl, $C_1$-$C_6$haloalkoxy, —($C_0$-$C_6$alkyl)cycloalkyl, —O($C_0$-$C_6$alkyl)cycloalkyl, —($C_0$-$C_6$alkyl)phenyl, —O—($C_0$-$C_6$alkyl)phenyl, —($C_0$-$C_6$alkyl)$CO_2R^{25}$, —($C_0$-$C_6$alkyl)C(O)$NR^{25}R^{26}$, —($C_0$-$C_6$alkyl)$NR^{25}R^{26}$, and —($C_1$-$C_6$alkyl)$OR^{25}$.

Y and Z can be taken together to be a bicyclic heteroaryl of 8 to 10 ring atoms, having 1, 2, or 3 ring atoms independently chosen from N, O, and S, wherein the bicyclic heteroaryl is substituted with 0-2 substituents independently chosen from hydroxyl, halogen, cyano, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)phenyl, —O—($C_0$-$C_6$alkyl)phenyl, —($C_0$-$C_6$alkyl)$CO_2R^{23}$, —($C_0$-$C_6$alkyl)C(O)$NR^{23}R^{24}$, —($C_0$-$C_6$alkyl)$NR^{23}R^{24}$, and —($C_1$-$C_6$alkyl)$OR^{23}$.

$R^{15}$ and $R^{16}$, are each independently chosen at each occurrence from hydrogen, $C_1$-$C_6$ alkyl, and —($C_0$-$C_6$alkyl)cycloalkyl; or when $X^2$ is absent and $X^1$ is $NR^{19}$, then $R^{19}$ and $R^{15}$ can be joined to form a pyrrolidine or piperidine ring, said pyrrolidine or piperidine ring substituted with 0 to 3 substituents chosen from $C_1$-$C_6$ alkyl, and —($C_0$-$C_6$alkyl)cycloalkyl.

$R^{17}$ and $R^{18}$ are each independently chosen at each occurrence from hydrogen, hydroxyl, $C_1$-$C_6$alkyl, $C_1$-$C_6$alkoxy, and —($C_0$-$C_6$alkyl)cycloalkyl, or $R^{17}$ and $R^{18}$ may be taken together to form an oxo group.

$R^{19}$, $R^{20}$, $R^{21}$, and $R^{22}$ are each independently chosen at each occurrence from hydrogen, $C_1$-$C_6$ alkyl, —($C_0$-$C_6$alkyl)cycloalkyl, —C(O)$C_1$-$C_6$alkyl, and —C(O)O$C_1$-$C_6$alkyl.

$R^{23}$ and $R^{24}$ are each independently chosen at each occurrence from hydrogen, $C_1$-$C_6$ alkyl, and —($C_0$-$C_6$alkyl)cycloalkyl.

$R^{25}$ and $R^{26}$ are each independently chosen at each occurrence from hydrogen, $C_1$-$C_6$ alkyl, and —($C_0$-$C_6$alkyl)cycloalkyl.

$R^{23}$ and $R^{24}$, or $R^{25}$ and $R^{26}$, bound to the same nitrogen atom may be taken together to form a 4 to 7-membered heterocycloalkyl ring, which heterocycloalkyl ring contains 0, 1, or 2 additional heteroatoms chosen from N, O, and S, and which heterocycloalkyl ring is optionally substituted at any carbon ring atom with halogen, hydroxyl, oxo, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)phenyl, —($C_0$-$C_6$alkyl)$CO_2R^{25}$, —($C_0$-$C_6$alkyl)C(O)$NR^{25}R^{26}$, —($C_1$-$C_6$alkyl)$OR^{25}$, or —($C_0$-$C_6$alkyl)$NR^{25}R^{26}$, and optionally substituted at any nitrogen ring atom available for substitution by $C_1$-$C_6$ alkyl or —($C_0$-$C_4$alkyl)cycloalkyl.

In this second aspect Y is not thiazole unless at least one of the following conditions is present:
  a) at least one of $X^1$ and $X^2$ is not a substituted carbon atom, or
  b) $R^{17}$ and $R^{18}$ are not taken together as a oxo group, or
  c) $R^{13}$ is not phenyl, or phenyl substituted only with one or two substituents chosen from halogen, $C_1$-$C_3$alkyl, and methoxy, or
  d) Z is not phenyl or phenyl substituted only with one or two substituents chosen from halogen, methyl, and methoxy.

In this second aspect the compound is not

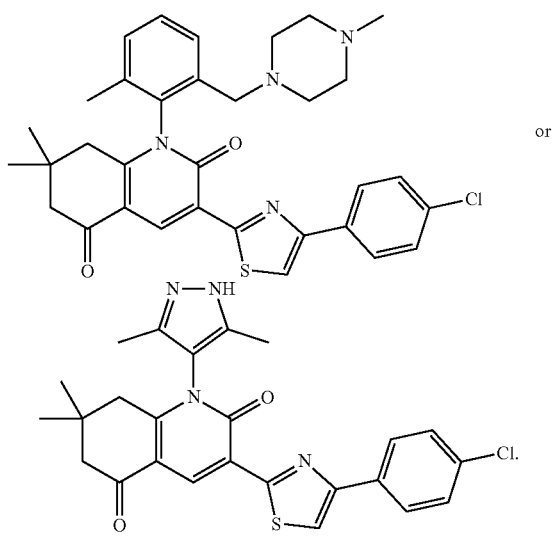

or

Pharmaceutical compositions comprising a compound or salt of Formula I or Formula II together with a pharmaceutically acceptable carrier are also disclosed.

Methods of treating a cancer characterized by the presence of an IDH1 mutation, wherein the IDH1 mutation results in a new ability of the enzyme to catalyze the NADPH-dependent reduction of a-ketoglutarate to R(−)-2-hydroxyglutarate in a patient, comprising the step of administering to the patient in need thereof a compound of Formula or II or a salt thereof, are also disclosed.

In some embodiments the IDH1 mutation is an IDH1 R132H or IDH1 R132C mutation.

Methods of treating cancer characterized by the presence of an IDH1 mutation, such as glioma (glioblastoma), acute myelogenous leukemia, acute myeloid leukemia, myelodysplastic/myeloproliferative neoplasms, sarcoma, chronic myelomonocytic leukemia, non-Hodgkin lymphoma, astrocytoma, melanoma, non-small cell lung cancer, cholangiocarcinomas, chondrosarcoma, or colon cancer, comprising administering a therapeutically effective amount of a compound or salt of Formula I or Formula II to a patient in need of such treatment are also disclosed.

DETAILED DESCRIPTION

Terminology

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or." The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in any suitable order unless otherwise indicated herein or otherwise clearly contradicted by context. The use of any and all examples, or exemplary language (e.g., "such as"), is intended for illustration and does not pose a limitation on the scope of the disclosure unless otherwise claimed. No language in the specification should be construed as indicating any non-claimed element as essential to the practice of the invention. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists. e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}$C, $^{13}$C, and $^{14}$C.

Formula I includes all pharmaceutically acceptable salts of Formula I.

Formula II includes all pharmaceutically acceptable salts of Formula II and all subformulae such as Formula III.

The opened ended term "comprising" includes the intermediate and closed terms "consisting essentially of" and "consisting of."

The term "substituted" means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Suitable groups that may be present on an "optionally substituted" position include, but are not limited to, e.g., halogen, cyano, hydroxyl, amino, nitro, oxo, azido, alkanoyl (such as a $C_2$-$C_6$ alkanoyl group such as acyl or the like (—(C=O)alkyl)); carboxamido; alkylcarboxamide; alkyl groups, alkoxy groups, alkylthio groups including those having one or more thioether linkages, alkylsulfinyl groups including those having one or more sulfinyl linkages, alkylsulfonyl groups including those having one or more sulfonyl linkages, mono- and di-aminoalkyl groups including groups having one or more N atoms, all of the foregoing optional alkyl substituents may have one or more methylene groups replaced by an oxygen or —NH—, and have from about 1 to about 8, from about 1 to about 6, or from 1 to about 4 carbon atoms, cycloalkyl; phenyl; phenylalkyl with benzyl being an exemplary phenylalkyl group, phenylalkoxy with benzyloxy being an exemplary phenylalkoxy group. Alkylthio and alkoxy groups are attached to the position they substitute by the sulfur or oxygen atom respectively.

A dash ("-") that is not between two letters or symbols is used to indicate a point of attachment for a substituent.

"Alkyl" includes both branched and straight chain saturated aliphatic hydrocarbon groups, having the specified number of carbon atoms, generally from 1 to about 8 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_8$alkyl, $C_1$-$C_4$alkyl, and $C_1$-$C_2$alkyl. When $C_0$-$C_n$ alkyl is used herein in conjunction with another group, for example, —$C_0$-$C_2$alkyl(phenyl), the indicated group, in this case phenyl, is either directly bound by a single covalent bond ($C_0$alkyl), or attached by an alkyl chain having the specified number of carbon atoms, in this case 1, 2, 3, or 4 carbon atoms. Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, 3-methylbutyl, t-butyl, n-pentyl, and sec-pentyl.

"Alkenyl" is a branched or straight chain aliphatic hydrocarbon group having one or more carbon-carbon double bonds that may occur at any stable point along the chain, having the specified number of carbon atoms. Examples of alkenyl include, but are not limited to, ethenyl and propenyl.

"Alkynyl" is a branched or straight chain aliphatic hydrocarbon group having one or more double carbon-carbon triple bonds that may occur at any stable point along the chain, having the specified number of carbon atoms.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "Alkylthio" or a "thioalkyl" group is an alkyl group as defined above with the indicated number of carbon atoms covalently bound to the group it substitutes by a sulfur bridge (—S—).

"Cycloalkyl" is a saturated hydrocarbon ring group, having the specified number of carbon atoms, usually from 3 to about 7 carbon atoms. Examples of cycloalkyl groups include cyclopropyl, cyclobutyl, cyclopentyl, or cyclohexyl as well as bridged or caged saturated ring groups such as norborane or adamantane. "—($C_0$-$C_n$alkyl)cycloalkyl" is a cycloalkyl group attached to the position it substitutes either by a single covalent bond ($C_0$) or by an alkylene linker having 1 to n carbon atoms.

"Halo" or "halogen" means fluoro, chloro, bromo, or iodo.

"Heteroaryl" is a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Heteroaryl groups include, but are not limited to, oxazolyl, piperazinyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, isothiazolyl, and isoxazolyl.

"Heterocycle" is a saturated, unsaturated, or aromatic cyclic group having the indicated number of ring atoms containing from 1 to about 3 heteroatoms chosen from N, O, and S, with remaining ring atoms being carbon. Examples of heterocycle groups include piperazine and thiazole groups.

"Heterocycloalkyl" is a saturated cyclic group having the indicated number of ring atoms containing from 1 to about 3 heteroatoms chosen from N, O, and S, with remaining ring atoms being carbon. Examples of heterocycloalkyl groups include tetrahydrofuranyl and pyrrolidinyl groups.

"Haloalkyl" means both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined above attached through an oxygen bridge (oxygen of an alcohol radical).

"Pharmaceutical compositions" means compositions comprising at least one active agent, such as a compound or salt of Formula (I), and at least one other substance, such as a carrier. Pharmaceutical compositions meet the U.S. FDA's GMP (good manufacturing practice) standards for human or non-human drugs.

"Carrier" means a diluent, excipient, or vehicle with which an active compound is administered. A "pharmaceutically acceptable carrier" means a substance, e.g., excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" includes both one and more than one such carrier.

A "patient" means a human or non-human animal in need of medical treatment. Medical treatment can include treatment of an existing condition, such as a disease or disorder or diagnostic treatment. In some embodiments the patient is a human patient.

"Providing" means giving, administering, selling, distributing, transferring (for profit or not), manufacturing, compounding, or dispensing.

"Treatment" or "treating" means providing an active compound to a patient in an amount sufficient to measurably reduce any cancer symptom, slow cancer progressionor cause cancer regression. In certain embodiments treatment of the cancer may be commenced before the patient presents symptoms of the disease.

A "therapeutically effective amount" of a pharmaceutical composition means an amount effective, when administered to a patient, to provide a therapeutic benefit such as an amelioration of symptoms, decrease cancer progression, or cause cancer regression.

A significant change is any detectable change that is statistically significant in a standard parametric test of statistical significance such as Student's T-test, where $p<0.05$.

Chemical Description

Compounds of Formula I or Formula II may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, tautomers, polymorphs, free compound and salts) of an active agent may be employed either alone or in combination.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

"Tautomers" or "tautomeric forms" are constitutional isomers that readily interconvert, commonly by the migration of a hydrogen atom combined with a switch of a single bond and a double bond.

"Pharmaceutically acceptable salts" include derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media such as ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)$_n$—COOH where n is 0-4, and the like. Lists of additional suitable salts may be found, e.g., in G. Steffen Paulekuhn, et al., *Journal of Medicinal Chemistry* 2007, 50, 6665 and *Handbook of Pharmaceutically Acceptable Salts: Properties, Selection and Use*, P. Heinrich Stahl and Camille G. Wemuth Editors, Wiley-VCH, 2002.

Chemical Description

Molecules which inhibit mutant IDH1 are disclosed herein.

In addition to compounds of Formula I, Formula II, and subformulae such as Formula III shown in the SUMMARY section, the disclosure also includes compounds in which the variables, e.g. A, B, X$^1$, X$^2$, Y, Z, R$^1$ to R$^{26}$ carry the following definitions. The disclosure includes all combinations of these definitions so long as a stable compound results. The disclosure includes the following particular embodiments of Formula (I)

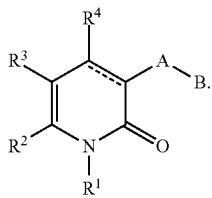

Formula (I)

In some embodiments the compound of Formula I is a compound of Formula (IA)

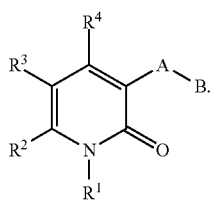

Formula (IA)

(A) R$^1$ is a phenyl, pyridyl, or tetrahydronaphthyl substituted by 0-3 substituents independently chosen from hydroxyl, halogen, cyano, nitro, oxo, —(C$_0$-C$_6$alkyl)phenyl, —O—(C$_0$-C$_6$alkyl)phenyl, C$_1$-C$_6$alkyl, C$_1$-C$_6$alkylthio, C$_1$-C$_6$alkoxy, —(C$_1$-C$_6$haloalkyl, C$_1$-C$_6$haloalkoxy, —(C$_0$-C$_6$alkyl)cycloalkyl, —O—(C$_0$-C$_6$alkyl)cycloalkyl, —(C$_0$-C$_2$alkyl)phenyl, —O—(C$_0$-C$_2$alkyl)phenyl, —(C$_0$-C$_6$alkyl)CO$_2$R$^5$, —(C$_0$-C$_6$alkyl)C(O)NR$^5$R$^6$, —(C$_1$-C$_6$alkyl)OR$^5$, —(C$_0$-C$_6$alkyl)NR$^5$R$^6$, —(C$_0$-C$_6$alkyl)NR$^5$C(O)R$^6$, and a monocyclic heterocycle of 4 to 6 ring atoms having 1, 2, or 3 ring atoms independently chosen from N, O, and S, wherein said monocyclic heterocycle of 4 to 6 ring atoms is optionally substituted with one or more substituents independently chosen from halogen, cyano, —CO$_2$H, C$_1$-C$_6$alkoxy, C$_1$-C$_6$haloalkyl, and C$_1$-C$_6$haloalkoxy.

R$^2$ is C$_1$-C$_6$alkyl, C$_2$-C$_6$alkenyl, C$_2$-C$_6$alkynyl, —(C$_0$-C$_6$alkyl)OR$^5$, —(C$_0$-C$_6$alkyl)SR$^5$, —(C$_0$-C$_6$alkyl)NR$^5$R$^6$, —(C$_0$-C$_6$alkyl)heterocycloalkyl or —(C$_0$-C$_6$alkyl)cycloalkyl.

A is a phenyl or a monocyclic heteroaryl of 5 or 6 ring atoms having 1 to 4 ring atoms independently chosen from N, O, and S, wherein A is substituted with 0-2 substituents chosen from halogen, C$_1$-C$_6$alkyl, C$_1$-C$_6$haloalkyl, —(C$_0$-C$_6$alkyl)cycloalkyl, —O(C$_0$-C$_6$alkyl)cycloalkyl, —(C$_0$-C$_6$alkyl)CO$_2$R$^5$, and —(C$_0$-C$_6$alkyl)C(O)NR$^5$R$^6$.

(B) R$^1$ is a phenyl or pyridyl substituted by 0-3 substituents independently chosen from hydroxyl, halogen, cyano, nitro, C$_1$-C$_6$alkyl, C$_1$-C$_6$alkylthio, C$_1$-C$_6$alkoxy, C$_1$-C$_2$haloalkyl, C$_1$-C$_2$haloalkoxy, —(C$_0$-C$_6$alkyl)C$_3$-C$_6$cycloalkyl, —O—(C$_0$-C$_6$alkyl) C$_3$-C$_6$cycloalkyl, —(C$_0$-C$_2$alkyl)phenyl, —O—(C$_0$-C$_2$alkyl)phenyl, —(C$_0$-C$_6$alkyl)CO$_2$R$^5$, —(C$_0$-C$_6$alkyl)C(O)NR$^5$R$^6$, —(C$_1$-C$_6$alkyl)OR$^5$, —(C$_0$-C$_6$alkyl)NR$^5$R$^6$, and —(C$_0$-C$_6$alkyl)NR$^5$C(O)R$^6$.

R$^2$ is C$_1$-C$_6$alkyl, C$_2$-C$_6$alkenyl, C$_2$-C$_6$alkynyl, or —(C$_0$-C$_6$alkyl)cycloalkyl.

R$^3$ is C(O)NR$^7$R$^8$.

R$^4$ is hydrogen or C$_1$-C$_6$alkyl.

A is a monocyclic heteroaryl of 5 or 6 ring atoms having 1 to 4 ring atoms independently chosen from N, O, and S, wherein A is substituted with 0-2 substituents independently chosen from halogen, cyano, C$_1$-C$_6$alkyl, C$_1$-C$_6$alkoxy, C$_1$-C$_6$haloalkyl, and C$_1$-C$_6$haloalkoxy, —(C$_0$-C$_6$alkyl)cycloalkyl, —O(C$_0$-C$_6$alkyl)cycloalkyl, —(C$_0$-C$_6$alkyl)CO$_2$R$^5$, and —(C$_0$-C$_6$alkyl)C(O)NR$^5$R$^6$.

B is a phenyl or pyridyl substituted with 0-3 substituents independently chosen from hydroxyl, halogen, cyano, C$_1$-C$_6$alkyl, C$_1$-C$_6$alkoxy, C$_1$-C$_6$haloalkyl, C$_1$-C$_6$haloalkoxy, —(C$_0$-C$_6$alkyl)cycloalkyl, —O—(C$_0$-C$_6$alkyl)cycloalkyl, —O—(C$_0$-C$_6$alkyl)phenyl, —O—(C$_0$-C$_6$alkyl)phenyl, —(C$_0$-C$_6$alkyl)cycloalkyl, —O(C$_0$-C$_6$alkyl)cycloalkyl, —(C$_0$-C$_6$alkyl)CO$_2$R$^9$, —(C$_0$-C$_6$alkyl)C(O)NR$^9$R$^{10}$, —(C$_0$-C$_6$alkyl)NR$^9$R$^{10}$, and —(C$_1$-C$_6$alkyl)OR$^9$.

(C) R$^1$ is a phenyl or pyridyl substituted with 0-3 substituents independently chosen from hydroxyl, halogen, cyano, C$_1$-C$_6$alkyl, C$_1$-C$_6$alkylthio, C$_1$-C$_6$alkoxy, C$_1$-C$_6$haloalkyl, C$_1$-C$_6$haloalkoxy, —(C$_0$-C$_6$alkyl)C$_3$-C$_6$cycloalkyl, —O—(C$_0$-C$_6$alkyl) C$_3$-C$_6$cycloalkyl, phenyl, phenoxy, benzyloxy, —(C$_0$-C$_6$alkyl)CO$_2$R$^5$, —(C$_0$-C$_6$alkyl)C(O)NR$^5$R$^6$, —(C$_1$-C$_6$alkyl)OR$^5$, —(C$_0$-C$_6$alkyl)NR$^5$R$^6$, and —(C$_0$-C$_6$alkyl)NR$^5$C(O)R$^6$.

R$^2$ is C$_1$-C$_6$alkyl, C$_2$-C$_6$alkenyl, or —(C$_0$-C$_6$alkyl)cycloalkyl.

R$^3$ is C(O)NR$^7$R$^8$; where R$^7$ and R$^8$ are taken together to form a 4- to 7-membered heterocycloalkyl ring, which heterocycloalkyl ring contains 0, 1, or 2 additional heteroatoms chosen from N, O, and S, which R$^7$/R$^8$ ring is optionally substituted at any carbon ring atom with halogen, hydroxyl, oxo, C$_1$-C$_6$alkyl, C$_1$-C$_6$alkoxy, C$_1$-C$_6$haloalkyl, C$_1$-C$_6$haloalkoxy, —(C$_0$-C$_6$alkyl)cycloalkyl, —(C$_0$-C$_6$alkyl)phenyl, —(C$_0$-C$_6$alkyl)CO$_2$R$^{11}$, —(C$_0$-C$_6$alkyl)C(O)NR$^{11}$R$^{12}$, —(C$_1$-C$_6$alkyl)OR$^{11}$, or —(C$_0$-C$_6$alkyl)NR$^{11}$R$^{12}$, and optionally substituted at any nitrogen ring atom available for substitution by C$_1$-C$_6$ alkyl or —(C$_0$-C$_4$alkyl)cycloalkyl.

R$^4$ is hydrogen;

A is a monocyclic heteroaryl of 5 ring atoms having 1 to 4 ring atoms independently chosen from N, O, and S, wherein A is substituted with 0-1 substituents chosen from halogen, C$_1$-C$_6$alkyl, C$_1$-C$_6$haloalkyl, —(C$_0$-C$_6$alkyl)cycloalkyl, —O(C$_0$-C$_6$alkyl)cycloalkyl, —(C$_0$-C$_6$alkyl)CO$_2$R$^5$, and —(C$_0$-C$_6$alkyl)C(O)NR$^5$R$^6$.

B is a phenyl or pyridyl substituted with 0-3 substituents independently chosen from hydroxyl, halogen, cyano, C$_1$-C$_6$alkyl, C$_1$-C$_6$alkoxy, C$_1$-C$_6$haloalkyl, C$_1$-C$_6$haloalkoxy, —(C$_0$-C$_6$alkyl)cycloalkyl, —(C$_0$-C$_6$alkyl)phenyl, —O—(C$_0$-C$_6$alkyl)phenyl, —(C$_0$-C$_6$alkyl)cycloalkyl, —O(C$_0$-C$_6$alkyl)cycloalkyl, —(C$_0$-C$_6$alkyl)CO$_2$R$^9$, —(C$_0$-C$_6$alkyl)C(O)NR$^9$R$^{10}$, —(C$_0$-C$_6$alkyl)NR$^9$R$^{10}$, and —(C$_1$-C$_6$alkyl)OR$^9$.

(C) $R^1$ is 2,6-diethylphenyl, 2-ethoxy-5-cholorophenyl, 2-chloro-5-ethoxyphenyl, or 2-ethyl-5-methoxyphenyl.

$R^2$ is isobutyl or 2,2-dimethylvinyl.

$R^3$ is

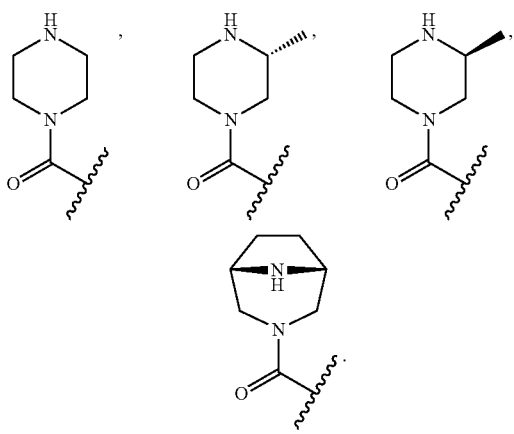

$R^4$ is hydrogen.

A is

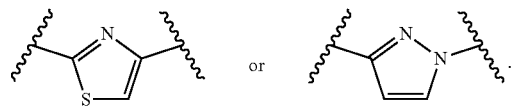 [SMILES: *c1csc(*)n1 ; *c1ccn(*)n1]

B is 4-chlorophenyl, 4-(trifluoromethyl)phenyl, 4-(difluoromethyl)phenyl, 6-(trifluoromethyl)-3-pyridyl, or 6-(difluoromethyl)-3-pyridyl.

The disclosure also includes compounds of Formula (I) in which the variables, e.g., A, B, and $R^1$-$R^4$ carry the following definitions.

The variable A

A is one of the following:

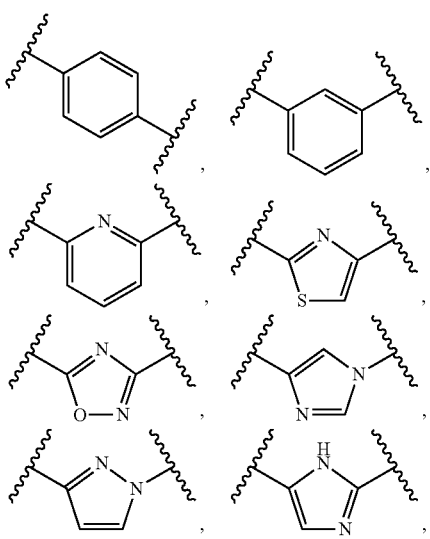

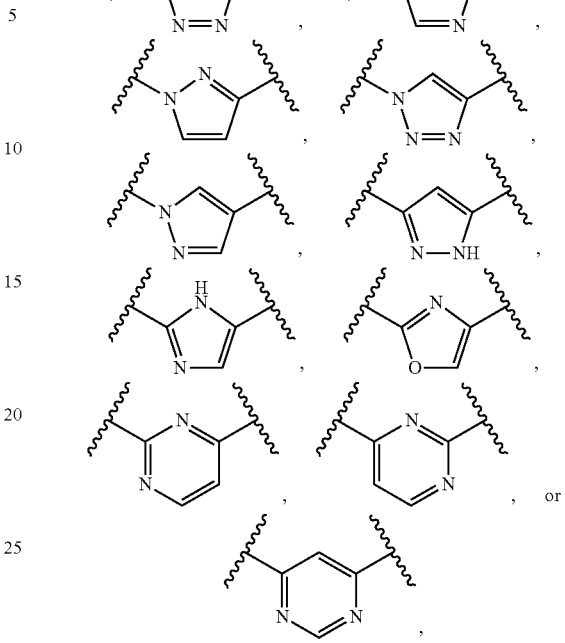

including tautomeric forms, and each A may be unsubstituted or substituted with a substituent independently chosen from halogen, $C_1$-$C_6$alkyl, $C_1$-$C_6$haloalkyl, and —($C_0$-$C_6$alkyl)cycloalkyl, —O($C_0$-$C_6$alkyl)cycloalkyl, —($C_0$-$C_6$alkyl)$CO_2R^5$, and —($C_0$-$C_6$alkyl)C(O)$NR^5R^6$.

(B) A is a thiazolyl, pyrazolyl, or imidazolyl group, each of which is optionally substituted with methyl or halogen.

(C) A is a phenyl or a monocyclic heteroaryl of 5 or 6 ring atoms having 1 to 4 ring atoms independently chosen from N, O, and S, wherein A is substituted with 0-2 substituents chosen from halogen, $C_1$-$C_6$alkyl, and $C_1$-$C_6$haloalkyl.

(D) A is a monocyclic heteroaryl of 5 or 6 ring atoms having 1 to 4 ring atoms independently chosen from N, O, and S, wherein A is substituted with 0-2 substituents independently chosen from halogen, cyano, $C_1$-$C_6$alkoxy, $C_1$-$C_6$haloalkyl, and $C_1$-$C_6$haloalkoxy.

(E) A is

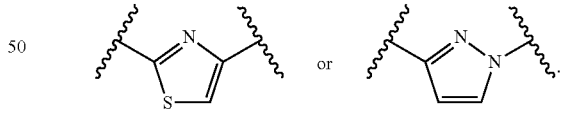

The Variable B

B is a phenyl substituted with 0-3 substituents independently chosen from hydroxyl, halogen, cyano, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —O—($C_0$-$C_6$alkyl)cycloalkyl, —($C_0$-$C_6$alkyl)phenyl, —O—($C_0$-$C_6$alkyl)phenyl, —($C_0$-$C_6$alkyl)$CO_2R^9$, —($C_0$-$C_6$alkyl)C(O)$NR^9R^{10}$, —($C_0$-$C_6$alkyl)$NR^9R^{10}$, and —($C_1$-$C_6$alkyl)$OR^9$.

(B) B is phenyl, which is unsubstituted or substituted with one or two substituents independently chosen from halogen, methyl, methoxy, trifluoromethyl, and trifluoromethoxy.

(C) B is phenyl substituted para to the point of attachment to A with one substituent chosen from chosen from halogen, methyl, methoxy, trifluoromethyl, and trifluoromethoxy.

(D) B is 4-chlorophenyl.

(E) B is 3-pyridyl substituted at the 4-position with halo or $C_1$haloalkyl.

(F) B is 4-chlorophenyl, 4-(trifluoromethyl)phenyl, 4-(difluoromethyl)phenyl, 6-(trifluoromethyl)-3-pyridyl, or 6-(difluoromethyl)-3-pyridyl.

The Variable $R^1$ $R^1$ is a phenyl, pyridyl, or tetrahydronaphthyl substituted by 0-3 substituents independently chosen from hydroxyl, halogen, cyano, nitro, —($C_0$-$C_6$alkyl)phenyl, —O—($C_0$-$C_6$alkyl)phenyl, $C_1$-$C_6$alkyl, $C_1$-$C_6$alkylthio, $C_1$-$C_6$alkoxy, $C_1$-$C_6$haloalkyl, $C_1$-$C_6$haloalkoxy, —($C_0$-$C_6$alkyl)cycloalkyl, —O—($C_0$-$C_6$alkyl)cycloalkyl, —($C_0$-$C_2$alkyl)phenyl, —O—($C_0$-$C_2$alkyl)phenyl, —($C_0$-$C_6$alkyl)$CO_2R^5$, —($C_0$-$C_6$alkyl)C(O)$NR^5R^6$, —($C_1$-$C_6$alkyl)$OR^5$, —($C_0$-$C_6$alkyl)$NR^5R^6$, —($C_0$-$C_6$alkyl)$NR^5$C(O)$R^6$, and a monocyclic heterocycle of 4 to 6 ring atoms having 1, 2, or 3 ring atoms independently chosen from N, O, and S.

$R^1$ is a phenyl or pyridyl substituted by 0-3 substituents independently chosen from hydroxyl, halogen, cyano, nitro, $C_1$-$C_6$alkyl, $C_1$-$C_6$alkylthio, $C_1$-$C_6$alkoxy, $C_1$-$C_2$haloalkyl, $C_1$-$C_2$haloalkoxy, —($C_0$-$C_6$alkyl)$C_3$-$C_6$cycloalkyl, —O—($C_0$-$C_6$alkyl) $C_3$-$C_6$cycloalkyl, —($C_0$-$C_2$alkyl)phenyl, —O—($C_0$-$C_2$alkyl)phenyl, —($C_0$-$C_6$alkyl)$CO_2R^5$, —($C_0$-$C_6$alkyl)C(O)$NR^5R^6$, —($C_1$-$C_6$alkyl)$OR^5$, —($C_0$-$C_6$alkyl) $NR^5R^6$, and —($C_0$-$C_6$alkyl)$NR^5$C(O)$R^6$ $R^1$ is a phenyl or pyridyl substituted by 1-3 substituents independently chosen from hydroxyl, halogen, cyano, $C_1$-$C_6$alkyl, $C_1$-$C_6$alkylthio, $C_1$-$C_6$alkoxy, $C_1$-$C_6$haloalkyl, $C_1$-$C_6$haloalkoxy, —($C_0$-$C_6$alkyl)cycloalkyl, —O—($C_0$-$C_6$alkyl)cycloalkyl, phenyl, phenyloxy, benzyloxy, —($C_0$-$C_6$alkyl)$CO_2R^5$, —($C_0$-$C_6$alkyl)C(O)$NR^5R^6$, —($C_1$-$C_6$alkyl)$OR^5$, —($C_0$-$C_6$alkyl)$NR^5R^6$, and —($C_0$-$C_6$alkyl) $NR^5$C(O)$R^6$; wherein at least one of the 1-3 $R^1$ substituents must be ortho to the point of $R^1$ attachment in Formula I.

(D) $R^1$ is a phenyl or pyridyl, substituted with 1-2 substituents independently chosen from halogen, hydroxyl, —COOH, $C_1$-$C_3$alkyl, $C_1$-$C_3$alkylthio, $C_1$-$C_3$alkoxy, —N($CH_3$)$_2$, —$CH_2CF_3$, —$CF_3$, —$OCF_3$, —($C_0$-$C_2$alkyl)cyclopropyl, —O—($C_0$-$C_2$alkyl)cyclopropyl, phenyl, phenoxy, and benzyloxy.

(E) $R^1$ is 2,6-diethylphenyl.

(F) $R^1$ is 5-methyl-2-ethoxypyridin-3-yl, 5-fluoro-2-ethoxypyridin-3-yl or 5-chloro-2-ethoxypyridin-3-yl.

(G) $R^1$ is 2-chloro-5-methoxyphenyl, 5 Chloro-2-ethoxyphenyl, or 5-chloro-2-isopropoxyphenyl.

(H) $R^1$ is 2,6-diethylphenyl, 2-ethoxy-5-cholorophenyl, 2-chloro-5-ethoxyphenyl, or 2-ethyl-5-methoxyphenyl.

(I) $R^1$ is phenyl or 3-pyridyl, which $R^1$ is unsubstituted or substituted with one or two substituents independently chosen from chloro, fluoro, methyl, ethyl, methoxy, ethoxy, and trifluoromethyl.

The Variable $R^2$ $R^2$ is $C_1$-$C_6$alkyl, $C_2$-$C_6$alkenyl, $C_2$-$C_6$alkynyl, —($C_0$-$C_6$alkyl)$OR^5$, —($C_0$-$C_6$alkyl)$SR^5$, —($C_0$-$C_6$alkyl)$NR^5R^6$, —($C_0$-$C_6$alkyl)heterocycloalkyl or —($C_0$-$C_6$alkyl)cycloalkyl.

$R^2$ is $C_1$-$C_6$alkyl, $C_2$-$C_6$alkenyl, $C_2$-$C_6$alkynyl, or —($C_0$-$C_6$alkyl)cycloalkyl.

$R^2$ is isobutyl or 2,2-dimethylvinyl.

$R^2$ is 2,2-dimethylvinyl.

The Variable $R^3$ $R^3$ is C(O)$NR^7R^8$; where $R^7$ and $R^8$ are taken together to form a 4- to 7-membered heterocycloalkyl ring, which heterocycloalkyl ring contains 0, 1, or 2 additional heteroatoms chosen from N, O, and S, which $R^7$/$R^8$ ring is optionally substituted at any carbon ring atom with halogen, hydroxyl, oxo, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)phenyl, —($C_0$-$C_6$alkyl)$CO_2R^{11}$, —($C_0$-$C_6$alkyl)C(O)$NR^{11}R^{12}$, —($C_1$-$C_6$alkyl)$OR^{11}$, or —($C_0$-$C_6$alkyl) $NR^{11}R^{12}$, and optionally substituted at any nitrogen ring atom available for substitution by $C_1$-$C_6$ alkyl or —($C_0$-$C_4$alkyl)cycloalkyl.

$R^3$ is C(O)$NR^7R^8$, where $R^7$ and $R^8$ and are taken together to form a piperazine ring which is optionally substituted at any carbon ring atom with 1 or 2 substituents independently chosen from halogen, hydroxyl, oxo, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)phenyl, —($C_0$-$C_6$alkyl) $CO_2R^{11}$, —($C_0$-$C_6$alkyl)C(O)$NR^{11}R^{12}$, —($C_1$-$C_6$alkyl) $OR^{11}$, and —($C_0$-$C_6$alkyl)$NR^{11}R^{12}$, and optionally substituted at any nitrogen ring atom available for substitution with $C_1$-$C_6$ alkyl or —($C_0$-$C_4$alkyl)cycloalkyl.

$R^3$ is C(O)$NR^7R^8$.

$R^3$ is

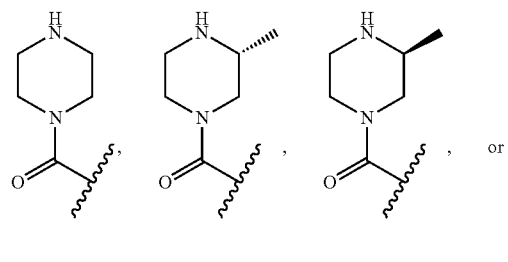

$R^3$ is

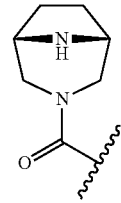

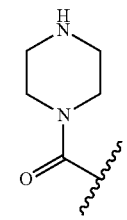

The Variable R $R^4$ is hydrogen, hydroxyl, halogen, cyano, —$CO_2H$, $C_1$-$C_6$alkyl, $C_2$-$C_6$alkenyl, $C_2$-$C_6$alkynyl, $C_1$-$C_6$alkoxy, or $C_1$-$C_6$haloalkyl.

$R^4$ is hydrogen or $C_1$-$C_6$alkyl.

$R^4$ is hydrogen.

The disclosure further includes compounds or salts of Formula(II) with the structure of Formula (III).

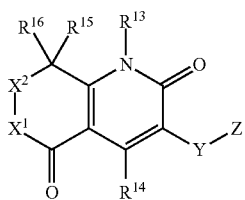

Formula (III)

The disclosure also includes compounds of Formula (II) and Formula (III) in which the variables, e.g., $X^1$, $X^2$, Y, Z, and $R^{13}$-$R^{26}$ carry the following definitions.

The variables $X^1$ and $X^2$ $X^1$ is $CR^{19}R^{20}$ and $X^2$ is $CR^{21}R^{22}$.

In certain embodiments $R^{15}$ and $R^{16}$ are both hydrogen; $R^{19}$ and $R^{20}$ are both hydrogen; and $R^{21}$ and $R^{22}$ are both hydrogen or both methyl.

The Variable Y

Y is one of the following:

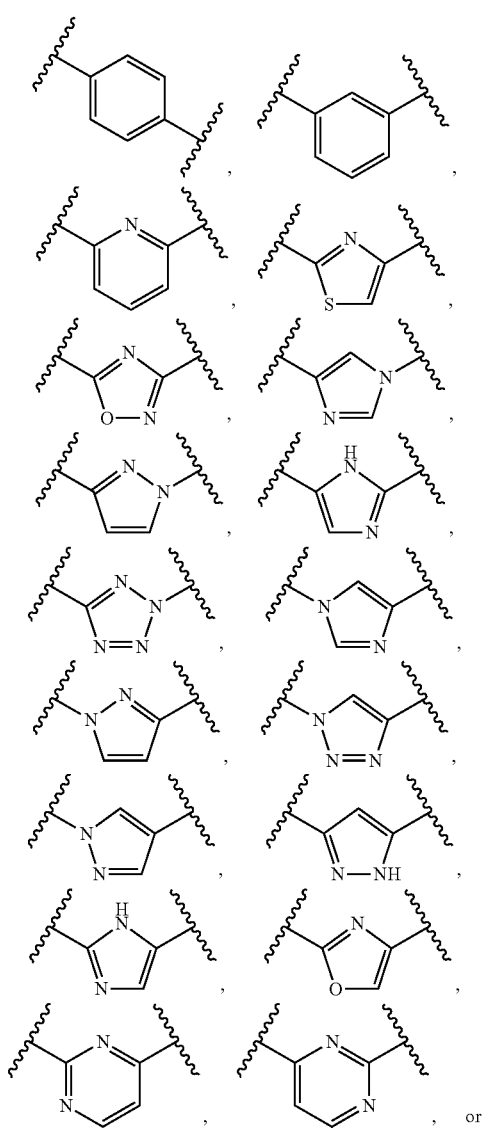

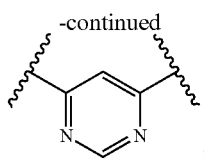

including tautomeric forms, and each Y may be substituted at open positions with 0-1 substituents chosen from halogen, $C_1$-$C_6$alkyl, or $C_1$-$C_6$haloalkyl.

(B) Y is one of the following:

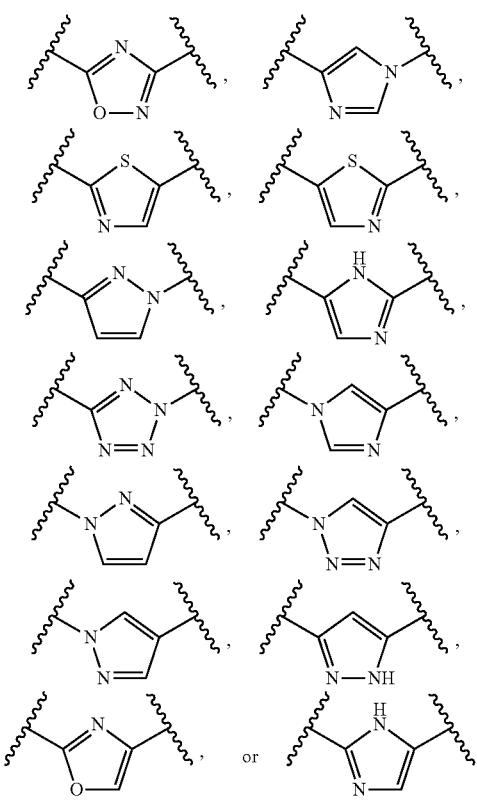

including tautomeric forms, and each Y may be substituted at open positions with 0-1 substituents chosen from halogen, $C_1$-$C_6$alkyl, or $C_1$-$C_6$haloalkyl.

(C) Y is

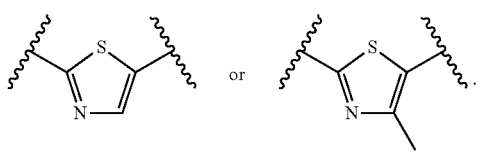

(D) Y is

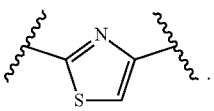 [SMILES: *c1csc(*)n1]

The Variable Z (A) Z is phenyl or pyridyl substituted with 0-3 substituents independently chosen from hydroxyl, halogen, cyano, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)phenyl, —O—($C_0$-$C_6$alkyl)phenyl, —($C_0$-$C_6$alkyl)$CO_2R^{23}$, —($C_0$-$C_6$alkyl)C(O)$NR^{23}R^{24}$, —($C_0$-$C_6$alkyl)$NR^{23}R^{24}$, and —($C_1$-$C_6$alkyl)$OR^{23}$.

(B) Z is 4-chlorophenyl, 4-(trifluoromethyl)phenyl, 4-(difluoromethyl)phenyl, 6-(trifluoromethyl)-3-pyridyl, or 6-(difluoromethyl)-3-pyridyl.

The Variable $R^{13}$ $R^{13}$ is phenyl, pyridyl, thiophenyl, or tetrahydronaphthyl, substituted by 0-3 substituents independently chosen from hydroxyl, halogen, cyano, —($C_0$-$C_6$alkyl)phenyl, —O—($C_0$-$C_6$alkyl)phenyl, $C_1$-$C_6$alkyl, $C_1$-$C_6$alkylthio, $C_1$-$C_6$alkoxy, $C_1$-$C_6$haloalkyl, $C_1$-$C_6$haloalkoxy, —($C_0$-$C_6$alkyl)cycloalkyl, —O—($C_0$-$C_6$alkyl)cycloalkyl, —($C_0$-$C_6$alkyl)$CO_2R^{23}$, —($C_0$-$C_6$alkyl)C(O)$NR^{23}R^{24}$, —($C_0$-$C_6$alkyl)$NR^{23}$C(O)$R^{24}$, —($C_1$-$C_6$alkyl)$OR^{23}$, —($C_0$-$C_6$alkyl)$NR^{23}R^{24}$, and monocyclic heterocycle of 4 to 6 ring atoms having 1, 2, or 3 ring atoms independently chosen from N, O, and S, wherein said monocyclic heterocycle of 4 to 6 ring atoms is optionally substituted with one or more substituents independently chosen from halogen, cyano, —$CO_2H$, $C_1$-$C_6$alkyl, $C_1$-$C_6$alkoxy, $C_1$-$C_6$haloalkyl, and $C_1$-$C_6$haloalkoxy.

$R^{13}$ is a phenyl substituted by 1-3 substituents independently chosen from hydroxyl, halogen, cyano, $C_1$-$C_6$alkyl, $C_1$-$C_6$alkylthio, $C_1$-$C_6$alkoxy, $C_1$-$C_6$haloalkyl, $C_1$-$C_6$haloalkoxy, —($C_0$-$C_6$alkyl)cycloalkyl, —O—($C_0$-$C_6$alkyl)cycloalkyl, phenyl, phenyloxy, benzyloxy, —($C_0$-$C_6$alkyl)$CO_2R^{23}$, —($C_0$-$C_6$alkyl)C(O)$NR^{23}R^{24}$, —($C_1$-$C_6$alkyl)$OR^{23}$, —($C_0$-$C_6$alkyl)$NR^{23}R^{24}$, and —($C_0$-$C_6$alkyl)$NR^{23}$C(O)$R^{24}$; wherein at least one of the 1-3 $R^{13}$ substituents must be ortho to the point of $R^{13}$ attachment in Formula II or Formula III.

$R^{13}$ is phenyl, substituted with 1-2 substituents independently chosen from halogen, hydroxyl, —COOH, $C_2$-$C_3$alkyl, $C_1$-$C_3$alkylthio, $C_1$-$C_3$alkoxy, —N($CH_3$)$_2$, —$CH_2CF_3$, —$CF_3$, —$OCF_3$, —($C_0$-$C_2$alkyl)cyclopropyl, and —O—($C_0$-$C_2$alkyl)cyclopropyl.

$R^{13}$ is phenyl substituted ortho to the point of $R^{13}$ attachment in Formula II with —$CF_3$, —$CH_2CF_3$, —COOH, cyclopropyl, or isopropyl.

In certain embodiments $R^{13}$ is 2,6-diethylphenyl, 2-ethoxy-5-cholorophenyl, 2-chloro ethoxyphenyl, or 2-ethyl-5-methoxyphenyl; $R^{14}$ is hydrogen. Y is

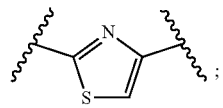

and Z is 4-chlorophenyl, 4-(trifluoromethyl)phenyl, 4-(difluoromethyl)phenyl, 6-(trifluoromethyl)-3-pyridyl, or 6-(difluoromethyl)-3-pyridyl.

$R^{13}$ 2,6-diethylphenyl, 2-ethoxy-5-cholorophenyl, 2-chloro-5-ethoxyphenyl, or 2-ethyl-5-methoxyphenyl, $R^{13}$ is 2,6-diethylphenyl.

The Variable $R^{14}$ $R^{14}$ is hydrogen.

The Variables $R^{19}$-$R^{22}$ $R^{19}$ and $R^{20}$ are both hydrogen and $R^{21}$ and $R^{22}$ are both methyl.

The disclosure includes compounds having a structure shown in Table 1 or a pharmaceutically acceptable salt thereof.

Treatment Methods

The compounds of Formula I, Formula II, or Formula III or a salt thereof, as well as pharmaceutical compositions comprising the compounds, are useful for treating cancer, including effecting tumor regression in vivo. The method of treating cancer or effecting tumor regression comprises providing to a patient an effective amount of a compound of Formula I, Formula II, or Formula III. In an embodiment the patient is a mammal, and more specifically a human. The disclosure also provides methods of treating non-human patients such as companion animals, e.g. cats, dogs, and livestock animals. An effective amount of a pharmaceutical composition may be an amount sufficient to inhibit the progression of cancer or a cancerous tumor; or cause a regression of a cancer or a cancerous tumor.

An effective amount of a compound or pharmaceutical composition described herein will also provide a sufficient concentration of a compound of Formula I, Formula II, or Formula III when administered to a patient. A sufficient concentration is a concentration of the compound in the patient's body necessary to combat the disorder. Such an amount may be ascertained experimentally, for example by assaying blood concentration of the compound, or theoretically, by calculating bioavailability.

Methods of treatment include providing certain dosage amounts of a compound of Formula I, Formula II, or Formula III to a patient. Dosage levels of each compound of from about 0.1 mg to about 140 mg per kilogram of body weight per day are useful in the treatment of the above-indicated conditions (about 0.5 mg to about 7 g per patient per day). The amount of compound that may be combined with the carrier materials to produce a single dosage form will vary depending upon the patient treated and the particular mode of administration. Dosage unit forms will generally contain between from about 1 mg to about 500 mg of each active compound. In certain embodiments 25 mg to 500 mg, or 25 mg to 200 mg of a compound of Formula I, Formula II, or Formula III are provided daily to a patient. Frequency of dosage may also vary depending on the compound used and the particular disease treated. However, for treatment of most diseases and disorders, a dosage regimen of 4 times daily or less can be used and in certain embodiments a dosage regimen of 1 or 2 times daily is used.

The compounds of Formula I, Formula II, or Formula III may be used to treat cancers and effect regression of tumors, including cancerous tumors. In certain embodiments, the patient is suffering from a cell proliferative disorder or disease. The cell proliferative disorder can be cancer, tumor (cancerous or benign), neoplasm, neovascularization, or melanoma. Cancers for treatment include both solid and disseminated cancers. Exemplary solid cancers (tumors) that may be treated by the methods provided herein include e.g. cancers of the lung, prostate, breast, liver, colon, breast, kidney, pancreas, brain, skin including malignant melanoma and Kaposi's sarcoma, testes or ovaries, carcinoma, kidney cancer (renal cell), and sarcoma. Cancers that may be treated with a compound of Formula I, Formula II, or Formula III also include bladder cancer, breast cancer, colon cancer, endometrial cancer, lung cancer, bronchial cancer, melanoma, Non-Hodgkins lymphoma, cancer of the blood, pancreatic cancer, prostate cancer, thyroid cancer, brain or spinal cancer, and leukemia. Exemplary disseminated cancers include leukemias or lymphoma including Hodgkin's disease, multiple myeloma and mantle cell lymphoma (MCL), chronic lymphocytic leukemia (CLL), T-cell leukemia, multiple myeloma, and Burkitt's lymphoma. Particularly included herein are methods of treating cancer by providing a compound of Formula I, Formula II, or Formula III to a patient wherein the cancer is a solid tumor or disseminated cancer.

Further included are methods of treating cancer by providing a compound of Formula I, Formula II, or Formula III to a patient wherein the cancer is selected from glioma (glioblastoma), acute myelogenous leukemia, acute myeloid leukemia, myelodysplastic/myeloproliferative neoplasms, sarcoma, chronic myelomonocytic leukemia, non-Hodgkin lymphoma, astrocytoma, melanoma, non-small cell lung cancer, cholangiocarcinomas, chondrosarcoma, or colon cancer.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A compound of Formula I, Formula II, or Formula III may be administered singularly (i.e., sole therapeutic agent of a regime) to treat diseases and conditions such as undesired cell proliferation, cancer, and/or tumor growth or may be administered in combination with another active agent. One or more compounds of Formula I, Formula II, or Formula III may be administered in coordination with a regime of one or more other chemotherapeutic agents such as an antineoplastic drug, e.g., an alkylating agent (e.g., mechloroethamine, chlorambucil, cyclophosamide, melphalan, or ifosfamide), an antimetabolite such as a folate antagonist (e.g., methotrexate), a purine antagonist (e.g. 6-mercaptopurine) or a pyrimidine antagonist (e.g., 5-fluorouracil). Other, non-limiting examples of chemotherapeutic agents that might be used in coordination with one or more compounds of Formula I, Formula II, or Formula III include taxanes and topoisomerase inhibitors. In addition, other non-limiting examples of active therapeutics include biological agents, such as monoclonal antibodies or IgG chimeric molecules, that achieve their therapeutic effect by specifically binding to a receptor or ligand in a signal transduction pathway associated with cancer (e.g. therapeutic antibodies directed against CD20 (e.g. rituximab) or against VEGF (e.g. bevacizumab)).

Methods of treatment provided herein are also useful for treatment of mammals other than humans, including for veterinary applications such as to treat horses and livestock e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

In an embodiment, the invention provides a method of treating a cancer disorder in a patient identified as in need of such treatment, the method comprising providing to the patient an effective amount of a compound of Formula I, Formula II, or Formula III. The compounds and salts of Formula I, Formula II, or Formula III provided herein may be administered alone, or in combination with one or more other active agent.

In an embodiment, the cancer to be treated is characterized by a mutant allele of IDH1 wherein the IDH1 mutation results in a new ability of the enzyme to catalyze the NADPH-dependent reduction of α-ketoglutarate to R(−)-2-hydroxyglutarate in a subject. In one aspect of this embodiment, the mutant IDH1 has an R132X mutation. In one aspect of this embodiment, the R132X mutation is selected from R132H, R132C, R132L, R132V, R132S and R132G. In another aspect, the R132X mutation is R132H or R132C. In yet another aspect, the R132X mutation is R132H.

In one aspect of this embodiment, the efficacy of cancer treatment is monitored by measuring the levels of 2HG in the subject. Typically levels of 2HG are measured prior to treatment, wherein an elevated level is indicative of the need to use a compound of Formula I to treat the cancer. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, these 2HG measurements will be utilized together with other well-known determinations of efficacy of cancer treatment, such as reduction in number and size of tumors and/or other cancer-associated lesions, improvement in the general health of the subject, and alterations in other biomarkers that are associated with cancer treatment efficacy. In different embodiments 2HG can be detected in a sample by direct measurement, or by measurement of derivatives or metabolites, such as by HPLC methods.

EXAMPLES

Abbreviations

AcOH Acetic Acid
BOC tert-butoxycarbonyl
BSA Bovine Serium Albumin
CBZ Benzyloxycarbonyl
DCM Dichloromethane
DIPEA Diisopropylethylamine
DMAP 4-(N,N-dimethylamino)pyridine
DMF Dimethylformamide
DMF-DMA Dimethylformamide Dimethylacetal
DMSO Dimethyl Sulfoxide
EtOAc Ethyl Acetate
LCMS Liquid Chromatography/Mass Spectrometry
LiHMDS Lithium bis(trimethylsilyl)amide
MP SPE Macroporous Solid Phase Extraction
NADPH Nicotinamide Adenine Dinucleotide Phosphate, Reduced Form
NaHMDS Sodium bis(trimethylsilyl)amide
NBS N-Bromosuccinimide
NCS N-Chlorosuccinimide
NMR Nuclear Magnetic Resonance
PEG Polyethyleneglycol
RPMI Roswell Park Memorial Institute medium (cell culture medium)
p-TsOH p-Toluenesulfonic acid
THF Tetrahydrofuran TFA Trifluoracetic acid General Methods All air- or moisture-sensitive reactions were performed under positive pressure of nitrogen with oven-dried glassware. Anhydrous solvents or reagents such as dichloromethane, N,N-dimethylformamide (DMF), acetonitrile, methanol, and triethylamine were purchased from Sigma-Aldrich. Preparative purification was performed on a Waters semi-preparative HPLC system. The column used was a Phenomenex Luna C18 (5 micron, 30×75 mm) at a flow rate of 45 mL/min. The mobile phase consisted of acetonitrile and water (each containing 0.1% trifluoroacetic acid). A gradient of 10% to 50% acetonitrile over 8 minutes was used during the purification. Fraction collection was triggered by UV detection (220 nM). Analytical analysis was performed on an Agilent LC/MS (Agilent Technologies, Santa Clara, Calif.). Purity analysis was determined using a 7 minute gradient of 4% to 100% acetonitrile (containing 0.025% trifluoroacetic acid) and water (containing 0.05% trifluoroacetic acid) with an 8 minute run time at a flow rate of 1 mL/min. A Phenomenex Luna C18 column (3 micron, 3×75 mm) was used at a temperature of 50° C. using an Agilent Diode Array Detector. Mass determination was performed using an Agilent 6130 mass spectrometer with electrospray ionization in the positive mode. $^1$H NMR spectra were recorded on Varian 400 MHz spectrometers. Chemical shifts are reported in ppm with non-deuterated solvent (DMSO-h6 at 2.50 ppm) as internal standard for DMSO-d6 solutions. All of the analogs tested in the biological assays have a purity greater than 95% based on LCMS analysis. High resolution mass spectrometry was recorded on Agilent 6210 Time-of-Flight LC/MS system. A gradient of 4% to 100% acetonitrile (containing 0.025% trifluoroacetic acid) and water (containing 0.05% trifluoroacetic acid) with a 4.5 minute run time at a flow rate of 1 mL/min was used. An Agilent Extend-C18 column (3.5 micron, 4.6×100 mm) was used at a temperature of 50° C. using an Agilent Diode Array Detector. Confirmation of molecular formulae was accomplished using electrospray ionization in the positive mode with the Agilent Masshunter software (version B.02).

EXAMPLES

Example 1. Synthesis of Selected Compounds

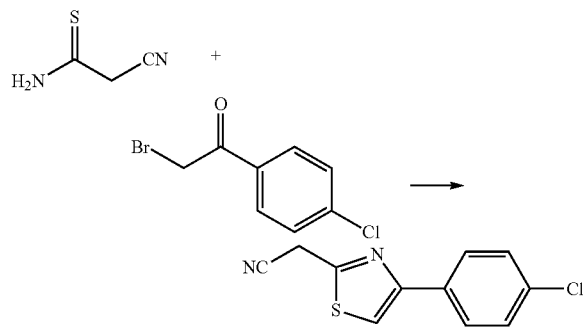

nitrile 1

Method 1-Nitrile 1:

To a solution of 2-bromo-1-(4-chlorophenyl)ethanone (2.33 g, 10 mmol) in ethanol (25 mL) was added 2-cyanoethanethioamide (1 g, 10 mmol). The reaction mixture was heated at reflux for 15.5 h. The reaction mixture was cooled to 0° C. A precipitate formed and was removed by filtration washing with hexanes and subsequently drying under vacuum. The product, 2-(4-(4-chlorophenyl)thiazol-2-yl)acetonitrile (nitrile N1), is a brown powder; LCMS: m/z (M+H)$^+$=235.0; $^1$H NMR (400 MHz, CDCl$_3$) δ 7.88-7.77 (m, 2H), 7.48 (s, 1H), 7.44-7.35 (m, 2H), 4.17 (s, 2H).

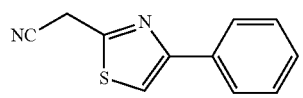

Nitrile 2

Nitrile 2: Synthesized by method 1 substituting 2-bromo-1-phenylethanone as a starting material. Following the reaction the mixture was concentrated and purified via silica gel chromatography (0 to 30% EtOAc/hexanes). Product is a red-orange solid (1.53 g, 77%); LCMS: m/z (M+H)$^+$=201.1.

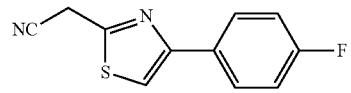

Nitrile 3

Nitrile 3: Synthesized by method 1 substituting 2-bromo-1-(4-fluorophenyl)ethanone as a starting material. Following the reaction the mixture was concentrated and purified via silica gel chromatography (0 to 40% EtOAc/hexanes). Product is a red-orange solid (1.53 g, 77%); LCMS: m/z (M+H)$^+$=219.0.

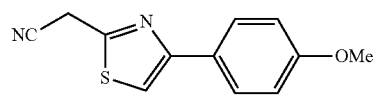

Nitrile 4

Nitrile 4: Synthesized by method 1 substituting 2-bromo-1-(4-methoxyphenyl)ethanone as a starting material. Following the reaction the mixture was concentrated and purified via silica gel chromatography (0 to 40% EtOAc/hexanes); LCMS: m/z (M+H)$^+$=231.1.

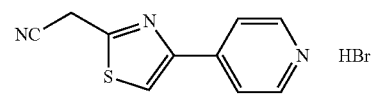

Nitrile 5

Nitrile 5: Synthesized by method 1 substituting 2-bromo-1-(pyridin-4-yl)ethanone hydrobromide as a starting material; LCMS: m/z (M+H)+=202.1.

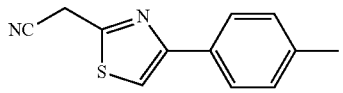

Nitrile 6

Nitrile 6: Synthesized by method 1 substituting 2-bromo-1-(4-methylphenyl)ethanone as a starting material. Following the reaction the mixture was concentrated and purified via silica gel chromatography (0 to 40% EtOAc/hexanes); LCMS: m/z (M+H)$^+$=215.1.

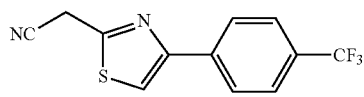

Nitrile 7

Nitrile 7: Synthesized by method 1 substituting 2-bromo-1-(4-trifluoromethylphenyl)ethanone as a starting material. Following the reaction the mixture was concentrated and purified via silica gel chromatography (0 to 40% EtOAc/hexanes); LCMS: m/z (M+H)$^+$=269.0.

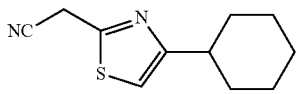

Nitrile 8

Nitrile 8: Synthesized by method 1 substituting 2-bromo-1-cyclohexylethanone as a starting material. The reaction was heated at 50° C. for 1 h, concentrated, and used without further purification; LCMS: m/z (M+H)$^+$=207.1.

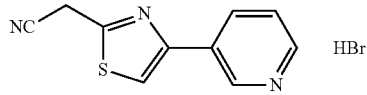

Nitrile 9

Nitrile 9: Synthesized by method 1 substituting 2-bromo-1-(pyridin-3-yl)ethanone hydrobromide as a starting material; LCMS: m/z (M+H)$^+$=202.1.

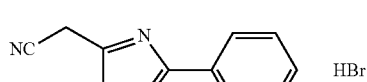

Nitrile 10

Nitrile 10: Synthesized by method 1 substituting 2-bromo-1-(pyridin-2-yl)ethanone hydrobromide as a starting material; LCMS: m/z (M+H)$^+$=202.1.

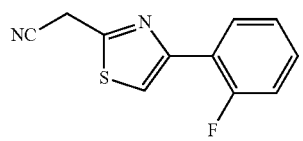

Nitrile 11

Nitrile 11: Synthesized by method 1 substituting 2-bromo-1-(2-fluorophenyl)ethanone as a starting material. Following the reaction the mixture was concentrated and purified via silica gel chromatography (0 to 40% EtOAc/hexanes); LCMS: m/z (M+H)$^+$=219.0.

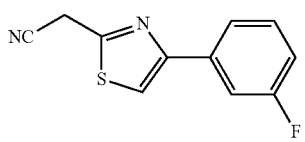

Nitrile 12

Nitrile 12: Synthesized by method 1 substituting 2-bromo-1-(3-fluorophenyl)ethanone as a starting material. Following the reaction the mixture was concentrated and purified via silica gel chromatography (0 to 40% EtOAc/hexanes); LCMS: m/z (M+H)$^+$=219.0.

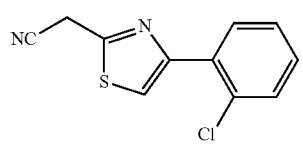

Nitrile 13

Nitrile 13: Synthesized by method 1 substituting 2-bromo-1-(2-chlorophenyl)ethanone as a starting material; LCMS: m/z (M+H)$^+$=235.0.

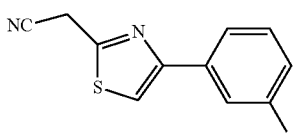

Nitrile 14

Nitrile 14: Synthesized by method 1 substituting 2-bromo-1-(3-chlorophenyl)ethanone as a starting material. Following the reaction the mixture was concentrated and purified via silica gel chromatography (0 to 40% EtOAc/hexanes); LCMS: m/z (M+H)$^+$=235.0.

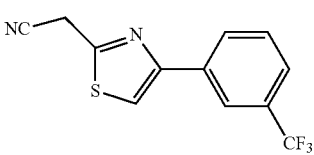

Nitrile 15

Nitrile 15: Synthesized by method 1 substituting 2-bromo-1-(3-trifluoromethylphenyl)ethanone as a starting material. Following the reaction the mixture was concentrated and purified via silica gel chromatography (0 to 40% EtOAc/hexanes); LCMS: m/z (M+H)$^+$=269.0.

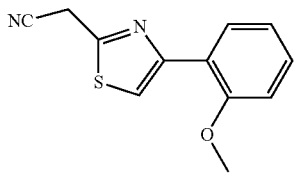

Nitrile 16

Nitrile 16: Synthesized by method 1 substituting 2-bromo-1-(2-methoxyphenyl)ethanone as a starting material. Following the reaction the mixture was concentrated and purified via silica gel chromatography (0 to 40% EtOAc/hexanes); LCMS: m/z (M+H)$^+$=231.0.

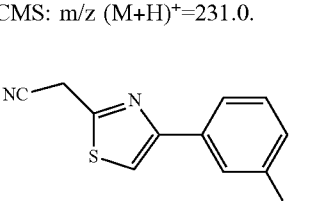

Nitrile 17

Nitrile 17: Synthesized by method 1 substituting 2-bromo-1-(3-methoxyphenyl)ethanone as a starting material. Following the reaction the mixture was concentrated and purified via silica gel chromatography (0 to 40% EtOAc/hexanes); LCMS: m/z (M+H)$^+$=231.1.

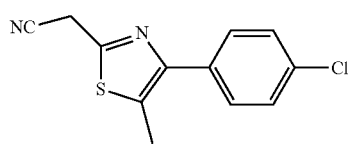

Nitrile 18

Nitrile 18: Synthesized by method 1 substituting 2-bromo-1-(4-chlorophenyl)propan-1-one as a starting material; LCMS: m/z (M+H)$^+$=249.0.

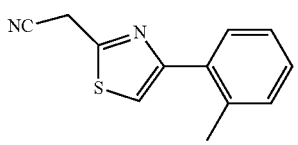

Nitrile 19

Nitrile 19: Synthesized by method 1 substituting 2-bromo-1-(2-methylphenyl)ethanone as a starting material. Following the reaction the mixture was concentrated and purified via silica gel chromatography (0 to 40% EtOAc/hexanes); LCMS: m/z (M+H)$^+$=215.0.

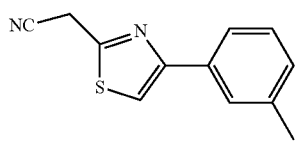

Nitrile 20

Nitrile 20: Synthesized by method 1 substituting 2-bromo-1-(3-methylphenyl)ethanone as a starting material. Following the reaction the mixture was concentrated and purified via silica gel chromatography (0 to 40% EtOAc/hexanes); LCMS: m/z (M+H)$^+$=215.0.

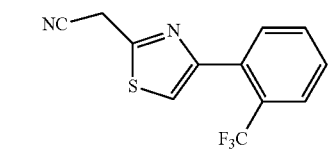

Nitrile 21

Nitrile 21: Synthesized by method 1 substituting 2-bromo-1-(2-trifluoromethylphenyl)ethanone as a starting material. Following the reaction the mixture was concentrated and purified via silica gel chromatography (0 to 40% EtOAc/hexanes); LCMS: m/z (M+H)$^+$=269.0.

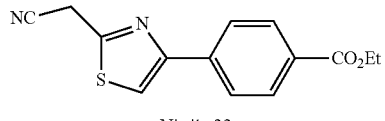

Nitrile 22

Nitrile 22: Synthesized by method 1 substituting 4-(2-bromoacetyl)benzoic acid as a starting material; concomitant esterification was observed (83% on 2 mmol scale); LCMS: m/z (M+H)$^+$=273.0.

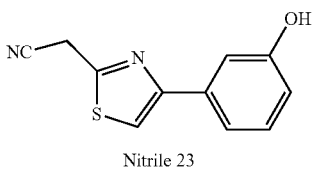 [SMILES: N#CCc1nc(-c2cccc(O)c2)cs1]

Nitrile 23

Nitrile 23: Synthesized by method 1 substituting 2-bromo-1-(3-hydroxyphenyl)ethanone as a starting material. Following the reaction the mixture was concentrated and purified via reverse phase chromatography (2 mmol scale, 60% yield); LCMS: m/z (M+H)$^+$=217.1.

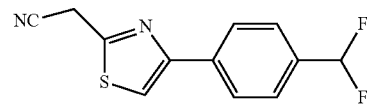

Nitrile 24

Nitrile 24: Synthesized by method 1 substituting 2-bromo-1-(4-(difluoromethyl)phenyl)ethanone as a starting material; LCMS: m/z (M+H)$^+$=251.0.

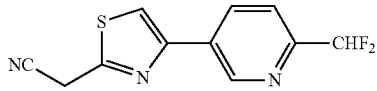

Nitrile 25

Nitrile 25: Synthesized by method 1 substituting 2-bromo-1-(6-(difluoromethyl)pyridin-3-yl)ethanone as a starting material: LCMS: m/z (M+H)$^+$=252.0.

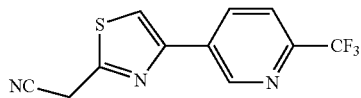

Nitrile 26

Nitrile 26: Synthesized by method 1 substituting 2-bromo-1-(6-(trifluoromethyl)pyridin-3-yl)ethanone as a starting material: LCMS: m/z (M+H)$^+$=270.0.

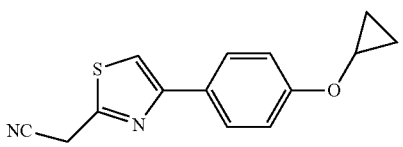

Nitrile 27

Nitrile 27: Synthesized by method 1 substituting 2-bromo-1-(4-cyclopropoxyphenyl)ethanone as a starting material: LCMS: m/z (M+H)$^+$=257.0.

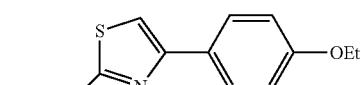

Nitrile 28

Nitrile 28: Synthesized by method 1 substituting 2-bromo-1-(4-ethoxyphenyl)ethanone as a starting material: LCMS: m/z (M+H)$^+$=245.0.

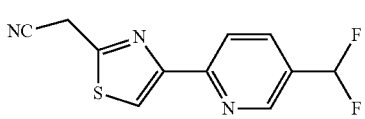

Nitrile 29

Nitrile 29: Synthesized by method 1 substituting 2-bromo-1-(5-(difluoromethyl)pyridin-2-yl)ethanone as a starting material (does not precipitate just concentrate): LCMS: m/z (M+H)$^+$=252.0.

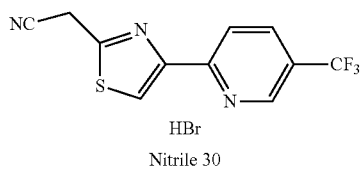 [SMILES: N#CCc1nc(-c2ccc(C(F)(F)F)cn2)cs1 ; Br]

Nitrile 30

Nitrile 30: Synthesized by method 1 substituting 2-bromo-1-(5-(trifluoromethyl)pyridin-2-yl)ethanone as a starting material (does not precipitate just concentrate): LCMS: m/z (M+H)$^+$=270.0.

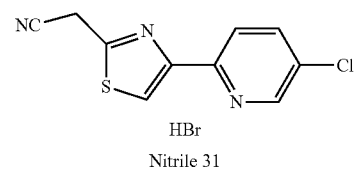 [SMILES: N#CCc1nc(-c2ccc(Cl)cn2)cs1 ; Br]

Nitrile 31

Nitrile 31: Synthesized by method 1 substituting 2-bromo-1-(5-chloropyridin-2-yl)ethanone hydrobromide as a starting material: LCMS: m/z (M+H)$^+$=236.0.

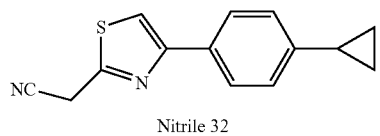

Nitrile 32

Nitrile 32: Synthesized by method 1 substituting 2-bromo-1-(4-cyclopropylphenyl)ethanone as a starting material: LCMS: m/z (M+H)$^+$=241.0.

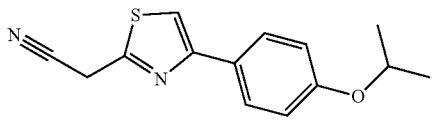

Nitrile 33

Nitrile 33: Synthesized by method 1 substituting 2-bromo-1-(4-isopropoxyphenyl)ethanone as a starting material: LCMS: m/z (M+H)$^+$=259.0.

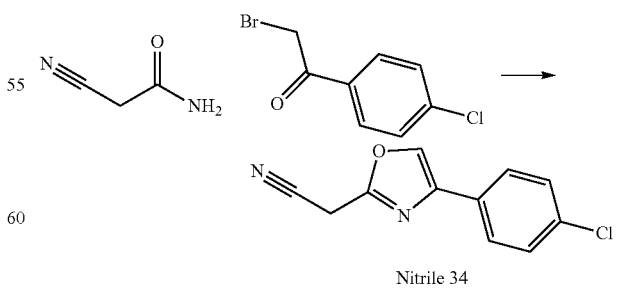

Nitrile 34

Nitrile 34: A mixture of 2-cyanoacetamide (1.440 g, 17.13 mmol) and 2-bromo-1-(4-chlorophenyl)ethanone (2 g, 8.57 mmol) were heated to 150° C. for 15 min. The crude product was dissolved in ethyl acetate and brine, and the organic layer was then washed with brine (3×), dried over MgSO$_4$ and concentrated. The crude product was purified by chormatography (20:80 EA/Hex to 100% EA) to afford nitrile 34 in 5% yield (95 mg, 0.435 mmol) mg as a yellowish solid: LCMS: m/z (M+H)$^+$=219.1.

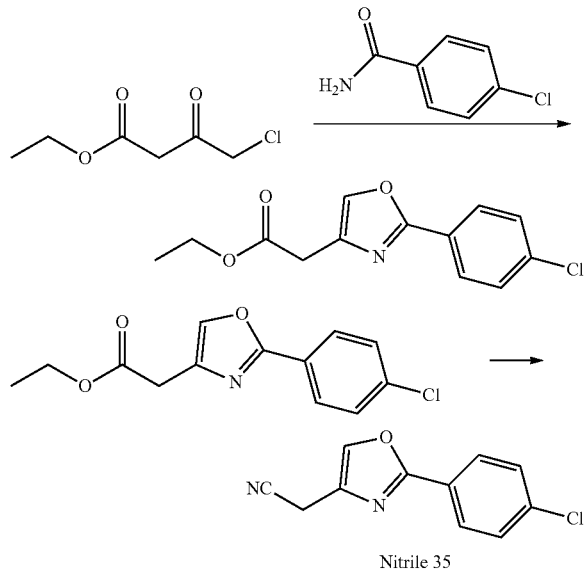

Nitrile 35

Nitrile 35: Step 1: A mixture of 4-chlorobenzamide (1 g, 6.43 mmol) and ethyl 4-chloro-3-oxobutanoate (0.869 ml, 6.43 mmol) were heated at 140° C. for 3 h, neat. The mixture was quenched with saturated NaHCO$_3$ solution and extracted with ethyl acetate. The organic extract was dried over MgSO$_4$ and concentrated. The crude material was purified by chromatography (20:80 to 80:20 EA/Hex) yielding in 28% yield (480 mg, 1.807 mmol) a white powder: LCMS: m/z (M+H)$^+$=266.0.

Step 2: To ethyl 2-(2-(4-chlorophenyl)oxazol-4-yl)acetate (480 mg, 1.807 mmol) was added 7M NH$_3$ in MeOH (Volume: 4517 µl). The mixture was heated to 60° C. for 16 h. The crude product was dissolved in ethyl acetate and brine, and the organic layer was then washed with brine (3×), dried over MgSO$_4$ and concentrated to afford 310 mg of a crude solid.

The crude intermediate was dissolved in DCM (Volume: 4517 µl) and treated with TRIETHYLAMINE (755 µl, 5.42 mmol) and then, TFAA (766 µl, 5.42 mmol). This mixture was stirred for 1 h at 0° C. The crude product was dissolved in ethyl acetate and brine, and the organic layer was then washed with brine (3×), dried over MgSO4 and concentrated to afford nitrile 35 in 87% yield (345 mg, 1.578 mmol): LCMS: m/z (M+H)$^+$219.1.

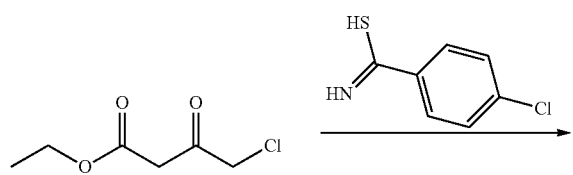

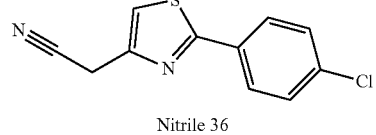

Nitrile 36

Nitrile 36: A mixture of 4-chlorobenzothioamide (1 g, 5.83 mmol) and ethyl 4-chloro-3-oxobutanoate (0.787 ml, 5.83 mmol) in EtOH (Volume: 5.83 ml) was heated at 80° C. for 16 h. The crude product was dissolved in ethyl acetate and saturated NaHCO$_3$ solution and the organic layer was then washed with brine (3×), dried over MgSO$_4$ and concentrated to afford the crude product as an oil.

To the crude intermediate was added 7M NH$_3$ in MeOH (Volume: 5.82 ml) and the mixture was heated to 60° C. for 16 h. The crude product was dissolved in ethyl acetate and saturated brine, and the organic layer was then washed with brine (3×), dried over MgSO$_4$ and concentrated to afford the crude product as white solid (1.1 g) which was taken to the next reaction.

The crude intermediate was dissolved in DCM (Volume: 5.82 ml) and treated with TRIETHYLAMINE (1.623 ml, 11.64 mmol) and then, TFAA (1.644 ml, 11.64 mmol). Stir for 1 h at 0° C. The crude product was dissolved in ethyl acetate and saturated brine, and the organic layer was then washed with brine (3×), dried over MgSO$_4$ and concentrated to afford 1.3 g of crude product. This material was purified by chromatography (10:90 EA/Hex t o 100% EA) to afford nitrile 36 in 88% yield (1.2 g, 5.11 mmol): LCMS: m/z (M+H)$^+$=235.1.

Bromoketones that aren't commercially available were prepared in the following ways:

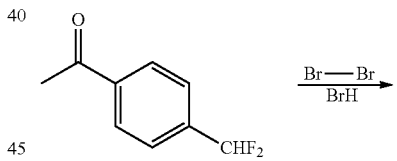

Bromo ketone 1

Bromo ketone 1: To a solution of 1-(4-(difluoromethyl)phenyl)ethanone (500 mg, 2.94 mmol) in CHCl$_3$ (Volume: 10 ml) was added dropwise bromine (0.151 ml, 2.94 mmol), and then HBr (0.484 ml, 2.94 mmol) (33% in AcOH) at 0° C. The mixture was stirred at 0° C. for 2 hrs. Additional of HBr (0.484 ml, 2.94 mmol) (33% in AcOH) was added to the mixture. The reaction mixture was stirred at r.t. for overnight. It was then diluted with DCM and washed with brine. The organic layer was dried and concentrated and the crude was used in the next step without further purification.

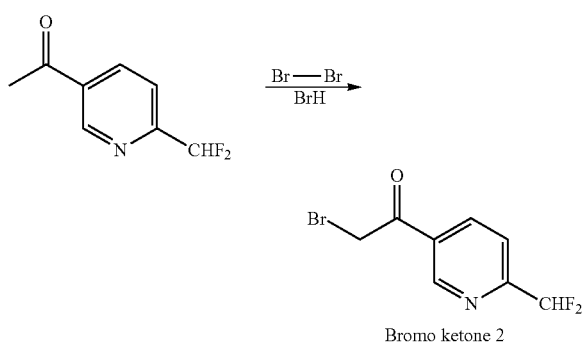

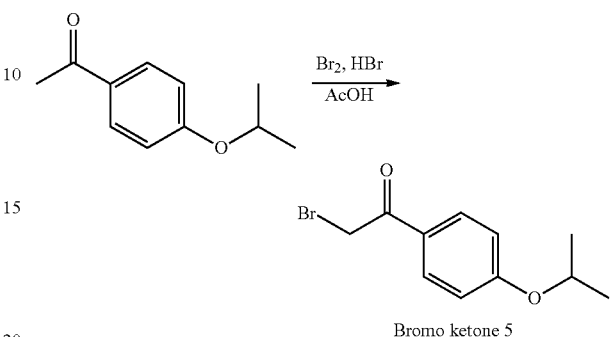

added a solution of bromine (0.300 ml, 5.82 mmol) in 5 mL chloroform, slowly at 0° C. Add HBr (1.740 ml, 10.57 mmol) in AcOH and slowly warm to RT and stir for 2 h. The solvent was evaporated and the crude product used in the next step without further purification.

Bromo ketone 2: To 1-(6-(difluoromethyl)pyridin-3-yl)ethanone (1 g, 5.84 mmol) in CHCl₃ (Volume: 25 ml) was added a solution of bromine (0.301 ml, 5.84 mmol) in 5 mL chloroform, slowly at 0° C. Add HBr (0.962 ml, 5.84 mmol) in AcOH and slowly warm to RT and stir for 2 h. It was then diluted with DCM and washed with brine. The organic layer was dried over MgSO₄ and concentrated, and the crude was used in the next step without further purification.

Bromo ketone 5: A mixture of 1-(4-isopropoxyphenyl)ethanone (2 g, 11.22 mmol) in AcOH (Volume: 11.22 ml) was treated with bromine (0.578 ml, 11.22 mmol) at 0° C., dropwise. The mixture was warmed to RT and stir for 16 h. The crude mixture was partitioned between ethyl acetate and saturated NaHCO₃ solution. The organic layer was washed with saturated NaHCO₃ solution, saturated NaS₂O₃ solution, and saturated brine, and was then dried over MgSO₄ and concentrated to afford the crude product, which was used in the next step without further purification.

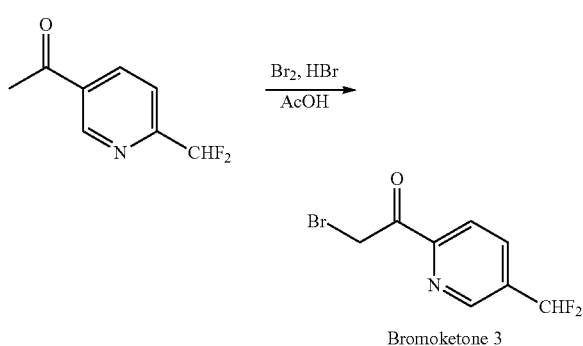

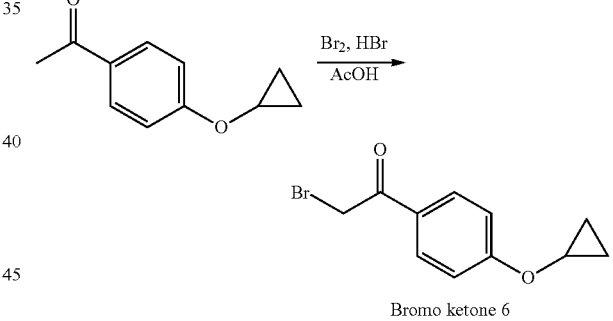

Bromo ketone 3: To a solution of 1-(5-(difluoromethyl)pyridin-2-yl)ethanone (0.2 g, 1.169 mmol) in CHCl₃ (Volume: 6 ml) was added dropwise bromine (0.060 ml, 1.169 mmol), and then HBr (0.192 ml, 1.169 mmol) (33% in AcOH) at 0° C. The mixture was stirred at 0° C. for 2 hrs. Additional HBr (0.192 ml, 1.169 mmol) was added to the mixture. The reaction mixture was stirred at r.t. for overnight. The solvent was evaporated and the crude product used in the next step without further purification.

Bromo ketone 6: A mixture of 1-(4-cyclopropoxyphenyl)ethanone (810 mg, 4.60 mmol) in AcOH (Volume: 4597 μl) was treated with bromine (237 μl, 4.60 mmol) at 0° C., dropwise. Let warm up to RT and stir for 16 h. The crude mixture was partitioned between ethyl acetate and saturated brine. The organic layer was washed with saturated brine, and was then dried over MgSO₄ and concentrated to afford the crude product, which was used in the next step without further purification.

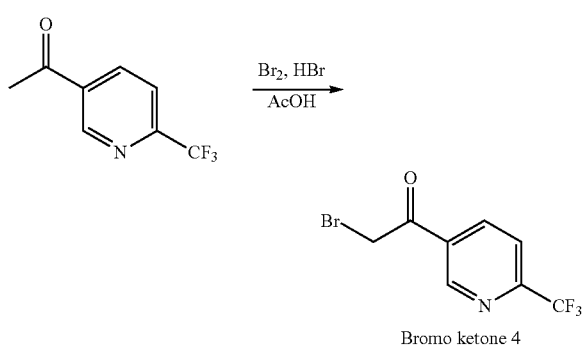

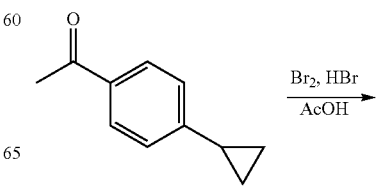

Bromo ketone 4: To 1-(6-(trifluoromethyl)pyridin-3-yl)ethanone (3 g, 15.86 mmol) in CHCl₃ (Volume: 50 ml) was

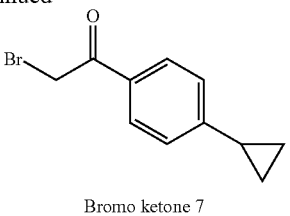

Bromo ketone 7

Bromo ketone 7: A mixture of 1-(4-cyclopropylphenyl)ethanone (580 mg, 3.62 mmol) in AcOH (Volume: 3620 µl) was treated with bromine (187 µl, 3.62 mmol) at 0° C., dropwise. Let warm up to RT and stir for 16 h. The crude mixture was partitioned between ethyl acetate and saturated brine. The organic layer was washed with saturated brine, and was then dried over MgSO₄ and concentrated to afford the crude product, which was used in the next step without further purification.

tion stirred for 15 min at rt, a precipitate formed almost immediately. The solvent was removed by blowing down under a stream of air with mild heating at 30° C. The residue was taken up in DMSO and subsequently purified by reverse phase chromatography to give Compound 12.

Method B-Similar to Method A, however the beginning of step 2 was initiated by moderate heating at 40° C. for 5 min to solubilize the nitrile prior to stirring at rt.

Method C-Similar to Method A, however the beginning of step 2 was initiated by moderate heating at 40° C. for 1 h prior to stirring at P. Additionally step 3 was heated at 45° C. for 1 h.

Method D-Similar to Method A, however the beginning of step 2 was initiated by moderate heating at 45° C. for 30 min prior to stirring at rt. Additionally step 3 was heated at 45° C. for 1 h.

Method E-Similar to Method A, however the beginning of step 2 was initiated by moderate heating at 40° C. for 30 min while simultaneously sonicating prior to stirring at it Additionally step 3 was heated at 50° C. for 1.5 h.

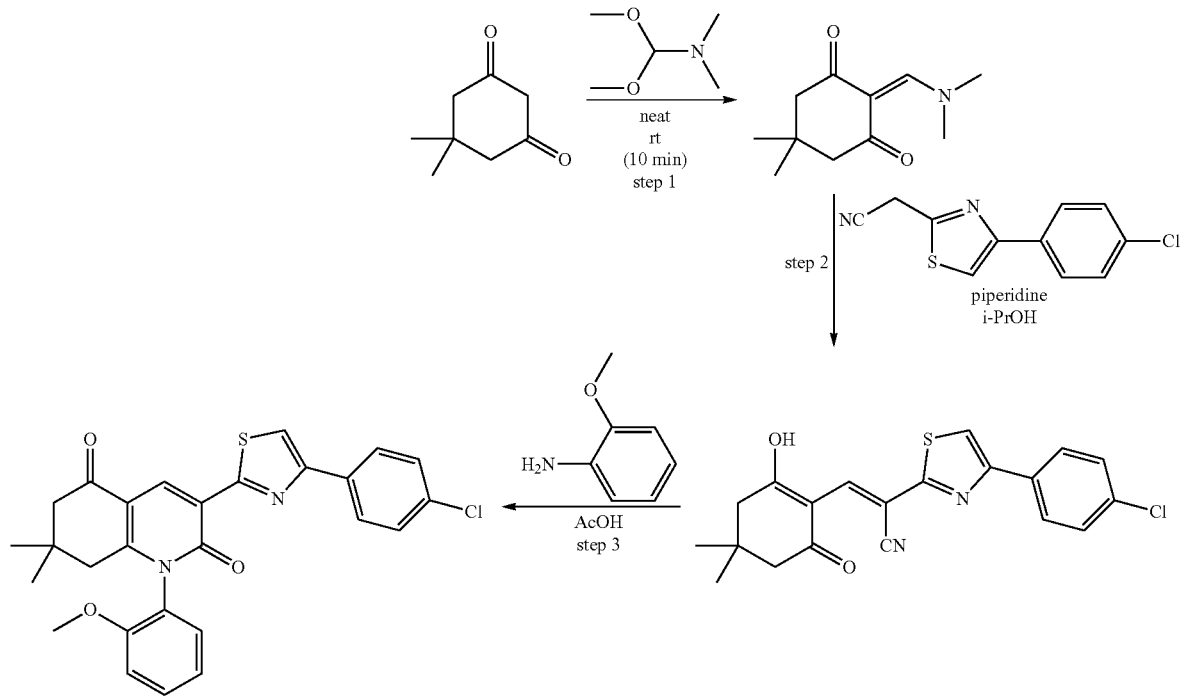

12

Method A-Compound 12:

Step 1: In a vial, 5,5-dimethylcyclohexane-1,3-dione (0.100 g, 0.713 mmol) and DMF-DMA (0.096 mL, 0.713 mmol) were mixed and stirred neat for 5 min. The reaction mixture became a yellow oil.

Step 2: To the mixture was added i-PrOH (2.55 mL), 2-(4-(4-chlorophenyl)thiazol-2-yl)acetonitrile (167 mg, 0.713 mmol), and piperidine (0.071 mL, 0.713 mmol). The reaction was allowed to stir at rt for 3 h. The solid went into solution. After 3 h, a precipitate formed at which point the solvent was removed by blowing down under a stream of air with mild heating at 30° C.

Step 3: To the resulting residue were added acetic acid (1 mL) and 2-methoxyaniline (80 µL, 0.713 mmol). The reac- Method F-Similar to Method A, however the beginning of step 2 was initiated by moderate heating at 40° C. for 30 min while simultaneously sonicating prior to stirring at rt. Additionally step 3 was heated at 100° C. for 1 h.

Method G-Similar to Method A, however the beginning of step 2 was initiated by moderate heating at 40° C. for 30 min while simultaneously sonicating prior to stirring at rt. Additionally step 3 was heated at 60° C. for 1 h.

Method H-Similar to Method A, however the beginning of step 2 was initiated by moderate heating at 40° C. for 30 min while simultaneously sonicating prior to stirring at rt. Additionally step 3 was heated at 50° C. for 1 h and at 100° C. for an additional 1 h.

Method I-Similar to Method A, however the beginning of step 2 was initiated by moderate heating at 40° C. for 30 min while simultaneously sonicating prior to stirring at rt. Additionally step 3 was heated at 50° C. for 1 h and at 100° C. for an additional 18 h.

Method J-Similar to Method A, however step 2 was carried out at 70° C. overnight (40° C. 4 h, 50° C. overnight, 60° C. 8 h prior to 70° C. overnight). Additionally step 3 was heated at 50° C. for 3.5 h.

Method K-Similar to Method A, however step 2 was carried out at 40° C. 2 h. Additionally step 3 was heated at 40° C. for 1 h and 100° C. for 1 h.

Method L-Similar to Method A, however potassium tert-butoxide was added after heating step 2 at 40° C. for 1.5 h and at 60° C. for an additional 1.5 h (little to no conversion). Upon addition of KOtBu, the mixture was heated at 40° C. for 1 h and at 60° C. for an additional 1 h. Step 3 was also heated at 40° C. for 1 h and 100° C. for 1 h.

Method M-Similar to Method A, however potassium tert-butoxide was added after heating step 2 at 40° C. for 1.5 h (little to no conversion). Upon addition of KOtBu, the mixture was heated at 55° C. for 3 h. Step 3 was also heated at 60° C. overnight.

Method N-Similar to Method A, however potassium tert-butoxide was used in place of piperidine in step 2. Additionally step 2 was heated at 40° C. for 1.5 h and step 3 was conducted at 50° C. overnight followed by 80° C. for 2.5 h and finally 110° C. overnight.

Method O-Similar to Method A, however potassium tert-butoxide was used in place of piperidine in step 2. Additionally step 2 was heated at 55° C. for 1 h and step 3 was conducted at 60° C. for 1.75 h followed by the addition of water and heating at 80° C. for 3 h.

Method P-Similar to Method A, however potassium tert-butoxide was used in place of piperidine in step 2. Additionally step 2 was heated at 55° C. for 1 h and step 3 was conducted at 60° C. for 1.75 h followed by the addition of water and heating at 100° C. for 1.5 h.

Method Q-Similar to Method A, however two equivalents of piperidine were used in step 2. Additionally step 2 was heated at 45° C. for 2 h and step 3 was conducted at 75° C. for 2.5 h.

Method R-Similar to Method A, however step 2 was heated at 45° C. for 3 h and step 3 was conducted at 55° C. overnight.

Method S

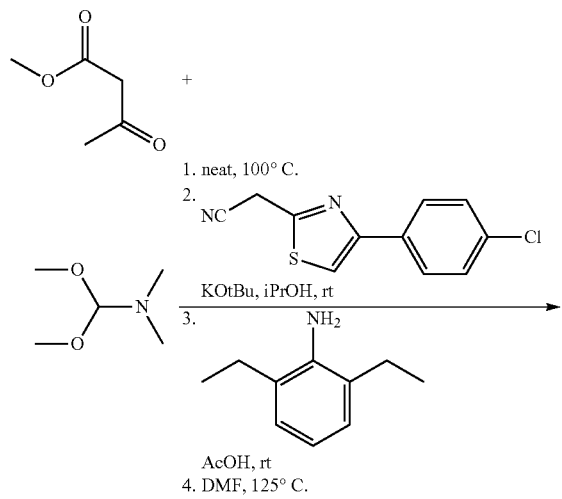

1. neat, 100° C.
2. 
KOtBu, iPrOH, rt
3. 
AcOH, rt
4. DMF, 125° C.

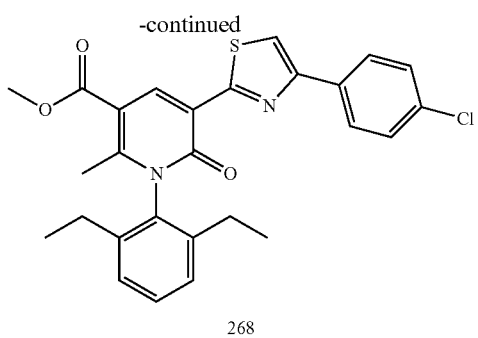

268

Method S-Compound 268:

Step 1: In a vial, methyl 3-oxobutanoate (0.385 mL, 3.57 mmol) and DMF-DMA (0.474 mL, 3.57 mmol) were mixed and heated neat at 100° C. for 15 min. The reaction mixture became a red oil.

Step 2: To the mixture was added i-PrOH (40 mL), 2-(4-(4-chlorophenyl)thiazol-2-yl)acetonitrile (837 mg, 3.57 mmol), and potassium tert-butoxide (400 mg, 3.57 mmol). The reaction was allowed to stir at rt for 2 h at which point the solvent was removed.

Step 3: To the resulting residue were added acetic acid (30 mL) and 2,6-dimethylaniline (646 μL, 3.9 mmol). The reaction stirred for 15 min and the mixture was diluted with water, extracted (EtOAc×2). The organic layers were combined (not dried with magesium sulfate) and concentrated. The residue was taken up in DMF (40 mL) and heated at 125° C. for 1.5 h. The reaction mixture was diluted with water and EtOAc, extracted (2×), the organic layers were combined, dried with magesium sulfate, concentrated and purified via silica gel chromatography (dry load) (0 to 25% EtOAc/hexanes) to afford methyl 5-(4-(4-chlorophenyl)thiazol-2-yl)-1-(2,6-diethylphenyl)-2-methyl-6-oxo-1,6-dihydropyridine-3-carboxylate (Compound 268, 1.05 g, 60%); LCMS: m/z (M+H)$^+$=493.0.

Method T-Similar to Method S, however step 1 was run with 3-oxo-3-phenylpropanenitrile and heating was done for a total of 45 min; step 2 was heated at 80° C. for 3.5 h and step 3 was conducted at 80° C. for 4 h. Final purification was done via reverse phase chromatography.

Method U

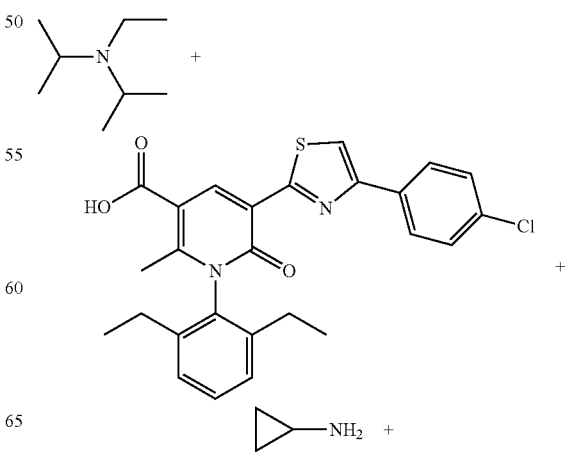

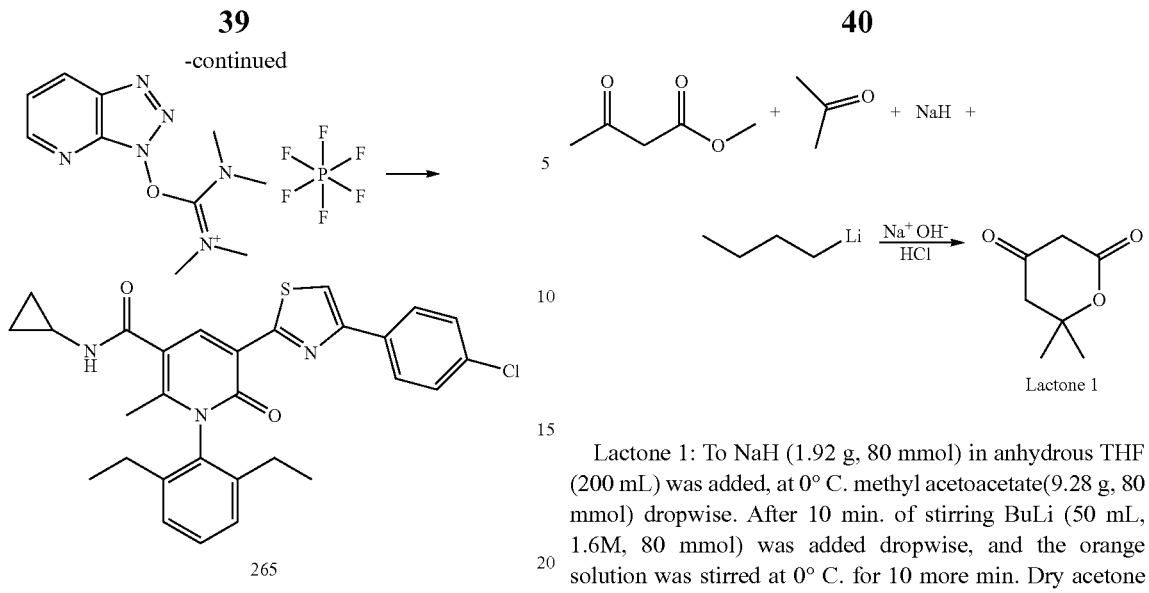

Method U-Compound 265: To a mixture of 5-(4-(4-chlorophenyl)thiazol-2-yl)-1-(2,6-diethylphenyl)-2-methyl-6-oxo-1,6-dihydropyridine-3-carboxylic acid (40 mg, 0.084 mmol), cyclopropanamine (0.009 mL, 0.125 mmol) in DMF (1.3 mL) were added diisopropylethylamine (0.044 mL, 0.25 mmol) and HATU (38 mg, 0.10 mmol). The reaction mixture stirred at rt 2.25 h and was concentrated partially by a stream of air. The residue was taken up in DMSO and subsequently purified by reverse phase chromatography to give Compound 265.

Lactone 1: To NaH (1.92 g, 80 mmol) in anhydrous THF (200 mL) was added, at 0° C. methyl acetoacetate(9.28 g, 80 mmol) dropwise. After 10 min. of stirring BuLi (50 mL, 1.6M, 80 mmol) was added dropwise, and the orange solution was stirred at 0° C. for 10 more min. Dry acetone (7.5 mL. 82 mmol) was added at once, and the mixture was stirred for 10 min. at 0° C. NaOH (80 mL, 2.5M) was then added, and the mixture was stirred at r.t. during 12 h, whereupon it was acidified (2.5M HCl) and extracted with ether (3×200 mL). The organic layer was washed (satd. NaCl) and dried (Na$_2$SO$_4$). After filtration, the solvent was evaporated. The residue was dissolved in a minimum of CH$_2$Cl$_2$ was precipitated with pentane as brownish solid (58% yield), m.p. 126-127° C.; H NMR (500 MHz, CDCl$_3$): 1.48 (s, 6H); 2.66 (s, 2H); 3.40 (s, 2H); LCMS: 142.0.

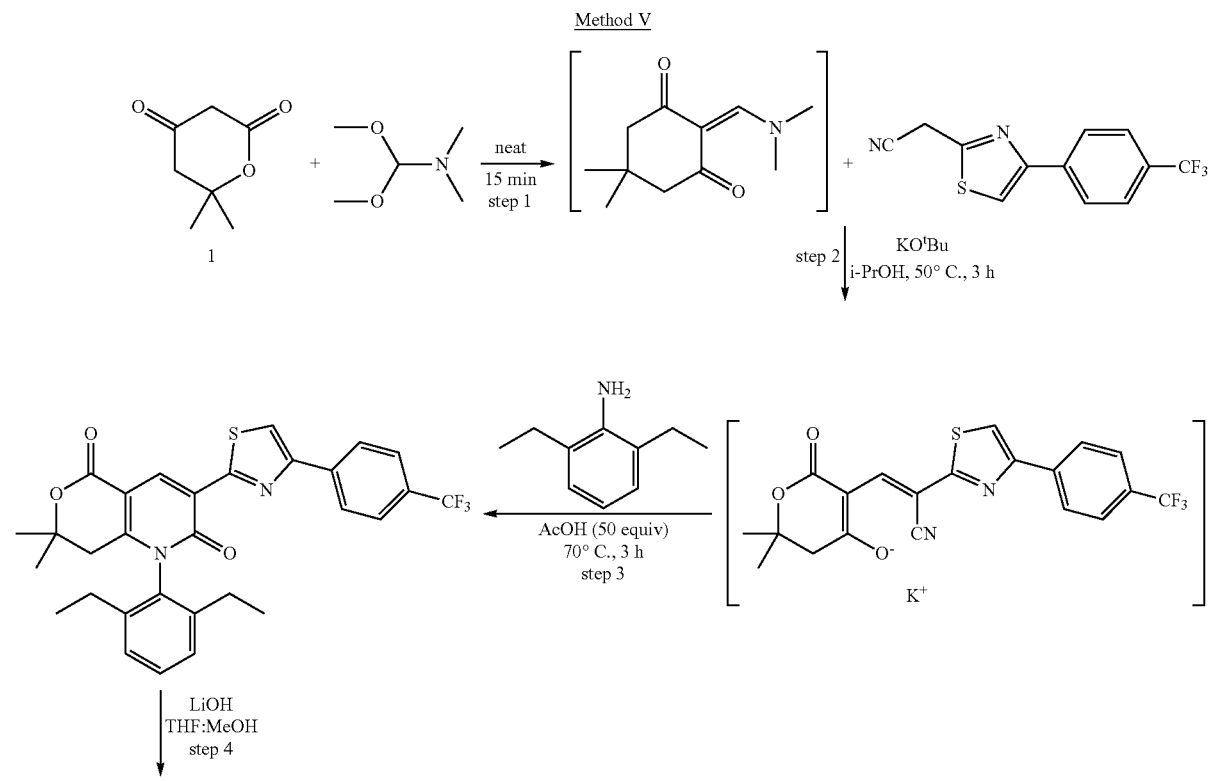

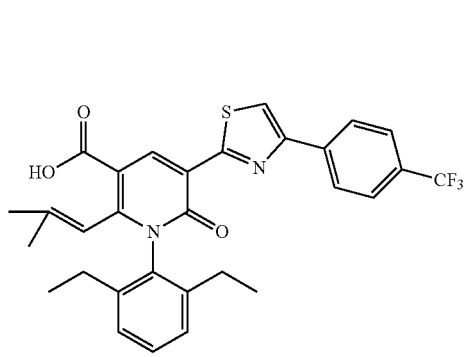
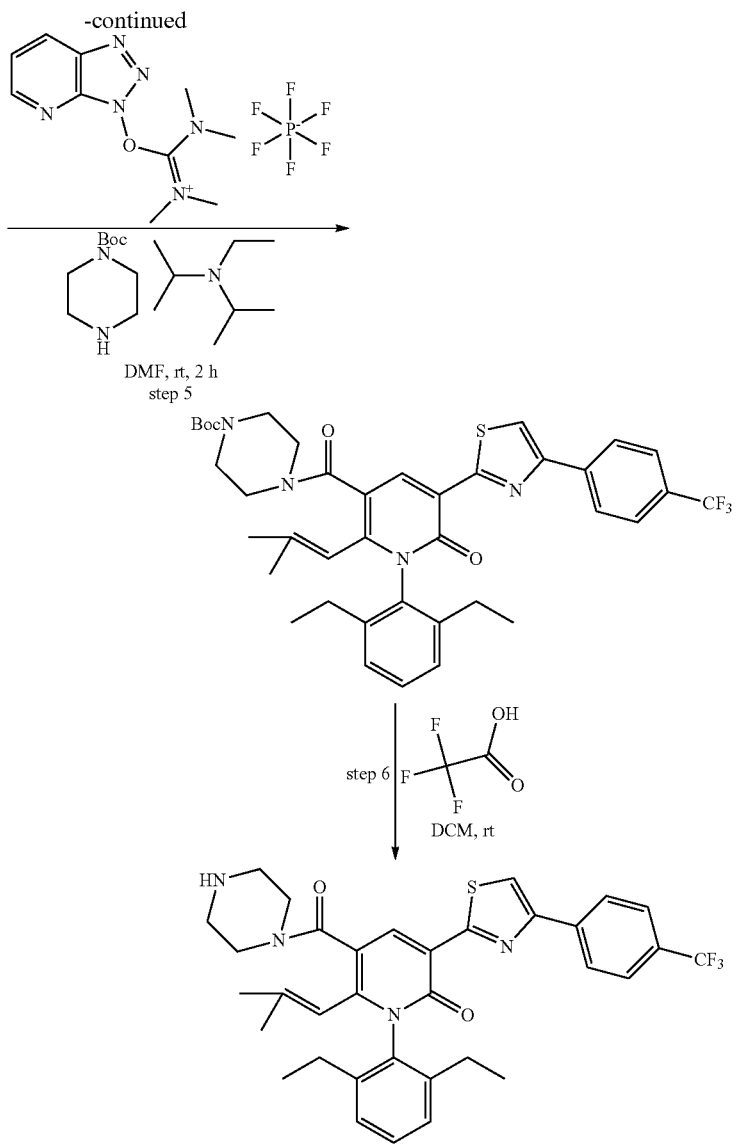

581

Method V-Compound 581:

Steps 1-3: The mixture of 6,6-dimethyldihydro-2H-pyran-2,4(3H)-dione (0.530 g, 3.73 mmol) and 1,1-dimethoxy-N,N-dimethylmethanamine (0.495 ml, 3.73 mmol) was stirred for 15 min at room temperature. To the mixture was diluted with IPA (Volume: 10 ml) and added 2-(2-(4-(trifluoromethyl)phenyl)thiazol-5-yl)acetonitrile (1.0 g, 3.73 mmol) and K'OBu (0.837 g, 7.46 mmol). The mixture was stirred at 50° C. for 3 hrs. The solvent was removed. To the residue was added 2,6-diethylaniline (0.665 ml, 4.10 mmol) and acetic acid (10.7 mL, 186 mmol). The mixture was stirred at 70° C. for 2 hrs and cooled to room temperature and diluted with EtOAc and washed with water. The organic layer was dried and concentrated and purified by column chromotography. The product, 1-(2,6-diethylphenyl)-7,7-dimethyl-3-(2-(4-(trifluoromethyl)phenyl)thiazol-4-yl)-7,8-dihydro-1H-pyrano[4,3-b]pyridine-2,5-dione; LCMS: m/z (M+H)$^+$ =553.0.

Step 4: To a solution of 1-(2,6-diethylphenyl)-7,7-dimethyl-3-(2-(4-(trifluoromethyl) phenyl)thiazol-4-yl)-7,8-dihydro-1H-pyrano[4,3-b]pyridine-2,5-dione (1 g, 1.810 mmol) in THF (10 ml) and MeOH (10 ml) was added lithium hydroxide (0.303 g, 12.67 mmol) and the mixture became yellow. Stir 1 h at 70° C. Concentrate with a stream of air and dilute with DCM. Adjust pH of aqueous layer to pH 7 using 1N HCl, extract 2×25 mL DCM, dry organic layers over magnesium sulfate, and concentrate. The product, 1-(2,6-diethylphenyl)-2-(2-methylprop-1-en-1-yl)-6-oxo-5-(2-(4-(trifluoromethyl)phenyl) thiazol-4-yl)-1,6-dihydropyridine-3-carboxylic acid; LCMS: m/z (M+H)$^+$=553.0. The crude was used in the next step without further purification.

Steps 5 and 6: To a solution of 1-(2,6-diethylphenyl)-2-(2-methylprop-1-en-1-yl)-6-oxo-5-(4-(4-(trifluoromethyl)phenyl)thiazol-2-yl)-1,6-dihydropyridine-3-carboxylic acid (1.0 g, 1.810 mmol) in DMF (Volume: 5 ml) was added 2-(3H-[1,2,3]triazolo[4,5-b]pyridin-3-yl)-1,1,3,3-tetramethylisouronium hexafluorophosphate(V) (1.376 g, 3.62 mmol) and N-ethyl-N-isopropylpropan-2-amine (0.740 ml, 4.52 mmol) and tert-butyl piperazine-1-carboxylate (0.674 g, 3.62 mmol) mixture became yellow the reaction mixture was stirred for 2 hrs at rt and dilute with water and extract with 3×10 mL DCM, washed with brine. The organic layer was dried and concentrated. The crude was used in the next step without further purification. The crude was diluted with DCM (5 ml) and treated with 2,2,2-trifluoroacetic acid (1.4 mL, 18.10 mmol) and the reaction mixture was stirred for 3 hrs at rt. The solvent was concentrated and purified by column chromatography. The product, 1-(2,6-diethylphenyl)-6-(2-methylprop-1-en-1-yl)-5-(piperazine-1-carbonyl)-3-(4-(4-(trifluoromethyl) phenyl)thiazol-2-yl)pyridin-2 (1H)-one, Compound 581; LCMS: m/z (M+H)$^+$=621.0.

-continued

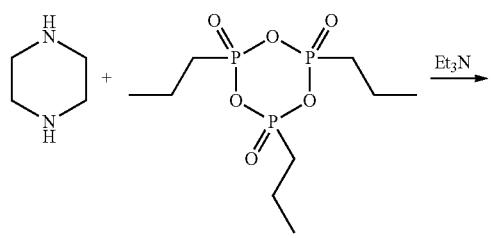

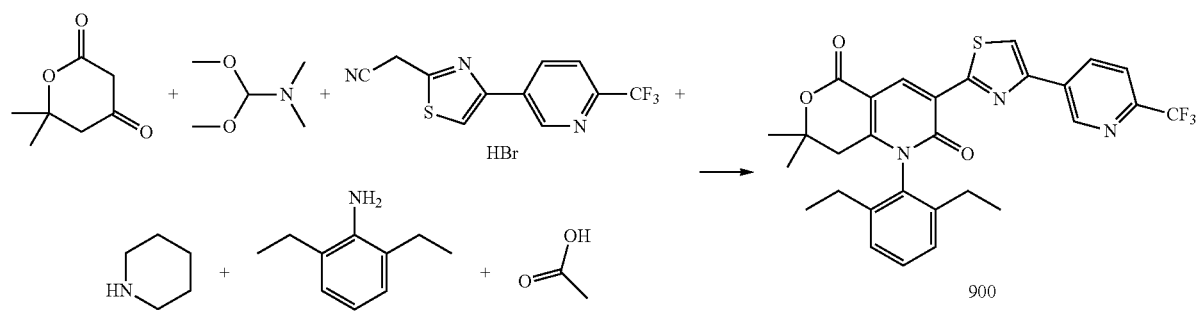

Method W-Compound 900:

Step 1: In a vial, 6,6-dimethyldihydro-2H-pyran-2,4(3H)-dione (24 mg, 0.168 mmol) and DMF-DMA (0.024 mL, 0.168 mmol) were mixed and stood neat for 5 min. The reaction mixture became a yellow/orange solid relatively quickly Step 2: To the mixture was added i-PrOH (2 mL), 2-(4-(6-(trifluoromethyl)pyridin-3-yl)thiazol-2-yl)acetonitrile hydrobromide (59 mg, 0.168 mmol), and piperidine (0.050 mL, 0.503 mmol). The reaction was heated at 70° C. for 5 h. The solid went into solution relatively quickly. The solvent was removed by blowing down under a stream of air with mild heating at 30° C.

Step 3: To the resulting residue were added 2,6-diethylaniline (0.033 mL, 0.201 mmol) and acetic acid (1.5 mL). The reaction was heated at 70° C. overnight. Following the reaction the mixture was concentrated and purified via silica gel chromatography (0 to 60% EtOAc/hexanes); LCMS: m/z (M+H)$^+$=554.1.

-continued

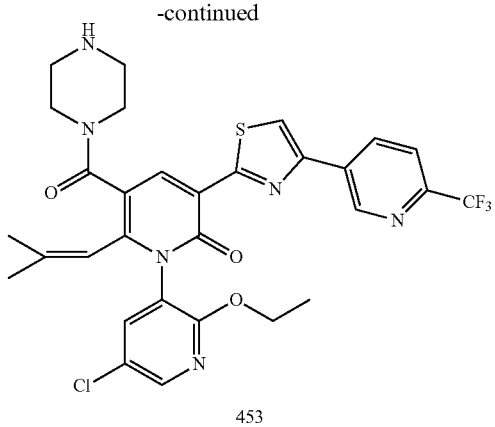

Method X-Compound 453:

A solution of 2,4,6-tripropyl-1,3,5,2,4,6-trioxatriphosphinane 2,4,6-trioxide (50% in EtOAc, 0.130 mL, 0.216 mmol) was added to a solution of 5'-chloro-2'-ethoxy-6-(2-methylprop-1-en-1-yl)-2-oxo-3-(4-(6-(trifluoromethyl)pyridin-3-yl)thiazol-2-yl)-2H-[1, 3'-bipyridine]-5-carboxylic acid (~83 mg, 0.144 mmol), piperazine (25 mg, 0.288 mmol), triethylamine (60 μL, 0.432 mmol) in EtOAc (1 mL). The reaction mixture stirred at rt and precipitate quickly formed. The reaction mixture stirred a total of 40 min and was concentrated under a stream of air. The residue was taken up in DMSO and subsequently purified by reverse phase chromatography to give Compound 453.

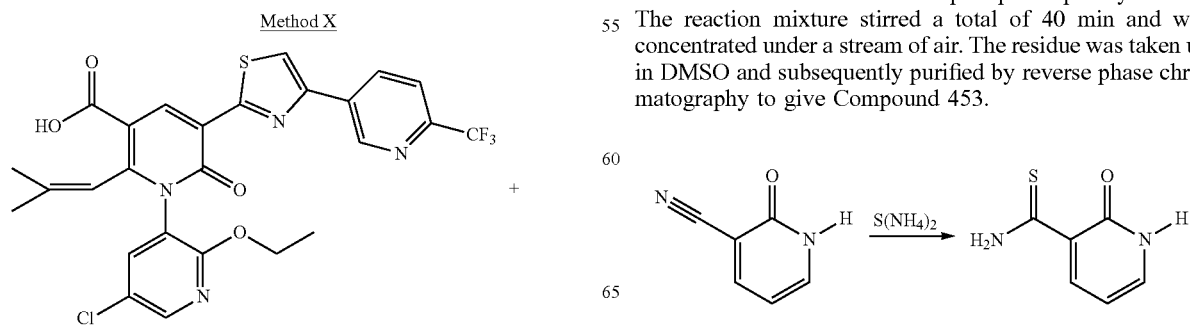

2-Oxo-1,2-dihydropyridine-3-carbothioamide: Ammonium sulfide (0.509 mL, 2.99 mmol) was added to a solution of 2-oxo-1,2-dihydropyridine-3-carbonitrile (211 mg, 1.757 mmol) in methanol (14 mL). The reaction was heated in a microwave at 130° C. for 2 h. The mixture stood overnight at rt and crystals formed. The mixture was further cooled to 0° C. for 4 h. The methanol was poured off and the solid was triturated with methanol and used as is in the following step. $^1$H NMR (400 MHz, DMSO-d$_6$) δ 12.60 (s, 1H), 11.31 (s, 1H), 9.98 (s, 1H), 8.93 (dd, J=7.4, 2.2 Hz, 1H), 7.77 (dd, J=6.2, 2.3 Hz, 1H), 6.52 (dd, J=7.4, 6.2 Hz, 1H).

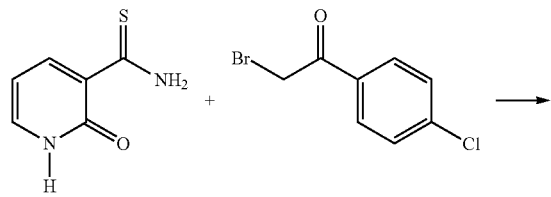

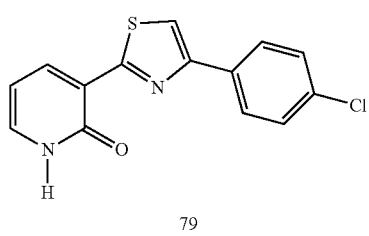

79

Method i-Compound 79: To 2-oxo-1,2-dihydropyridine-3-carbothioamide (124 mg, 0.804 mmol) in ethanol (2 mL) was added 2-bromo-1-(4-chlorophenyl)ethanone (188 mg, 0.804 mmol). The reaction mixture was heated at reflux for 17.5 h. The reaction mixture was cooled to rt and diluted with hexanes. The solid was removed by filtration washing with hexanes. Dry on high vacuum. The product (compound 79; 213 mg [65%]) is a red-brown powder. $^1$H NMR (400 MHz, DMSO-d$_6$) δ 12.10 (s, 1H), 8.28 (dd, J=7.2, 2.1 Hz, 1H), 7.80 (s, 1H), 7.76-7.68 (m, 2H), 7.30 (s, 1H), 7.20-7.11 (m, 2H), 6.15 (dd, J=7.2, 6.3 Hz, 1H).

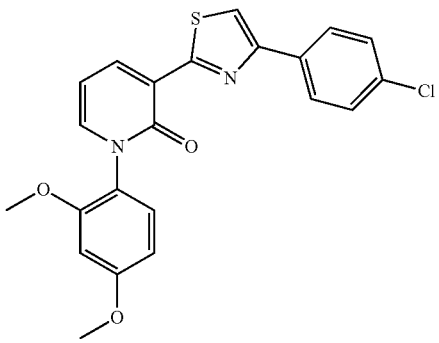

165

Method ii-Compound 165: To a mixture of 3-(4-(4-chlorophenyl) thiazol-2-yl)pyridin-2(1H)-one (compound 79) (60 mg, 0.208 mmol), copper (II) acetate (56.6 mg, 0.312 mmol), and 2,4-dimethoxyphenylboronic acid (76 mg, 0.416 mmol) were added 1,4-dioxane (2 mL) and pyridine (0.2 mL). The reaction mixture was sealed and heated at 80° C. for 60 h. The reaction mixture was filtered through a Agilent PL-Thiol MP SPE cartridge, to remove copper, washing with EtOAc. The mixture was concentrated under a stream of air. The residue was taken up in DMSO and subsequently purified by reverse phase chromatography to give Compound 165. $^1$H NMR (400 MHz, DMSO-d$_6$) δ 8.73 (dd, J=7.2, 2.1 Hz, 1H), 8.20 (s, 1H), 8.16-8.07 (m, 2H), 7.79 (dd, J=6.6, 2.1 Hz, 1H), 7.59-7.51 (m, 2H), 7.33 (d, J=8.6 Hz, 1H), 6.81 (d, J=2.6 Hz, 1H), 6.72-6.58 (m, 2H), 3.87 (s, 3H), 3.78 (s, 3H).

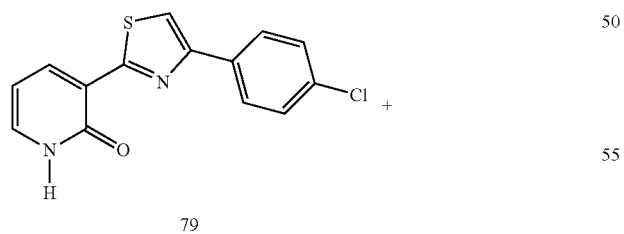

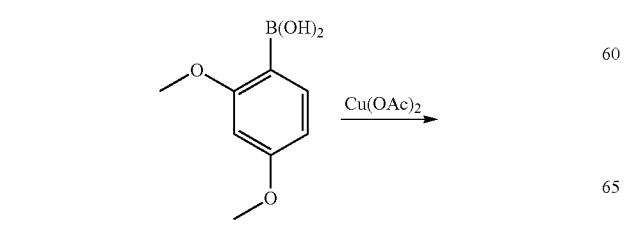

Method iii: In a microwave vial, combine 2-(3-bromophenyl)acetonitrile (300 mg, 1.53 mmol), (4-chlorophenyl)boronic acid (287 mg, 1.84 mmol), tetrakis(triphenylphosphine)palladium(0) (88 mg, 0.077 mmol), 2M aqueous sodium carbonate solution (2.3 mL), and dimethoxyethane (10 mL). The reaction mixture was heated in a microwave with stirring at 140° C. for 1 h. The reaction mixture was diluted with water and DCM, extracted (2×), the organic layers were combined, dried with magesium sulfate, concentrated and purified via silica gel chromatography (0 to 25% EtOAc/hexanes) to afford 2-(4'-chloro-[1,1'-biphenyl]-3-yl)acetonitrile (298 mg, 86%); $^1$H NMR (400 MHz, CDCl$_3$) δ 7.62-7.38 (m, 7H), 7.37-7.28 (m, 1H), 3.82 (t, J=0.7 Hz, 2H).

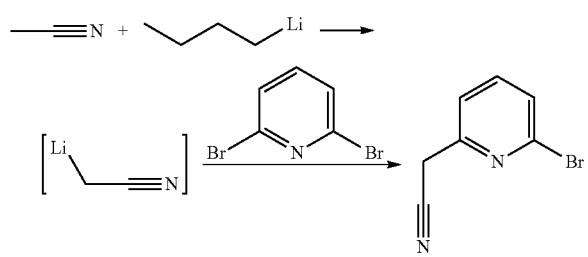

Method iv: A solution of n-butyllithium in hexanes (1.6M, 17.4 mL, 27.9 mmol) was added slowly to a solution of acetonitrile (1.5 mL, 28.7 mmol) in THF (40 mL) at −78° C. A precipitate formed. The slurry stirred at this temperature for 30 min. A solution of 2,6-dibromopyridine (2 g, 8.4 mmol) in THF (10 mL) was added slowly to the slurry. The reaction mixture stirred at −78° C. for 45 min. The mixture was allowed to warm slowly to rt over 30 min. The reaction mixture was diluted with water and EtOAc, extracted (2×), the organic layers were combined, dried with magnesium sulfate, concentrated and purified via silica gel chromatography (0 to 40% EtOAc/hexanes) to afford 2-(6-bromopyridin-2-yl)acetonitrile (1.65 g, 99%) as a yellow oil that solidified upon cooling; LCMS: m/z (M+H)$^+$=197.0.

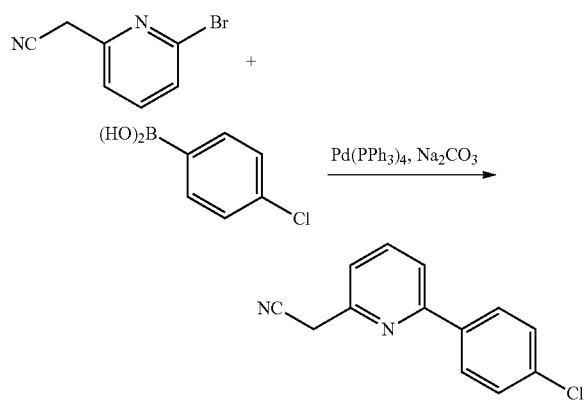

Compound 2-(6-(4-chlorophenyl)pyridin-2-yl)acetonitrile was prepared according to method iii and the purification utilized was a gradient from 0 to 40% EtOAc/hexanes (1.5 mmol scale, quant.); LCMS: m/z (M+H)$^+$=229.1.

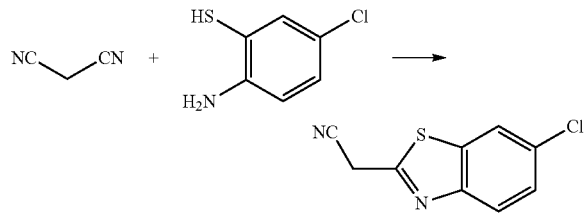

Method v: Malononitrile (65 mg, 0.98 mmol) and 2-amino-5-chlorobenzenethiol (157 mg, 0.98 mmol) were heated at 50° C. for 4 h and at reflux for 1 h in a mixture of EtOH and AcOH. The reaction mixture was concentrated under a stream of air and used without further purification.

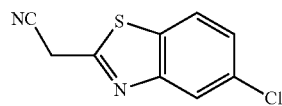 [SMILES: N#CCc1nc2cc(Cl)ccc2s1]

Compound 2-(5-chlorobenzo[d]thiazol-2-yl)acetonitrile was prepared according to method v, however refluxing was conducted overnight followed by heating in a microwave at 120° C. for 1h and at 150° C. for 1 h. The reaction mixture was concentrated under a stream of air and used without further purification; LCMS: m/z (M+H)$^+$=209.0.

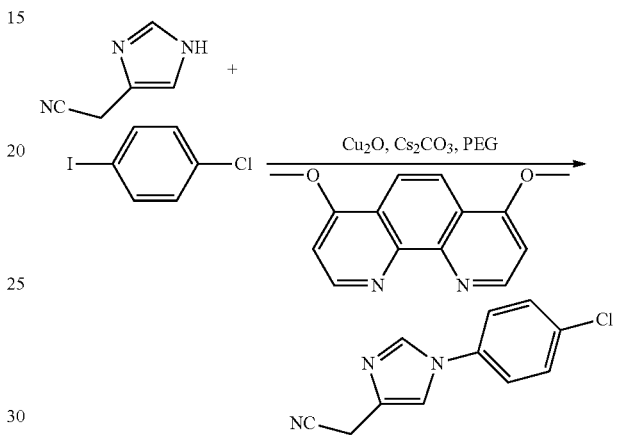

Method vi: A mixture of 2-(1H-imidazol-4-yl)acetonitrile (150 mg, 1.4 mmol), 1-chloro-4-iodobenzene (467 mg, 1.96 mmol), 4,7-dimethoxy-1,10-phenanthroline (101 mg, 0.42 mmol), copper (I) oxide (20 mg, 0.14 mmol), cesium carbonate (776 mg, 2.38 mmol), PEG (250 mg) and DMSO (1.5 mL) was heated with stirring at 110° C. for 24 h. The reaction mixture was diluted with water, 0.1N HCl, and EtOAc, extracted (2×). The organic layers were combined, dried with magnesium sulfate, concentrated and purified via reverse phase chromatography (C18) (5 to 100% acetonitrile/water [0.1% TFA]) to afford 2-(1-(4-chlorophenyl)-1H-imidazol-4-yl)acetonitrile (35 mg, 12%) as a yellow oil; LCMS: m/z (M+H)$^+$=218.0.

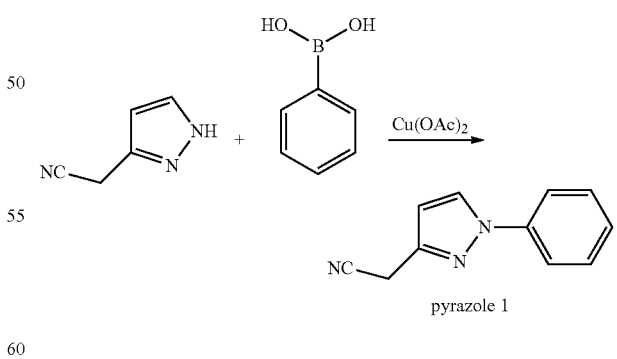

pyrazole 1

Method vii-pyrazole 1: A mixture of copper (II) acetate 382 mg, 2.1 mmol), 2-(1H-pyrazol-3-yl)acetonitrile (150 mg, 1.4 mmol), phenylboronic acid (341 mg, 2.8 mmol), triethylamine (0.390 mL, 2.8 mmol), pyridine (0.227 mL, 2.8 mmol), 4 Angstrom molecular sieves (500 mg), and dichloromethane (10 mL) was heated at 55° C. overnight. The reaction mixture was filtered, extracted (DCM/1 N HCl), dried with magnesium sulfate, concentrated and 2-(1-phenyl-1H)-pyrazol-3-yl)acetonitrile used without further purification; LCMS: m/z (M+H)$^+$=184.1.

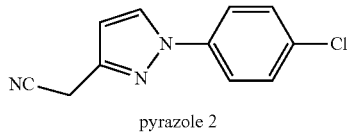 [SMILES: N#CCc1ccn(-c2ccc(Cl)cc2)n1]

pyrazole 2

Pyrazole 2: Synthesized by method vii substituting (4-chlorophenyl)boronic acid as a starting material and purification was necessary by silica gel chromatography; LCMS: m/z (M+H)$^+$=218.0.

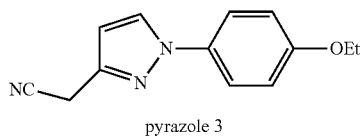

pyrazole 3

Pyrazole 3: Synthesized by method vii substituting (4-ethoxyphenyl)boronic acid as a starting material and purification was necessary by silica gel chromatography; LCMS: m/z (M+H)$^+$=228.1.

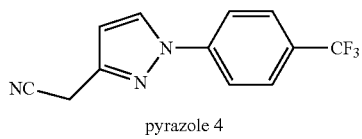 [SMILES: N#CCc1ccn(-c2ccc(C(F)(F)F)cc2)n1]

pyrazole 4

Pyrazole 4: Synthesized by method vii substituting (4-(trifluoromethyl)phenyl)boronic acid as a starting material and purification was necessary by silica gel chromatography; LCMS: m/z (M+H)$^+$=252.1.

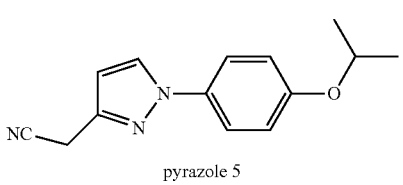 [SMILES: CC(C)Oc1ccc(-n2ccc(CC#N)n2)cc1]

pyrazole 5

Pyrazole 5: Synthesized by method vii substituting (4-isopropoxyphenyl)boronic acid as a starting material and purification was necessary by silica gel chromatography; LCMS: m/z (M+H)$^+$=242.1.

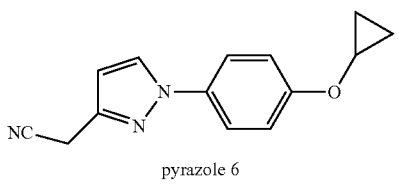 [SMILES: N#CCc1ccn(-c2ccc(OC3CC3)cc2)n1]

pyrazole 6

Pyrazole 6: Synthesized by method vii substituting (4-cyclopropoxyphenyl)boronic acid as a starting material and purification was necessary by silica gel chromatography; LCMS: m/z (M+H)$^+$=240.0.

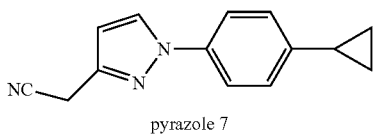 [SMILES: N#CCc1ccn(-c2ccc(C3CC3)cc2)n1]

pyrazole 7

Pyrazole 7: Synthesized by method vii substituting (4-cyclopropylphenyl)boronic acid as a starting material and purification was necessary by silica gel chromatography; LCMS: m/z (M+H)$^+$=224.1.

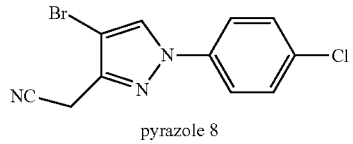 [SMILES: N#CCc1nn(-c2ccc(Cl)cc2)cc1Br]

pyrazole 8

Pyrazole 8: Synthesized by the bromination of pyrazole 2 with NBS (1.3 eq) in acetonitrile followed by silica gel chromatography; LCMS: m/z (M+H)$^+$=297.9.

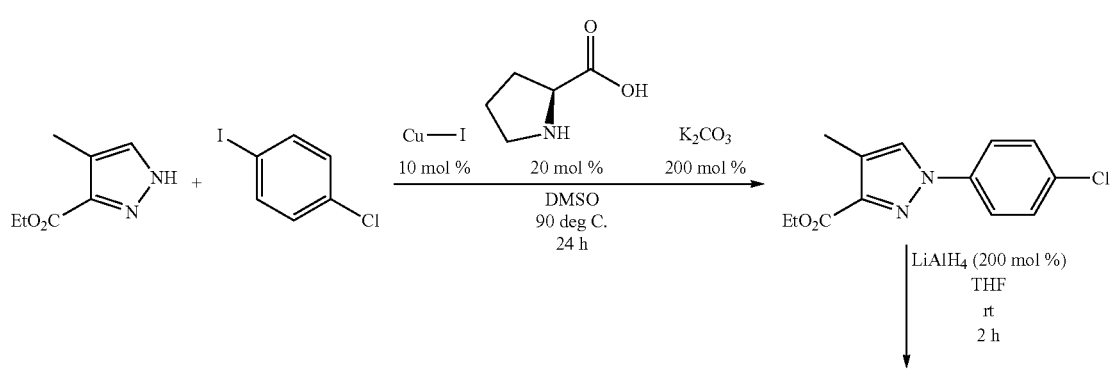

 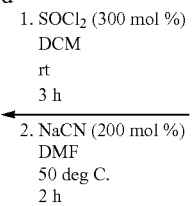 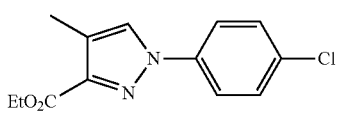

Pyrazole 9: Synthesized by copper catalyzed N-arylation, subsequent ester reduction with lithium aluminum hydride, chlorination of the resulting alchol, and finally displacement with cyanide anion; LCMS: m/z (M+H)$^+$=232.0.

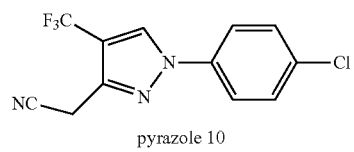 [SMILES: N#CCc1nn(-c2ccc(Cl)cc2)cc1C(F)(F)F]

Pyrazole 10: Synthesized in the same manner as pyrazole 9 substituting ethyl 4-(trifluoromethyl)-1H-pyrazole-3-carboxylate as a starting material in the N-arylation: LCMS: m/z (M+H)$^+$=286.0.

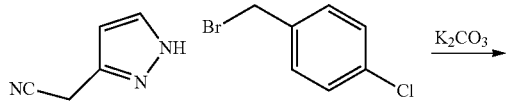

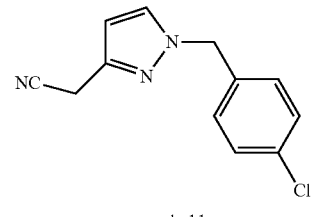

Pyrazole 11: To a solution of 2-(1H-pyrazol-3-yl)acetonitrile (50 mg, 0.467 mmol) in MeCN (Volume: 4.5 ml) were added POTASSIUM CARBONATE (77 mg, 0.560 mmol), and then 1-(bromomethyl)-4-chlorobenzene (96 mg. 0.467 mmol). The mixture was stirred at 80° C. for 3 days. Water was added to the mixture, and extracted with EtOAc. The organic layer was dried over MgSO$_4$ and concentrated. The crude product was purified by Biotage (0-3% MeOH/DCM). LCMS: m/z (M+H)$^+$=232.0.

Method viii: A mixture of 5-(chloromethyl)-2-phenyl-1H-imidazole hydrochloride (197 mg, 0.86 mmol) and sodium cyanide (127 mg, 2.58 mmol) in DMSO (3 mL) was stirred at rt overnight. The reaction mixture was diluted with water and saturated aqueous sodium bicarbonate solution, extracted (EtOAc×2), dried with magnesium sulfate, concentrated and 2-(2-phenyl-1H-imidazol-5-yl)acetonitrile used without further purification.

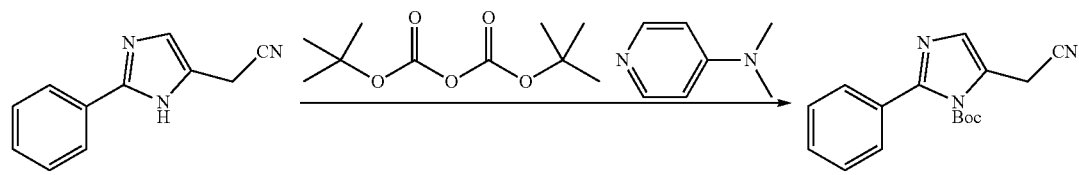

Method ix: A mixture of 2-(2-phenyl-1H-imidazol-5-yl)acetonitrile (50 mg, 0.27 mmol), Boc$_2$O (0.070 mL. 0.3 mmol), and DMAP (trace) in acetonitrile (3 mL) and sodium cyanide (127 mg, 2.58 mmol) in DMSO (3 mL) was stirred at rt for 40 min and concentrated under a stream of air. Tert-butyl 5-(cyanomethyl)-2-phenyl-1H-imidazole-1-carboxylate was used without further purification; LCMS: m/z (M+H)$^+$=284.1 (weak).

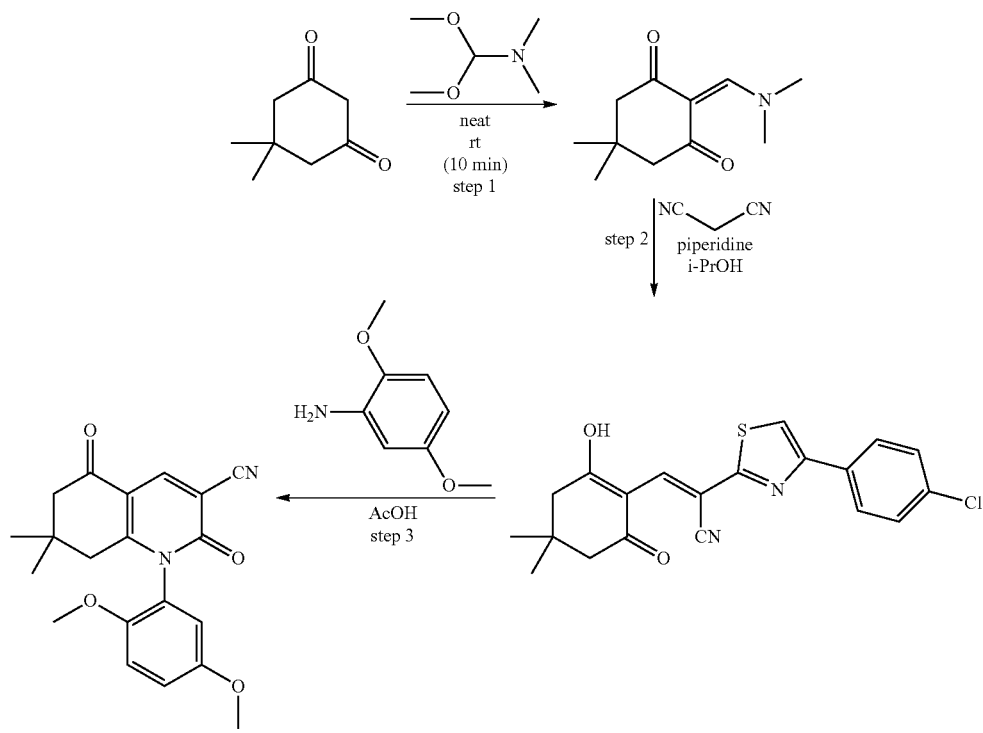

1-(2,5-Dimethoxyphenyl)-7,7-dimethyl-2,5-dioxo-1,2,5,6,7,8-hexahydroquinoline-3-carbonitrile: Step 1. Similar to method A; Step 2: Similar to method A with stirring only for 1 h. Also, add aniline prior to concentration; Step 3: Add acetic acid and stir overnight at rt. The reaction mixture was diluted with water and DCM, extracted (2×), the organic layers were combined, dried with magnesium sulfate, concentrated and purified via silica gel chromatography (10 to 100% EtOAc/hexanes) to afford 1-(2,5-dimethoxyphenyl)-7,7-dimethyl-2,5-dioxo-1,2,5,6,7,8-hexahydroquinoline-3-carbonitrile (70% on 2.85 mmol scale); LCMS: m/z (M+H)+=353.1.

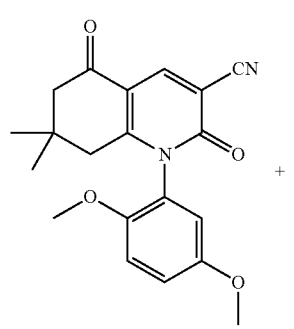

+

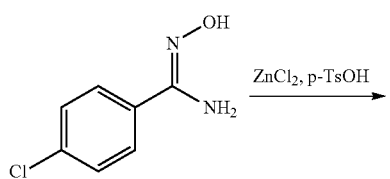

-continued

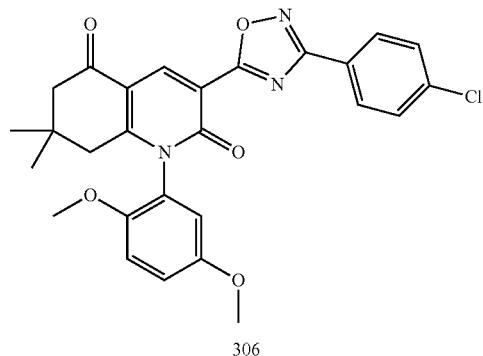

306

Method x-Compound 306: Zinc chloride solution (0.5M, 0.182 mL, 0.091 mmol) was placed in a vial and the ethereal solvent was removed under a stream of nitrogen. To the solid was added DMF (1 mL) as well as 1-(2,5-dimethoxyphenyl)-7,7-dimethyl-2,5-dioxo-1,2,5,6,7,8-hexahydroquinoline-3-carbonitrile (80 mg, 0.227 mmol), p-TsOH (17 mg, 0.091 mmol), and 4-chloro-N'-hydroxybenzimidamide (46.5 mg, 0.272 mmol). The reaction mixture was heated at 80° C. overnight and at 100° C. for 8 h. The reaction mixture was filtered through a Agilent PL-Thiol MP SPE cartridge, to remove zinc, washing with EtOAc. The mixture was concentrated under a stream of air. The residue was taken up in DMSO and subsequently purified by reverse phase chromatography to give Compound 306.

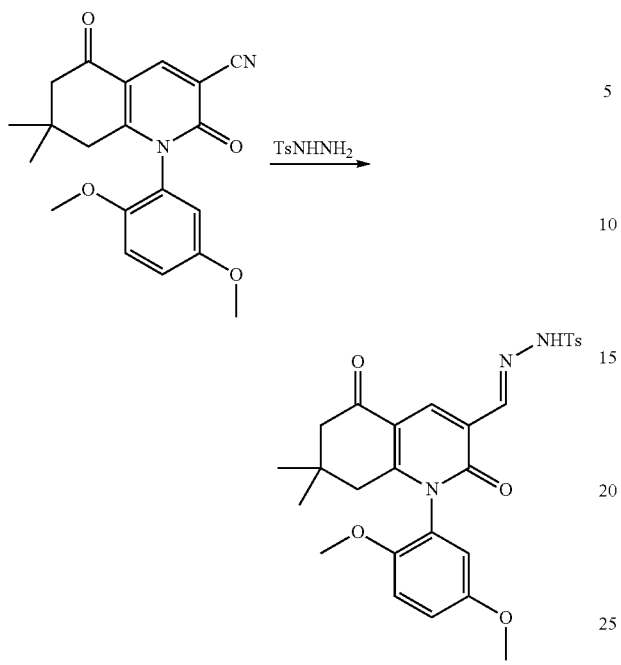

N'-((1-(2,5-Dimethoxyphenyl)-7,7-dimethyl-2,5-dioxo-1,2,5,6,7,8-hexahydroquinolin-3-yl)methylene)-4-methylbenzenesulfonohydrazide: A mixture of 1-(2,5-dimethoxyphenyl)-7,7-dimethyl-2,5-dioxo-1,2,5,6,7,8-hexahydroquinoline-3-carbonitrile (80 mg, 0.227 mmol), 4-methylbenzenesulfonohydrazide (46.5 mg, 0.25 mmol), sodium hydrophosphite (205 mg, 1.3 mmol), pyridine (1.3 mL), water (0.8 mL), and acetic acid (0.8 mL) was added to a slurry of Raney Ni (0.4 g, 0.23 mmol). The mixture evolved bubbles and was stirred at rt for 2 h. The mixture was filtered washing with DCM. The filtrate was concentrated and N'-((1-(2,5-dimethoxyphenyl)-7,7-dimethyl-2,5-dioxo-1,2,5,6,7,8-hexahydroquinolin-3-yl)methylene)-4-methylbenzenesulfonohydrazide was used without further purification; LCMS: m/z (M+H)$^+$=524.2.

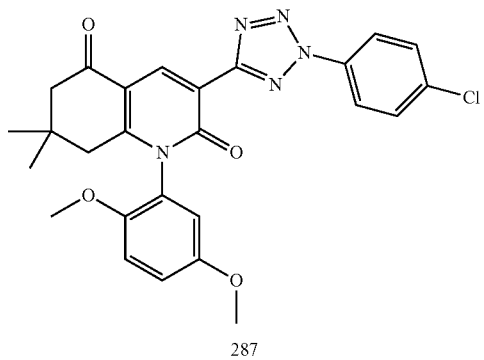

287

Method xi-Compound 287: A solution of sodium nitrite (32 mg, 0.465 mmol) in water (0.25 mL) was added slowly to a solution of 4-chloroaniline (58 mg, 0.454 mmol) and conc. aq. HCl (0.3 mL) in ethanol (0.5 mL) and water (0.5 mL) at 0° C. The reaction stirred at rt 10 min. A faint yellow mixture resulted. This was cooled further to −15° C. and a solution of N'-(1-(2,5-dimethoxyphenyl)-7,7-dimethyl-2,5-dioxo-1,2,5,6,7,8-hexahydroquinolin-3-yl)methylene)-4-methylbenzenesulfonohydrazide (0.227 mmol) in pyridine (2 mL) was added slowly. This formed an orange slurry which was allowed to warm slowly to rt and stir a total of 2 h. The reaction mixture was diluted with water and 1N aq. HCl, extracted (DCM×2), dried with magnesium sulfate, concentrated, and submitted in DMSO for reverse phase purification to afford Compound 287.

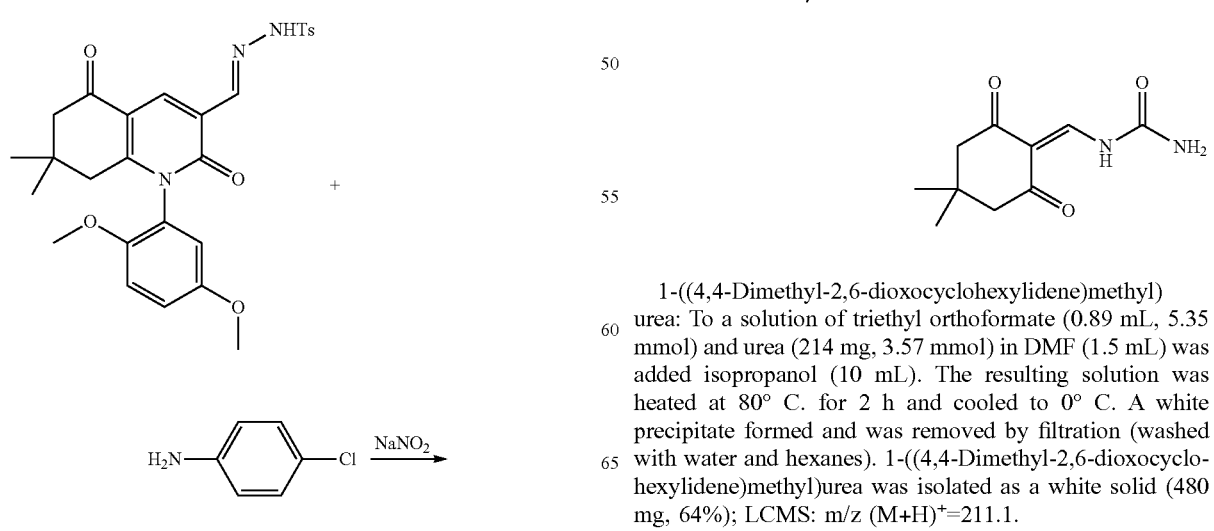

1-((4,4-Dimethyl-2,6-dioxocyclohexylidene)methyl)urea: To a solution of triethyl orthoformate (0.89 mL, 5.35 mmol) and urea (214 mg, 3.57 mmol) in DMF (1.5 mL) was added isopropanol (10 mL). The resulting solution was heated at 80° C. for 2 h and cooled to 0° C. A white precipitate formed and was removed by filtration (washed with water and hexanes). 1-((4,4-Dimethyl-2,6-dioxocyclohexylidene)methyl)urea was isolated as a white solid (480 mg, 64%); LCMS: m/z (M+H)$^+$=211.1.

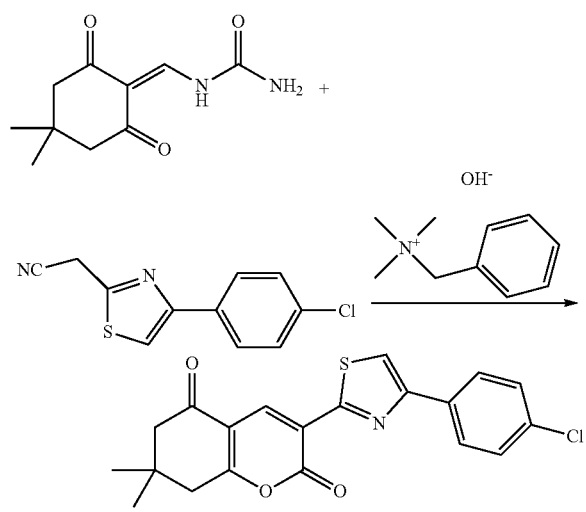

3-(4-(4-Chlorophenyl)thiazol-2-yl)-7,7-dimethyl-7,8-dihydro-2H-chromene-2,5(6H)-dione: A mixture of 1-((4,4-dimethyl-2,6-dioxocyclohexylidene)methyl)urea (40 mg, 0.19 mmol), nitrile 1 (54 mg, 0.23 mmol), and a solution of benzyltrimethylammonium hydroxide solution (40% in MeOH, 0.113 mL, 0.285 mmol) in DMF/MeOH (1:1-1 mL) was heated at 140° C. for 1 h 20 min. Upon cooling, the mixture was diluted with water, acidified at 0° C. with 1N HCl, stirred overnight, and filtered to afford a brown solid (3-(4-(4-chlorophenyl)thiazol-2-yl)-7,7-dimethyl-7,8-dihydro-2H-chromene-2,5(6H)-dione, 61 mg, 91%); LCMS: m/z (M+H)$^+$=386.0.

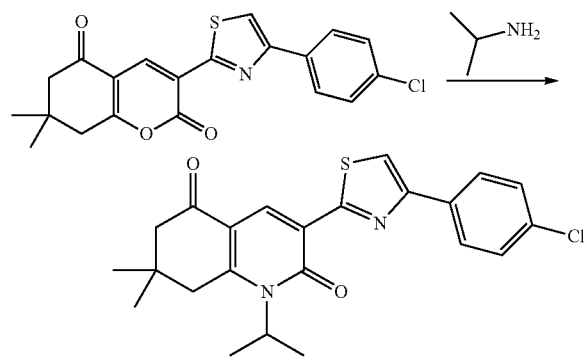

Method xii-Compound 55: A solution of 3-(4-(4-chlorophenyl)thiazol-2-yl)-7,7-dimethyl-7,8-dihydro-2H-chromene-2,5(6H)-dione (34 mg, 0.088 mmol) and isopropylamine (0.03 mL, 0.35 mmol) in DMF (0.5 mL) was heated at 150° C. for 2 h and submitted in DMF for reverse phase purification to afford Compound 55.

Method xiii-Same as method xii except heat in microwave at 130° C. for 30 min.

Method xiv-Same as method xii except heat neat at 180° C. for 30 min.

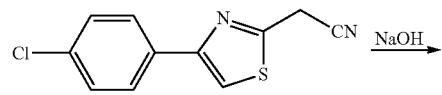

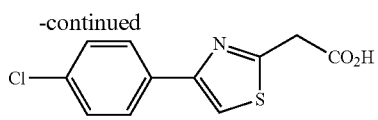

2-(4-(4-Chlorophenyl)thiazol-2-yl)acetic acid: A solution of 2-(4-(4-chlorophenyl)thiazol-2-yl)acetonitrile (100 mg, 0.426 mmol) and sodium hydroxide (170 mg, 4.3 mmol) in ethanol/water (1:1-4 mL) was heated at 100° C. overnight. The mixture was cooled, concentrated, acidified (1N HCl), and filtered to afford 2-(4-(4-chlorophenyl) thiazol-2-yl) acetic acid; LCMS: m/z (M+H)$^+$=254.0.

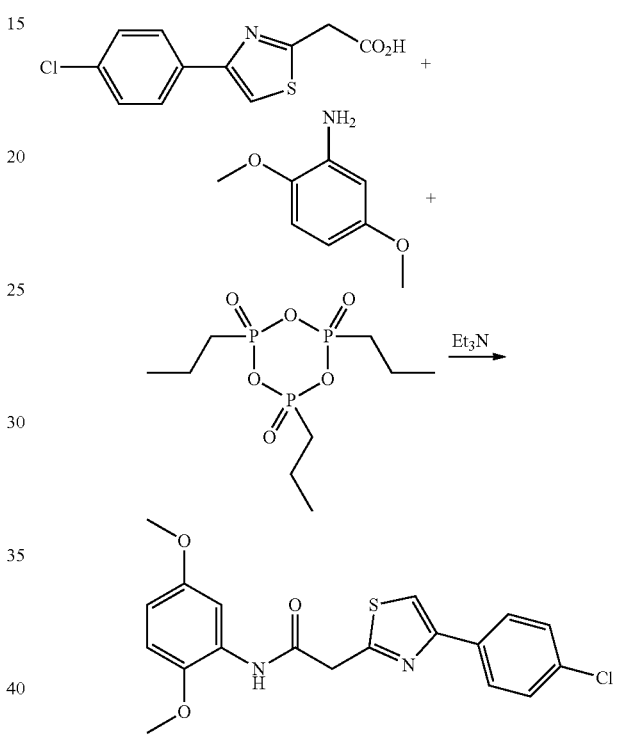

2-(4-(4-Chlorophenyl)thiazol-2-yl)-N-(2,5-dimethoxyphenyl)acetamide: A solution of 2,4,6-tripropyl-1,3,5,2,4,6-trioxatriphosphinane 2,4,6-trioxide (50% in DMF, 0.455 mL, 0.765 mmol) was added to a solution of 2-(4-(4-chlorophenyl)thiazol-2-yl)acetic acid (97 mg, 0.38 mmol), 2,5-dimethoxyaniline (64 mg, 0.42 mmol), triethylamine (0.21 mL, 1.6 mmol) in DMF (2 mL). The mixture was heated with stirring at 60° C. for 2.25 h. The reaction mixture was diluted with water, extracted (EtOAc×2), dried with magnesium sulfate, concentrated and 2-(4-(4-chlorophenyl)thiazol-2-yl)-N-(2,5-dimethoxyphenyl)acetamide was used without further purification; LCMS: m/z (M+H)$^+$=389.0.

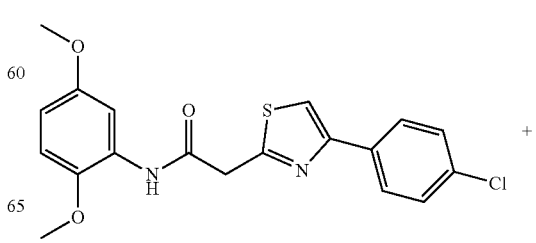

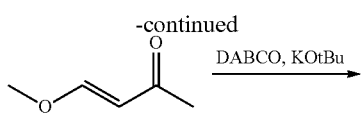

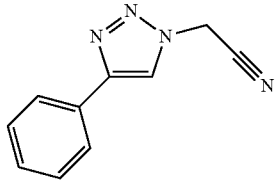

62

Method xv-Compound 62: A solution of 2-(4-(4-chlorophenyl) thiazol-2-yl)-N-(2,5-dimethoxyphenyl)acetamide (74 mg, 0.19 mmol), 4-methoxybut-3-en-2-one (0.043 mL, 0.38 mmol), and DABCO (21 mg, 0.19 mmol) in DME (2 mL) was heated at 125° C. for 2 h with little to no reaction. Potassium tert-butoxide (21 mg, 0.19 mmol) was added and heating resumed at 80° C. for 3.5 h. The reaction mixture was diluted with water, MeOH, 1N HCl, and DCM, extracted (DCM/MeOH×2), dried with magnesium sulfate, concentrated and submitted in DMSO for reverse phase purification to afford Compound 62.

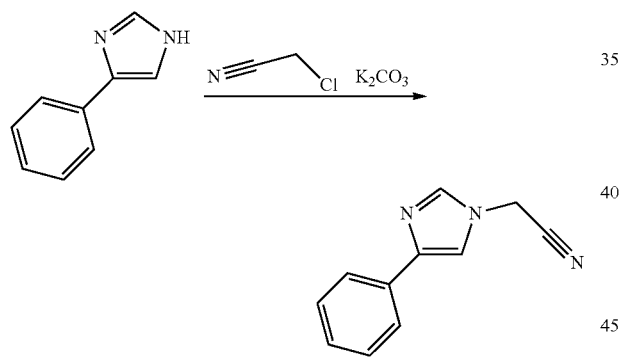

Method xvi-2-(4-phenyl-1H-imidazol-1-yl)acetonitrile: A mixture of 4-phenyl-1H-imidazole (250 mg, 1.7 mmol), chloroacetonitrile (0.22 mL, 3.5 mmol), and potassium carbonate (1.2 g, 8.7 mmol) in DMF (8 mL) was stirred at rt for 22 h. The reaction mixture was diluted with water, extracted (EtOAc×2), dried with magnesium sulfate, concentrated to afford 2-(4-phenyl-1H-imidazol-1-yl)acetonitrile as a brown solid which was used without further purification; LCMS: m/z (M+H)$^+$=184.1.

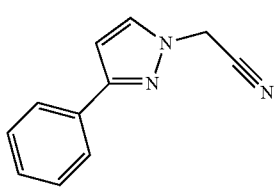 [SMILES: N#CCn1ccc(-c2ccccc2)n1]

2-(3-phenyl-1H-pyrazol-1-yl)acetonitrile was synthesized by method xvi; LCMS: m/z (M+H)$^+$=184.1 (weak).

2-(4-phenyl-1H-1,2,3-triazol-1-yl)acetonitrile was synthesized by method xvi; LCMS: m/z (M+H)$^+$=185.1 (weak).

2-(4-phenyl-1H-pyrazol-1-yl)acetonitrile was synthesized by method xvi; LCMS: m/z (M+H)$^+$=184.1 (weak).

1-(2,5-Dimethoxyphenyl)-7,7-dimethyl-2,5-dioxo-1,2,5,6,7,8-hexahydroquinoline-3-carboxylic acid: A mixture of 1-(2,5-dimethoxyphenyl)-7,7-dimethyl-2,5-dioxo-1,2,5,6,7,8-hexahydroquinoline-3-carbonitrile (60 mg, 0.17 mmol) in concentrated HCl (3 mL) was heated at 80° C. for 22 h. The reaction mixture was diluted with water, extracted (DCM/MeOH×3), dried with magnesium sulfate, concentrated to afford 1-(2,5-dimethoxyphenyl)-7,7-dimethyl-2,5-dioxo-1,2,5,6,7,8-hexahydroquinoline-3-carboxylic acid which was used without further purification; LCMS: m/z (M+H)$^+$=372.1.

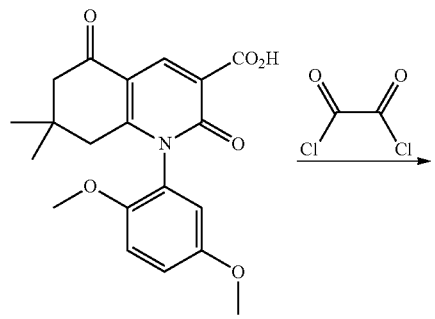

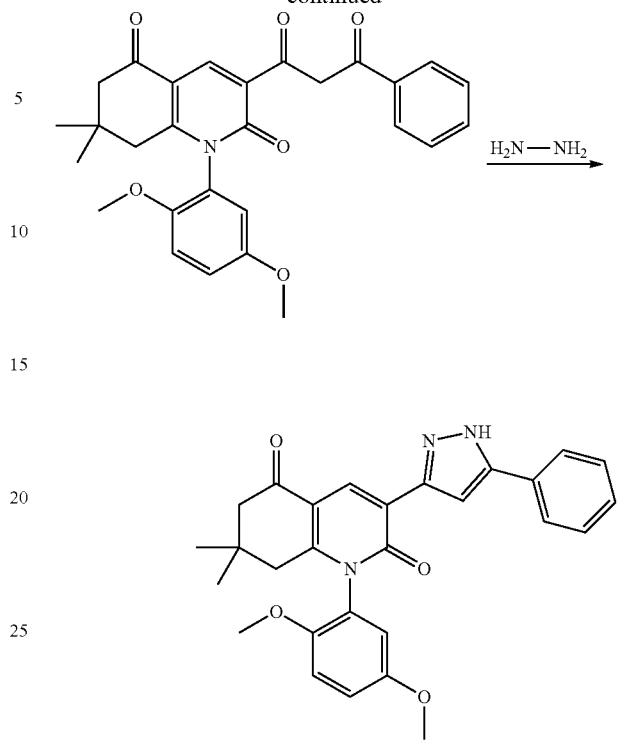

1-(2,5-Dimethoxyphenyl)-7,7-dimethyl-2,5-dioxo-1,2,5,6,7,8-hexahydroquinoline-3-carbonyl chloride: To a mixture of 1-(2,5-dimethoxyphenyl)-7,7-dimethyl-2,5-dioxo-1,2,5,6,7,8-hexahydroquinoline-3-carboxylic acid (28 mg, 0.075 mmol) in DCM (3 mL) was added a drop of DMF and oxalyl chloride (0.033 mL, 0.38 mmol). The reaction stirred at rt 1.2 h. The reaction mixture was concentrated under a stream of argon, rediluted with DCM, and reconcentrated to afford 1-(2,5-dimethoxyphenyl)-7,7-dimethyl-2,5-dioxo-1,2,5,6,7,8-hexahydroquinoline-3-carbonyl chloride; LCMS shows formation of methyl ester when aliquot added to MeOH.

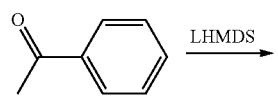

Method xvii-Compound 294: To a solution of acetophenone (0.026 mL, 0.23 mmol) in THF (1 mL) that had been cooled to −78° C. was added a solution of LiHMDS (1M THF, 0.225 mL, 0.225 mmol) slowly. The reaction continued to stir at this temperature for 1 h (faint yellow solution) at which point a solution of 1-(2,5-dimethoxyphenyl)-7,7-dimethyl-2,5-dioxo-1,2,5,6,7,8-hexahydroquinoline-3-carbonyl chloride (0.075 mmol) in THF (1.5 mL) was added. The reaction became more yellow and was allowed to warm slowly 1.5 h. The reaction went from yellow to red (likely red is doubly deprotonated trione). Hydrazine (3 eq) in ethanol was added and stirring resumed for 1 h. Acetic acid (3 drops) was added and the reaction went from red to yellow along with the formation of a precipitate. The reaction was heated at 50° C. for 1 h and stood at rt for 1 wk. The reaction mixture was concentrated and submitted in DMSO for reverse phase purification to afford Compound 294.

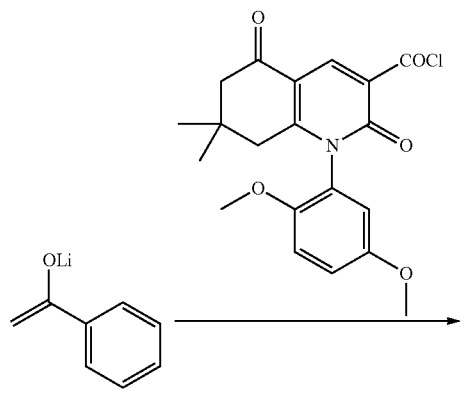

-continued

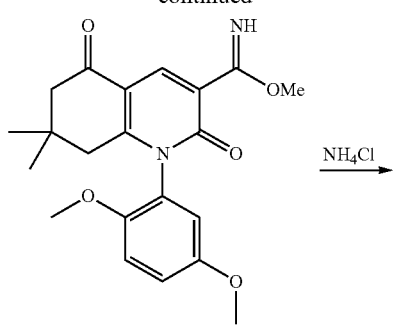

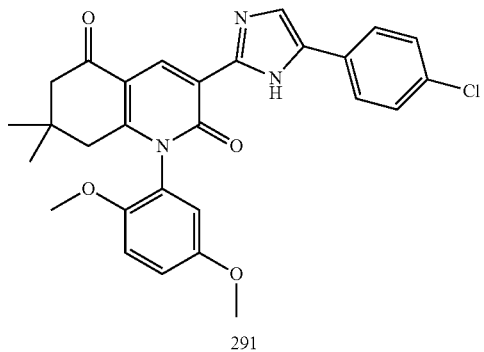

Method xviii-Compound 291: 2-Bromo-1-(4-chlorophenyl)ethanone (7 mg, 0.03 mmol) was added to a solution of 1-(2,5-dimethoxyphenyl)-7,7-dimethyl-2,5-dioxo-1,2,5,6,7,8-hexahydroquinoline-3-carboximidamide (11 mg, 0.03 mmol) in THF (1 mL) along with 3 drops of sat. aq. sodium bicarbonate solution. The reaction was heated at 70° C. for 1.5 h, acetic acid (5 drops) was added and heating resumed at this temp for 2 h. The reaction mixture was concentrated and submitted in DMSO for reverse phase purification to afford Compound 291.

1-(2,5-Dimethoxyphenyl)-7,7-dimethyl-2,5-dioxo-1,2,5,6,7,8-hexahydroquinoline-3-carboximidamide: A solution of sodium methoxide in methanol (25%, 0.389 mL, 1.7 mmol) was added to a mixture of 1-(2,5-dimethoxyphenyl)-7,7-dimethyl-2,5-dioxo-1,2,5,6,7,8-hexahydroquinoline-3-carbonitrile (60 mg, 0.17 mmol) in methanol (1.5 mL). The red mixture was heated at 45° C. for 45 min. Ammonium chloride (182 mg, 3.4 mmol) and acetic acid (1 mL) were added and the red color disipated. The mixture was heated at 60° C. overnight. The reaction mixture was diluted with water, extracted (EtOAc to remove organic impurities), basified (1N NaOH), extracted (DCM/MeOH×5; difficult to get amidine out of water layer), dried with magnesium sulfate, and concentrated to afford 1-(2,5-dimethoxyphenyl)-7,7-dimethyl-2,5-dioxo-1,2,5,6,7,8-hexahydroquinoline-3-carboximidamide which was used without further purification.

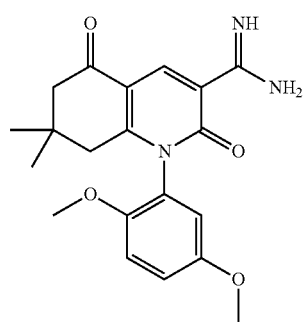

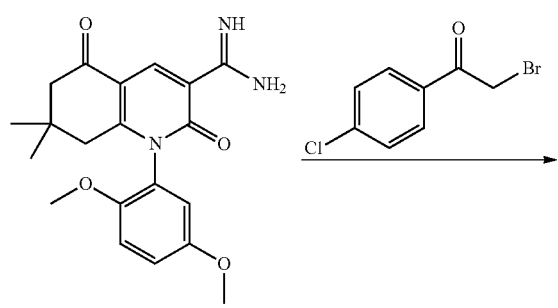

2-(4-Bromo-5-methylthiazol-2-yl)acetonitrile: Step 1-NBS (4.22 g, 24 mmol) was added to a solution of 5-methylthiazole (2 mL, 23 mmol) in acetonitrile (50 mL) and the mixture was heated at 50° C. for 5 h at which point NCS (3.77 g, 28 mmol) was added. The mixture was heated at 80° C. for 18 h and cooled to rt, diluted with diethylether (200 mL), and succinimide was removed by filtration. Upon concentration, the residue was dry loaded for purification via silica gel chromatography (0 to 20% EtOAc/hexanes) to afford the 4-bromo-2-chloro-5-methylthiazole (1.7 g, 36%) (LCMS: m/z (M+H)$^+$=212.9); Step 2—To a cooled (−60° C.) solution of NaHMDS (1M in THF, 24 mL, 24 mmol) in THF (50 mL) was added acetonitrile (0.85 mL, 16 mmol) slowly. The reaction stirred at this temp for 30 min at which point a solution of 4-bromo-2-chloro-5-methythiazole (1.72 g, 8.1 mmol) in THF (20 mL) was added slowly. The mixture became deep red brown. The mixture was allowed to warm slowly to 0° C. and it remained at this temperature for a further 1.5 h. The reaction mixture was diluted with water and EtOAc, extracted (2×), the organic layers were combined, dried with magnesium sulfate, concentrated and purified via silica gel chromatography (0 to 60% EtOAc/hexanes) to afford 2-(4-bromo-5-methylthiazol-2-yl)acetonitrile (1.16 g, 66%) as a dark red semisolid; LCMS: m/z (M+H)$^+$=216.9.

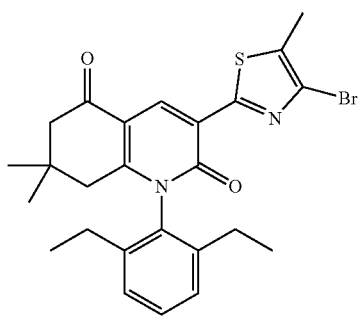

3-(4-bromo-5-methylthiazol-2-yl)-1-(2,6-diethylphenyl)-7,7-dimethyl-7,8-dihydroquinoline-2,5(1H,6H)-dione was prepared according to method N (no heating of step 2, step 3-heated at 80° C. 4 h) by utilizing 2-(4-bromo-5-methylthiazol-2-yl)acetonitrile; LCMS: m/z (M+H)⁺=499.0.

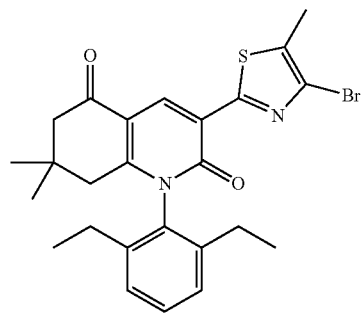 [SMILES: CCc1cccc(CC)c1-n1c2c(cc(-c3nc(Br)c(C)s3)c1=O)C(=O)CC(C)(C)C2]

+

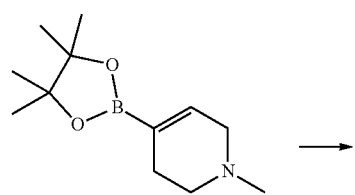

→

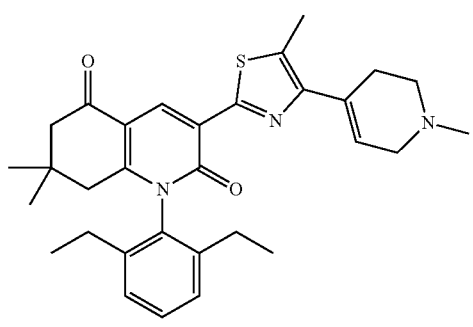

208

Method xix-Compound 208 was prepared according to method iii (130° C. for 1.5 h), and filtered through an Agilent PL-Thiol MP SPE cartridge to remove palladium. The organic layer was concentrated under a stream of air. The residue was taken up in DMSO and subsequently purified by reverse phase chromatography to afford Compound 208.

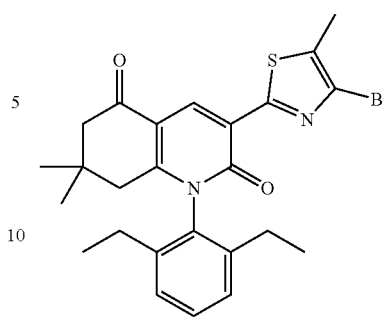

+

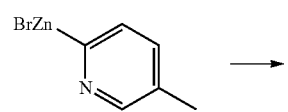

→

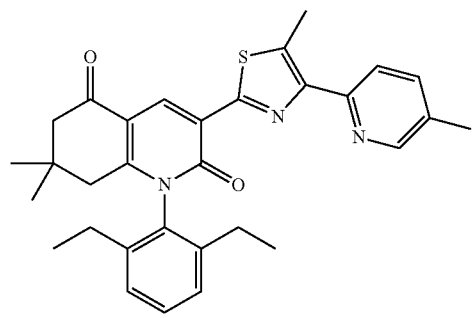

292

Method xx-Compound 292 was prepared according to method iii however sodium carbonate solution was omitted and dry DME was utilized (110° C. for 2 h), and filtered through an Agilent PL-Thiol MP SPE cartridge to remove palladium. The organic layer was concentrated under a stream of air. The residue was taken up in DMSO and subsequently purified by reverse phase chromatography to afford Compound 292.

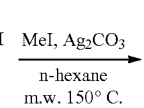

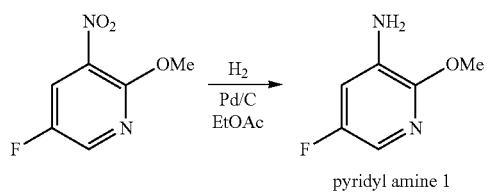

pyridyl amine 1

Method xxi-pyridyl amine 1: To a solution of 5-fluoro-3-nitropyridin-2-ol (158 mg, 1 mmol) in n-hexane (1 mL)

was added silver carbonate (331 mg, 1.2 mmol) and methyl iodide (0.2 mL, 2 mmol). The resulting mixture was stirred at 150° C. under microwave irradiation (Power 250 W) for 1 hour. Solvent was removed and the residue was dissolved in ethyl acetate (2 ml) and washed with water (2×). Solvent was removed and the residue was purified on ISCO affording 5-fluoro-2-methoxy-3-nitropyridine (100 mg, 58%) as a colorless oil. $^1$H NMR (400 MHz, CDCl$_3$) δ 8.31 (d, J=2.8 Hz, 1H), 8.09 (dd, J=7.2, 2.8 Hz, 1H), 4.11 (s, 3H).

5-Fluoro-2-methoxy-3-nitropyridine (100 mg, 0.58 mmol) was dissolved in EtOAc (3 ml) and Pd/C (10 wt. % loading, 20 mg) was added to above solution. The flask was evacuated and backfilled with H$_2$ gas using H$_2$ balloon. The mixture was stirred at room temperature under H$_2$ for 2 hours and filtered. The filtrate was concentrated affording pyridyl amine 1 (75 mg, 91%) as a crude product which was used without further purification.

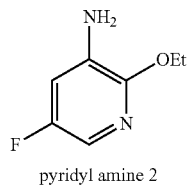 [SMILES: CCOc1ncc(F)cc1N]

pyridyl amine 2

Pyridyl amine 2: Synthesized by method xxi using 5-fluoro-3-nitropyridin-2-ol (158 mg, 1 mmol) and bromoethane (0.15 ml, 0.2 mmol) as colorless oil (59% yield over 2 steps).

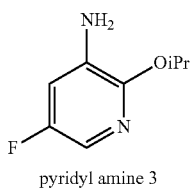

pyridyl amine 3

Pyridyl amine 3: Synthesized by method xxi using 5-fluoro-3-nitropyridin-2-ol (158 mg, 1 mmol) and 2-iodopropane (0.2 ml, 0.2 mmol) as colorless oil (58% yield over 2 steps).

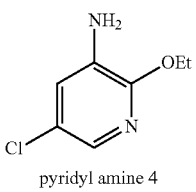 [SMILES: CCOc1ncc(Cl)cc1N]

pyridyl amine 4

Pyridyl amine 4: Synthesized by method xxi using 5-chloro-3-nitropyridin-2-ol (158 mg, 1 mmol) and bromoethane (0.15 ml, 0.2 mmol). After hydrogenation, the crude product was purified on ISCO affording pyridyl amine 4 as a colorless oil (26% yield over 2 steps).

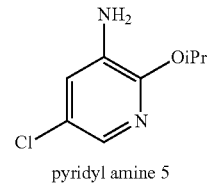 [SMILES: CC(C)Oc1ncc(Cl)cc1N]

pyridyl amine 5

Pyridyl amine 5: Synthesized by method xxi using 5-chloro-3-nitropyridin-2-ol (158 mg, 1 mmol) and 2-iodopropane (0.2 ml, 0.2 mmol). After hydrogenation, the crude product was purified on ISCO affording pyridyl amine 5 as a colorless oil (25% yield over 2 steps).

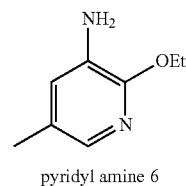

pyridyl amine 6

Pyridyl amine 6: Synthesized by method xxi using 5-methyl-3-nitropyridin-2-ol (154 mg, 1 mmol) and bromoethane (0.15 ml, 0.2 mmol) as a colorless oil (91% yield over 2 steps).

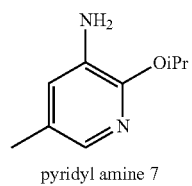

pyridyl amine 7

Pyridyl amine 7: Synthesized by method xxi using 5-methyl-3-nitropyridin-2-ol (154 mg, 1 mmol) and 2-iodopropane (0.2 ml, 0.2 mmol) as colorless oil (52% yield over 2 steps).

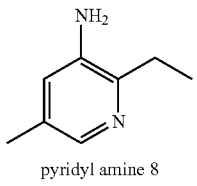

pyridyl amine 8

Pyridyl amine 8: Synthesized by the same method that was used to make pyridyl amine 9 below using 2-chloro-5-methyl-3-nitropyridine (see procedure below). Product is a tan oil (67% over two steps).

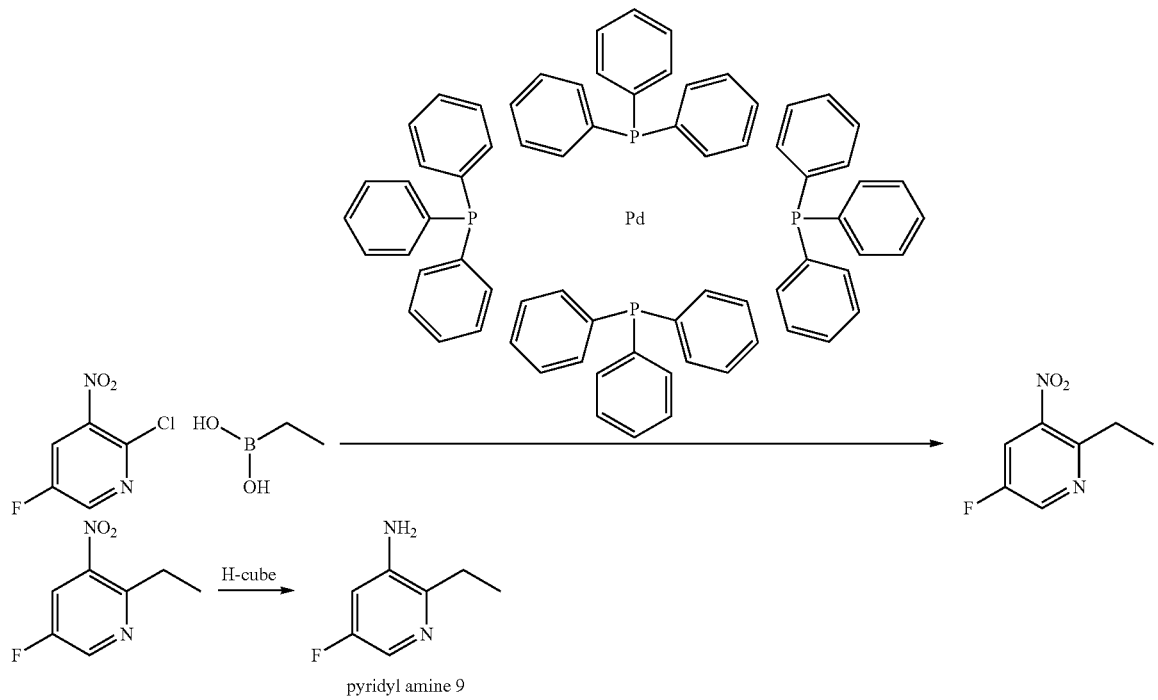

pyridyl amine 9

Pyridyl amine 9: Step 1: A mixture of 2-chloro-5-fluoro-3-nitropyridine (2 g, 11.33 mmol) and ethylboronic acid (1.674 g, 22.66 mmol) in Dioxane (Volume: 28.3 ml) was treated with potassium carbonate (6.26 g, 45.3 mmol) and Pd(Ph3P)4 (0.393 g, 0.340 mmol). The mixture was heated at 140° C. for 16 h, cooled to rt, and then, filtered through celite with ethyl acetate. The concentrated filtrate was purified by chromatography (hexanes to 10:90 EA/Hex) to afford the product in 39% yield (750 mg, 4.41 mmol).

Step 2: A solution of 2-ethyl-5-fluoro-3-nitropyridine (340 mg, 1.998 mmol) in MeOH (Volume: 4.00E+04 μl) was run through the H-cube (40 psi, 40° C., 0.8 mL/min). After concentrating the collected material, pyridyl amine 9 was obtained as a solid in 91% yield (255 mg, 1.82 mmol).

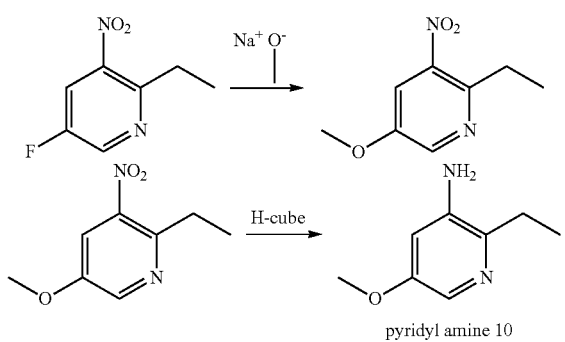

pyridyl amine 10

Pyridyl amine 10: Step 1: To 2-ethyl-5-fluoro-3-nitropyridine (650 mg, 3.82 mmol) in MeOH (Dry) (Volume: 19.100 mL) was added sodium methoxide (1032 mg. 19.10 mmol). The mixture was stirred at 80° C. for 16 h in a sealed tube. The crude was diluted with brine and sat NH4Cl. The aqueous layer was extracted with ethyl acetate (3×) and then, the organic layer was washed with brine (2×), dried over MgSO4, and concentrated to afford the crude product (430 mg). The crude was purified by chromatography (hexanes to 40:60 EA/hex) to afford 210 mg of pure product as a solid.

Step 2: A solution of 2-ethyl-5-methoxy-3-nitropyridine (210 mg, 1.153 mmol) in MeOH (Volume: 2.31E+04 μl) was run through the H-cube (40 psi, 40° C. 0.8 mL/min). After concentrating the collected material, pyridyl amine 10 was obtained as a pale yellow oil in 86% yield (150 mg, 0.986 mmol).

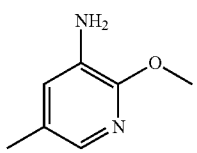

pyridyl amine 11

Pyridyl amine 11: Commercially available.

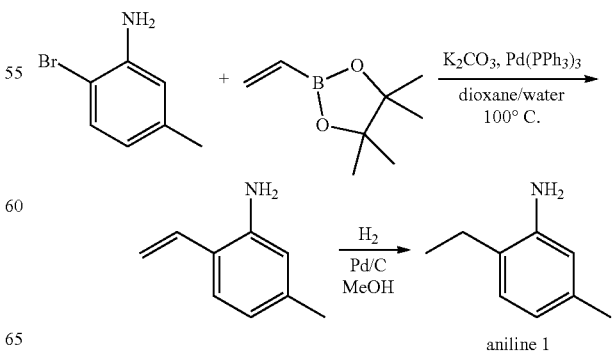

aniline 1

Aniline 1: Step 1: A mixture of 2-bromo-5-methylaniline (220 mg, 1 mmol) and vinylboronic acid pinacol ester (185 mg, 1.2 mmol) in Dioxane/Water (4:1, Volume: 2.5 ml) was treated with potassium carbonate (276 mg, 2 mmol) and Pd(Ph$_3$P)$_4$ (12 mg, 0.01 mmol). The mixture was heated at 100° C. for 16 h and cooled to rt. The reaction was quenched with water and the aqueous layer was extracted with ethyl acetate. The organic layer was washed with brine, dried over Na$_2$SO$_4$, and concentrated. The crude product was purified by chromatography (hexanes to 10:90 EA/Hex) to afford the product in 17% yield (28 mg, 0.17 mmol).

Step 2: Pd/C (10 wt. % loading, 5 mg) was added to a solution of 5-fluoro-2-vinylaniline (28 mg, 0.17 mmol) in MeOH (Volume: 2.0 ml). The flask was evacuated and backfilled with H$_2$ gas using H$_2$ balloon. The mixture was stirred at room temperature under H$_2$ for 2 hours and filtered. The filtrate was concentrated affording aniline 1 as an oil.

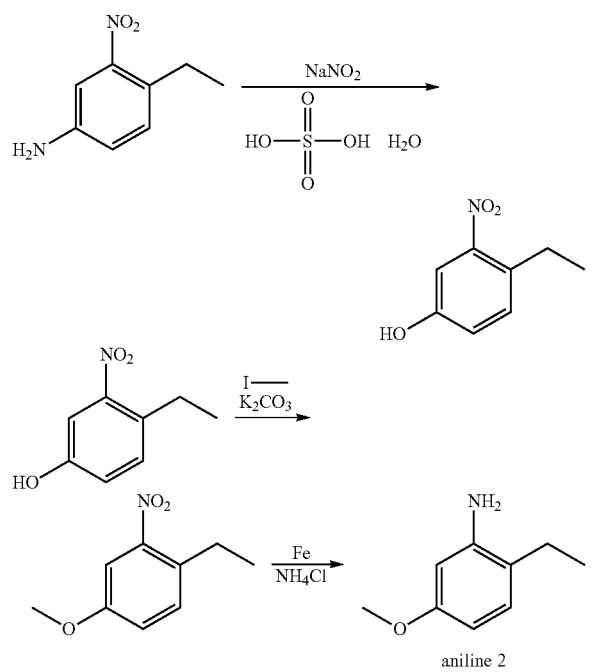

aniline 2

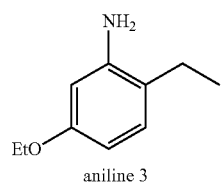

aniline 3

Aniline 3: Synthesized by the same method used to make aniline 2 substituting iodoethane in step 2 (yield 17% over 3 steps).

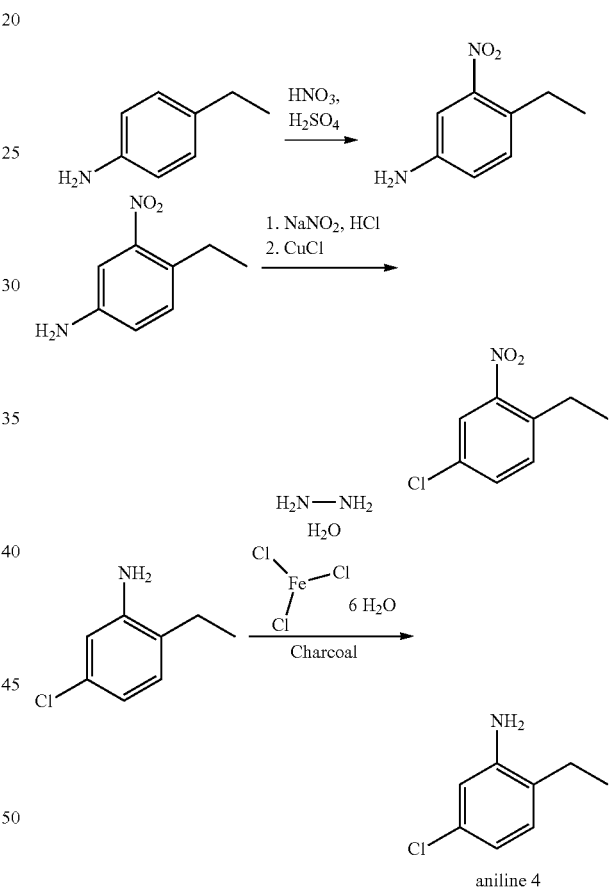

aniline 4

Aniline 2: Step 1: In a mixture of 5 ml. of 55% sulfuric acid and 4-ethyl-3-nitroaniline (1.2 g, 7.22 mmol) was suspended and then was diazotized with 2 ml of 20% sodium nitrite at 0° C. This diazonium salt solution then was added slowly to a boiling solution of 25 ml of 55% sulfuric acid. After the addition was completed the mixture was boiled for 30 min, cooled, and then was extracted with ether. The ether solution was washed with water, and then was extracted with dilute sodium hydroxide solution which on acidification yielded the phenol. This was extracted with ether, and the ether solution was dried over sodium sulfate and distilled.

Step 2: 4-ethyl-3-nitrophenol (460 mg, 2.75 mmol) was dissolved in acetone (25 ml), then K$_2$CO$_3$ (1141 mg, 8.26 mmol) and MeI (0.344 ml, 5.50 mmol) was added and reflux for 12 h and the solvent was concentrated and 4-methoxy-1-ethyl-2-nitrobenzene used next step without further purification.

Step 3: To a suspension of 4-methoxy-1-ethyl-2-nitrobenzene in THF (Volume: 10 ml) and Water (Volume: 3.33 ml) were added AMMONIUM CHLORIDE (294 mg, 5.50 mmol) followed by iron (768 mg, 13.76 mmol). The mixture was stirred at 80° C. for overnight. After cooling, EtOAc was added and the reaction mixture was passed through Celite. The organic layer was dried and concentrated and purified by column chromotography to yield aniline 2 (20% over 3 steps).

Aniline 4: Step 1: 4-Ethylaniline (1.8 ml, 14.5 mmol) was added slowly to sulfuric acid (11 ml) at 0 deg C. The material clumped up and made a thick dark brown mixture. This was sonicated to get mostly into solution. To the mixture which was maintained at 0 deg C. was added nitric acid (0.7 ml) as well as additional sulfuric acid (1.75 ml). Reaction stirred 15 min and was sonnicated to get the remainder of the material into solution. The mixture stirred at 0 deg C. 1 h and was subsequently poured onto ice and a brown precipitate was formed. The precipitate was removed by filtration and washed with a small amount of water. The solid was resuspended and neutralized with ammonium hydroxide solution. The solid was filtered and dried. Some product was dissolved by the ammonium hydroxide and this layer was combined with the initial precipitate washings (which were acidic) following its basification with sodium hydroxide pellets. The solid was redissolved in this aqueous solution. The combined aqueous layers were extracted with DCM (4×), dried with magnesium sulfate (subsequent filtration), and concentrated to yield a brown oil, 4-ethyl-3-nitroaniline, which was used in the subsequent step without further purification (2.14 g, 89%); LCMS: m/z (M+H)$^+$=167.1.

Step 2: 4-Ethyl-3-nitroaniline (1 g, 6 mmol) was dissolved in concentrated HCl (20 ml). The compound initially solidified but most of material eventually was soluble. Cool mixture to 0 deg C. Add sodium nitrite (0.57 g, 8.3 mmol) in water (2.3 ml) and a gas was evolved. The mixture was sonicated to dissolve material further (**this should not be repeated as this material could be explosive!). Mixture was stirred at this temperature for 1 hr. Diazonium intermediate visible by (LCMS: m/z (M)$^+$=178.0). Copper (I) chloride (1 g, 10.5 mmol) was added to the mixture and a large amount of gas was evolved. Reaction mixture became dark green. Gass evolution ceased within 3 minutes but stirring was continued at rt for 1.5 h. The mixture was extracted with DCM (3×)/water, dried with magnesium sulfate (subsequent filtration), concentrated, and subsequently purified by silica gel chromatography (gradient 0 to 20% EtOAc/hexanes) to yield a light yellow oil, 4-chloro-1-ethyl-2-nitrobenzene (0.9 g, 81%).

Step 3: To a mixture of 4-chloro-1-ethyl-2-nitrobenzene (0.9 g, 4.9 mmol), iron (III) chloride (0.13 g, 0.49 mmol), and charcoal (80 mg, 6.6 mmol) in methanol (17 ml) was added hydrazine hydrate (0.95 ml, 20 mmol) in methanol (7 ml). The reaction mixture was stirred at rt as gas was evolved. When gas evolution ceased, the vial was sealed and heated at 80 deg C. for 5 h (**pressure builds over time and vial needed to be vented frequently). The mixture was cooled to rt and filtered through celite washing with methanol, concentrated, and purified by silica gel chromatography (gradient 0 to 50% EtOAc/hexanes). The product, aniline 4, is a light yellow oil (quant.); $^1$H NMR (400 MHz, DMSO-d$_6$) δ 6.86 (dd, J=8.0, 0.7 Hz, 1H), 6.59 (d, J=2.2 Hz, 1H), 6.44 (dd, J=8.0, 2.2 Hz, 1H), 5.11 (s, 2H), 2.43-2.31 (m, 2H), 1.06 (t, J=7.5 Hz, 3H).

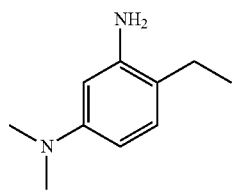

aniline 5

Aniline 5: Synthesized by the same method used to make aniline 2 substituting 4-ethyl-3-nitroaniline as a starting material in step 2 (90% yield over 2 steps).

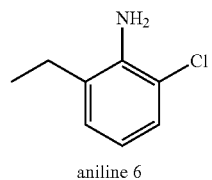

aniline 6

Amine 6: Synthesized by the same method used to make aniline 1 substituting 2-bromo-6-chloroaniline as a starting material, tricyclohexylphosphine as ligand, Pd$_2$(dba)$_3$ as catalyst, and potassium phosphate tribasic as base in step 1 (49% yield over 2 steps).

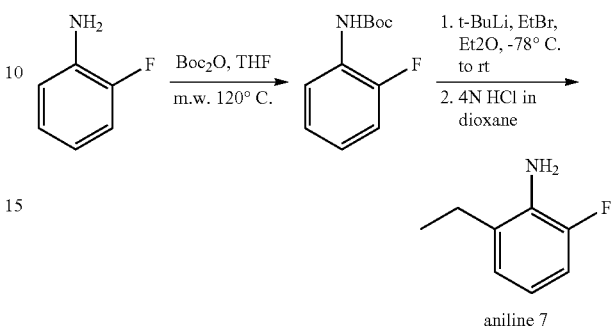

aniline 7

Aniline 7: Step 1: To a solution of 2-fluoroaniline (333 mg, 3.0 mmol) in THF (Volume: 2 ml) was added di-tert-butyl dicarbonate (655 mg, 3.0 ml). The mixture was heated to 120° C. under microwave irradiation for 6 hours, cooled and concentrated. The crude product was purified by ISCO affording desired product as an oil (450 mg).

Step 2: Boc protected 2-fluoroaniline (450 mg, 2.13 mmol) was dissolved in diethylether (Volume: 10 ml) and cooled to −78° C. t-Butyl lithium (1.7 M, 2.76 ml) was added to above solution and the reaction mixture was allowed to warm to −20° C. for 3 hours. The mixture was then cooled to −78° C. and ethylbromide (1.16 g, 10.65 mmol) was added. The resulting mixture was stirred at room temperature overnight and quenched with ammonium chloride. The aqueous layer was extracted with ethyl acetate and the combined organic layer was dried and concentrated. The residue was purified by ISCO affording the product as a yellow oil.

Step 3: Above product was dissolved in 4 N HCl in dioxane (Volume 2 ml), and the resulting mixture was stirred at rt for 1 hour. Solvent was removed and the crude product was used without purification (5% over 3 steps).

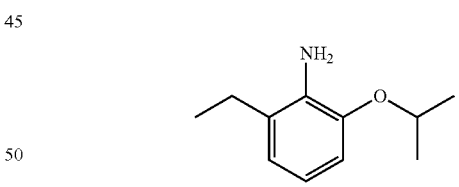

aniline 8

Aniline 8: Synthesized by the same method used to make aniline 7 substituting 2-isopropoxyaniline in step 1 (yield 66% over 3 steps).

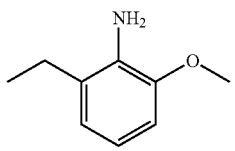

aniline 9

Aniline 9: Synthesized by the same method used to make aniline 7 substituting 2-methoxyaniline in step 1 (yield 46% over 3 steps).

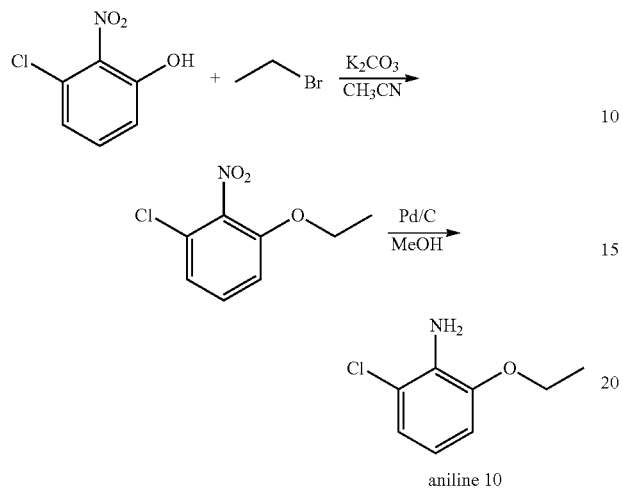

aniline 10

Aniline 10: Step 1: A mixture of 3-chloro-2-nitrophenol (173 mg, 1 mmol) and ethyl bromide (109 mg, 1.2 mmol) in acetonitrile (4:1, Volume: 2.5 ml) was treated with potassium carbonate (276 mg, 2 mmol). The mixture was stirred at rt for 2 h. The reaction was quenched with water and the aqueous layer was extracted with ethyl acetate. The organic layer was washed with brine, dried over $Na_2SO_4$, and concentrated. The crude product was purified by chromatography (hexanes to 10:90 EA/Hex) to afford the product.

Step 2: Same as step 2 in the synthesis of aniline 1 affording aniline 10 as an oil (15% over 2 steps).

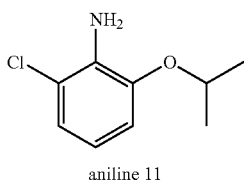

aniline 11

Aniline 11: Synthesized by the same method used to make aniline 10 substituting 2-iodopropane as a starting material in step 1 (75% yield over 2 steps).

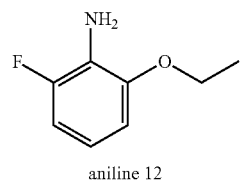

aniline 12

Aniline 12: Synthesized by the same method used to make aniline 10 substituting 3-fluoro-2-nitrophenol as a starting material in step 1 (23% yield over 2 steps).

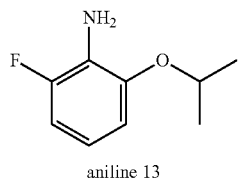

aniline 13

Aniline 13: Synthesized by the same method used to make aniline 10 substituting 3-fluoro-2-nitrophenol and 2-iodopropane as a starting material in step 1 (95% yield over 2 steps).

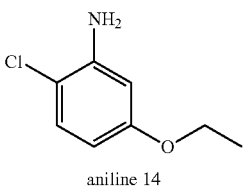

aniline 14

Aniline 14: Synthesized by the same method used to make aniline 10 substituting 4-chloro-3-nitrophenol as a starting material in step 1 (30% yield over 2 steps).

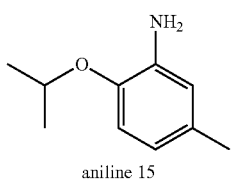

aniline 15

Aniline 15: Synthesized by the same method used to make aniline 10 substituting 4-methyl-2-nitrophenol as a starting material in step 1 (33% yield over 2 steps).

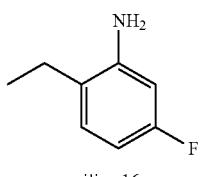

aniline 16

Aniline 16: Synthesized by the same method used to make aniline 1 substituting 2-bromo-5-fluoroaniline as a starting material in step 1 (22% yield over 2 steps).

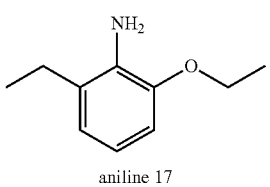

aniline 17

Aniline 17: Synthesized by the same method used to make aniline 7 substituting 2-ethoxyaniline in step 1 (yield 40% over 3 steps).

Method xxii-Compound 412—The mixture of tert-butyl 4-(5-(4-bromo-5-methylthiazol-2-yl)-1-(2,6-diethylphenyl)-2-isobutyl-6-oxo-1,6-dihydropyridine-3-carbonyl)piperazine-1-carboxylate (100 mg, 0.149 mmol), 4-chloroaniline (57.0 mg, 0.447 mmol), Pd2(dba)3 (6.13 mg, 6.70 mol), BINAP (9.27 mg, 0.015 mmol) and potassium tert-butoxide (25.06 mg, 0.223 mmol) in toluene (Volume: 0.75 ml) was stirred at 80° C. for overnight in seal tube. Water was added to the mixture, and extracted with EtOAc. The organic layer was dried over MgSO4 and concentrated. The crude product was used in the next reaction without purification.

Method xxiii

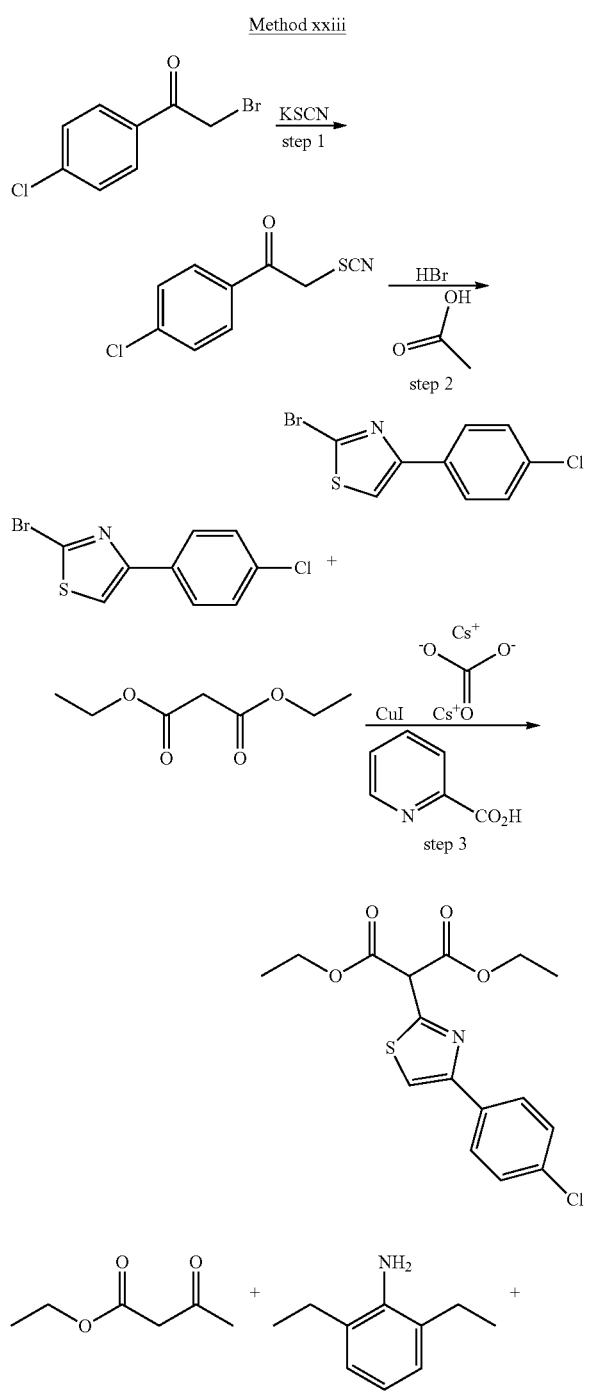

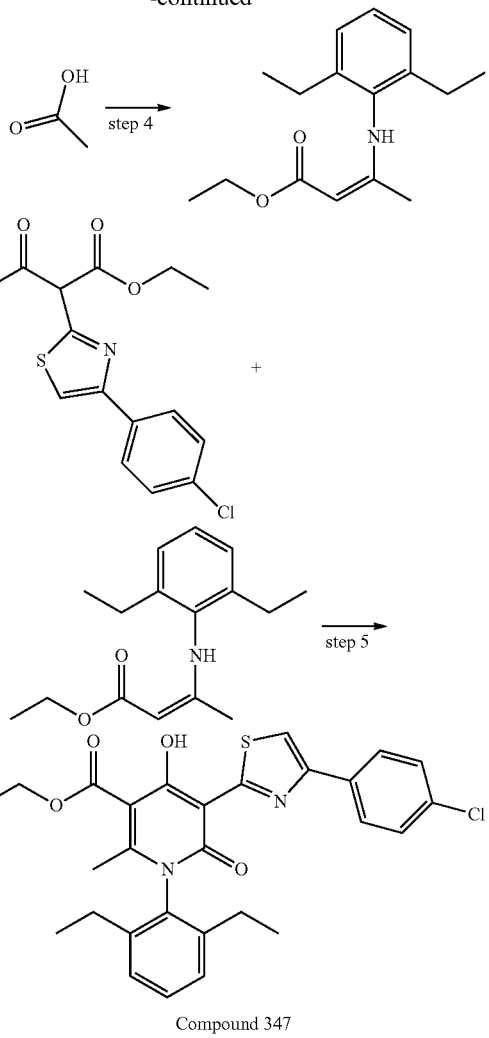

Compound 347

Method xxiii-Compound 347-Step 1: A mixture of 2-bromo-1-(4-chlorophenyl) ethanone (7.5 g, 32.1 mmol), potassium thiocyanate (3.12 g, 32.1 mmol), and Ethanol (Volume: 30 ml) was stirred at 80° C. for 2.0 h, diluted with water, and extracted with dichloromethane. The organic layer was washed with water, dried over anhydrous MgSO4, and concentrated in vacuo to give a colorless solid.

Step 2: To a stirred solution of 1-(4-chlorophenyl)-2-thiocyanatoethanone in AcOH (10 mL) was added 25% HBr in AcOH (10 mL) dropwise at room temperature. The mixture was stirred at 130° C. for 2.0 h and at room temperature for 1.0 h. The mixture was diluted with water, and extracted with chloroform. The organic layer was washed with water, dried over anhydrous MgSO4, and concentrated in vacuo. The residue was purified by silica gel column chromatography (hexane-EtOAc) to give the 2-bromo-4-(4-chlorophenyl)thiazole (75% yield); LCMS: m/z (M+H)+=273.0.

Step 3: To a solution of 2-bromo-4-(4-chlorophenyl) thiazole (880 mg, 3.21 mmol) in 1,4-Dioxane (Volume: 5 ml) were added, copper(I) iodide (61.0 mg, 0.321 mmol), picolinic acid (79 mg, 0.641 mmol), followed by cesium carbonate (3133 mg, 9.62 mmol) and refluxed for 32 h. The reaction mixture was filtered through an Agilent PL-Thiol MP SPE cartridge, to remove copper, washing with EtOAc.

The mixture was concentrated under reduced pressure. The residue was purified by passing through a silica gel column to give the diethyl 2-(4-(4-chlorophenyl)thiazol-2-yl)malonate (50% yield); LCMS: m/z (M+H)$^+$=354.0.

Step 4: A mixture of ethyl 3-oxobutanoate (1.0 g, 7.68 mmol), 2,6-diethylaniline (1.266 ml, 7.68 mmol) and acetic acid (0.044 ml, 0.768 mmol) was placed in a ultrasound bath Branson 1510 for 3 h. At the end of the reaction, 5 mL of ethanol was added. The solution was dried with Na2SO4, filtered and concentrated with reduced pressure. The residue was purified by passing through a silica gel column to give the (Z)-ethyl 3-((2,6-diethylphenyl)amino)but-2-enoate (50% yield); LCMS: m/z (M+H)$^+$=262.0

Step 5: A mixture of diethyl 2-(4-(4-chlorophenyl)thiazol-2-yl)malonate (10 mg, 0.028 mmol), (Z)-ethyl 3-((2,6-diethylphenyl)amino)but-2-enoate (7.39 mg, 0.028 mmol) as a neat was heated up to 250° C. The residue was taken up in DMSO and subsequently purified by reverse phase chromatography to give ethyl 5-(4-(4-chlorophenyl)thiazol-2-yl)-1-(2,6-diethylphenyl)-4-hydroxy-2-methyl-6-oxo-1,6-dihydropyridine-3-carboxylate, compound 347; LCMS: m/z (M+H)$^+$=523.0.

Method xxiv

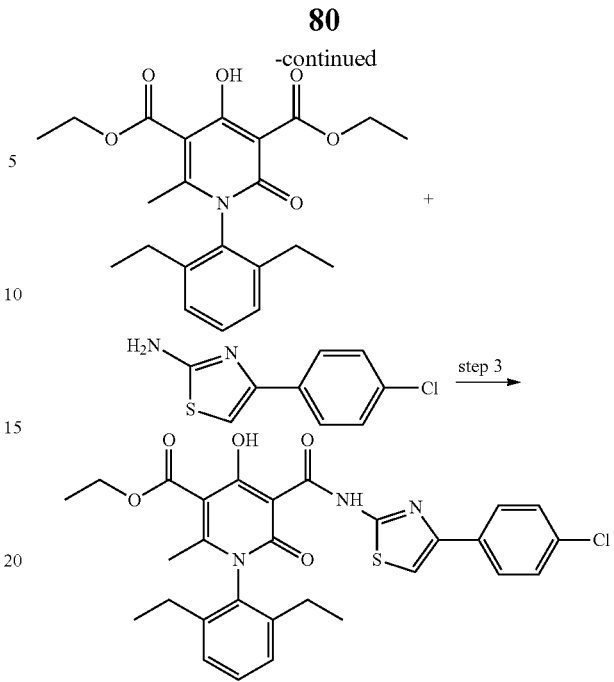

Method xxiv-Step 1: A mixture of 2-bromo-1-(4-chlorophenyl)ethanone (1 g, 4.28 mmol) and thiourea (0.326 g, 4.28 mmol) were placed in a MW test tube containing a magnetic stirring bar, rubber cap, and EtOH (Volume: 15 ml). The test tube was placed in the microwave cavity and subjected to MW irradiation at 50° C. (100 W) for 5 min. After completion of the reaction, the tube was removed, cooled to room temperature, and the contents added to water (10 mL). The product was extracted into methylene chloride (15 mL), which was filtered though a short silica column to afford the 2-aminothiazole (90% yield); LCMS: m/z (M+H)$^+$=211.0

Step 2: A mixture of (Z)-ethyl 3-((2,6-diethylphenyl)amino)but-2-enoate (200 mg, 0.765 mmol) and triethyl methanetricarboxylate (162 μl, 0.765 mmol) was kept at 200-210° C. for 12 h. It was cooled, hexane (30 ml) was added, and the mixture was vigorously stirred. The amino ether was filtered off, washed on the filter several times with hexane, and dried to give the diethyl 1-(2,6-diethylphenyl)-4-hydroxy-6-methyl-2-oxo-1,2-dihydropyridine-3,5-dicarboxylate (40% yield); LCMS: m/z (M+H)$^+$=402.0.

Step 3: A mixture of diethyl 1-(2,6-diethylphenyl)-4-hydroxy-6-methyl-2-oxo-1,2-dihydropyridine-3,5-dicarboxylate (65 mg, 0.162 mmol), 4-(4-chlorophenyl)thiazol-2-amine (34.1 mg, 0.162 mmol) and DMF (Volume: 50 μL) was stirred an kept on a metal bath at 180° C. for 10 min. At the end of the reaction, 10 mL of EtOAc was added, concentrated with reduced pressure. The residue was purified by passing through a silica gel column to give the ethyl 5-((4-(4-chlorophenyl)thiazol-2-yl)carbamoyl)-1-(2,6-diethylphenyl)-4-hydroxy-2-methyl-6-oxo-1,6-dihydropyridine-3-carboxylate (60% yield); LCMS: m/z (M+H)$^+$=566.0.

Example 2. Enzymatic Assays

Assays were conducted in a 1536-well black solid-bottom plate with a final assay volume of 9 μL. The depletion of the cofactor NADPH by the mutant IDH1 enzyme was coupled to a second enzyme diaphorase and its corresponding substrate resazurin.

Specifically, for IDH1 R132H, 3 μL of enzyme (4 mM β-ME, 0.0005 mg/mL IDH1 R132H, 150 mM NaCl, 20 mM Tris pH 7.5, 10 mM $MgCl_2$, 0.05% BSA) were added to the plate, followed by the addition of 23 nL of test compound in DMSO. The plate was lidded and incubated at room temperature for 30 minutes at which time 3 μL of substrate were added (0.016 mM NADPH, 2 mM α-KG, 150 mM NaCl, 20 mM Tris pH 7.5, 10 mM $MgCl_2$, 0.05% BSA). This reaction was incubated at room-temperature for 60 minutes at which time the detection mix was added (0.06 mg/mL diaphorase, 0.036 mM resazurin, 150 mM NaCl, 20 mM Tris pH 7.5, 10 mM $MgCl_2$, 0.05% BSA). After a 5-minute incubation, the fluorescence generated by the conversion of resazurin to resorufin was detected (ex 544 nm, emission 590 nm).

For IDH1 R132C, 3 μL of enzyme (0.00032 mg/mL IDH1 R132H, 10% glycerol, 50 mM potassium phosphate pH 6.5, 5 mM $MgCl_2$, 0.03% BSA) were added to the plate, followed by the addition of 23 nL of test compound in DMSO. The plate was lidded and incubated at room temperature for 30 minutes at which time 3 μL of substrate were added (0.012 mM NADPH, 0.6 mM α-KG, 10% glycerol, 50 mM potassium phosphate pH 6.5, 5 mM $MgCl_2$, 0.03% BSA). This reaction was incubated at room-temperature for 105 minutes at which time the detection mix was added (0.03 mg/mL diaphorase, 0.03 mM resazurin, 10% glycerol, 50 mM potassium phosphate pH 6.5, 5 mM $MgCl_2$, 0.03% BSA). After a 5-minute incubation, the fluorescence generated by the conversion of resazurin to resorufin was detected (ex 544 nm, emission 590 nm).

Example 3. Cell-Based Assays

Cell-based 2HG quantification assays were conducted in 96-well clear plates with a final assay volume of 100 μL. 2HG levels in cultured cells were determined using LC/MS-based detection.

Briefly, 4,000 cells/well (either transgenic U87 cells expressing mutant R132H IDH1, or HT1080 cells endogenously expressing the R132C mutant IDH1) were plated in 96-well clear tissue culture plates, and allowed to attached overnight at 37° C. The overlaying media was then removed and replaced with 100 μL fresh RPMI (10% FBS, no phenol red) containing titrations of compound, and incubated at 37° C. for 48 hours. Following incubation, 75 μL of the overlaying media was removed for 2HG analysis and snap-frozen on dry ice.

Samples were thawed, mixed with 2× volume of 100% acetonitrile, and centrifuged at 4,000 rpm for 15 minutes at 4° C. The resulting supernatant was collected to assess 2-hydroxyglutarate levels on a RF-MS system. The RF-MS system consists of RapidFire RF200 system (Agilent, Santa Clara, Calif.) interfaced with an API4000 mass spectrometer (AB Sciex, Foster City, Calif.). A Zymark Twister robotic arm is present to handle standard microtiter plates. The entire system is run with RapidFire software and Analyst software for the RF200 system and the mass spectrometer, respectively. The mobile phase consisted of 0.1% formic acid in 100% acetonitrile (solvent A) and 0.1% formic acid in water (solvent B). Samples were aspirated directly from 384-well plates into a 10 μL sample loop, and passed through an in-line purification SPE system with graphite carbon cartridges (Agilent) with solvent A at a flow rate of 1.5 mL/min for 1 s. After the de-salting step, analyte retained on the cartridge was eluted to the mass spectrometer with solvent B at a flow rate of 0.4 mL/min for 8 s. The cartridge was re-equilibrated with solvent A at a flow rate of 1.5 mL/min for 0.5 s. In total, the entire sampling cycle was 10 s per well. Each metabolite can be monitored by negative electrospray ionization on an API4000 triple-quadrupole mass spectrometer operating in multiple reaction monitoring (MRM) mode, with MS parameters optimized on infused metabolite standard solutions. Metabolites can be quantified by comparison of peak areas with pure metabolite standards at known concentration.

2HG metabolite levels were then determined and quantified using a 2HG standard curve, and % inhibition of 2HG was production was calculated using vehicle-treated and media-only controls.

Example 4. Additional Compounds

Table 1 shows compounds of Example 1 with biological and other data, and shows additional compounds prepared by the methods shown in Example 1. Hindered rotation as well as solvent peaks (DMSO and water) both complicate NMR signals and hide some proton resonances in many of the spectra. Table 2 shows further additional compounds which could be prepared by the methods shown in Example 1. Routine changes in starting materials and reaction conditions, readily apparent to those of one skilled in the art, were used to make the particular compounds disclosed in Table 1. An "A" is used to denote compounds with an $IC_{50}$ less than 0.3 micromolar, a "B" indicates compound with an $IC_{50}$ between 0.3 micromolar and 1.0 micromolar, a "C" denotes compounds with an $IC_{50}$ between 1.0 micromolar and 5.0 micromolar, a "D" denotes compounds with an $IC_{50}$ between 5.0 micromolar and 20 micromolar, and an "E" denotes compounds with an $IC_{50}$ greater than 20 micromolar. A standard enzymatic inhibition assay, such as the assay of Example 2, is used to determine the $IC_{50}$'s for the compounds.

TABLE 1
Characterization and Enzymatic Inhibition Data for Selected Compounds
| Cpd # | Structure | Data for R132H (μM) | Data for R132C (μM) | MZ | RT (min) | Synthesis Method | 1H-NMR |
|---|---|---|---|---|---|---|---|
| 1 | 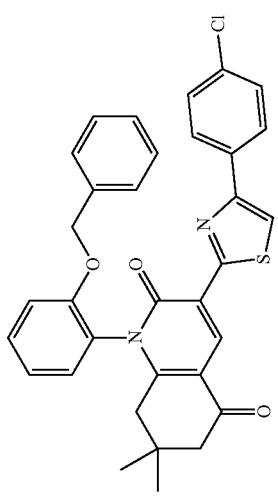 | E | B | 567.1516 | 3.99 | Starting materials: nitrile-1, aniline-2-benzyloxyaniline; Method: E | |
| 2 | 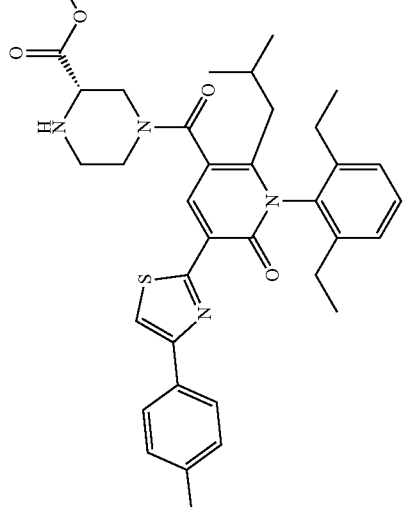 | C | B | 647.2426 | 3.148 | Starting materials: acid-compound 14, amine-(S)-1-tert-butyl 2-methyl piperazine-1,2-dicarboxylate; Methods: U, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 3 | 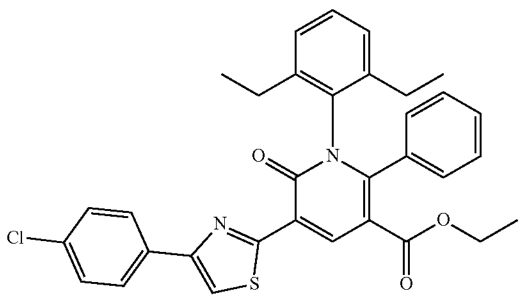 [SMILES: CCOC(=O)c1cc(-c2nc(-c3ccc(Cl)cc3)cs2)c(=O)n(-c2c(CC)cccc2CC)c1-c1ccccc1] | E | E | 569.1643 | 4.366 | Starting material: step 1 with ethyl 3-oxo-3-phenylpropanoate; Method: T | |
| 4 | 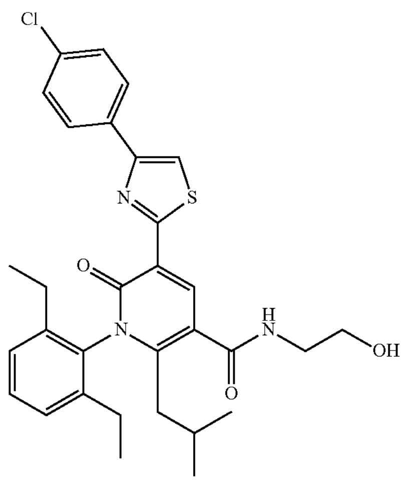 [SMILES: CCc1cccc(CC)c1-n1c(CC(C)C)c(C(=O)NCCO)cc(-c2nc(-c3ccc(Cl)cc3)cs2)c1=O] | A | B | 564.2069 | 3.749 | Starting materials: acid-compound 14, amine-2-aminoethanol; Method: U | $^1$H NMR (400 MHz, DMSO-$d_6$) δ 8.75-8.70 (m, 1H), 8.70 (d, J = 0.6 Hz, 1H), 8.21 (d, J = 0.6 Hz, 1H), 8.14-8.08 (m, 2H), 7.57-7.52 (m, 2H), 7.52-7.45 (m, 1H), 7.37 (s, 1H), 7.35 (s, 1H), 4.79-4.73 (m, 1H), 3.55 (q, J = 6.0 Hz, 2H), 3.34 (t, J = 5.9 Hz, 2H), 3.17 (dd, J = 5.3, 0.7 Hz, 2H), 2.34 (dq, J = 15.1, 7.6 Hz, 2H), 2.15 (dq, J = 15.0, 7.4 Hz, 2H), 1.34 (dq, J = 13.5, 6.7 Hz, 1H), 1.09 (d, J = 7.5, 0.6 Hz, 6H), 0.63 (d, J = 6.6 Hz, 6H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 5 | 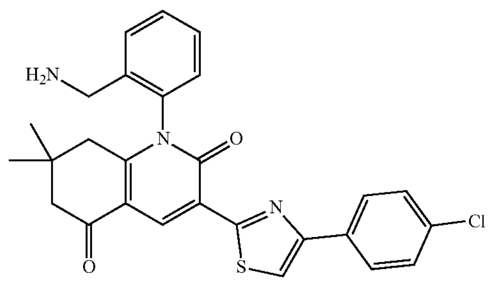 [SMILES: CC1(C)CC(=O)c2cc(-c3nc(-c4ccc(Cl)cc4)cs3)c(=O)n(-c3ccccc3CN)c2C1] | D | D | 512.117 | 2.693 | Starting materials: nitrile-1, aniline-2-(aminomethyl)aniline; Method: A (step 2-45° C., step 3-70° C. 2.5 h) | |
| 6 | 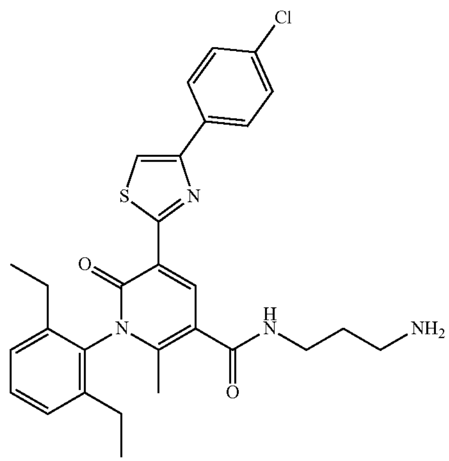 [SMILES: CCc1cccc(CC)c1-n1c(C)c(C(=O)NCCCN)cc(-c2nc(-c3ccc(Cl)cc3)cs2)c1=O] | C | C | 535.1914 | 2.686 | Starting materials: acid-compound 143, amine-propane-1,3-diamine; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 7 | 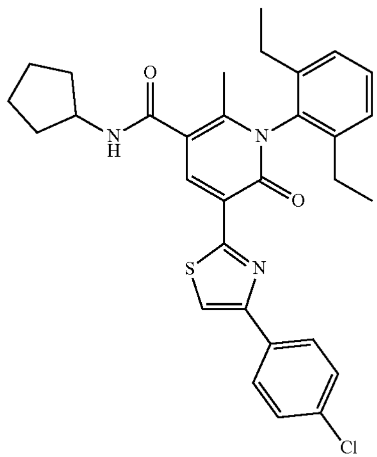 [SMILES: CCc1cccc(CC)c1-n1c(C)c(C(=O)NC2CCCC2)cc(-c2nc(-c3ccc(Cl)cc3)cs2)c1=O] | E | C | 546.2002 | 4.033 | Starting materials: acid-compound 143, amine-cyclopentanamine; Method: U | |
| 8 | 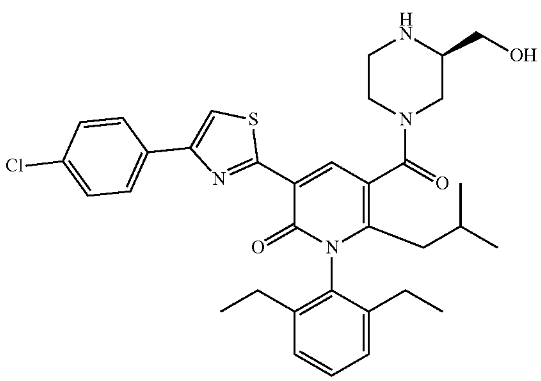 [SMILES: CCc1cccc(CC)c1-n1c(CC(C)C)c(C(=O)N2CCN[C@@H](CO)C2)cc(-c2nc(-c3ccc(Cl)cc3)cs2)c1=O] | A | A | 619.2526 | 2.824 | Starting materials: acid-compound 14, amine-(R)-tert-butyl 2-(hydroxymethyl)piperazine-1-carboxylate; Method: U, then Boc removal with TFA/DCM rt | |

TABLE 1-continued
Characterization and Enzymatic Inhibition Data for Selected Compounds
| Cpd # | Structure | Data for R132H (μM) | Data for R132C (μM) | MZ | RT (min) | Synthesis Method | ¹H-NMR |
|---|---|---|---|---|---|---|---|
| 9 | 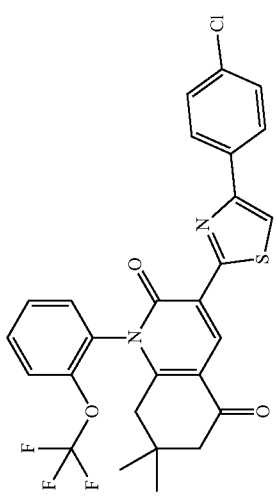 | C | B | 567.0755 | 3.96 | Starting materials: nitrile-1, aniline-2-trifluoromethoxyaniline; Method: H | |
| 10 | 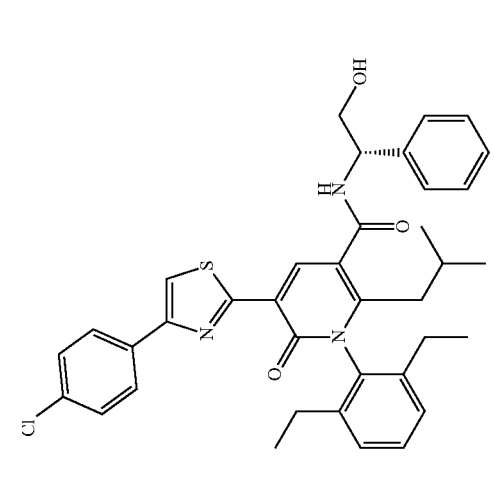 | B | A | 640.2395 | 3.922 | Starting materials: acid-compound 14, amine-(S)-2-amino-2-phenylethanol; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 11 | 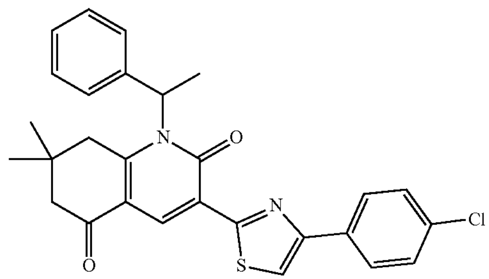 [SMILES: CC(c1ccccc1)n1c2c(cc(-c3nc(-c4ccc(Cl)cc4)cs3)c1=O)C(=O)CC(C)(C)C2] | E | D | 489.1375 | 4.042 | Method: xiii | |
| 12 | 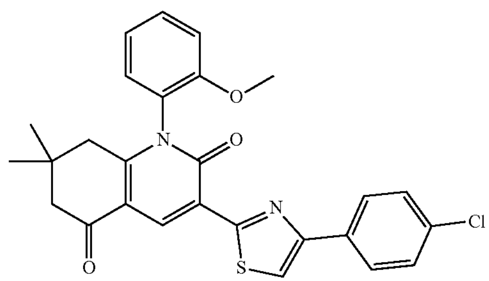 [SMILES: COc1ccccc1-n1c2c(cc(-c3nc(-c4ccc(Cl)cc4)cs3)c1=O)C(=O)CC(C)(C)C2] | C | C | 491.1203 | 3.86 | Starting materials: nitrile-1, aniline-2-methoxyaniline; Method: A | |
| 13 | 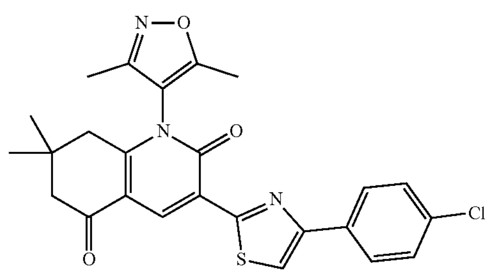 [SMILES: Cc1noc(C)c1-n1c2c(cc(-c3nc(-c4ccc(Cl)cc4)cs3)c1=O)C(=O)CC(C)(C)C2] | E | C | 480.1145 | 3.853 | Starting materials: nitrile-1, amine-3,5-dimethylisoxazol-4-amine; Method: R (step 2-50° C. 2 h, step 3-80° C. 3 h) | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 14 | 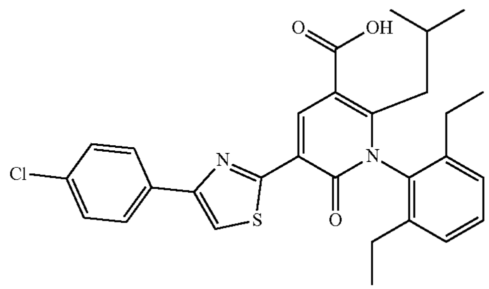 [SMILES: CCc1cccc(CC)c1-n1c(CC(C)C)c(C(=O)O)cc(-c2nc(-c3ccc(Cl)cc3)cs2)c1=O] | C | D | 521.166 | 4.059 | Methods: S, then ester hydrolyzed with LiOH (3 eq), THF/MeOH/water, 50° C. 6 h | |
| 15 | 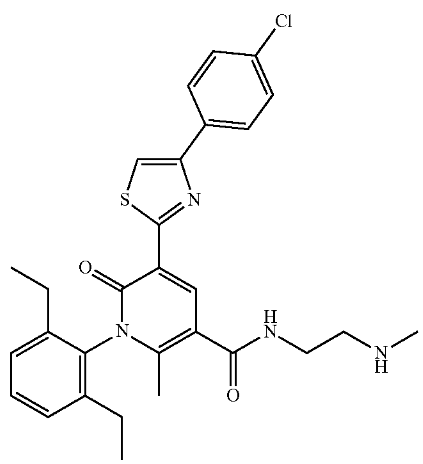 [SMILES: CCc1cccc(CC)c1-n1c(C)c(C(=O)NCCNC)cc(-c2nc(-c3ccc(Cl)cc3)cs2)c1=O] | C | A | 535.1938 | 2.712 | Starting materials: acid-compound 143, amine-tert-butyl (2-aminoethyl)(methyl)carbamate; Method: U, then Boc removal with TFA/DCM rt | |

TABLE 1-continued
Characterization and Enzymatic Inhibition Data for Selected Compounds
| Cpd # | Structure | Data for R132H (µM) | Data for R132C (µM) | MZ | RT (min) | Synthesis Method | 1H-NMR |
|---|---|---|---|---|---|---|---|
| 16 | 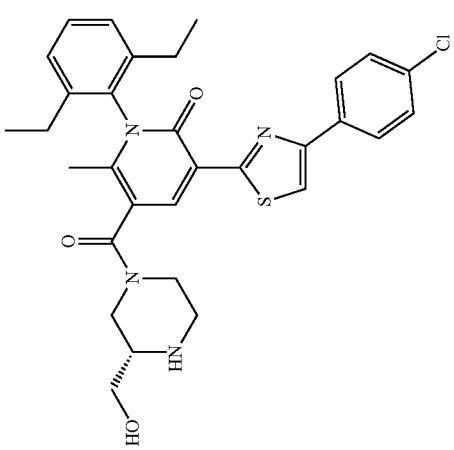 | C | B | 577.2054 | 2.678 | Starting materials: acid-compound 143, amine-(S)-tert-butyl 2-(hydroxymethyl)piperazine-1-carboxylate; Methods: U, then Boc removal with TFA/DCM rt | |
| 17 | 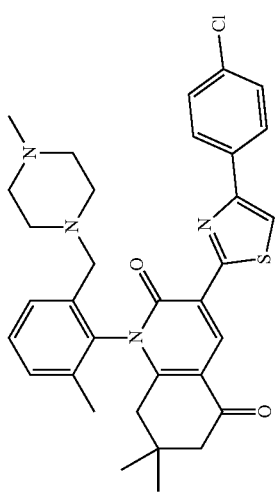 Comparative example | D | D | 587.2264 | 2.808 | | |

TABLE 1-continued
Characterization and Enzymatic Inhibition Data for Selected Compounds
| Cpd # | Structure | Data for R132H (µM) | Data for R132C (µM) | MZ | RT (min) | Synthesis Method | ¹H-NMR |
|---|---|---|---|---|---|---|---|
| 18 | 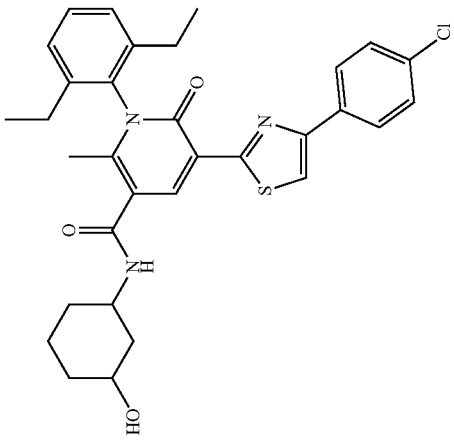 | D | C | 576.2108 | 3.67 | Starting materials: acid-compound 143, amine-3-aminocyclohexanol; Method: U | |
| 19 | 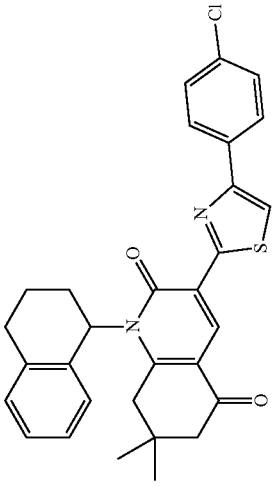 | E | B | 515.156 | 4.172 | Method: xiii | |

TABLE 1-continued
Characterization and Enzymatic Inhibition Data for Selected Compounds
| Cpd # | Structure | Data for R132H (μM) | Data for R132C (μM) | MZ | RT (min) | Synthesis Method | 1H-NMR |
|---|---|---|---|---|---|---|---|
| 20 | 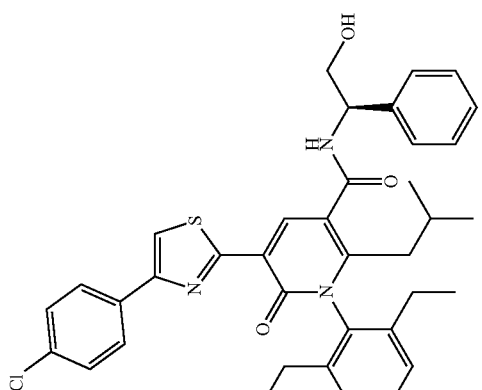 | B | A | 640.2394 | 3.913 | Starting materials: acid-compound 14, amine-(R)-2-amino-2-phenylethanol; Method: U | |
| 21 | 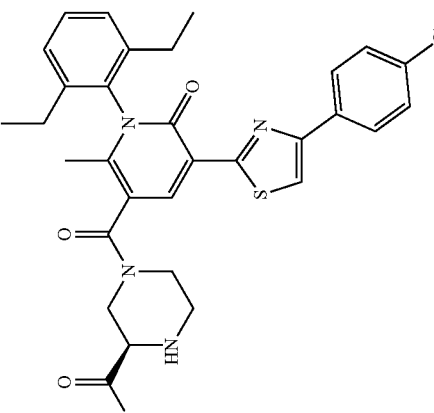 | B | C | 591.1808 | 2.896 | compound 83 was hydrolyzed with LiOH (0.5M), THF, rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | $^1$H-NMR |
|---|---|---|---|---|---|---|---|
| 22 | 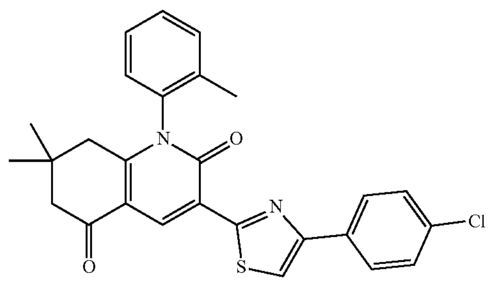 [SMILES: Cc1ccccc1-n1c2c(cc(-c3nc(-c4ccc(Cl)cc4)cs3)c1=O)C(=O)CC(C)(C)C2] | C | B | 475.1249 | 3.934 | Starting materials: nitrile-1, aniline-2-methylaniline; Method: E | |
| 23 | 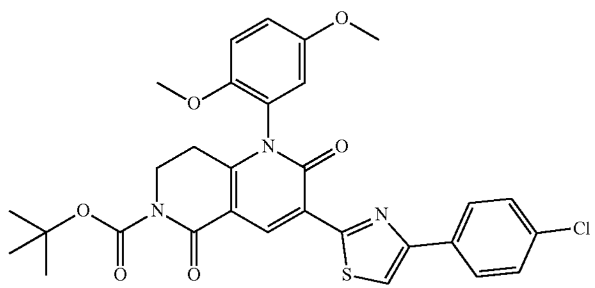 [SMILES: COc1ccc(OC)c(-n2c3c(cc(-c4nc(-c5ccc(Cl)cc5)cs4)c2=O)C(=O)N(C(=O)OC(C)(C)C)CC3)c1] | E | D | 594.1442 | 3.866 | Starting materials: nitrile-1, aniline-2,5-dimethoxyaniline, tert-butyl 2,4-dioxopiperidine-1-carboxylate; Method: C | |
| 24 | 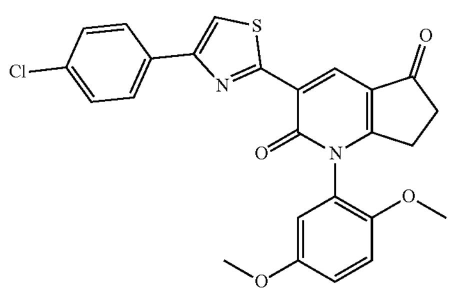 [SMILES: COc1ccc(OC)c(-n2c3c(cc(-c4nc(-c5ccc(Cl)cc5)cs4)c2=O)C(=O)CC3)c1] | E | D | 479.084 | 3.672 | Starting materials: nitrile-1, aniline-2,5-dimethoxyaniline, cyclopentane-1,3-dione; Method: B | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 25 | 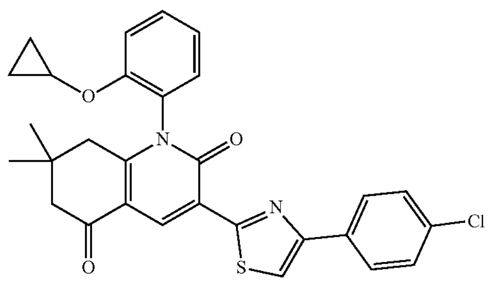 [SMILES: CC1(C)CC(=O)c2cc(-c3nc(-c4ccc(Cl)cc4)cs3)c(=O)n(-c3ccccc3OC3CC3)c2C1] | C | B | 517.1368 | 3.94 | Starting materials: nitrile-1, aniline-2-cyclopropoxyaniline; Method: G | |
| 26 | 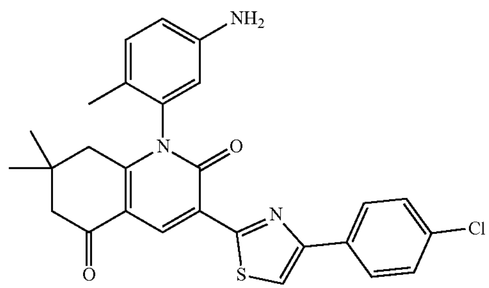 [SMILES: Cc1ccc(N)cc1-n1c2c(cc(-c3nc(-c4ccc(Cl)cc4)cs3)c1=O)C(=O)CC(C)(C)C2] | C | C | 490.1374 | 3.753 | Nitro reduction of compound 182 with SnCl2 (5 eq), EtOH 70° C. 0.5 h | |
| 27 | 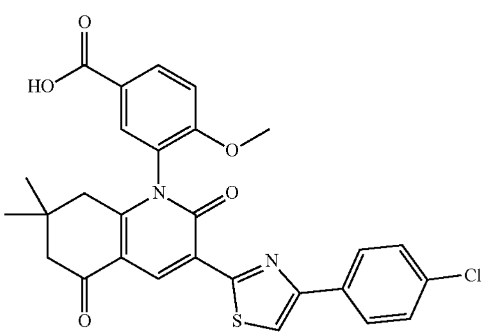 [SMILES: COc1ccc(C(=O)O)cc1-n1c2c(cc(-c3nc(-c4ccc(Cl)cc4)cs3)c1=O)C(=O)CC(C)(C)C2] | D | D | 535.1112 | 3.596 | Starting materials: nitrile-1, aniline-3-amino-4-methoxybenzoic acid; Method: A (step 2-45° C., step 3-70° C. 2.5 h) | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 28 | 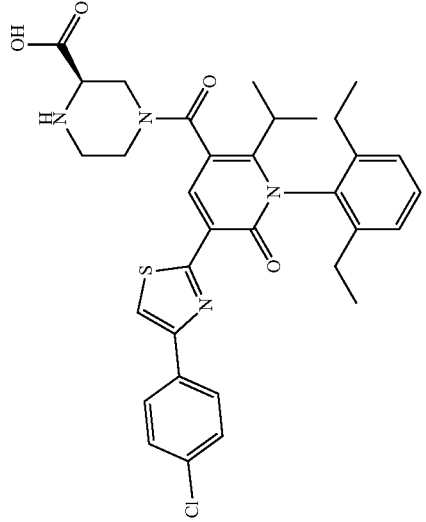 | A | A | 619.2136 | 3.02 | compound 222 was hydrolyzed with LiOH (0.5M), THF, rt | 1H NMR (400 MHz, DMSO-d6) δ 8.75 (s, 1H), 8.60 (d, J = 14.6 Hz, 1H), 8.23 (d, J = 2.6 Hz, 1H), 8.19-8.09 (m, 2H), 7.57-7.44 (m, 3H), 7.37 (dd, J = 7.7, 4.5 Hz, 2H), 4.79-4.26 (m, 2H), 4.15-3.53 (m, 4H), 2.44-2.27 (m, 2H), 2.30-2.04 (m, 2H), 1.23-0.97 (m, 15H). Aliphatic region complicated significantly by amide rotamers. |
| 29 | 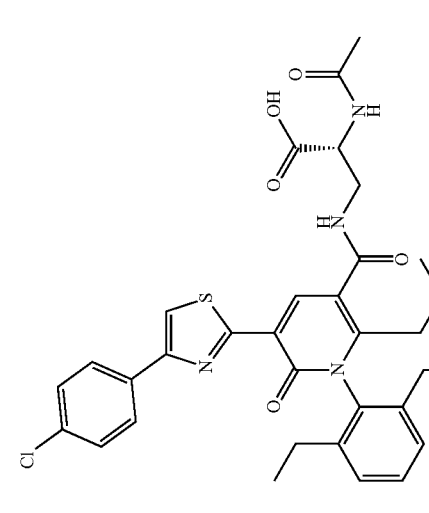 | C | C | 649.2241 | 3.572 | Starting materials: acid-compound 14, amine-(R)-3-amino-2-((tert-butoxycarbonyl)amino)propanoic acid hydrochloride; Methods: U, then Boc removal with TFA/DCM rt, then acetylation with AcCl/NEt₃ rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 30 | 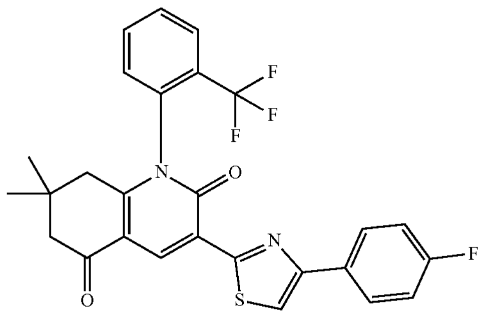 [SMILES: CC1(C)CC(=O)c2cc(-c3nc(-c4ccc(F)cc4)cs3)c(=O)n(-c3ccccc3C(F)(F)F)c2C1] | B | B | 535.1083 | 3.804 | Starting materials: nitrile-3, aniline-2-trifluoromethylaniline; Method: I | |
| 31 | 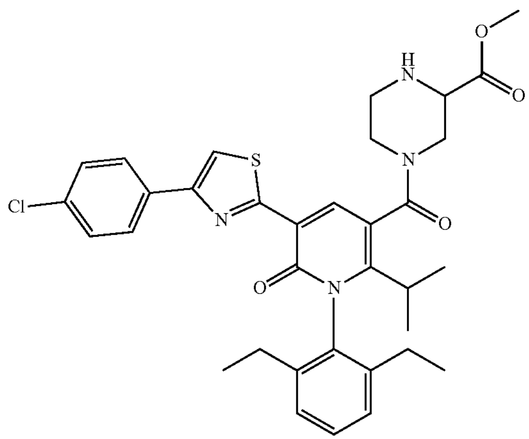 [SMILES: CCc1cccc(CC)c1-n1c(C(C)C)c(C(=O)N2CCNC(C(=O)OC)C2)cc(-c2nc(-c3ccc(Cl)cc3)cs2)c1=O] | C | B | 633.229 | 3.045 | Starting materials: acid-compound 98, amine-1-tert-butyl 2-methyl piperazine-1,2-dicarboxylate; Method: U, then Boc removal with TFA/DCM rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 32 | 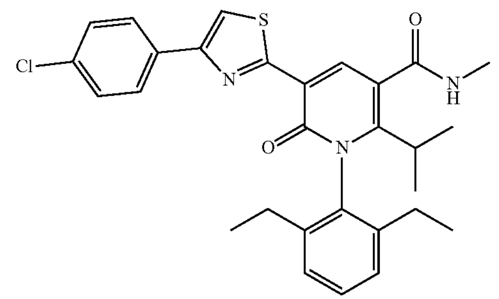 [SMILES: CCc1cccc(CC)c1-n1c(C(C)C)c(C(=O)NC)cc(-c2nc(-c3ccc(Cl)cc3)cs2)c1=O] | B | B | 520.1827 | 3.898 | Amide coupling of acid 98 with methylamine similar to method used to synthesize 2-(4-(4-chlorophenyl)thiazol-2-yl)-N-(2,5-dimethoxyphenyl)acetamide (70° C. 24 h) | |
| 33 | 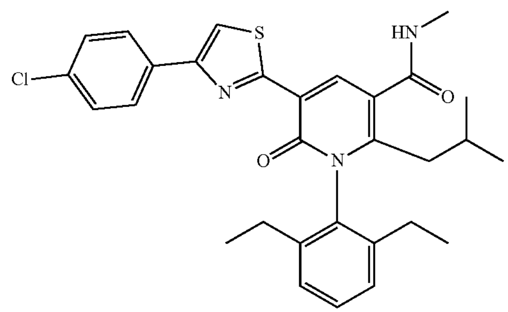 [SMILES: CCc1cccc(CC)c1-n1c(CC(C)C)c(C(=O)NC)cc(-c2nc(-c3ccc(Cl)cc3)cs2)c1=O] | B | A | 534.1959 | 3.979 | Amide coupling of acid 14 with methylamine similar to method used to synthesize 2-(4-(4-chlorophenyl)thiazol-2-yl)-N-(2,5-dimethoxyphenyl)acetamide (70° C. 24 h) | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 34 | (structure) | C | B | 618.2532 | 3.971 | Starting materials: acid-compound 14, amine-piperidin-3-ylmethanol; Method: U | |
| 35 | (structure) | C | C | 589.2391 | 2.132 | Starting materials: acid-compound 98, amine-tert-butyl 4-aminopiperidine-1-carboxylate; Method: U, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 36 | 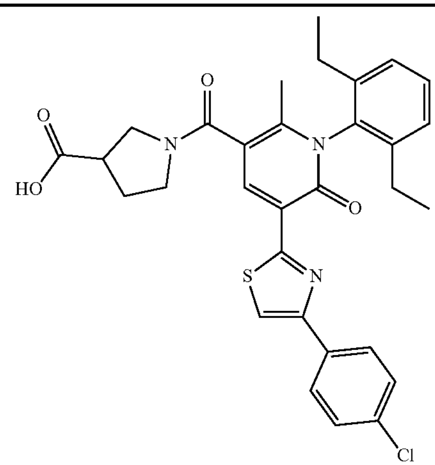 | E | E | 576.1731 | 2.415 | Starting materials: acid-compound 143, amine-methyl pyrrolidine-3-carboxylate; Method: U, then hydrolyzed with LiOH (0.5M), THF, rt | |
| 37 | 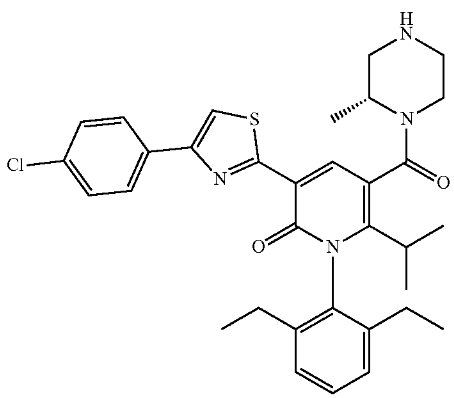 [SMILES: CCc1cccc(CC)c1-n1c(C(C)C)c(C(=O)N2CCNC[C@H]2C)cc(-c2nc(-c3ccc(Cl)cc3)cs2)c1=O] | C | B | 589.2393 | 2.841 | Starting materials: acid-compound 98, amine-(R)-tert-butyl 3-methylpiperazine-1-carboxylate; Methods: U, then Boc removal with TFA/DCM rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 38 | 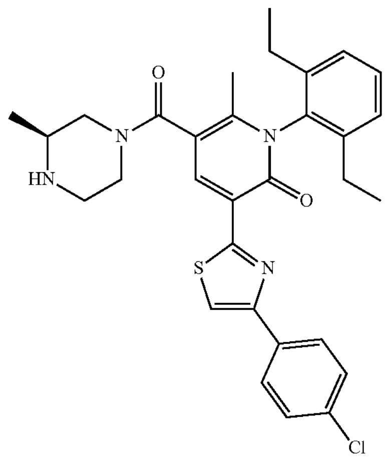 [SMILES: CCc1cccc(CC)c1-n1c(C)c(C(=O)N2CCN[C@@H](C)C2)cc(-c2nc(-c3ccc(Cl)cc3)cs2)c1=O] | A | B | 583.1912 | 2.734 | Starting materials: acid-compound 143, amine-(S)-tert-butyl 2-methylpiperazine-1-carboxylate; Methods: U, then Boc removal with TFA/DCM rt | ¹H NMR of TFA salt (400 MHz, DMSO-d₆) δ 9.09 (m, 1H), 8.71 (m, 2H), 8.21 (s, 1H), 8.10 (d, J = 8.6 Hz, 2H), 7.56-7.42 (m, 3H), 7.35 (d, J = 7.7 Hz, 2H), 3.75 (m, 1H), 2.96 (m, 2H), 2.37-2.02 (m, 5H), 1.87 (s, 3H), 1.27 (m, 1H), 1.14 (s, 2H), 1.06 (t, J = 7.5 Hz, 6H). Aliphatic region complicated significantly by amide rotamers. |
| 39 | 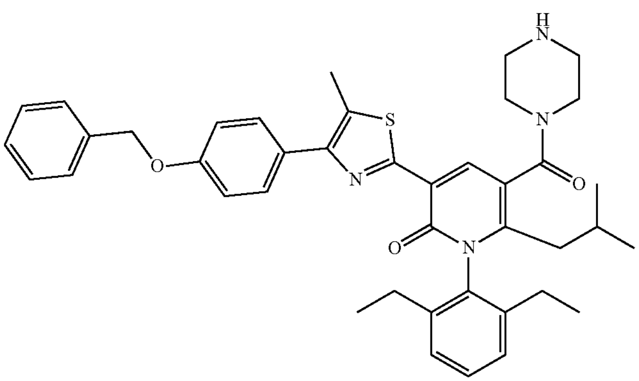 [SMILES: CCc1cccc(CC)c1-n1c(CC(C)C)c(C(=O)N2CCNCC2)cc(-c2nc(-c3ccc(OCc4ccccc4)cc3)c(C)s2)c1=O] | D | D | 675.3361 | 3.374 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-(benzyloxy)phenyl)(boronic acid (method xix); Methods: S, then ester hydrolyzed with LiOH (0.5M), THF, rt, U, xix, then Boc removal with TFA/DCM rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 40 | 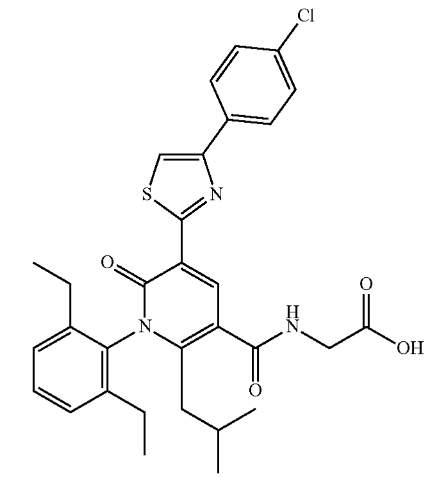 [SMILES: CCc1cccc(CC)c1-n1c(CC(C)C)c(C(=O)NCC(=O)O)cc(-c2nc(-c3ccc(Cl)cc3)cs2)c1=O] | C | D | 536.1417 | 3.491 | Starting materials: acid-compound 143, amine-methyl 2-aminoacetate; Method: U, then hydrolyzed with LiOH (0.5M), THF, rt | |
| 41 | 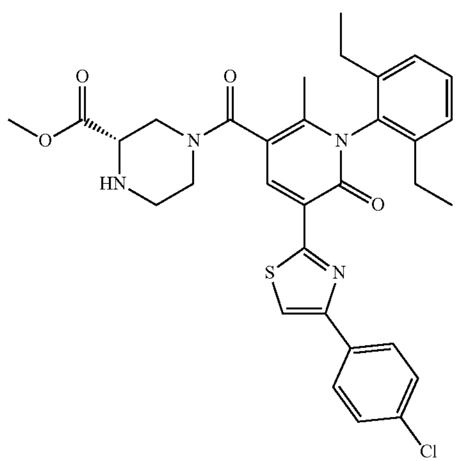 [SMILES: CCc1cccc(CC)c1-n1c(C)c(C(=O)N2CCN[C@H](C(=O)OC)C2)cc(-c2nc(-c3ccc(Cl)cc3)cs2)c1=O] | D | C | 627.1828 | 2.875 | Starting materials: acid-compound 143, amine-(S)-1-tert-butyl 2-methyl piperazine-1,2-dicarboxylate; Methods: U, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 42 | 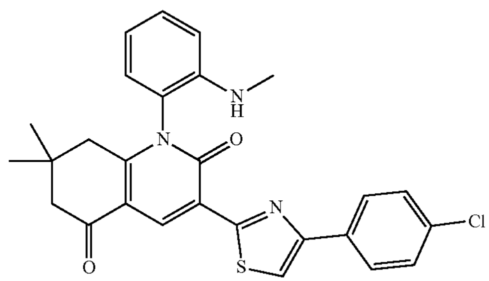 [SMILES: CNc1ccccc1-n1c2c(cc(-c3nc(-c4ccc(Cl)cc4)cs3)c1=O)C(=O)CC(C)(C)C2] | C | C | 490.136 | 3.845 | Starting materials: nitrile-1, aniline-2-(methylamino)aniline; Method: E | |
| 43 | 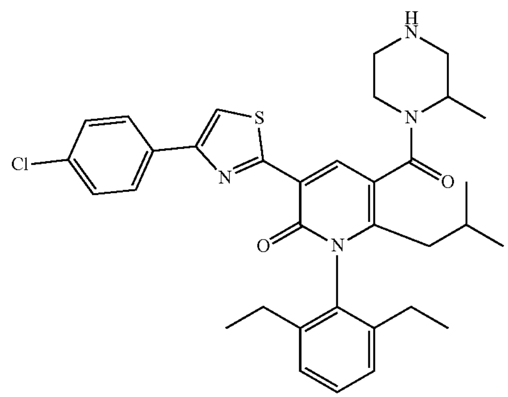 [SMILES: CCc1cccc(CC)c1-n1c(CC(C)C)c(C(=O)N2CCNCC2C)cc(-c2nc(-c3ccc(Cl)cc3)cs2)c1=O] | B | A | 603.255 | 2.9 | Starting materials: acid-compound 14, amine-tert-butyl 3-methylpiperazine-1-carboxylate; Method: U, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 44 | 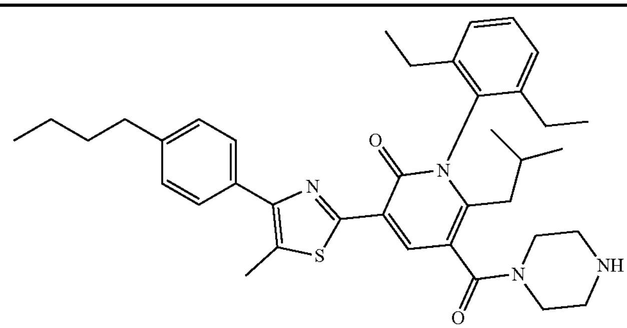 | C | C | 625.3576 | 3.471 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-butylphenyl)boronic acid (method xix); Methods: S, then ester hydrolyzed with LiOH (0.5M), THF, rt, U, xix, then Boc removal with TFA/DCM rt | |
| 45 | 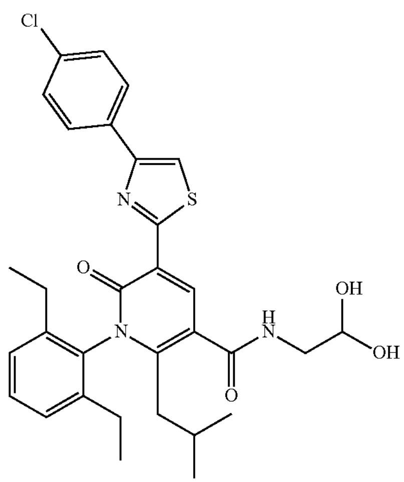 [SMILES: CCc1cccc(CC)c1-n1c(CC(C)C)c(C(=O)NCC(O)O)cc(-c2nc(-c3ccc(Cl)cc3)cs2)c1=O] | B | A | 578.2244 | 3.845 | Starting materials: acid compound 14, amine-1-aminopropan-2-ol; Method: U | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 46 | 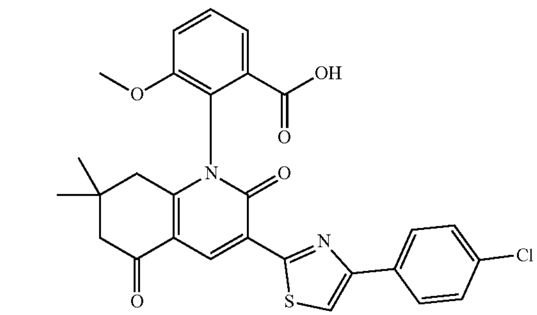 [SMILES: COc1cccc(C(=O)O)c1-n1c2c(cc(-c3nc(-c4ccc(Cl)cc4)cs3)c1=O)C(=O)CC(C)(C)C2] | C | C | 535.1089 | 3.55 | Starting materials: nitrile-1, aniline-2-amino-3-methoxybenzoic acid; Method: A (step 2-45° C., step 3-70° C. 2.5 h) | |
| 47 | 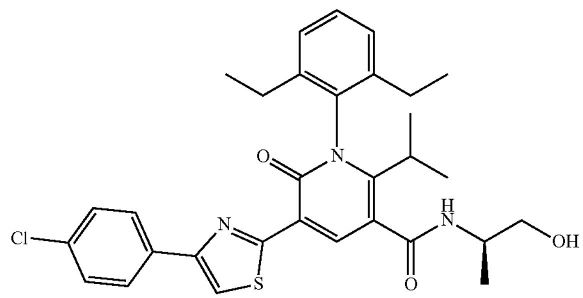 [SMILES: CCc1cccc(CC)c1-n1c(C(C)C)c(C(=O)N[C@H](C)CO)cc(-c2nc(-c3ccc(Cl)cc3)cs2)c1=O] | C | C | 564.2074 | 3.744 | Starting materials: acid-compound 98, amine-(R)-2-aminopropan-1-ol; Method: U | |

TABLE 1-continued
Characterization and Enzymatic Inhibition Data for Selected Compounds
| Cpd # | Structure | Data for R132H (µM) | Data for R132C (µM) | MZ | RT (min) | Synthesis Method | ¹H-NMR |
|---|---|---|---|---|---|---|---|
| 48 | 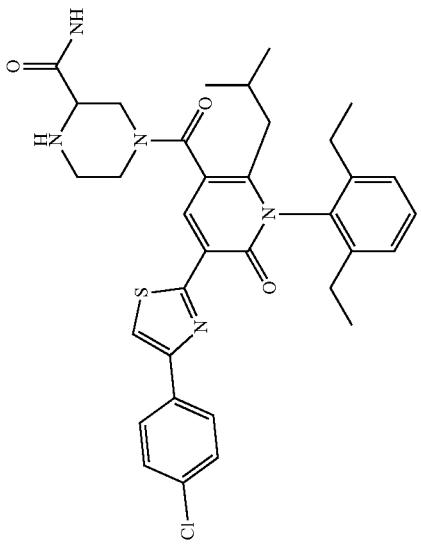 | B | A | 632.2441 | 2.845 | Starting materials: acid-compound 14, amine-piperazine-2-carboxamide; Method: U | |
| 49 | 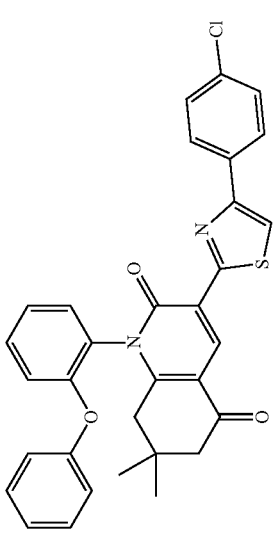 | A | A | 553.1347 | 4.048 | Starting materials: nitrile-1, aniline-2-phenoxyaniline; Method: E | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 50 | 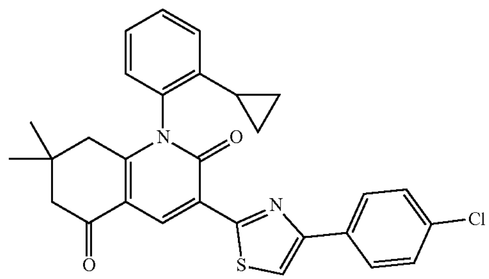 [SMILES: CC1(C)CC(=O)c2cc(-c3nc(-c4ccc(Cl)cc4)cs3)c(=O)n(-c3ccccc3C3CC3)c2C1] | B | B | 501.1402 | 3.993 | Starting materials: nitrile-1, aniline-2-cyclopropylaniline; Method: E | |
| 51 | 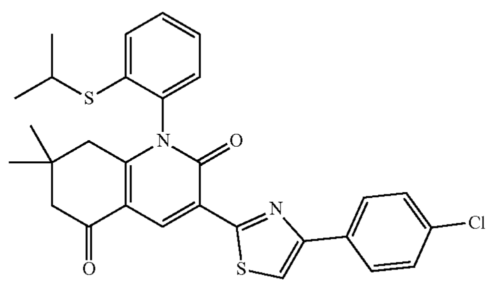 [SMILES: CC(C)Sc1ccccc1-n1c2c(cc(-c3nc(-c4ccc(Cl)cc4)cs3)c1=O)C(=O)CC(C)(C)C2] | E | C | 535.1279 | 4.087 | Starting materials: nitrile-1, aniline-2-(isopropylthio)aniline; Method: E | |
| 52 | 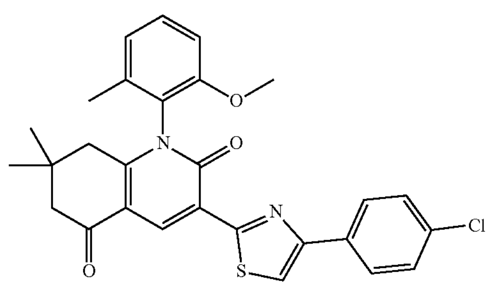 [SMILES: COc1cccc(C)c1-n1c2c(cc(-c3nc(-c4ccc(Cl)cc4)cs3)c1=O)C(=O)CC(C)(C)C2] | C | C | 505.135 | 3.963 | Starting materials: nitrile-1, aniline-2-methoxy-6-ethylaniline; Method: R | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 53 | 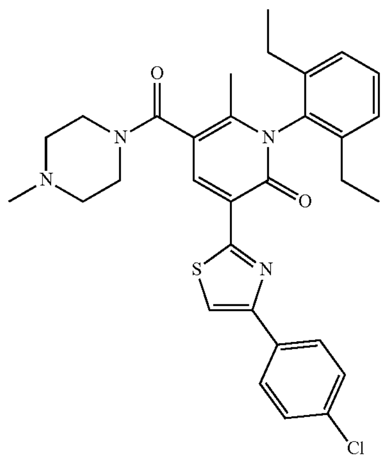 [SMILES: CCc1cccc(CC)c1-n1c(C)c(C(=O)N2CCN(C)CC2)cc(-c2nc(-c3ccc(Cl)cc3)cs2)c1=O] | C | B | 561.2076 | 2.74 | Starting materials: acid-compound 143, amine-1-methylpiperazine; Method: U | |
| 54 | 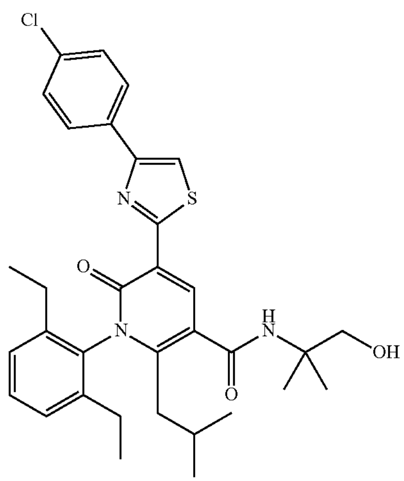 [SMILES: CCc1cccc(CC)c1-n1c(CC(C)C)c(C(=O)NC(C)(C)CO)cc(-c2nc(-c3ccc(Cl)cc3)cs2)c1=O] | B | B | 592.2403 | 3.964 | Starting materials: acid-compound 14, amine-2-amino-2-methylpropan-1-ol; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 55 | 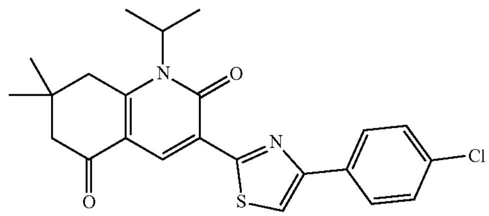 [SMILES: CC(C)n1c2c(cc(-c3nc(-c4ccc(Cl)cc4)cs3)c1=O)C(=O)CC(C)(C)C2] | E | C | 427.1242 | 3.952 | Method: xii | |
| 56 | 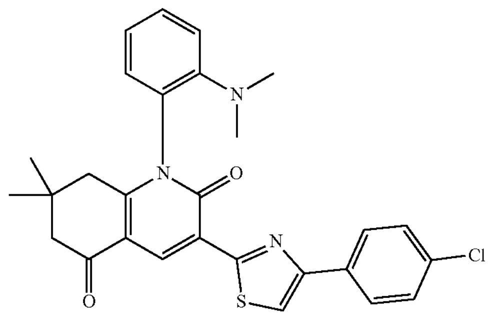 [SMILES: CN(C)c1ccccc1-n1c2c(cc(-c3nc(-c4ccc(Cl)cc4)cs3)c1=O)C(=O)CC(C)(C)C2] | B | B | 504.1516 | 4.019 | Starting materials: nitrile-1, aniline-2-dimethylaminoaniline; Method: E | |
| 57 | 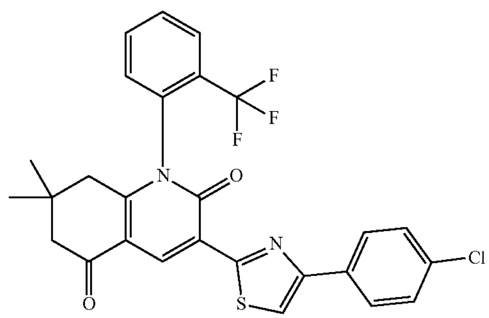 [SMILES: CC1(C)CC(=O)c2cc(-c3nc(-c4ccc(Cl)cc4)cs3)c(=O)n(-c3ccccc3C(F)(F)F)c2C1] | B | A | 529.0976 | 3.936 | Starting materials: nitrile-1, aniline-2-trifluoroaniline; Method: E | |

TABLE 1-continued
Characterization and Enzymatic Inhibition Data for Selected Compounds
| Cpd # | Structure | Data for R132H (μM) | Data for R132C (μM) | MZ | RT (min) | Synthesis Method | 1H-NMR |
|---|---|---|---|---|---|---|---|
| 58 | 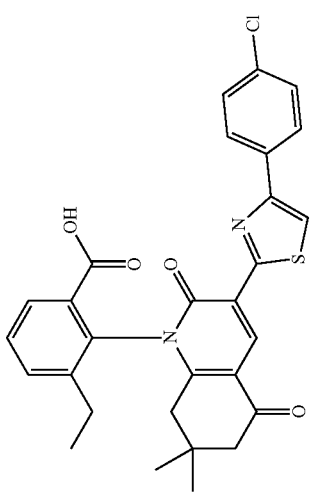 | B | C | 533.131 | 3.741 | Starting materials: nitrile-1, aniline-2-amino-3-ethylbenzoic acid; Method: K (step 3 80° C. 2 h) | |
| 59 | 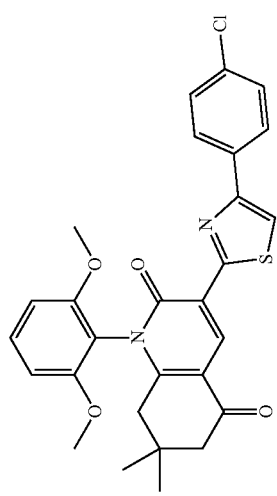 | C | C | 521.1318 | 3.864 | Starting materials: nitrile-1, aniline-2,6-dimethoxyaniline; Method: G | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 60 | 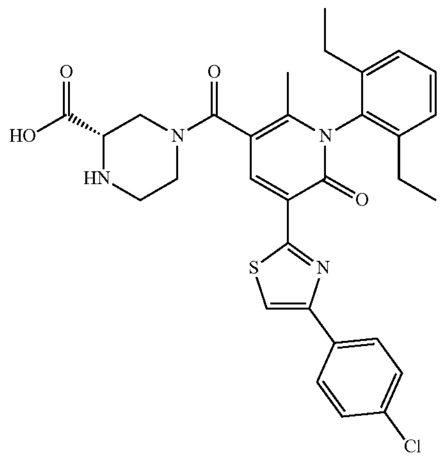 [SMILES: CCc1cccc(CC)c1-n1c(C)c(C(=O)N2CCN[C@H](C(=O)O)C2)cc(-c2nc(-c3ccc(Cl)cc3)cs2)c1=O] | B | B | 591.1831 | 2.89 | Compound 41 was hydrolyzed with LiOH (xs), THF/MeOH/water, 50° C. 1.75 h | |
| 61 | 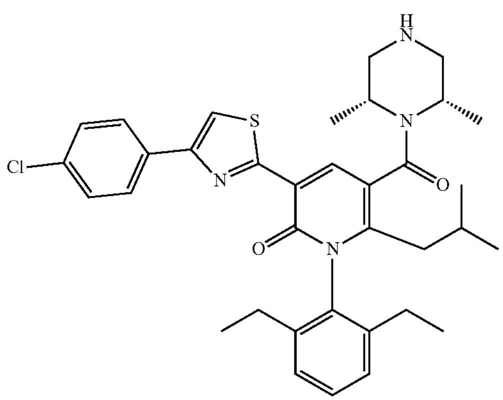 [SMILES: CCc1cccc(CC)c1-n1c(CC(C)C)c(C(=O)N2[C@H](C)CNC[C@@H]2C)cc(-c2nc(-c3ccc(Cl)cc3)cs2)c1=O] | B | A | 617.2714 | 2.966 | Starting materials: acid-compound 14, amine-(3S,5R)-tert-butyl 3,5-dimethylpiperazine-1-carboxylate [made by Boc2O of piperazine deriv]; Methods: U, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 62 | 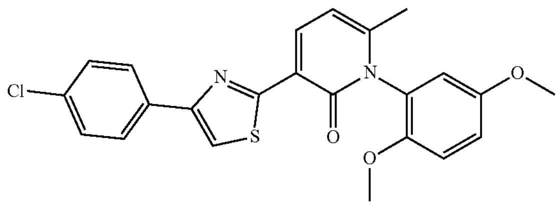 [SMILES: COc1ccc(OC)c(-n2c(C)ccc(-c3nc(-c4ccc(Cl)cc4)cs3)c2=O)c1] | E | D | 439.0987 | 3.822 | Method: xv | |
| 63 | 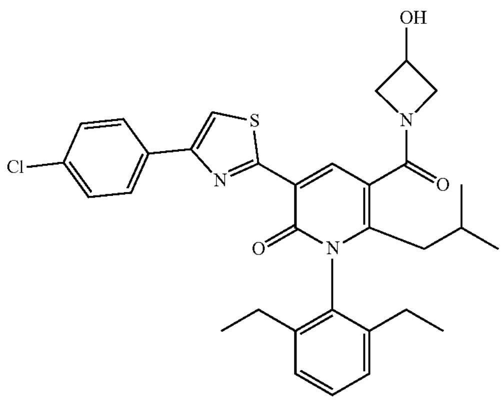 [SMILES: CCc1cccc(CC)c1-n1c(CC(C)C)c(C(=O)N2CC(O)C2)cc(-c2nc(-c3ccc(Cl)cc3)cs2)c1=O] | C | B | 576.2075 | 3.798 | Starting materials: acid-compound 14, amine-azetidin-3-ol; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 64 | *structure* | C | B | 578.2227 | 3.813 | Starting materials: acid-compound 14, amine-(R)-2-aminopropan-1-ol; Method: U | |
| 65 | *structure* | E | D | 504.1678 | 3.343 | Starting materials: nitirle-2-(1-(4-chlorophenyl)-1H-imidazol-4-yl)acetonitrile (see experimental for synthesis), aniline-2,5-dimethoxyaniline; Method: L | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 66 | 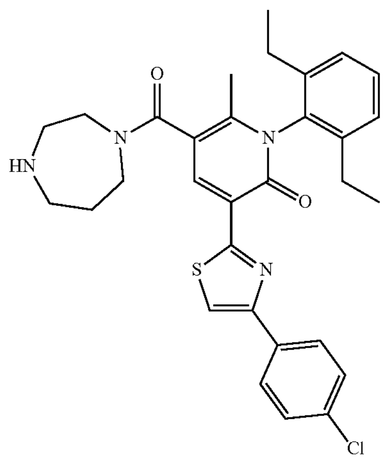 [SMILES: CCc1cccc(CC)c1-n1c(C)c(C(=O)N2CCCNCC2)cc(-c2nc(-c3ccc(Cl)cc3)cs2)c1=O] | B | B | 561.2062 | 2.685 | Starting materials: acid-compound 143, amine-tert-butyl 1,4-diazepane-1-carboxylate; Method: U, then Boc removal with TFA/DCM rt | |
| 67 | 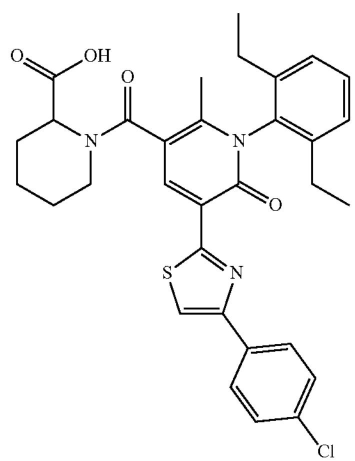 [SMILES: CCc1cccc(CC)c1-n1c(C)c(C(=O)N2CCCCC2C(=O)O)cc(-c2nc(-c3ccc(Cl)cc3)cs2)c1=O] | C | D | 590.1904 | 3.745 | Starting materials: acid-compound 143, amine-methyl piperidine-2-carboxylate; Method: U, then hydrolyzed with LiOH (0.5M), THF, rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | $^1$H-NMR |
|---|---|---|---|---|---|---|---|
| 68 | 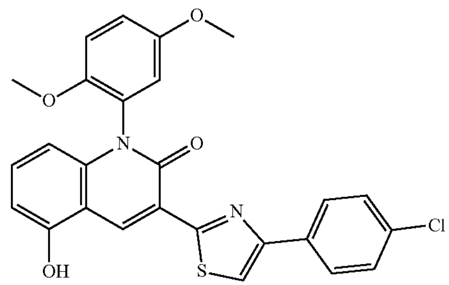 [SMILES: COc1ccc(OC)c(-n2c(=O)c(-c3nc(-c4ccc(Cl)cc4)cs3)cc3c(O)cccc32)c1] | E | E | 491.0817 | 3.619 | Starting materials: nitrile-1, aniline-2,5-dimethoxyaniline, cyclohexane-1,3-dione; Methods: B, then oxidation with DDQ (1.5 eq) in dioxane, 70° C. 17.5 h | |
| 69 | 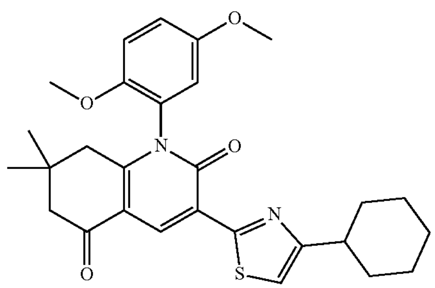 [SMILES: COc1ccc(OC)c(-n2c3c(cc(-c4nc(C5CCCCC5)cs4)c2=O)C(=O)CC(C)(C)C3)c1] | C | C | 493.2156 | 3.92 | Starting materials: nitirle-8, aniline-2,5-dimethoxyaniline; Method: K | |
| 70 | 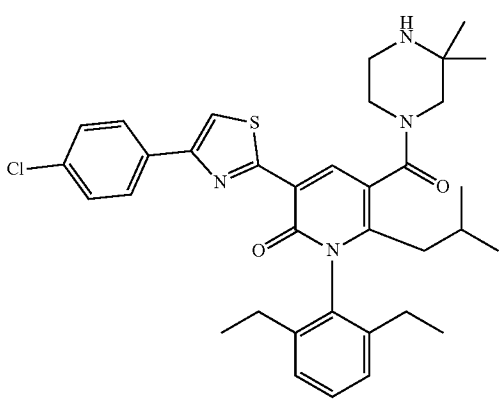 [SMILES: CCc1cccc(CC)c1-n1c(CC(C)C)c(C(=O)N2CCNC(C)(C)C2)cc(-c2nc(-c3ccc(Cl)cc3)cs2)c1=O] | B | A | 617.2708 | 2.914 | Starting materials: acid-compound 14, amine-2, 2-dimethylpiperazine; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 71 | 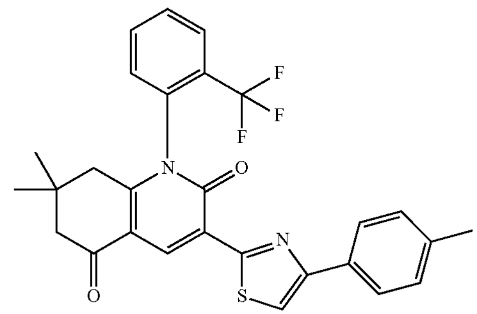 | B | B | 509.1512 | 3.89 | Starting materials: nitrile-6, aniline-2-trifluoromethylaniline; Method: I | |
| 72 | 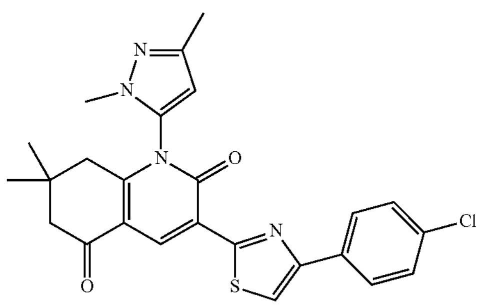 [SMILES: Cc1cc(-n2c3c(cc(-c4nc(-c5ccc(Cl)cc5)cs4)c2=O)C(=O)CC(C)(C)C3)n(C)n1] | C | C | 479.1326 | 3.738 | Starting materials: nitrile-, amine-1,3-dimethyl-1H-pyrazol-5-amine; Method: R (step 2-50° C. 2 h, step 3-80° C. 3 h then 100° C. overnight) | |
| 73 | 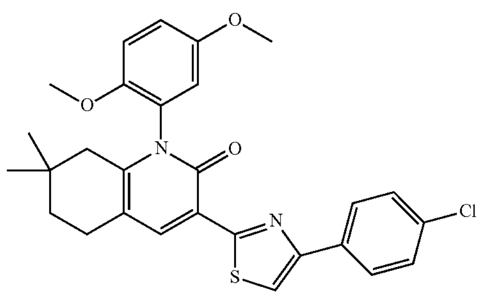 [SMILES: COc1ccc(OC)c(-n2c3c(cc(-c4nc(-c5ccc(Cl)cc5)cs4)c2=O)CCC(C)(C)C3)c1] | C | C | 507.1509 | 4.196 | Starting materials: nitrile-1, aniline-2,5-dimethoxyaniline; Methods: A, then complete ketone reduction to methylene with LiAlH4 (1.5 eq) in THF, 60° C. 48 h | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 74 | 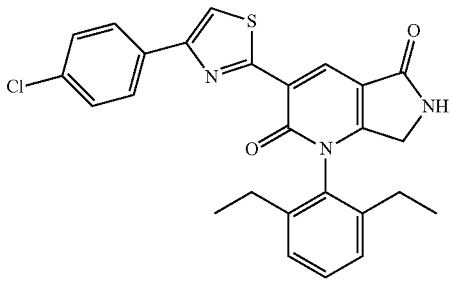 [SMILES: CCc1cccc(CC)c1-n1c2c(cc(-c3nc(-c4ccc(Cl)cc4)cs3)c1=O)C(=O)NC2] | C | D | 476.119 | 3.704 | Starting materials: nitrile-1, aniline-2,6-diethylaniline, dicarbonyl-4-hydroxy-1H-pyrrol-2(5H)-one; Method: N (step 1-60° C. 0.33 h, step 2-60° C. 1 h, step 3-80° C. 2 h) | |
| 75 | 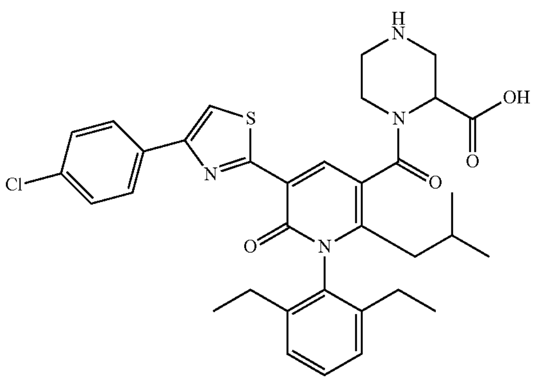 [SMILES: CCc1cccc(CC)c1-n1c(CC(C)C)c(C(=O)N2CCNCC2C(=O)O)cc(-c2nc(-c3ccc(Cl)cc3)cs2)c1=O] | C | B | 633.2306 | 2.966 | compound 147 was hydrolyzed with LiOH (0.5M), THF, rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 76 | 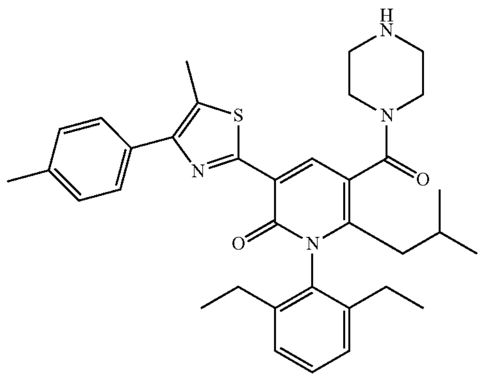 [SMILES: CCc1cccc(CC)c1-n1c(CC(C)C)c(C(=O)N2CCNCC2)cc(-c2nc(-c3ccc(C)cc3)c(C)s2)c1=O] | A | A | 292.1579 | 3.239 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), p-tolylboronic acid (method xix); Methods: S, then ester hydrolyzed with LiOH (0.5M), THF, rt, U, xix, then Boc removal with TFA/DCM rt | ¹H NMR (400 MHz, DMSO-d₆) δ 8.82 (d, J = 50.5 Hz, 1H), 8.56 (d, J = 1.2 Hz, 1H), 7.66 (dd, J = 8.1, 1.3 Hz, 2H), 7.53-7.46 (m, 1H), 7.36 (d, J = 7.6 Hz, 2H), 7.30 (d, J = 7.8 Hz, 2H), 4.04 (s, 1H), 3.77 (s, 1H), 3.58 (s, 4H), 3.14 (d, J = 50.4 Hz, 3H), 2.55 (d, J = 1.2 Hz, 3H), 2.37 (s, 3H), 2.28-1.91 (m, 4H), 1.32 (dq, J = 14.2, 7.1 Hz, 1H), 1.10 (d, J = 8.4 Hz, 7H), 0.62 (d, J = 6.5 Hz, 6H). Aliphatic region complicated significantly by amide rotamers. |
| 77 | 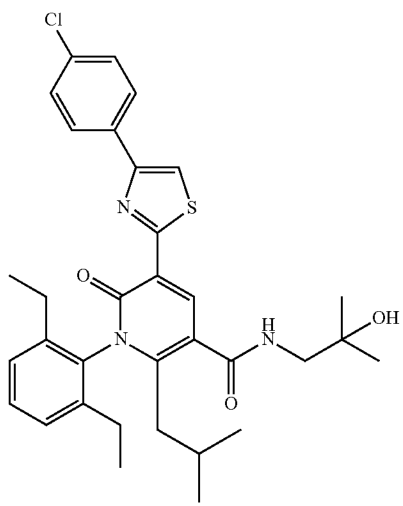 [SMILES: CCc1cccc(CC)c1-n1c(CC(C)C)c(C(=O)NCC(C)(C)O)cc(-c2nc(-c3ccc(Cl)cc3)cs2)c1=O] | B | A | 592.2383 | 3.922 | Starting materials: acid-compound 14, amine-1-amino-2-methylpropan-2-ol; Method: U | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 78 | 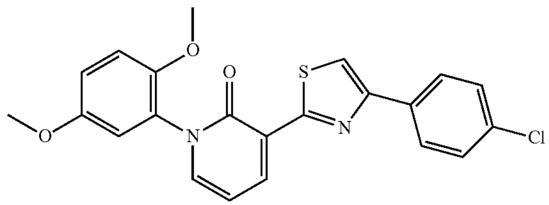 [SMILES: COc1ccc(OC)c(-n2cccc(-c3nc(-c4ccc(Cl)cc4)cs3)c2=O)c1] | E | E | 425.0723 | 3.787 | Method: ii | |
| 79 | 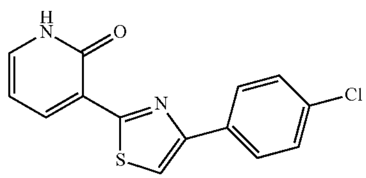 [SMILES: O=c1[nH]cccc1-c1nc(-c2ccc(Cl)cc2)cs1] | E | E | 289.0201 | 3.347 | Method: i | (400 MHz, DMSO-d₆) δ 12.10 (s, 1H), 8.28 (dd, J = 7.2, 2.1 Hz, 1H), 7.80 (s, 1H), 7.76-7.68 (m, 2H), 7.30 (s, 1H), 7.20-7.11 (m, 2H), 6.15 (dd, J = 7.2, 6.3 Hz, 1H) |
| 80 | 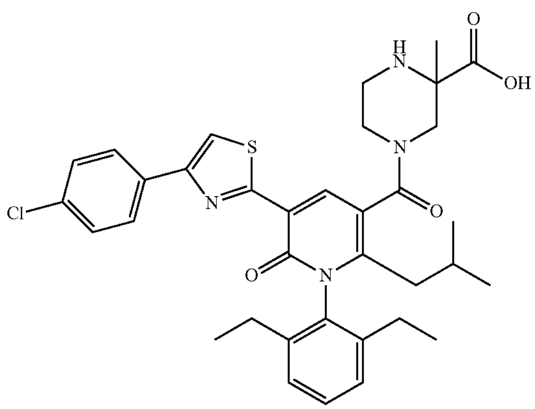 [SMILES: CCc1cccc(CC)c1-n1c(CC(C)C)c(C(=O)N2CCNC(C)(C(=O)O)C2)cc(-c2nc(-c3ccc(Cl)cc3)cs2)c1=O] | B | A | 647.2459 | 3.135 | Starting materials: acid-compound 14, amine-1-tert-butyl 2-methyl 2-methylpiperazine-1,2-dicarboxylate (xxii); Methods: U, then Boc removal with TFA/DCM rt, then ester cleavage with LiOH/water/THF rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | $^1$H-NMR |
|---|---|---|---|---|---|---|---|
| 81 | 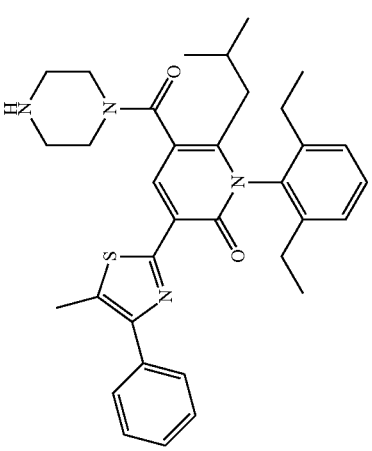 | A | B | 591.2785 | 3.155 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), phenylboronic acid (method xix); Methods: S, then ester hydrolyzed with LiOH (0.5M), THF, rt, U, xix, then Boc removal with TFA/DCM rt | $^1$H NMR (400 MHz, DMSO-d$_6$) δ 8.83 (d, J = 40.8 Hz, 1H), 8.57 (d, J = 1.0 Hz,1H), 7.77 (dt, J = 8.3, 1.3 Hz, 2H), 7.50 (ddd, J = 7.8, 6.9, 1.3 Hz, 3H), 7.44-7.39 (m, 1H), 7.36 (d, J = 7.8 Hz, 2H), 4.04 (s, 1H), 3.77 (s, 1H), 3.59 (s, 2H), 3.20 (s, 3H), 3.06 (d, J = 13.6 Hz, 1H), 2.57 (d, J = 1.0 Hz, 3H), 2.44-1.88 (m, 6H), 1.33 (p, J = 6.7 Hz, 1H), 1.10 (d, J = 8.8 Hz, 6H), 0.62 (d, J = 6.5 Hz, 6H). Aliphatic region complicated significantly by amide rotamers. |
| 82 | 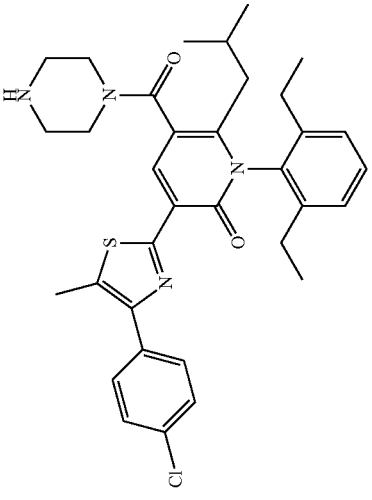 | A | A | 302.1324 | 3.26 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), 4-chlorophenylboronic acid (method xix); Methods: S, then ester hydrolyzed with LiOH (xs), THF/MeOH/water, 50 °Q U, xix, then Boc removal with TFA/DCM rt | $^1$H NMR of TFA salt (400 MHz, DMSO-d$_6$) δ 8.80 (m, 2H), 8.56 (d, J = 1.0 Hz, 1H), 7.80 (dd, J = 8.5, 1.1 Hz, 2H), 7.57-7.43 (m, 3H), 7.35 (d, J = 7.7 Hz, 2H), 4.01 (s, 1H), 3.74 (s, 1H), 3.55 (s, 1H), 3.19 (s, 2H), 3.06 (s, 1H), 2.65 (s, 1H), 2.56 (d, J = 1.1 Hz, 3H), 2.46-2.24 (m, 1H), 2.24-1.89 (m, 3H), 1.31 (dt, J = 13.2,6.6 Hz, 1H), 1.08 (m, 7H), 0.60 (d, J = 6.5 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 83 | 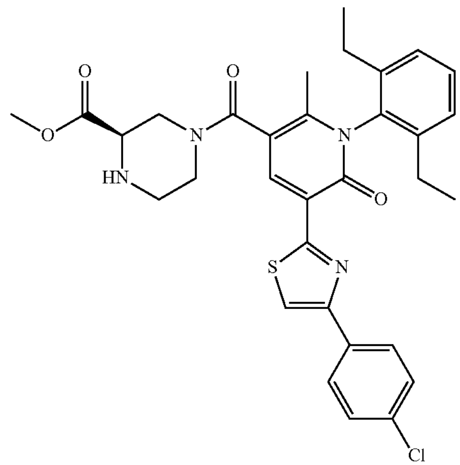 [SMILES: CCc1cccc(CC)c1-n1c(C)c(C(=O)N2CCN[C@@H](C(=O)OC)C2)cc(-c2nc(-c3ccc(Cl)cc3)cs2)c1=O] | C | B | 627.1826 | 2.882 | Starting materials: acid-compound 143, amine-(R)-1-tert-butyl 2-methyl piperazine-1,2-dicarboxylate; Method: U, then Boc removal with TFA/DCM rt | |
| 84 | 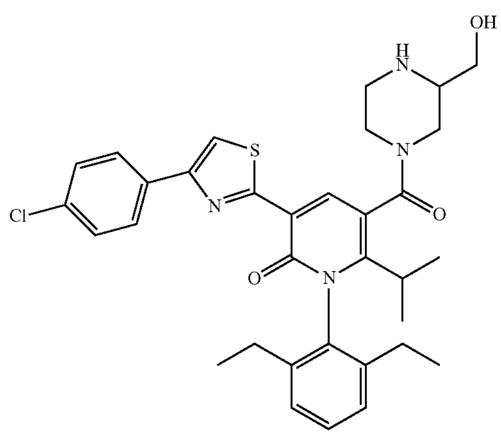 [SMILES: CCc1cccc(CC)c1-n1c(C(C)C)c(C(=O)N2CCNC(CO)C2)cc(-c2nc(-c3ccc(Cl)cc3)cs2)c1=O] | B | A | 605.2364 | 2.764 | Starting materials: acid-compound 98, amine-tert-butyl 2-(hydroxymethyl)piperazine-1-carboxylate; Methods: U, then Boc removal with TFA/DCM rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 85 | 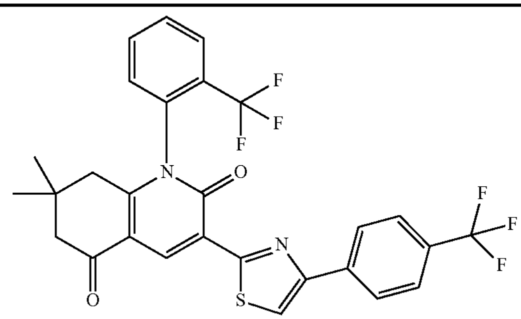 | B | B | 563.124 | 3.902 | Starting materials: nitrile-7, aniline-2-trifluoromethylaniline; Method: I | |
| 86 | 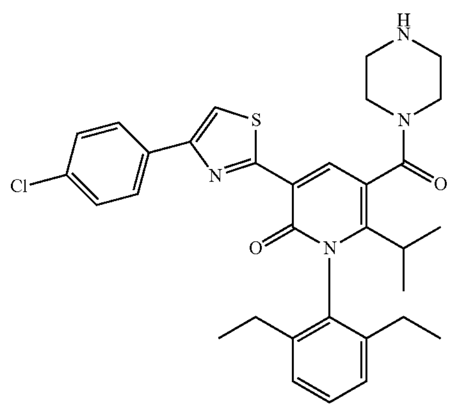 [SMILES: CCc1cccc(CC)c1-n1c(C(C)C)c(C(=O)N2CCNCC2)cc(-c2nc(-c3ccc(Cl)cc3)cs2)c1=O] | B | A | 575.2225 | 2.79 | Starting materials: acid-compound 98, amine-tert-butyl piperazine-1-carboxylate; Method: U; then Boc removal with TFA/DCM rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 87 | 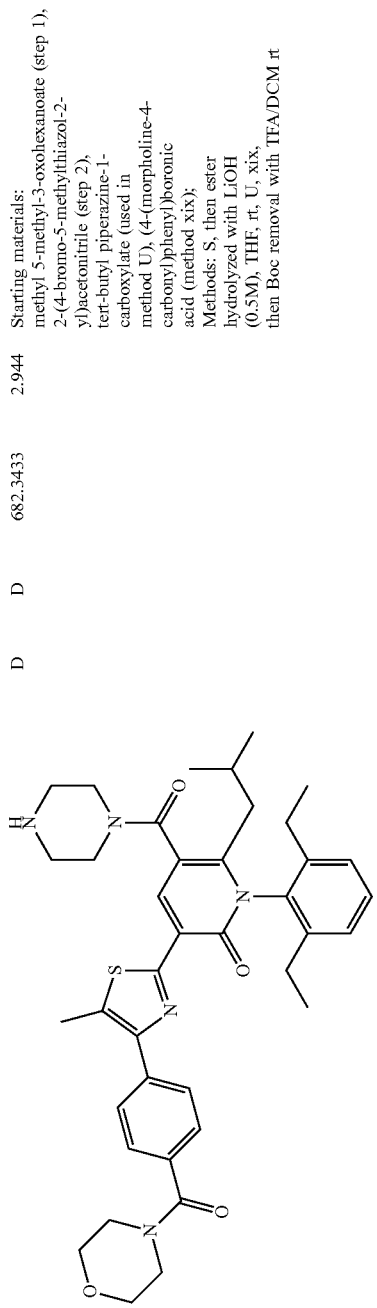 | D | D | 682.3433 | 2.944 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-(morpholine-4-carbonyl)phenyl)boronic acid (method xix); Methods: S, then ester hydrolyzed with LiOH (0.5M), THF, rt, U, xix, then Boc removal with TFA/DCM rt | |
| 88 | 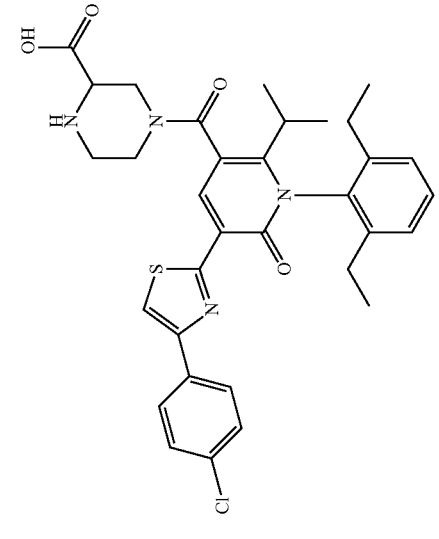 | A | A | 619.2139 | 3.023 | compound 31 was hydrolyzed with LiOH (0.5M), THF, rt | 1H NMR (400 MHz, DMSO-d6) δ 8.74 (s, 1H), 8.58 (d, J = 15.9 Hz, 1H), 8.21 (s, 1H), 8.17-8.09 (m, 2H), 7.54-7.43 (m, 3H), 7.37 (q, J = 6.9 Hz, 2H), 4.59 (dd, J = 58.1, 15.3 Hz, 2H), 4.30-3.49 (m, 6H), 2.42-2.25 (m, 2H), 2.24-1.96 (m, 2H), 1.08 (ddt, J = 16.4, 13.8,6.1 Hz, 13H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 89 | 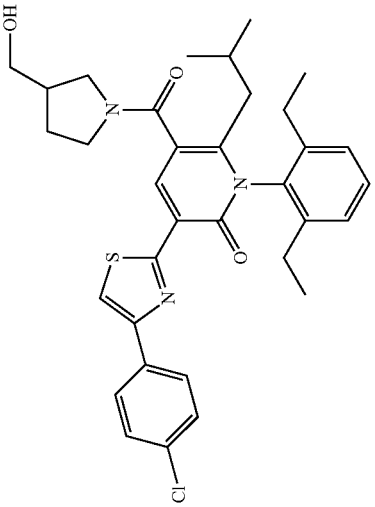 | C | B | 604.2392 | 3.819 | Starting materials: acid-compound 14, amine-pyrrolidin-3-ylmethanol; Method: U | |
| 90 | 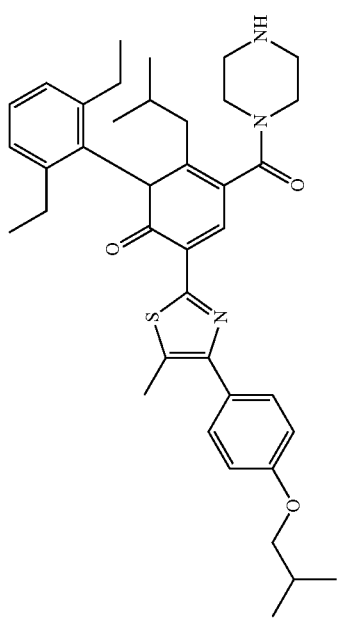 | C | C | 641.3532 | 3.421 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-isobutoxyphenyl)boronic acid (method xix); Methods: S, then ester hydrolyzed with LiOH (0.5M), THF, rt, U, xix, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 91 | 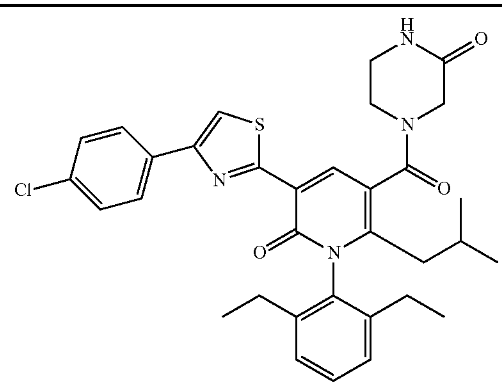 | A | A | 603.2193 | 3.706 | Starting materials: acid-compound 14, amine-piperazin-2-one; Method: U | ¹H NMR (400 MHz, DMSO-d₆) δ 8.65 (d, J = 29.1 Hz, 1H), 8.22 (s, 1H), 8.17 (d, J = 2.6 Hz, 1H), 8.15-8.09 (m, 2H), 7.57-7.50 (m, 2H), 7.49 (d, J = 7.6 Hz, 1H), 7.38 (s, 1H), 7.36 (s, 1H), 4.32-3.95 (m, 3H), 3.77 (d, J = 18.2 Hz, 2H), 2.42-2.08 (m, 5H), 1.35 (s, 1H), 1.09 (d, J = 7.8 Hz, 7H), 0.62 (t, J = 7.2 Hz, 7H). Aliphatic region complicated significantly by amide rotamers. |
| 92 | 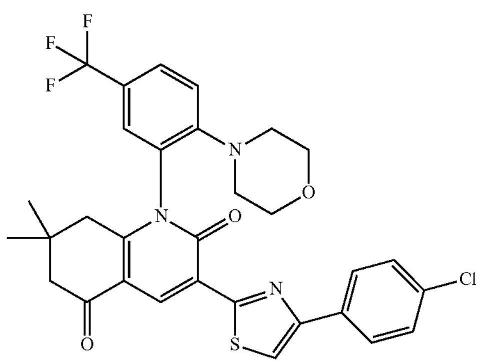 [SMILES: CC1(C)CC(=O)c2cc(-c3nc(-c4ccc(Cl)cc4)cs3)c(=O)n(-c3cc(C(F)(F)F)ccc3N3CCOCC3)c2C1] | C | C | 614.1487 | 3.905 | Starting materials: nitrile-1, aniline-2-morpholino-5-trifluoromethylaniline; Method: G | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 93 | 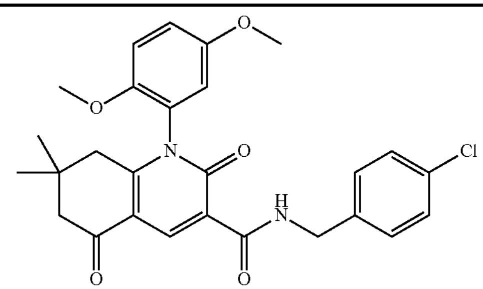 | D | D | 495.1691 | 3.467 | Starting materials: nitrile-N-(4-chlorobenzyl)-2-cyanoacetamide, aniline-2,5-dimethoxyaniline; Method: D | |
| 94 | 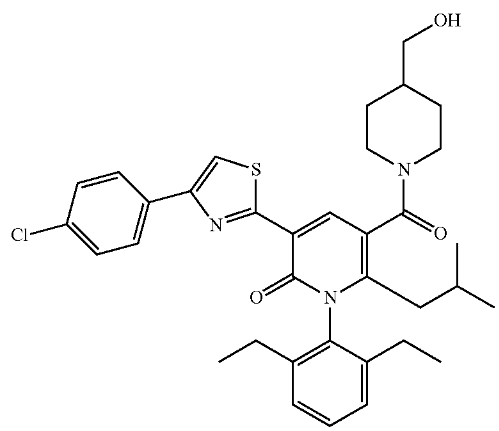 [SMILES: CCc1cccc(CC)c1-n1c(CC(C)C)c(C(=O)N2CCC(CO)CC2)cc(-c2nc(-c3ccc(Cl)cc3)cs2)c1=O] | C | A | 618.2552 | 3.892 | Starting materials: acid-compound 14, amine-piperidin-4-ylmethanol; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 95 | 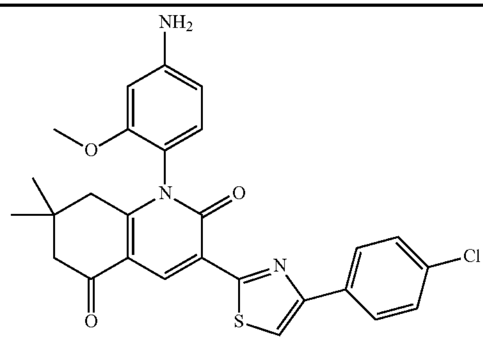 | C | C | 506.134 | 3.676 | Starting materials: nitrile-1, aniline-2-methoxy-4-nitroaniline; Methods: A (step 2-45° C., step 3-70° C. 2.5 h), then Nitro reduction with SnCl2 (5 eq), EtOH 70° C. 0.5 h | |
| 96 | 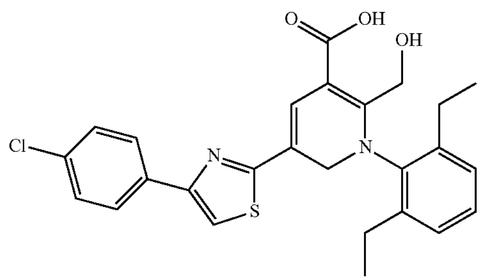 [SMILES: CCc1cccc(CC)c1N1CC(c2nc(-c3ccc(Cl)cc3)cs2)=CC(C(=O)O)=C1CO] | D | D | 495.1146 | 3.762 | Lactone hydrolysis of compound 194 using LiOH (xs), THF/MeOH/water 50° C. 3 h (reverse phase purify with ammonium hydroxide modifier and not TFA) | |
| 97 | 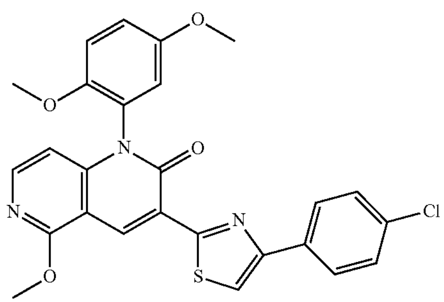 [SMILES: COc1ccc(OC)c(-n2c(=O)c(-c3nc(-c4ccc(Cl)cc4)cs3)cc3c(OC)nccc32)c1] | D | C | 506.0953 | 3.562 | O-Methylation with concomitant oxidation of compound 244-NaH (1.5 eq), THF/DMF then iodomethane (1.5 eq) rt 2.5 h | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 98 | 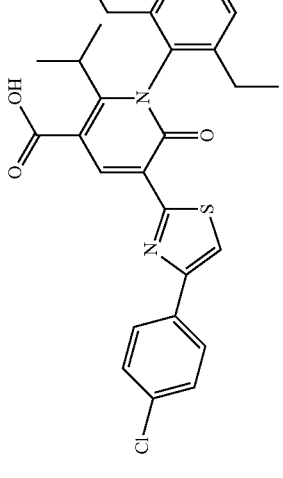 | C | D | 507.1527 | 3.946 | Compound 125 was hydrolyzed with LiOH (~5 eq). THF/MeOH/water, 50° C. 48 h then 70° C. 2.5 h | |
| 99 | 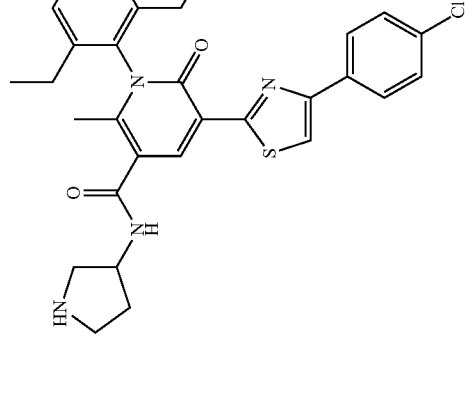 | C | B | 547.1936 | 2.714 | Starting materials: acid-compound 143, amine-tert-butyl 3-aminopyrrolidine-1-carboxylate; Method: U, then Boc removal with TFA/DCM rt | |

TABLE 1-continued
Characterization and Enzymatic Inhibition Data for Selected Compounds
| Cpd # | Structure | Data for R132H (µM) | Data for R132C (µM) | MZ | RT (min) | Synthesis Method | 1H-NMR |
|---|---|---|---|---|---|---|---|
| 100 | 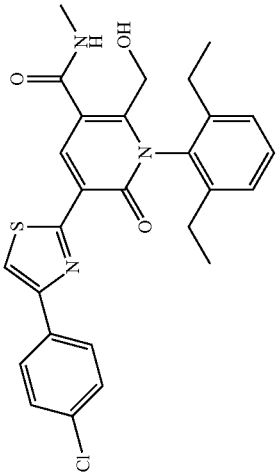 | C | C | 508.1456 | 2.482 | Lactone aminolysis of compound 194 by heating with methylamine (xs), THF 50° C. 1 h | |
| 101 | 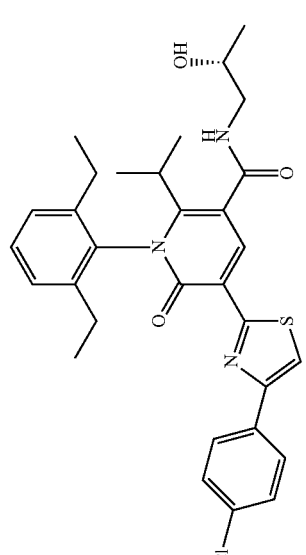 | C | B | 564.2099 | 3.767 | Starting materials: acid-compound 98, amine-(R)-1-aminopropan-2-ol; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 102 | 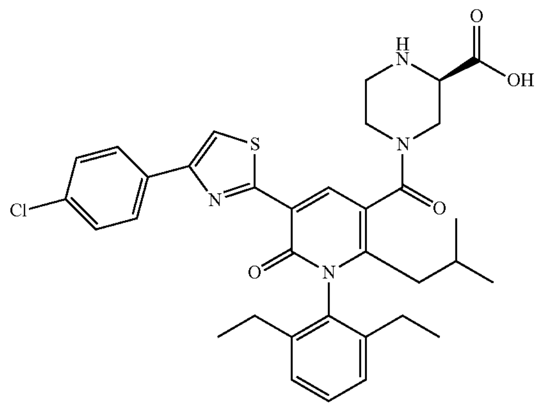 [SMILES: CCc1cccc(CC)c1-n1c(CC(C)C)c(C(=O)N2CCN[C@@H](C(=O)O)C2)cc(-c2nc(-c3ccc(Cl)cc3)cs2)c1=O] | B | A | 633.2309 | 3.125 | compound 131 was hydrolyzed with LiOH (0.5M), THF, rt | |
| 103 | 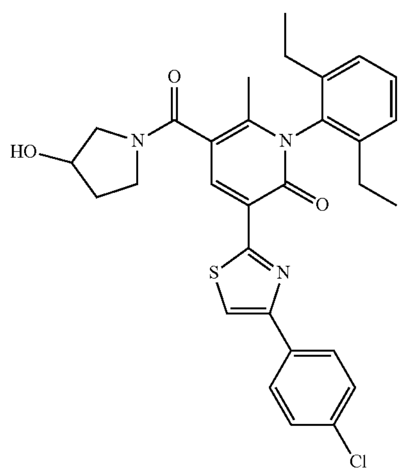 [SMILES: CCc1cccc(CC)c1-n1c(C)c(C(=O)N2CCC(O)C2)cc(-c2nc(-c3ccc(Cl)cc3)cs2)c1=O] | C | D | 548.1764 | 3.522 | Starting materials: acid-compound 143, amine-pyrrolidin-3-ol; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 104 | 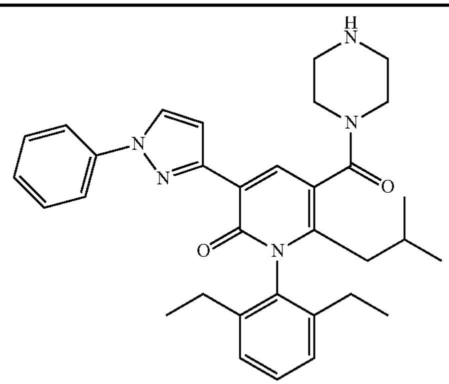 | C | C | 269.6615 | 2.933 | Starting materials: methyl 5-methyl-3-oxohexanoate (step 1), 2-(1-phenyl-1H-pyrazol-3-yl)acetonitrile (step 2), piperazine (used in method U); Methods: S (following addition of acetic acid and aniline heat 45° C. 3 h then extract and heat in DMF), then ester hydrolyzed with LiOH (xs), THF/MeOH/water,50° C., U | |
| 105 | 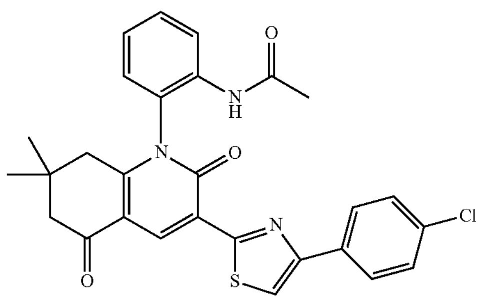 [SMILES: CC(=O)Nc1ccccc1-n1c2c(cc(-c3nc(-c4ccc(Cl)cc4)cs3)c1=O)C(=O)CC(C)(C)C2] | C | D | 518.1321 | 3.611 | Starting materials: nitrile-1, aniline-N-(2-aminophenyl)acetamide; Method: E | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | $^1$H-NMR |
|---|---|---|---|---|---|---|---|
| 106 | 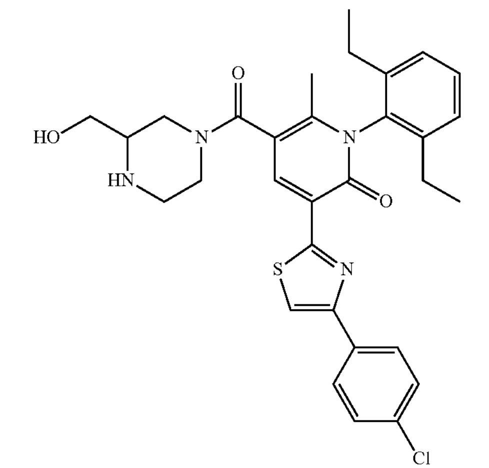 [SMILES: CCc1cccc(CC)c1-n1c(C)c(C(=O)N2CCNC(CO)C2)cc(-c2nc(-c3ccc(Cl)cc3)cs2)c1=O] | A | B | 577.2026 | 2.664 | Starting materials: acid-compound 143, amine-tert-butyl 2-(hydroxymethyl)piperazine-1-carboxylate; Methods: U; then Boc removal with TFA/DCM rt | $^1$H NMR of TFA salt (400 MHz, DMSO-d$_6$) δ 9.17 (s, 1H), 8.74 (s, 2H), 8.21 (s, 1H), 8.10 (d, J = 8.6 Hz, 2H), 7.55-7.42 (m, 3H), 7.35 (d, J = 7.7 Hz, 2H), 5.47 (d, J = 58.7 Hz, 1H), 4.48 (m, 1H), 3.51 (s, 2H), 2.37-2.02 (m, 4H), 1.86 (m, 3H), 1.06 (t, J = 7.5 Hz, 6H). Aliphatic region complicated significantly by amide rotamers. |
| 107 | 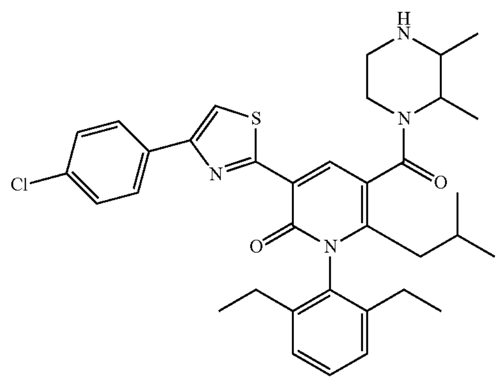 [SMILES: CCc1cccc(CC)c1-n1c(CC(C)C)c(C(=O)N2CCNC(C)C2C)cc(-c2nc(-c3ccc(Cl)cc3)cs2)c1=O] | B | A | 617.2726 | 2.944 | Starting materials: acid-compound 14, amine-2,3-dimethylpiperazine; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 108 | 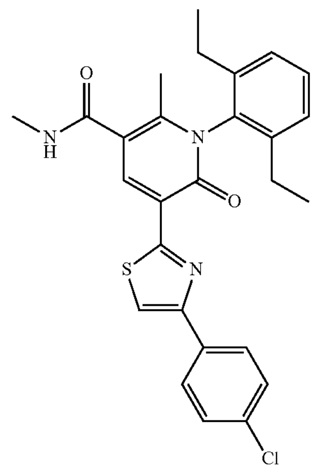 [SMILES: CCc1cccc(CC)c1-n1c(C)c(C(=O)NC)cc(-c2nc(-c3ccc(Cl)cc3)cs2)c1=O] | C | C | 492.1506 | 3.75 | Amide coupling of acid 143 with methylamine similar to method used to synthesize 2-(4-(4-chlorophenyl)thiazol-2-yl)-N-(2,5-dimethoxyphenyl)acetamide | |
| 109 | 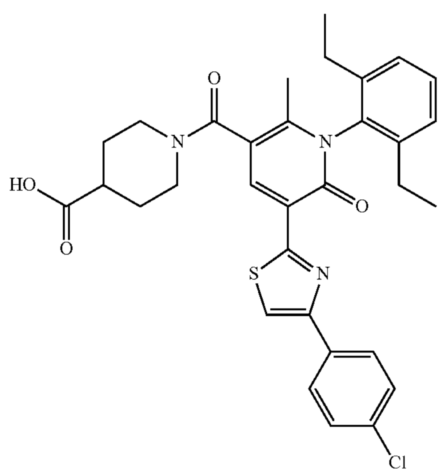 [SMILES: CCc1cccc(CC)c1-n1c(C)c(C(=O)N2CCC(C(=O)O)CC2)cc(-c2nc(-c3ccc(Cl)cc3)cs2)c1=O] | C | D | 590.1859 | 3.552 | Starting materials: acid-compound 143, amine-methyl piperidine-4-carboxylate; Method: U, then hydrolyzed with LiOH (0.5M), THF, rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 110 | 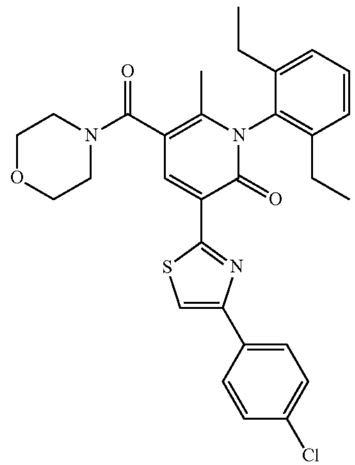 [SMILES: CCc1cccc(CC)c1-n1c(C)c(C(=O)N2CCOCC2)cc(-c2nc(-c3ccc(Cl)cc3)cs2)c1=O] | C | C | 570.1605 | 3.787 | Starting materials: acid-compound 143, amine-morpholine; Method: U | |
| 111 | 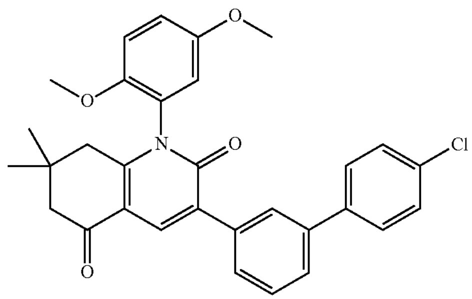 | E | D | 514.1777 | 3.835 | Starting materials: nitrile-2(4'-chloro-[1,1'-biphenyl]-3-yl)acetonitrile (method iii), aniline-2,5-dimethoxyaniline; Method: J | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 112 | 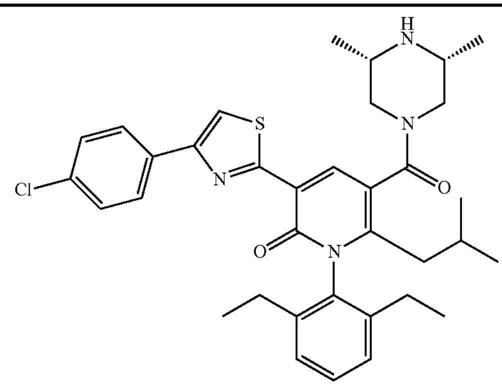 | B | A | 617.2725 | 2.925 | Starting materials: acid-compound 14, amine-(2S,6R)-2,6-dimethylpiperazine; Method: U | |
| 113 | 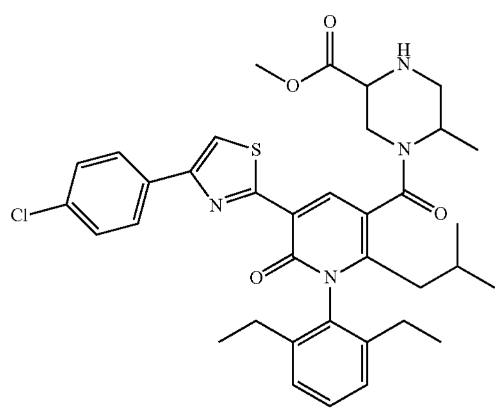 [SMILES: CCc1cccc(CC)c1-n1c(CC(C)C)c(C(=O)N2CC(C(=O)OC)NCC2C)cc(-c2nc(-c3ccc(Cl)cc3)cs2)c1=O] | C | B | 661.2615 | 3.469 | Starting materials: acid-compound 14, amine-1-tert butyl 2 methyl 5-methylpiperazine-1,2-dicarboxylate; Methods: U, then Boc removal with TFA/DCM rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 114 | 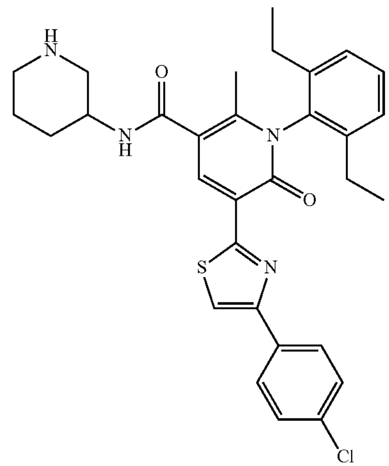 [SMILES: CCc1cccc(CC)c1-n1c(C)c(C(=O)NC2CCCNC2)cc(-c2nc(-c3ccc(Cl)cc3)cs2)c1=O] | C | B | 561.2107 | 2.723 | Starting materials: acid-compound 143, amine-tert-butyl 3-aminopiperidine-1-carboxylate; Method: U, then Boc removal with TFA/DCM rt | |
| 115 | 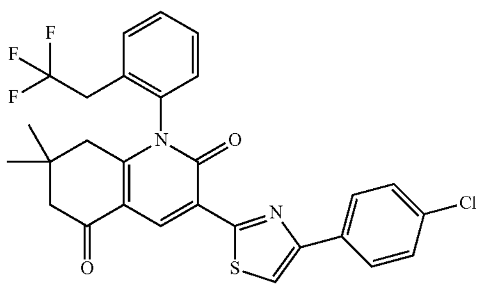 [SMILES: CC1(C)CC(=O)c2cc(-c3nc(-c4ccc(Cl)cc4)cs3)c(=O)n(-c3ccccc3CC(F)(F)F)c2C1] | B | B | 543.1107 | 3.911 | Starting materials: nitrile-1, aniline-2-(2,2,2-trifluoroethyl)aniline; Method: E | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 116 | 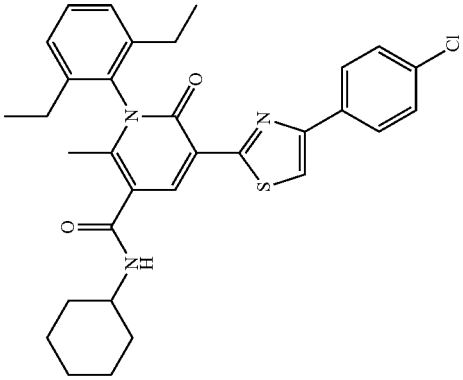 | E | C | 560.2134 | 4.151 | Starting materials: acid-compound 143, amine-cyclohexanamine; Method: U | |
| 117 | 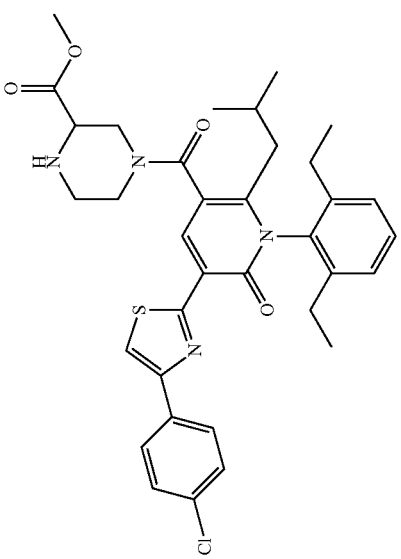 | C | A | 647.2452 | 3.163 | Starting materials: acid-compound 14, amine-1-tert-butyl 2-methyl piperazine-1,2-dicarboxylate; Method: U, then Boc removal with TFA/DCM rt | |

TABLE 1-continued
Characterization and Enzymatic Inhibition Data for Selected Compounds
| Cpd # | Structure | Data for R132H (μM) | Data for R132C (μM) | MZ | RT (min) | Synthesis Method | ¹H-NMR |
|---|---|---|---|---|---|---|---|
| 118 | 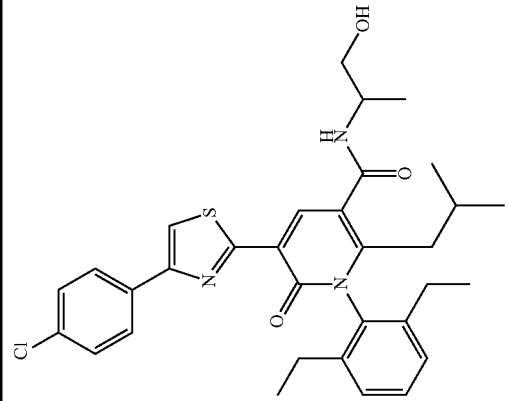 | B | A | 578.2212 | 3.821 | Starting materials: acid compound 14, amine-2 aminopropan-1-ol; Method: U | |
| 119 | 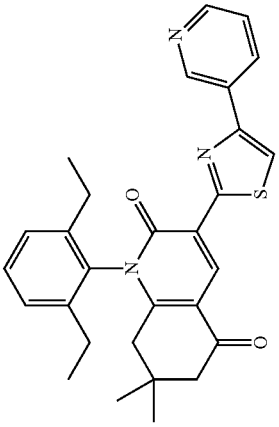 | D | C | 484.2055 | 3.476 | Starting materials: nitrile-9, aniline-2,6-diethylaniline; Method: Q | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 120 | 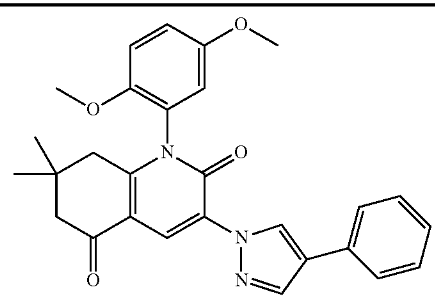 | E | E | 470.208 | 3.608 | Starting materials: nitrile-2-(4-phenyl-1H-pyrazol-1-yl)acetonitrile (synthesized by method xvi), aniline-2,5-dimethoxyaniline; Method: P | |
| 121 | 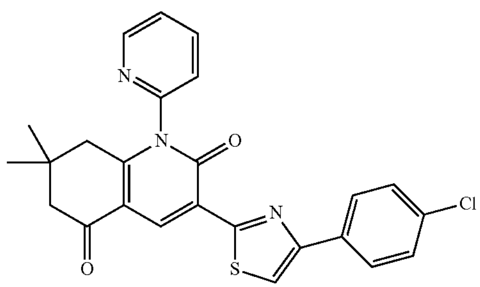 [SMILES: CC1(C)CC(=O)c2cc(-c3nc(-c4ccc(Cl)cc4)cs3)c(=O)n(-c3ccccn3)c2C1] | D | D | 462.1057 | 3.723 | Method: xiv | |
| 122 | 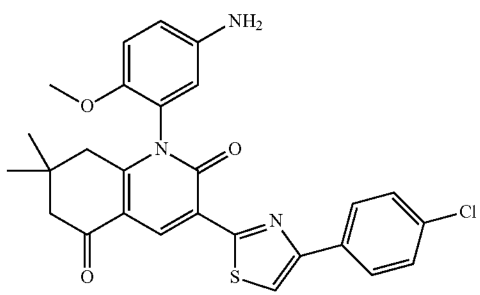 [SMILES: COc1ccc(N)cc1-n1c2c(cc(-c3nc(-c4ccc(Cl)cc4)cs3)c1=O)C(=O)CC(C)(C)C2] | C | B | 506.1315 | 3.54 | Nitro reduction of compound 128 with SnCl2 (5 eq), EtOH 70° C. 0.5 h | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 123 | 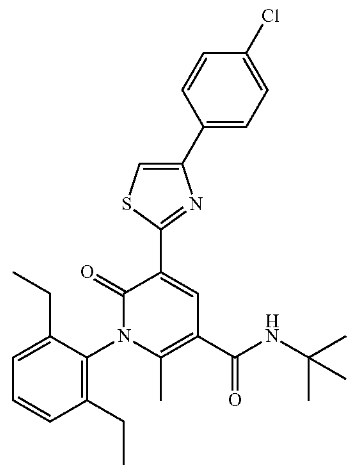 [SMILES: CCc1cccc(CC)c1-n1c(C)c(C(=O)NC(C)(C)C)cc(-c2nc(-c3ccc(Cl)cc3)cs2)c1=O] | D | C | 534.1983 | 4.032 | Starting materials: acid-compound 143, amine-2-methylpropan-2-amine; Method: U | |
| 124 | 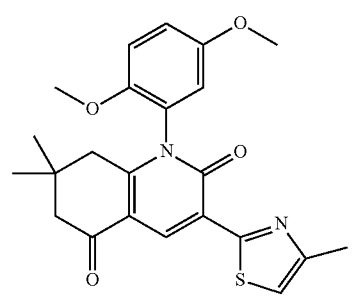 | E | D | 447.1364 | 3.364 | Starting materials: nitrile-2-(4-methylthiazol 2 yl)acetonitrile, aniline-2,5-dimethoxyaniline; Method: A | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 125 | 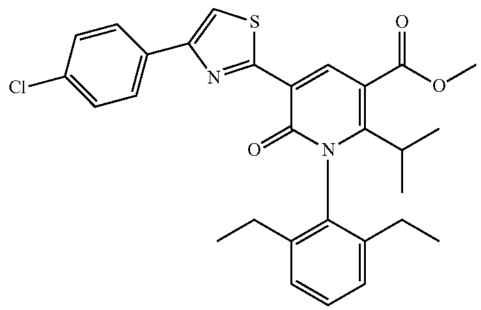 [SMILES: CCc1cccc(CC)c1-n1c(C(C)C)c(C(=O)OC)cc(-c2nc(-c3ccc(Cl)cc3)cs2)c1=O] | C | C | 521.1655 | 4.445 | Starting materia: step 1 with methyl 4-methyl-3-oxopentanoate; Method: S | |
| 126 | 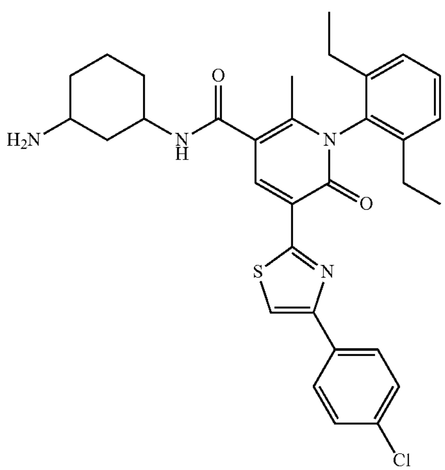 [SMILES: CCc1cccc(CC)c1-n1c(C)c(C(=O)NC2CCCC(N)C2)cc(-c2nc(-c3ccc(Cl)cc3)cs2)c1=O] | D | C | 575.2244 | 2.728 | Starting materials: acid-compound 143, amine-cyclohexane-1,3-diamine (cis and trans mixture); Method: U | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 127 | 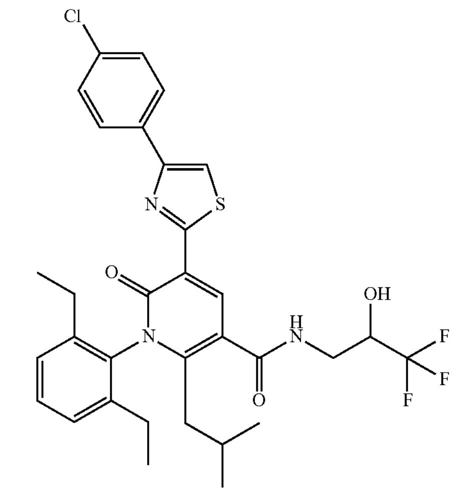 [SMILES: CCc1cccc(CC)c1-n1c(CC(C)C)c(C(=O)NCC(O)C(F)(F)F)cc(-c2nc(-c3ccc(Cl)cc3)cs2)c1=O] | B | A | 632.1942 | 3.919 | Starting materials: acid-compound 14, amine-3-amino-1,1,1-trifluoropropan-2-ol; Method: U | |
| 128 | 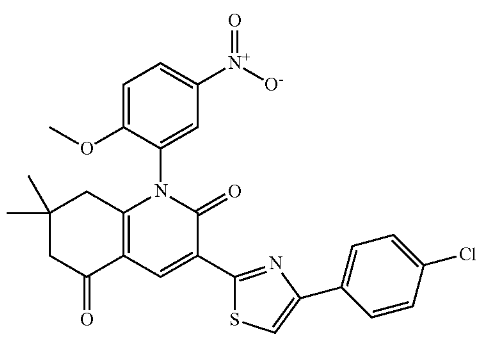 [SMILES: COc1ccc([N+](=O)[O-])cc1-n1c2c(cc(-c3nc(-c4ccc(Cl)cc4)cs3)c1=O)C(=O)CC(C)(C)C2] | C | C | 536.1049 | 3.781 | Starting materials: nitrile-1, aniline-2-methoxy-5-nitroaniline; Method: A (step 2-45° C., step 3-70° C. 2.5 h) | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 129 | 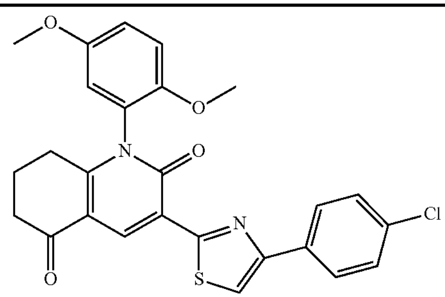 | C | C | 493.0973 | 3.741 | Starting materials: nitrile-1, aniline-2,5-dimethoxyaniline, cyclohexane-1,3-dione; Method: A | |
| 130 | 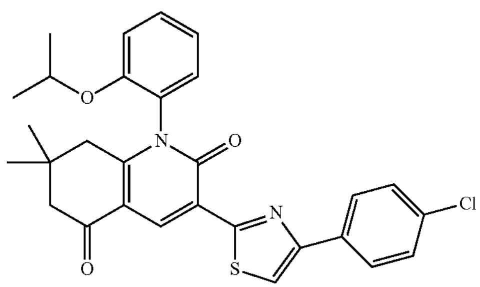 [SMILES: CC(C)Oc1ccccc1-n1c2c(cc(-c3nc(-c4ccc(Cl)cc4)cs3)c1=O)C(=O)CC(C)(C)C2] | C | B | 519.1492 | 4.026 | Starting materials: nitrile-1, aniline-2-isopropoxyaniline; Method: E | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 131 | 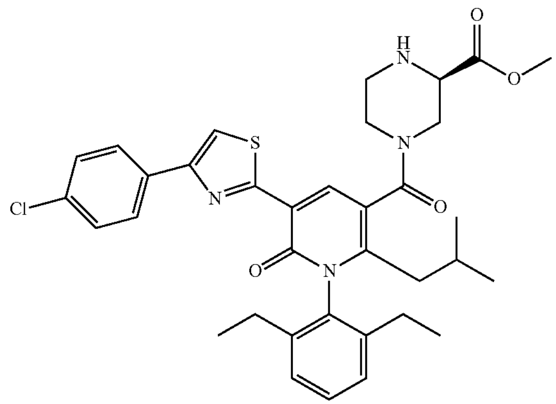 [SMILES: CCc1cccc(CC)c1-n1c(CC(C)C)c(C(=O)N2CCN[C@@H](C(=O)OC)C2)cc(-c2nc(-c3ccc(Cl)cc3)cs2)c1=O] | C | A | 647.2476 | 3.16 | Starting materials: acid-compound 14, amine-(R)-1-tert-butyl 2-methyl piperazine-1,2-dicarboxylate; Method: U, then Boc removal with TFA/DCM rt | |
| 132 | 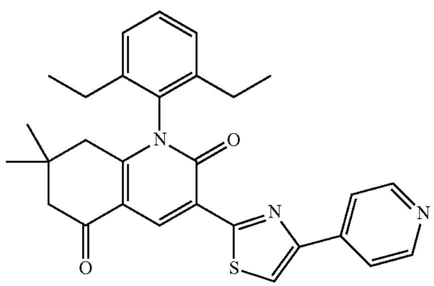 [SMILES: CCc1cccc(CC)c1-n1c2c(cc(-c3nc(-c4ccncc4)cs3)c1=O)C(=O)CC(C)(C)C2] | C | C | 506.1896 | 3.024 | Starting materials: nitrile-4, aniline-2,6-diethylaniline; Method: Q | |

TABLE 1-continued
Characterization and Enzymatic Inhibition Data for Selected Compounds
| Cpd # | Structure | Data for R132H (µM) | Data for R132C (µM) | MZ | RT (min) | Synthesis Method | ¹H-NMR |
|---|---|---|---|---|---|---|---|
| 133 | 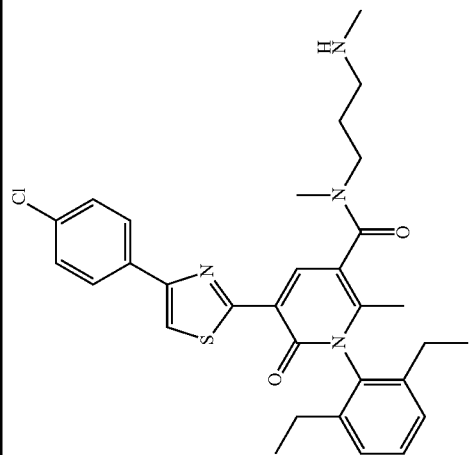 | D | C | 563.2247 | 2.72 | Starting materials: acid-compound 143, amine-N1,N3-dimethylpropane-1,3-diamine; Method: U | |
| 134 | 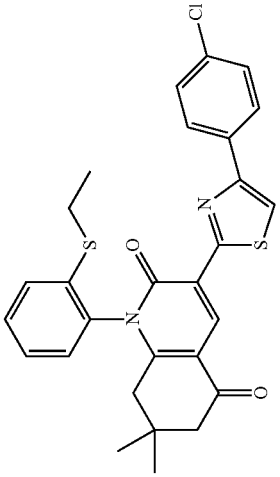 | C | B | 521.1119 | 4.006 | Starting materials: nitrile-1, aniline-2-(ethylthio)aniline; Method: E | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 135 | *structure* | C | B | 535.1287 | 4.096 | Starting materials: nitrile-1, aniline-2-(propylthio)aniline; Method: E | |
| 136 | *structure* | E | E | 535.1099 | 3.643 | Starting materials: nitrile-1, aniline-4-amino-3 methoxybenzoic acid; Method: A (step 2-45° C., step 3-70° C. 2.5 h) | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 137 | 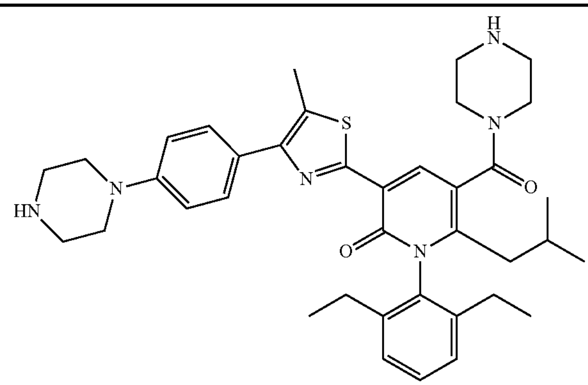 | E | E | 653.3652 | 2.658 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), tert-butyl 4-(4-(4,4,5,5-tetramethyl-1,3,2-dioxaborolan-2-yl)phenyl)piperazine-1-carboxylate (method xix); Methods: S, then ester hydrolyzed with LiOH (0.5M), THF, rt, U, xix, then Boc removal with TFA/DCM rt | |
| 138 | 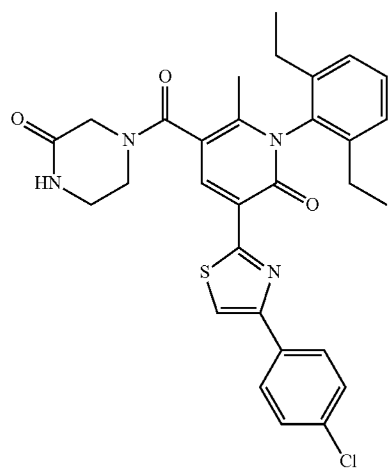 [SMILES: CCc1cccc(CC)c1-n1c(C)c(C(=O)N2CCNC(=O)C2)cc(-c2nc(-c3ccc(Cl)cc3)cs2)c1=O] | A | C | 561.1731 | 3.413 | Starting materials: acid-compound 143, amine-piperazin-2-one; Method: U | 1H NMR (400 MHz, DMSO-d6) δ 8.65 (d, J = 11.4 Hz, 1H), 8.20 (s, 1H), 8.16-8.06 (m, 3H), 7.55-7.42 (m, 3H), 7.34 (d, J = 7.7 Hz, 2H), 3.95 (m, 1H), 3.80 (m, 1H), 3.63 (m, 2H), 3.28 (m, 2H), 2.34-2.24 (m, 1H), 2.18 (m, 3H), 1.86 (s, 3H), 1.06 (t, J = 7.5 Hz, 6H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 139 | 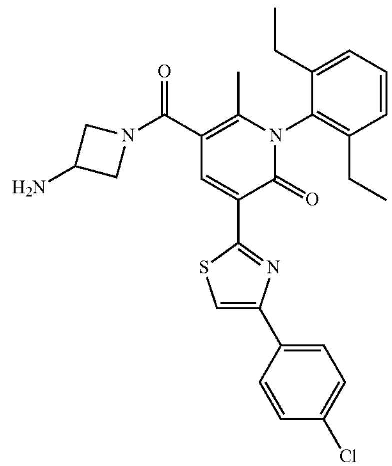 [SMILES: CCc1cccc(CC)c1-n1c(C)c(C(=O)N2CC(N)C2)cc(-c2nc(-c3ccc(Cl)cc3)cs2)c1=O] | C | C | 533.1776 | 2.65 | Starting materials: acid-compound 143, amine-tert-butyl azetidin-3-ylcarbamate; Method: U, then Boc removal with TFA/DCM rt | |
| 140 | 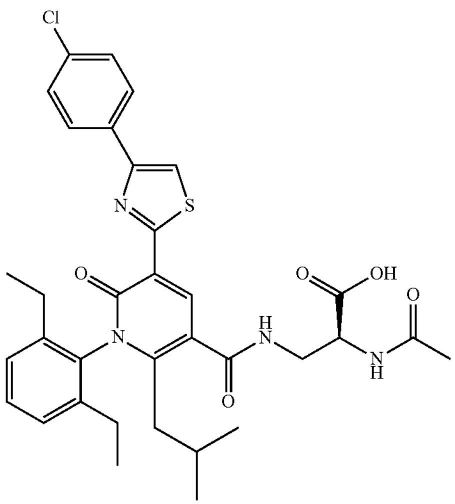 [SMILES: CCc1cccc(CC)c1-n1c(CC(C)C)c(C(=O)NC[C@H](NC(C)=O)C(=O)O)cc(-c2nc(-c3ccc(Cl)cc3)cs2)c1=O] | D | D | 649.2243 | 3.57 | Starting materials: acid-compound 14, amine-(S)-3-amino-2-((tert-butoxycarbonyl)amino)propanoic acid hydrochloride; Methods: U, then Boc removal with TFA/DCM rt, then acetylation with AcCl/NEt3 rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 141 | 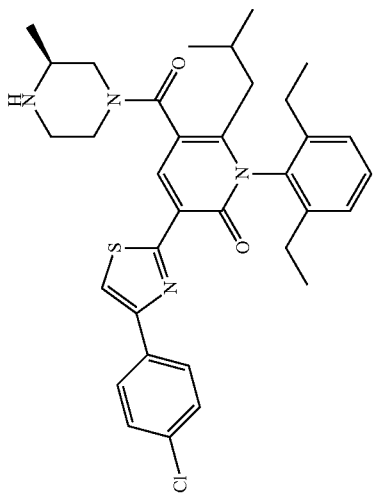 | B | A | 603.2546 | 2.876 | Starting materials: acid-compound 14, amine-(S)-tert-butyl 2-methylpiperazine-1-carboxylate; Method: U, then Boc removal with TFA/DCM rt | |
| 142 | 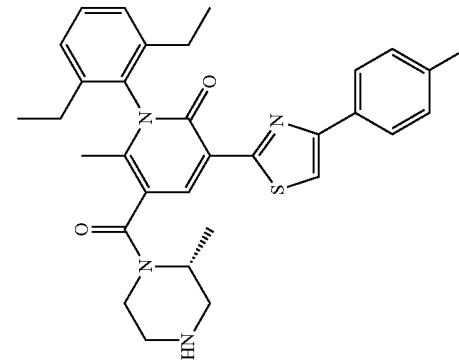 | A | B | 561.2091 | 2.727 | Starting materials: acid-compound 143, amine-(R)-tert-butyl 3-methylpiperazine-1-carboxylate; Methods: U, then Boc removal with TFA/DCM rt | 1H NMR of TFA salt (400 MHz, DMSO-d6) δ 9.10 (m, 1H), 8.60 (m, 2H), 8.21 (s, 1H), 8.10 (d, J = 8.2 Hz, 2H), 7.55-7.42 (m, 3H), 7.35 (d, J = 7.8 Hz, 2H), 3.31 (m, 5H), 2.38-2.03 (m, 5H), 1.86 (m, 3H), 1.31 (m, 4H), 1.06 (q, J = 7.1 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 143 | 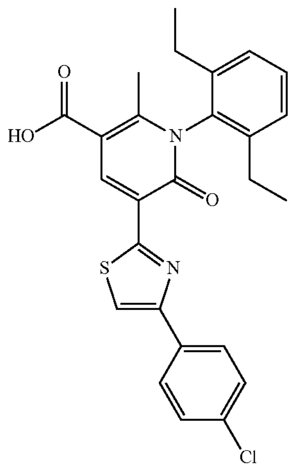 [SMILES: CCc1cccc(CC)c1-n1c(C)c(C(=O)O)cc(-c2nc(-c3ccc(Cl)cc3)cs2)c1=O] | D | D | 479.1186 | 3.835 | Compound 268 was hydrolyzed with LiOH (3 eq), THF/MeOH/water, 60° C. 22 h | |
| 144 | 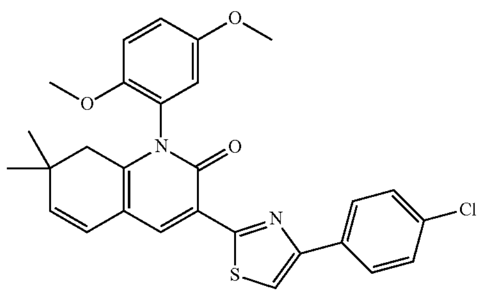 [SMILES: COc1ccc(OC)c(-n2c3c(cc(-c4nc(-c5ccc(Cl)cc5)cs4)c2=O)C=CC(C)(C)C3)c1] | C | C | 505.1351 | 4.152 | Starting materials: nitrile-1, aniline-2,5-dimethoxyaniline; Methods: A, then ketone reduction with NaBH4 (xs) in EtOH, 50° C. 24 h, then alcohol elimination with p-TsOH hydrate (cat.), dioxane, rt 4 h | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 145 | 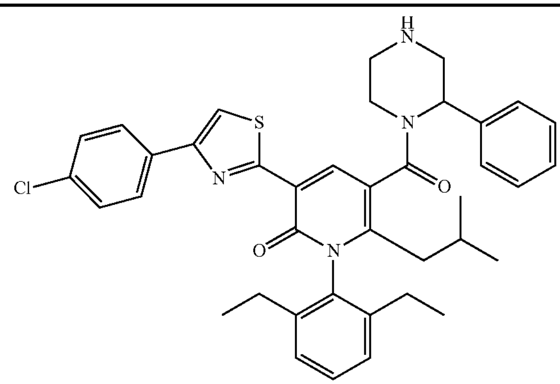 | B | A | 665.2721 | 3.024 | Starting materials: acid-compound 14, amine-tert-butyl 3-phenylpiperazine-1-carboxylate; Method: U, then Boc removal with TFA/DCM rt | |
| 146 | 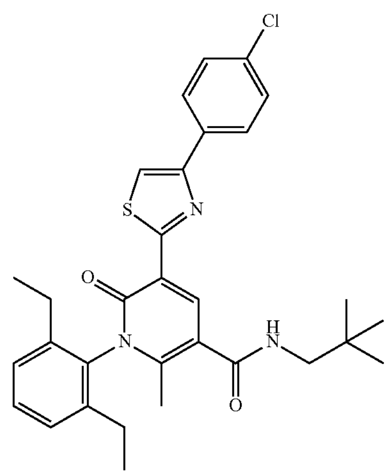 [SMILES: CCc1cccc(CC)c1-n1c(C)c(C(=O)NCC(C)(C)C)cc(-c2nc(-c3ccc(Cl)cc3)cs2)c1=O] | E | C | 548.2137 | 4.097 | Starting materials: acid-compound 143, amine-2,2-dimethylpropan-1-amine; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 147 | 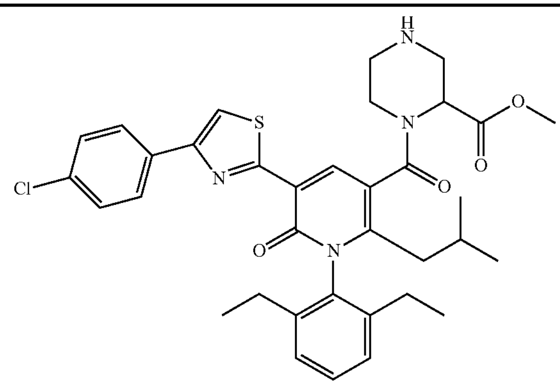 | C | A | 647.247 | 2.97 | Starting materials: acid-compound 14, amine-1-tert-butyl 3-methyl piperazine-1,3-dicarboxylate; Method: U, then Boc removal with TFA/DCM rt | |
| 148 | 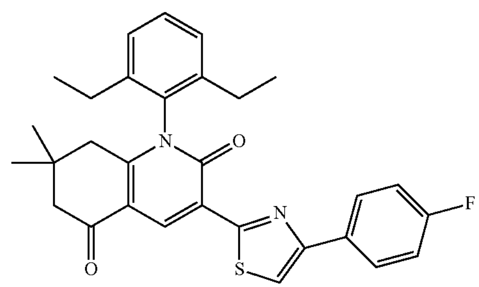 [SMILES: CCc1cccc(CC)c1-n1c2c(cc(-c3nc(-c4ccc(F)cc4)cs3)c1=O)C(=O)CC(C)(C)C2] | B | B | 501.1991 | 4.028 | Starting materials: nitrile-3, aniline-2,6-diethylaniline; Method: R | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 149 | 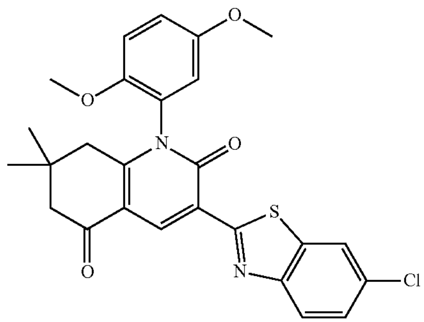 [SMILES: COc1ccc(OC)c(-n2c3c(cc(-c4nc5ccc(Cl)cc5s4)c2=O)C(=O)CC(C)(C)C3)c1] | E | C | 495.1159 | 3.787 | Starting materials: nitrile-2-(6-chlorobenzo[d]thiazol-2-yl)acetonitrile (synthesized by method v), aniline-2,5-dimethoxyaniline; Method: K | |
| 150 | 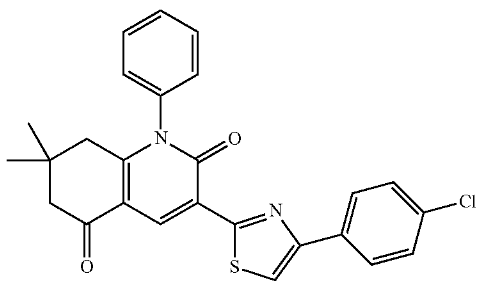 [SMILES: CC1(C)CC(=O)c2cc(-c3nc(-c4ccc(Cl)cc4)cs3)c(=O)n(-c3ccccc3)c2C1] | D | D | 461.1086 | 3.853 | Starting materials: nitrile-1, aniline-aniline; Method: A | |

TABLE 1-continued
Characterization and Enzymatic Inhibition Data for Selected Compounds
| Cpd # | Structure | Data for R132H (μM) | Data for R132C (μM) | MZ | RT (min) | Synthesis Method | 1H-NMR |
|---|---|---|---|---|---|---|---|
| 151 | 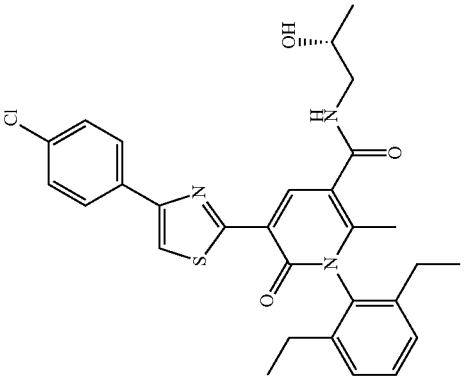 | C | B | 536.1768 | 3.595 | Starting materials: acid-compound 143, amine-(R)-1-aminopropan-2-ol; Method: U | |
| 152 | 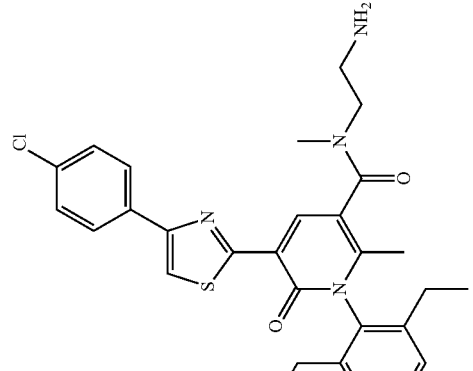 | C | C | 557.1734 | 2.696 | Starting materials: acid-compound 143, amine-tert butyl (2-(methylamino)ethyl)carbamate; Method: U, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 153 | 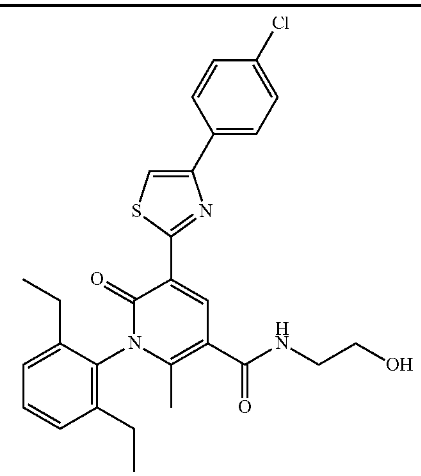 | B | C | 522.1627 | 3.505 | Starting materials: acid-compound 143, amine-2-aminoethanol; Method: U | |
| 154 | 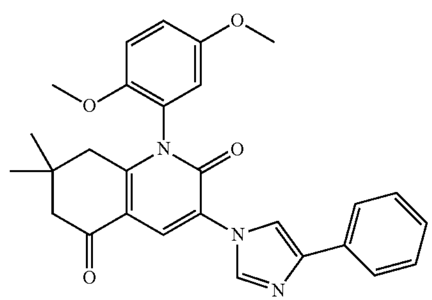 [SMILES: COc1ccc(OC)c(-n2c3c(cc(-n4cnc(-c5ccccc5)c4)c2=O)C(=O)CC(C)(C)C3)c1] | D | D | 470.2095 | 3.02 | Starting materials: nitrile-2-(4-phenyl-1H-imidazol-1-yl)acetonitrile (synthesized by method xvi), aniline-2,5-dimethoxyaniline; Method: O | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 155 | 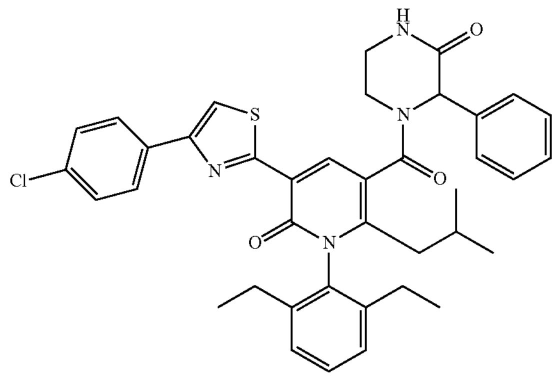 [SMILES: CCc1cccc(CC)c1-n1c(CC(C)C)c(C(=O)N2CCNC(=O)C2c2ccccc2)cc(-c2nc(-c3ccc(Cl)cc3)cs2)c1=O] | B | A | 679.2475 | 3.911 | Starting materials: acid-compound 14, amine-3-phenylpiperazin-2-one; Method: U | |
| 156 | 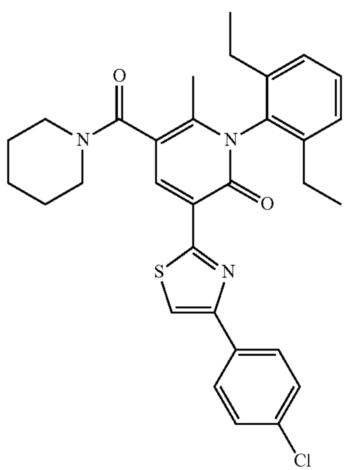 [SMILES: CCc1cccc(CC)c1-n1c(C)c(C(=O)N2CCCCC2)cc(-c2nc(-c3ccc(Cl)cc3)cs2)c1=O] | C | C | 546.1998 | 4.064 | Starting materials: acid-compound 143, amine-piperidine; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 157 | 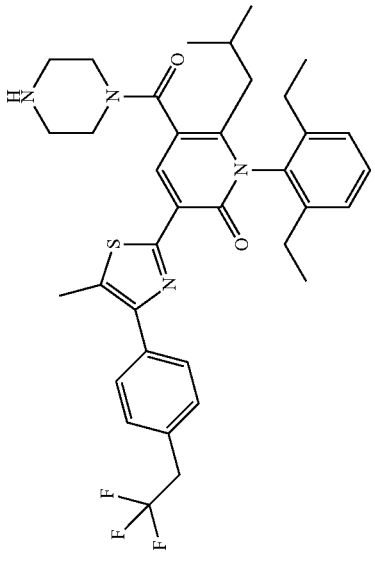 | B | A | 653.2787 | 3.335 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-(trifluoromethoxy)phenyl)boronic acid (method xix); Methods: S, then ester hydrolyzed with LiOH (0.5M), THF, rt, U, xix, then Boc removal with TFA/DCM rt | |
| 158 | 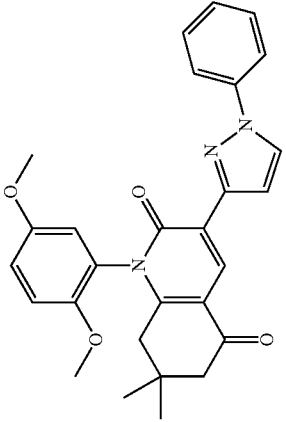 | C | C | 470.2074 | 3.539 | Starting materials: nitrile-2-(1-phenyl-1H)-pyrazol-3-yl)acetonitrile (synthesized by method vii), aniline-2,5-dimethoxyaniline; Method: M | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 159 | 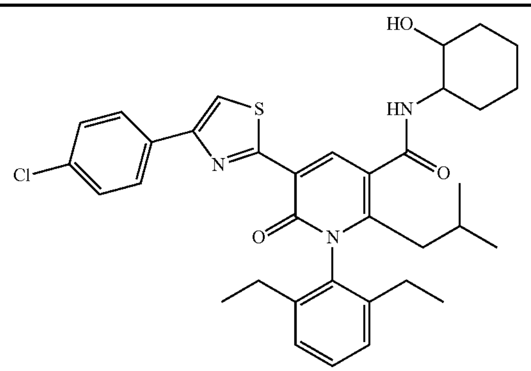 | C | C | 618.2541 | 4.006 | Starting materials: acid compound 14, amine-2 aminocyclohexanol; Method: U | |
| 160 | 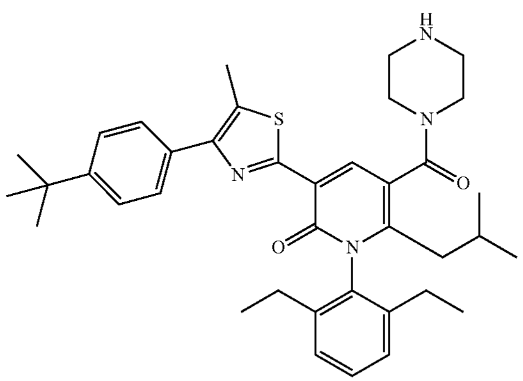 [SMILES: CCc1cccc(CC)c1-n1c(CC(C)C)c(C(=O)N2CCNCC2)cc(-c2nc(-c3ccc(C(C)(C)C)cc3)c(C)s2)c1=O] | C | C | 647.3407 | 3.438 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-(tert-butyl)phenyl)boronic acid (method xix); Methods: S, then ester hydrolyzed with LiOH (0.5M), THF, rt, U, xix, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 161 | 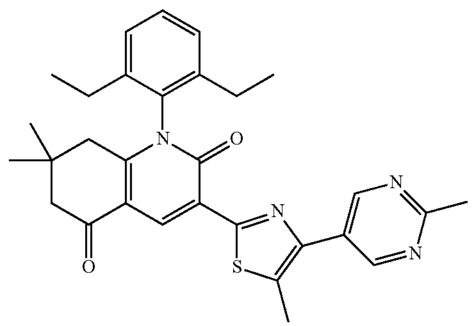 | D | C | 513.2321 | 3.813 | Starting material: boryl species-2-methyl-5-(4,4,5,5-tetramethyl-1,3,2-dioxaborolan-2-yl)pyrimidine; Method: xix | |
| 162 | 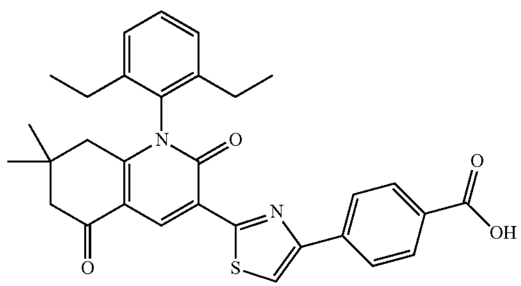 [SMILES: CCc1cccc(CC)c1-n1c2c(cc(-c3nc(-c4ccc(C(=O)O)cc4)cs3)c1=O)C(=O)CC(C)(C)C2] | E | D | 527.2023 | 3.688 | Starting materials: nitrile-22, aniline-2,6-diethylaniline; Methods: (Q, then hydrolysis of the ester with LiOH (5 eq), THF/MeOH/water | |
| 163 | 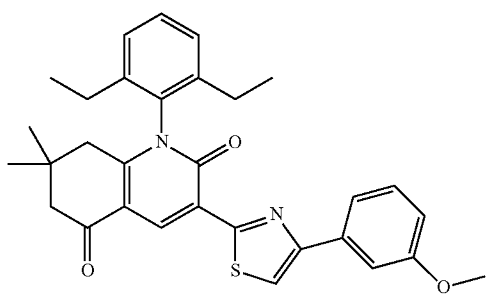 | E | E | 513.2186 | 3.981 | Starting materials: nitrile-17, aniline-2,6-diethylaniline; Method: R | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 164 | 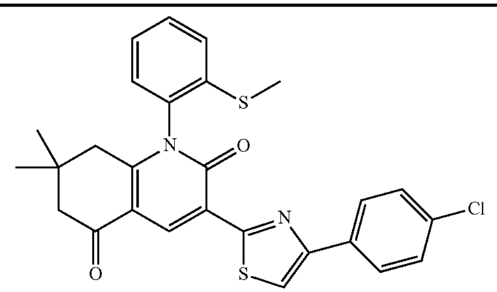 | C | B | 507.0971 | 3.917 | Starting materials: nitrile-1, aniline-2-(methylthio)aniline; Method: E | (400 MHz, DMSO-d6) δ 8.73 (dd, J = 7.2, 2.1Hz, 1H), 8.20 (s, 1H), 8.16-8.07 (m, 2H), 7.79 (dd, J = 6.6, 2.1 Hz, 1H), 7.59-7.51 (m, 2H), 7.33 (d, J = 8.6 Hz, 1H), 6.81 (d, J = 2.6 Hz, 1H), 6.72-6.58 (m, 2H), 3.87 (s, 3H), 3.78 (s, 3H) |
| 165 | 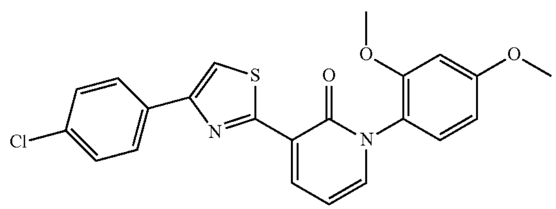 [SMILES: COc1ccc(-n2cccc(-c3nc(-c4ccc(Cl)cc4)cs3)c2=O)c(OC)c1] | E | E | 425.0717 | 3.801 | Method: ii | |
| 166 | 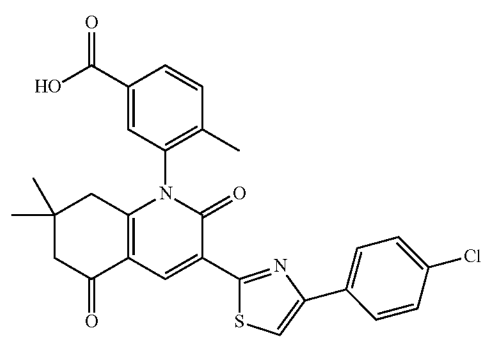 [SMILES: Cc1ccc(C(=O)O)cc1-n1c2c(cc(-c3nc(-c4ccc(Cl)cc4)cs3)c1=O)C(=O)CC(C)(C)C2] | E | D | 519.1148 | 3.682 | Starting materials: nitrile-1, aniline-3-amino-4-methylbenzoic acid; Method: A (step 2-45° C., step 3-70° C. 2.5 h) | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 167 | 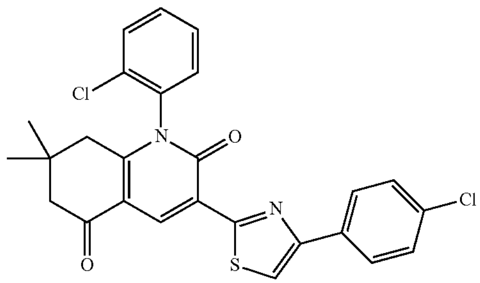 [SMILES: CC1(C)CC(=O)c2cc(-c3nc(-c4ccc(Cl)cc4)cs3)c(=O)n(-c3ccccc3Cl)c2C1] | A | A | 495.0716 | 3.956 | Starting materials: nitrile-1, aniline-2-chloroaniline; Method: E | |
| 168 | 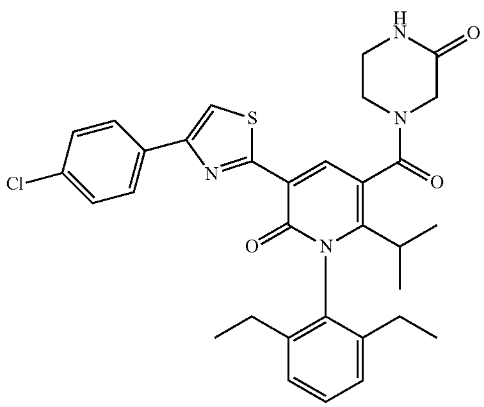 [SMILES: CCc1cccc(CC)c1-n1c(C(C)C)c(C(=O)N2CCNC(=O)C2)cc(-c2nc(-c3ccc(Cl)cc3)cs2)c1=O] | B | B | 589.2019 | 3.625 | Starting materials: acid-compound 98, amine-piperazin-2-one; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 169 | 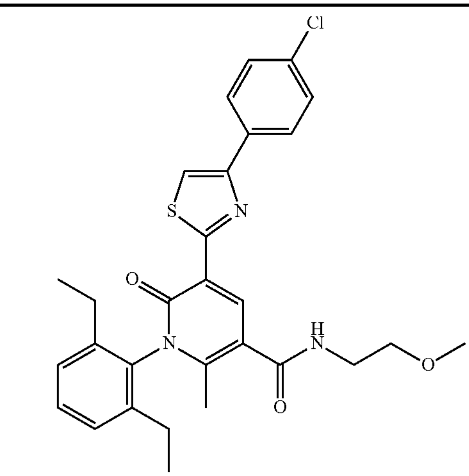 | C | B | 536.1774 | 3.789 | Starting materials: acid-compound 143, amine-2-methoxyethanamine; Method: U | |
| 170 | 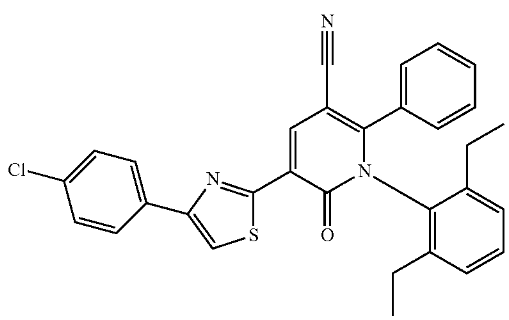 [SMILES: CCc1cccc(CC)c1-n1c(-c2ccccc2)c(C#N)cc(-c2nc(-c3ccc(Cl)cc3)cs2)c1=O] | D | C | 522.1404 | 4.11 | Method: T | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 171 | 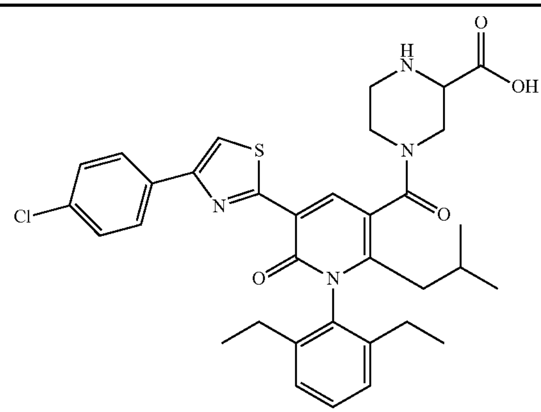 | A | A | 633.2325 | 3.122 | Starting materials: acid-compound 14, amine-1-tert-butyl 2-methyl piperazine-1,2-dicarboxylate; Method: U, then Boc removal with TFA/DCM rt, then hydrolyzed with LiOH (0.5M), THF, rt | ¹H NMR (400 MHz, DMSO-$d_6$) δ 8.71 (d, J = 46.4 Hz, 1H), 8.24 (s, 1H), 8.13 (d, J = 8.1 Hz, 2H), 7.51 (dd, J = 15.7, 8.0 Hz, 3H), 7.37 (d, J = 7.2 Hz, 2H), 4.72-3.76 (m, 2H), 3.69-3.38 (m, 7H), 2.45-1.98 (m, 4H), 1.34 (s, 1H), 1.22-1.00 (m, 7H), 0.77-0.49 (m, 7H). Aliphatic region complicated significantly by amide rotamers. |
| 172 | 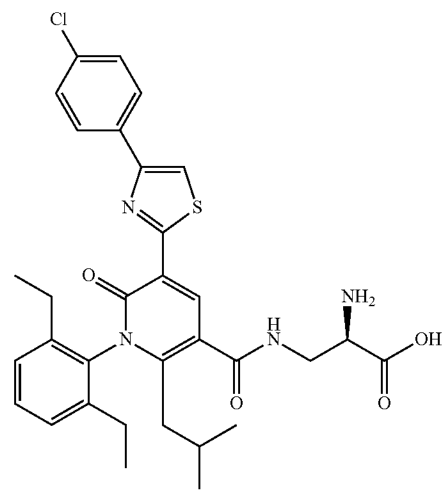 [SMILES: CCc1cccc(CC)c1-n1c(CC(C)C)c(C(=O)NC[C@@H](N)C(=O)O)cc(-c2nc(-c3ccc(Cl)cc3)cs2)c1=O] | B | A | 607.2155 | 3.056 | Starting materials: acid-compound 14, amine-(R)-3-amino-2-((tert-butoxycarbonyl)amino)propanoic acid hydrochloride; Methods: U, then Boc removal with TFA/DCM rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 173 | 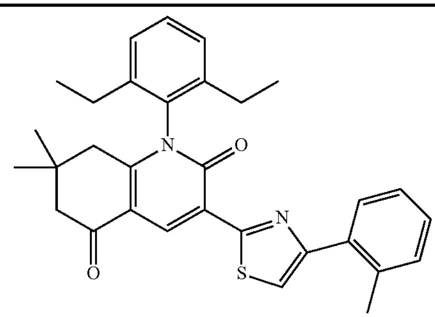 | C | C | 497.2258 | 4.099 | Starting materials: nitrile-19, aniline-2,6-diethylaniline; Method: R | |
| 174 | 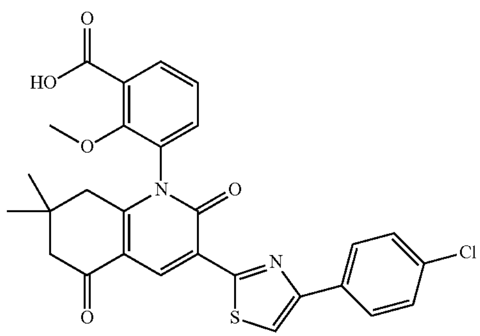 [SMILES: COc1c(C(=O)O)cccc1-n1c2c(cc(-c3nc(-c4ccc(Cl)cc4)cs3)c1=O)C(=O)CC(C)(C)C2] | E | D | 535.1078 | 3.604 | Starting materials: nitrile-1, aniline-3-amino-2-methoxybenzoic acid; Method: A (step 2-45° C., step 3-70° C. 2.5 h) | |
| 175 | 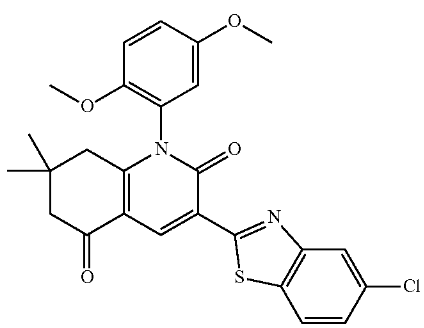 [SMILES: COc1ccc(OC)c(-n2c3c(cc(-c4nc5cc(Cl)ccc5s4)c2=O)C(=O)CC(C)(C)C3)c1] | A | B | 495.1138 | 3.795 | Starting materials: nitrile-2-(5-chlorobenzo[d]thiazol-2-yl)acetonitrile (synthesized by method v), aniline-2,5-dimethoxyaniline; Method-K | |

TABLE 1-continued
Characterization and Enzymatic Inhibition Data for Selected Compounds
| Cpd # | Structure | Data for R132H (μM) | Data for R132C (μM) | MZ | RT (min) | Synthesis Method | 1H-NMR |
|---|---|---|---|---|---|---|---|
| 176 | 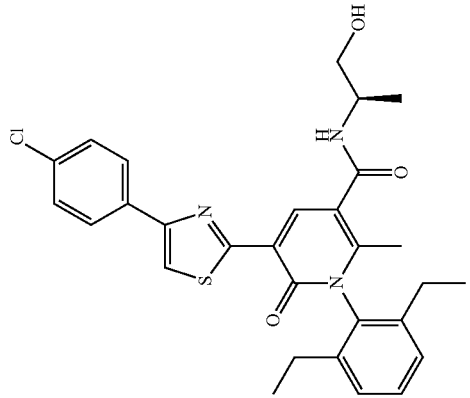 | C | C | 536.1778 | 3.576 | Starting materials: acid-compound 143, amine-(R)-2-aminopropan-1-ol; Method: U | |
| 177 | 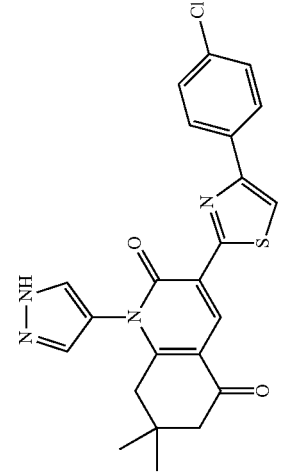 Comparative example | D | D | 479.1303 | 3.56 | | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 178 | 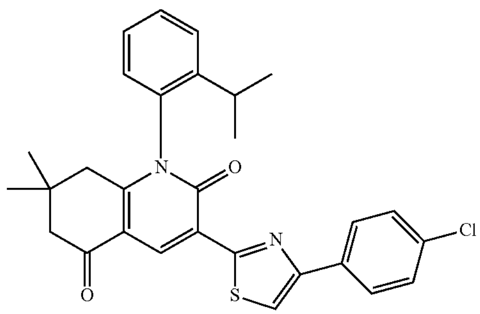 [SMILES: CC(C)c1ccccc1-n1c2c(cc(-c3nc(-c4ccc(Cl)cc4)cs3)c1=O)C(=O)CC(C)(C)C2] | B | B | 503.1558 | 4.121 | Starting materials: nitrile-1, aniline-2-isopropylaniline; Method: E | |
| 179 | 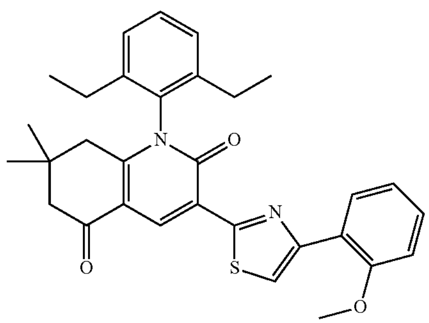 [SMILES: CCc1cccc(CC)c1-n1c2c(cc(-c3nc(-c4ccccc4OC)cs3)c1=O)C(=O)CC(C)(C)C2] | C | C | 535.2006 | 4.034 | Starting materials: nitrile-16, aniline-2,6-diethylaniline; Method: R | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 180 | 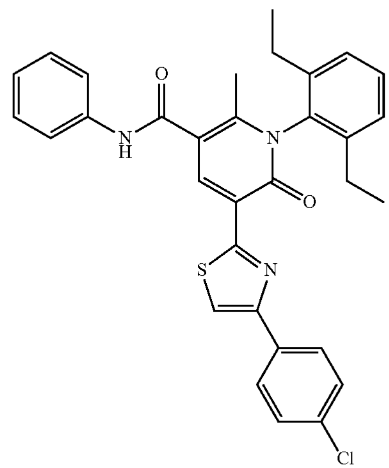 [SMILES: CCc1cccc(CC)c1-n1c(C)c(C(=O)Nc2ccccc2)cc(-c2nc(-c3ccc(Cl)cc3)cs2)c1=O] | E | E | 554.1682 | 4.043 | Starting materials: acid-compound 143, amine-aniline; Method: U | |
| 181 | 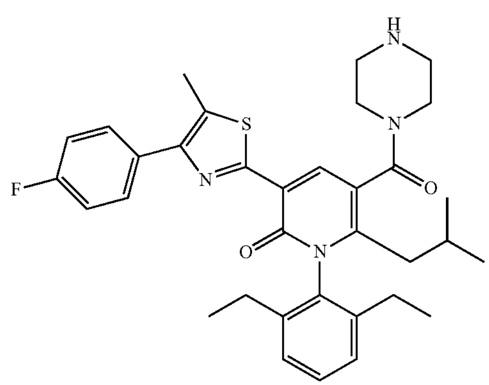 [SMILES: CCc1cccc(CC)c1-n1c(CC(C)C)c(C(=O)N2CCNCC2)cc(-c2nc(-c3ccc(F)cc3)c(C)s2)c1=O] | A | A | 587.285 | 3.187 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-fluorophenyl)boronic acid (method xix); Methods: S, then ester hydrolyzed with LiOH (0.5M), THF, rt, U, xix, then Boc removal with TFA/DCM rt | ¹H NMR (400 MHz, DMSO-$d_6$) δ 8.82 (d, J = 52.4 Hz, 1H), 8.57 (d, J = 1.0 Hz, 1H), 7.86-7.77 (m, 2H), 7.50 (t, J = 7.6 Hz, 1H), 7.40-7.28 (m, 4H), 4.03 (s, 1H), 3.76 (s, OH), 3.60 (d, J = 29.2 Hz, 2H), 3.14 (d, J = 55.3 Hz, 5H), 2.56 (d, J = 1.0 Hz, 3H), 2.42-2.26 (m, 2H), 2.26-1.93 (m, 4H), 1.33 (dt, J = 13.6, 6.8 Hz, 1H), 1.10 (d, J = 8.8 Hz, 6H), 0.62 (d, J = 6.5 Hz, 6H). Aliphatic region complicated significantly by amide rotamers. |

TABLE 1-continued
Characterization and Enzymatic Inhibition Data for Selected Compounds
| Cpd # | Structure | Data for R132H (μM) | Data for R132C (μM) | MZ | RT (min) | Synthesis Method | 1H-NMR |
|---|---|---|---|---|---|---|---|
| 182 | 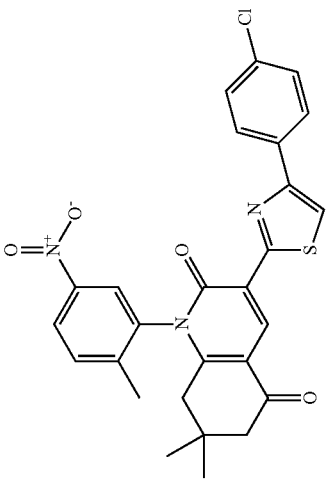 | C | C | 520.1104 | 3.834 | Starting materials: nitrile-1, aniline-2-methyl-5-nitroaniline; Method: A (step 2-45° C., step 3-70° C. 2.5 h) | |
| 183 | 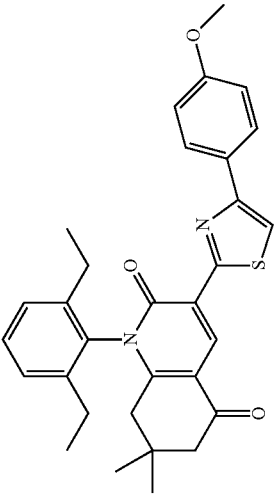 | B | B | 513.22 | 3.98 | Starting materials: nitrile-4, aniline-2,6-diethylaniline; Method: R | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 184 | 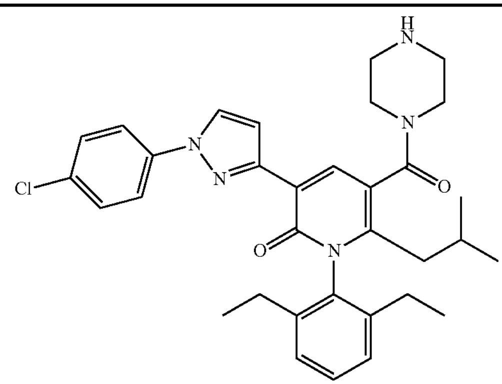 | A | A | 572.2776 | 3.026 | Starting materials: methyl 5-methyl-3-oxohexanoate (step 1), 2-(1-(4-chlorophenyl)-1H-pyrazol-3-yl)acetonitrile (used in method U); Methods: S (following additon of acetic acid and aniline heat 45° C. 3 h then extract and heat in DMF), then ester hydrolyzed with LiOH (xs), THF/MeOH/water, 50° C.; U | 1H NMR of TFA salt (400 MHz, DMSO-d6) δ 8.73 (br s, 2H), 8.54 (d, J = 2.5 Hz, 1H), 8.29 (s, 1H), 8.00-7.93 (m, 2H), 7.61-7.54 (m, 2H), 7.50-7.38 (m, 1H), 7.32 (d, J = 7.7 Hz, 2H), 7.20-7.12 (m, 1H), 4.01 (s, 1H), 3.74 (s, 1H), 3.57 (m, 2H), 3.20 (m, 2H), 3.07 (m, 1H), 2.91 (m, 1H), 2.28 (m, 2H), 1.93 (m, 1H), 1.35-1.19 (m, 1H), 1.09 (s, 6H), 0.60 (d, J = 6.6 Hz, 6H). Aliphatic region complicated significantly by amide rotamers. |
| 185 | 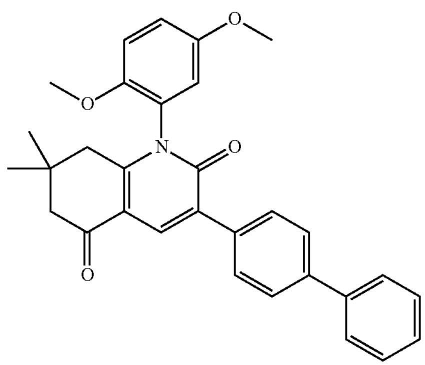 [SMILES: COc1ccc(OC)c(-n2c3c(cc(-c4ccc(-c5ccccc5)cc4)c2=O)C(=O)CC(C)(C)C3)c1] | E | E | 480.2176 | 3.719 | Starting materials: nitrile-2-([1,1'-biphenyl]-4-yl)acetonitrile, aniline-2,5-dimethoxyaniline; Method: M | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 186 | 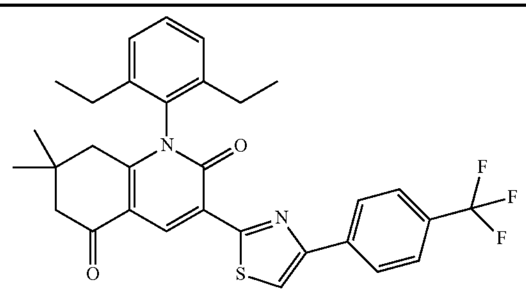 | B | A | 551.1968 | 4.121 | Starting materials: nitrile-7, aniline-2,6-diethylaniline; Method: R | |
| 187 | 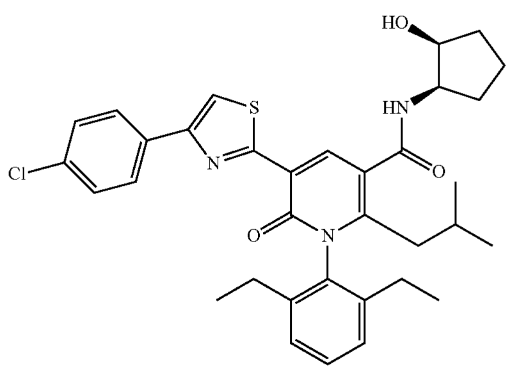 [SMILES: CCc1cccc(CC)c1-n1c(CC(C)C)c(C(=O)N[C@@H]2CCC[C@@H]2O)cc(-c2nc(-c3ccc(Cl)cc3)cs2)c1=O] | B | B | 604.2377 | 4.009 | Starting materials: acid-compound 14, amine-cis-2-aminocyclopentanol; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 188 | 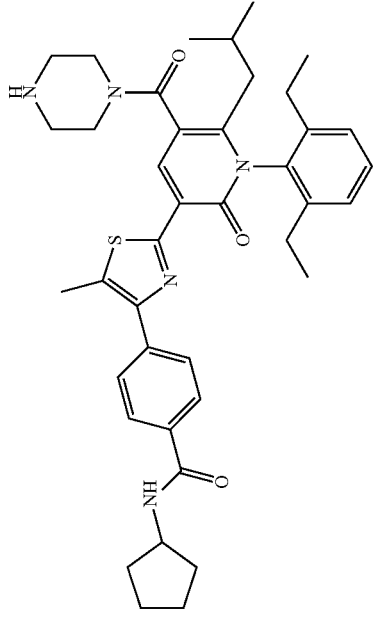 | D | D | 340.6861 | 3.112 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-(cyclopentylcarbamoyl)phenyl)boronic acid (method xix); Methods: S, then ester hydrolyzed with LiOH (0.5M), THF, rt, U, xix, then Boc removal with TFA/DCM rt | |
| 189 | 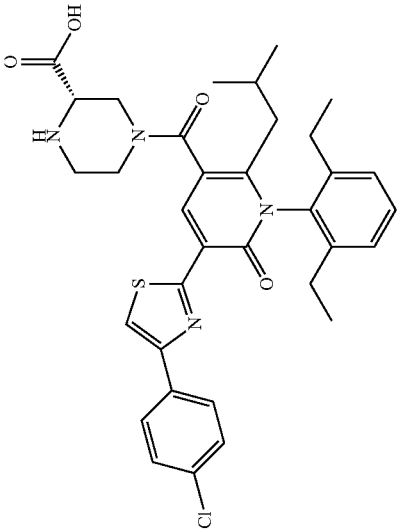 | B | A | 633.2321 | 3.129 | Compound 2 was hydrolyzed with LiOH (xs), THF/MeOH/water, 50° C. 1.75 h | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 190 | 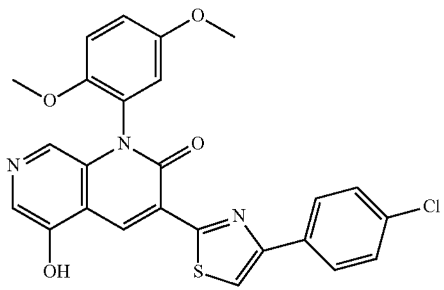 [SMILES: COc1ccc(OC)c(-n2c(=O)c(-c3nc(-c4ccc(Cl)cc4)cs3)cc3c(O)cncc32)c1] | E | E | 492.0784 | 3.457 | This oxidized product is produced as a byproduct in the course of the Boc deprotection to generate compound 280 | |
| 191 | 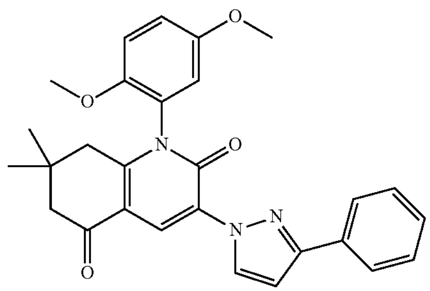 [SMILES: COc1ccc(OC)c(-n2c3c(cc(-n4ccc(-c5ccccc5)n4)c2=O)C(=O)CC(C)(C)C3)c1] | C | C | 470.2074 | 3.66 | Starting materials: nitrile-2-(3-phenyl-1H-pyrazol-1-yl)acetonitrile (synthesized by method xvi), aniline-2,5-dimethoxyaniline; Method: O | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 192 | 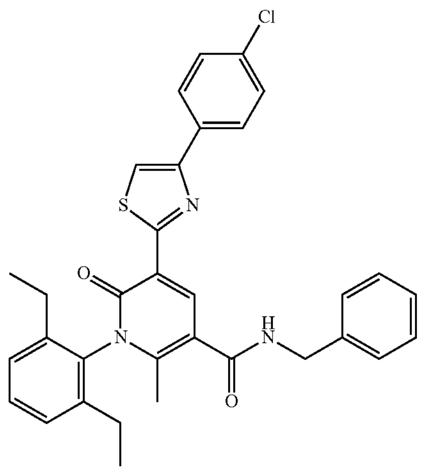 [SMILES: CCc1cccc(CC)c1-n1c(C)c(C(=O)NCc2ccccc2)cc(-c2nc(-c3ccc(Cl)cc3)cs2)c1=O] | E | C | 568.1842 | 3.966 | Starting materials: acid-compound 143, amine-benzylamine; Method: U | |
| 193 | 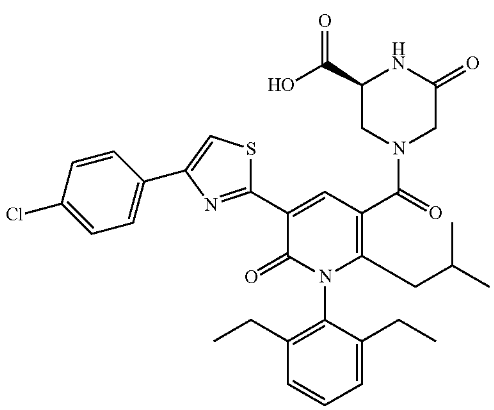 [SMILES: CCc1cccc(CC)c1-n1c(CC(C)C)c(C(=O)N2CC(=O)N[C@H](C(=O)O)C2)cc(-c2nc(-c3ccc(Cl)cc3)cs2)c1=O] | B | B | 647.2077 | 3.592 | Starting materials: acid-compound 14, amine-(S)-methyl 6-oxopiperazine-2-carboxylate (xxi); Methods: U, then ester cleavage with LiOH/water/THF rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 194 | 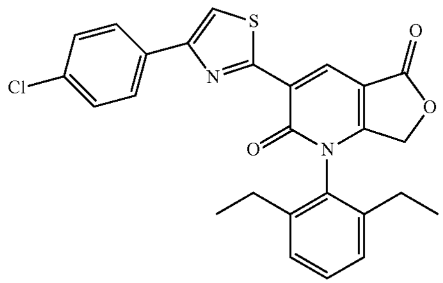 [SMILES: CCc1cccc(CC)c1-n1c2c(cc(-c3nc(-c4ccc(Cl)cc4)cs3)c1=O)C(=O)OC2] | E | D | 477.1041 | 3.925 | Starting materials: nitrile-1, aniline-2,6-diethylaniline, dicarbonyl-4-hydroxyfuran-2(5H)-one; Method: N (step 1- 50° C. 0.25 h, step 3-50° C. 1 h then 80° C. 3 h) | |
| 195 | 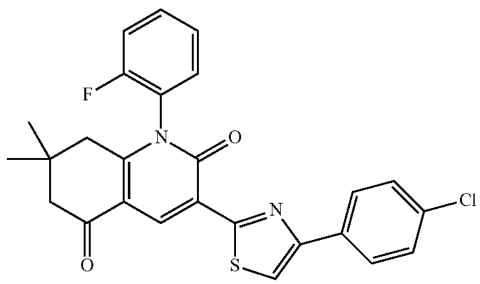 | B | B | 479.0991 | 3.885 | Starting materials: nitrile-1, aniline-2-fluoroaniline; Method: E | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 196 | 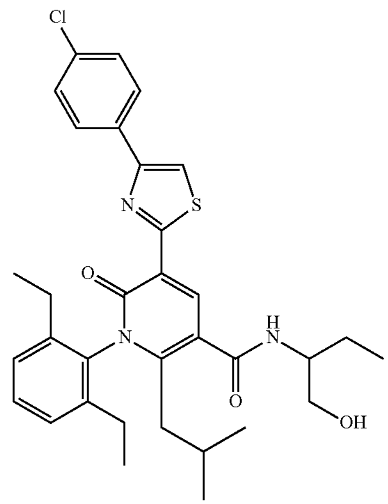 [SMILES: CCc1cccc(CC)c1-n1c(CC(C)C)c(C(=O)NC(CC)CO)cc(-c2nc(-c3ccc(Cl)cc3)cs2)c1=O] | C | A | 592.2381 | 3.896 | Starting materials: acid compound 14, amine-2-aminobutan-1-ol; Method: U | |
| 197 | 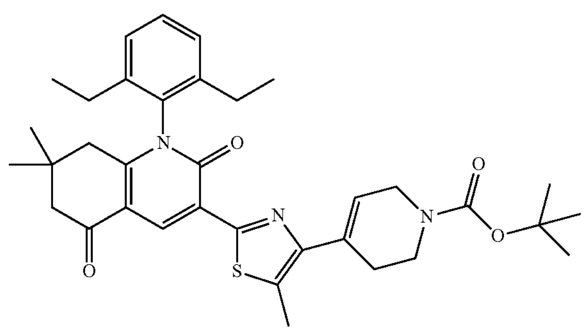 [SMILES: CCc1cccc(CC)c1-n1c2c(cc(-c3nc(C4=CCN(C(=O)OC(C)(C)C)CC4)c(C)s3)c1=O)C(=O)CC(C)(C)C2] | C | D | 602.3029 | 4.203 | Starting material: boryl species-tert-butyl 4-(4,4,5,5-tetramethyl-1,3,2-dioxaborolan-2-yl)-5,6-dihydropyridine-1(2H)-carboxylate; Method: xix | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 198 | 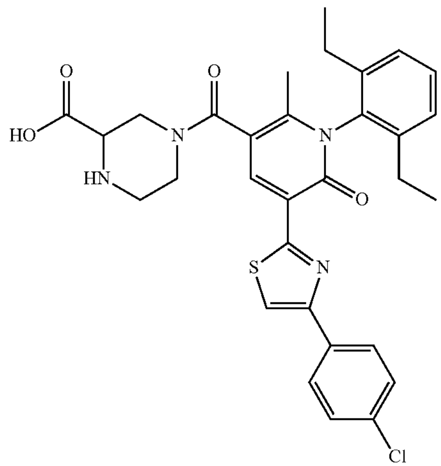 [SMILES: CCc1cccc(CC)c1-n1c(C)c(C(=O)N2CCNC(C(=O)O)C2)cc(-c2nc(-c3ccc(Cl)cc3)cs2)c1=O] | B | B | 591.1846 | 2.894 | Starting materials: acid-compound 143, amine-1-tert butyl 2-methyl piperazine-1,2-dicarboxylate; Method: U, then Boc removal with TFA/DCM rt, then hydrolyzed with LiOH(0.5M), THF, rt | |
| 199 | 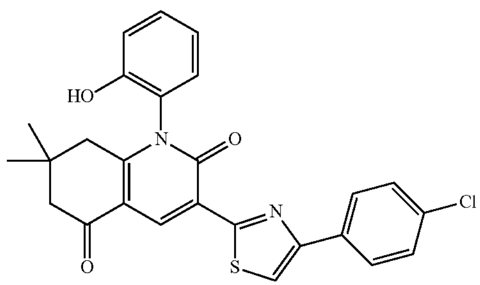 [SMILES: CC1(C)CC(=O)c2cc(-c3nc(-c4ccc(Cl)cc4)cs3)c(=O)n(-c3ccccc3O)c2C1] | D | D | 477.1046 | 3.642 | Starting materials: nitrile-1, aniline-2-hydroxyaniline; Method: E | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 200 | 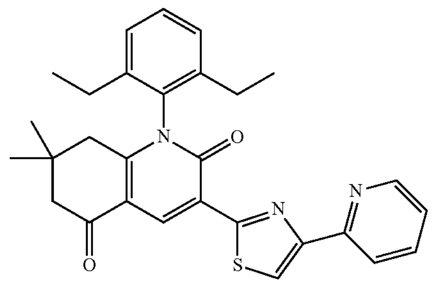 [SMILES: CCc1cccc(CC)c1-n1c2c(cc(-c3nc(-c4ccccn4)cs3)c1=O)C(=O)CC(C)(C)C2] | D | C | 506.1872 | 3.732 | Starting materials: nitrile-10, aniline-2,6-diethylaniline; Method: Q | |
| 201 | 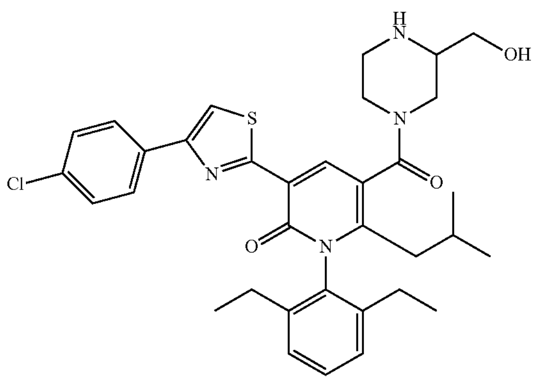 [SMILES: CCc1cccc(CC)c1-n1c(CC(C)C)c(C(=O)N2CCNC(CO)C2)cc(-c2nc(-c3ccc(Cl)cc3)cs2)c1=O] | A | A | 641.2333 | 2.82 | Starting materials: acid-compound 14, amine-tert-butyl 2-(hydroxymethyl)piperazine-1-carboxylate; Method: U, then Boc removal with TFA/DCM rt | ¹H NMR (400 MHz, DMSO-d₆) δ 9.26 (s, 1H), 8.89-8.61 (m, 1H), 8.24 (s, 1H), 8.14 (d, J = 8.0 Hz, 2H), 7.58-7.51 (m, 2H), 7.49 (d, J = 7.7 Hz, 1H), 7.38 (s, 1H), 7.36 (s, 1H), 5.52 (d, J = 38.4 Hz, 2H), 4.59 (s, 1H), 3.93 (s, 1H), 3.82-3.55 (m, 2H), 3.36-2.91 (m, 4H), 2.47-1.90 (m, 3H), 1.34 (d, J = 18.8 Hz, 1H), 1.10 (dq, J = 7.8, 4.5 Hz, 8H), 0.67 (dd, J = 31.1, 7.9 Hz, 7H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 202 | 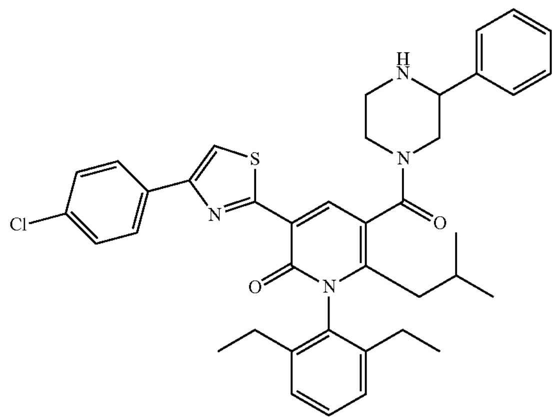 [SMILES: CCc1cccc(CC)c1-n1c(CC(C)C)c(C(=O)N2CCNC(c3ccccc3)C2)cc(-c2nc(-c3ccc(Cl)cc3)cs2)c1=O] | B | A | 665.2727 | 3.061 | Starting materials: acid compound 14, amine 2, amine-2 phenylpiperazine; Method: U | |
| 203 | 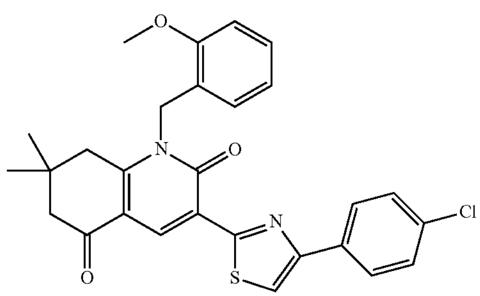 [SMILES: COc1ccccc1Cn1c2c(cc(-c3nc(-c4ccc(Cl)cc4)cs3)c1=O)C(=O)CC(C)(C)C2] | C | C | 505.1334 | 3.997 | Starting materials: nitrile-1, amine subst for aniline-(2-methoxyphenyl)methan amine; Method: F | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 204 | 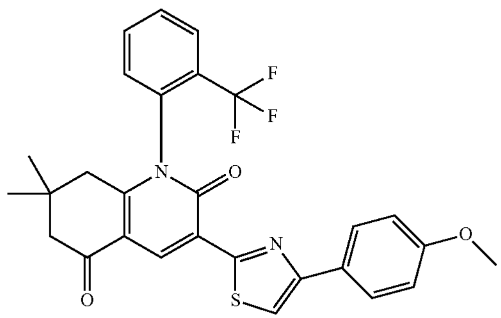 | C | B | 525.1452 | 3.766 | Starting materials: nitrile-4, aniline-2-trifluoromethylaniline; Method: I | |
| 205 | 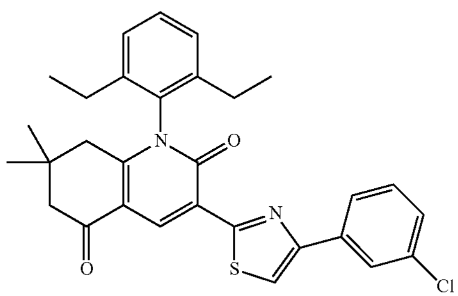 [SMILES: CCc1cccc(CC)c1-n1c2c(cc(-c3nc(-c4cccc(Cl)c4)cs3)c1=O)C(=O)CC(C)(C)C2] | E | C | 517.1713 | 4.179 | Starting materials: nitrile-14, aniline-2,6-diethylaniline; Method: R | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 206 | 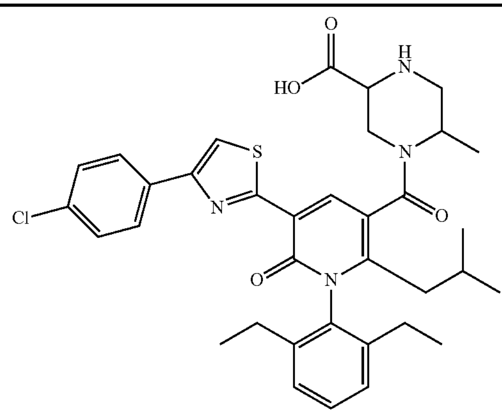 | B | A | 647.2478 | 3.23 | Compound 113 was hydrolyzed with LiOH (xs), THF/MeOH/water, 50° C 1.75 h | |
| 207 | 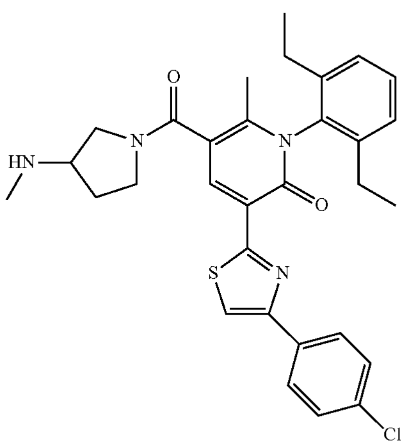 [SMILES: CCc1cccc(CC)c1-n1c(C)c(C(=O)N2CCC(NC)C2)cc(-c2nc(-c3ccc(Cl)cc3)cs2)c1=O] | C | C | 583.1914 | 2.679 | Starting materials: acid-compound 143, amine-tert-butyl methyl(pyrrolidin-3-yl)carbamate; Method: U, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 208 | 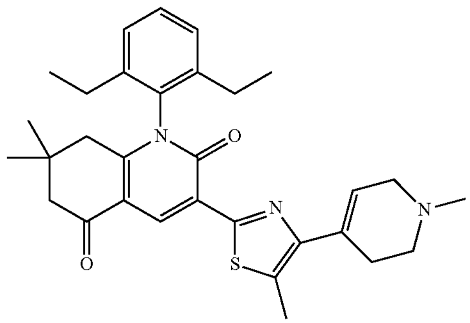 | E | D | 516.2666 | 2.725 | Method: xix | |
| 209 | 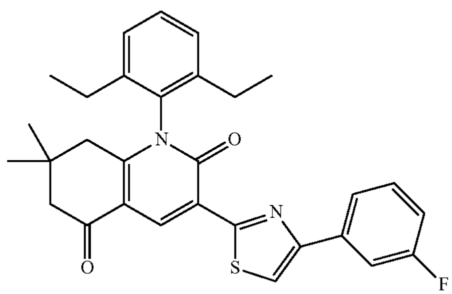 [SMILES: CCc1cccc(CC)c1-n1c2c(cc(-c3nc(-c4cccc(F)c4)cs3)c1=O)C(=O)CC(C)(C)C2] | C | C | 501.1988 | 4.039 | Starting materials: nitrile-12, aniline-2,6-diethylaniline; Method: R | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | $^1$H-NMR |
|---|---|---|---|---|---|---|---|
| 210 | 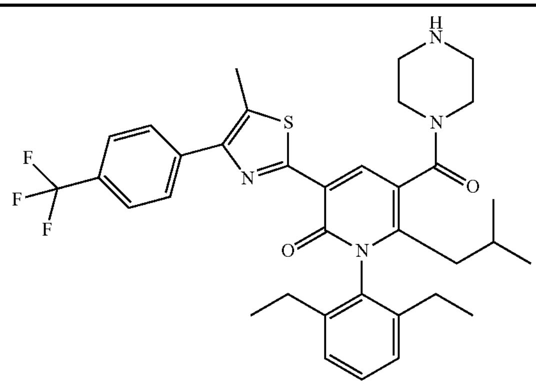 | B | A | NA | NA | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-(trifluoromethyl)phenyl) boronic acid (method xix); Methods: S, then ester hydrolyzed with LiOH (0.5M), THF, rt, U, xix, then Boc removal with TFA/DCM rt | |
| 211 | 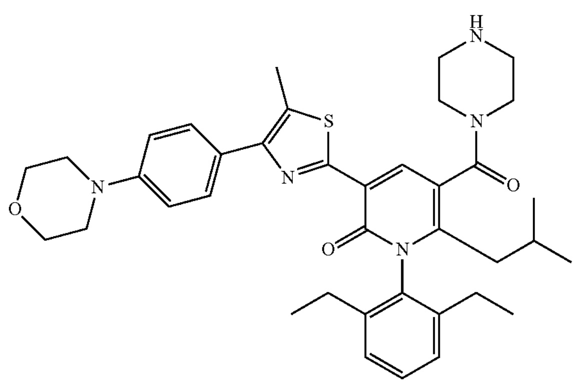 [SMILES: CCc1cccc(CC)c1-n1c(CC(C)C)c(C(=O)N2CCNCC2)cc(-c2nc(-c3ccc(N4CCOCC4)cc3)c(C)s2)c1=O] | D | D | 654.3449 | 3.071 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), 4-(4-(4,4,5,5-tetramethyl-1,3,2-dioxaborolan-2-yl)phenyl) morpholine (method xix); Methods: S, then ester hydrolyzed with LiOH (0.5M), THF, rt, U, xix, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 212 | 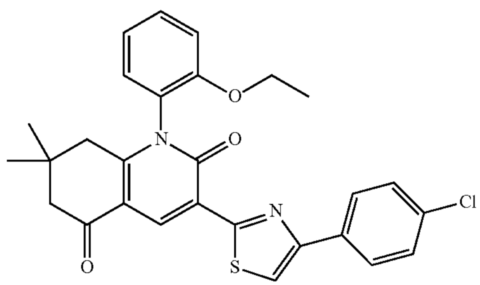 [SMILES: CCOc1ccccc1-n1c2c(cc(-c3nc(-c4ccc(Cl)cc4)cs3)c1=O)C(=O)CC(C)(C)C2] | B | B | 505.1354 | 3.927 | Starting materials: nitrile-1, aniline-2-ethoxyaniline; Method: E | |
| 213 | 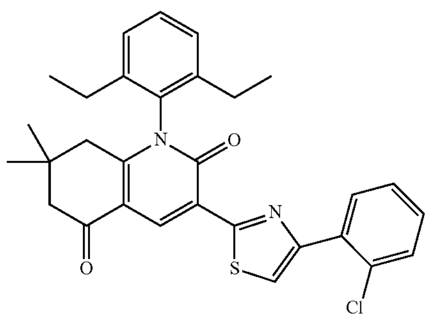 [SMILES: CCc1cccc(CC)c1-n1c2c(cc(-c3nc(-c4ccccc4Cl)cs3)c1=O)C(=O)CC(C)(C)C2] | C | C | 539.1508 | 4.155 | Starting materials: nitrile-13, aniline-2,6-diethylaniline; Method: R | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 214 | 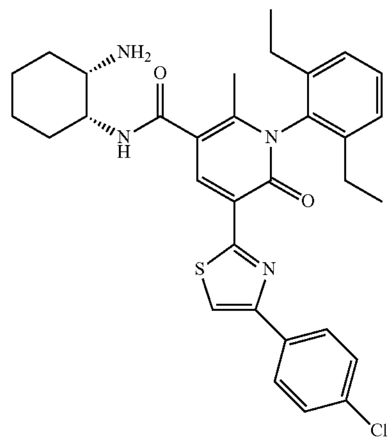 [SMILES: CCc1cccc(CC)c1-n1c(C)c(C(=O)N[C@@H]2CCCC[C@@H]2N)cc(-c2nc(-c3ccc(Cl)cc3)cs2)c1=O] | D | B | 288.116 | 2.782 | Starting materials: acid-compound 143, amine-(1R,2S)-cyclohexane-1,2 diamine; Method: U | |
| 215 | 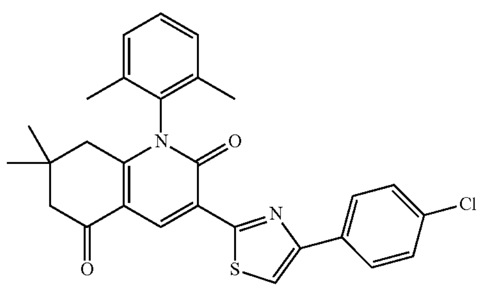 [SMILES: Cc1cccc(C)c1-n1c2c(cc(-c3nc(-c4ccc(Cl)cc4)cs3)c1=O)C(=O)CC(C)(C)C2] | C | C | 489.1402 | 4.013 | Starting materials: nitrile-1, aniline-2,6-dimethylaniline; Method: R | |

TABLE 1-continued
Characterization and Enzymatic Inhibition Data for Selected Compounds
| Cpd # | Structure | Data for R132H (μM) | Data for R132C (μM) | MZ | RT (min) | Synthesis Method | 1H-NMR |
|---|---|---|---|---|---|---|---|
| 216 | 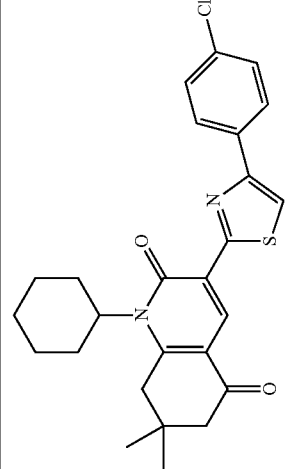 | E | D | 467.1555 | 4.193 | Method: xii | |
| 217 | 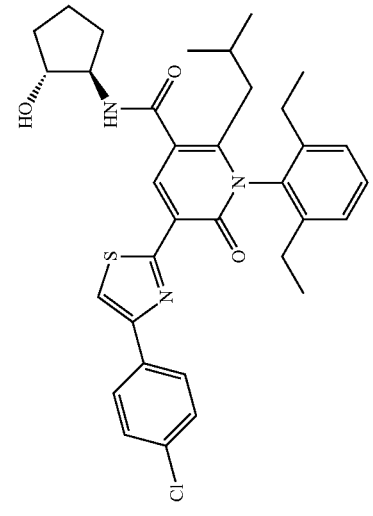 | C | B | 604.2399 | 3.923 | Starting materials: acid-compound 14, amine-trans-2-aminocyclopentanol hydrochloride; Method: U | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 218 | (structure) | A | B | 550.1934 | 3.667 | Starting materials: acid-compound 198, amine-2-aminoethanol; Method: U | ¹H NMR (400 MHz, DMSO-d₆) δ 8.67 (t, J = 5.5 Hz, 1H), 8.56 (d, J = 0.6 Hz, 1H), 8.19 (d, J = 0.6 Hz, 1H), 8.13-8.07 (m, 2H), 7.56-7.51 (m, 2H), 7.48 (dd, J = 8.2, 7.1 Hz, 1H), 7.37 (s, 1H), 7.35 (s, 1H), 4.82-4.72 (m, 1H), 3.57 (q, J = 5.9 Hz, 2H), 3.35 (q, J = 6.0 Hz, 2H), 2.54 (d, J = 7.0 Hz, 1H), 2.34 (dq, J = 15.1, 7.6 Hz, 2H), 2.16 (dq, J = 15.0, 7.5 Hz, 2H), 1.15 (d, J = 7.1Hz, 6H), 1.12-1.06 (m, 6H). |
| 219 | (structure) | C | C | 598.1914 | 3.574 | Starting materials: acid-compound 143, amine-4-aminocyclohexanol; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 220 | 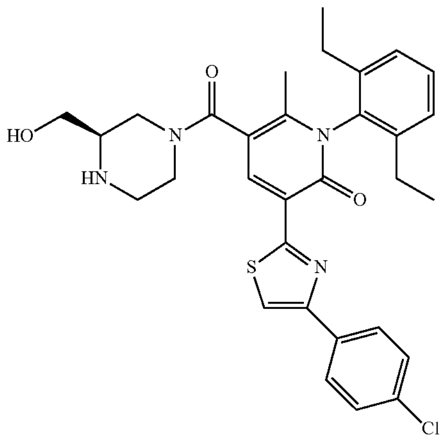 [SMILES: CCc1cccc(CC)c1-n1c(C)c(C(=O)N2CCN[C@@H](CO)C2)cc(-c2nc(-c3ccc(Cl)cc3)cs2)c1=O] | A | B | 577.2014 | 2.673 | Starting materials: acid-compound 143, amine-(R)-tert-butyl 2-(hydroxymethyl)piperazine-1-carboxylate; Method: U, then Boc removal with TFA/DCM rt | ¹H NMR (400 MHz, DMSO-$d_6$) δ 9.18 (s, 1H), 8.75 (s, 2H), 8.22 (s, 1H), 8.11 (d, J = 8.4 Hz, 2H), 7.56-7.50 (m, 2H), 7.48 (t, J = 7.7 Hz, 1H), 7.37 (s, 1H), 7.35 (s, 1H), 5.48 (d, J = 59.3 Hz, 1H), 4.54 (s, 1H), 3.61 (d, J = 73.6 Hz, 2H), 3.15 (d, J = 100.0 Hz, 5H), 2.40-2.09 (m, 4H), 1.88 (d, J = 12.7 Hz, 3H), 1.07 (t, J = 7.5 Hz, 6H). Aliphatic region complicated significantly by amide rotamers. |
| 221 | 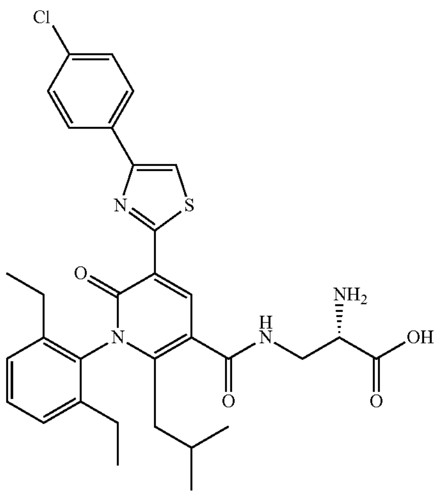 [SMILES: CCc1cccc(CC)c1-n1c(CC(C)C)c(C(=O)NC[C@H](N)C(=O)O)cc(-c2nc(-c3ccc(Cl)cc3)cs2)c1=O] | C | B | 607.2121 | 3.047 | Starting materials: acid-compound 14, amine-(S)-3-amino-2-((tert-butoxycarbonyl)amino)propanoic acid hydrochloride; Methods: U, then Boc removal with TFA/DCM rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 222 | 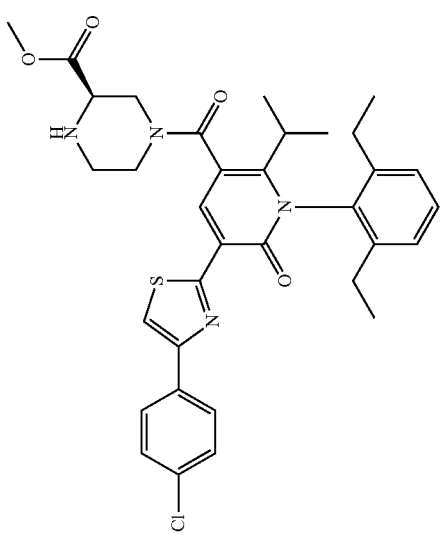 | C | A | 633.2305 | 3.043 | Starting materials: acid-compound 98, amine-(R)-1-tert-butyl 2-methyl piperazine-1,2-dicarboxylate; Method: U, then Boc removal with TFA/DCM rt | |
| 223 | 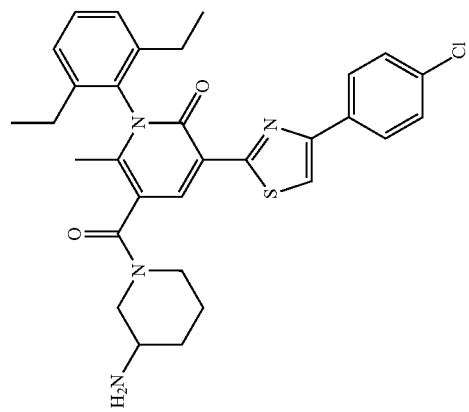 | C | A | 561.2089 | 2.699 | Starting materials: acid-compound 143, amine-tert-butyl piperidin-3-ylcarbamate; Method: U, then Boc removal with TFA/DCM rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 224 | 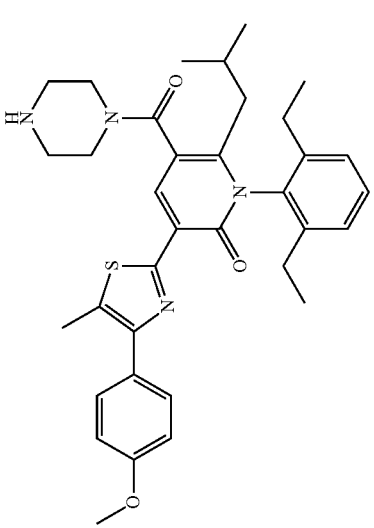 | B | B | 599.3049 | 3.163 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-methoxyphenyl)boronic acid (method xix); Methods: S, then ester hydrolyzed with LiOH (0.5M), THF, rt, U, xix, then Boc removal with TFA/DCM rt | |
| 225 | 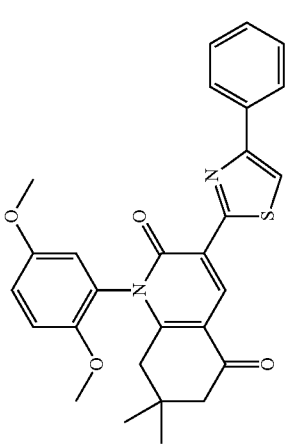 | C | C | 509.1529 | 3.718 | Starting materials: nitrile-2, aniline-2,5-dimethoxyaniline; Method: A | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 226 | 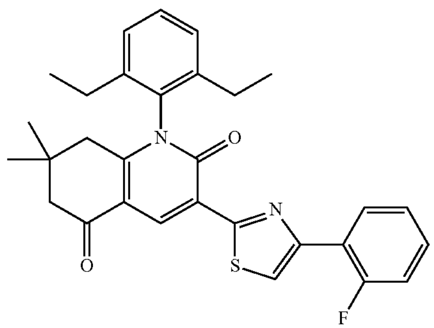 [SMILES: CCc1cccc(CC)c1-n1c2c(cc(-c3nc(-c4ccccc4F)cs3)c1=O)C(=O)CC(C)(C)C2] | C | C | 523.1819 | 4.116 | Starting materials: nitrile-11, aniline-2,6-diethylaniline; Method: R | |
| 227 | 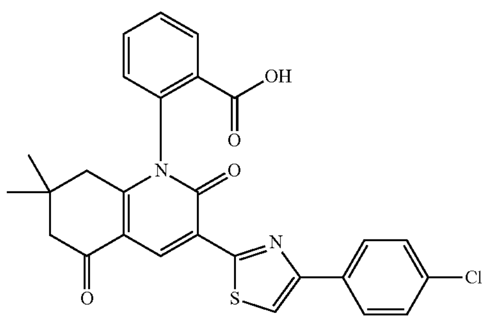 [SMILES: CC1(C)CC(=O)c2cc(-c3nc(-c4ccc(Cl)cc4)cs3)c(=O)n(-c3ccccc3C(=O)O)c2C1] | D | D | 505.1001 | 3.523 | Starting materials: nitrile-1, aniline-2-aminobenzoic acid; Method: E | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 228 | 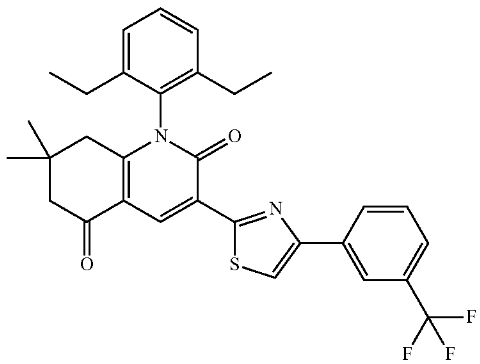 [SMILES: CCc1cccc(CC)c1-n1c2c(cc(-c3nc(-c4cccc(C(F)(F)F)c4)cs3)c1=O)C(=O)CC(C)(C)C2] | E | E | 551.1987 | 4.109 | Starting materials: nitrile-15, aniline-2,6-diethylaniline; Method: R | |
| 229 | 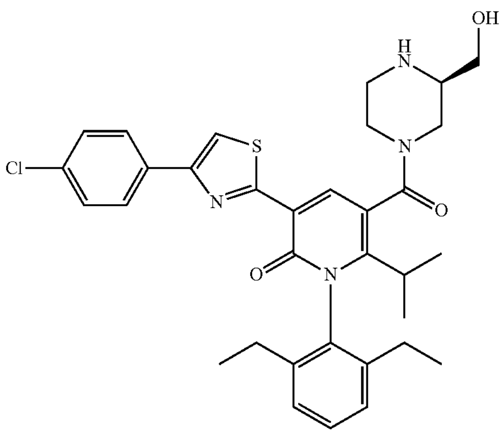 [SMILES: CCc1cccc(CC)c1-n1c(C(C)C)c(C(=O)N2CCN[C@@H](CO)C2)cc(-c2nc(-c3ccc(Cl)cc3)cs2)c1=O] | B | A | 605.2327 | 2.758 | Starting materials: acid-compound 98, amine-(R)-tert-butyl 2-(hydroxymethyl)piperazine-1-carboxylate; Method: U, then Boc removal with TFA/DCM rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 230 | 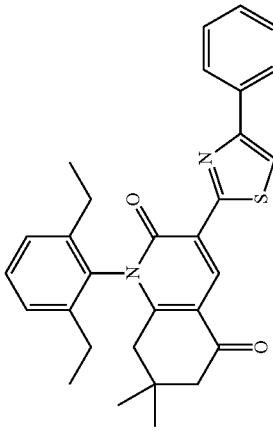 | D | C | 573.1822 | 4.018 | Starting materials: nitrile-21, aniline-2,6-diethylaniline; Method: R | |
| 231 | 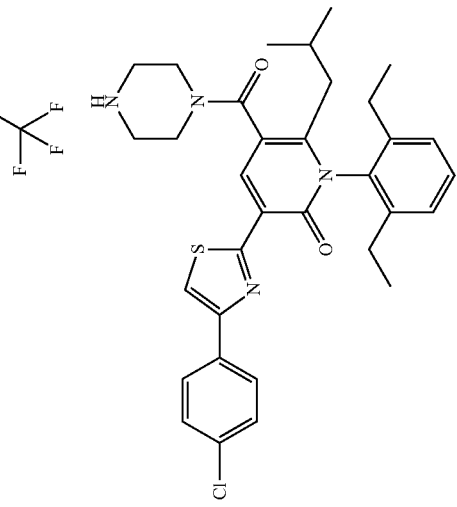 | A | A | 589.2381 | 1.982 | Starting materials: acid-compound 14, amine-tert-butyl piperazine-1-carboxylate; Method: U; then Boc removal with TFA/DCM rt | 1H NMR (400 MHz, DMSO-$d_6$) δ 8.93 (s, 1H), 8.73 (d, J = 0.7 Hz, 1H), 8.24 (d, J = 0.7 Hz, 1H), 8.14 (d, J = 8.4 Hz, 2H), 7.55-7.52 (m, 2H), 7.49 (d, J = 7.7 Hz, 1H), 7.38 (s, 1H), 7.36 (s, 1H), 4.06 (s, 1H), 3.93-3.51 (m, 3H), 3.16 (d, J = 64.2 Hz, 5H), 2.42-1.94 (m, 3H), 1.34 (dq, J = 13.5, 6.7 Hz, 1H), 1.10 (d, J = 7.9 Hz, 8H), 0.63 (d, J = 6.5 Hz, 6H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 232 | 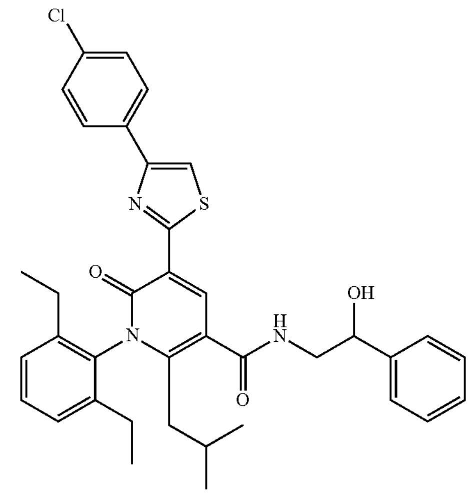 [SMILES: CCc1cccc(CC)c1-n1c(CC(C)C)c(C(=O)NCC(O)c2ccccc2)cc(-c2nc(-c3ccc(Cl)cc3)cs2)c1=O] | B | A | 640.2379 | 3.992 | Starting materials: acid-compound 14, amine-2-amino-1-phenylethanol; Method: U | |
| 233 | 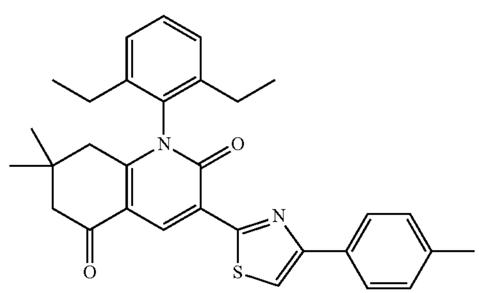 | B | B | 497.2257 | 4.121 | Starting materials: nitrile-6, aniline-2,6-diethylaniline; Method: R | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 234 | 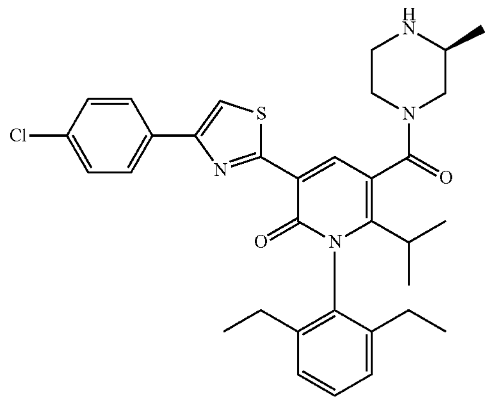 [SMILES: CCc1cccc(CC)c1-n1c(C(C)C)c(C(=O)N2CCN[C@@H](C)C2)cc(-c2nc(-c3ccc(Cl)cc3)cs2)c1=O] | C | B | 489.2426 | 2.838 | Starting materials: acid-compound 98, amine-(S)-tert-butyl 2-methylpiperazine-1-carboxylate; Methods: U, then Boc removal with TFA/DCM rt | |
| 235 | 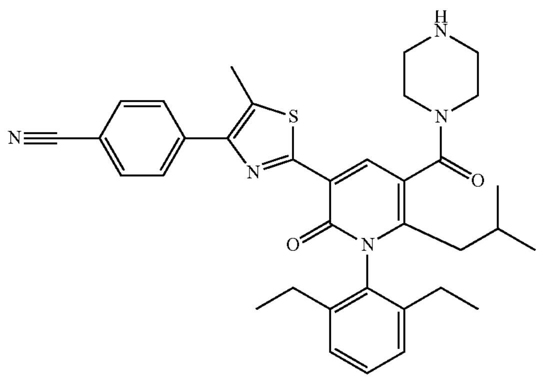 [SMILES: CCc1cccc(CC)c1-n1c(CC(C)C)c(C(=O)N2CCNCC2)cc(-c2nc(-c3ccc(C#N)cc3)c(C)s2)c1=O] | A | A | 594.2916 | 3.12 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-cyanophenyl)boronic acid (method xix); Methods: S, then ester hydrolyzed with LiOH (0.5M), THF, rt, U, xix, then Boc removal with TFA/DCM rt | 1H NMR (400 MHz, DMSO-$d_6$) δ 8.86 (s, 1H), 8.61 (s, 1H), 8.05-7.98 (m, 2H), 7.98-7.92 (m, 2H), 7.50 (t, J =7.7 Hz, 1H), 7.37 (s, 1H), 7.35 (s, 1H), 4.02 (s, 1H), 3.76 (s, 1H), 3.58 (t, J = 30.1 Hz, 2H), 3.21 (s, 3H), 3.06 (s, 1H), 2.62 (s, 3H), 2.40-1.91 (m, 6H), 1.33 (dt, J = 13.4, 6.7 Hz, 1H), 1.10 (s, 6H), 0.62 (d, J = 6.6 Hz, 6H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 236 | 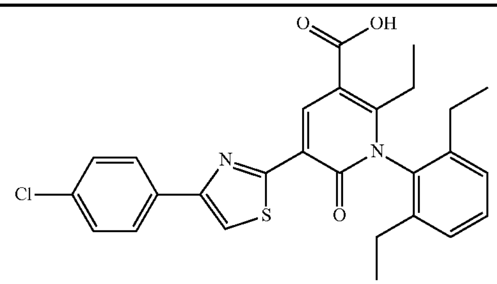 | C | D | 493.1347 | 3.927 | Methods: S, then ester hydrolyzed with LiOH (3 eq), THF/MeOH/water, 50° C. 3.5 h | |
| 237 | 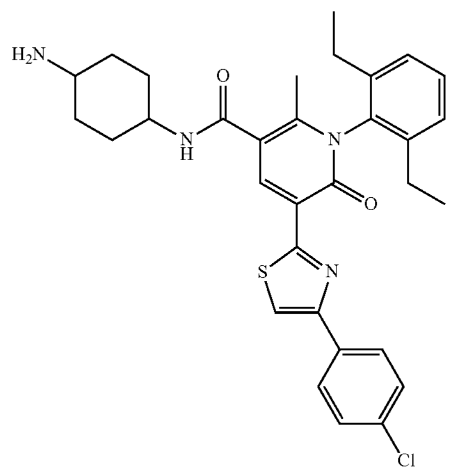 [SMILES: CCc1cccc(CC)c1-n1c(C)c(C(=O)NC2CCC(N)CC2)cc(-c2nc(-c3ccc(Cl)cc3)cs2)c1=O] | D | D | 575.2241 | 2.707 | Starting materials: acid-compound 143, amine-cyclohexane-1,4-diamine (cis); Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 238 | 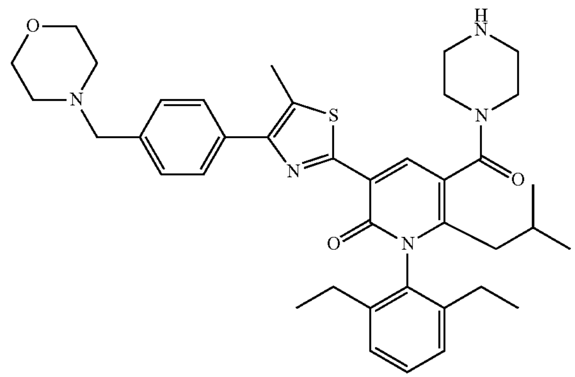 [SMILES: CCc1cccc(CC)c1-n1c(CC(C)C)c(C(=O)N2CCNCC2)cc(-c2nc(-c3ccc(CN4CCOCC4)cc3)c(C)s2)c1=O] | D | D | 668.36 | 2.637 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), 4-(4-(4,4,5,5-tetramethyl-1,3,2-dioxaborolan-2-yl)benzyl)morpholine (method xix); Methods: S, then ester hydrolyzed with LiOH (0.5M), THF, rt, U, xix, then Boc removal with TFA/DCM rt | |
| 239 | 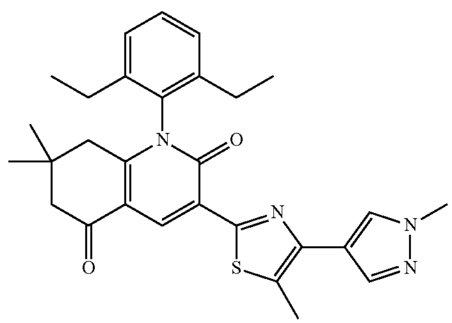 | C | C | 501.231 | 3.736 | Starting material: boryl species-(1-methyl-1H-pyrazol-4-yl)boronic acid; Method: xix | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 240 | 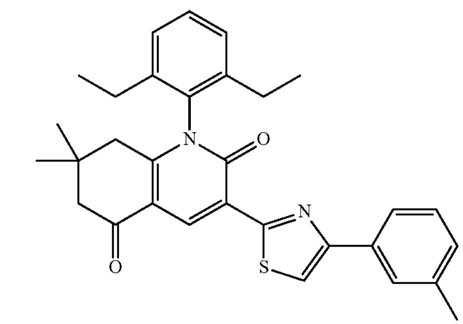 | D | C | 497.2252 | 4.115 | Starting materials: nitrile-20, aniline-2,6-diethylaniline; Method: R | |
| 241 | 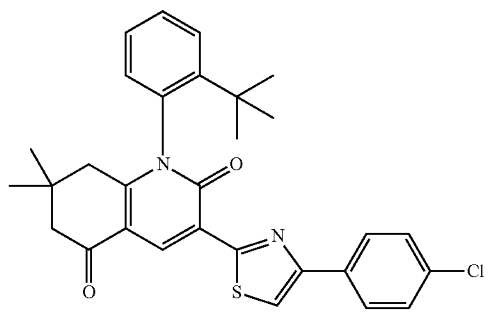 [SMILES: CC1(C)CC(=O)c2cc(-c3nc(-c4ccc(Cl)cc4)cs3)c(=O)n(-c3ccccc3C(C)(C)C)c2C1] | C | B | 517.1711 | 4.158 | Starting materials: nitrile-1, aniline-2-tert-butylaniline; Method: E | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 242 | 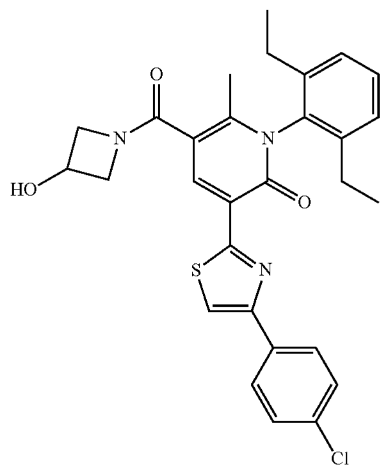 [SMILES: CCc1cccc(CC)c1-n1c(C)c(C(=O)N2CC(O)C2)cc(-c2nc(-c3ccc(Cl)cc3)cs2)c1=O] | C | C | 534.1637 | 3.532 | Starting materials: acid-compound 143, amine-azetidin-3-ol; Method: U | |
| 243 | 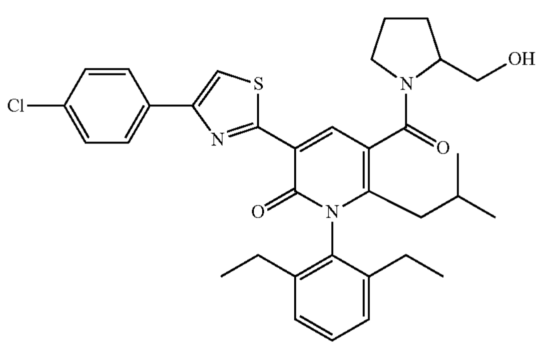 [SMILES: CCc1cccc(CC)c1-n1c(CC(C)C)c(C(=O)N2CCCC2CO)cc(-c2nc(-c3ccc(Cl)cc3)cs2)c1=O] | C | C | 604.2369 | 3.993 | Starting materials: acid-compound 14, amine-pyrrolidin-2-ylmethanol; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 244 | 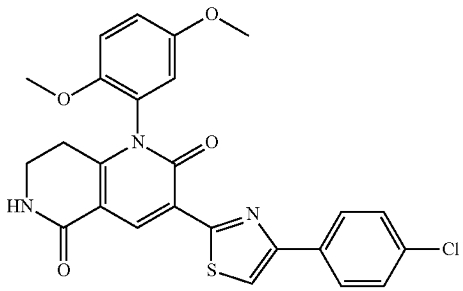 [SMILES: COc1ccc(OC)c(-n2c3c(cc(-c4nc(-c5ccc(Cl)cc5)cs4)c2=O)C(=O)NCC3)c1] | C | C | 516.0768 | 3.34 | Boc removal of Compound 23 with TFA/DCM rt | |
| 245 | 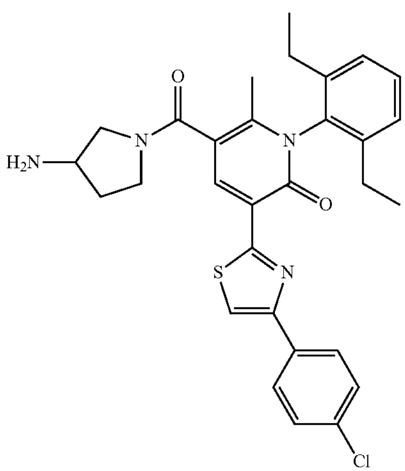 [SMILES: CCc1cccc(CC)c1-n1c(C)c(C(=O)N2CCC(N)C2)cc(-c2nc(-c3ccc(Cl)cc3)cs2)c1=O] | C | C | 547.1939 | 2.643 | Starting materials: acid-compound 143, amine-tert-butyl pyrrolidin-3-ylcarbamate; Method: U, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 246 | 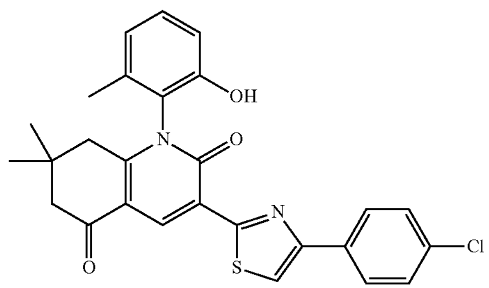 [SMILES: Cc1cccc(O)c1-n1c2c(cc(-c3nc(-c4ccc(Cl)cc4)cs3)c1=O)C(=O)CC(C)(C)C2] | C | C | 491.1214 | 3.754 | Starting materials: nitrile-1, aniline-2-amino-3-methylphenol; Method: A (step 2-45° C., step 3-70° C. 2.5 h) | |
| 247 | 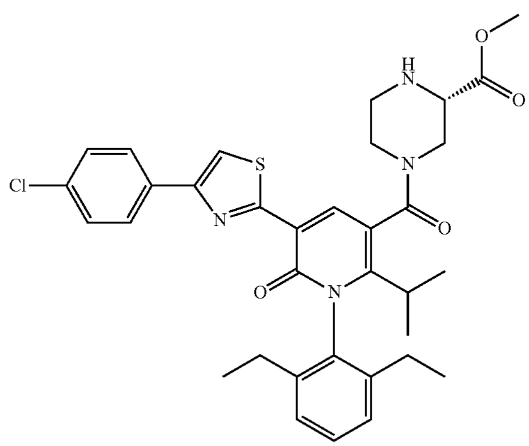 [SMILES: CCc1cccc(CC)c1-n1c(C(C)C)c(C(=O)N2CCN[C@H](C(=O)OC)C2)cc(-c2nc(-c3ccc(Cl)cc3)cs2)c1=O] | D | C | 633.2274 | 3.051 | Starting materials: acid-compound 98, amine-(S)-1-tert-butyl 2-methyl piperazine-1,2-dicarboxylate; Methods: U, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 248 | 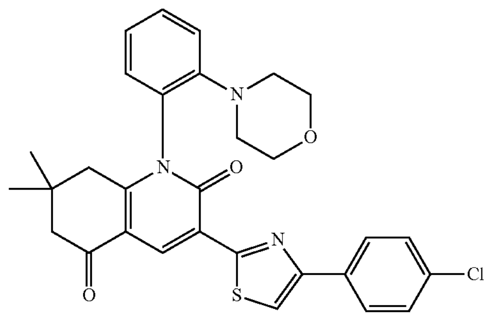 [SMILES: CC1(C)CC(=O)c2cc(-c3nc(-c4ccc(Cl)cc4)cs3)c(=O)n(-c3ccccc3N3CCOCC3)c2C1] | C | B | 546.1637 | 3.878 | Starting materials: nitrile-1, aniline-2-morpholinoaniline; Method: G | |
| 249 | 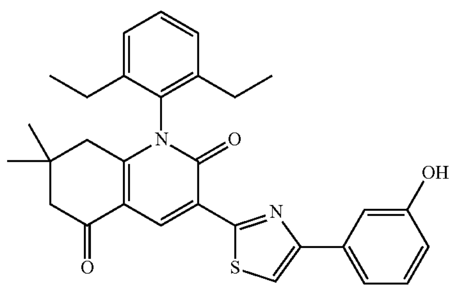 [SMILES: CCc1cccc(CC)c1-n1c2c(cc(-c3nc(-c4cccc(O)c4)cs3)c1=O)C(=O)CC(C)(C)C2] | C | C | 521.1881 | 3.715 | Starting materials: nitrile-23, aniline-2,6-diethylaniline; Method: Q | |

TABLE 1-continued
Characterization and Enzymatic Inhibition Data for Selected Compounds
| Cpd # | Structure | Data for R132H (µM) | Data for R132C (µM) | MZ | RT (min) | Synthesis Method | ¹H-NMR |
|---|---|---|---|---|---|---|---|
| 250 | 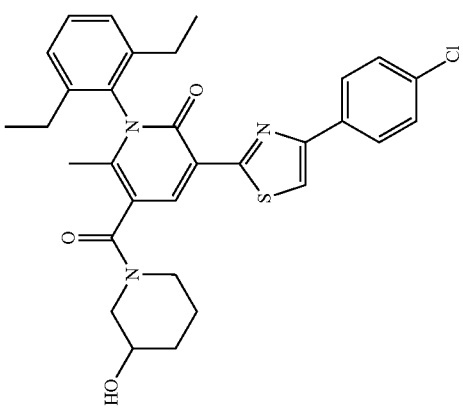 | C | C | 562.1921 | 3.657 | Starting materials: acid-compound 143, amine-piperidin-3-ol; Method: U | |
| 251 | 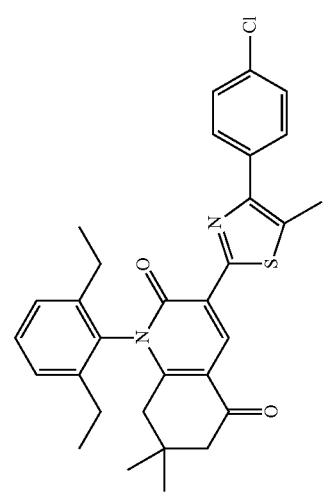 | B | A | 531.1885 | 4.257 | Starting materials: nitrile-18, aniline-2,6-diethylaniline; Method: R | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | $^1$H-NMR |
|---|---|---|---|---|---|---|---|
| 252 | 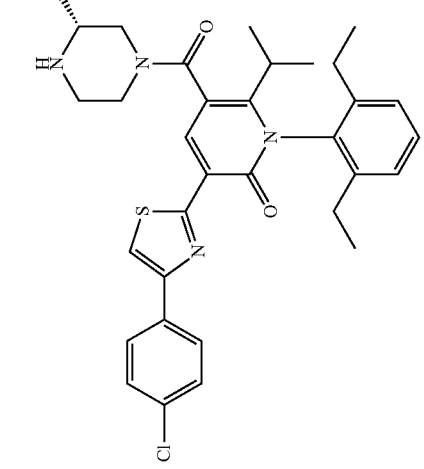 | B | B | 605.2354 | 2.764 | Starting materials: acid-compound 98, amine-(S)-tert-butyl 2-(hydroxymethyl)piperazine-1-carboxylate; Methods: U, then Boc removal with TFA/DCM rt | |
| 253 | 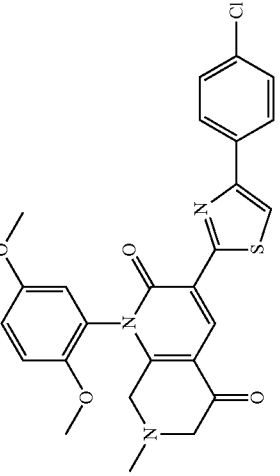 | C | C | 530.0928 | 1.995 | N-Methylation of compound 280-formalin, MeOH, NaBH3CN, AcOH, rt 1 h | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 254 | 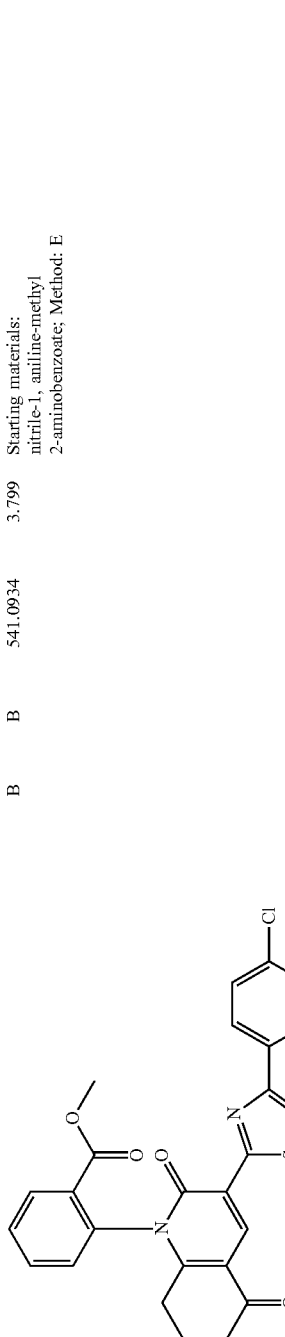 | B | B | 541.0934 | 3.799 | Starting materials: nitrile-1, aniline-methyl 2-aminobenzoate; Method: E | |
| 255 | 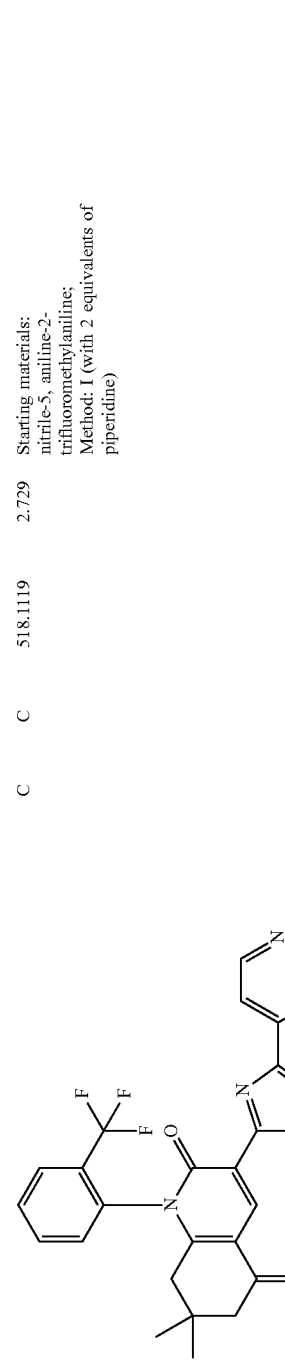 | C | C | 518.1119 | 2.729 | Starting materials: nitrile-5, aniline-2-trifluoromethylaniline; Method: I (with 2 equivalents of piperidine) | |
| 256 | 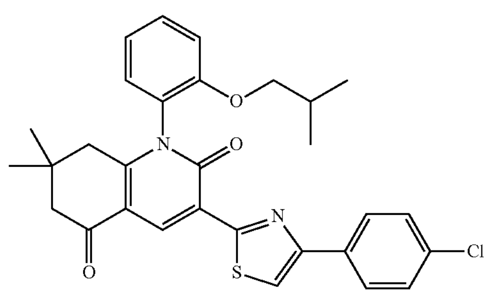 [SMILES: CC(C)COc1ccccc1-n1c2c(cc(-c3nc(-c4ccc(Cl)cc4)cs3)c1=O)C(=O)CC(C)(C)C2] | B | B | 533.1656 | 4.079 | Starting materials: nitrile-1, aniline-2-isobutoxyaniline; Method: E | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 257 | 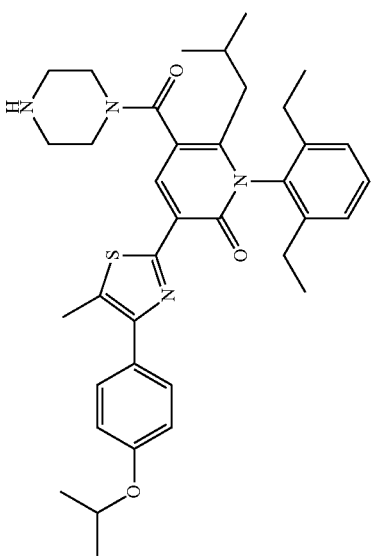 | B | A | 649.3215 | 3.31 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-isopropoxyphenyl) boronic acid (method xix); Methods: S, then ester hydrolyzed with LiOH (0.5M), THF, rt, U, xix, then Boc removal with TFA/DCM rt | |
| 258 | 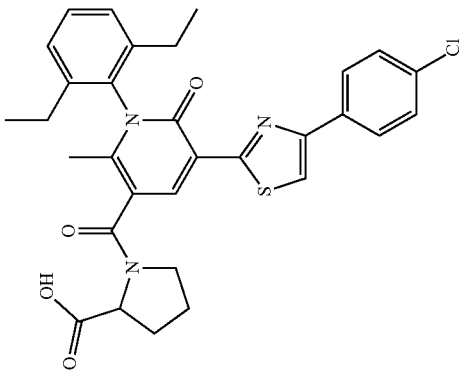 | C | C | 576.1709 | 3.624 | Starting materials: acid-compound 143, amine-methyl pyrrolidine-2-carboxylate; Method: U, then hydrolyzed with LiOH (0.5M), THF, rt | |

TABLE 1-continued
Characterization and Enzymatic Inhibition Data for Selected Compounds
| Cpd # | Structure | Data for R132H (μM) | Data for R132C (μM) | MZ | RT (min) | Synthesis Method | $^1$H-NMR |
|---|---|---|---|---|---|---|---|
| 259 | 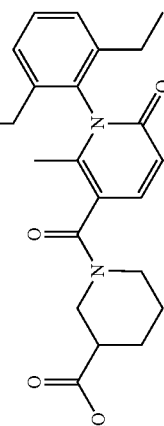 | D | D | 590.1848 | 3.625 | Starting materials: acid-compound 143, amine-ethyl piperidine-3-carboxylate; Method: U, then hydrolyzed with LiOH (0.5M), THF, rt | |
| 260 | 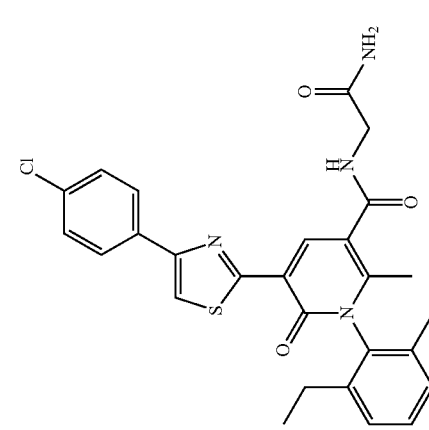 | C | C | 535.155 | 3.378 | Starting materials: acid-compound 143, amine-2-aminoacetamide; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 261 | 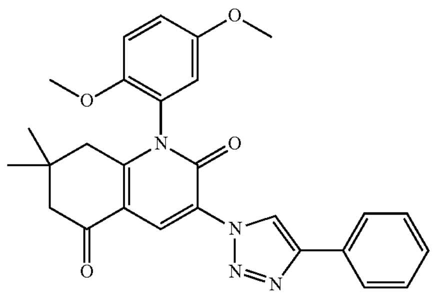 [SMILES: COc1ccc(OC)c(-n2c3c(cc(-n4cc(-c5ccccc5)nn4)c2=O)C(=O)CC(C)(C)C3)c1] | D | D | 471.2024 | 3.464 | Starting materials: nitrile-2-(4-phenyl-1H-1,2,3-triazol-1-yl)acetonitrile (synthesized by method xvi), aniline-2,5-dimethoxyaniline; Method: P | |
| 262 | 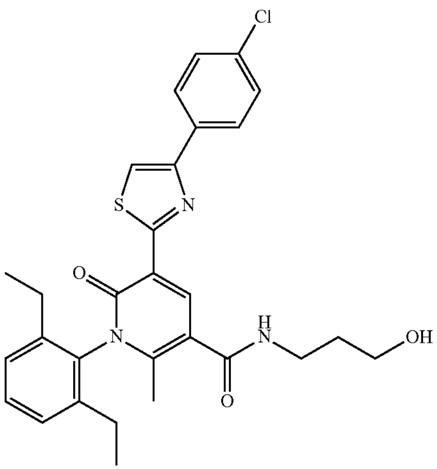 [SMILES: CCc1cccc(CC)c1-n1c(C)c(C(=O)NCCCO)cc(-c2nc(-c3ccc(Cl)cc3)cs2)c1=O] | C | B | 536.1746 | 3.545 | Starting materials: acid-compound 143, amine-3-aminopropan-1-ol; Method: U | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 263 | 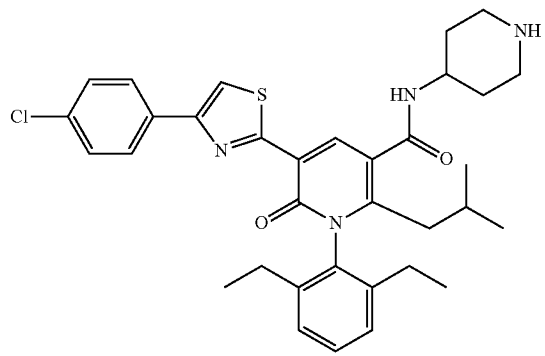 [SMILES: CCc1cccc(CC)c1-n1c(CC(C)C)c(C(=O)NC2CCNCC2)cc(-c2nc(-c3ccc(Cl)cc3)cs2)c1=O] | B | A | 603.2566 | 2.621 | Starting materials: acid-compound 14, amine-tert-butyl 4-aminopiperidine-1-carboxylate; Method: U, then Boc removal with TFA/DCM rt | |
| 264 | 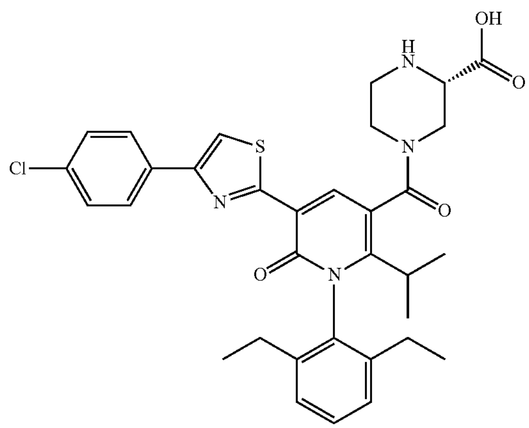 [SMILES: CCc1cccc(CC)c1-n1c(C(C)C)c(C(=O)N2CCN[C@H](C(=O)O)C2)cc(-c2nc(-c3ccc(Cl)cc3)cs2)c1=O] | B | A | 619.2125 | 3.028 | Compound 247 was hydrolyzed with LiOH (xs), THF/MeOH/water, 50° C. 1.75 h | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 265 | 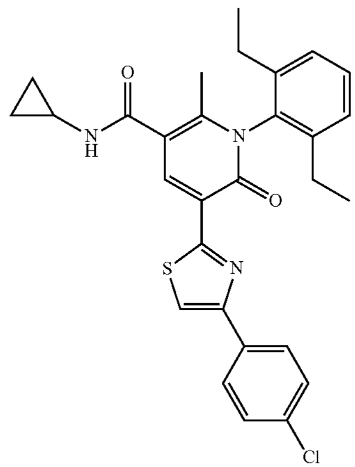 [SMILES: CCc1cccc(CC)c1-n1c(C)c(C(=O)NC2CC2)cc(-c2nc(-c3ccc(Cl)cc3)cs2)c1=O] | C | C | 518.1654 | 3.818 | Method: U | |
| 266 | 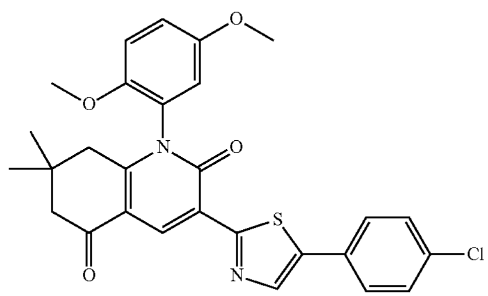 [SMILES: COc1ccc(OC)c(-n2c3c(cc(-c4ncc(-c5ccc(Cl)cc5)s4)c2=O)C(=O)CC(C)(C)C3)c1] | E | E | 543.113 | 3.811 | Starting materials: nitrile-2-(thiazol-2-yl)acetonitrile, aniline-2,5-dimethoxyaniline; Method: G, then arylation of the thiazole-1-bromo-4-chlorobenzene (3 eq), potassium acetate (3 eq), palladium (II) acetate (0.1 eq), DMA, 150° C. 1 h | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 267 | 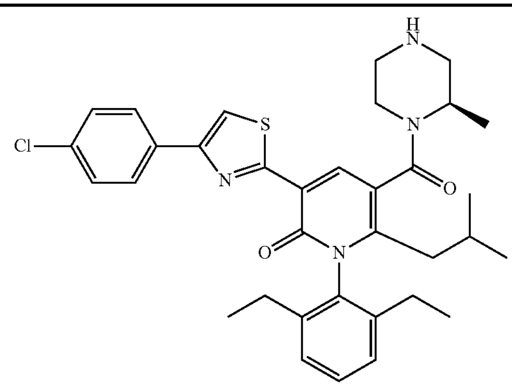 | B | A | 603.2571 | 2.888 | Starting materials: acid-compound 14, amine-(R)-tert-butyl 3-methylpiperazine-1-carboxylate; Method: U, then Boc removal with TFA/DCM rt | |
| 268 | 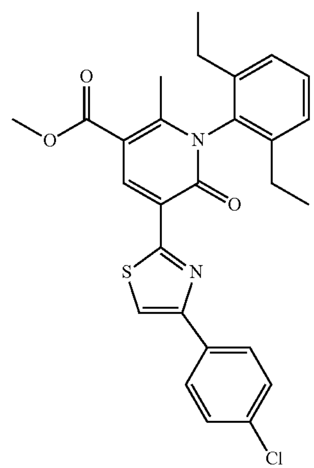 [SMILES: CCc1cccc(CC)c1-n1c(C)c(C(=O)OC)cc(-c2nc(-c3ccc(Cl)cc3)cs2)c1=O] | E | D | 493.1338 | 4.247 | Method: S | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 269 | 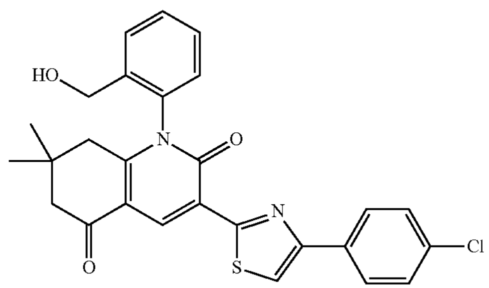 [SMILES: CC1(C)CC(=O)c2cc(-c3nc(-c4ccc(Cl)cc4)cs3)c(=O)n(-c3ccccc3CO)c2C1] | D | C | 513.1011 | 3.641 | Starting materials: nitrile-1, aniline-2-(aminophenyl) methanol; Method: A (step 2-45° C., step 3-70° C. 2.5 h) | |
| 270 | 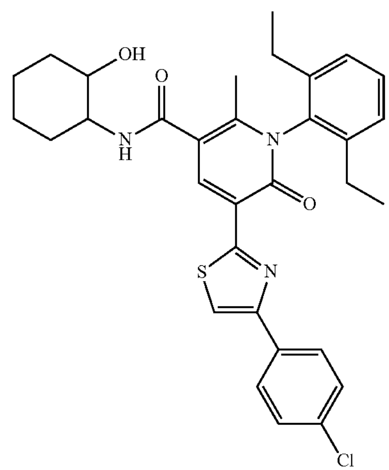 [SMILES: CCc1cccc(CC)c1-n1c(C)c(C(=O)NC2CCCCC2O)cc(-c2nc(-c3ccc(Cl)cc3)cs2)c1=O] | C | C | 576.208 | 3.763 | Starting materials: acid-compound 143, amine-2-aminocyclohexanol; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 271 | 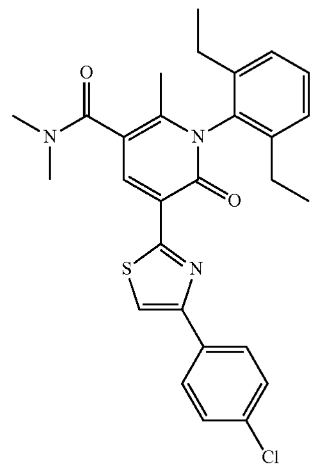 [SMILES: CCc1cccc(CC)c1-n1c(C)c(C(=O)N(C)C)cc(-c2nc(-c3ccc(Cl)cc3)cs2)c1=O] | C | C | 506.1659 | 3.819 | Starting materials: acid-compound 143, amine-dimethylamine; Method: U | |
| 272 | 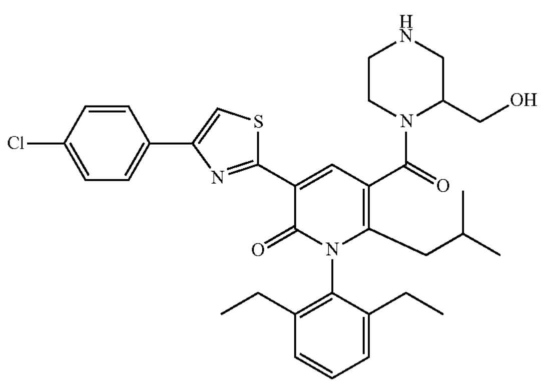 [SMILES: CCc1cccc(CC)c1-n1c(CC(C)C)c(C(=O)N2CCNCC2CO)cc(-c2nc(-c3ccc(Cl)cc3)cs2)c1=O] | B | A | 619.2492 | 2.847 | Starting materials: acid-compound 14, amine-tert-butyl 3-(hydroxymethyl)piperazine-1-carboxylate; Method: U, then Boc removal with TFA/DCM rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 273 | 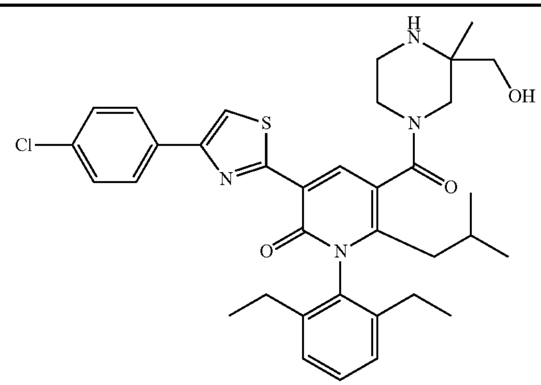 | B | A | 633.2682 | 2.866 | Starting materials: acid-compound 14, tert-butyl 2-(hydroxymethyl)-2-methylpiperazine-1-carboxylate (xxiii); Methods: U, then Boc removal with TFA/DCM rt | |
| 274 | 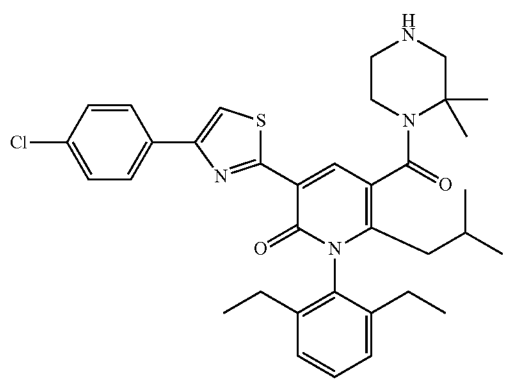 [SMILES: CCc1cccc(CC)c1-n1c(CC(C)C)c(C(=O)N2CCNCC2(C)C)cc(-c2nc(-c3ccc(Cl)cc3)cs2)c1=O] | B | A | 617.2719 | 2.972 | Starting materials: acid-compound 14, amine-tert-butyl 3,3-dimethylpiperazine-1-carboxylate; Method: U, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 275 | 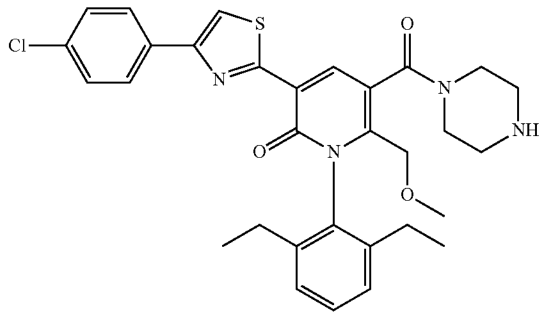 [SMILES: CCc1cccc(CC)c1-n1c(COC)c(C(=O)N2CCNCC2)cc(-c2nc(-c3ccc(Cl)cc3)cs2)c1=O] | A | A | 577.2035 | 3.018 | Starting materials: methyl 4-methoxy-3-oxobutanoate (step 1), PIPERAZINE (used in method U); Methods: S, then ester hydrolyzed with LiOH (0.5M), THF, rt, U, xix | ¹H NMR (400 MHz, DMSO-$d_6$) δ 8.83 (s, 1H), 8.75-8.70 (m, 1H), 8.28 (d, J = 2.1 Hz, 1H), 8.13 (dd, J = 8.6, 2.0 Hz, 2H), 7.59-7.52 (m, 2H), 7.49 (td, J = 7.8,1.9 Hz, 1H), 7.36 (s, 1H), 7.34 (s, 1H), 4.05 (d, J = 12.6 Hz, 1H), 3.91 (s, 1H), 3.69 (d, J =13.1 Hz, 2H), 3.52 (s, 0H), 3.18 (s, 3H), 3.03 (s, 1H), 2.92 (t, J = 1.3 Hz, 3H), 2.41-2.02 (m, 6H), 1.08 (d, J = 8.5 Hz, 6H). Aliphatic region complicated significantly by amide rotamers. |
| 276 | 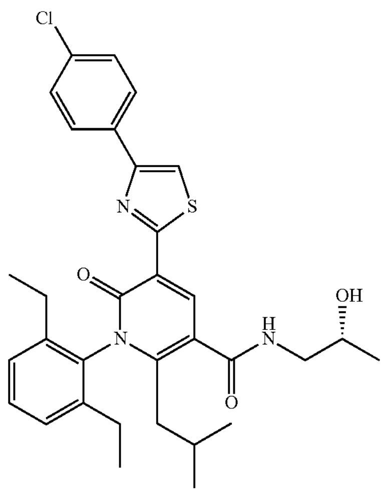 [SMILES: CCc1cccc(CC)c1-n1c(CC(C)C)c(C(=O)NC[C@@H](C)O)cc(-c2nc(-c3ccc(Cl)cc3)cs2)c1=O] | B | A | 578.2263 | 3.84 | Starting materials: acid-compound 14, amine-(R)-1-aminopropan-2-ol; Method: U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 277 | 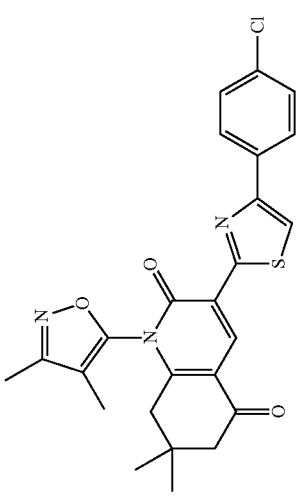 | C | C | 480.114 | 3.777 | Starting materials: nitrile-1, amine-3,4-dimethylisoxazol-5-amine; Method: R (step 2-50° C. 2 h, step 3-80° C. 3 h then 100° C. overnight) | |
| 278 | 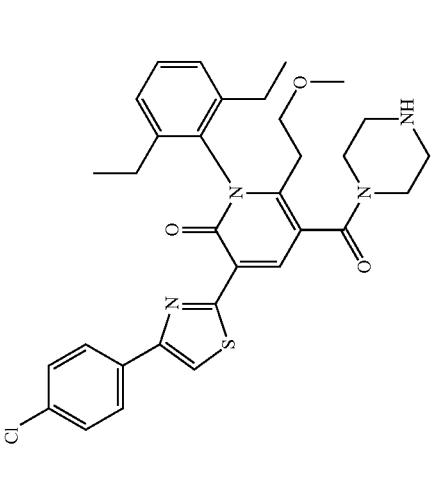 | A | A | 591.2195 | 3.741 | Starting materials: methyl 5-methoxy-3-oxopentanoate (step 1), PIPERAZINE (used in method U); Methods: S, then ester hydrolyzed with LiOH (0.5M), THF, rt, U, xix | 1H NMR (400 MHz, DMSO-d6) δ 8.74 (d, J = 0.5 Hz, 2H), 8.24 (d, J = 0.5 Hz, 1H), 8.18-8.10 (m, 2H), 7.58-7.47 (m, 3H), 7.39 (s, 1H), 7.37 (s, 1H), 4.04 (s, 1H), 3.85-3.43 (m, 3H), 3.16 (d, J =35.4 Hz, 6H), 3.02 (d, J = 0.6 Hz, 3H), 2.85 (s, 1H), 2.17 (s, 2H), 1.9 Hz, 2H), 2.33 (t, J = 1.11 (s,7H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 279 | 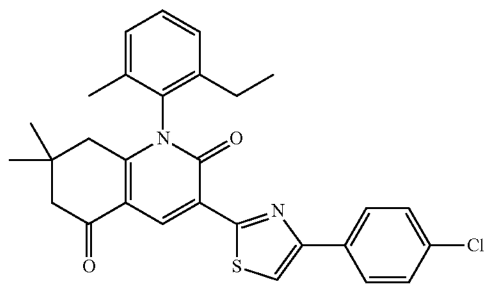 [SMILES: CCc1cccc(C)c1-n1c2c(cc(-c3nc(-c4ccc(Cl)cc4)cs3)c1=O)C(=O)CC(C)(C)C2] | C | B | 503.1562 | 4.101 | Starting materials: nitrile-1, aniline-2-methyl-6-ethylaniline; Method: R | |
| 280 | 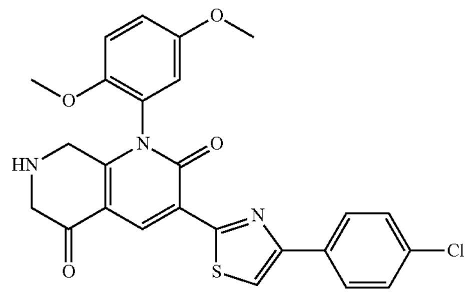 [SMILES: COc1ccc(OC)c(-n2c3c(cc(-c4nc(-c5ccc(Cl)cc5)cs4)c2=O)C(=O)CNC3)c1] | D | D | 247.5513 | 3.148 | Starting materials: nitrile-1, aniline-2,5-dimethoxyaniline, tert-butyl 3,5-dioxopiperidine-1-carboxylate; Methods: D, then Boc removal with TFA/DCM rt | |
| 281 | 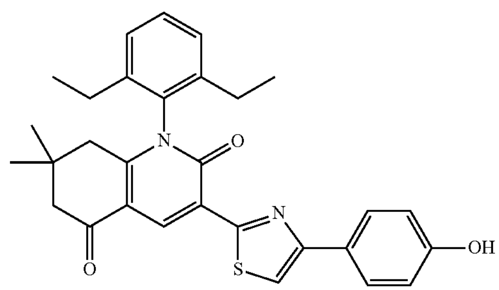 [SMILES: CCc1cccc(CC)c1-n1c2c(cc(-c3nc(-c4ccc(O)cc4)cs3)c1=O)C(=O)CC(C)(C)C2] | D | D | 499.2034 | 3.682 | Demethylation of cmpd 183 using BBr3 (3 eq) in DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 282 | 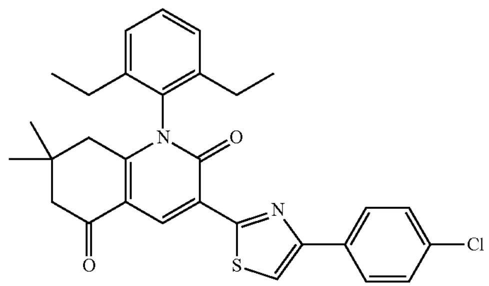 [SMILES: CCc1cccc(CC)c1-n1c2c(cc(-c3nc(-c4ccc(Cl)cc4)cs3)c1=O)C(=O)CC(C)(C)C2] | B | A | 517.1699 | 4.187 | Starting materials: nitrile-1, aniline-2,6-diethylaniline; Method: E | |
| 283 | 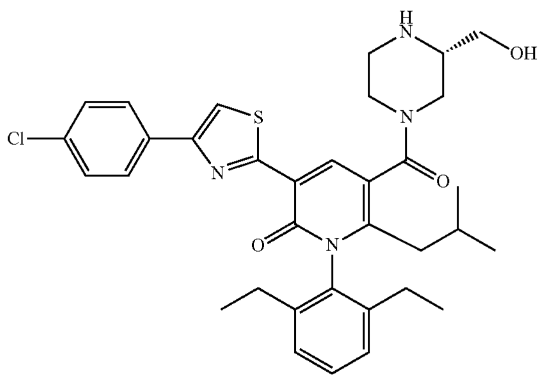 [SMILES: CCc1cccc(CC)c1-n1c(CC(C)C)c(C(=O)N2CCN[C@H](CO)C2)cc(-c2nc(-c3ccc(Cl)cc3)cs2)c1=O] | B | A | 619.2519 | 2.825 | Starting materials: acid-compound 14, amine-(S)-tert-butyl 2-(hydroxymethyl) piperazine-1-carboxylate; Methods: U, then Boc removal with TFA/DCM rt | |
| 284 | 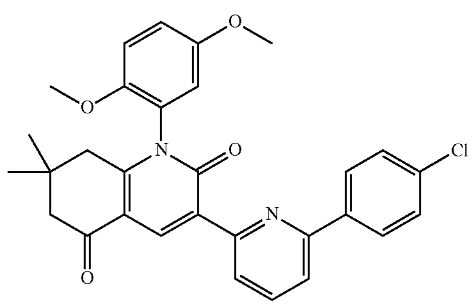 [SMILES: COc1ccc(OC)c(-n2c3c(cc(-c4cccc(-c5ccc(Cl)cc5)n4)c2=O)C(=O)CC(C)(C)C3)c1] | D | D | 515.175 | 3.8 | Starting materials: nitrile-2-(6-(4-chlorophenyl)pyridin-2-yl)acetonitrile (method iii with 2-(6-bromopyridin-2-yl(acetonitrile), aniline-2,5-dimethoxyaniline; Method: J | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 285 | 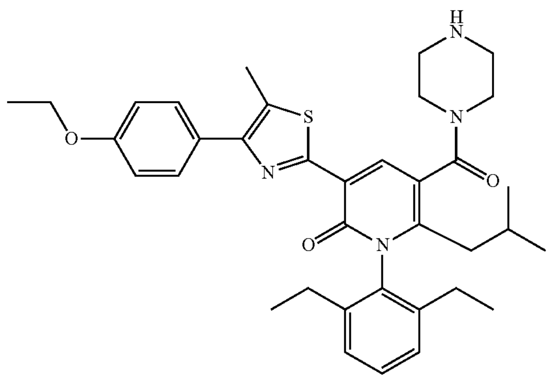 [SMILES: CCOc1ccc(-c2nc(-c3cc(C(=O)N4CCNCC4)c(CC(C)C)n(-c4c(CC)cccc4CC)c3=O)sc2C)cc1] | A | A | 613.3187 | 3.247 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-ethxyphenyl)boronic acid (method xix); Methods: S, then ester hydrolyzed with LiOH (0.5M), THF, rt, U, xix, then Boc removal with TFA/DCM rt | 1H NMR (400 MHz, DMSO-d6) δ 8.98-8.69 (m, 1H), 8.56 (s, 1H), 7.74-7.62 (m, 2H), 7.49 (t, J = 7.7 Hz, 1H), 7.36 (d, J = 7.7 Hz, 2H), 7.03 (d, J = 8.8 Hz, 2H), 4.09 (q, J = 6.9 Hz, 4H), 3.76 (s, 1H), 3.60 (d, J = 28.8 Hz, 1H), 3.14 (d, J = 53.2 Hz, 4H), 2.54 (s, 3H), 2.42-1.91 (m, 6H), 1.36 (t, J = 7.0 Hz, 4H), 1.10 (d, J = 7.3 Hz, 6H), 0.62 (d, J = 6.6 Hz, 6H). Aliphatic region complicated significantly by amide rotamers. |
| 286 | 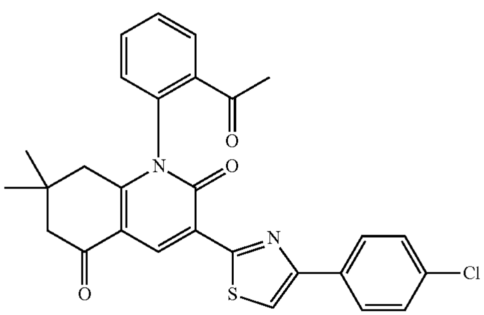 [SMILES: CC(=O)c1ccccc1-n1c2c(cc(-c3nc(-c4ccc(Cl)cc4)cs3)c1=O)C(=O)CC(C)(C)C2] | C | C | 525.1025 | 3.767 | Starting materials: nitrile-1, aniline-2-acetylaniline; Method: E | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 287 | 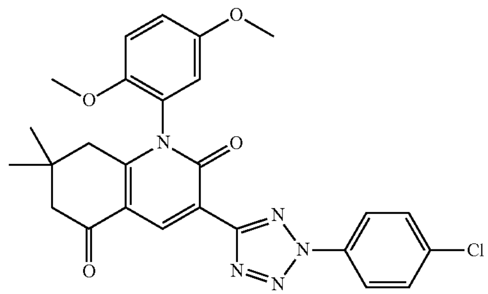 [SMILES: COc1ccc(OC)c(-n2c3c(cc(-c4nnn(-c5ccc(Cl)cc5)n4)c2=O)C(=O)CC(C)(C)C3)c1] | E | C | 528.1383 | 3.572 | Method: xi | |
| 288 | 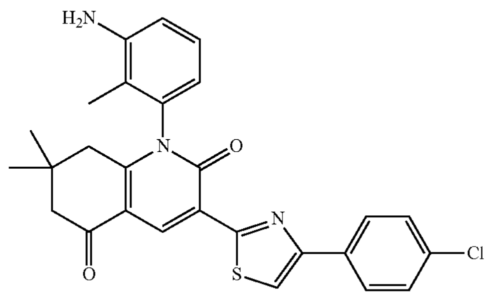 [SMILES: Cc1c(N)cccc1-n1c2c(cc(-c3nc(-c4ccc(Cl)cc4)cs3)c1=O)C(=O)CC(C)(C)C2] | C | C | 512.1182 | 3.748 | Starting materials: nitrile-1, aniline-2-methyl-3-nitroaniline; Methods: A (step 2-45° C., step 3-70° C. 2.5 h), then Nitro reduction with SnCl2 (5 eq), EtOH 70° C. 2 h | |
| 289 | 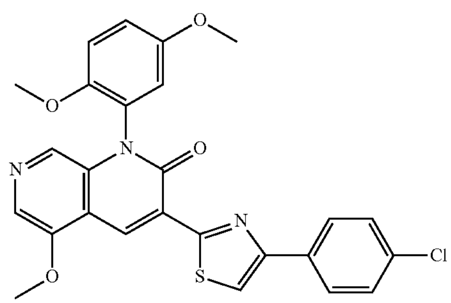 [SMILES: COc1ccc(OC)c(-n2c(=O)c(-c3nc(-c4ccc(Cl)cc4)cs3)cc3c(OC)cncc32)c1] | E | D | 506.0936 | 2.868 | O-Methylation with concomitant oxidation of compound 280 formalin, formic acid (1:1), 70° C. 2 h | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 290 | 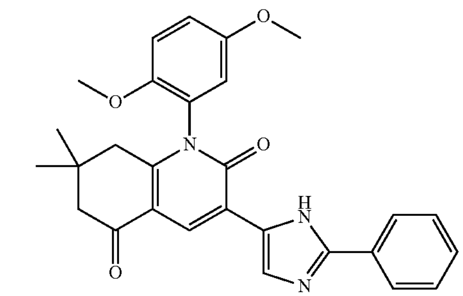 [SMILES: COc1ccc(OC)c(-n2c3c(cc(-c4cnc(-c5ccccc5)[nH]4)c2=O)C(=O)CC(C)(C)C3)c1] | C | C | 470.2054 | 2.59 | Starting materials: nitrile-tert-butyl 5-(cyanomethyl)-2-phenyl-1H-imidazole-1-carboxylate (synthesized by method ix), aniline-2,5-dimethoxyaniline; Method: N (Boc falls off during reaction sequence) | |
| 291 | 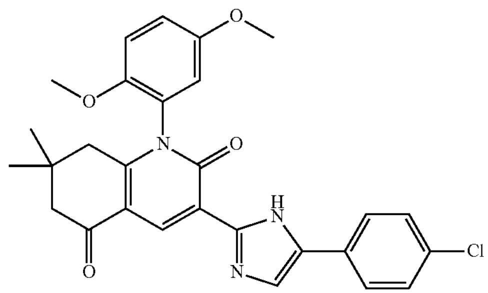 [SMILES: COc1ccc(OC)c(-n2c3c(cc(-c4ncc(-c5ccc(Cl)cc5)[nH]4)c2=O)C(=O)CC(C)(C)C3)c1] | C | C | 504.1709 | 3.171 | Method: xviii | |
| 292 | 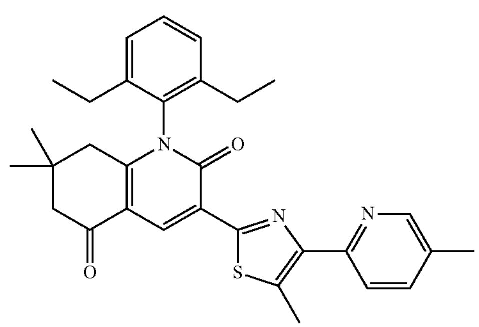 | C | C | 512.2377 | 3.766 | Method: xx | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 293 | 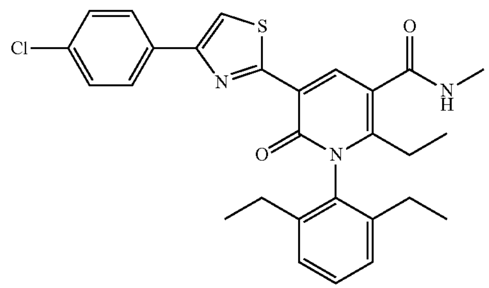 [SMILES: CCc1cccc(CC)c1-n1c(CC)c(C(=O)NC)cc(-c2nc(-c3ccc(Cl)cc3)cs2)c1=O] | B | B | 506.1654 | 3.862 | Amide coupling of acid 236 with methylamine similar to method used to synthesize 2-(4-(4-chlorophenyl)thiazol-2-yl)-N-(2,5-dimethoxyphenyl)acetamide (70° C, 24 h) | |
| 294 | 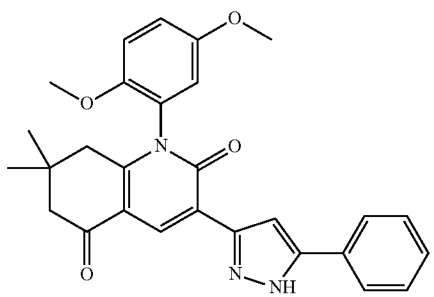 [SMILES: COc1ccc(OC)c(-n2c3c(cc(-c4cc(-c5ccccc5)[nH]n4)c2=O)C(=O)CC(C)(C)C3)c1] | E | D | 470.2073 | 3.428 | Method: xvii | |
| 295 | 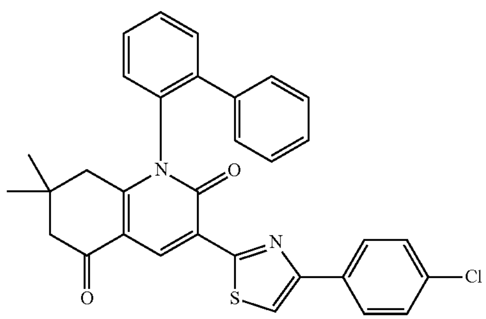 [SMILES: CC1(C)CC(=O)c2cc(-c3nc(-c4ccc(Cl)cc4)cs3)c(=O)n(-c3ccccc3-c3ccccc3)c2C1] | C | B | 537.139 | 4.037 | Starting materials: nitrile-1, aniline-2-phenylaniline; Method: E | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 296 | 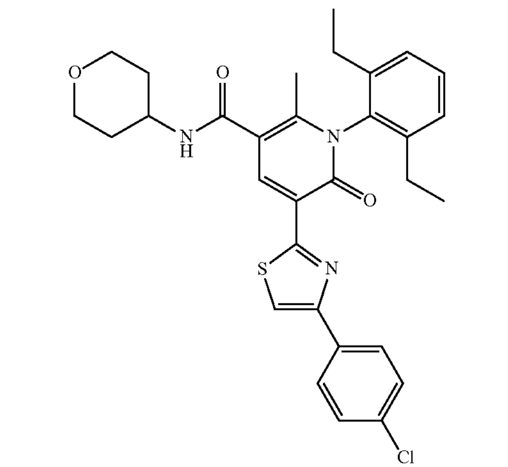 [SMILES: CCc1cccc(CC)c1-n1c(C)c(C(=O)NC2CCOCC2)cc(-c2nc(-c3ccc(Cl)cc3)cs2)c1=O] | C | C | 562.1936 | 3.788 | Starting materials: acid-compound 143, amine-tetrahydro-2H-pyran-4-amine hydrochloride; Method: U | |
| 297 | 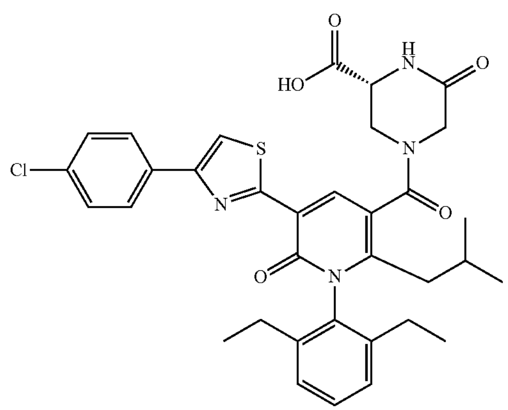 [SMILES: CCc1cccc(CC)c1-n1c(CC(C)C)c(C(=O)N2CC(=O)N[C@@H](C(=O)O)C2)cc(-c2nc(-c3ccc(Cl)cc3)cs2)c1=O] | B | B | 647.2089 | 3.597 | Starting materials: acid-compound 14, amine-(R)-ethyl 6-oxopiperazine-2-carboxylate (xxi); Methods: U, then ester cleavage with LiOH/water/THF rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 298 | 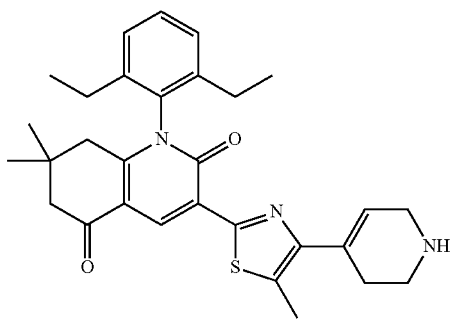 [SMILES: CCc1cccc(CC)c1-n1c2c(cc(-c3nc(C4=CCNCC4)c(C)s3)c1=O)C(=O)CC(C)(C)C2] | E | D | 524.236 | 2.704 | Boc removal of compound 197 with TFA/DCM rt | |
| 299 | 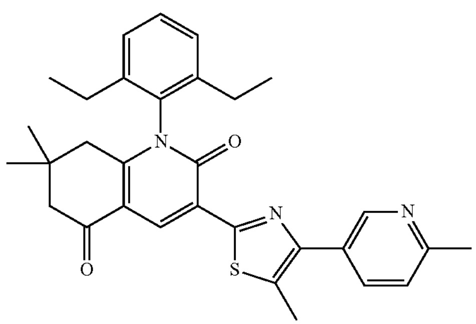 | C | C | 512.2377 | 3.209 | Starting material: boryl species-(6-methylpyridin-3-yl)boronic acid hydrate; Method: xix | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | $^1$H-NMR |
|---|---|---|---|---|---|---|---|
| 300 | 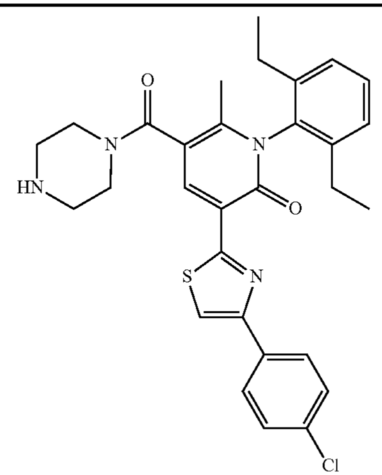 | A | B | 547.1942 | 2.691 | Starting materials: acid-compound 143, amine-piperazine; Method: U | |
| 301 | 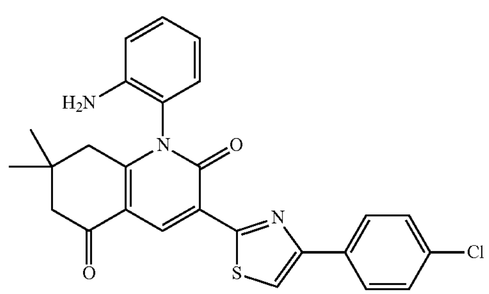 [SMILES: CC1(C)CC(=O)c2cc(-c3nc(-c4ccc(Cl)cc4)cs3)c(=O)n(-c3ccccc3N)c2C1] | C | C | 476.1207 | 3.721 | Starting materials: nitrile-1, aniline-2-aminoaniline; Method: E | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 302 | 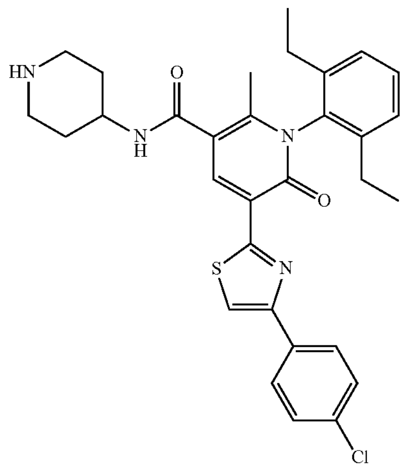 [SMILES: CCc1cccc(CC)c1-n1c(C)c(C(=O)NC2CCNCC2)cc(-c2nc(-c3ccc(Cl)cc3)cs2)c1=O] | B | B | 561.2062 | 2.708 | Starting materials: acid-compound 143, amine-tert-butyl 4-aminopiperidine-1-carboxylate; Method: U, then Boc removal with TFA/DCM rt | |
| 303 | 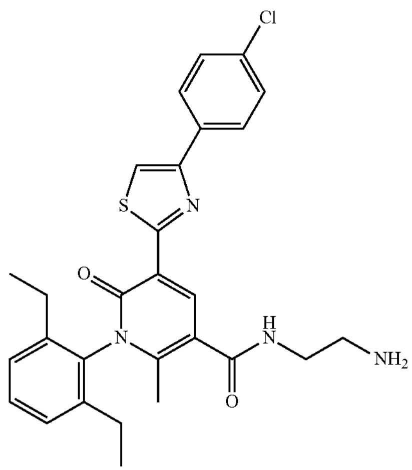 | B | C | 521.1787 | 2.669 | Starting materials: acid-compound 143, amine-tert-butyl (2-aminoethyl)carbamate; Method: U, then Boc removal with TFA/DCM rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 304 | 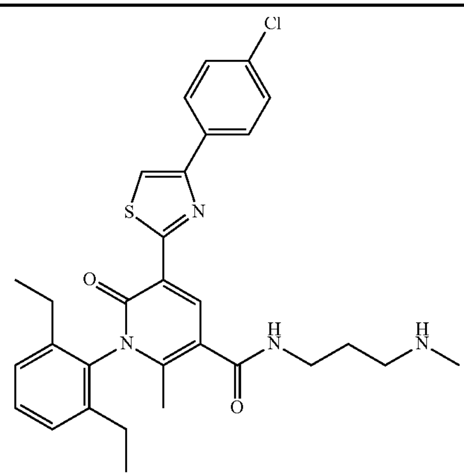 | C | B | 571.1919 | 2.708 | Starting materials: acid-compound 143, amine-tert-butyl (3-aminopropyl)(methyl) carbamate; Method: U, then Boc removal with TFA/DCM rt | |
| 305 | 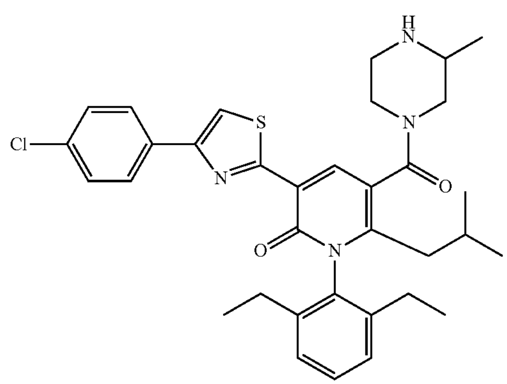 [SMILES: CCc1cccc(CC)c1-n1c(CC(C)C)c(C(=O)N2CCNC(C)C2)cc(-c2nc(-c3ccc(Cl)cc3)cs2)c1=O] | B | A | 603.2546 | 2.881 | Starting materials: acid-compound 14, amine-tert-butyl 2-methylpiperazine-1-carboxylate; Method: U, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 306 | 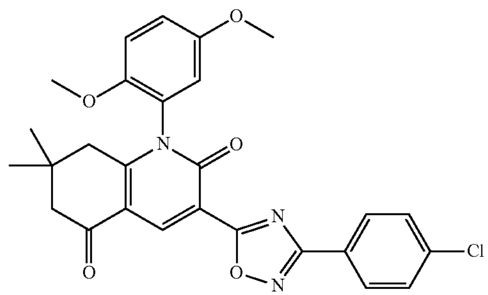 [SMILES: COc1ccc(OC)c(-n2c3c(cc(-c4nc(-c5ccc(Cl)cc5)no4)c2=O)C(=O)CC(C)(C)C3)c1] | D | D | 506.1493 | 3.697 | Method: x | |
| 307 | 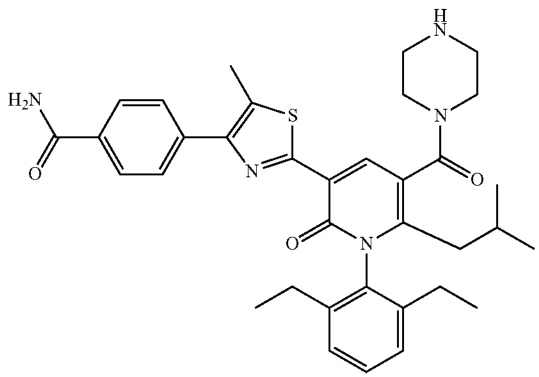 [SMILES: CCc1cccc(CC)c1-n1c(CC(C)C)c(C(=O)N2CCNCC2)cc(-c2nc(-c3ccc(C(N)=O)cc3)c(C)s2)c1=O] | D | D | 612.3003 | 2.846 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-carbamoylphenyl)boronic acid (method xix); Methods: S, then ester hydrolyzed with LiOH (0.5M), THF, rt, xix, then Boc removal with TFA/DCM rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 308 | 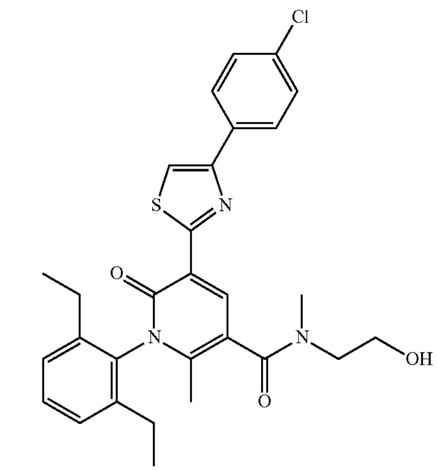 [SMILES: CCc1cccc(CC)c1-n1c(C)c(C(=O)N(C)CCO)cc(-c2nc(-c3ccc(Cl)cc3)cs2)c1=O] | C | C | 536.1783 | 3.563 | Starting materials: acid-compound 143, amine-2-(methylamino)ethanol; Method: U | |
| 309 | 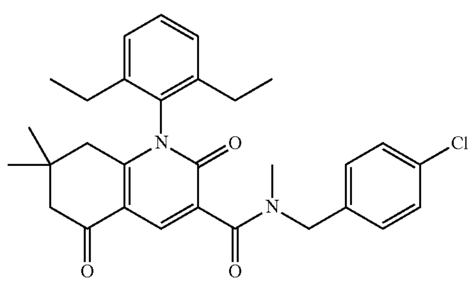 [SMILES: CCc1cccc(CC)c1-n1c2c(cc(C(=O)N(C)Cc3ccc(Cl)cc3)c1=O)C(=O)CC(C)(C)C2] | D | D | 505.226 | 3.676 | Starting materials: nitrile-N-(4-chlorobenzyl)-2-cyano-N-methylacetamide, aniline-2,6-diethylaniline; Method: 379R | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 310 | 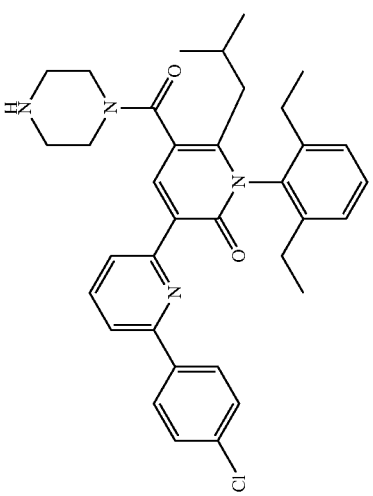 | C | C | 583.2852 | 2.917 | Starting materials: methyl 5-methyl-3-oxohexanoate (step 1), 2-(6-(4-chlorophenyl)pyridin-2-yl)acetonitrile (step 2), piperazine (used in method U); Methods: S, then ester hydrolyzed with LiOH (xs), THF/MeOH/water, 50° C.; U | |
| 311 | 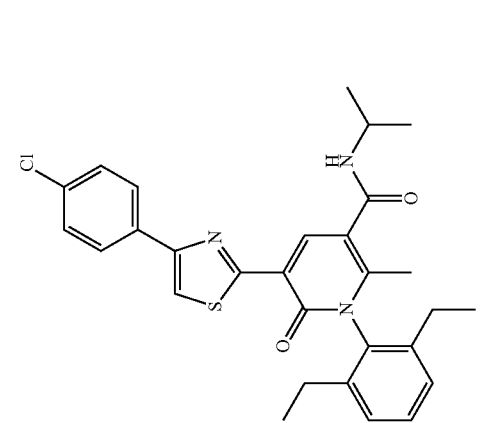 | C | C | 520.1817 | 3.916 | Starting materials: acid-compound 143, amine-propan-2 amine; Method: U | |

TABLE 1-continued
Characterization and Enzymatic Inhibition Data for Selected Compounds
| Cpd # | Structure | Data for R132H (μM) | Data for R132C (μM) | MZ | RT (min) | Synthesis Method | 1H-NMR |
|---|---|---|---|---|---|---|---|
| 312 | 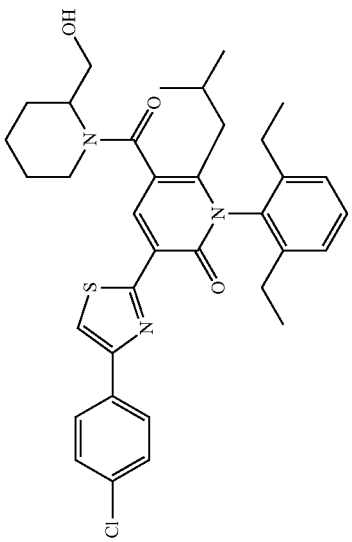 | C | B | 618.2536 | 4.034 | Starting materials: acid-compound 14, amine-piperidin-2-ylmethanol; Method: U | |
| 313 | 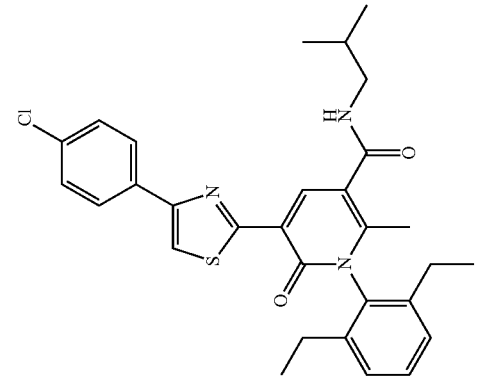 | E | C | 534.1974 | 4.012 | Starting materials: acid-compound 143, amine-2-methylpropan-1-amine; Method: U | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 314 | 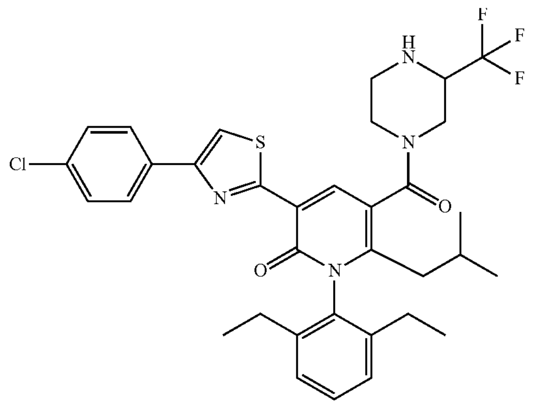 [SMILES: CCc1cccc(CC)c1-n1c(CC(C)C)c(C(=O)N2CCNC(C(F)(F)F)C2)cc(-c2nc(-c3ccc(Cl)cc3)cs2)c1=O] | B | B | 657.2259 | 4.042 | Starting materials: acid-compound 14, amine-2-(trifluoromethyl)piperazine; Method: U | |
| 315 | 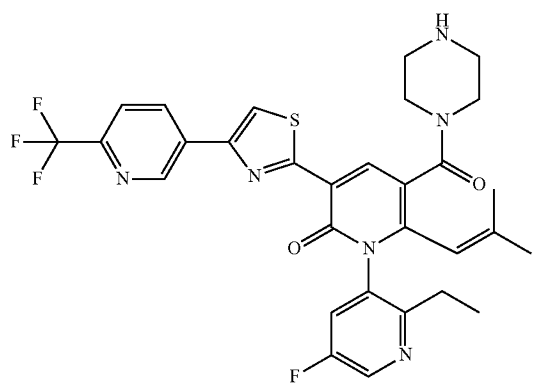 [SMILES: CCc1ncc(F)cc1-n1c(C=C(C)C)c(C(=O)N2CCNCC2)cc(-c2nc(-c3ccc(C(F)(F)F)nc3)cs2)c1=O] | B | C | 613.1999 | 2.523 | Starting materials: nitrile 26 (step 2 method W); pyridyl amine 9 (step 3 methodW), Methods: W, then steps 4-6 in method V | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 316 | 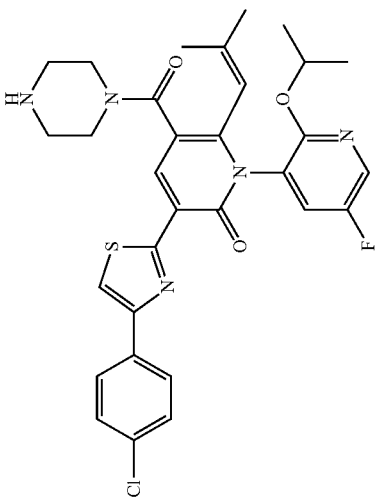 | A | A | 608.1914 | 2.725 | Starting materials: nitrile 1 (step2 method V); pyridyl amine 3 (step 3 method V); piperidine (step 5 method V), Methods: V, no step 7 | |
| 317 | 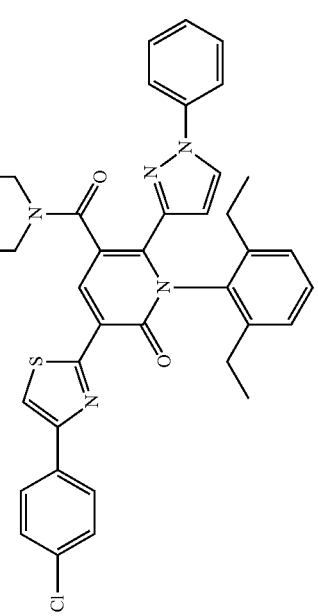 | D | C | 675.2301 | 2.84 | Starting materials: ethyl 3-oxo-3-(1-phenyl-1H-pyrazol-3-yl)propanoate (step 1), Nitrile 1 (step 2), piperazine (used in method U); Methods: S, ester hydrolyzed with LiOH (xs), THF/MeOH/water, 60° C.; U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 318 | 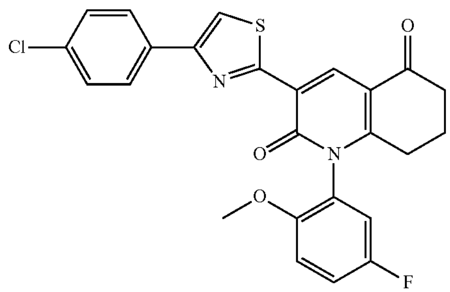 [SMILES: COc1ccc(F)cc1-n1c2c(cc(-c3nc(-c4ccc(Cl)cc4)cs3)c1=O)C(=O)CCC2] | C | C | 481.096 | 3.733 | Starting material: cyclohexane-1,3-dione (step1 method M); nitrile 1 (step2 method M); 2,4-dimethylaniline (step 3 method M), Methods: M | 1H NMR (400 MHz, CD3OD) δ 9.33 (s, 1H), 7.98 (d, J = 8.4 Hz, 2H), 7.56 (s, 1H), 7.41 (d, J = 8.4 Hz, 2H), 7.22-7.23 (m, 1H), 7.08-7.01 (m, 2H), 3.79 (s, 3H), 2.63-2.52 (m, 4H), 2.12-2.11 (m, 2H). Aliphatic region complicated significantly by amide rotamers. |
| 319 | 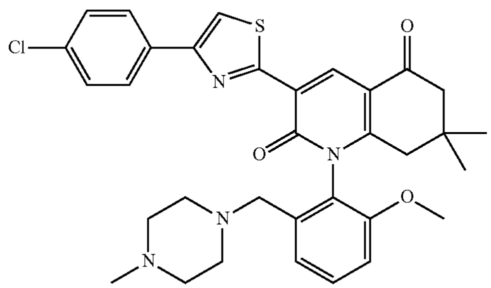 [SMILES: COc1cccc(CN2CCN(C)CC2)c1-n1c2c(cc(-c3nc(-c4ccc(Cl)cc4)cs3)c1=O)C(=O)CC(C)(C)C2] | D | D | 603.2185 | 2.775 | Starting material: 5,5-dimethylcyclohexane-1,3-dione (step1 method M); nitrile 1 (step2 method M); 2-methoxy-6-((4-methylpiperazin-1-yl)methyl)aniline (step 3 method M), Methods: M | HCl salt: 1H NMR (400 MHz, dmso) δ 9.09 (s, 1H), 8.26 (s, 1H), 8.14-8.07 (m, 2H), 7.63-7.53 (m, 3H), 7.37 (s, 1H), 7.30 (d, J = 8.4 Hz, 1H), 3.78 (s, 3H), 3.32 (s,4H), 2.96-2.70 (m, 4H), 2.55 (t, J = 10.5 Hz, 2H), 2.50-2.40 (m, 5H), 2.25 (d, J = 17.5 Hz, 2H), 0.99 (d, J = 20.6 Hz, 6H). Aliphatic region complicated significantly by amide rotamers. |

TABLE 1-continued
Characterization and Enzymatic Inhibition Data for Selected Compounds
| Cpd # | Structure | Data for R132H (µM) | Data for R132C (µM) | MZ | RT (min) | Synthesis Method | 1H-NMR |
|---|---|---|---|---|---|---|---|
| 320 | 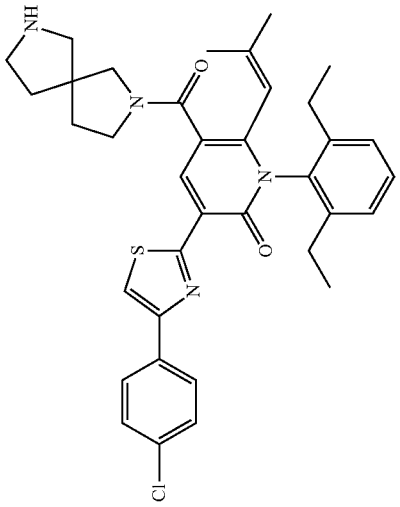 | B | A | 627.2555 | 2.787 | Starting materials: 6,6-dimethyldihydro-2H-pyran 2,4(3H)-dione (step 1), Nitrile 1 (step 2), tert-butyl 2,7-diazaspiro[4.4]nonane-2-carboxylate (used in methods V, step 5); Methods: V | |
| 321 | 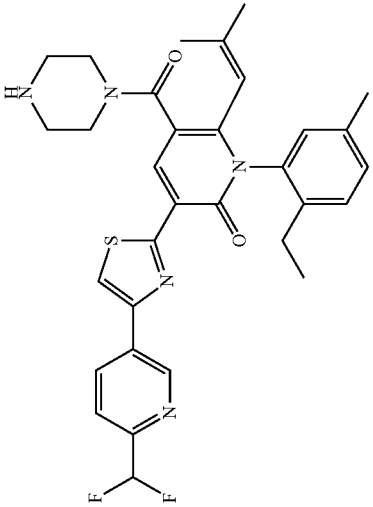 | | | | | | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | $^1$H-NMR |
|---|---|---|---|---|---|---|---|
| 322 | 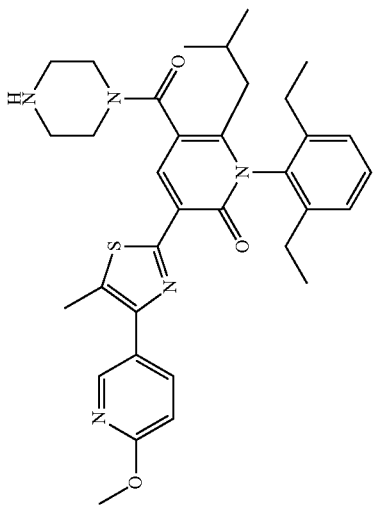 | B | B | 600.3026 | 2.728 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (6-methoxypyridin-3-yl)boronic acid (method xix); Methods: S, then Boc removal with TFA/DCM rt | |
| 323 | 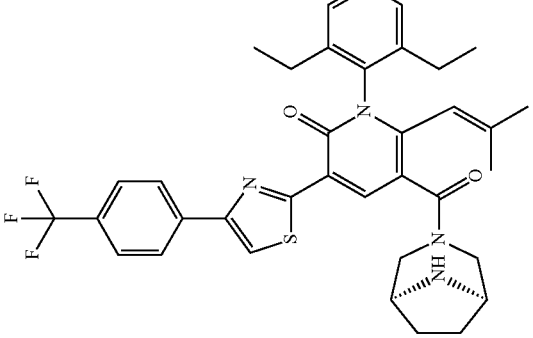 | A | A | 647.2642 | 2.853 | Starting materials: 6,6-dimethyldihydro-2H-pyran-2,4(3H)-dione (step 1), Nitrile 7 (step 2), (1R,5S)-tert-butyl 3,8-diazabicyclo[3.2.1]octane-8-carboxylate (used in methods V, step 5); Methods: V. | 1H NMR (400 MHz, DMSO-d6) δ 8.75 (s, 1H), 8.40 (s, 1H), 8.29 (d, J = 8.1 Hz, 2H), 7.83 (d, J = 8.1 Hz, 2H), 7.43 (t, J = 7.7 Hz, 1H), 7.39-7.20 (m, 2H), 5.24 (s, 1H), 4.49-4.39 (m, 2H), 4.16-3.88 (m, 2H), 3.62-3.48 (m, 1H), 3.01-2.91 (m, 1H), 2.66-2.54 (m, 2H), 2.43-2.28 (m, 2H), 2.18-1.73 (m, 5H), 1.59-1.50 (m, 7H), 1.19-1.06 (m, 3H), 1.04-0.90 (m, 3H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 324 | 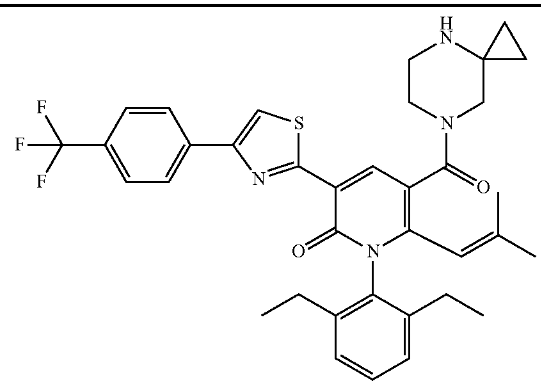 | A | A | 647.2691 | 2.874 | Starting materials: 6,6-dimethyldihydro-2H-pyran-2,4(3H)-dione (step 1), Nitrile 7 (step 2), tert-butyl 4,7-diazaspiro[2.5]octane-4-carboxylate (used in methods V, step 5); Methods: V. | 1H NMR (400 MHz, DMSO-d6) δ 8.71 (s, 1H), 8.41 (s, 1H), 8.29 (d, J = 8.1 Hz, 2H), 7.83 (d, J = 8.2 Hz, 2H), 7.48-7.21 (m, 3H), 5.33 (s, 1H), 4.43-4.33 (m, 1H), 3.70-3.37 (m, 3H), 3.07-2.90 (m, 2H), 2.71-2.59 (m, 2H), 2.44-1.90 (m, 4H), 1.58 (d, J = 10.3 Hz, 6H), 1.26-0.72 (m, 9H). |
| 325 | 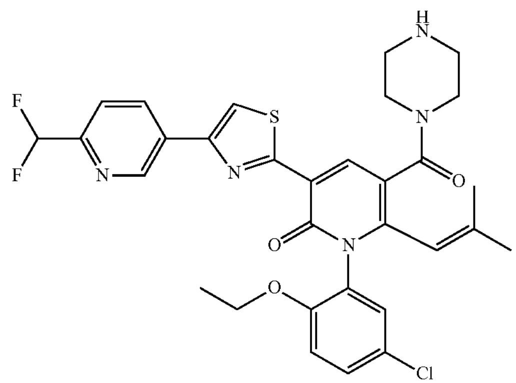 [SMILES: CCOc1ccc(Cl)cc1-n1c(C=C(C)C)c(C(=O)N2CCNCC2)cc(-c2nc(-c3ccc(C(F)F)nc3)cs2)c1=O] | | | | | | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 326 | 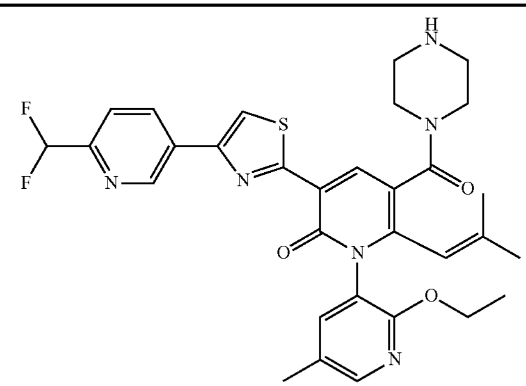 | A | B | 607.2309 | 2.471 | Starting materials: 6,6-dimethyldihydro-2H-pyran-2,4(3H)-dione (step 1), Nitrile 25 (step 2), pyridyl amine 6 (step 3 of methods V); Methods: V, no step 6. | |
| 328 | 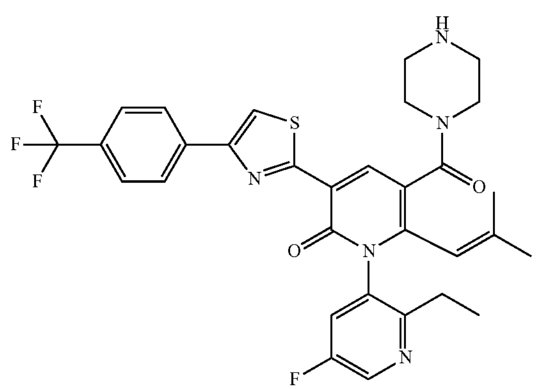 | A | A | 612.2066 | 2.65 | Starting materials: 6,6-dimethyldihydro-2H-pyran-2,4(3H)-dione (step 1), 2-(4-(trifluoromethyl)phenyl)thiazol-2-yl)acetonitrile (step 2), 2-ethyl-5-fluoropyridin-3-amine (step 3); Methods: W, then V (steps 4-6) | TFA salt: 1H NMR (400 MHz, DMSO-d6) δ 8.80 (bs, 1H), 8.76 (s, 1H), 8.73 (d, J = 2.8 Hz, 1H), 8.45 (s, 1H), 8.31 (d, J = 8.0 Hz, 2H), 8.03 (d, J = 8.6 Hz, 1H), 7.85 (d, J = 8.2 Hz, 2H), 5.61-5.41 (m, 1H), 4.15-3.91 (m, 1H), 3.75-2.81 (s, 8H), 2.34-2.25 (m, 1H), 1.63 (s, 3H), 1.59 (s, 3H), 1.23-0.98 (m, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 329 | 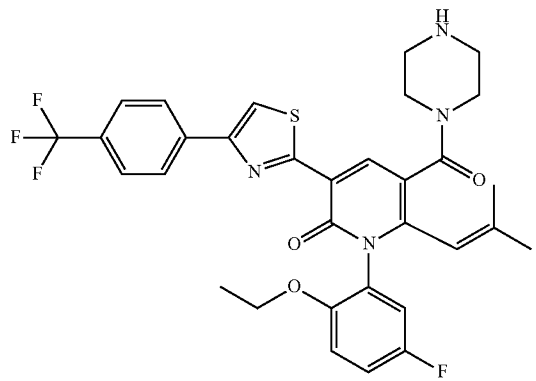 [SMILES: CCOc1ccc(F)cc1-n1c(C=C(C)C)c(C(=O)N2CCNCC2)cc(-c2nc(-c3ccc(C(F)(F)F)cc3)cs2)c1=O] | A | A | 627.21 | 2.708 | Starting materials: nitrile 7 (step 2 method W); 2-ethoxy-5-fluoroaniline (step 3 method W). Methods: W, then steps 4-6 in method V | 1H NMR (400 MHz, DMSO-d6) δ 8.80 (s, 1H), 8.70 (s, 1H), 8.42 (s, 1H), 8.31 (d, J = 8.2 Hz, 2H), 7.85 (d, J = 8.2 Hz, 2H), 7.44 (d, J = 8.5 Hz, 1H), 7.34 (td, J = 8.8, 3.0 Hz, 1H), 7.28-7.14 (m, 1H), 5.58 (s, 1H), 4.18-3.95 (m, 3H), 3.91-3.83 (m, 1H), 3.69-3.61 (m, 1H), 3.26-3.00 (m, 4H), 2.96 (s, 1H), 1.61 (d, J = 1.4 Hz, 3H), 1.54 (d, J = 1.2 Hz, 3H), 1.20-1.05 (m, 3H). |
| 330 | 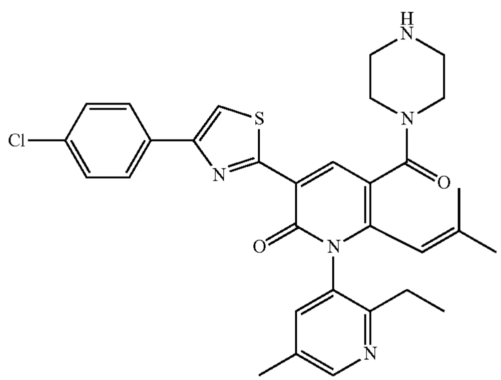 [SMILES: CCc1ncc(C)cc1-n1c(C=C(C)C)c(C(=O)N2CCNCC2)cc(-c2nc(-c3ccc(Cl)cc3)cs2)c1=O] | A | B | 574.2032 | 2.526 | Starting materials: 6,6-dimethyldihydro-2H-pyran-2,4(3H)-dione (step 1), Nitrile 1 (step 2), pyridyl amine 8 (step 3 of methods V); Methods: V, no step 6. | 1H NMR (400 MHz, DMSO-d6) δ 8.59 (s, 1H), 8.06 (dd, J = 9.2, 5.6 Hz, 1H), 7.86-7.75 (m, 2H), 7.75-7.65 (m, 2H), 7.48-7.29 (m, 2H), 5.40 (s, 1H), 4.92 (d, J = 29.8 Hz, 1H), 3.54-3.31 (m, 2H), 3.30-2.97 (m, 2H), 2.93-2.64 (m, 3H), 2.10-1.80 (m, 7H), 1.62-1.44 (d, J = 2.6 Hz, 2H), 1.35-1.19 (m, 4H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 331 | 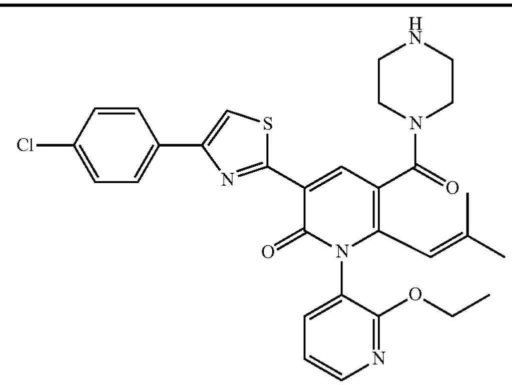 | A | B | 576.1808 | 2.583 | Starting materials: 6,6-dimethyldihydro-2H-pyran-2,4(3H)-dione (step 1), 2-(4-(4-chlorophenyl)thiazol-2-yl)acetonitrile (step 2), 2-ethoxypyridin-3-amine (step 3); Methods: W, then V (steps 4-6) | TFA salt: 1H NMR (400 MHz, DMSO-d6) δ 8.87-8.60 (m, 2H), 8.29 (dd, J = 5.0, 1.8 Hz, 1H), 8.26 (s, 1H), 8.11 (d, J = 8.5 Hz, 2H), 8.03-7.86 (m, 1H), 7.55 (d, J = 8.6 Hz, 2H), 7.23-7.02 (m, 1H), 5.54 (s, 1H), 4.51-4.38 (m, 1H), 4.34-4.18 (m, 3H), 4.06-3.91 (m, 1H), 3.74-2.89 (m, 5H), 1.61 (s, 3H), 1.55 (s, 3H), 1.25-1.09 (m, 3H). |
| 332 | 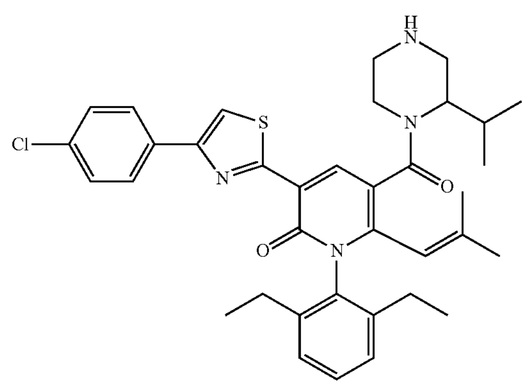 [SMILES: CCc1cccc(CC)c1-n1c(C=C(C)C)c(C(=O)N2CCNCC2C(C)C)cc(-c2nc(-c3ccc(Cl)cc3)cs2)c1=O] | B | A | 629.2715 | 2.913 | Starting materials: 6,6-dimethyldihydro-2H-pyran-2,4(3H)-dione (step 1), Nitrile 1 (step 2), tert-butyl 3-isopropylpiperazine-1-carboxylate (used in methods V, step 5); Methods: V | 1H NMR (400 MHz, DMSO-d6) δ 8.79 (s, 1H), 8.25 (s, 1H), 8.18-7.99 (m, 2H), 7.53 (dd, J = 8.6, 3.2 Hz, 2H), 7.48-7.16 (m, 3H), 5.30 (d, J = 12.1 Hz, 1H), 4.44 (dd, J = 73.5, 12.5 Hz, 1H), 3.71-3.37 (m, 2H), 3.27-2.83 (m, 2H), 2.70-2.51 (m, 2H), 2.44-2.01 (m, 3H), 1.62 (dd, J = 12.6, 6.9 Hz, 3H), 1.48 (dd, J = 52.3,1.3 Hz, 3H), 1.16-1.05 (m, 3H), 1.06-0.91 (m, 6H), 0.85-0.64 (m, 5H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 333 | 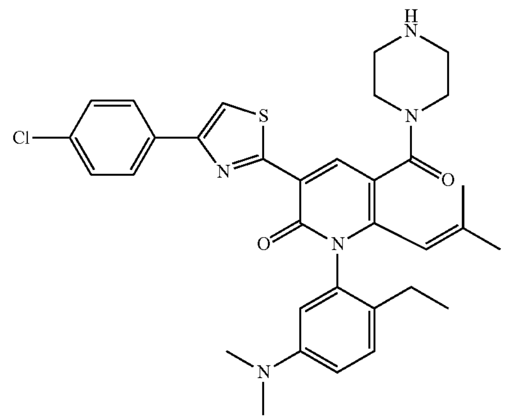 [SMILES: CCc1ccc(N(C)C)cc1-n1c(C=C(C)C)c(C(=O)N2CCNCC2)cc(-c2nc(-c3ccc(Cl)cc3)cs2)c1=O] | A | A | 602.2367 | 2.69 | Starting materials: 6,6-dimethyldihydro-2H-pyran-2,4(3H)-dione (step 1), Nitrile 1 (step 2), aniline 5 (step 3 of methods V); Methods: V, | |
| 334 | 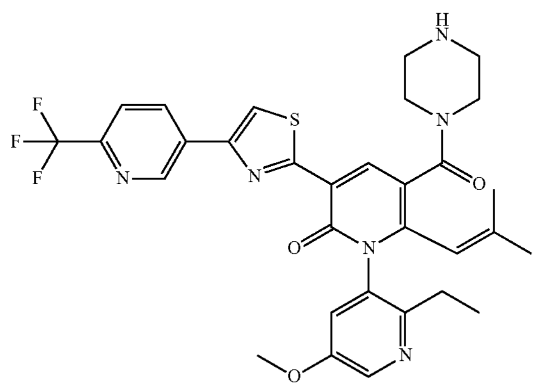 [SMILES: CCc1ncc(OC)cc1-n1c(C=C(C)C)c(C(=O)N2CCNCC2)cc(-c2nc(-c3ccc(C(F)(F)F)nc3)cs2)c1=O] | B | C | 625.218 | 2.468 | Starting materials: 6,6-dimethyldihydro-2H-pyran-2,4(3H)-dione (step 1), 2-(4-(6-(trifluoromethyl)pyridin-3-yl)thiazol-2-yl)acetonitrile hydrobromide (step 2), 2-ethyl-5-methoxypyridin-3-amine (step 3); Methods: W, then V (steps 4-6) | 1H NMR (400 MHz, Chloroform-d) δ 9.30 (s, 1H), 8.83 (bs, 1H), 8.50 (d, J = 8.1 Hz, 1H), 8.41 (d, J = 2.7 Hz, 1H), 7.82 (s, 1H), 7.77 (d, J = 8.2 Hz, 1H), 7.08-6.87 (m, 1H), 5.44-5.40 (m, 1H), 4.05-3.74 (m, 4H), 3.57-3.23 (m, 3H), 3.07-2.79 (m, 4H), 2.60-2.26 (m, 2H), 1.70 (s, 3H), 1.66 (s, 3H), 1.35-1.11 (m, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 336 | 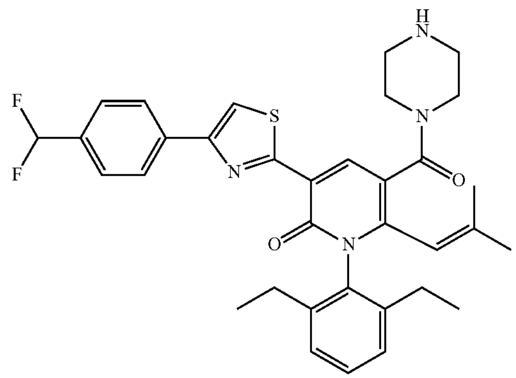 [SMILES: CCc1cccc(CC)c1-n1c(C=C(C)C)c(C(=O)N2CCNCC2)cc(-c2nc(-c3ccc(C(F)F)cc3)cs2)c1=O] | A | A | 603.2598 | 2.741 | Starting materials: 6,6-dimethyldihydro-2H-pyran-2,4(3H)-dione (step 1), Nitrile 24 (step 2), Methods: V, no step 6. | |
| 337 | 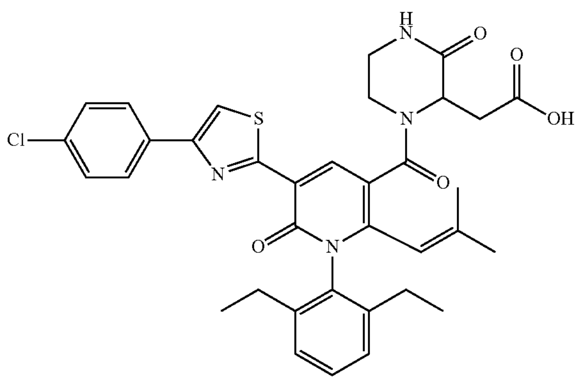 [SMILES: CCc1cccc(CC)c1-n1c(C=C(C)C)c(C(=O)N2CCNC(=O)C2CC(=O)O)cc(-c2nc(-c3ccc(Cl)cc3)cs2)c1=O] | A | A | 659.21 | 3.474 | Starting materials: 6,6-dimethyldihydro-2H-pyran-2,4(3H)-dione (step 1), Nitrile 1 (step 2), ethyl 2-(3-oxopiperazin-2-yl)acetate (used in methods V, step 5); Methods: V, no step 6, then ester hydrolyzed with LiOH (xs). THF/MeOH/water, 60° C. | 1H NMR (400 MHz, DMSO-d6) δ 8.63 (s, 1H), 8.23 (d, J = 1.8 Hz, 1H), 8.15-8.06 (m, 2H), 7.56-7.50 (m, 2H), 7.41 (td, J = 7.7, 3.0 Hz, 1H), 7.35-7.22 (m, 2H), 5.23 (s, 1H), 4.79 (t, J = 4.4 Hz, 1H), 4.54-4.33 (m, 1H), 3.63-3.62 (m, 1H), 3.25-3.03 (m, 1H), 2.97-2.53 (m, 3H), 2.42-2.20 (m, 2H), 1.64-1.43 (m, 7H), 1.11 (t, J = 7.5, 3H), 0.99 (t, J = 7.6 Hz, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 338 | 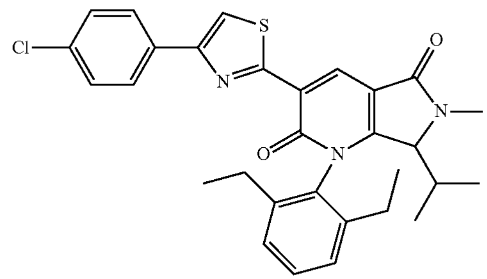 [SMILES: CCc1cccc(CC)c1-n1c2c(cc(-c3nc(-c4ccc(Cl)cc4)cs3)c1=O)C(=O)N(C)C2C(C)C] | C | B | 632.1835 | 4.101 | Starting materials: ethyl 4-((tert-butoxycarbonyl)(methyl)amino)-5-methyl-3-oxohexanoate (step 1), piperazine (used in method U); Methods: S, then ester hydrolyzed with LiOH (xs), THF/MeOH/water, 60° C.; U; Boc removal with TFA (xs)/DCM rt resulted in lactam formation (expulsion of piperazine) | 1H NMR (400 MHz, DMSO-d6) δ 8.84 (s, 1H), 8.25 (s, 1H), 8.16-8.09 (m, 2H), 7.58-7.48 (m, 3H), 7.39 (ddd, J = 7.6, 6.1, 1.4 Hz, 2H), 4.20 (d, J = 1.6 Hz, 1H), 3.00 (s, 3H), 2.45 (m, 1H), 2.31 (q, J = 7.5 Hz, 2H), 2.06 (dq, J = 14.9, 7.4 Hz, 1H), 1.66-1.54 (m, 1H), 1.16 (t, J = 7.5 Hz, 3H), 0.98 (t, J = 7.5 Hz, 3H), 0.85 (d, J = 7.3 Hz, 3H), 0.52 (d, J = 6.8 Hz, 3H). |
| 339 | 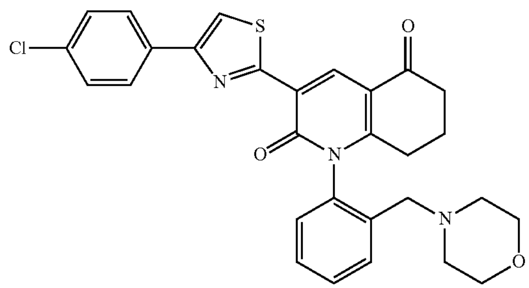 [SMILES: O=C1CCCc2c1cc(-c1nc(-c3ccc(Cl)cc3)cs1)c(=O)n2-c1ccccc1CN1CCOCC1] | D | C | 532.1444 | 3.139 | Starting material: cyclohexane-1,3-dione (step1 method M); nitrile 1 (step2 method M); 2-(morpholinomethyl)aniline (step 3 method M); Methods: M | |
| 340 | 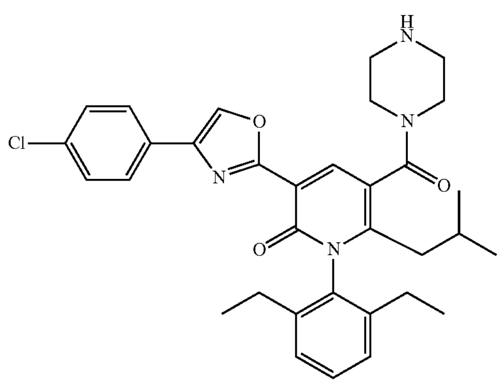 [SMILES: CCc1cccc(CC)c1-n1c(CC(C)C)c(C(=O)N2CCNCC2)cc(-c2nc(-c3ccc(Cl)cc3)co2)c1=O] | B | B | 573.2632 | 2.661 | Starting materials: methyl 5-methyl-3-oxohexanoate (step 1), piperazine (used in method U); nitrile 34 (step 2), piperazine (used in method U); Methods: S, then ester hydrolyzed with LiOH (xs), THF/MeOH/water, 60° C.; U | TFA salt: 1H NMR (400 MHz, DMSO-d6) δ 8.74 (m, 2H), 8.31 (s, 1H), 7.87-7.80 (m, 2H), 7.55-7.40 (m, 3H), 7.32 (d, J = 7.7 Hz, 2H), 4.13-2.82 (br m, 10H), 2.42-1.69 (br m, 3H), 1.31 (dt, J = 13.6, 6.8 Hz, 1H), 1.10 (br s, 6H), 0.60 (d, J = 6.6 Hz, 6H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 341 | 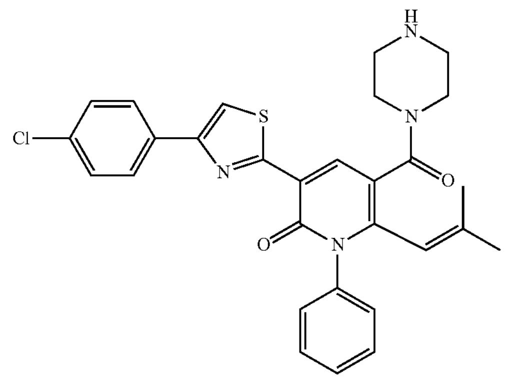 [SMILES: CC(C)=Cc1c(C(=O)N2CCNCC2)cc(-c2nc(-c3ccc(Cl)cc3)cs2)c(=O)n1-c1ccccc1] | B | C | 531.1631 | 2.583 | Starting material: 6,6-dimethyldihydro-2H-pyran-2,4(3H) dione (step1 method V); nitrile 1 (step2 method V); aniline (step 3 method V), Methods: V | TFA salt: 1H NMR (400 MHz, cd3od) δ 8.82 (s, 1H), 8.06-8.01 (m, 2H), 7.93 (d, J = 1.8 Hz, 1H), 7.61-7.49 (m, 3H), 7.48-7.42 (m, 2H), 7.37 (s, 1H), 7.19 (s, 1H), 5.59 (s, 1H), 4.25 (s, 2H), 3.84 (s, 2H), 3.64 (d, J = 18.3 Hz, 2H), 3.14 (s,2H), 1.63 (dd, J = 9.4,1.1 Hz, 6H). Aliphatic region complicated significantly by amide rotamers. |
| 342 | 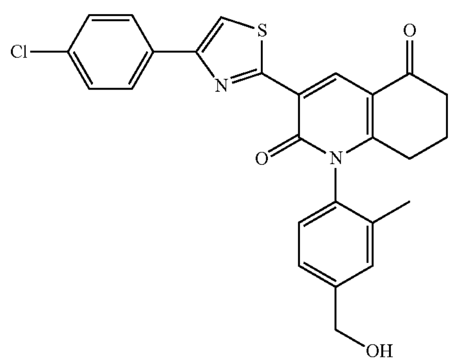 [SMILES: Cc1cc(CO)ccc1-n1c2c(cc(-c3nc(-c4ccc(Cl)cc4)cs3)c1=O)C(=O)CCC2] | D | D | 477.1016 | 3.52 | Starting material: cyclohexane-1,3-dione (step1 method M); nitrile 1 (step2 method M); (4-amino-3-methylphenyl)methanol (step 3 method M), Methods: M | 1H NMR (400 MHz, cdcl3) δ 9.38 (s, 1H), 8.03-7.95 (m, 2H), 7.58 (s, 1H), 7.47 (s, 1H), 7.45-7.40 (m, 3H), 7.18 (d, J = 8.0 Hz, 1H), 4.79 (d, J = 3.7Hz, 2H), 2.72-2.56 (m, 3H), 2.43-2.29 (m, 1H), 2.20-2.07 (m, 5H), 1.79 (s, 1H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 343 | 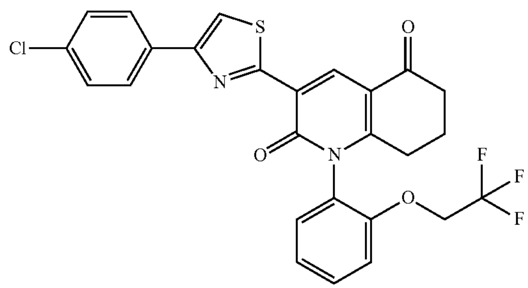 [SMILES: O=C1CCCc2c1cc(-c1nc(-c3ccc(Cl)cc3)cs1)c(=O)n2-c1ccccc1OCC(F)(F)F] | C | C | 531.0732 | 3.771 | Starting material: cyclohexane-1,3-dione (step1 method M); nitrile 1 (step2 method M); 2-(2,2,2-trifluoroethoxy)aniline (step 3 method M); Methods: M | 1H NMR (400 MHz, CD3OD) δ 9.35 (s, 1H), 7.98 (d, J = 8.4 Hz, 2H), 7.54-7.50 (m, 2H), 7.40 (d, J = 8.4 Hz, 2H), 7.30-7.28 (m, 2H), 7.13 (d, J = 8.4 Hz, 1H), 4.46-4.41 (m, 1H), 4.36-4.31 (m, 1H), 2.61-2.46 (m, 4H), 2.12-2.07 (m, 2H). Aliphatic region complicated significantly by amide rotamers. |
| 344 | 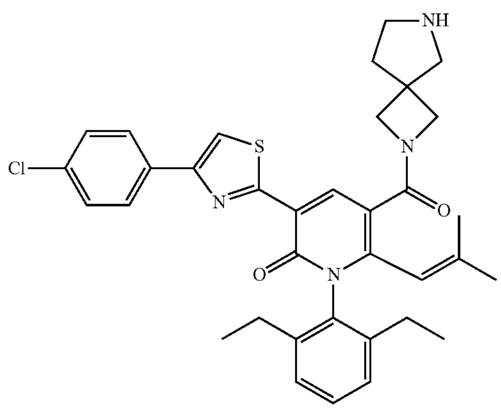 [SMILES: CCc1cccc(CC)c1-n1c(C=C(C)C)c(C(=O)N2CC3(CCNC3)C2)cc(-c2nc(-c3ccc(Cl)cc3)cs2)c1=O] | B | A | 613.24 | 2.758 | Starting materials: 6,6-dimethyldihydro-2H-pyran-2,4(3H)-dione (step 1), Nitrile 1 (step 2), tert-butyl 2,6-diazaspiro[3.4]octane-6-carboxylate (used in methods V, step 5); Methods: V | 1H NMR (400 MHz, DMSO-d6) δ 8.74 (s, 1H), 8.28 (s, 1H), 8.14-8.05 (m, 2H), 7.59-7.47 (m, 3H), 7.35-7.24 (m, 2H), 5.33 (d, J = 2.0 Hz, 1H), 4.03-3.84 (m, 3H), 3.22-3.01 (m, 2H), 2.70-2.50 (m, 2H), 2.37-2.00 (m, 3H), 1.61 (s, 6H), 1.40-1.28 (m, 4H), 1.15-0.99 (m, 6H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 345 | 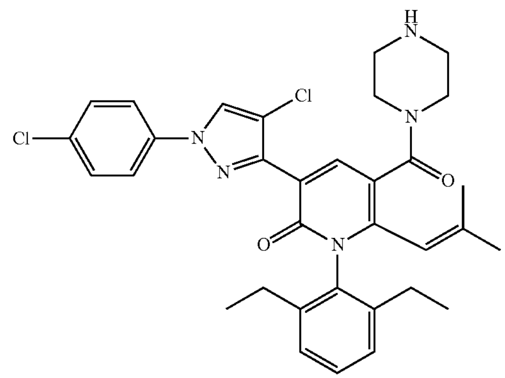 [SMILES: CCc1cccc(CC)c1-n1c(C=C(C)C)c(C(=O)N2CCNCC2)cc(-c2nn(-c3ccc(Cl)cc3)cc2Cl)c1=O] | C | C | 626.2061 | 2.634 | Starting materials: pyrazole 2 (step 2); Methods: V, step 4 with NaOH (xs), following step 4 chlorination-NCS (2 eq) in acetonitrile reflux overnight, then cleave Boc by addition of TFA (xs). | TFA salt: 1H NMR (400 MHz, DMSO-d6) δ 8.84 (s, 1H), 8.78 (br s, 1H), 8.68 (br s, 1H), 7.91-7.81 (m, 2H). 7.78 (s, 1H), 7.63-7.50 (m, 2H), 7.37 (t, J = 7.6 Hz, 1H), 7.24 (s,2H), 5.30-5.13 (m, 1H), 4.06-3.78 (m, 1H), 3.56 (m, 1H), 3.05 (m, 5H), 2.44-1.97 (m, 5H), 1.54 (dd, J = 5.6, 1.3 Hz, 6H), 1.20-0.91 (m, 6H). |
| 346 | 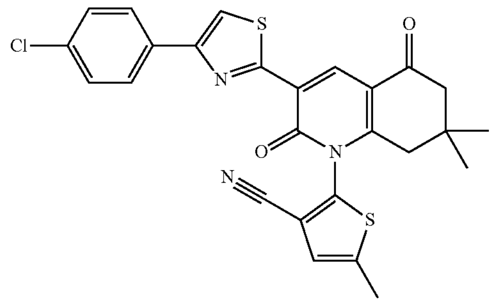 [SMILES: Cc1cc(C#N)c(-n2c3c(cc(-c4nc(-c5ccc(Cl)cc5)cs4)c2=O)C(=O)CC(C)(C)C3)s1] | B | B | 506.077 | 3.858 | Starting material: 5,5-dimethylcyclohexane-1,3-dione (step1 method M); nitrile 1 (step2 method M); 2-amino-5-methylthiophene-3-carbonitrile (step 3 method M), Methods: M | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 347 | 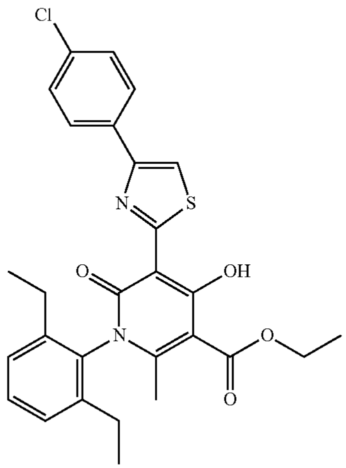 [SMILES: CCOC(=O)c1c(O)c(-c2nc(-c3ccc(Cl)cc3)cs2)c(=O)n(-c2c(CC)cccc2CC)c1C] | D | D | 523.1446 | 4.233 | Method xxiii | |
| 348 | 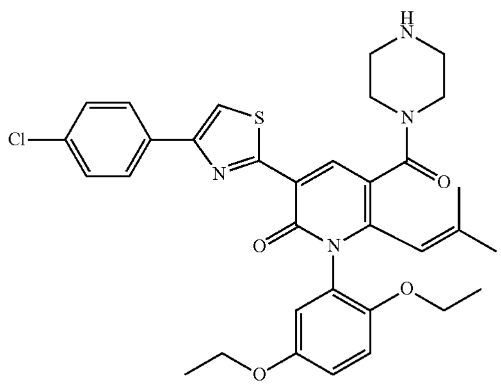 [SMILES: CCOc1ccc(OCC)c(-n2c(C=C(C)C)c(C(=O)N3CCNCC3)cc(-c3nc(-c4ccc(Cl)cc4)cs3)c2=O)c1] | A | A | 619.2161 | 2.703 | Starting material: 6,6-dimethyldihydro-2H-pyran-2,4(3H)-dione (step1 method V); nitrile 1 (step2 method V); 2,5-diethoxyaniline (step 3 method V), Methods: V | TFA salt: 1H NMR (400 MHz, CD3OD) δ 8.82 (s, 1H), 8.07-8.01 (m, 2H), 7.93 (s, 1H), 7.49-7.42 (m, 2H), 7.16-6.98 (m, 3H), 5.65 (s, 1H), 4.25 (s, 2H), 4.03 (d, J = 6.9 Hz, 4H), 3.81 (s, 2H), 3.60 (s, 2H), 3.26 (s, 2H), 1.66 (d, J = 5.7Hz,6H), 1.45-1.34 (m, 3H), 1.27-1.13 (m, 3H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 349 | 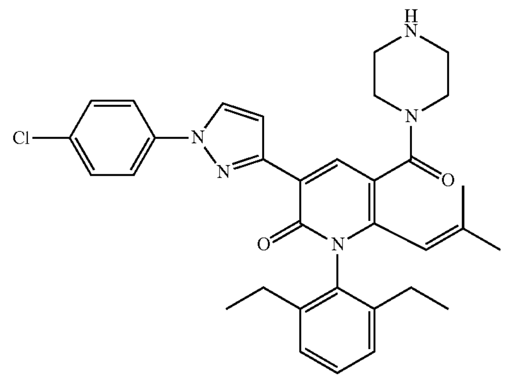 [SMILES: CCc1cccc(CC)c1-n1c(C=C(C)C)c(C(=O)N2CCNCC2)cc(-c2ccn(-c3ccc(Cl)cc3)n2)c1=O] | A | A | 570.2619 | 2.649 | Starting materials: pyrazole 2 (step 2), piperazine (step 5); Methods: V, step 4 with NaOH (xs), no step 6. | TFA salt: 1H NMR (400 MHz, DMSO-d6) δ 8.79 (br s, 1H), 8.69 (br s, 1H), 8.54 (d, J = 2.6 Hz, 1H), 8.34 (s, 1H), 8.00-7.87 (m, 2H), 7.62-7.50 (m, 2H), 7.37 (t, J = 7.6 Hz, 1H), 7.33-7.11 (m, 3H), 5.27-5.12 (m, 1H), 3.99 (m, 1H), 3.53 (m, 1H), 3.21-2.85 (m, 4H), 2.42-1.98 (m, 2H), 1.53 (t, J = 1.5 Hz, 6H), 1.21-0.85 (m, 6H). |
| 350 | 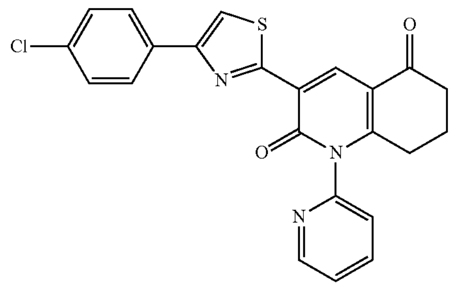 [SMILES: O=C1CCCc2c1cc(-c1nc(-c3ccc(Cl)cc3)cs1)c(=O)n2-c1ccccn1] | E | E | 434.0715 | 3.559 | Starting material: cyclohexane-1,3-dione (step1 method M); nitrile 1 (step2 method M); pyridin-2-amine (step 3 method M); Methods: M | |

| Cpd # | Structure | Data for R132H (μM) | Data for R132C (μM) | MZ | RT (min) | Synthesis Method | ¹H-NMR |
|---|---|---|---|---|---|---|---|
| 351 | 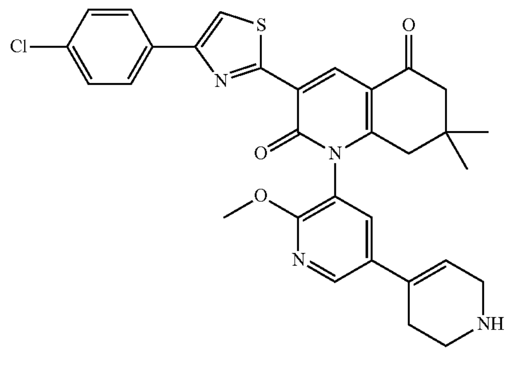 [SMILES: COc1ncc(C2=CCNCC2)cc1-n1c2c(cc(-c3nc(-c4ccc(Cl)cc4)cs3)c1=O)C(=O)CC(C)(C)C2] | D | D | 573.1709 | 2.771 | Starting material: 5,5-dimethylcyclohexane-1,3-dione (step1 method M); nitrile 1 (step2 method M); 6-methoxy-1',2',3',6'-tetrahydro-[3,4'-bipyridin]-5-amine (step 3 method M), Methods: M | TFA salt: 1H NMR(400 MHz, CD3OD) δ 9.07 (s, 1H), 8.85-8.84 (br, 1H), 8.54 (s, 1H), 8.24 (s, 1H), 8.18 (s, 1H), 8.08 (d, J = 8.4 Hz, 2H), 7.54 (d, J = 8.4 Hz, 2H), 6.29 (s, 1H), 3.90 (s, 3H), 3.77 (br, 2H), 2.71 (br, 2H), 2.61 (d, J = 16 Hz, 1H), 2.26 (d, J = 16 Hz, 1H), 1.00 (s, 3H), 0.96 (s, 3H). Two proton overlapped with water and two other proton overlapped with DMSO. Aliphatic region complicated significantly by amide rotamers. |
| 352 | 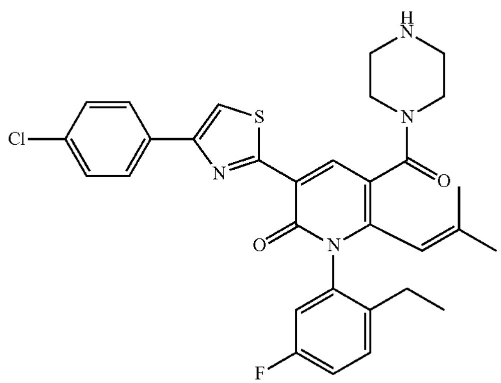 [SMILES: CCc1ccc(F)cc1-n1c(C=C(C)C)c(C(=O)N2CCNCC2)cc(-c2nc(-c3ccc(Cl)cc3)cs2)c1=O] | A | A | 577.182 | 2.706 | Starting material: 6,6-dimethyldihydro-2H-pyran-2,4(3H)-dione (step1 method V); nitrile 1 (step2 method V); aniline 16 (step 3 method V), Methods: V | TFA salt: 1H NMR (400 MHz, CD3OD) δ 8.87 (s, 1H), 8.05 (d, J = 8.4 Hz, 2H), 7.95 (s, 1H), 7.52-7.44 (m, 3H), 7.29-7.19 (m, 2H), 5.66-5.48 (m, 1H), 4.33-4.13 (m, 4H), 3.87-3.49 (m, 4H), 3.27-3.10 (m, 3H), 2.47-2.21 (m, 2H), 1.68 (s, 6H), 1.27-1.05 (m, 3H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 353 | 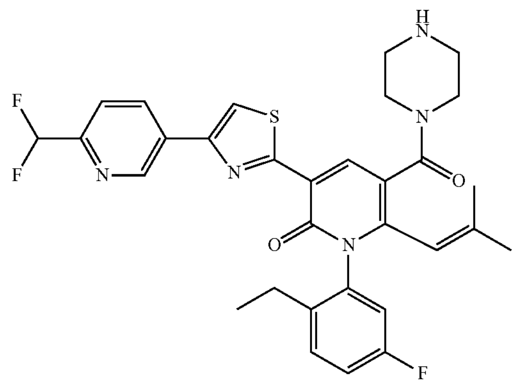 [SMILES: CCc1ccc(F)cc1-n1c(C=C(C)C)c(C(=O)N2CCNCC2)cc(-c2nc(-c3ccc(C(F)F)nc3)cs2)c1=O] | | | | | | |
| 354 | 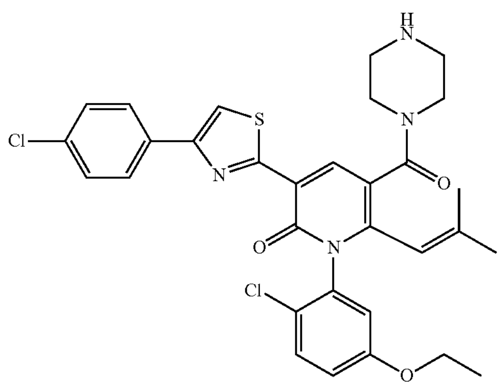 [SMILES: CCOc1ccc(Cl)c(-n2c(C=C(C)C)c(C(=O)N3CCNCC3)cc(-c3nc(-c4ccc(Cl)cc4)cs3)c2=O)c1] | A | A | 609.1506 | 2.7 | Starting material: 6,6-dimethyldihydro-2H-pyran-2,4(3H)-dione (step1 method V); nitrile 1 (step2 method V); aniline 14 (step 3 method V), Methods: V | TFA salt: 1H NMR (400 MHz, CD3OD) δ 8.86 (s, 1H), 8.05 (d, J = 8.4 Hz, 1H), 7.96 (s, 1H), 7.56-7.40 (m, 2H), 7.18-6.99 (m, 3H), 5.63 (s, 1H), 4.35-3.99 (m, 4H), 3.86-3.54 (m, 4H), 3.25-3.10 (m, 2H), 1.70 (s, 6H), 1.40 (m, 3H), Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 356 | 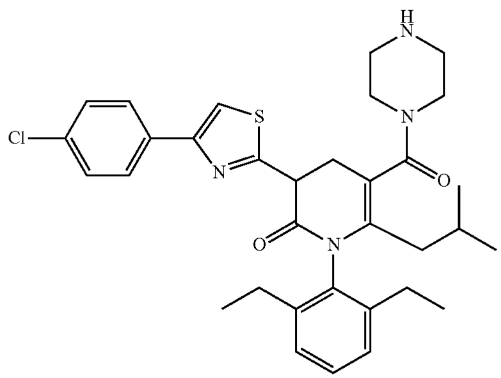 [SMILES: CCc1cccc(CC)c1N1C(=O)C(c2nc(-c3ccc(Cl)cc3)cs2)CC(C(=O)N2CCNCC2)=C1CC(C)C] | B | A | 591.2528 | 2.793 | Compound 231 was reduced with LiAlH4 (2 eq), THF, rt | |
| 357 | 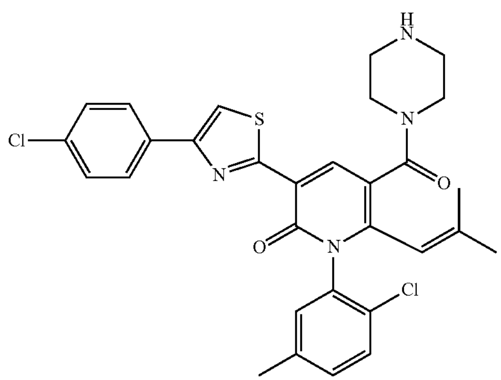 [SMILES: CC(C)=Cc1c(C(=O)N2CCNCC2)cc(-c2nc(-c3ccc(Cl)cc3)cs2)c(=O)n1-c1cc(C)ccc1Cl] | A | A | 579.1369 | 2.676 | Starting material: 6,6-dimethyldihydro-2H-pyran-2,4(3H)-dione (step1 method V); nitrile 1 (step2 method V); 2-chloro-5-methylaniline (step 3 method V), Methods: V | TFA salt: 1H NMR (400 MHz, CD3OD) δ 8.82 (s, 1H), 8.00 (d, J = 8.6 Hz, 2H), 7.92 (s, 1H), 7.55-7.45 (m, 1H), 7.43 (d, J = 8.7 Hz, 2H), 7.38-7.14 (m, 2H), 5.62-5.51 (m, 1H), 4.35-4.15 (m, 1H), 3.86-3.70 (m, 1H), 3.66-3.55 (m, 2H), 3.35-3.10 (m, 4H), 2.46-2.34 (m, 3H), 1.70-1.60 (m, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 358 | 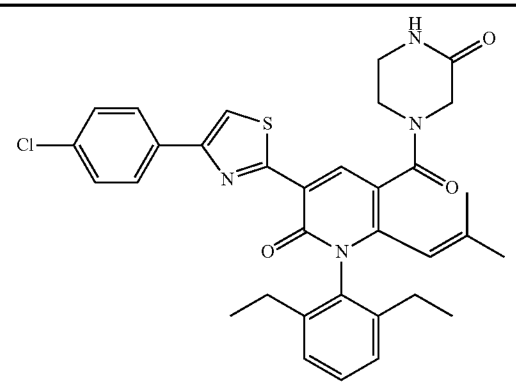 | A | A | 601.2049 | 3.612 | Starting materials: 6,6-dimethyldihydro-2H-pyran-2,4(3H)-dione (step 1), Nitrile 1 (step 2), piperazin-2-one (used in methods V; step 5); Methods: V, no step 6. | 1H NMR (400 MHz, DMSO-d6) δ 8.70 (d, J = 8.2 Hz, 1H), 8.24 (d, J = 1.8 Hz, 1H), 8.17-7.97 (m, 3H), 7.58-7.36 (m, 4H), 5.23 (s, 1H), 3.89-3.79 (s, 2H), 3.26-2.95 (m, 4H), 2.41-2.00 (m, 4H), 1.61-1.42 (m, 7H), 1.20-0.86 (m, 6H). |
| 359 | 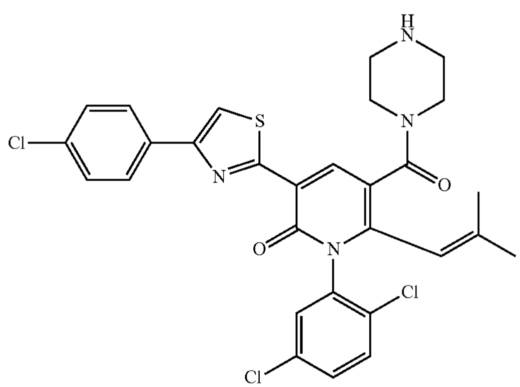 [SMILES: CC(C)=Cc1c(C(=O)N2CCNCC2)cc(-c2nc(-c3ccc(Cl)cc3)cs2)c(=O)n1-c1cc(Cl)ccc1Cl] | A | A | 601.0793 | 2.715 | Starting material: 6,6-dimethyldihydro-2H-pyran-2,4(3H)-dione (step1 method V); nitrile 1 (step2 method V); 2,5-dichloroaniline (step 3 method V), Methods: V | TFA salt: 1H NMR (400 MHz, CD3OD) δ 8.86 (s, 1H), 8.09-8.01 (m, 2H), 7.96 (s, 1H), 7.77-7.57 (m, 3H), 7.49-7.42 (m, 2H), 5.62 (s, 1H), 4.23 (s, 2H), 3.81 (s, 2H), 3.62 (s, 3H), 3.27 (s, 2H), 1.71 (s, 6H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 360 | 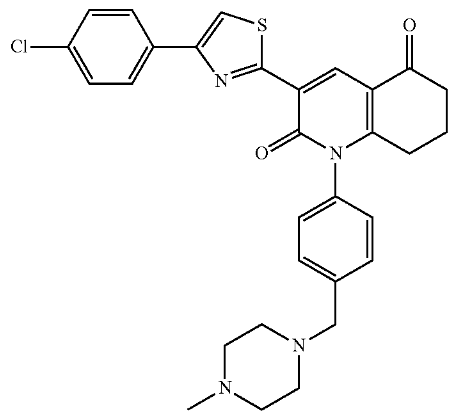 [SMILES: CN1CCN(Cc2ccc(-n3c4c(cc(-c5nc(-c6ccc(Cl)cc6)cs5)c3=O)C(=O)CCC4)cc2)CC1] | E | E | 545.1765 | 2.623 | Starting material: cyclohexane-1,3-dione (step1 method M); nitrile 1 (step2 method M); 4-((4-methylpiperazin-1-yl)methyl)aniline (step 3 method M), Methods: M | HCl salt: 1H NMR (400 MHz, DMSO-d6) δ 9.10 (s, 1H), 8.23 (s, 1H), 8.13-8.07 (m, 2H), 7.76 (s, 2H), 7.55 (dd, J = 12.0, 5.3 Hz, 4H), 4.21 (s,6H), 3.57 (s, 5H), 2.83 (s, 3H), 2.54 (dd, J = 12.9, 6.7 Hz, 4H), 2.05-1.94 (m, 3H). Aliphatic region complicated significantly by amide rotamers. |
| 361 | 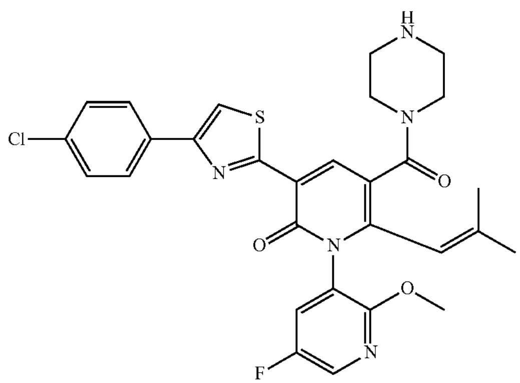 [SMILES: COc1ncc(F)cc1-n1c(C=C(C)C)c(C(=O)N2CCNCC2)cc(-c2nc(-c3ccc(Cl)cc3)cs2)c1=O] | A | A | 602.1371 | 2.598 | Starting materials: nitrile 1 (step2 method V); pyridyl amine 1 (step 3 method V); piperidine (step 5 method V), Methods: V, no step 7 | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 363 | 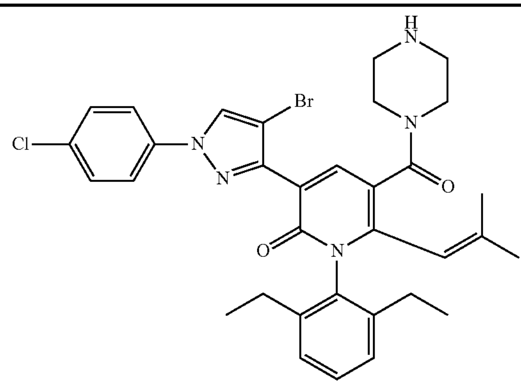 | C | D | 650.1705 | 2.644 | Starting materials: pyrazole 2 (step 2); Methods: V, step 4 with NaOH (xs), following step 4 bromination-NBS (3.3 eq) in acetonitrile 50 deg C. 3days, then cleave Boc by addition of TFA (xs). | TFA salt: 1H NMR (400 MHz, DMSO-d6) δ 8.84 (s, 1H), 8.79 (brs, 1H), 8.68 (br s, 1H), 7.94-7.80 (m, 2H), 7.76 (s, 1H), 7.64-7.51 (m, 2H), 7.37 (t, J = 7.6 Hz, 1H), 7.21 (br s, 2H), 5.24-5.16 (m, 1H), 3.97 (m, 1H), 3.55 (m, 1H), 3.23-2.80 (m, 5H), 2.44-2.04 (m, 5H), 1.54 (dd, J = 6.5, 1.3 Hz, 6H), 1.19-0.89 (m, 6H). |
| 364 | 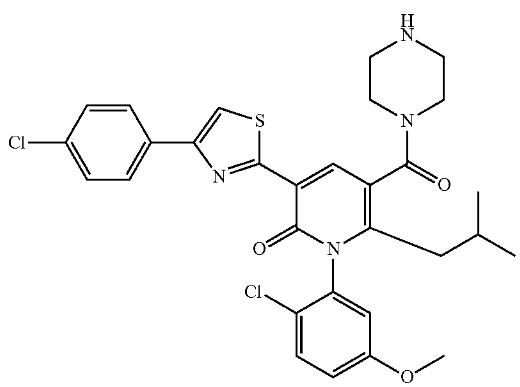 [SMILES: COc1ccc(Cl)c(-n2c(CC(C)C)c(C(=O)N3CCNCC3)cc(-c3nc(-c4ccc(Cl)cc4)cs3)c2=O)c1] | A | B | 597.1494 | 2.682 | Starting materials: methyl 5-methyl-3-oxohexanoate (step 1), Nitrile 1 (step 2), 2-chloro-5-methoxyaniline (step 3), piperazine (used in method U); Methods: S, ester hydrolyzed with LiOH (xs), THF/MeOH/water, 60° C.; U | 1H NMR (400 MHz, DMSO-d6) δ 8.47 (d, J = 2.0 Hz, 1H), 8.18 (s, 1H), 8.01-7.96 (m, 2H), 7.95-7.90 (m, 2H), 7.59-7.49 (m, 2H), 7.32 (d, J = 7.7Hz, 1H), 3.81-3.48 (m, 6H), 3.14 (d, J = 33.7 Hz, 6H), 2.38-2.10 (m, 2H), 1.06 (td, J = 7.6, 2.2 Hz, 6H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 365 | 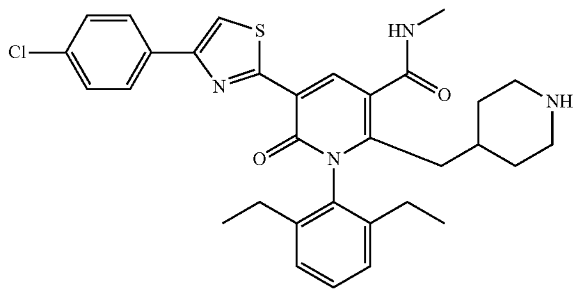 [SMILES: CCc1cccc(CC)c1-n1c(CC2CCNCC2)c(C(=O)NC)cc(-c2nc(-c3ccc(Cl)cc3)cs2)c1=O] | D | D | 575.2222 | 2.722 | Starting materials: tert-butyl 4-(4-ethoxy-2,4-dioxobutyl)piperidine-1-carboxylate (step 1), methylamine (used in method U); Methods: S, then ester hydrolyzed with LiOH (xs), THF/MeOH/water, 60° C.; U; Boc removal with TFA (xs)/DCM rt | TFA salt: 1H NMR(400 MHz, DMSO-d6) δ 8.70 (s, 1H), 8.63 (q, J = 4.4 Hz, 1H), 8.38 (d, J = 11.3 Hz, 1H), 8.21 (s, 1H), 8.17-7.90 (m, 3H), 7.61-7.43 (m, 3H), 7.35 (d, J = 7.7 Hz, 2H), 3.12 (d, J = 12.5 Hz, 2H), 2.79 (d, J = 4.5 Hz, 3H), 2.69-2.51 (m, 3H), 2.45-2.23 (m, 2H), 2.10 (dq, J = 15.0, 7.5 Hz, 2H), 1.31 (d, J = 12.4 Hz, 2H), 1.25-1.12 (m, 2H), 1.08 (t, J = 7.5 Hz, 6H). |
| 366 | 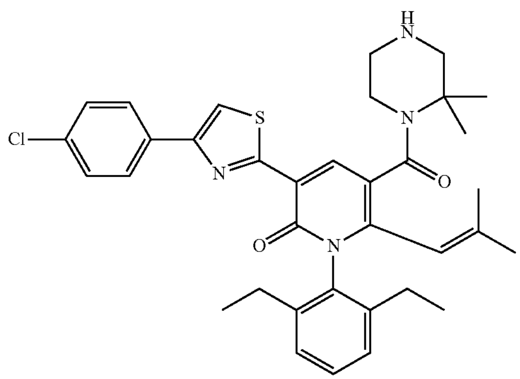 [SMILES: CCc1cccc(CC)c1-n1c(C=C(C)C)c(C(=O)N2CCNCC2(C)C)cc(-c2nc(-c3ccc(Cl)cc3)cs2)c1=O] | A | A | 615.255 | 2.894 | Starting materials: 6,6-dimethyldihydro-2H-pyran-2,4(3H)-dione (step 1), Nitrile 1 (step 2), tert-butyl 3,3-dimethylpiperazine-1-carboxylate (used in methods V, step 5); Methods: V | 1H NMR (400 MHz, DMSO-d6) δ 8.63 (s, 1H), 8.24 (s, 1H), 8.14-8.05 (m, 2H), 7.58-7.47 (m, 2H), 7.42 (t, J = 7.7 Hz, 1H), 7.29 (dd, J = 15.9, 7.5 Hz, 2H), 5.25 (s, 1H), 3.61-3.41 (m, 2H), 3.22-3.14 (m, 1H), 3.10-3.00 (m, 2H), 2.69-2.61 (m, 1H), 2.37-2.01 (m, 7H), 1.65-1.53 (m, 7H), 1.41 (s, 3H), 1.14-1.06 (m, 6H), 1.01 (t, J = 7.5 Hz, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 367 | 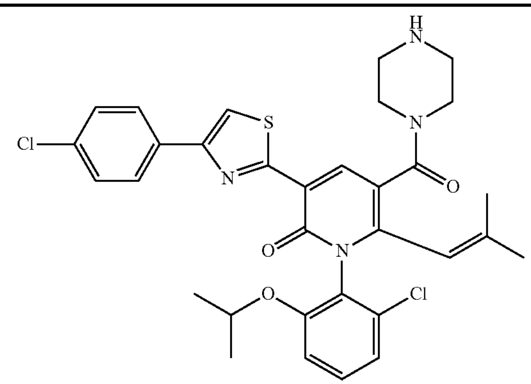 | A | A | 623.1661 | 2.735 | Starting material: 6,6-dimethyldihydro-2H-pyran-2,4(3H)-dione (step1 method V); nitrile 1 (step2 method V); aniline 11 (step 3 method V), Methods: V | TFA salt: 1H NMR (400 MHz, CD3OD) δ 8.87 (s, 1H), 8.05 (d, J = 8.4 Hz, 2H), 7.95 (s, 1H), 7.50-7.44 (m, 3H), 7.21-7.16 (m, 2H), 5.64-5.52 (s, 1H), 4.76-4.61 (m, 1H), 4.30 (s, 1H), 3.83-3.52 (m, 3H), 3.26-3.18 (m, 4H), 1.70 (s, 6H), 1.30-1.13 (m, 6H). Aliphatic region complicated significantly by amide rotamers. |
| 368 | 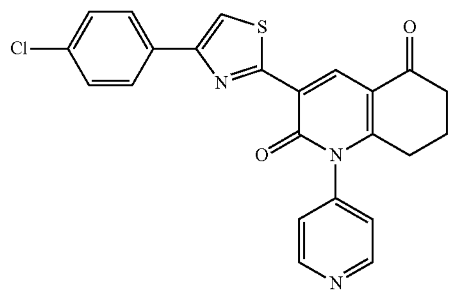 [SMILES: O=C1CCCc2c1cc(-c1nc(-c3ccc(Cl)cc3)cs1)c(=O)n2-c1ccncc1] | E | E | 434.0735 | 3.407 | Starting material: cyclohexane-1,3-dione (step1 method M); nitrile 1 (step2 method M); pyridin-4-amine (step 3 method M), Methods: M | |
| 369 | 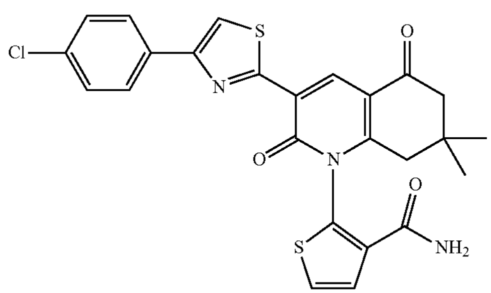 [SMILES: CC1(C)CC(=O)c2cc(-c3nc(-c4ccc(Cl)cc4)cs3)c(=O)n(-c3sccc3C(N)=O)c2C1] | D | D | 510.0727 | 3.514 | Starting material: 5,5-dimethylcyclohexane-1,3-dione (step1 method M); nitrile 1 (step2 method M); 2-aminothiophene-3-carboxamide (step 3 method M), Methods: M | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | $^1$H-NMR |
|---|---|---|---|---|---|---|---|
| 370 | 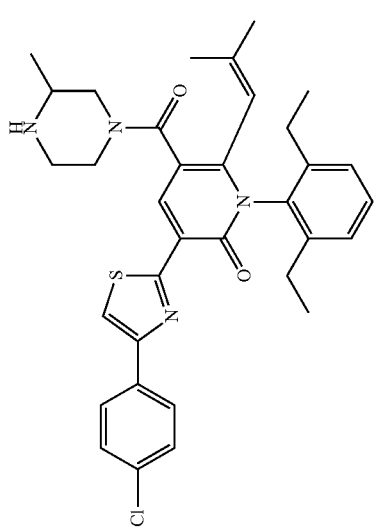 | A | A | 601.2395 | 2.805 | Starting materials: 6,6-dimethyldihydro-2H-pyran-2,4(3H)-dione (step 1), Nitrile 1 (step 2), tert-butyl 2-methylpiperazine-1-carboxylate (used in methods V, step 5); Methods: V | 1H NMR (400 MHz, DMSO-d6) δ 8.73 (d, J = 9.4 Hz, 1H), 8.25 (s, 1H), 8.09 (dd, J = 8.9, 2.3 Hz, 2H), 7.53 (dd, J = 8.7, 2.3 Hz, 2H), 7.43 (t, J = 7.7 Hz, 1H), 7.29 (dd, J = 22.5, 7.7 Hz, 2H), 5.30 (s, 1H), 4.55 (dd, J = 32.5, 13.8 Hz, 1H), 4.33-4.23 (m, 1H), 3.72-3.48 (m, 1H), 3.23-2.62 (m, 3H), 2.42-2.24 (m, 2H), 2.16-1.97 (m, 2H), 1.63-1.52 (m, 6H), 1.24 (dd, J = 12.0, 6.4 Hz, 1H), 1.11 (dt, J = 11.5, 7.3 Hz, 6H), 0.98 (t, J = 7.5 Hz, 3H). |
| 371 | 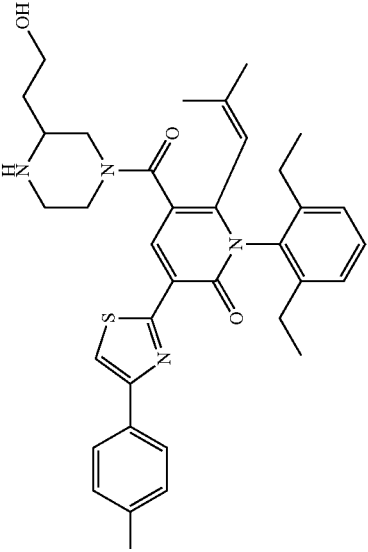 | A | A | 631.2501 | 2.749 | Starting materials: 6,6-dimethyldihydro-2H-pyran-2,4(3H)-dione (step 1), Nitrile 1 (step 2), 2-(piperazin-2-yl)ethanol (used in methods V, step 5); Methods: V, no step 6. | 1H NMR (400 MHz, DMSO-d6) δ 8.75 (s, 1H), 8.25 (s, 1H), 8.14-8.04 (m, 2H), 7.53 (d, J = 8.5Hz, 2H), 7.43 (t, J = 7.7 Hz, 1H), 7.29 (dd, J = 21.9, 7.5 Hz, 2H), 5.31 (d, J = 10.2 Hz, 1H), 4.96-4.20 (m, 1H), 3.82-3.35 (m, 4H), 3.23-3.07 (m, 2H), 2.86-2.57 (m, 2H), 2.46-2.19 (m, 2H), 2.18-1.96 (m, 2H), 1.82-1.48 (m, 8H), 1.12 (t, J = 6.9 Hz, 3H), 0.98 (t, J = 7.6 Hz, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 372 | 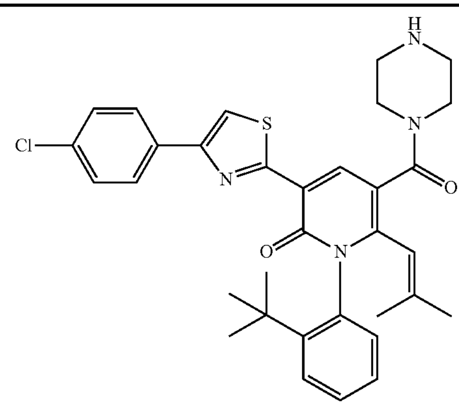 | A | A | 587.2225 | 2.785 | Starting material: 6,6-dimethyldihydro-2H-pyran-2,4(3H)-dione (step1 method V); nitrile 1 (step2 method V); 2-tert-butylaniline (step 3 method V), Methods: V | TFA salt: 1H NMR(400 MHz, CD3OD) δ 8.84 (s, 1H), 8.03 (d, J = 8.6 Hz, 2H), 7.93 (s, 1H), 7.77-7.73 (m, 1H), 7.55-7.30 (m, 4H), 7.15-6.85 (m, 1H), 5.65-5.50 (m, 1H), 4.40-4.25 (m, 1H), 3.90-3.73 (m, 1H), 3.65-3.50 (m, 2H), 3.35-3.10 (m, 4H), 1.77-1.60 (m, 6H), 1.40-1.10 (m, 9H). Aliphatic region complicated significantly by amide rotamers. |
| 373 | 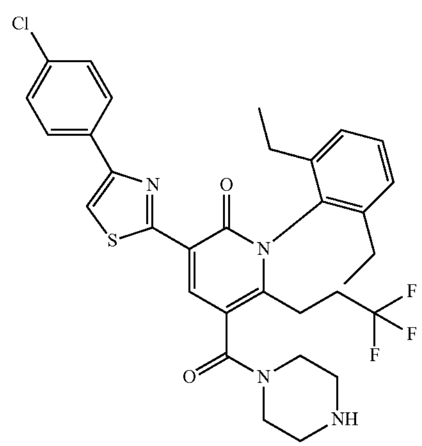 [SMILES: CCc1cccc(CC)c1-n1c(CCC(F)(F)F)c(C(=O)N2CCNCC2)cc(-c2nc(-c3ccc(Cl)cc3)cs2)c1=O] | B | B | 629.195 | 2.851 | Starting materials: ethyl 6,6,6-trifluoro-3-oxohexanoate (step 1), piperazine (used in method U); Methods: S, then ester hydrolyzed with LiOH (xs), THF/MeOH/water, 60° C.; U | TFA salt: 1H NMR (400 MHz, DMSO-d6) δ 8.77 (m, 3H), 8.24 (s, 1H), 8.16-8.08 (m, 2H), 7.55-7.47 (m, 3H), 7.38 (d, J = 7.7 Hz, 2H), 3.72 (br m, 5H), 3.17 (br m, 2H), 2.36 (dt, J = 15.1, 7.6 Hz, 2H), 2.02 (br m, 3H), 1.08 (t, J = 7.5 Hz, 6H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 374 | 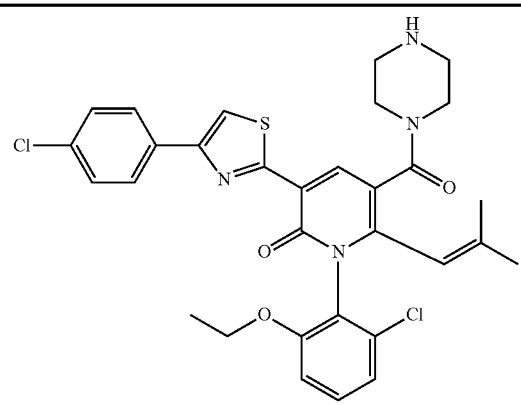 | A | A | 631.1309 | 2.683 | Starting material: 6,6-dimethyldihydro-2H-pyran-2,4(3H)-dione (step1 method V); nitrile 1 (step2 method V); aniline 10 (step 3 method V), Methods: V | TFA salt: 1H NMR (400 MHz, CD3OD) δ 8.87 (s, 1H), 8.05 (d, J = 8.4 Hz, 2H), 7.95 (s, 1H), 7.51-7.45 (m, 3H), 7.26-7.10 (m, 2H), 5.55 (s, 1H), 4.37-3.47 (m, 7H), 3.26-3.19 (m, 3H), 1.68 (s, 6H), 1.24 (m, 3H). Aliphatic region complicated significantly by amide rotamers. |
| 375 | 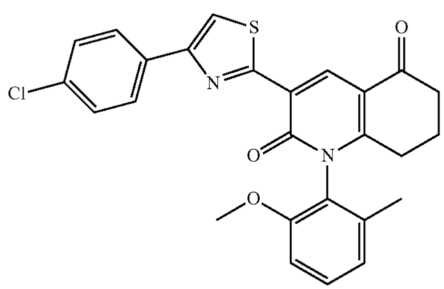 [SMILES: COc1cccc(C)c1-n1c2c(cc(-c3nc(-c4ccc(Cl)cc4)cs3)c1=O)C(=O)CCC2] | C | C | 477.1042 | 3.834 | Starting material: cyclohexane-1,3-dione (step1 method M); nitrile 1 (step2 method M); 2-ethyl-6-methylaniline (step 3 method M), Methods: M | 1H NMR (400 MHz, CD3OD) δ 9.34 (s, 1H), 7.98 (d, J = 8.4 Hz, 2H), 7.54 (s, 1H), 7.41-7.35 (m, 3H), 7.00-6.98 (m, 1H), 6.93-6.91 (m, 1H), 3.76 (s, 3H), 2.37-2.62 (m, 4H), 1.60-1.24 (m, 5H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 376 | 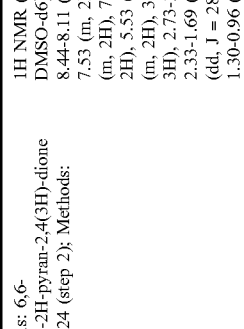 | A | A | 609.22 | 2.609 | Starting materials: 6,6-dimethyldihydro-2H-pyran-2,4(3H)-dione (step 1), Nitrile 24 (step 2); Methods: V, no step 6. | 1H NMR (400 MHz, DMSO-d6) δ 8.71 (s, 1H), 8.44-8.11 (m, 2H), 7.75-7.53 (m, 2H), 7.49-7.26 (m, 2H), 7.26-6.86 (m, 2H), 5.53 (s, 1H), 4.09-3.91 (m, 2H), 3.26-2.74 (m, 3H), 2.73-2.54 (m, 3H), 2.33-1.69 (m, 6H), 1.56 (dd, J = 28.9, 1.3 Hz, 5H), 1.30-0.96 (m, 2H). |
| 377 | 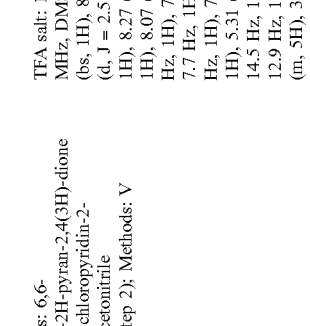 | A | A | 610.2024 | 2.668 | Starting materials: 6,6-dimethyldihydro-2H-pyran-2,4(3H)-dione (step 1), 2-(4-(5-chloropyridin-2-yl)thiazol-2-yl)acetonitrile hydrobromide (step 2); Methods: V | TFA salt: 1H NMR (400 MHz, DMSO-d6) δ 8.78 (bs, 1H), 8.77 (s, 1H), 8.70 (d, J = 2.5 Hz, 1H), 8.37 (s, 1H), 8.27 (d, J = 8.5 Hz, 1H), 8.07 (dd, J = 8.5, 2.5 Hz, 1H), 7.45 (dd, J = 7.7, 7.7 Hz, 1H), 7.34 (d, J = 7.7 Hz, 1H), 7.29 (s, 1H), 4.06 (d, J = 14.5 Hz, 1H), 3.61 (d, J = 12.9 Hz, 1H), 3.48-3.30 (m, 5H), 3.24-3.05 (m, 2H), 3.05-2.93 (m, 1H), 2.45-2.25 (m, 1H), 2.19-2.13 (m, 1H), 1.59 (s, 6H), 1.14 (t, J = 7.5 Hz, 3H), 1.01 (t, J = 7.6 Hz, 3H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 378 | 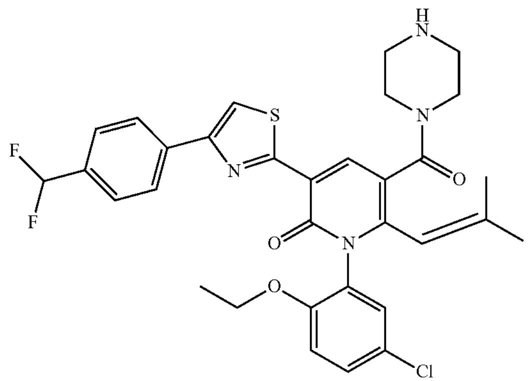 [SMILES: CCOc1ccc(F)cc1-n1c(C=C(C)C)c(C(=O)N2CCNCC2)cc(-c2nc(-c3ccc(C(F)F)cc3)cs2)c1=O] | A | A | 625.19 | 2.664 | Starting materials: 6,6-dimethyldihydro-2H-pyran-2,4(3H)-dione (step 1), Nitrile 24 (step 2); Methods: V, no step 6. | 1H NMR (400 MHz, DMSO-d6) δ 8.71 (s, 1H), 8.31 (s, 1H), 8.21 (d, J = 8.0 Hz, 2H), 7.75-7.42 (m, 4H), 7.32-7.14 (m, 1H), 7.14-6.85 (m, 1H), 5.54 (s, 1H), 4.17-3.70 (m, 3H), 3.23-2.84 (m, 5H), 2.65 (p, J = 1.9 Hz, 1H), 2.38-1.70 (m, 1H), 1.56 (dd, J = 30.7, 1.4 Hz, 6H), 1.21 (dt, J = 104.5, 6.9 Hz, 3H). |
| 379 | 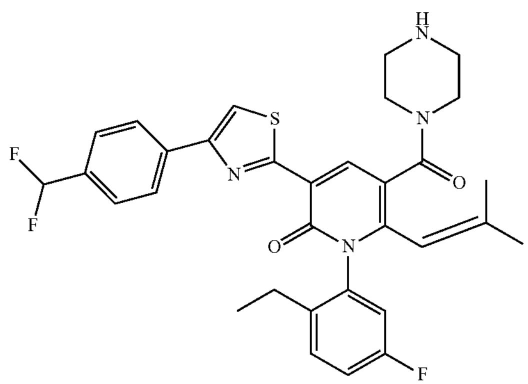 [SMILES: CCc1ccc(F)cc1-n1c(C=C(C)C)c(C(=O)N2CCNCC2)cc(-c2nc(-c3ccc(C(F)F)cc3)cs2)c1=O] | A | A | 297.11 | 2.667 | Starting materials: 6,6-dimethyldihydro-2H-pyran-2,4(3H)-dione (step 1), 2-(4-(4-(difluoromethyl)phenyl)thiazol-2-yl)acetonitrile (step 2), 2-ethyl-5-fluoroaniline (step 3); Methods: W, then V (steps 4-6) | ¹H NMR (400 MHz, DMSO-d₆) δ 8.79 (bs, 2H), 8.70 (s, 1H), 8.31 (s, 1H), 8.20 (d, J = 7.9 Hz, 2H), 7.66 (d, J = 7.8 Hz, 2H), 7.55-7.15 (m, 3H), 7.07 (t, J = 56.0 Hz, 1H), 5.60-5.33 (m, 1H), 4.16-3.87 (m, 1H), 3.73-2.83 (m, 7H), 2.19-1.92 (m, 2H), 1.59 (s, 3H), 1.55 (s, 3H), 1.13-0.90 (m, 3H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | $^1$H-NMR |
|---|---|---|---|---|---|---|---|
| 380 | 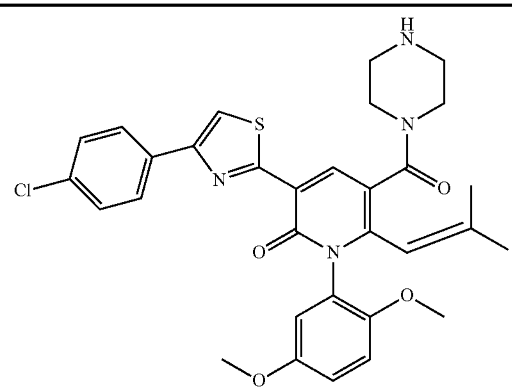 | A | A | 591.1824 | 2.577 | Starting material: 6,6-dimethyldihydro-2H-pyran-2,4(3H)-dione (step1 method V); nitrile 1 (step2 method V); 2,5-dimethoxyaniline (step 3 method V), Methods: V | TFA salt: 1H NMR (400 MHz, CD3OD) δ 8.82 (s, 1H), 8.04 (d, J = 8.6 Hz, 2H), 7.93 (s, 1H), 7.45 (d, J = 8.6 Hz, 2H), 7.09 (d, J = 2.6 Hz, 2H), 6.90 (d, J = 63.2 Hz, 1H), 5.63 (s, 1H), 4.26 (s, 1H), 3.89-3.48 (m, 10H), 3.29-3.19 (m, 3H), 1.66 (d, J = 2.3 Hz, 7H), 1.31 (s, 1H). Aliphatic region complicated significantly by amide rotamers. |
| 381 | 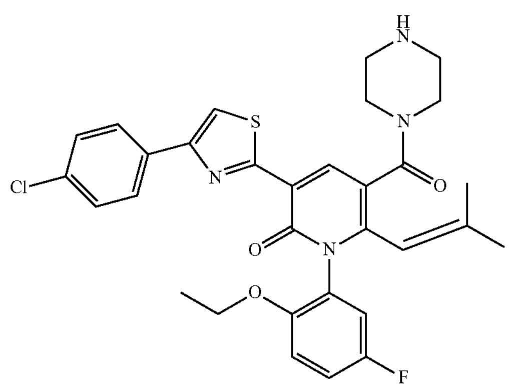 [SMILES: CCOc1ccc(F)cc1-n1c(C=C(C)C)c(C(=O)N2CCNCC2)cc(-c2nc(-c3ccc(Cl)cc3)cs2)c1=O] | A | A | 593.1776 | 2.648 | Starting material: 6,6-dimethyldihydro-2H-pyran-2,4(3H)-dione (step1 method V); nitrile 1 (step2 method V); 5-fluoro-2-methoxyaniline (step 3 method V), Methods: V | TFA salt: 1H NMR (400 MHz, CD3OD) δ 8.81 (s, 1H), 8.02 (d, J = 8.6 Hz, 2H), 7.92 (s, 1H), 7.43 (d, J = 8.7 Hz, 2H), 7.27-7.02 (m, 3H), 5.63 (s, 1H), 4.30-4.15 (m, 1H), 4.10-3.90 (m, 2H), 3.85-3.70 (m, 1H), 3.65-3.50 (m, 2H), 3.35-3.10 (m, 4H), 1.67-1.60 (m, 6H), 1.30-1.15 (m, 3H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 382 | 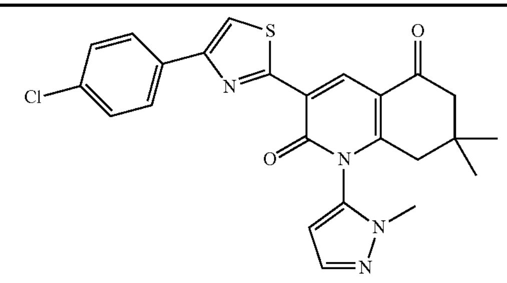 | D | C | 465.1153 | 3.702 | Starting material: 5,5-dimethylcyclohexane-1,3-dione (step1 method M); nitrile 1 (step2 method M); 1-methyl-1H-pyrazol-5-amine (step 3 method M), Methods: M | 1H NMR (400 MHz, cdcl3) δ 9.34 (s, 1H), 8.03-7.96 (m, 2H), 7.71 (d, J = 2.0 Hz, 1H), 7.62 (s, 1H), 7.47-7.40 (m, 2H), 6.35 (d, J = 2.0 Hz, 1H), 3.70 (s, 3H), 2.67 (d, J = 18.1 Hz, 1H), 2.52 (s, 2H), 2.17 (d, J = 18.1 Hz, 1H), 1.11 (d, J = 14.8 Hz, 3H), 1.08 (s,3H). Aliphatic region complicated significantly by amide rotamers. |
| 383 | 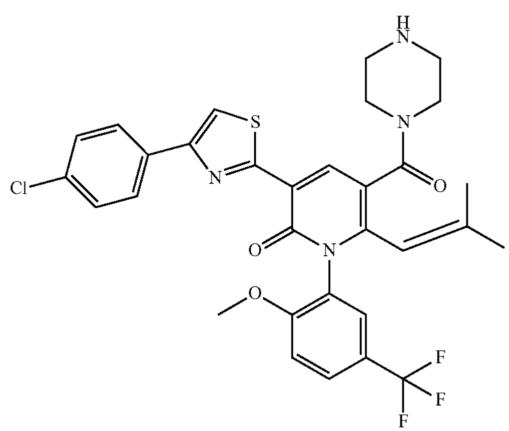 [SMILES: COc1ccc(C(F)(F)F)cc1-n1c(C=C(C)C)c(C(=O)N2CCNCC2)cc(-c2nc(-c3ccc(Cl)cc3)cs2)c1=O] | B | B | 629.1626 | 2.703 | Starting material: 6,6-dimethyldihydro-2H-pyran-2,4(3H)-dione (step1 method V); nitrile 1 (step2 method V); 2-methoxy-5-(trifluoromethyl)aniline (step 3 method V), Methods: V | TFA salt: 1H NMR(400 MHz, CD3OD) δ 8.83 (s, 1H), 8.08-7.99 (m, 2H), 7.94 (s, 1H), 7.84 (dd, J = 8.8, 1.7 Hz, 2H), 7.51-7.42 (m, 2H), 7.39 (s, 1H), 5.58 (s, 1H), 4.23 (s, 2H), 3.87 (d, J = 20.7 Hz, 4H), 3.62 (s, 3H), 3.31-3.20 (m, 3H), 1.65 (s, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 384 | 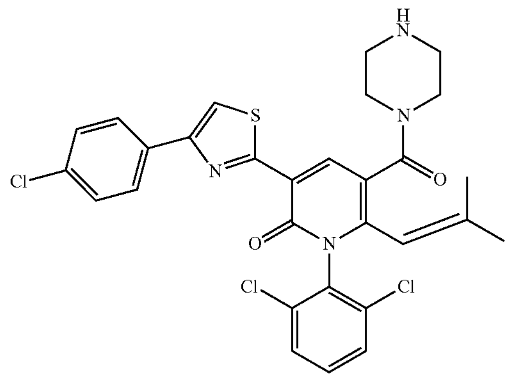 [SMILES: CC(C)=Cc1c(C(=O)N2CCNCC2)cc(-c2nc(-c3ccc(Cl)cc3)cs2)c(=O)n1-c1c(Cl)cccc1Cl] | A | A | 623.0648 | 2.679 | Starting material: 6,6-dimethyldihydro-2H-pyran-2,4(3H)-dione (step1 method V); nitrile 1 (step2 method V); 2,6-dichloroaniline (step 3 method V). Methods: V | TFA salt: 1H NMR (400 MHz, CD3OD) δ 8.87 (s, 1H), 8.02 (d, J = 8.6 Hz, 2H), 7.96 (s, 1H), 7.70-7.60 (m, 2H), 7.56 (t, J = 8.2 Hz, 1H), 7.44 (d, J = 8.6 Hz, 2H), 5.53-5.50 (m, 1H), 4.34-4.22 (m, 1H), 3.80-3.67 (m, 1H), 3.65-3.50 (m, 2H), 3.35-3.10 (m, 4H), 1.74-1.68 (m, 6H). Aliphatic region complicated significantly by amide rotamers. |
| 385 | 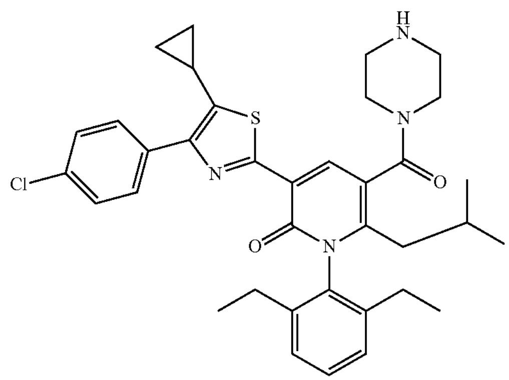 [SMILES: CCc1cccc(CC)c1-n1c(CC(C)C)c(C(=O)N2CCNCC2)cc(-c2nc(-c3ccc(Cl)cc3)c(C3CC3)s2)c1=O] | B | A | 629.2738 | 2.978 | Starting material: methyl 5-methyl-3-oxohexanoate (step1 method V); nitrile V (step2 method V); 2,6-diethylaniline (step 3 method V). Methods: V(step1-5), bromination with NBS in DCM, followed by treatment with cyclopropyltrifluoro-I4-borane potassium salt, Pd(dppf)Cl2-DCM, and Cs2CO3 in THF at 70° C., then V (step 6) | TFA salt: 1H NMR(400 MHz, CD3OD) δ 8.61 (s, 1H), 7.93-7.87 (m, 2H), 7.55-7.47 (m, 3H), 7.39 (d, J = 7.7 Hz, 2H), 4.29 (s, 2H), 4.00 (s, 2H), 3.72 (s, 2H), 3.39 (s, 2H), 2.66 (s, 2H), 2.41 (dt, J = 22.7, 7.5 Hz, 2H), 2.35-2.21 (m, 2H), 2.21-2.02 (m, 4H), 1.65 (d, J = 7.1 Hz, 1H), 1.53-1.40 (m, 1H), 1.25-1.11 (m, 6H), 0.81-0.73 (m, 3H), 0.70 (d, J = 6.4 Hz, 5H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 386 | 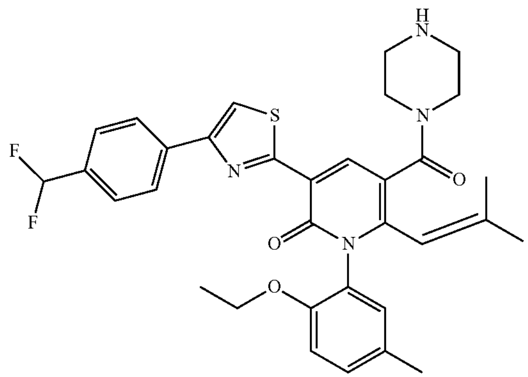 [SMILES: CCOc1ccc(C)cc1-n1c(C=C(C)C)c(C(=O)N2CCNCC2)cc(-c2nc(-c3ccc(C(F)F)cc3)cs2)c1=O] | A | A | 605.24 | 2.635 | Starting materials: 6,6-dimethyldihydro-2H-pyran-2,4(3H)-dione (step 1), Nitrile 24 (step 2); Methods: V, no step 6. | 1H NMR (400 MHz, DMSO-d6) δ 8.64 (s, 1H), 8.30 (s, 1H), 8.21 (d, J = 8.0 Hz, 2H), 7.66 (dd, J = 8.0, 1.5 Hz, 2H), 7.32-7.12 (m, 2H), 7.14-6.87 (m, 2H), 5.50 (s, 1H), 4.14-3.53 (m, 3H), 3.23-2.81 (m, 3H), 2.74-2.55 (m, 2H), 2.36-2.16 (m, 3H), 1.81 (d, J = 62.2 Hz, 3H), 1.62-1.43 (m, 6H), 1.29-0.92 (m, 3H). |
| 387 | 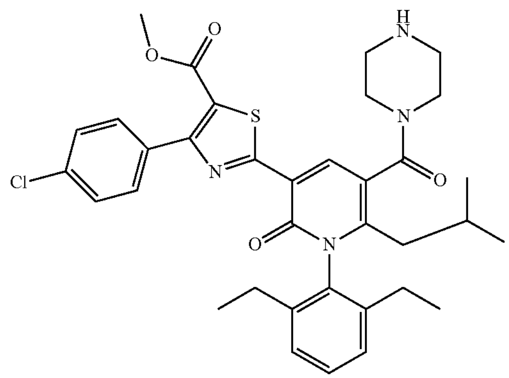 [SMILES: CCc1cccc(CC)c1-n1c(CC(C)C)c(C(=O)N2CCNCC2)cc(-c2nc(-c3ccc(Cl)cc3)c(C(=O)OC)s2)c1=O] | A | A | 647.2451 | 2.847 | Starting material: methyl 5-methyl-3-oxohexanoate (step1 method V; nitrile 1 (step2 method V); 2,6-diethylaniline (step 3 method V), Methods: V(step1-5), treated with CuCN in pyridine at 150° C., followed by 6M NaOH at 90° C., and MeOH with H2SO4 (5 drops) at 80° C., then V (step 6) | TFA salt: 1H NMR (400 MHz, CD3OD) δ 8.76 (s, 1H), 7.81-7.75 (m, 2H), 7.57-7.50 (m, 1H), 7.50-7.44 (m, 2H), 7.41 (d, J = 7.7 Hz, 2H), 4.27 (s, 2H), 3.99 (s, 2H), 3.81 (s, 3H), 3.74 (s,2H), 3.38 (s, 2H), 2.71 (s, 2H), 2.43 (dt, J = 22.5, 7.4 Hz, 2H), 2.28 (s, 2H), 1.66 (d, J = 7.0 Hz, 1H), 1.56-1.44 (m, 2H), 1.20 (t, J = 7.3 Hz, 6H), 0.71 (d, J = 6.4 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 388 | 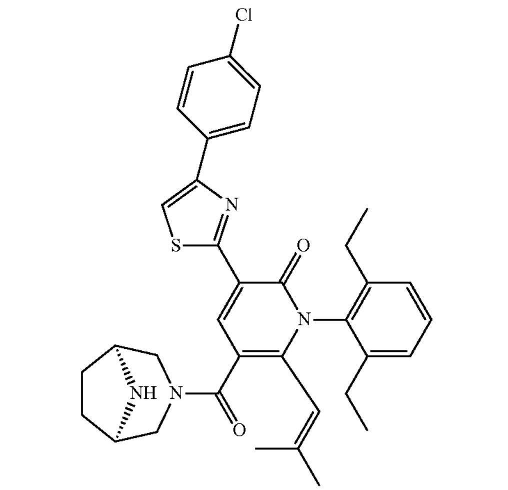 [SMILES: CCc1cccc(CC)c1-n1c(C=C(C)C)c(C(=O)N2C[C@H]3CC[C@@H](C2)N3)cc(-c2nc(-c3ccc(Cl)cc3)cs2)c1=O] | A | A | 635.2206 | 2.823 | Starting materials: 6,6-dimethyldihydro-2H-pyran-2,4(3H)-dione (step 1), Nitrile 1 (step 2), (1R,5S)-tert-butyl 3,8-diazabicyclo[3.2.1]octane-8-carboxylate (used in methods V, step 5); Methods: V | 1H NMR (400 MHz, DMSO-d6) δ 8.73 (s, 1H), 8.24 (s, 1H), 8.15-8.04 (m, 2H), 7.58-7.48 (m, 2H), 7.42 (t, J = 7.7 Hz, 1H), 7.29 (dd, J = 26.3, 7.7 Hz, 2H), 5.23 (s, 1H), 4.44 (d, J = 14.0 Hz, 1H), 4.14-3.86 (m, 2H), 3.61-3.34 (m, 2H), 2.96 (d, J = 14.0 Hz, 1H), 2.65 (p, J = 1.9 Hz, 1H), 2.44-2.27 (m, 2H), 2.15-1.97 (m, 2H), 1.96-1.71 (m, 3H), 1.55 (dd, J = 10.4, 1.3 Hz, 6H), 1.14 (t, J = 7.7 Hz, 3H), 0.96 (t, J = 7.5 Hz, 3H). |
| 389 | 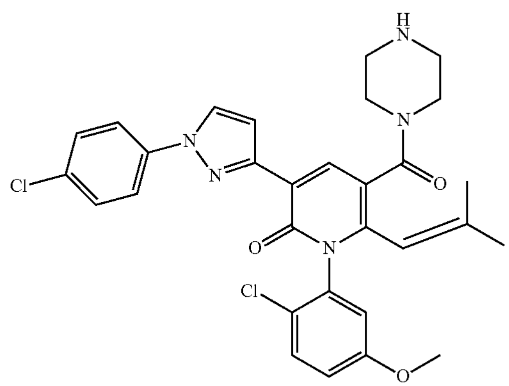 [SMILES: COc1ccc(Cl)c(-n2c(C=C(C)C)c(C(=O)N3CCNCC3)cc(-c3ccn(-c4ccc(Cl)cc4)n3)c2=O)c1] | A | B | 578.1713 | 2.525 | Starting materials: 6,6-dimethyldihydro-2H-pyran-2,4(3H)-dione (step 1), pyrazole 2 (step 2), 2-chloro-5-methoxyaniline (step 3 of methods V); Methods: V, no step 6. | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 391 | 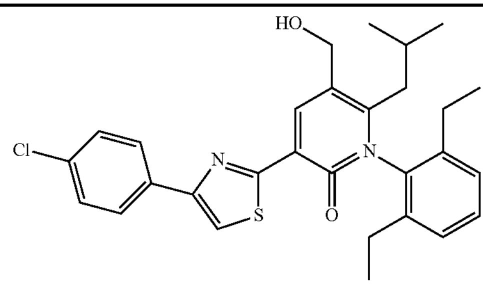 | B | B | 507.1868 | 4.08 | Compound 231 was reduced with BH3-THF complex (4.3 eq), THF, rt | |
| 392 | 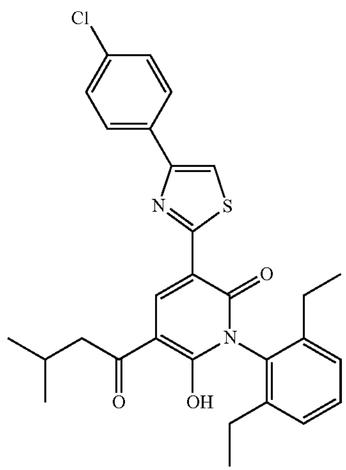 [SMILES: CCc1cccc(CC)c1-n1c(O)c(C(=O)CC(C)C)cc(-c2nc(-c3ccc(Cl)cc3)cs2)c1=O] | D | D | 521.1654 | 4.596 | | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 393 | 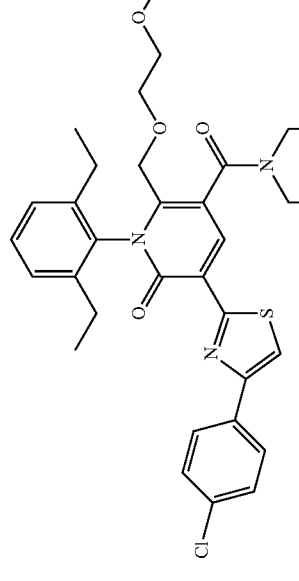 | A | B | 621.2268 | 2.706 | Starting materials: ethyl 4-(2-methoxyethoxy)-3-oxobutanoate(step 1), Nitrile 1 (step 2), piperazine (used in method U); Methods: S, ester hydrolyzed with LiOH (xs), THF/MeOH/water, 60° C.; U | 1H NMR (400 MHz, DMSO-d6) δ 8.71 (s, 1H), 8.25 (s, 1H), 8.15-8.07 (m, 2H), 7.53-7.42 (m, 2H), 7.32 (d, J = 7.7 Hz, 3H), 4.14 (s, 2H), 3.97-3.43 (m, 8H), 3.21-3.03 (m, 6H), 2.42-2.05 (m, 6H), 1.10-0.99 (m, 6H). |
| 394 | 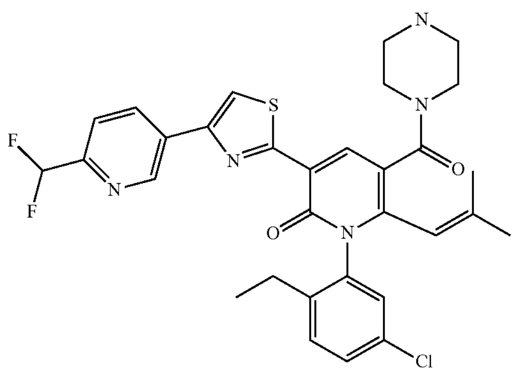 [SMILES: CCc1ccc(Cl)cc1-n1c(C=C(C)C)c(C(=O)N2CCNCC2)cc(-c2nc(-c3ccc(C(F)F)nc3)cs2)c1=O] | | | | | | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 395 | 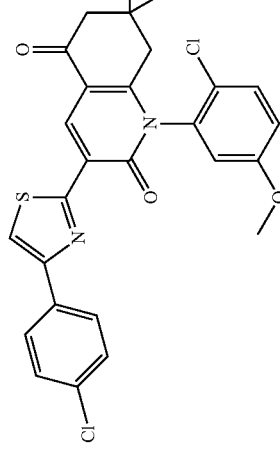 | B | A | 525.0805 | 3.981 | Starting material: 5,5-dimethylcyclohexane-1,3-dione (step1 method M); nitrile 1 (step2 method M); 2-chloro-5-methoxyaniline (step 3 method M), Methods: M | 1H NMR (400 MHz, CDCl3) δ 9.36 (s, 1H), 8.03-7.96 (m, 2H), 7.59 (s, 1H), 7.55 (d, J = 9.0Hz, 1H), 7.46-7.38 (m, 2H), 7.08 (dd, J = 9.0, 2.9 Hz, 1H), 6.86 (d, J = 2.9 Hz, 1H), 3.86 (s, 3H), 2.55-2.44 (m, 3H), 2.32 (d, J = 17.8 Hz, 1H), 1.09 (d, J = 1.3 Hz, 6H). Aliphatic region complicated significantly by amide rotamers. |
| 396 | 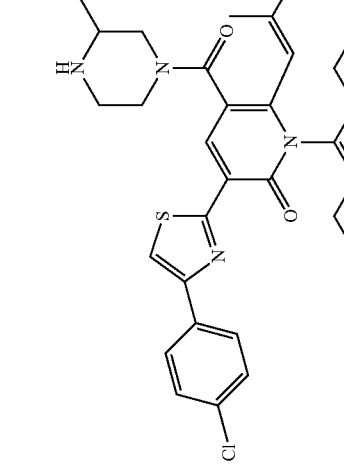 | A | A | 655.214 | 3.952 | Starting materials: 6,6-dimethyldihydro-2H-pyran-2,4(3H)-dione (step 1), Nitrile 1 (step 2), 2-(trifluoromethyl)piperazine (used in methods V, step 5); Methods: V, no step 6. | 1H NMR (400 MHz, DMSO-d6) δ 8.75 (s, 1H), 8.24 (s, 1H), 8.10 (dd, J = 9.1, 2.5 Hz, 2H), 7.57-7.48 (m, 2H), 7.43 (td, J = 7.7, 4.6 Hz, 1H), 7.30 (dd, J = 18.6, 7.0 Hz, 2H), 5.25 (s, 1H), 4.52-4.44 (m, 1H), 4.15-3.98 (m, 1H), 3.23-2.56 (m, 5H), 2.38-2.17 (m, 2H), 2.16-1.99 (m, 2H), 1.56 (d, J = 11.2 Hz, 6H), 1.16-0.91 (m, 6H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 397 | 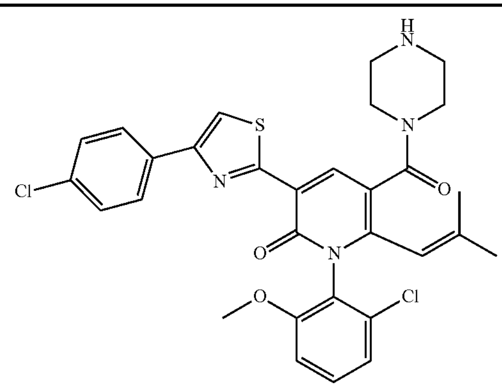 | A | A | 595.1354 | 2.634 | Starting material: 6,6-dimethyldihydro-2H-pyran-2,4(3H)-dione (step1 method V); nitrile 1 (step2 method V); 2-chloro-6-methoxyaniline (step 3 method V), Methods: V | TFA salt: 1H NMR (400 MHz, CD3OD) δ 8.84 (s, 1H), 8.03 (d, J = 8.6 Hz, 2H), 7.93 (s, 1H), 7.50 (t, J = 8.4 Hz, 1H), 7.43 (d, J = 8.7 Hz, 2H), 7.26-7.11 (m, 2H), 5.51 (s, 1H), 4.37-4.20 (m, 1H), 3.90-3.70 (m, 4H), 3.60-3.45 (m, 2H), 3.35-3.10 (m, 4H), 1.71-1.60 (m, 6H). Aliphatic region complicated significantly by amide rotamers. |
| 398 | 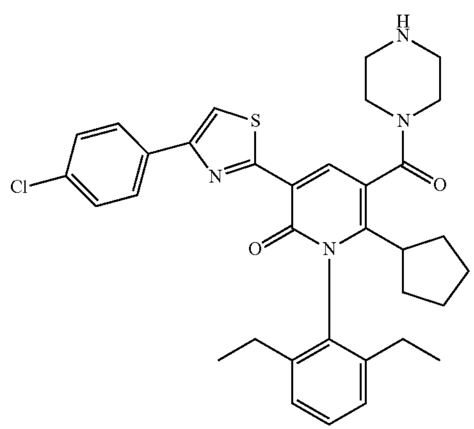 [SMILES: CCc1cccc(CC)c1-n1c(C2CCCC2)c(C(=O)N2CCNCC2)cc(-c2nc(-c3ccc(Cl)cc3)cs2)c1=O] | B | A | 601.2424 | 2.843 | Starting materials: ethyl 3-cyclopentyl-3-oxopropanoate (step 1), piperazine (used in method U); Methods: S, then ester hydrolyzed with LiOH (xs), THF/MeOH/water, 60° C.; U | TFA salt: 1H NMR (400 MHz, DMSO-d6) δ 8.91 (br s, 1H), 8.73 (br s, 1H), 8.65 (d, J = 2.0 Hz, 1H), 8.20 (d, J = 2.2 Hz, 1H), 8.15-8.04 (m, 2H), 7.48 (dd, J = 19.1, 7.7 Hz, 3H), 7.33 (d, J = 7.3 Hz, 2H), 4.06 (br d, J = 14.0 Hz, 1H), 3.77 (m, 1H), 3.61 (m, 1H), 3.46 (m, 3H), 3.13 (m, 3H), 2.29 (m, 3H), 2.07 (m, 2H), 1.70 (m, 1H), 1.56 (m, 4H), 1.43 (m, 1H), 1.23 (m, 3H), 1.14-0.91 (m, 6H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 399 | 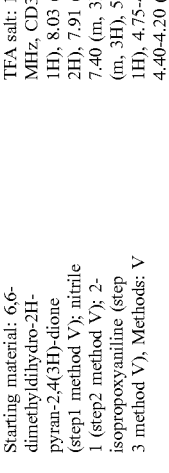 | A | A | 589.2052 | 2.682 | Starting material: 6,6-dimethyldihydro-2H-pyran-2,4(3H)-dione (step1 method V); nitrile 1 (step2 method V); 2-isopropoxyaniline (step 3 method V), Methods: V | TFA salt: 1H NMR (400 MHz, CD3OD) δ 8.82 (s, 1H), 8.03 (d, J = 8.6 Hz, 2H), 7.91 (s, 1H), 7.50-7.40 (m, 3H), 7.35-7.05 (m, 3H), 5.70-5.55 (m, 1H), 4.75-4.50 (m, 1H), 4.40-4.20 (m, 1H), 3.90-3.70 (m, 1H), 3.68-3.50 (m, 2H), 3.35-3.10 (m, 4H), 1.70-1.58 (m, 6H), 1.30-1.10 (m, 6H). Aliphatic region complicated significantly by amide rotamers. |
| 400 | 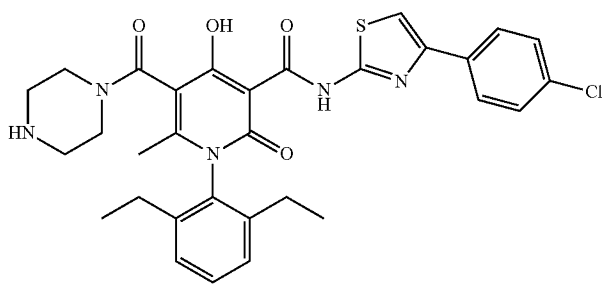 [SMILES: CCc1cccc(CC)c1-n1c(C)c(C(=O)N2CCNCC2)c(O)c(C(=O)Nc2nc(-c3ccc(Cl)cc3)cs2)c1=O] | E | E | 606.1925 | 2.871 | Starting materials: piperazine (method U); Methods: xxiv; ester hydrolyzed with LiOH (xs), THF/MeOH/water, 60° C.; U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 401 | 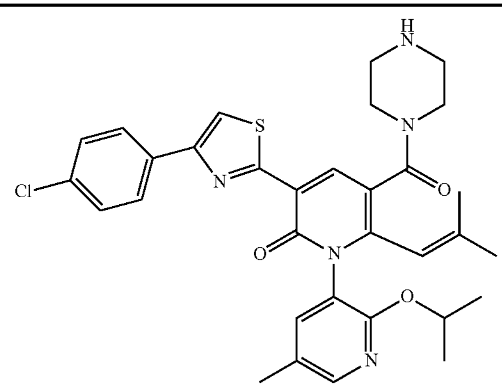 | A | A | 604.2145 | 2.708 | Starting matericals: nitrile 1 (step2 method V); pyridyl amine 7 (step 3 method V); piperidine (step 5 method V), Methods: V, no step 7 | |
| 402 | 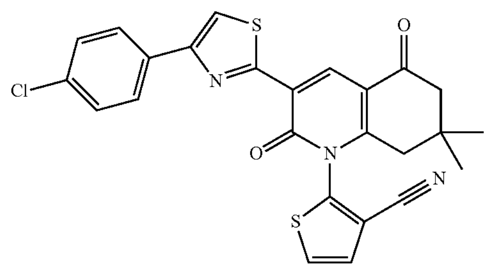 [SMILES: CC1(C)CC(=O)c2cc(-c3nc(-c4ccc(Cl)cc4)cs3)c(=O)n(-c3sccc3C#N)c2C1] | B | A | 492.0606 | 3.776 | Starting material: 5,5-dimethylcyclohexane-1,3-dione (step1 method M); nitrile 1 (step2 method M); 2-aminothiophene-3-carbonitrile (step 3 method M), Methods: M | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 403 | 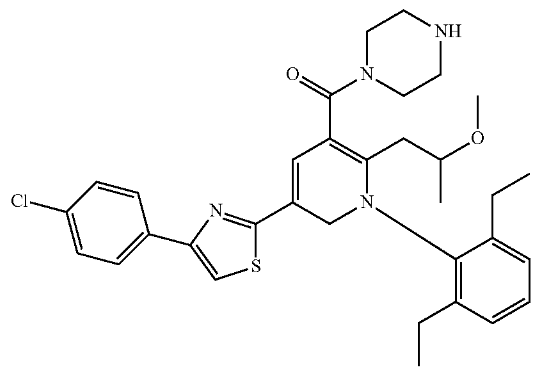 [SMILES: CCc1cccc(CC)c1N1CC(c2nc(-c3ccc(Cl)cc3)cs2)=CC(C(=O)N2CCNCC2)=C1CC(C)OC] | A | B | 605.2338 | 2.752 | Starting materials: ethyl 5-methoxy-3-oxohexanoate (step 1), Nitrile 1 (step 2), piperazine (used in method U); Methods: S, ester hydrolyzed with LiOH (xs), THF/MeOH/water, 60° C.; U | |
| 404 | 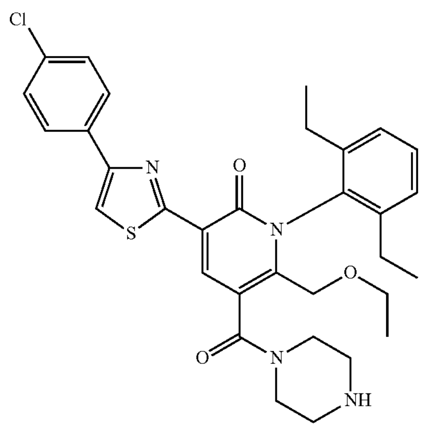 [SMILES: CCOCc1c(C(=O)N2CCNCC2)cc(-c2nc(-c3ccc(Cl)cc3)cs2)c(=O)n1-c1c(CC)cccc1CC] | A | A | 296.112 | 2.757 | Starting materials: ethyl 4-ethoxy-3-oxobutanoate (step 1), Nitrile 1 (step 2), piperazine (used in method U); Methods: S, ester hydrolyzed with LiOH (xs), THF/MeOH/water, 60° C.; U | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | $^1$H-NMR |
|---|---|---|---|---|---|---|---|
| 405 | 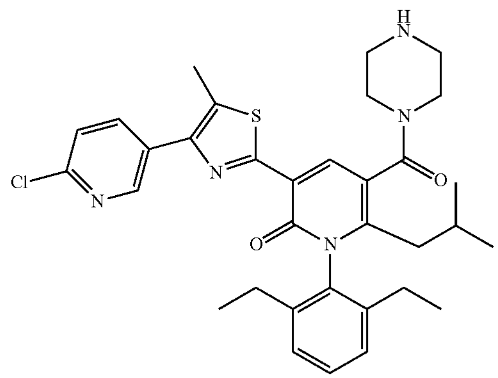 [SMILES: CCc1cccc(CC)c1-n1c(CC(C)C)c(C(=O)N2CCNCC2)cc(-c2nc(-c3ccc(Cl)nc3)c(C)s2)c1=O] | A | A | 626.2339 | 2.74 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (6-chloropyridin-3-yl)boronic acid (method xix); Methods: S, then Boc removal with TFA/DCM rt | |
| 406 | 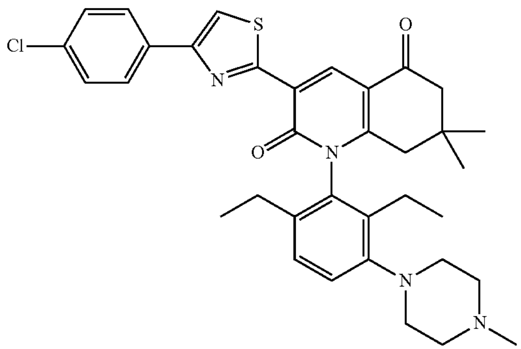 [SMILES: CCc1ccc(N2CCN(C)CC2)c(CC)c1-n1c2c(cc(-c3nc(-c4ccc(Cl)cc4)cs3)c1=O)C(=O)CC(C)(C)C2] | D | D | 615.2558 | 2.968 | Starting material: 5,5-dimethylcyclohexane-1,3-dione (step1 method M); nitrile 1 (step2 method M); 2,6-diethyl-3-(4-methylpiperazin-1-yl)aniline (step 3 method M); Methods: M | HCl salt: 1H NMR (400 MHz, CD3OD) δ 9.35 (s, 1H), 8.09-8.04 (m, 2H), 7.94 (s, 1H), 7.53 (d, J = 8.4 Hz, 1H), 7.47 (dd, J = 8.9, 2.3 Hz, 3H), 3.61 (d, J = 10.2 Hz, 2H), 3.35 (dd, J = 7.9, 6.0 Hz, 2H), 3.30-3.17 (m, 4H), 3.00 (s, 3H), 2.75 (td, J = 15.1, 7.6 Hz, 2H), 2.45-2.14 (m, 6H), 1.17 (t, J =7.5 Hz, 3H), 1.07 (dd, J = 10.7, 5.6 Hz, 9H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 407 | 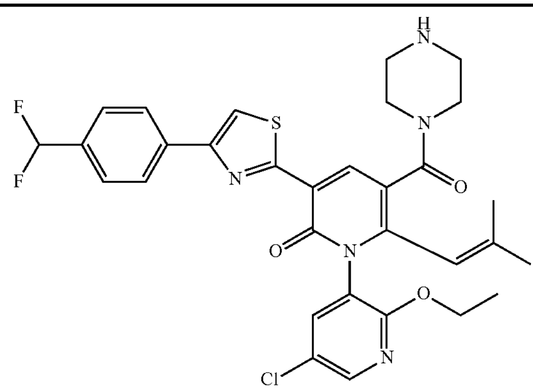 | A | B | 626.1786 | 2.67 | Starting materials: 6,6-dimethyldihydro-2H-pyran-2,4(3H)-dione (step 1), Nitrile 24 (step 2), pyridyl amine 4 (step 3 of methods V); Methods: V, no step 6. | |
| 408 | 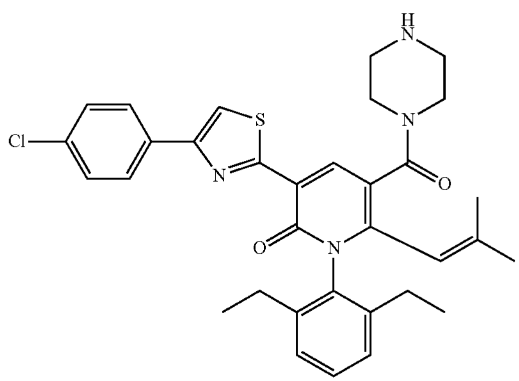 [SMILES: CCc1cccc(CC)c1-n1c(C=C(C)C)c(C(=O)N2CCNCC2)cc(-c2nc(-c3ccc(Cl)cc3)cs2)c1=O] | A | A | 587.2243 | 2.781 | Starting material: 6,6-dimethyldihydro-2H-pyran-2,4(3H)-dione (step1 method V); nitrile 1 (step2 method V); 2,6-diethylaniline (step 3 method V), Methods: V | TFA salt: 1H NMR (400 MHz, CD3OD) δ 8.91 (s, 1H), 8.08-8.02 (m, 2H), 7.95 (s, 1H), 7.53-7.43 (m, 3H), 7.39-7.29 (m, 2H), 5.39 (s, 1H), 4.38 (s, 1H), 3.78 (s, 2H), 3.52 (d, J = 29.4 Hz, 3H), 3.24 (s, 1H), 2.31 (d, J = 61.9 Hz, 4H), 1.67 (dd, J = 21.3, 1.1 Hz, 6H), 1.31 (s, 2H), 1.26-1.06 (m, 6H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 409 | 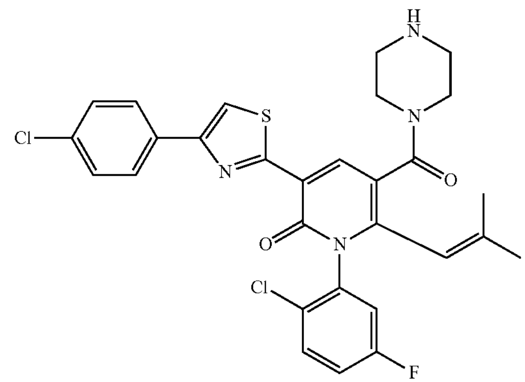 [SMILES: CC(C)=Cc1c(C(=O)N2CCNCC2)cc(-c2nc(-c3ccc(Cl)cc3)cs2)c(=O)n1-c1cc(F)ccc1Cl] | A | A | 583.1128 | 2.648 | Starting material: 6,6-dimethyldihydro-2H-pyran-2,4(3H)-dione (step1 method V); nitrile 1 (step2 method V); 2-chloro-5-fluoroaniline (step 3 method V), Methods: V | TFA salt: 1H NMR (400 MHz, CD3OD) δ 8.84 (s, 1H), 8.02 (d, J = 8.7 Hz, 2H), 7.94 (s, 1H), 7.72-7.62 (m, 1H), 7.50-7.40 (m, 3H), 7.38-7.32 (m, 1H), 5.61 (s, 1H), 4.35-4.15 (m, 1H), 3.90-3.70 (m, 1H), 3.65-3.50 (m, 2H), 3.35-3.10 (m, 4H), 1.72-1.62 (m, 6H). Aliphatic region complicated significantly by amide rotamers. |
| 410 | 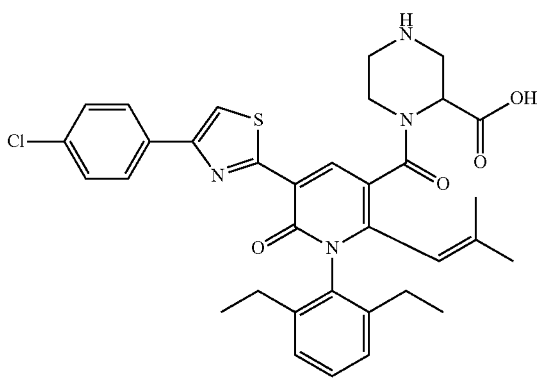 [SMILES: CCc1cccc(CC)c1-n1c(C=C(C)C)c(C(=O)N2CCNCC2C(=O)O)cc(-c2nc(-c3ccc(Cl)cc3)cs2)c1=O] | A | A | 631.2138 | 2.863 | Starting materials: 6,6-dimethyldihydro-2H-pyran-2,4(3H)-dione (step 1), Nitrile 1 (step 2), 1-tert-butyl 3-methyl piperazine-1,3-dicarboxylate (used in methods V, step 5); Methods: V, then ester hydrolyzed with LiOH (xs), THF/MeOH/water, 60° C. | 1H NMR (400 MHz, DMSO-d6) δ 8.72 (s, 1H), 8.25 (s, 1H), 8.13-8.03 (m, 2H), 7.59-7.47 (m, 2H), 7.42 (td, J = 7.5, 4.3 Hz, 1H), 7.28 (dd, J = 20.7, 7.6 Hz, 2H), 5.22 (s, 1H), 3.72 (t, J = 14.6 Hz, 2H), 3.12-2.95 (m, 2H), 2.72-2.52 (m, 2H), 2.43-2.20 (m, 2H), 2.19-1.97 (m, 2H), 1.66-1.46 (m, 7H), 1.35-1.18 (m, 2H), 1.16-1.05 (m, 3H), 1.00 (td, J = 7.5, 4.4 Hz, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 411 | 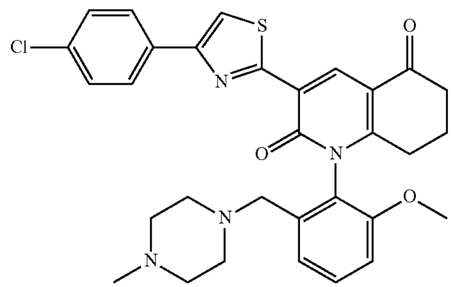 [SMILES: COc1cccc(CN2CCN(C)CC2)c1-n1c2c(cc(-c3nc(-c4ccc(Cl)cc4)cs3)c1=O)C(=O)CCC2] | D | D | 575.1865 | 2.666 | Starting material: cyclohexane-1,3-dione (step1 method M); nitrile 1 (step2 method M); 2-methoxy-6-((4-methylpiperazin-1-yl)methyl)aniline (step 3 method M), Methods: M | |
| 412 | 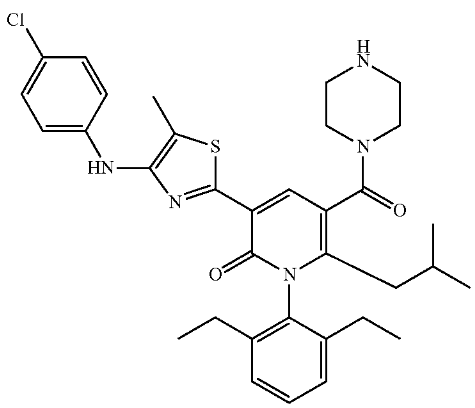 [SMILES: CCc1cccc(CC)c1-n1c(CC(C)C)c(C(=O)N2CCNCC2)cc(-c2nc(Nc3ccc(Cl)cc3)c(C)s2)c1=O] | D | D | 309.6354 | 2.845 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U); Methods: S, then ester hydrolyzed with LiOH (0.5M), THF, rt, U, xxii, then Boc removal with TFA/DCM rt | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 413 | 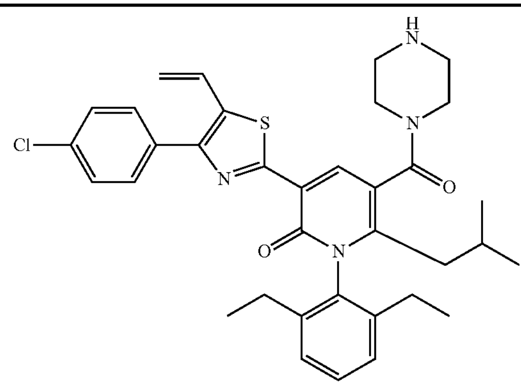 | B | A | 615.2543 | 2.977 | Starting material: methyl 5-methyl-3-oxohexanoate (step 1 method V); nitrile 1 (step2 method V); 2,6-diethylaniline (step 3 method V), Methods: V(step1-5), bromination with NBS in DCM, followed by step 1 of aniline 1 synthesis, then V (step 6) | TFA salt: 1H NMR (400 MHz, CD3OD) δ 8.67 (s, 1H), 7.71-7.62 (m, 2H), 7.52 (dd, J = 11.8, 4.9 Hz, 3H), 7.42 (t, J = 8.9 Hz, 2H), 6.91 (dd, J = 17.3, 11.0 Hz, 2H), 5.71 (d, J = 17.3 Hz, 1H), 5.36 (d, J = 11.1 Hz, 1H), 4.29 (s, 2H), 3.99 (s, 2H), 3.73 (s, 2H), 3.39 (s, 2H), 2.66 (s, 2H), 2.43 (dt, J = 22.7, 7.6 Hz, 2H), 2.28 (dd, J = 14.6, 7.0 Hz, 2H), 1.66 (d, J = 7.0 Hz, 1H), 1.54-1.40 (m, 1H), 1.30-1.08 (m, 6H), 0.71 (d, J = 6.2 Hz, 6H). Aliphatic region complicated significantly by amide rotamers. |
| 414 | 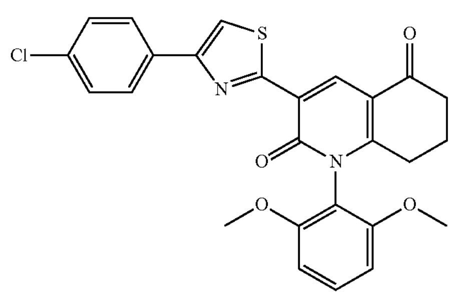 [SMILES: COc1cccc(OC)c1-n1c2c(cc(-c3nc(-c4ccc(Cl)cc4)cs3)c1=O)C(=O)CCC2] | C | C | 493.0979 | 3.757 | Starting material: cyclohexane-1,3-dione (step1 method M); nitrile 1 (step2 method M); 2,6-dimethoxyaniline (step 3 method M), Methods: M | 1H NMR (400 MHz, CD3OD) δ 9.32 (s, 1H), 7.98 (d, J = 8.4 Hz, 2H), 7.53 (s, 1H), 7.45-7.39 (m, 3H), 6.71 (d, J = 8.4 Hz, 2H), 3.78 (s, 6H), 2.59 (t, J = 8.0 Hz, 2H), 2.10 (t, J = 8.0 Hz, 2H), 2.09-2.03 (m, 2H), Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 415 | 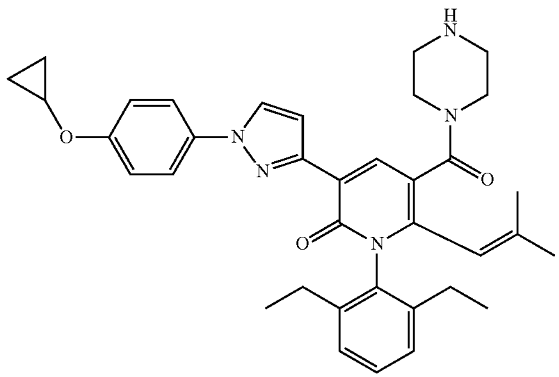 [SMILES: CCc1cccc(CC)c1-n1c(C=C(C)C)c(C(=O)N2CCNCC2)cc(-c2ccn(-c3ccc(OC4CC4)cc3)n2)c1=O] | A | A | 296.6664 | 2.662 | Starting materials: pyrazole 6 (step 2), piperazine (step 5); Methods: V, step 4 with NaOH (xs), no step 6. | TFA salt: 1H NMR (400 MHz, DMSO-d6) δ 8.78 (br s, 1H), 8.68 (br s, 1H), 8.39 (d, J = 2.5 Hz, 1H), 8.31 (s, 1H), 7.86-7.70 (m, 2H), 7.37 (t, J = 7.7 Hz, 1H), 7.25 (dd, J = 16.6, 7.5 Hz, 2H), 7.18-7.07 (m, 3H), 5.24-5.13 (m, 1H), 4.08-3.93 (m, 1H), 3.88 (tt, J = 6.1, 2.9 Hz, 1H), 3.54 (m, 1H), 3.10 (m, 4H), 2.97 (m, 1H), 2.43-2.19 (m, 1H), 2.09 (m, 2H), 1.53 (dd, J = 2.6, 1.4 Hz, 6H), 1.19-0.90 (m, 6H), 0.87-0.74 (m, 2H), 0.66 (tt, J = 4.9, 3.0 Hz, 2H). |
| 416 | 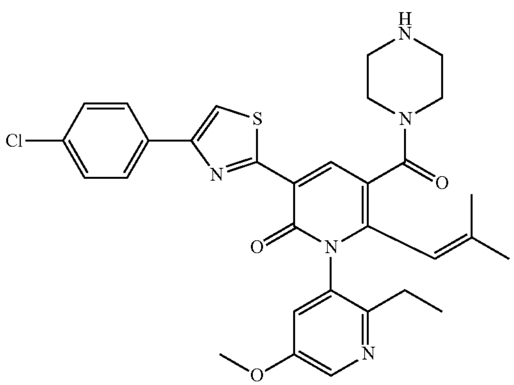 [SMILES: CCc1ncc(OC)cc1-n1c(C=C(C)C)c(C(=O)N2CCNCC2)cc(-c2nc(-c3ccc(Cl)cc3)cs2)c1=O] | A | A | 590.1996 | 2.561 | Starting materials: 6,6-dimethyldihydro-2H-pyran-2,4(3H)-dione (step 1), 2-(4-(4-chlorophenyl)thiazol-2-yl)acetonitrile (step 2), 2-ethyl-5-methoxypyridin-3-amine (step 3); Methods: W, then V (steps 4-6) | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 417 | 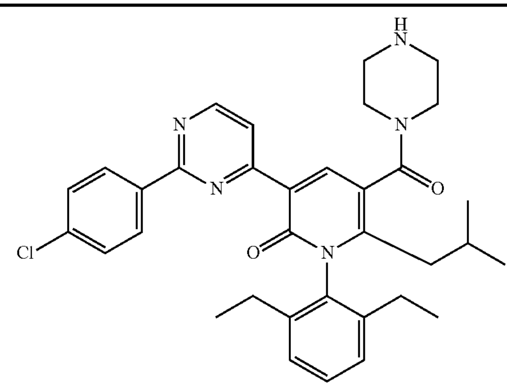 | B | B | 584.2784 | 2.785 | Starting materials: methyl 5-methyl-3-oxohexanoate (step 1), 2-(2-(4-chlorophenyl)pyrimidin-4-yl)acetonitrile (step 2), tert-butyl piperazine-1-carboxylate (used in method U), then Boc removal with TFA/DCM rt | 1H NMR (400 MHz, DMSO-d6) δ 8.98 (s, 1H), 8.91 (d, J = 5.4 Hz, 1H), 8.83 (s, 1H), 8.57-8.47 (m, 2H), 8.39 (d, J = 5.3 Hz, 1H), 7.65-7.57 (m, 2H), 7.50-7.41 (m, 1H), 7.34 (s, 1H), 7.32 (s, 1H), 4.17-4.05 (m, 1H), 3.90-3.81 (m, 1H), 3.62-3.43 (m, 2H), 3.27-3.06 (m, 4H), 2.33 (dq, J = 15.2, 7.5 Hz, 2H), 2.21 (d, J = 12.2 Hz, 3H), 2.03-1.92 (m, 1H), 1.33 (hept, J = 6.9 Hz, 1H), 1.09 (t, J = 7.5 Hz, 6H), 0.61 (d, J = 6.5 Hz, 6H). Aliphatic region complicated significantly by amide rotamers. |
| 418 | 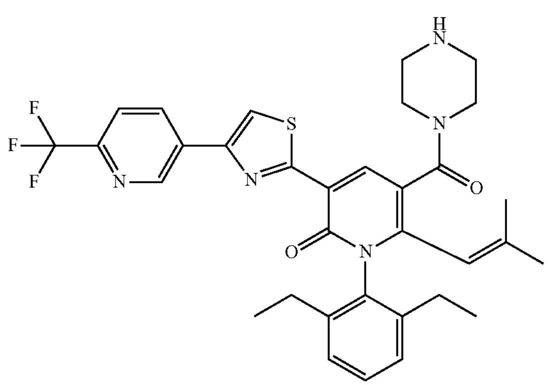 [SMILES: CCc1cccc(CC)c1-n1c(C=C(C)C)c(C(=O)N2CCNCC2)cc(-c2nc(-c3ccc(C(F)(F)F)nc3)cs2)c1=O] | A | A | 622.2488 | 2.686 | Starting materials: piperazine (step 5 of method V); Methods: W, then step 4 of method V with NaOH (xs), then step 5 of method V and no step 6. | TFA salt: 1H NMR(400 MHz, DMSO-d6) δ 9.46 (dt, J = 2.2, 0.6 Hz, 1H), 8.87-8.60 (m, 4H), 8.57 (s, 1H), 8.02 (dd, J = 8.3, 0.8 Hz, 1H), 7.43 (t, J = 7.7 Hz, 1H), 7.30 (dd, J = 16.8, 7.7 Hz, 2H), 5.34-5.21 (m, 1H), 4.04 (br d, J = 14.3 Hz, 1H), 3.73-3.32 (m, 2H), 3.24-2.87 (m, 4H), 2.44-1.96 (m, 3H), 1.57 (t, J = 1.6 Hz, 6H), 1.06 (dt, J = 46.0, 7.3 Hz, 6H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 419 | 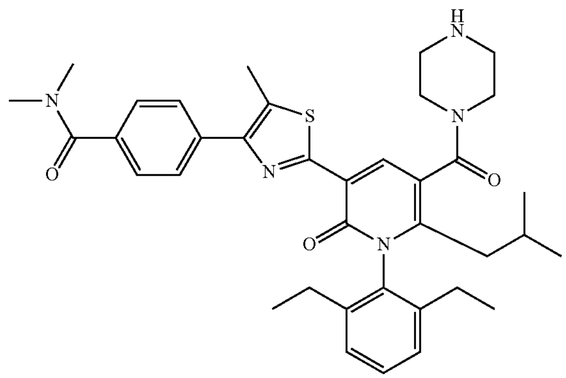 [SMILES: CCc1cccc(CC)c1-n1c(CC(C)C)c(C(=O)N2CCNCC2)cc(-c2nc(-c3ccc(C(=O)N(C)C)cc3)c(C)s2)c1=O] | C | C | 640.3339 | 2.663 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-(dimethylcarbamoyl)phenyl)boronic acid (method xix); Methods: S, then Boc removal with TFA/DCM rt | |
| 420 | 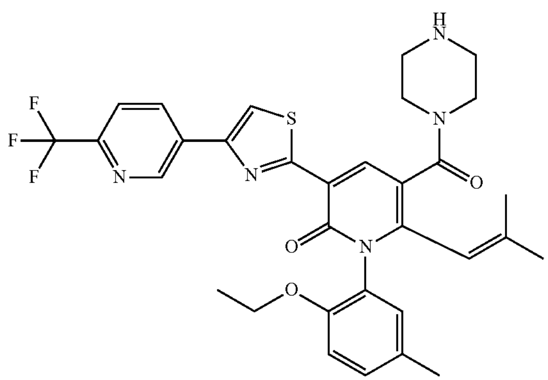 [SMILES: CCOc1ccc(C)cc1-n1c(C=C(C)C)c(C(=O)N2CCNCC2)cc(-c2nc(-c3ccc(C(F)(F)F)nc3)cs2)c1=O] | A | A | 624.23 | 2.603 | Starting materials: nitrile 26 (step 2 method W); 2-ethoxy-5-methylaniline (step 3 method W). Methods: W, then steps 4-6 in method V | 1H NMR (400 MHz, DMSO-d6) δ 9.47 (s, 1H), 8.79 (s, 1H), 8.70 (dd, J = 8.3, 2.1 Hz, 2H), 8.56 (s, 1H), 8.03 (d, J = 8.2 Hz, 1H), 7.26 (dd, J = 8.5, 2.2 Hz, 1H), 7.21 (d, J = 3.3 Hz, 1H), 7.05 (d, J = 8.1 Hz, 1H), 5.53 (s, 1H), 4.07-3.93 (m, 1H), 3.87-3.81 (m, 1H), 3.67-3.61 (m, 1H), 3.49-3.42 (m, 2H), 3.24-3.05 (m, 5H), 2.35-2.26 (m, 3H), 1.59 (s, 3H), 1.54 (s, 3H), 1.11 (q, J = 10.6, 7.1 Hz, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 421 | 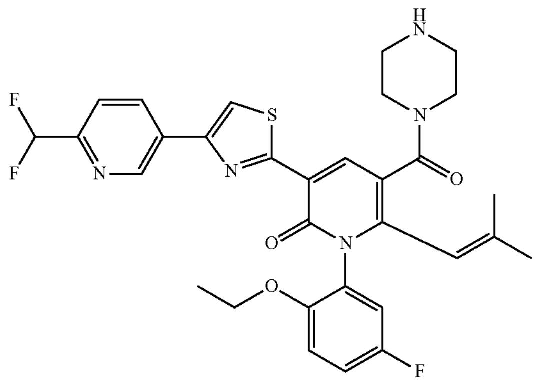 [SMILES: CCOc1ccc(F)cc1-n1c(C=C(C)C)c(C(=O)N2CCNCC2)cc(-c2nc(-c3ccc(C(F)F)nc3)cs2)c1=O] | | | | | | |
| 422 | 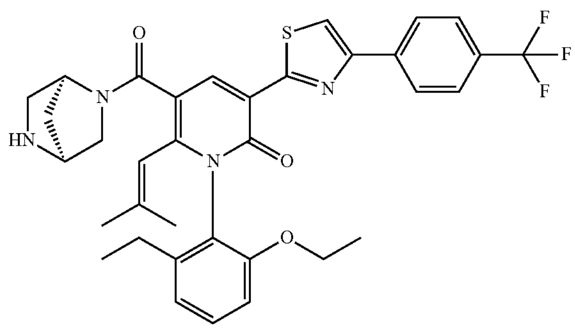 [SMILES: CCOc1cccc(CC)c1-n1c(C=C(C)C)c(C(=O)N2C[C@@H]3C[C@H]2CN3)cc(-c2nc(-c3ccc(C(F)(F)F)cc3)cs2)c1=O] | B | A | 633.2506 | 2.815 | Starting materials: 6,6-dimethyldihydro-2H-pyran-2,4(3H)-dione (step 1), Nitrile 7 (step 2), (1S,4S)-tert-butyl 2,5-diazabicyclo[2.2.1]heptane-2-carboxylate (used in methods V, step 5); Methods: V. | 1H NMR (400 MHz, DMSO-d6) δ 8.72 (s, 1H), 8.41 (s, 1H), 8.28 (dd, J = 8.4, 4.2 Hz, 2H), 7.88-7.77 (m, 2H), 7.44 (td, J = 7.6, 4.0 Hz, 1H), 7.31 (t, J = 8.3 Hz, 2H), 5.34 (s, 1H), 4.81-4.71 (m, 1H), 4.46-4.24 (m, 2H), 3.43-3.33 (m, 1H), 3.23-3.16 (m, 1H), 2.70-2.54 (m, 1H), 2.36-2.01 (m, 3H), 1.89-1.74 (m, 2H), 1.65-1.52 (m, 6H), 1.24-0.93 (m, 6H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 423 | 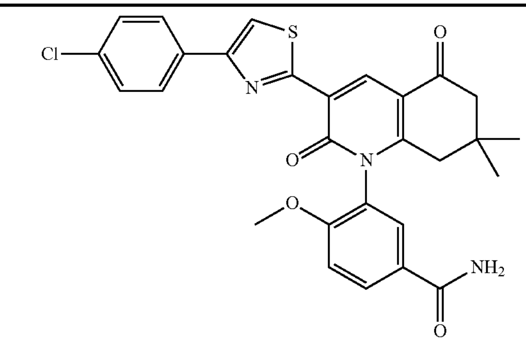 | C | C | 534.1271 | 3.474 | Starting material: 5,5-dimethylcyclohexane-1,3-dione (step1 method M); nitrile 1 (step2 method M); 3-amino-4-methoxybenzamide (step 3 method M), Methods: M | |
| 424 | 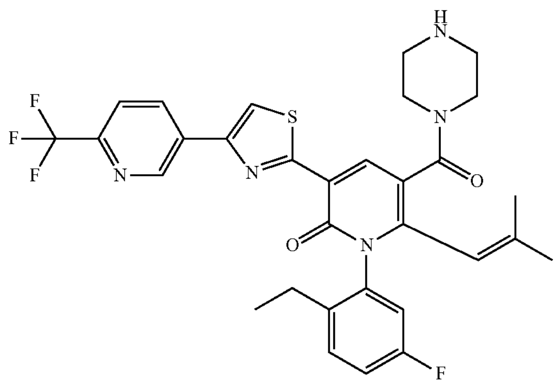 [SMILES: CCc1ccc(F)cc1-n1c(C=C(C)C)c(C(=O)N2CCNCC2)cc(-c2nc(-c3ccc(C(F)(F)F)nc3)cs2)c1=O] | A | B | 612.2 | 2.62 | Starting materials: 6,6-dimethyldihydro-2H-pyran-2,4(3H)-dione (step 1), 2-(4-(6-(trifluoromethyl)pyridin-3-yl)thiazol-2-yl)acetonitrile (step 2), 2-ethyl-5-fluoroaniline (step 3); Methods: W, then V (steps 4-6) | 1H NMR (400 MHz, DMSO-d6) δ 9.44 (s, 1H), 8.75 (bs, 1H), 8.74 (s, 1H), 8.68 (d, J = 8.4 Hz, 1H), 8.56 (s, 1H), 8.00 (d, J = 8.3 Hz, 1H), 7.55-7.11 (m, 3H), 5.57-5.35 (m, 1H), 4.12-3.91 (m, 1H), 3.77-3.58 (m, 1H), 3.46-2.86 (m, 6H), 2.41-1.99 (m, 2H), 1.59 (s, 3H), 1.55 (s, 3H), 1.13-0.91 (m, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 425 | (structure) | A | A | 635.2659 | 2.841 | Starting materials: 6,6-dimethyldihydro-2H-pyran-2,4(3H)-dione (step 1), Nitrile 7 (step 2), (S)-tert-butyl 2-methylpiperazine-1-carboxylate (used in methods V, step 5); Methods: V. | 1H NMR (400 MHz, DMSO-d6) δ 8.75 (s, 1H), 8.41 (s, 1H), 8.29 (d, J = 8.1 Hz, 2H), 7.83 (d, J = 8.1 Hz, 2H), 7.50-7.21 (m, 3H), 5.30 (s, 1H), 4.64-4.47 (m, 1H), 4.35-4.24 (m, 1H), 3.73-3.61 (m, 1H), 3.57-3.38 (m, 1H), 3.24-2.86 (m, 2H), 2.44-2.20 (m, 1H), 2.19-2.09 (m, 1H), 1.64-1.49 (m, 6H), 1.31-1.19 (m, 2H), 1.19-1.04 (m, 6H), 1.02-0.93 (m, 3H). |
| 426 | (structure) | A | A | 630.2311 | 2.753 | Starting materials: 6,6-dimethyldihydro-2H-pyran-2,4(3H)-dione (step 1), Nitrile 1 (step 2), tert-butyl 3-isopropylpiperazine-1-carboxylate (used in methods V, step 5); Methods: V | 1H NMR (400 MHz, DMSO-d6) δ 8.76 (s, 1H), 8.26 (s, 1H), 8.09 (dd, J = 8.0, 6.0 Hz, 2H), 7.53 (dd, J = 8.0, 6.2 Hz, 2H), 7.43 (t, J = 7.7 Hz, 1H), 7.37-7.20 (m, 2H), 5.29 (d, J = 9.5 Hz, 1H), 4.72-4.55 (m, 1H), 4.02-3.72 (m, 1H), 3.66-3.54 (m, 1H), 3.17-2.99 (m, 2H), 2.82 (t, J = 13.0 Hz, 1H), 2.68-2.62 (m, 1H), 2.42-2.22 (m, 2H), 2.15-1.99 (m, 2H), 1.67-1.50 (m, 6H), 1.11 (t, J = 7.5 Hz, 3H), 1.05-0.91 (m, 3H), |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 427 | 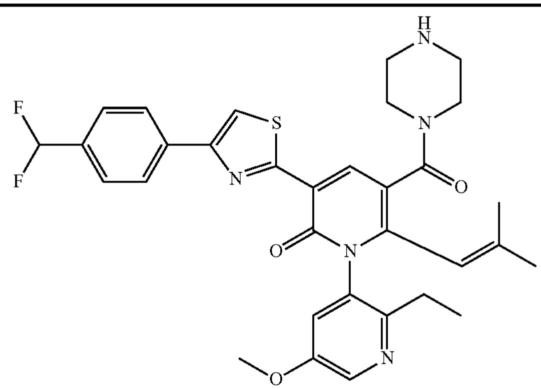 | A | B | 606.2342 | 2.523 | Starting materials: 6,6-dimethyldihydro-2H-pyran-2,4(3H)-dione (step 1), 2-(4-(4-(difluoromethyl)phenyl)thiazol-2-yl)acetonitrile (step 2), 2-ethyl-5-methoxypyridin-3-amine (step 3); Methods: W, then V (steps 4-6) | 1H NMR (400 MHz, Chloroform-d) δ 8.85 (bs, 1H), 8.40 (d, J = 2.7 Hz, 1H), 8.10 (d, J = 8.0 Hz, 2H), 7.69 (s, 1H), 7.59 (d, J = 8.0 Hz, 2H), 7.08-6.87 (m, 1H), 6.70 (t, J = 56.5 Hz, 1H), 5.45-5.40 (m, 1H), 3.96-3.82 (m, 4H), 3.59-3.27 (m, 3H), 3.06-2.75 (m, 4H), 2.59-2.28 (m, 2H), 1.75-1.54 (m, 6H), 1.30-1.07 (m, 3H). |
| 428 | 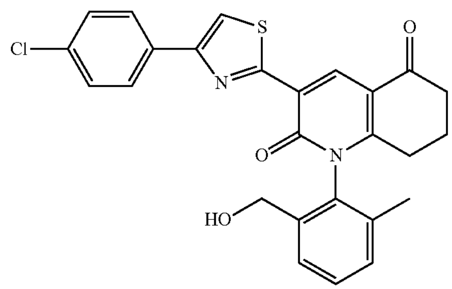 [SMILES: Cc1cccc(CO)c1-n1c2c(cc(-c3nc(-c4ccc(Cl)cc4)cs3)c1=O)C(=O)CCC2] | C | C | 477.1034 | 3.593 | Starting material: cyclohexane-1,3-dione (step1 method M); nitrile 1 (step2 method M); (2-amino-3-methylphenyl)methanol (step 3 method M), Methods: M | 1H NMR (400 MHz, CDCl3) δ 9.41 (s, 1H), 7.99 (t, J = 5.5 Hz, 2H), 7.58 (s, 1H), 7.53-7.38 (m, 6H), 5.30 (s, 1H), 4.51-4.35 (m, 2H), 2.60 (ddd, J = 18.4, 9.9, 5.8 Hz, 4H), 2.39 (dt, J = 18.2, 6.1 Hz, 2H), 2.17-2.06 (m, 6H). Aliphatic region complicated significantly by amide rotamers. |
| 429 | 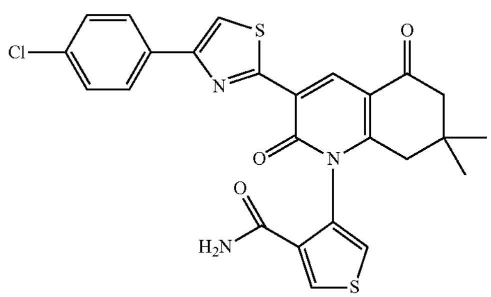 [SMILES: CC1(C)CC(=O)c2cc(-c3nc(-c4ccc(Cl)cc4)cs3)c(=O)n(-c3cscc3C(N)=O)c2C1] | D | D | 510.0724 | 3.432 | Starting material: 5,5-dimethylcyclohexane-1,3-dione (step1 method M); nitrile 1 (step2 method M); 4-aminothiophene-3-carboxamide (step 3 method M), Methods: M | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 430 | 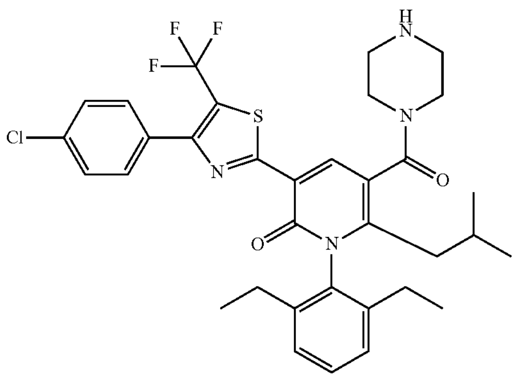 [SMILES: CCc1cccc(CC)c1-n1c(CC(C)C)c(C(=O)N2CCNCC2)cc(-c2nc(-c3ccc(Cl)cc3)c(C(F)(F)F)s2)c1=O] | B | B | 657.226 | 3.033 | Starting material: methyl 5-methyl-3-oxohexanoate (step1 method V); nitrile 1 (step2 method V); 2,6-diethylaniline (step 3 method V). Methods: V(step1-5), bromination with NBS in DCM, followed by treatment with Hartwig's Trifluoromethylator in DMF, then V (step 6) | TFA salt: 1H NMR(400 MHz, CD3OD) δ 8.77 (s, 1H), 7.71 (d, J = 8.5 Hz, 2H), 7.54 (t, J = 8.2 Hz, 3H), 7.41 (d, J = 7.7 Hz, 2H), 4.27 (s, 2H), 3.97 (s, 2H), 3.75 (t, J = 25.4 Hz, 2H), 3.37 (s, 2H), 2.72 (s, 2H), 2.43 (dt, J = 22.6, 7.6 Hz, 2H), 2.28 (s, 3H), 1.58-1.43 (m, 1H), 1.19 (t, J = 6.6 Hz, 6H), 0.72 (d, J = 6.5 Hz, 6H). Aliphatic region complicated significantly by amide rotamers. |
| 431 | 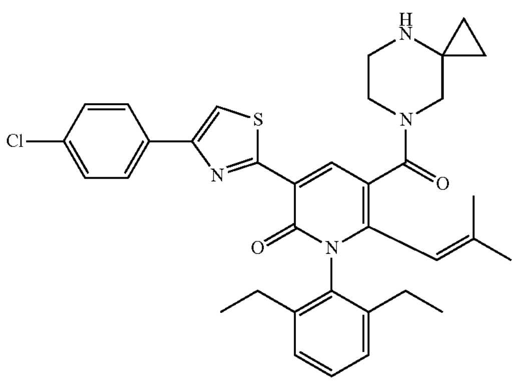 [SMILES: CCc1cccc(CC)c1-n1c(C=C(C)C)c(C(=O)N2CCNC3(CC3)C2)cc(-c2nc(-c3ccc(Cl)cc3)cs2)c1=O] | A | A | 613.2427 | 2.85 | Starting materials: 6,6-dimethyldihydro-2H-pyran-2,4(3H)-dione (step 1), Nitrile 1 (step 2), tert-butyl 4,7-diazaspiro[2.5]octane-4-carboxylate (used in methods V, step 5); Methods: V | 1H NMR (400 MHz, DMSO-d6) δ 8.70 (s, 1H), 8.25 (s, 1H), 8.16-8.05 (m, 2H), 7.59-7.49 (m, 2H), 7.43 (t, J = 7.6 Hz, 1H), 7.30 (dd, J = 21.4, 7.9 Hz, 2H), 5.33 (s, 1H), 4.41-4.31(m, 1H), 3.69-3.40 (m, 3H), 3.04-2.90 (m, 1H), 2.68-2.52 (m, 1H), 2.44-2.21 (m, 3H), 2.19-1.98 (m, 2H), 1.62-1.51 (m, 7H), 1.18-1.04 (m, 3H), 0.99 (t, J = 7.5 Hz, 6H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 432 | 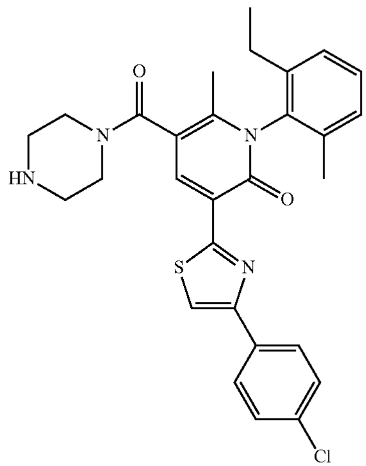 [SMILES: CCc1cccc(C)c1-n1c(C)c(C(=O)N2CCNCC2)cc(-c2nc(-c3ccc(Cl)cc3)cs2)c1=O] | B | C | 633.1792 | 2.6 | Starting material: methyl 3-oxobutanoate (step1 method M); nitrile 1 (step2 method M); 2-ethyl-6-methylaniline (step 3 method M), Methods: M | TFA salt: 1H NMR (400 MHz, dmso-d6) δ 8.95 (s, 2H), 8.71 (d, J = 6.5 Hz, 1H), 8.22 (s, 1H), 8.12 (d, J = 8.6 Hz, 2H), 7.52 (t, J = 8.4 Hz, 2H), 7.43 (t, J = 7.6 Hz, 1H), 7.33 (dd, J = 15.7, 8.1 Hz, 2H), 3.57 (d, J = 87.5 Hz, 4H), 3.16 (t, J = 47.1Hz, 4H), 2.20 (t, J = 39.9 Hz, 1H), 1.98 (s,3H), 1.90 (s, 3H), 1.08 (t, J = 7.5 Hz, 3H). Aliphatic region complicated significantly by amide rotamers. |
| 433 | 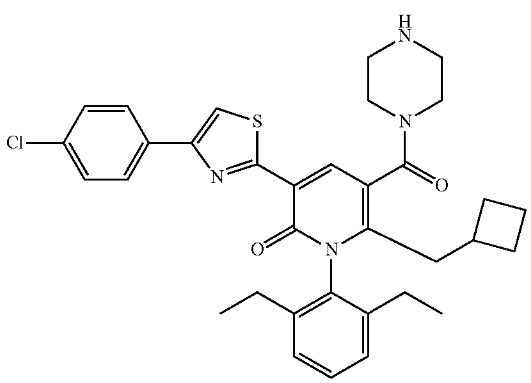 [SMILES: CCc1cccc(CC)c1-n1c(CC2CCC2)c(C(=O)N2CCNCC2)cc(-c2nc(-c3ccc(Cl)cc3)cs2)c1=O] | A | A | 601.2391 | 2.86 | Starting materials: ethyl 4-cyclobutyl-3-oxobutanoate (step 1), piperazine (used in method U); Methods: S, then ester hydrolyzed with LiOH (xs), THF/MeOH/water, 60° C.; U | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | $^1$H-NMR |
|---|---|---|---|---|---|---|---|
| 434 | 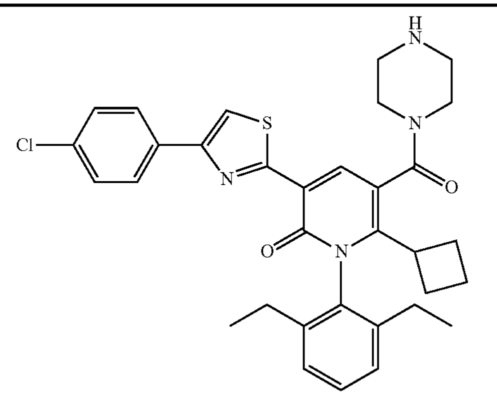 | B | A | 587.223 | 2.772 | Starting materials: ethyl 3-cyclobutyl-3-oxopropanoate (used in method U); Methods: S, then ester hydrolyzed with LiOH (xs), THF/MeOH/water, 60° C.; U | 1H NMR (400 MHz, DMSO-d6) δ 8.42 (d, J = 2.4 Hz, 1H), 8.18 (d, J = 1.9 Hz, 1H), 8.08 (m, 3H), 7.59-7.36 (m, 4H), 7.31 (m, 2H), 3.69 (m, 1H), 3.41 (m, 2H), 3.01 (m, 1H), 2.70 (m, 3H), 2.40-2.26 (m, 1H), 2.26-1.94 (m, 3H), 1.46 (m, 3H), 1.05 (m, 6H). |
| 435 | 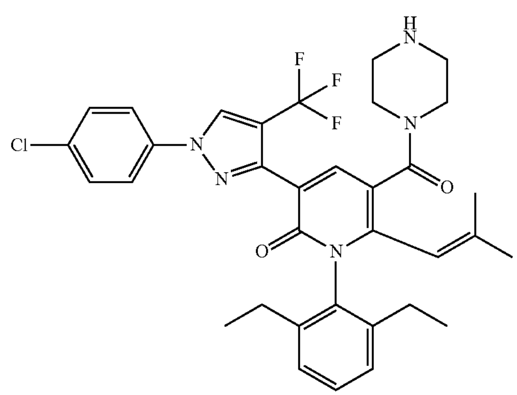 [SMILES: CCc1cccc(CC)c1-n1c(C=C(C)C)c(C(=O)N2CCNCC2)cc(-c2nn(-c3ccc(Cl)cc3)cc2C(F)(F)F)c1=O] | C | D | 638.251 | 2.681 | Starting materials: pyrazole 10 (step 2), piperazine (step 5); Methods: V, step 4 with NaOH (xs), no step 6. | TFA salt: 1H NMR (400 MHz, DMSO-d6) δ 9.23 (d, J = 0.9 Hz, 1H), 8.80 (br s, 1H), 8.69 (br s, 1H), 8.02-7.88 (m, 2H), 7.78 (s, 1H), 7.68-7.54 (m, 2H), 7.37 (t, J = 7.6 Hz, 1H), 7.24 (br m, 2H), 5.24-5.13 (m, 1H), 3.90 (m, 1H), 3.53 (m, 1H), 3.21-2.73 (m, 5H), 2.41-1.97 (m, 4H), 1.53 (dd, J = 5.0, 1.3 Hz, 6H), 1.17-0.89 (m, 6H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 436 | 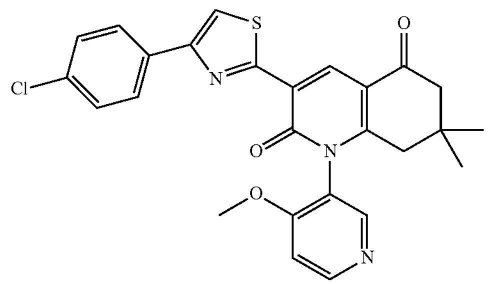 [SMILES: COc1ccncc1-n1c2c(cc(-c3nc(-c4ccc(Cl)cc4)cs3)c1=O)C(=O)CC(C)(C)C2] | E | D | 492.1148 | 3.133 | Starting material: 5,5-dimethylcyclohexane-1,3-dione (step1 method M); nitrile 1 (step2 method M); 4-methoxypyridin-3-amine (step 3 method M), Methods: M | HCl salt: 1H NMR (400 MHz, CD3OD) δ 9.01 (s, 1H), 8.21-8.19 (m, 2H), 8.08-8.06 (m, 2H), 7.88-7.86 (m, 1H), 7.52 (d, J = 8.4 Hz, 2H), 6.48 (d, J = 8.4 Hz, 1H), 3.76 (s, 3H), 3.68-3.64 (m, 1H), 2.77-2.73 (m, 2H), 2.41-2.41 (m, 1H), 1.20-0.96 (m, 6H). Aliphatic region complicated significantly by amide rotamers. |
| 437 | 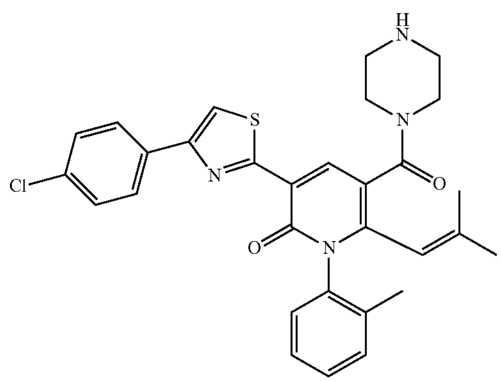 [SMILES: CC(C)=Cc1c(C(=O)N2CCNCC2)cc(-c2nc(-c3ccc(Cl)cc3)cs2)c(=O)n1-c1ccccc1C] | A | B | 567.1593 | 2.618 | Starting material: 6,6-dimethyldihydro-2H-pyran-2,4(3H)-dione (step1 method V); nitrile 1 (step2 method V); 2-methylaniline (step 3 method V), Methods: V | TFA salt: 1H NMR(400 MHz, CD3OD) δ 8.86 (s, 1H), 8.03 (d, J = 8.6 Hz, 2H), 7.92 (s, 1H), 7.47-7.03 (m, 6H), 5.63-5.43 (m, 1H), 4.40-4.20 (m, 1H), 3.90-3.73 (m, 1H), 3.65-3.50 (m, 2H), 3.35-3.10 (m, 4H), 2.20-1.95 (m, 3H), 1.70-1.58 (m, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 438 | 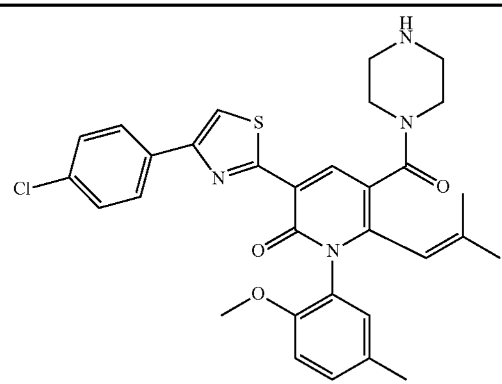 | A | A | 575.1889 | 2.624 | Starting material: 6,6-dimethyldihydro-2H-pyran-2,4(3H)-dione (step1 method V); nitrile 1 (step2 method V); 2-methoxy-5-methylaniline (step 3 method V), Methods: V | TFA salt: 1H NMR(400 MHz, dmso-d6) δ 8.66 (s, 1H), 8.23 (S,1H), 8.11 (d, J = 8.6Hz,2H), 7.57-7.51 (m, 2H), 7.28 (d, J = 8.4 Hz, 1H), 7.20 (S,1H), 7.06 (s, 1H), 5.49 (s, 1H), 3.97 (s, 1H), 3.81-3.56 (m, 4H), 3.43 (s, 2H), 3.26-2.85 (m, 4H), 2.32 (s, 3H), 1.58 (S, 3H), 1.53 (S, 3H). Aliphatic region complicated significantly by amide rotamers. |
| 439 | 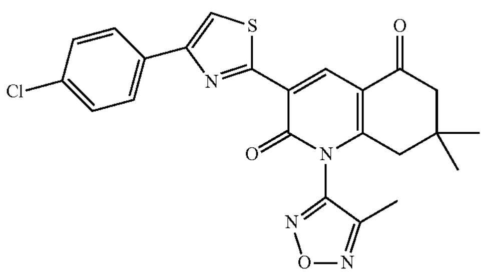 [SMILES: Cc1nonc1-n1c2c(cc(-c3nc(-c4ccc(Cl)cc4)cs3)c1=O)C(=O)CC(C)(C)C2] | E | C | 467.0923 | 3.889 | Starting material: 5,5-dimethylcyclohexane-1,3-dione (step1 method M); nitrile 1 (step2 method M); 4-methyl-1,2,5-oxadiazol-3-amine (step 3 method M), Methods: M | 1H NMR (400 MHz, CDCl3) δ 9.34 (s, 1H), 8.02-7.95 (m, 2H), 7.63 (s, 1H), 7.46-7.39 (m, 2H), 2.96-2.80 (m, 1H), 2.53 (t, J = 4.6 Hz, 2H), 2.38 (s,3H), 2.02 (d, J = 15.3 Hz, 1H), 1.12 (d, J = 40.2 Hz, 6H). Aliphatic region complicated significantly by amide rotamers. |
| 440 | 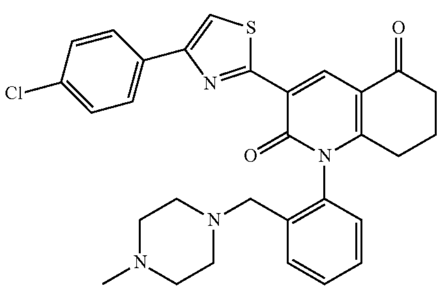 [SMILES: CN1CCN(Cc2ccccc2-n2c3c(cc(-c4nc(-c5ccc(Cl)cc5)cs4)c2=O)C(=O)CCC3)CC1] | D | D | 545.1771 | 2.655 | Starting material: cyclohexane-1,3-dione (step1 method M); nitrile 1 (step2 method M); 2-((4-methylpiperazin-1-yl)methyl)aniline (step 3 method M), Methods: M | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 441 | 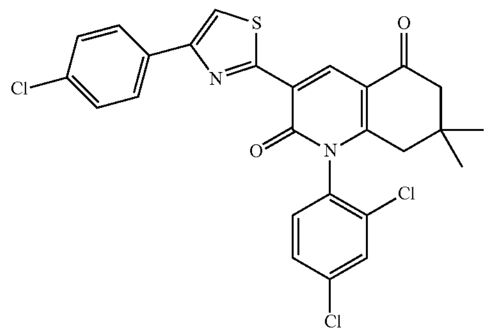 [SMILES: CC1(C)CC(=O)c2cc(-c3nc(-c4ccc(Cl)cc4)cs3)c(=O)n(-c3ccc(Cl)cc3Cl)c2C1] | E | D | 531.0291 | 4.091 | Starting material: 5,5-dimethylcyclohexane-1,3-dione (step1 method M); nitrile 1 (step2 method M); 2,4-dichloroaniline (step 3 method M). Methods: M | 1H NMR (400 MHz, CDCl3) δ 9.36 (s, 1H), 8.03-7.95 (m, 2H), 7.70 (d, J = 2.2Hz, 1H), 7.59 (s, 1H), 7.52 (dd, J = 8.4, 2.2 Hz, 1H), 7.46-7.39 (m, 2H), 7.28 (t, J = 6.2 Hz, 1H), 2.57-2.40 (m, 3H), 2.28 (d, J = 17.8 Hz, 1H), 1.10 (d, J = 1.9 Hz, 6H). Aliphatic region complicated significantly by amide rotamers. |
| 442 | 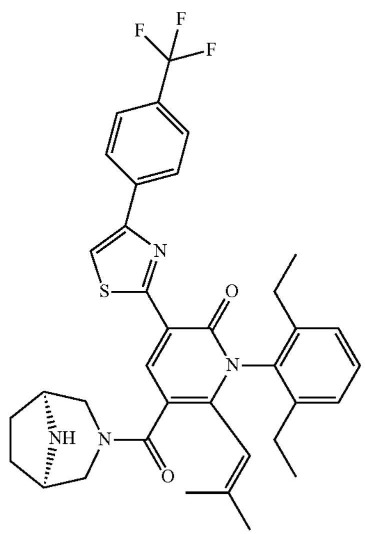 [SMILES: CCc1cccc(CC)c1-n1c(C=C(C)C)c(C(=O)N2C[C@H]3CC[C@@H](C2)N3)cc(-c2nc(-c3ccc(C(F)(F)F)cc3)cs2)c1=O] | A | A | 613.2389 | 2.798 | Starting materials: 6,6-dimethyldihydro-2H-pyran-2,4(3H)-dione (step 1), Nitrile 1 (step 2), (1R,5S)-tert-butyl 3,8-diazabicyclo[3.2.1]octane-3-carboxylate (used in methods V, step 5); Methods: V | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 443 | 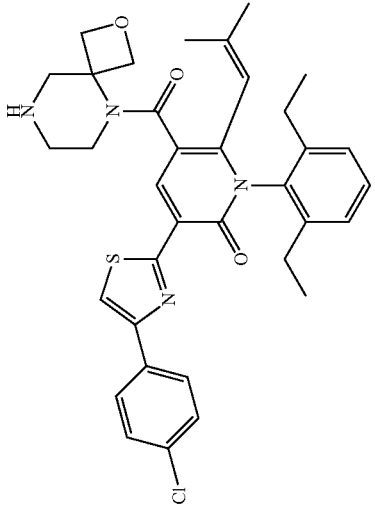 | B | A | 651.2177 | 3.494 | Starting materials: 6,6-dimethyldihydro-2H-pyran-2,4(3H)-dione (step 1), Nitrile 1 (step 2), tert-butyl 2-oxa-5,8-diazaspiro[3.5]nonane-8-carboxylate (used in methods V, step 5); Methods: V | 1H NMR (400 MHz, DMSO-d6) δ 9.13 (s, 1H), 8.27 (s, 1H), 8.16-8.04 (m, 2H), 7.63-7.51 (m, 2H), 7.44 (t, J = 7.7 Hz, 1H), 7.30 (d, J = 7.7 Hz, 2H), 5.41-5.25 (m, 1H), 4.57-4.02 (m, 2H), 3.13-2.96 (m, 6H), 2.42-1.90 (m, 6H), 1.64-1.30 (m, 6H), 1.10-0.97 (m, 6H). |
| 444 | 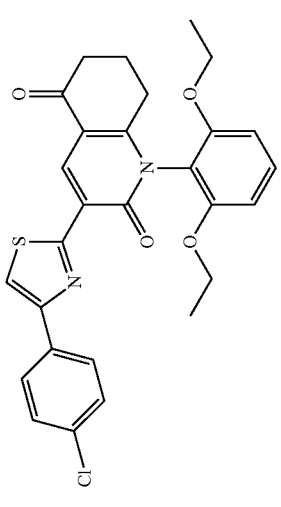 | B | B | 521.1296 | 3.914 | Starting material: cyclohexane-1,3-dione (step1 method M); nitrile 1 (step2 method M); 2,6-diethoxyaniline (step 3 method M), Methods: M | 1H NMR (400 MHz,CDCl) δ 9.35 (s, 1H), 8.00 (d, J = 8.6 Hz, 2H), 7.56 (s, 1H), 7.40 (dd, J = 17.1, 8.6 Hz, 3H), 6.69 (d, J = 8.5 Hz, 2H), 4.12-4.02 (m, 4H), 2.66-2.59 (m, 2H), 2.56 (t, J = 6.2 Hz, 2H), 2.16-2.06 (m, 2H), 1.23 (t, J = 7.0 Hz, 6H). Aliphatic region complicated significantly by amide rotamers. |
| 445 | 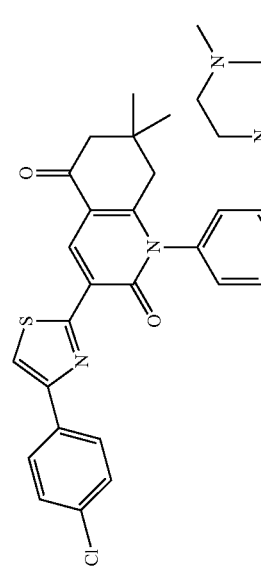 | D | D | 573.2092 | 2.748 | Starting material: 5,5-dimethylcyclohexane-1,3-dione (step1 method M); nitrile 1 (step2 method M); 3-((4-methylpiperazin-1-yl)methyl)aniline (step 3 method M), Methods: M | HCl salt: 1H NMR (400 MHz, dmso-d6) δ 9.09 (s, 1H), 8.24 (s, 1H), 8.13-8.07 (m, 2H), 7.80 (s, 1H), 7.72 (t, J = 7.8 Hz, 1H), 7.66 (s, 1H), 7.59-7.53 (m, 3H), 4.37 (s, 4H), 3.59 (d, J = 17.0 Hz, 4H), 2.82 (s, 3H), 2.70 (d, J = 18.6 Hz, 2H), 2.49-2.34 (m, 4H), 1.00 (d, J = 8.7 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | $^1$H-NMR |
|---|---|---|---|---|---|---|---|
| 446 | 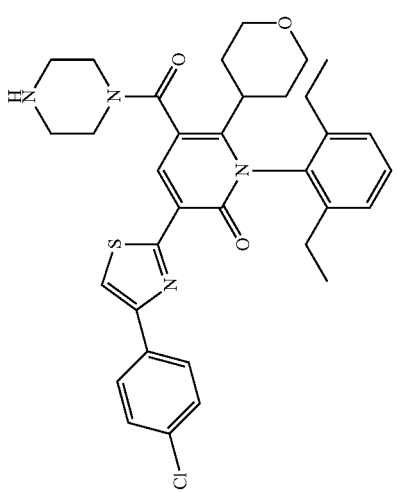 | C | B | 617.2343 | 2.727 | Starting materials: ethyl 3-oxo-3-((tetrahydro-2H-pyran-4-yl)propanoate (step 1), Nitrile 1 (step 2), piperazine (used in method U); Methods: S, ester hydrolyzed with LiOH (xs), THF/MeOH/water, 60° C.; U | 1H NMR (400 MHz, DMSO-d6) δ 8.66 (s, 1H), 8.21 (s, 1H), 8.17-8.06 (m, 2H), 7.49 (dd, J = 8.2, 6.4 Hz, 3H), 7.36 (dd, J = 10.2, 7.7 Hz, 2H), 4.11-3.99 (m, 1H), 3.84-3.64 (m, 4H), 3.53 (dd, J = 13.1, 5.9 Hz, 1H), 3.09-3.01 (m, 1H), 2.90-2.80 (m, 2H), 2.65-2.51 (m, 2H), 2.39-2.14 (m, 5H), 2.03 (tt, J = 15.0, 7.5 Hz, 2H), 1.72 (td, J = 13.4, 12.4, 9.1 Hz, 1H), 1.46 (d, J = 12.2 Hz, 1H), 1.22 (d, J = 11.9 Hz, 1H), 1.06 (dt, J = 22.1, 7.5 Hz, 6H). |
| 447 | 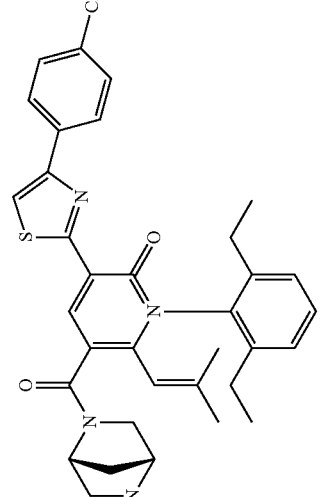 | A | A | 599.2253 | 2.765 | Starting materials: 6,6-dimethyldihydro-2H-pyran-2,4(3H)-dione (step 1), Nitrile 1 (step 2), (1R,4R)-tert-butyl 2,5-diazabicyclo[2.2.1]heptane-2-carboxylate (used in methods V, step 5); Methods: V | 1H NMR (400 MHz, DMSO-d6) δ 8.70 (s, 1H), 8.25 (d, J = 4.4 Hz, 1H), 8.14-8.04 (m, 2H), 7.58-7.49 (m, 2H), 7.43 (td, J = 7.7, 4.1 Hz, 1H), 7.31 (t, J = 8.2 Hz, 2H), 5.34 (s, 1H), 4.78-4.72 (m, 1H), 4.44-4.24 (m, 1H), 3.42-3.32 (m, 1H), 3.26-3.16 (m, 2H), 2.68-2.63(m, 1H), 2.34-2.24 (m, 2H), 2.21-2.06 (m, 3H), 1.84-1.76 (m, 2H), 1.63-1.54 (m, 6H), 1.04-0.97 (m, 6H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 448 | 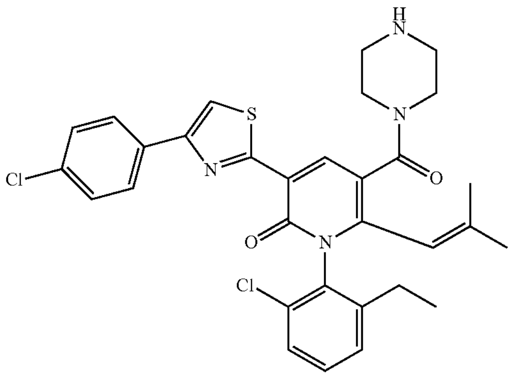 [SMILES: CCc1cccc(Cl)c1-n1c(C=C(C)C)c(C(=O)N2CCNCC2)cc(-c2nc(-c3ccc(Cl)cc3)cs2)c1=O] | A | A | 593.1528 | 2.726 | Starting material: 6,6-dimethyldihydro-2H-pyran-2,4(3H)-dione (step1 method V); nitrile 1 (step2 method V); aniline 6 (step 3 method V), Methods: V | TFA salt: 1H NMR (400 MHz, CD3OD) δ 8.88 (s, 1H), 8.03 (d, J = 8.7 Hz, 2H), 7.94 (s, 1H), 7.55-7.39 (m, 5H), 5.55-5.35 (m, 1H), 4.40-4.20 (m, 1H), 3.85-3.70 (m, 1H), 3.60-3.45 (m, 2H), 3.35-3.10 (m, 4H), 2.60-2.25 (m, 2H), 1.74-1.63 (m, 6H), 1.30-1.05 (m, 3H). Aliphatic region complicated significantly by amide rotamers. |
| 449 | 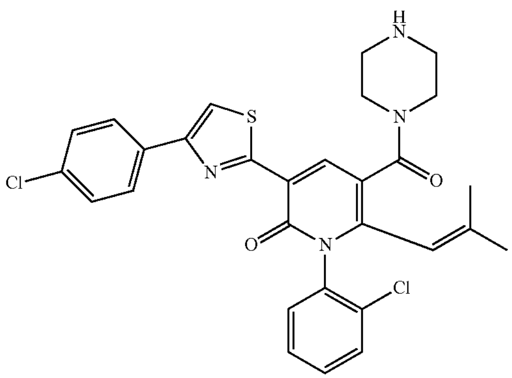 [SMILES: CC(C)=Cc1c(C(=O)N2CCNCC2)cc(-c2nc(-c3ccc(Cl)cc3)cs2)c(=O)n1-c1ccccc1Cl] | A | A | 565.1235 | 2.636 | Starting material: 6,6-dimethyldihydro-2H-pyran-2,4(3H)-dione (step1 method V); nitrile 1 (step2 method V); 2-chloroaniline (step 3 method V), Methods: V | TFA salt: 1H NMR (400 MHz, CD3OD) δ 8.86 (s, 1H), 8.07-8.02 (m, 2H), 7.95 (s, 1H), 7.68 (d, J = 8.7 Hz, 2H), 7.56 (t, J = 6.3 Hz, 2H), 7.48-7.43 (m, 2H), 5.58 (s, 1H), 4.28 (s, 2H), 3.83 (s, 2H), 3.63 (d, J = 25.9 Hz, 2H), 1.68 (d, J = 13.7 Hz, 6H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 450 | 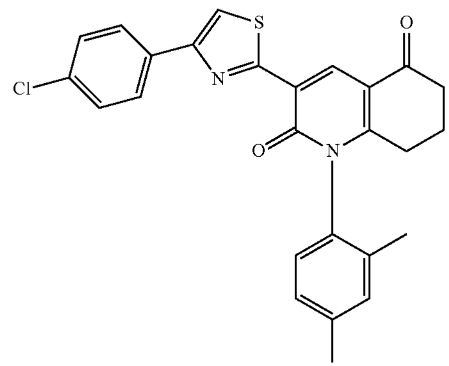 [SMILES: Cc1ccc(-n2c3c(cc(-c4nc(-c5ccc(Cl)cc5)cs4)c2=O)C(=O)CCC3)c(C)c1] | E | E | 461.1083 | 3.931 | Starting material: cyclohexane-1,3-dione (step1 method M); nitrile 1 (step2 method M); 2,4-dimethylaniline (step 3 method M), Methods: M | 1H NMR (400 MHz, CD3OD) δ 9.34 (s, 1H), 7.98 (d, J = 8.4 Hz, 2H), 7.55 (s, 1H), 7.40 (d, J = 8.4 Hz, 2H), 7.24-7.19 (m, 2H), 7.03 (d, J = 8.4 Hz, 1H), 2.62-2.57 (m, 3H), 2.40-2.35 (m, 4H), 2.11-2.07 (m, 2H), 2.04 (s, 3H). Aliphatic region complicated significantly by amide rotamers. |
| 451 | 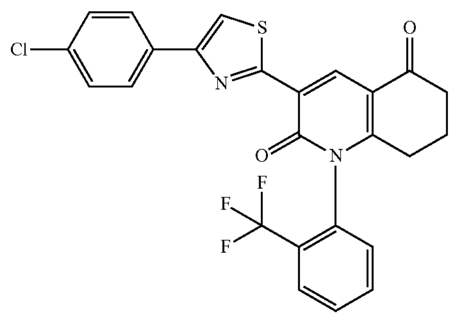 [SMILES: O=C1CCCc2c1cc(-c1nc(-c3ccc(Cl)cc3)cs1)c(=O)n2-c1ccccc1C(F)(F)F] | B | C | 501.0633 | 3.827 | Starting material: cyclohexane-1,3-dione (step1 method M); nitrile 1 (step2 method M); 2,6-diethyl-4-methylaniline (step 3 method M), Methods: M | 1H NMR (400 MHz, CD3OD) δ 9.36 (s, 1H), 7.97 (d, J = 8.4 Hz, 2H), 7.93-7.91 (m, 1H), 7.78-7.82 (m, 1H), 7.72-7.69 (m, 1H), 7.56 (s, 1H), 7.42-7.38 (m, 3H), 2.64-2.45 (m, 4H), 2.11-2.03 (m, 2H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 452 | 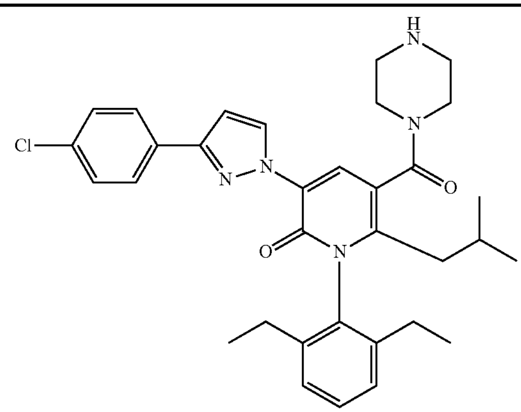 | A | A | 572.2794 | 2.81 | Starting materials: methyl 5-methyl-3-oxohexanoate (step 1), 2-(3-phenyl-1H-pyrazol-1-yl)acetonitrile (step 2), piperazine (used in method U); Methods: S, then ester hydrolyzed with LiOH (xs), THF/MeOH/water, 60° C.; U | 1H NMR (400 MHz, DMSO-d6) δ 8.72 (d, J = 2.6 Hz, 1H), 8.26 (s, 1H), 8.09-7.86 (m, 1H), 7.61-7.38 (m, 3H), 7.32 (d, J = 7.7 Hz, 3H), 7.00 (d, J = 2.6 Hz, 1H), 3.77-3.66 (m, 1H), 3.56-3.46 (m, 3H), 3.07 (m, 3H), 2.75-2.57 (m, 1H), 2.30 (dt, J = 3.7,1.9 Hz, 1H), 2.00-1.82 (m, 1H), 1.31-1.16 (m, 1H), 1.14-1.04 (m, 9H), 1.01 (dd, J = 11.4, 7.0 Hz, 2H), 0.59 (d, J = 6.6 Hz, 6H). |
| 454 | 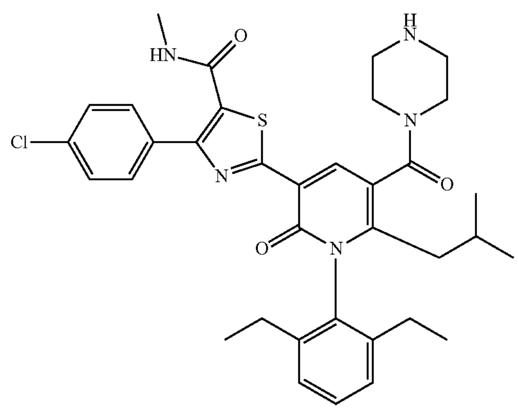 [SMILES: CCc1cccc(CC)c1-n1c(CC(C)C)c(C(=O)N2CCNCC2)cc(-c2nc(-c3ccc(Cl)cc3)c(C(=O)NC)s2)c1=O] | B | C | 668.2458 | 2.599 | Starting material: methyl 5-methyl-3-oxohexanoate (step1 method V); nitrile 1 (step2 method V); 2,6-diethylaniline (step 3 method V), Methods: V(step1-5), treated with CuCN in pyridine at 150° C., followed by methylamine, HATU in DMF, then V (step 6) | TFA salt: 1H NMR(400 MHz, CD3OD) δ 8.74 (s, 1H), 7.80-7.74 (m, 2H), 7.57-7.43 (m, 4H), 7.40 (d, J = 7.7 Hz, 2H), 4.27 (s, 2H), 3.98 (s, 2H), 3.75 (s, 2H), 3.37 (d, J = 18.9 Hz, 3H), 2.83 (d, J = 3.8 Hz, 3H), 2.42 (td, J = 15.1, 7.6 Hz, 2H), 2.28 (s, 2H), 1.66 (d, J = 7.0 Hz, 1H), 1.55-1.43 (m, 2H), 1.20 (d, J = 6.8 Hz, 6H), 0.71 (d, J = 6.5 Hz, 6H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 455 | 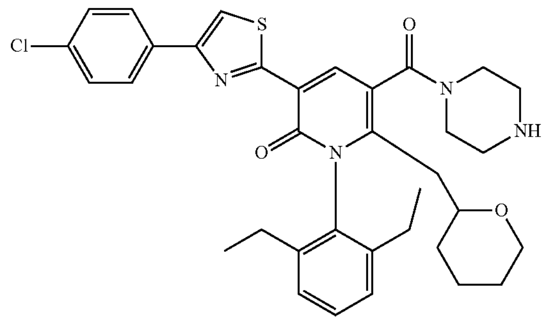 [SMILES: CCc1cccc(CC)c1-n1c(CC2CCCCO2)c(C(=O)N2CCNCC2)cc(-c2nc(-c3ccc(Cl)cc3)cs2)c1=O] | C | B | 631.2525 | 2.81 | Starting materials: ethyl 3-oxo-4-(tetrahydro-2H-pyran-2-yl)butanoate (step 1), piperazine (used in method U); Methods: S, then ester hydrolyzed with LiOH (xs), THF/MeOH/water, 60° C.; U | |
| 456 | 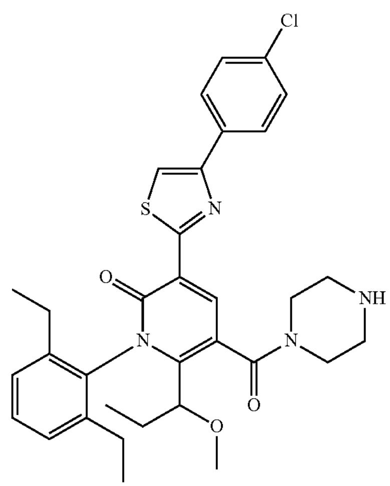 [SMILES: CCc1cccc(CC)c1-n1c(C(CC)OC)c(C(=O)N2CCNCC2)cc(-c2nc(-c3ccc(Cl)cc3)cs2)c1=O] | B | B | 605.2326 | 2.769 | Starting materials: ethyl 4-methoxy-3-oxohexanoate (step 1), Nitrile 1 (step 2), piperazine (used in method U); Methods: S, ester hydrolyzed with LiOH (xs), THF/MeOH/water, 60° C.; U | 1H NMR (400 MHz, DMSO-d6) δ 8.69 (s, 1H), 8.23 (s, 1H), 8.16-8.11 (m, 2H), 7.53-7.47 (m, 3H), 7.37 (dd, J = 7.4, 5.6 Hz, 2H), 3.61-3.50 (m, 1H), 3.42-3.32 (m, 1H), 3.19 (s, 3H), 3.11-3.03 (m, 4H), 2.35-2.21 (m, 4H), 2.06-1.86 (m, 2H), 1.14-1.01 (m, 11H), 0.50 (t, J = 7.3 Hz, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 457 | 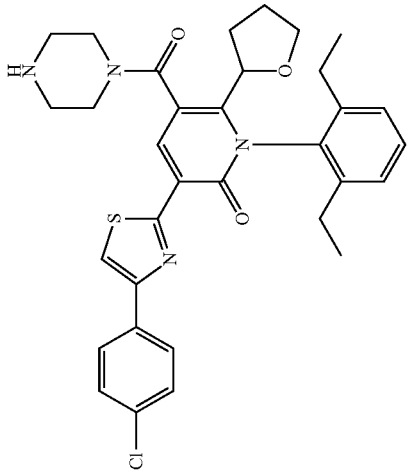 | A | A | 625.1991 | 2.747 | Starting materials: ethyl 3-oxo-3-(tetrahydrofuran-2-yl)propanoate (step 1), piperazine (used in method U); Methods: S, then ester hydrolyzed with LiOH (xs), THF/MeOH/water, 60° C.; U | TFA salt: 1H NMR(400 MHz, DMSO-d6) δ 8.82 (br s, 1H), 8.65 (br s, 1H), 8.57 (s, 1H), 8.23 (s, 1H), 8.14-8.07 (m, 2H), 7.55-7.44 (m, 3H), 7.39-7.30 (m, 2H), 4.06 (dd, J = 8.9, 6.5 Hz, 1H), 3.88-3.79 (m, 1H), 3.77-3.56 (m, 2H), 3.48-3.36 (m, 1H), 3.01 (m, 4H), 2.47-2.23 (m, 3H), 2.18-1.82 (m, 3H), 1.71-1.51 (m, 2H), 1.07 (td, J = 7.5, 2.3 Hz, 6H). |
| 458 | 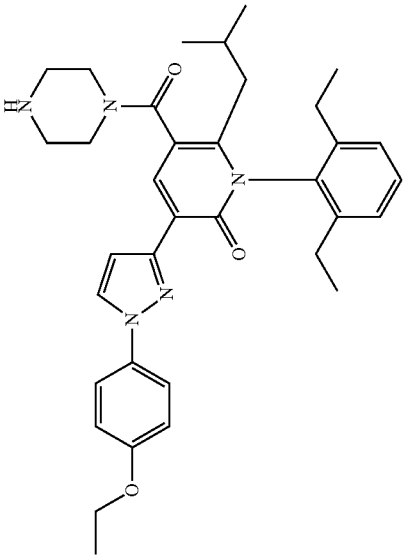 | A | A | 604.3267 | 2.693 | Starting materials: methyl 5-methyl-3-oxohexanoate (step 1), pyrazole 3 (step 2), piperazinee (used in method U), Methods: S, then ester hydrolyzed with LiOH (4 eq), THF/MeOH, 50 C., U | 1H NMR (400 MHz, DMSO-d6) δ 8.78 (s, 1H), 8.37 (d, J = 2.4 Hz, 1H), 8.24 (s, 1H), 7.84-7.75 (m, 2H), 7.43 (t, J = 7.6 Hz, 1H), 7.31 (s, 1H), 7.29 (s, 1H), 7.12 (d, J = 2.4 Hz, 1H), 7.07-6.97 (m, 2H), 4.05 (q, J = 7.0 Hz, 2H), 3.79-3.67 (m, 1H), 3.67-3.45 (m, 3H), 3.24-3.12 (m, 2H), 3.12-3.00 (m, 2H), 2.38-2.24 (m, 3H), 2.22-2.13 (m, 2H), 1.97-1.85 (m, 1H), 1.33 (t, J = 6.9 Hz, 3H), 1.30-1.22 (m, 6H), 1.08 (s, 6H), 0.58 (d, J = 6.6 Hz, 6H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 459 | 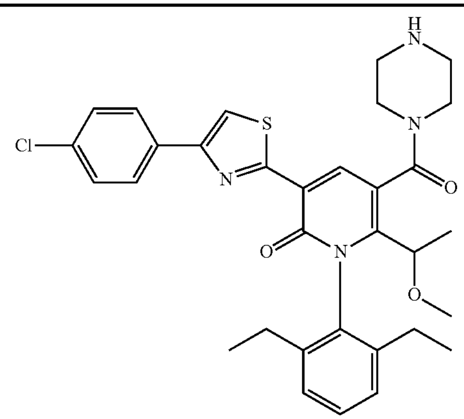 | A | A | 591.2217 | 2.732 | Starting materials: ethyl 4-methoxy-3-oxopentanoate (step 1), Nitrile 1 (step 2), piperazine (used in method U); Methods: S, ester hydrolyzed with LiOH (xs), THF/MeOH/water, 60° C.; U | 1H NMR (400 MHz, DMSO-d6) δ 8.60 (s, 1H), 8.19 (s, 1H), 8.14-8.06 (m, 2H), 7.54-7.45 (m, 3H), 6.87 (dd, J = 8.6, 5.2 Hz, 2H), 3.78 (s, 3H), 3.67-3.39 (m, 9H), 2.44-2.00 (m, 8H), 0.62 (s, 6H). |
| 460 | 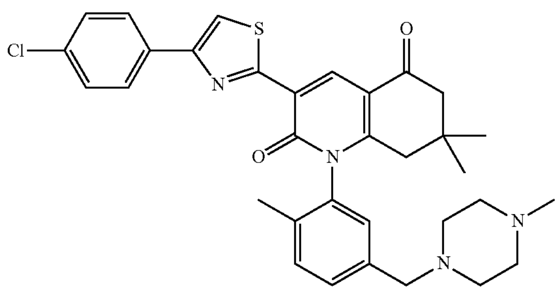 [SMILES: Cc1ccc(CN2CCN(C)CC2)cc1-n1c2c(cc(-c3nc(-c4ccc(Cl)cc4)cs3)c1=O)C(=O)CC(C)(C)C2] | D | D | 587.2235 | 2.83 | Starting material: 5,5-dimethylcyclohexane-1,3-dione (step1 method M); nitrile 1 (step2 method M); 2-methyl-5-((4-methylpiperazin-1-yl)methyl)aniline (step 3 method M), Methods: M | HCl salt: 1H NMR (400 MHz, dmso-d6) δ 9.11 (s, 1H), 8.27 (s, 1H), 8.15-8.08 (m, 2H), 7.60-7.54 (m, 2H), 7.51 (d, J = 3.9 Hz, 3H), 3.25 (s, 4H), 2.67 (s, 3H), 2.57 (d, J = 16.2 Hz, 2H), 2.39 (t, J = 20.5 Hz, 5H), 2.26 (d, J = 17.5 Hz, 2H), 2.04 (s, 3H), 1.93 (d, J = 19.3 Hz, 1H), 1.00 (d, J = 13.6 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 461 | 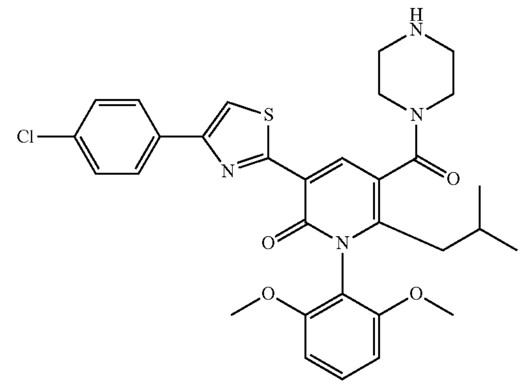 [SMILES: COc1cccc(OC)c1-n1c(CC(C)C)c(C(=O)N2CCNCC2)cc(-c2nc(-c3ccc(Cl)cc3)cs2)c1=O] | A | B | 593.1968 | 2.609 | Starting materials: methyl 5-methyl-3-oxohexanoate (step 1), Nitrile 1 (step 2), 2,6-dimethoxyaniline (step 3), piperazine (used in method U); Methods: S, ester hydrolyzed with LiOH (xs), THF/MeOH/water, 60° C.; U | 1H NMR (400 MHz, DMSO-d6) δ 8.23 (s, 1H), 8.13-8.08 (m, 2H), 7.63 (d, J = 9.0 Hz, 1H), 7.53-7.48 (m, 3H), 7.18 (dd, J = 9.0, 3.0 Hz, 2H), 3.80 (s, 6H), 3.74-3.42 (m, 4H), 3.23-2.89 (m, 4H), 2.34-1.98 (m, 3H), 0.78-0.57 (m, 6H). |
| 462 | 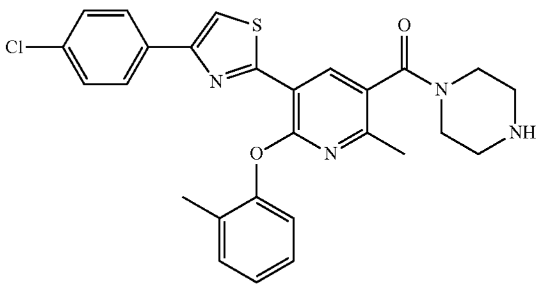 [SMILES: Cc1ccccc1Oc1nc(C)c(C(=O)N2CCNCC2)cc1-c1nc(-c2ccc(Cl)cc2)cs1] | D | D | 505.1459 | 2.763 | Starting material: methyl 3-oxobutanoate (step1 method F); nitrile 1 (step2 method F). Methods: F (step 1-2), V (step 5-6) followed by treatment with tBuOK, dichlorotri-o-tolylbismuth in THF under reflux | TFA salt: 1H NMR (400 MHz, CD3OD) δ 8.77 (s, 1H), 8.04 (d, J = 8.4 Hz, 2H), 7.99 (s, 1H), 7.44 (d, J = 8.4 Hz, 2H), 7.25-7.24 (m, 1H), 7.21-7.19 (m, 2H), 7.09-7.07 (m, 1H), 4.10-3.95 (m, 4H), 3.39-3.30 (m, 4H), 2.32 (s,3H), 2.19 (s, 3H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 463 | 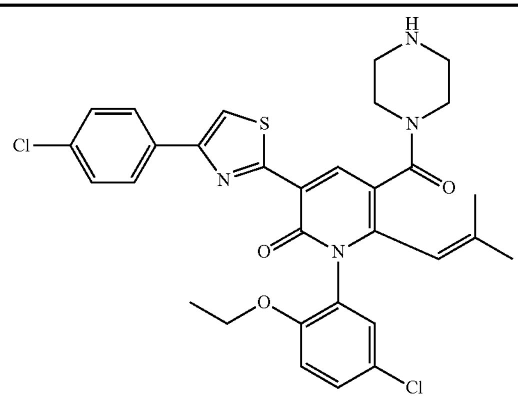 | A | A | 609.15 | 2.709 | Starting material: 6,6-dimethyldihydro-2H-pyran-2,4(3H)-dione (step1 method V); nitrile 1 (step2 method V); 5-chloro-2-methoxyaniline (step 3 method V), Methods: V | TFA salt: 1H NMR(400 MHz, CD3OD) δ 8.82 (s, 1H), 8.03 (d, J = 8.6 Hz, 2H), 7.93 (s, 1H), 7.50-7.43 (m, 4H), 7.30-7.10 (m, 1H), 5.65 (s, 1H), 4.40-3.90 (m, 3H), 3.89-3.75 (m, 1H), 3.70-3.50 (m, 2H), 3.35-3.10 (m, 4H), 1.69-1.63 (m, 6H), 1.30-1.15 (m, 3H). Aliphatic region complicated significantly by amide rotamers. |
| 464 | 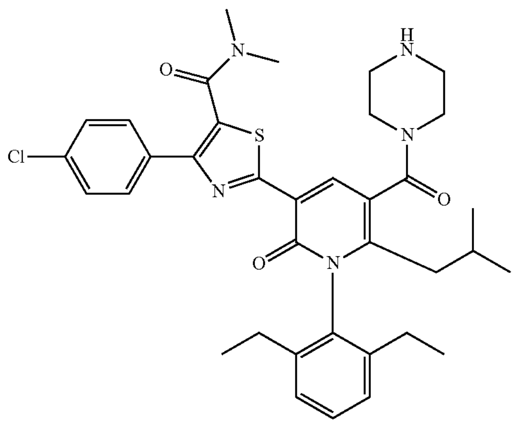 [SMILES: CCc1cccc(CC)c1-n1c(CC(C)C)c(C(=O)N2CCNCC2)cc(-c2nc(-c3ccc(Cl)cc3)c(C(=O)N(C)C)s2)c1=O] | B | C | 660.2776 | 2.681 | Starting material: methyl 5-methyl-3-oxohexanoate (step1 method V); nitrile 1 (step2 method V); 2,6-diethylaniline (step 3 method V), Methods: V(step1-5), treated with CuCN in pyridine at 150° C., followed by dimethylamine, HATU in DMF, then V (step 6) | TFA salt: 1H NMR(400 MHz, CD3OD) δ 8.77 (s, 1H), 7.79-7.74 (m, 2H), 7.56-7.48 (m, 3H), 7.40 (d, J = 7.7 Hz, 2H), 4.29 (s, 2H), 3.98 (s, 2H), 3.77 (s, 2H), 3.41 (s, 2H), 3.07 (s, 3H), 2.74 (s, 3H), 2.42 (dt, J = 22.5, 7.5 Hz, 2H), 2.28 (s, 2H), 1.66 (d, J = 7.0 Hz, 1H), 1.54-1.43 (m, 2H), 1.19 (t, J = 7.0 Hz, 6H), 0.72 (d, J = 6.6 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 465 | 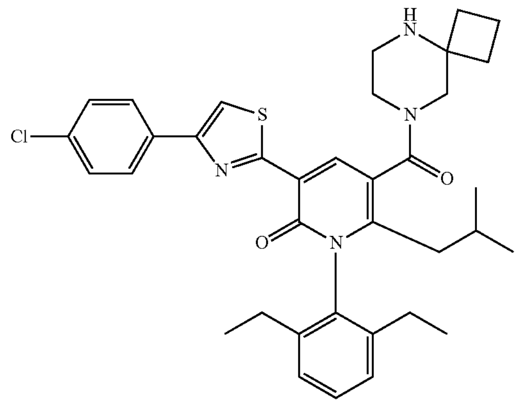 [SMILES: CCc1cccc(CC)c1-n1c(CC(C)C)c(C(=O)N2CCNC3(CCC3)C2)cc(-c2nc(-c3ccc(Cl)cc3)cs2)c1=O] | A | A | 627.2526 | 2.871 | Starting materials: 6,6-dimethyldihydro-2H-pyran-2,4(3H)-dione (step 1), Nitrile 1 (step 2), tert-butyl 5,8-diazaspiro[3.5]nonane-5-carboxylate (used in methods V, step 5); Methods: V | 1H NMR (400 MHz, DMSO-d6) δ 8.70 (s, 1H), 8.25 (s, 1H), 8.10 (d, J = 8.3 Hz, 2H), 7.57-7.50 (m, 2H), 7.43 (t, J = 7.6 Hz, 1H), 7.29 (dd, J = 20.7, 8.0 Hz, 2H), 5.33 (s, 1H), 4.41-4.32 (m, 1H), 4.02-3.92 (m, 1H), 3.68-3.40 (m, 2H), 3.16-2.86 (m, 2H), 2.69-2.51 (m, 1H), 2.45-2.01 (m, 6H), 2.00-1.78 (m, 3H), 1.56 (d, J = 11.1 Hz, 6H), 1.37 (d, J = 1.2 Hz, 1H), 1.11 (tt, J = 7.6, 5.5 Hz, 4H), 1.05-0.94 (m, 3H). |
| 466 | 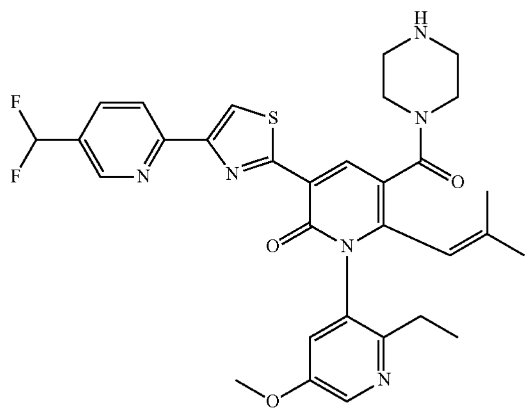 [SMILES: CCc1ncc(OC)cc1-n1c(C=C(C)C)c(C(=O)N2CCNCC2)cc(-c2nc(-c3ccc(C(F)F)cn3)cs2)c1=O] | C | D | 607.2321 | 2.398 | Starting materials: nitrile 29 (step 2 method W); pyridyl amine 10 (step 3 method W); Methods: W, then steps 4-6 in method V | 1H NMR (400 MHz, DMSO-d6) δ 8.84-8.81 (m, 1H), 8.74 (s, 1H), 8.69 (s, 1H), 8.45 (s, 1H), 8.37 (d, J = 7.1 Hz, 2H), 8.13 (d, J = 8.2 Hz, 1H), 7.58 (s, 1H), 7.19 (s, 1H), 5.52 (s, 1H), 4.10-3.89 (m, 1H), 3.86 (s, 3H), 3.81-3.73 (m, 2H), 3.71-3.62 (m, 1H), 3.24-2.81 (m, 4H), 2.26-2.15 (m, 1H), 1.56 (s, 6H), 1.13 (s, 1H), 1.01 (t, J = 7.5 Hz, 3H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 467 | 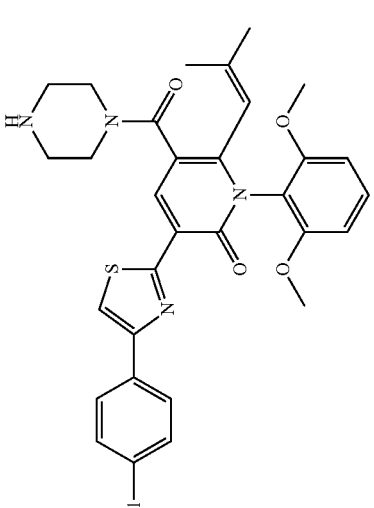 | A | A | 591.1836 | 2.564 | Starting material: 6,6-dimethyldihydro-2H-pyran-2,4(3H)-dione (step1 method V); nitrile 1 (step2 method V); 2,6-dimethoxylaniline (step 3 method V), Methods: V | TFA salt: 1H NMR(400 MHz, CD3OD) δ 8.82 (s, 1H), 8.07-8.01 (m, 2H), 7.92 (d, J = 2.4 Hz, 1H), 7.53-7.40 (m, 3H), 6.84 (d, J = 8.5 Hz, 2H), 5.53 (s, 1H), 4.31 (s, 2H), 3.80 (dd, J = 23.5, 8.0 Hz, 7H), 3.57 (s, 2H), 3.29-3.20 (m, 4H), 1.64 (d, J = 1.2 Hz, 6H). Aliphatic region complicated significantly by amide rotamers. |
| 468 | 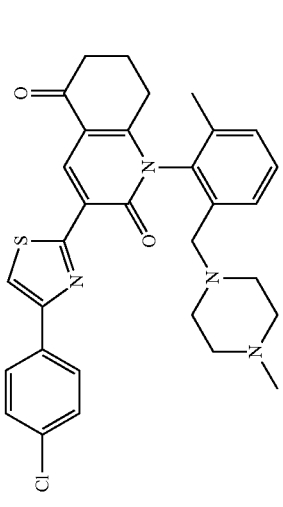 | D | D | 559.1951 | 2.727 | Starting material: cyclohexane-1,3-dione (step1 method M); nitrile 1 (step2 method M); 2-methyl-6-((4-methylpiperazin-1-yl)methyl)aniline (step 3 method M), Methods: M | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 469 | 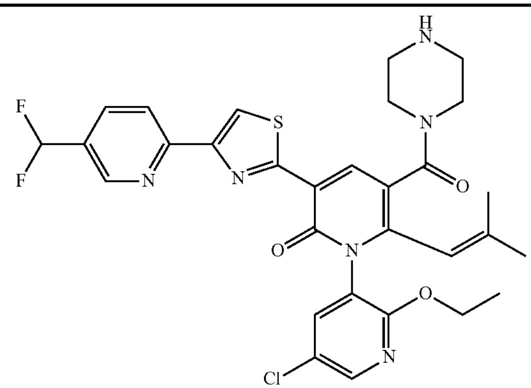 | B | C | 627.1739 | 2.563 | Starting materials: nitrile 29 (step 2 method W); pyridyl amine 4 (step 3 method W), Methods: W, then steps 4-6 in method V | 1H NMR (400 MHz, DMSO-d6) δ 8.82 (t, J = 1.2 Hz, 1H), 8.72 (d, J = 7.8 Hz, 2H), 8.46 (s, 1H), 8.40-8.34 (m, 2H), 8.17-8.09 (m, 2H), 7.19 (t, J = 55.3 Hz, 1H), 5.60 (s, 1H), 4.24 (d, J = 16.9 Hz, 2H), 3.94 (d, J = 25.7 Hz, 1H), 3.40 (s, 2H), 3.24-2.82 (m, 5H), 1.62 (d, J = 1.5 Hz, 3H), 1.53 (s, 3H), 1.25-1.05 (m, 3H). Aliphatic region complicated significantly by amide rotamers. |
| 470 | 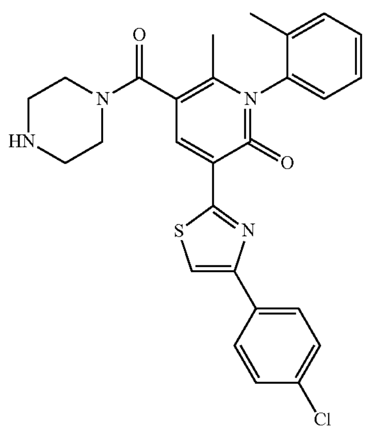 | C | D | 505.1485 | 2.521 | Starting material: methyl 3-oxobutanoate (step1 method F); nitrile 1 (step2 method F), Methods: F (step 1-2), V (step 5-6) followed by treatment with tBuOK, dichlorotri-o-tolylbismuth in THF under reflux | TFA salt: 1H NMR (400 MHz, CD3OD) δ 8.73 (s, 1H), 8.02 (d, J = 8.4 Hz, 2H), 7.90 (s, 1H), 7.49-7.42 (m, 5H), 7.27 (d, J = 8.4 Hz, 1H), 3.95-3.75 (m, 4H), 3.22-3.29 (m, 4H), 2.09 (s, 3H), 2.04 (s, 3H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 472 | 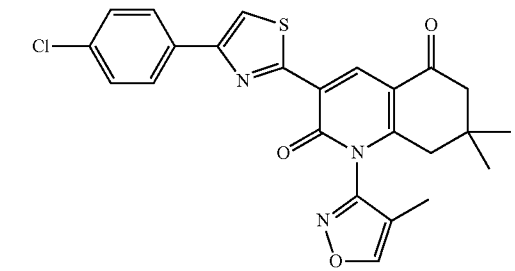 [SMILES: Cc1conc1-n1c2c(cc(-c3nc(-c4ccc(Cl)cc4)cs3)c1=O)C(=O)CC(C)(C)C2] | C | C | 466.0997 | 3.839 | Starting material: 5,5-dimethylcyclohexane-1,3-dione (step1 method M); nitrile 1 (step2 method M); 4-methylisoxazol-3-amine (step 3 method M), Methods: M | |
| 473 | 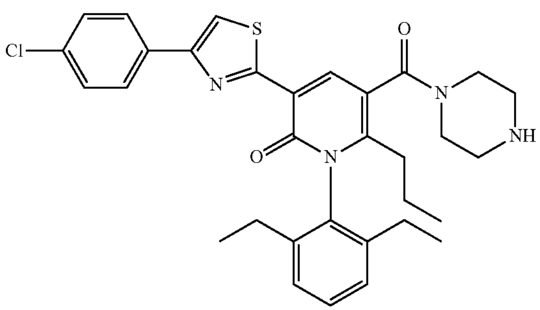 [SMILES: CCCc1c(C(=O)N2CCNCC2)cc(-c2nc(-c3ccc(Cl)cc3)cs2)c(=O)n1-c1c(CC)cccc1CC] | A | A | 575.2223 | 2.804 | Starting materials: ethyl 3-oxohexanoate (step 1), piperazine (used in method U); Methods: S, then ester hydrolyzed with LiOH (xs), THF/MeOH/water, 60° C.; U | 1H NMR (400 MHz, DMSO-d6) δ 8.54 (d, J = 2.1 Hz, 1H), 8.18 (d, J = 2.0 Hz, 1H), 8.09 (d, J = 7.8 Hz, 2H), 7.49 (dd, J = 16.9, 7.7 Hz, 3H), 7.34 (d, J = 7.9 Hz, 2H), 3.79-3.31 (m, 4H), 2.76 (br m, 6H), 2.29 (dt, J = 15.3, 7.3 Hz, 3H), 2.14 (br m, 3H), 1.13-1.07 (m, 2H), 1.07 (t, J = 7.4 Hz, 6H), 0.60 (t, J = 7.1 Hz, 3H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 474 | 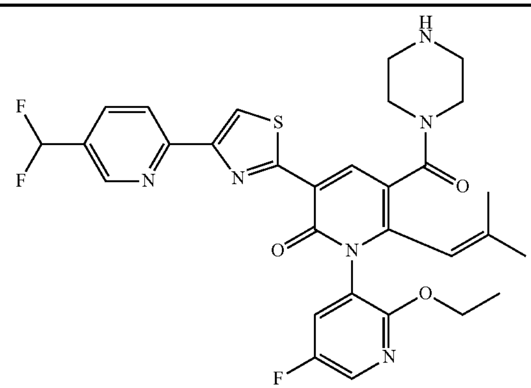 | B | C | 611.2061 | 2.502 | Starting materials: nitrile 29 (step 2 method W); pyridyl amine 2 (step 3 method W), Methods: W, then steps 4-6 in method V | 1H NMR (400 MHz, DMSO-d6) δ 8.82 (d, J = 2.1Hz, 1H), 8.71 (s, 1H), 8.45 (s, 1H), 8.36 (d, J = 8.2 Hz, 1H), 8.34 (d, J = 2.9 Hz, 1H), 8.13 (dd, J = 8.4, 2.1Hz, 1H), 8.04 (dd, J = 8.1, 3.0 Hz, 1H), 7.19 (t, J = 55.4 Hz, 1H), 7.22-6.91 (m, 1H), 5.61 (s, 1H), 4.51-4.09 (m, 2H), 4.09-3.75 (m, 1H), 3.70-3.46 (m, 3H), 3.27-3.06 (m, 2H), 3.09-2.95 (m, 1H), 2.98-2.80 (m, 1H), 1.62 (s, 3H), 1.53 (s, 3H), 1.11 (t, J = 7.2 Hz, 3H). Aliphatic region complicated significantly by amide rotamers. |
| 475 | 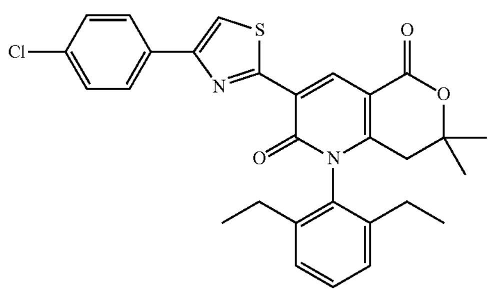 [SMILES: CCc1cccc(CC)c1-n1c2c(cc(-c3nc(-c4ccc(Cl)cc4)cs3)c1=O)C(=O)OC(C)(C)C2] | B | B | 519.1492 | 4.005 | Starting material: 5,5-dimethylcyclohexane-1,3-dione (step1 method M); nitrile 1 (step2 method M); 2,6-diethylaniline (step 3 method M), Methods: M | 1H NMR (400 MHz,CDCl3) δ 9.39 (s, 1H), 8.02-7.96 (m, 2H), 7.62-7.59 (m, 1H), 7.53-7.46 (m, 1H), 7.45-7.40 (m, 2H), 7.35 (t, J = 7.2 Hz, 2H), 2.47 (s, 2H), 2.31 (q,J = 7.9 Hz, 4H), 1.47 (s, 6H), 1.19 (t, J = 7.5 Hz, 6H). MS m/z 519.2 [M + H]+. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 476 | 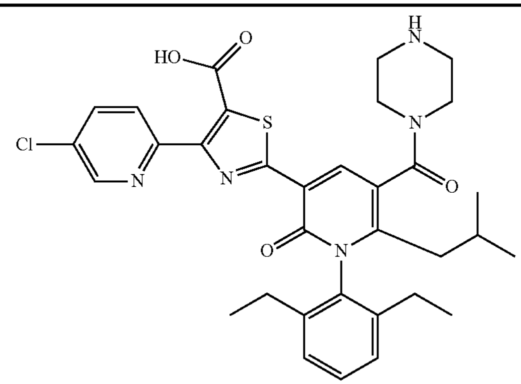 | D | D | 317.1178 | 2.587 | Starting material: methyl 5-methyl-3-oxohexanoate (step1 method V); nitrile 1 (step2 method V); 2,6-diethylaniline (step 3 method V), Methods: V(step1-5), treated with CuCN in pyridine at 150° C., followed by 6M NaOH at 90° C., then V (step 6) | TFA salt: 1H NMR(400 MHz, CD3OD) δ 8.75 (s, 1H), 7.81-7.75 (m, 2H), 7.57-7.50 (m, 1H), 7.49-7.43 (m, 2H), 7.41 (d, J = 7.8 Hz, 2H), 4.27 (s, 2H), 3.98 (s, 2H), 3.74 (s, 2H), 3.38 (s, 2H), 2.72 (s, 2H), 2.43 (dt, J = 22.7, 7.5 Hz, 2H), 2.22 (d, J = 50.9 Hz, 4H), 1.66 (d, J = 7.0 Hz, 1H), 1.55-1.43 (m, 1H), 1.22 (dd, J = 24.6,17.4 Hz, 6H), 0.71 (d, J = 6.4 Hz, 6H). Aliphatic region complicated significantly by amide rotamers. |
| 477 | 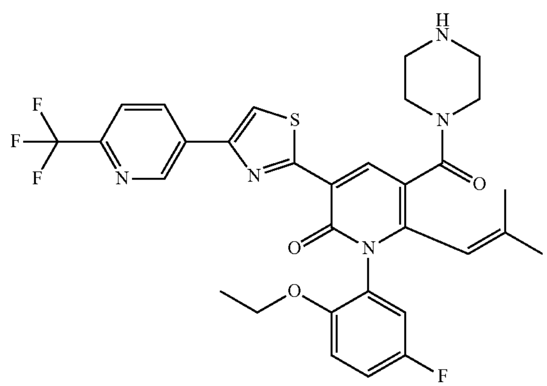 [SMILES: CCOc1ccc(F)cc1-n1c(C=C(C)C)c(C(=O)N2CCNCC2)cc(-c2nc(-c3ccc(C(F)(F)F)nc3)cs2)c1=O] | A | B | 628.2 | 2.571 | Starting materials: nitrile 26 (step 2 method W); 2-ethoxy-5-fluoroaniline (step 3 method W), Methods: W, then steps 4-6 in method V | ¹H NMR (400 MHz, DMSO-d₆) δ 9.47 (s, 1H), 8.90-8.67 (m, 3H), 8.58 (s, 1H), 8.03 (d, J = 8.2 Hz, 1H), 7.43 (d, J = 8.1 Hz, 1H), 7.34 (td, J = 8.6,3.1Hz, 1H), 7.20 (q, J = 7.4, 5.6 Hz, 1H), 5.59 (s, 1H), 4.05-3.96 (m, 2H), 3.91-3.82 (m, 1H), 3.69-3.61 (m, 1H), 3.51-3.44 (m, 2H), 3.25-3.02 (m, 4H), 1.61 (s, 3H), 1.54 (s, 3H), 1.11 (q, J = 10.9, 7.0 Hz, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 478 | 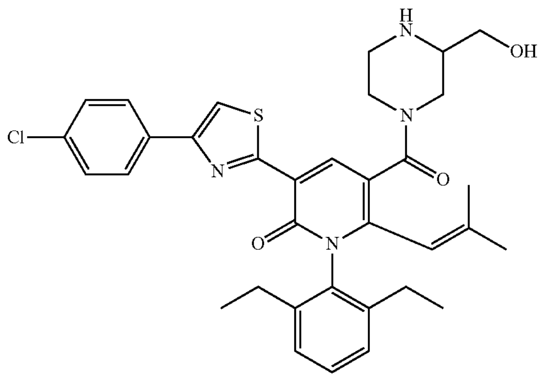 [SMILES: CCc1cccc(CC)c1-n1c(C=C(C)C)c(C(=O)N2CCNC(CO)C2)cc(-c2nc(-c3ccc(Cl)cc3)cs2)c1=O] | A | A | 617.2376 | 2.743 | Starting materials: 6,6-dimethyldihydro-2H-pyran-2,4(3H)-dione (step 1), Nitrile 1 (step 2), tert-butyl 2-(hydroxymethyl)piperazine-1-carboxylate (used in methods V, step 5); Methods: V | 1H NMR (400 MHz, DMSO-d6) δ 8.73 (s, 1H), 8.25 (s, 1H), 8.09 (d, J = 8.5 Hz, 1H), 7.53 (d, J = 8.5 Hz, 2H), 7.43 (t, J = 7.7 Hz, 1H), 7.29 (dd, J = 20.5, 7.7 Hz, 2H), 5.29 (s, 1H), 4.63-4.53 (m, 1H), 3.73-3.39 (m, 3H), 3.21-2.63 (m, 2H), 2.44-2.18 (m, 4H), 2.16-1.99 (m, 2H), 1.63-1.51 (m, 7H), 1.16-1.05 (m, 3H), 0.98 (t, J = 7.5 Hz, 3H). |
| 480 | 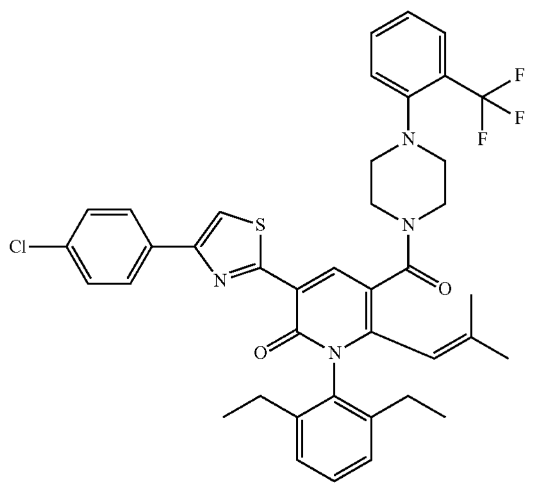 [SMILES: CCc1cccc(CC)c1-n1c(C=C(C)C)c(C(=O)N2CCN(c3ccccc3C(F)(F)F)CC2)cc(-c2nc(-c3ccc(Cl)cc3)cs2)c1=O] | D | D | 731.2432 | 4.294 | Starting materials: 6,6-dimethyldihydro-2H-pyran-2,4(3H)-dione (step 1), Nitrile 1 (step 2), 1(2-(trifluoromethyl)phenyl)piperazine (used in methods V, step 5); Methods: V, no step 6. | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 481 | 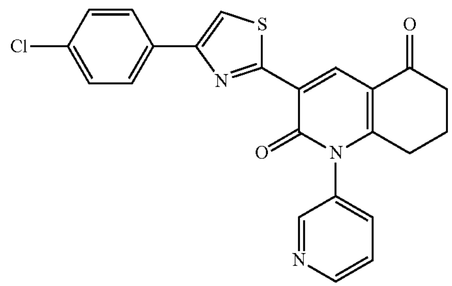 [SMILES: O=C1CCCc2c1cc(-c1nc(-c3ccc(Cl)cc3)cs1)c(=O)n2-c1cccnc1] | E | E | 434.0732 | 3.431 | Starting material: cyclohexane-1,3-dione (step1 method M); nitrile 1 (step2 method M); pyridin-3-amine (step 3 method M). Methods: M | |
| 482 | 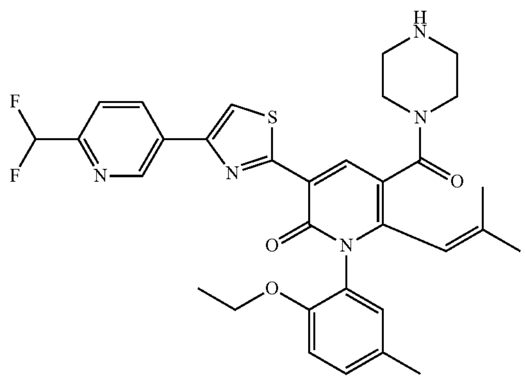 [SMILES: CCOc1ccc(C)cc1-n1c(C=C(C)C)c(C(=O)N2CCNCC2)cc(-c2nc(-c3ccc(C(F)F)nc3)cs2)c1=O] | | | | | | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 483 | 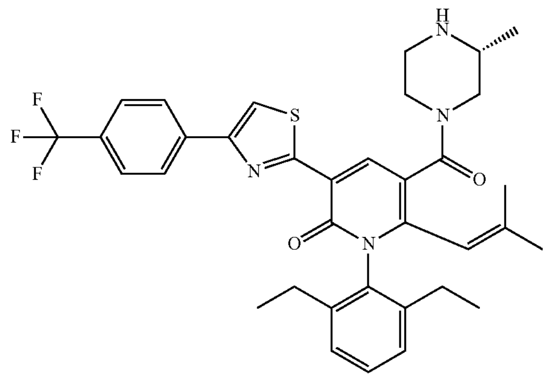 [SMILES: CCc1cccc(CC)c1-n1c(C=C(C)C)c(C(=O)N2CCN[C@H](C)C2)cc(-c2nc(-c3ccc(C(F)(F)F)cc3)cs2)c1=O] | A | A | 635.2686 | 2.852 | Starting materials: 6,6-dimethyldihydro-2H-pyran-2,4(3H)-dione (step 1), Nitrile 7 (step 2), (R)-tert-butyl 2-methylpiperazine-1-carboxylate (used in methods V, step 5); Methods: V. | 1H NMR (400 MHz, DMSO-d6) δ 8.75 (s, 1H), 8.41 (s, 1H), 8.29 (d, J = 8.1 Hz, 2H), 7.83 (d, J = 8.1 Hz, 2H), 7.47-7.22 (m, 3H), 5.30 (s, 1H), 4.64-4.47 (m, 1H), 4.35-4.24 (m, 1H), 3.73-3.46 (m, 1H), 3.23-2.86 (m, 4H), 2.81-2.57 (m, 2H), 2.43-2.22 (m, 2H), 2.09 (s, 3H), 1.66-1.50 (m, 6H), 1.31-0.92 (m, 6H). |
| 485 | 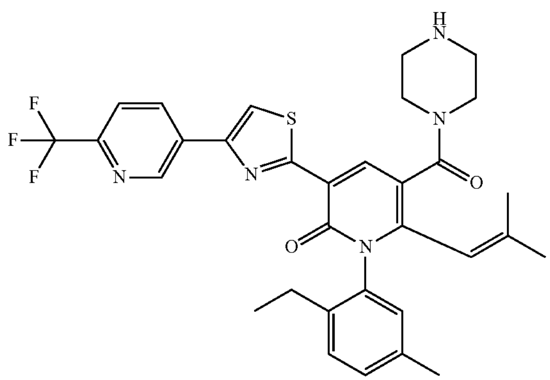 [SMILES: CCc1ccc(C)cc1-n1c(C=C(C)C)c(C(=O)N2CCNCC2)cc(-c2nc(-c3ccc(C(F)(F)F)nc3)cs2)c1=O] | | | | | | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 486 | 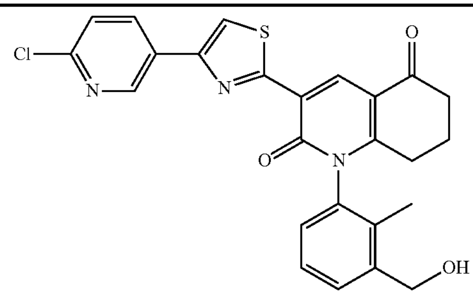 | D | D | 477.1046 | 3.506 | Starting material: cyclohexane-1,3-dione (step1 method M); nitrile 1 (step2 method M); (3-amino-2-methylphenyl)methanol (step 3 method M), Methods: M | 1H NMR (400 MHz, CDCl3) δ 9.39 (s, 1H), 8.03-7.96 (m, 2H), 7.60 (t, J = 6.5 Hz, 1H), 7.58 (s, 1H), 7.48-7.39 (m, 3H), 7.15 (d, J = 7.8 Hz, 1H), 4.87-4.75 (m, 2H), 2.69-2.55 (m, 3H), 2.42-2.31 (m, 1H), 2.19-2.09 (m, 2H), 2.08 (d, J = 5.1 Hz, 3H). Aliphatic region complicated significantly by amide rotamers. |
| 487 | 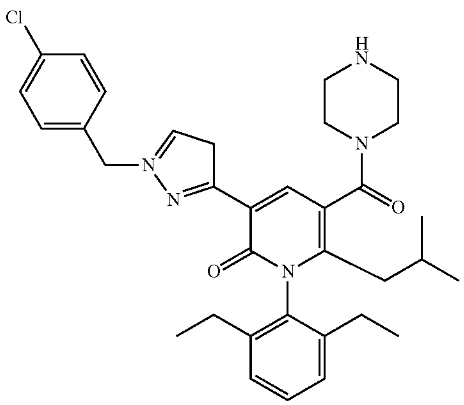 | E | E | 586.2962 | 2.591 | Starting materials: methyl 5-methyl-3-oxohexanoate (step 1 method S), pyrazole 11 (step 2 method S), tert-butyl piperazine-1-carboxylate (used in method U), Methods: S, then ester hydrolyzed with LiOH (4 eq), THF, 50 C., U, then Boc removal with TFA/DCM rt | 1H NMR (400 MHz, DMSO-d6) δ 8.66 (s, 1H), 7.68 (s, 1H), 7.53 (d, J = 1.9 Hz, 1H), 7.42 (t, J = 7.7 Hz, 1H), 7.34-7.25 (m, 4H), 6.99-6.91 (m, 2H), 6.42 (d, J = 1.9 Hz, 1H), 5.27 (d, J = 4.5 Hz, 2H), 3.95-3.85 (m, 1H), 3.60-3.50 (m, 3H), 3.23-3.12 (m, 3H), 3.04-2.97 (m, 1H), 2.26-1.76 (m, 6H), 1.31-1.19 (m, 1H), 1.10-1.01 (m, 6H), 0.56 (d, J = 6.5 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 488 | 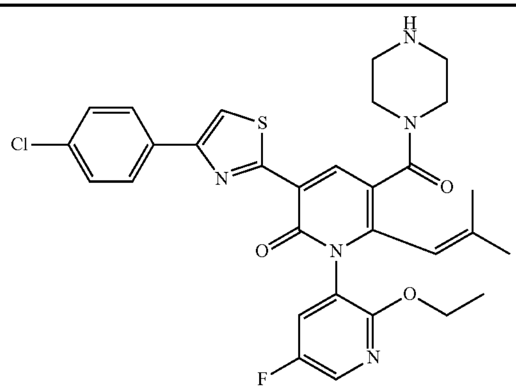 | A | A | 594.1745 | 2.655 | Starting materials: nitrile 1 (step2 method V); pyridyl amine 2 (step 3 method V); piperidine (step 5 method V), Methods: V, no step 7 | |
| 489 | 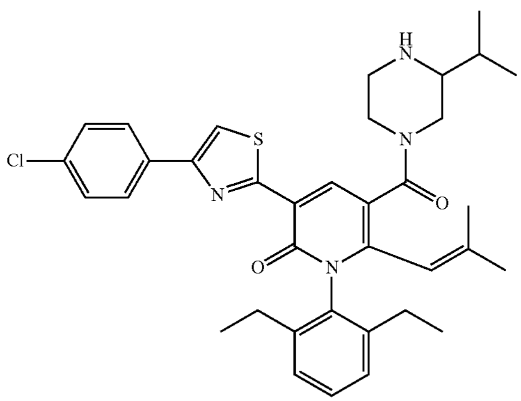 [SMILES: CCc1cccc(CC)c1-n1c(C=C(C)C)c(C(=O)N2CCNC(C(C)C)C2)cc(-c2nc(-c3ccc(Cl)cc3)cs2)c1=O] | A | A | 629.2716 | 2.892 | Starting materials: 6,6-dimethyldihydro-2H-pyran-2,4(3H)-dione (step 1), Nitrile 1 (step 2), tert-butyl 2-isopropylpiperazine-1-carboxylate (used in methods V, step 5); Methods: V | 1H NMR (400 MHz, DMSO-d6) δ 8.75 (s, 1H), 8.25 (s, 1H), 8.10 (dd, J = 9.1, 2.5 Hz, 2H), 7.53 (dd, J = 8.7, 2.4 Hz, 2H), 7.43 (td, J = 7.7, 2.4 Hz, 1H), 7.34-7.23 (m, 2H), 5.28 (s, 1H), 3.72-361 (m, 1H), 3.20-3.01 (m, 2H), 2.81-2.51 (m, 2H), 2.43-2.25 (m, 2H), 2.14-2.08 (m, 2H), 1.92-1.72 (m, 2H), 1.63-1.52 (m, 7H), 1.23-1.06 (m, 4H), 1.06-0.80 (m, 9H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 490 | 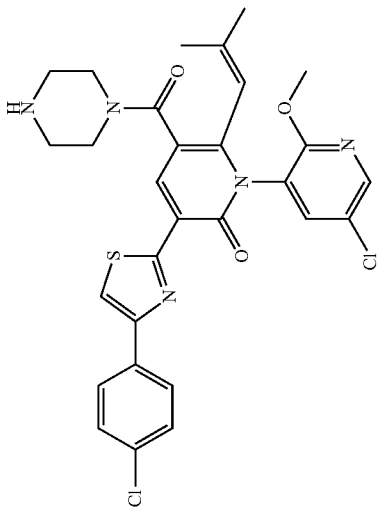 | A | A | 596.1272 | 2.671 | Starting materials: nitrile 1 (step2 method V); 5-chloro-2-methoxypyridin-3-amine (step 3 method V); piperidine (step 5 method V), Methods: V, no step 7 | |
| 491 | 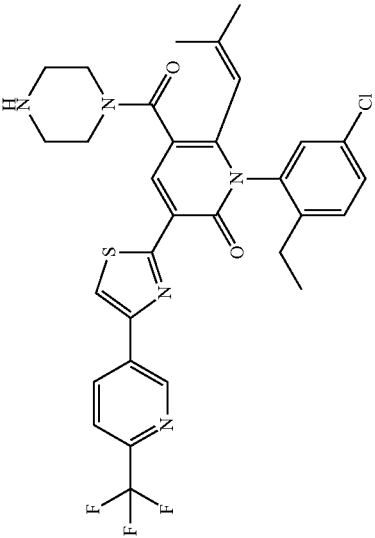 | A | A | 628.17 | 2.673 | Starting materials: nitrile 26 (step 2 method W); Aniline 4 (step 3 method W), Methods: W, then steps 4-6 in method V | 1H NMR (400MHz, DMSO-$d_6$) δ 9.47 (s, 1H), 8.88-8.67 (m, 3H), 8.59 (s, 1H), 8.04 (d, J = 8.2 Hz, 1H), 7.65 (s, 1H), 7.59-7.45 (m, 2H), 5.53 (s, 1H), 4.06-3.97 (m, 1H), 3.75-3.66 (m, 1H), 3.49-3.42 (m, 2H), 3.22-3.05 (m, 4H), 3.02-2.92 (m, 1H), 2.14 (p, J = 7.1 Hz, 1H), 1.61 (d, J = 7.8 Hz, 3H), 1.58 (s, 3H), 1.00 (t, J = 7.5 Hz, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 492 | (structure) | A | A | 587.2255 | 2.803 | Starting materials: ethyl 4-cyclopropyl-3-oxobutanoate (step 1), piperazine (used in method U); Methods: S, then ester hydrolyzed with LiOH (xs), THF/MeOH/water, 60° C.; U | TFA salt: 1H NMR (400 MHz, DMSO-d6) δ 8.79 (br s, 2H), 8.73 (s, 1H), 8.21 (s, 1H), 8.16-8.07 (m, 2H), 7.55-7.44 (m, 3H), 7.34 (d, J = 7.7 Hz, 2H), 4.07 (m, 1H), 3.74 (m, 1H), 3.51 (m, 3H), 3.12 (m, 3H), 2.35 (m, 2H), 2.12 (m, 5H), 1.07 (t, J = 7.5 Hz, 6H), 0.52-0.12 (m, 2H), −0.05 (m, 1H), −0.27 (m, 1H). |
| 493 | (structure) | D | D | 627.1828 | 2.888 | Starting material: 5,5-dimethylcyclohexane-1,3-dione (step1 method M); nitrile 1 (step2 method M); 4-(4-methylpiperazin-1-yl)-2-(trifluoromethyl)aniline (step 3 method M), Methods: M | HCl salt: 1H NMR (400 MHz, dmso-d6) δ 9.06 (s, 1H), 8.24 (s, 1H), 8.09 (m, 2H), 7.54 (m, 5H), 4.14 (d, J = 13.1 Hz, 2H), 3.55 (d, J = 9.8 Hz, 3H), 3.21 (dd, J = 21.4, 11.7 Hz, 4H), 2.87 (t, J = 5.7 Hz, 3H), 2.70 (m, 2H), 2.53 (d, J = 13.2 Hz, 1H), 2.44 (d, J = 16.3 Hz, 1H), 2.20 (d, J = 17.8 Hz, 1H), 1.02 (s, 3H), 0.93 (s, 3H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 494 | 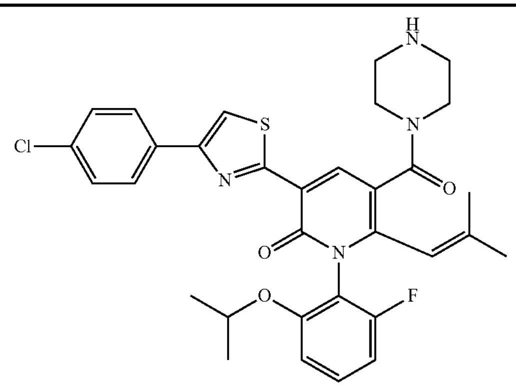 | A | A | 607.1962 | 2.701 | Starting material: 6,6-dimethyldihydro-2H-pyran-2,4(3H)-dione (step1 method V); nitrile 1 (step2 method V); aniline 13 (step 3 method V), Methods: V | TFA salt: 1H NMR (400 MHz, CD3OD) δ 8.85 (s, 1H), 8.04 (d, J = 8.8 Hz, 2H), 7.94 (s, 1H), 7.53-7.43 (m, 3H), 7.10-7.00 (m, 1H), 6.94-6.85 (m, 1H), 5.65 (s, 1H), 4.79-4.55 (m, 1H), 4.37-4.21 (m, 1H), 3.82-3.47 (m, 4H), 3.28-3.18 (m, 3H), 1.72-1.60 (m, 6H), 1.34-1.11 (m, 6H). Aliphatic region complicated significantly by amide rotamers. |
| 496 | 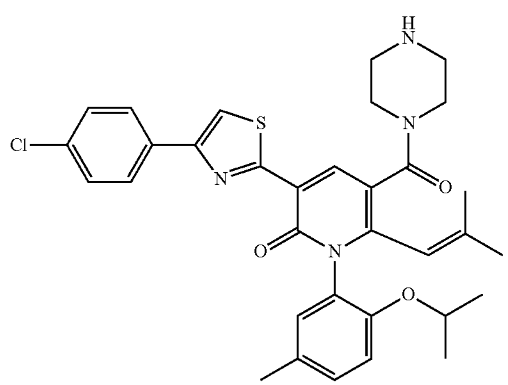 [SMILES: CC(C)=Cc1c(C(=O)N2CCNCC2)cc(-c2nc(-c3ccc(Cl)cc3)cs2)c(=O)n1-c1cc(C)ccc1OC(C)C] | A | A | 603.219 | 2.728 | Starting material: 6,6-dimethyldihydro-2H-pyran-2,4(3H)-dione (step1 method V); nitrile 1 (step2 method V); aniline 15 (step 3 method V), Methods: V | TFA salt: 1H NMR (400 MHz, CD3OD) δ 8.83 (s, 1H), 8.04 (d, J = 8.4 Hz, 2H), 7.92 (s, 1H), 7.45 (d, J = 8.8 Hz, 2H), 7.27 (m, 1H), 7.15-6.98 (m, 2H), 5.64 (s, 1H), 4.69-4.44 (m, 1H), 4.24 (s, 1H), 3.91-3.45 (m, 3H), 3.23-3.11 (m, 4H), 2.35 (s, 3H), 1.65 (s, 6H), 1.34-0.97 (m, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | $^1$H-NMR |
|---|---|---|---|---|---|---|---|
| 497 | 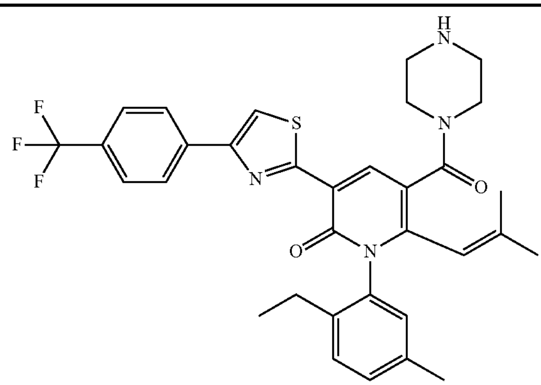 | | | | | | |
| 498 | 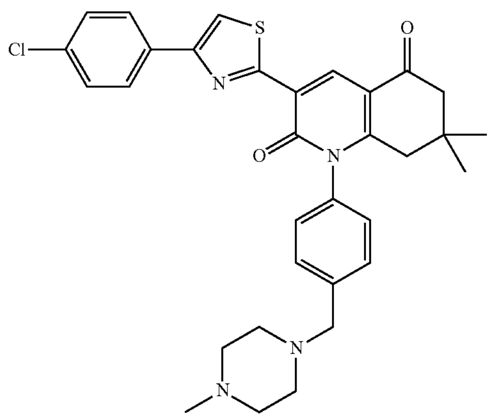 [SMILES: CN1CCN(Cc2ccc(-n3c4c(cc(-c5nc(-c6ccc(Cl)cc6)cs5)c3=O)C(=O)CC(C)(C)C4)cc2)CC1] | C | D | 573.2076 | 2.728 | Starting material: 5,5-dimethylcyclohexane-1,3-dione (step1 method M); nitrile 1 (step2 method M); 4-((4-methylpiperazin-1-yl)methyl)aniline (step 3 method M), Methods: M | HCl salt: 1H NMR (400 MHz, dmso-d6) δ 9.09 (d, J = 5.5 Hz, 1H), 8.24 (s, 1H), 8.14-8.08 (m, 2H), 7.85 (s, 3H), 7.59-7.52 (m, 3H), 4.40 (s, 4H), 3.63 (s, 4H), 2.81 (d, J = 23.0 Hz, 5H), 2.44 (t, J = 18.2 Hz, 4H), 1.07-0.89 (m, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 499 | 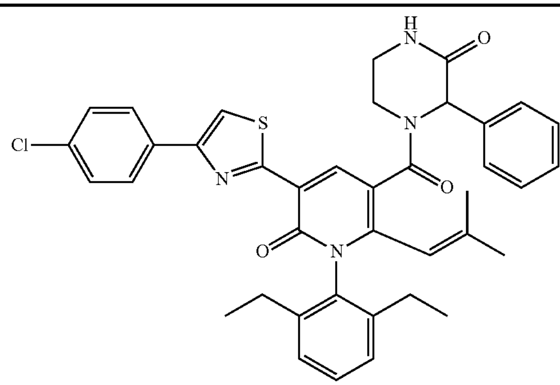 | B | A | 677.2338 | 3.839 | Starting materials: 6,6-dimethyldihydro-2H-pyran-2,4(3H)-dione (step 1), Nitrile 1 (step 2), 3-phenylpiperazin-2-one (used in methods V, step 5); Methods: V, no step 6. | 1H NMR (400 MHz, DMSO-d6) δ 8.79 (s, 1H), 8.39-8.27 (m, 1H), 8.23 (s, 1H), 8.18-8.00 (m, 2H), 7.58-7.48 (m, 2H), 7.46-7.18 (m, 7H), 5.92 (s, 1H), 5.13 (s, 1H), 4.34-4.25 (m, 1H), 3.71-3.43 (m, 2H), 3.23-3.07 (m, 2H), 2.68-2.60 (m, 1H), 2.40-2.18 (m, 2H), 2.18-1.96 (m, 2H), 1.59 (d, J = 40.8 Hz, 2H), 1.36-1.17 (m, 1H), 1.16-1.02 (m, 4H), 0.97 (t, J = 7.6 Hz, 3H). |
| 500 | 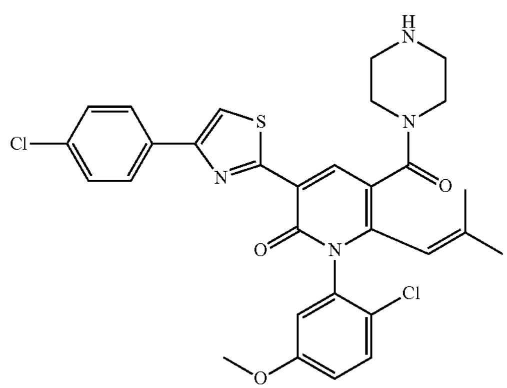 [SMILES: COc1ccc(Cl)c(-n2c(C=C(C)C)c(C(=O)N3CCNCC3)cc(-c3nc(-c4ccc(Cl)cc4)cs3)c2=O)c1] | A | A | 595.1312 | 2.666 | Starting material: 6,6-dimethyldihydro-2H-pyran-2,4(3H)-dione (step1 method V); nitrile 1 (step2 method V); 2-chloro-5-methoxyaniline (step 3 method V), Methods: V | TFA salt: 1H NMR(400 MHz, CD3OD) δ 8.85 (s, 1H), 8.08-8.01 (m, 2H), 7.95 (s, 1H), 7.53 (s, 2H), 7.49-7.43 (m, 2H), 7.12 (dd, J = 9.0, 3.0 Hz, 1H), 5.64 (s, 1H), 4.27 (s, 2H), 3.84 (s,4H), 3.60 (s, 3H), 3.28-3.15 (m, 3H), 1.70 (d, J = 3.8 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | $^1$H-NMR |
|---|---|---|---|---|---|---|---|
| 501 | 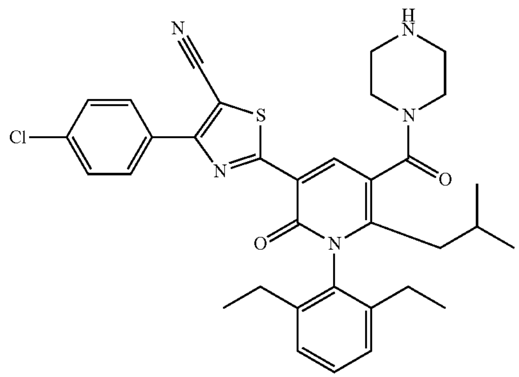 [SMILES: CCc1cccc(CC)c1-n1c(CC(C)C)c(C(=O)N2CCNCC2)cc(-c2nc(-c3ccc(Cl)cc3)c(C#N)s2)c1=O] | B | B | 614.2335 | 2.889 | Starting material: methyl 5-methyl-3-oxohexanoate (step1 method V); nitrile 1 (step2 method V); 2,6-diethylaniline (step 3 method V), Methods: V(step1-5), followed by treatment with CuCN in pyridine at 150° C., then V (step 6) | TFA salt: 1H NMR(400 MHz, CD3OD) δ 8.86 (s, 1H), 8.19 (d, J = 8.5 Hz, 2H), 7.61-7.55 (m, 2H), 7.54 (d, J = 7.7 Hz, 1H), 7.41 (d, J = 7.7 Hz, 2H), 4.28 (s, 2H), 3.98 (s, 2H), 3.78 (s, 2H), 3.49-3.35 (m, 2H), 2.71 (s, 2H), 2.49-2.35 (m, 2H), 2.27 (s, 2H), 1.66 (d, J = 7.0 Hz, 1H), 1.57-1.45 (m, 1H), 1.19 (d, J = 3.3 Hz, 6H), 0.72 (d, J = 6.6 Hz, 6H). Aliphatic region complicated significantly by amide rotamers. |
| 502 | 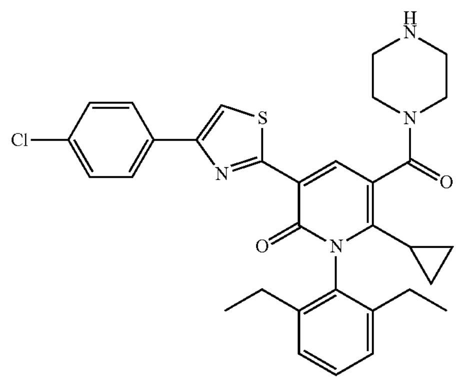 [SMILES: CCc1cccc(CC)c1-n1c(C2CC2)c(C(=O)N2CCNCC2)cc(-c2nc(-c3ccc(Cl)cc3)cs2)c1=O] | A | A | 287.1067 | 2.726 | Starting materials: methyl 3-cyclopropyl-3-oxopropanoate (step 1), piperazine (used in method U); Methods: S, then ester hydrolyzed with LiOH in THF/MeOH/water, 60° C.; U | TFA salt: 1H NMR (400 MHz, DMSO-d6) δ 8.80 (br s, 2H), 8.58 (s, 1H), 8.21 (s, 1H), 8.12-8.05 (m, 2H), 7.55-7.40 (m, 3H), 7.36-7.28 (m, 2H), 4.09 (m, 1H), 3.72 (m, 1H), 3.63-3.46 (m, 1H), 3.25-3.05 (m, 2H), 2.45-2.17 (m, 2H), 2.09 (m, 1H), 1.31 (ddd, J = 14.6, 8.4, 6.0 Hz, 1H), 1.09 (dt, J = 12.2, 7.5 Hz, 6H), 0.71-0.61 (m, 2H), 0.47-0.26 (m, 2H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 503 | 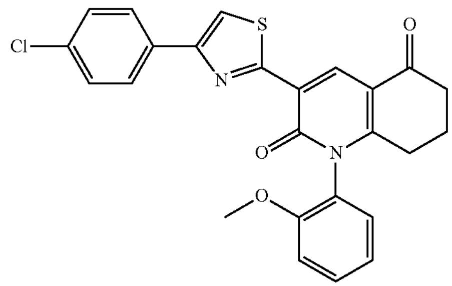 [SMILES: COc1ccccc1-n1c2c(cc(-c3nc(-c4ccc(Cl)cc4)cs3)c1=O)C(=O)CCC2] | C | C | 463.0886 | 3.746 | Starting material: cyclohexane-1,3-dione (step1 method M); nitrile 1 (step2 method M); 2-methoxyaniline (step 3 method M), Methods: M | 1H NMR (400 MHz, CD3OD) δ 9.33 (s, 1H), 7.97 (d, J = 8.4 Hz, 2H), 7.54-7.50 (m, 2H), 7.40 (d, J = 8.4 Hz, 2H), 7.21-7.20 (m, 1H), 7.09-7.16 (m, 2H), 3.80 (s, 3H), 2.61-2.46 (m, 4H), 2.11-2.07 (m, 2H). Aliphatic region complicated significantly by amide rotamers. |
| 505 | 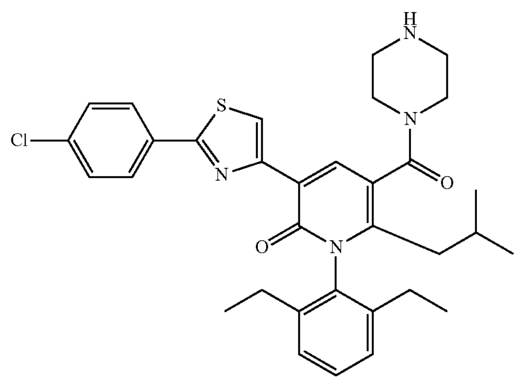 [SMILES: CCc1cccc(CC)c1-n1c(CC(C)C)c(C(=O)N2CCNCC2)cc(-c2csc(-c3ccc(Cl)cc3)n2)c1=O] | A | A | 589.2404 | 2.875 | Starting materials: methyl 5-methyl-3-oxohexanoate (step 1), nitrile 36 (step 2), piperazine (used in method U); Methods: S, then ester hydrolyzed with LiOH THF/MeOH/water, 60° C.; U | TFA salt: 1H NMR(400 MHz, DMSO-d6) δ 8.78 (br s, 2H), 8.54 (s, 1H), 8.50 (s, 1H), 8.12-8.04 (m, 2H), 7.62-7.54 (m, 2H), 7.49-7.40 (m, 1H), 7.32 (d, J = 7.7 Hz, 2H), 4.02 (br m, 1H), 3.90-3.42 (m, 3H), 3.20 (br m, 2H), 2.39-2.24 (br m, 2H), 2.24-2.06 (m, 1H), 1.91 (br m, 1H), 1.43-1.19 (m, 1H), 1.08 (t, J = 7.2 Hz, 7H), 0.60 (d, J = 6.7 Hz, 6H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 506 | 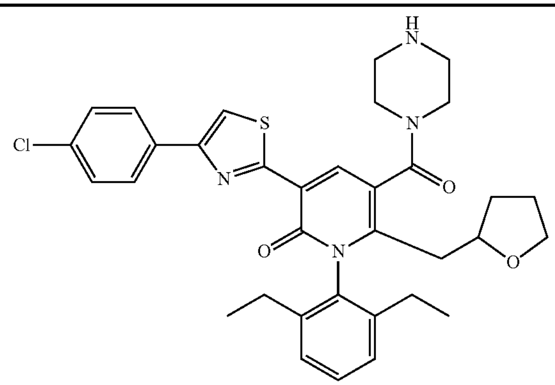 | A | A | 617.2377 | 2.759 | Starting materials: ethyl 3-oxo-4-(tetrahydrofuran-2-yl)butanoate (step 1), piperazine (used in method U); Methods: S, then ester hydrolyzed with LiOH (xs), THF/MeOH/water, 60° C.; U | |
| 507 | 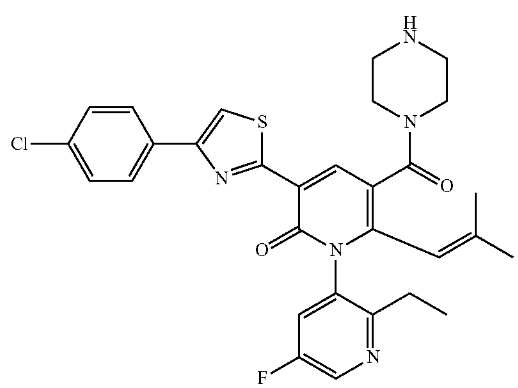 [SMILES: CCc1ncc(F)cc1-n1c(C=C(C)C)c(C(=O)N2CCNCC2)cc(-c2nc(-c3ccc(Cl)cc3)cs2)c1=O] | A | A | 600.1601 | 2.603 | Starting materials: 6,6-dimethyldihydro-2H-pyran-2,4(3H)-dione (step 1), Nitrile 1 (step 2), pyridyl amine 9 (step 3 of methods V); Methods: V, no step 6. | 1H NMR (400 MHz, DMSO-d6) δ 8.71 (d, J = 4.3 Hz, 2H), 8.26 (s, 1H), 8.10 (d, J = 8.3 Hz, 3H), 8.06-7.96 (m, 1H), 7.57-7.45 (m, 2H), 5.56 (s, 1H), 4.02-3.95 (m, 1H), 3.72-3.36 (m, 4H), 3.23-2.86 (m, 1H), 2.40-2.20 (m, 2H), 1.66-1.53 (m, 7H), 1.20-1.00 (m, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | $^1$H-NMR |
|---|---|---|---|---|---|---|---|
| 508 | (structure) | A | A | 309.1225 | 2.777 | Starting material: 6,6-dimethyldihydro-2H-pyran-2,4(3H)-dione (step1 method V); nitrile 1 (step2 method V); aniline 8 (step 3 method V), Methods: V | TFA salt: 1H NMR(400 MHz, CD3OD) δ 8.85 (s, 1H), 8.03 (d, J = 8.7 Hz, 2H), 7.91 (s, 1H), 7.46-7.38 (m, 3H), 7.10-6.93 (m, 2H), 5.51 (s, 1H), 4.75-4.65 (m, 1H), 4.40-4.20 (m, 1H), 3.85-3.65 (m, 1H), 3.60-3.45 (m, 2H), 3.35-3.10 (m, 4H), 2.50-2.20 (m, 2H), 1.68-1.61 (m, 6H), 1.30-1.10 (m, 9H). Aliphatic region complicated significantly by amide rotamers. |
| 509 | (structure) | C | C | 516.1154 | 3.773 | Starting material: 5,5-dimethylcyclohexane-1,3-dione (step1 method M); nitrile 1 (step2 method M); 3-amino-4-methoxybenzonitrile (step 3 method M), Methods: M | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 511 | 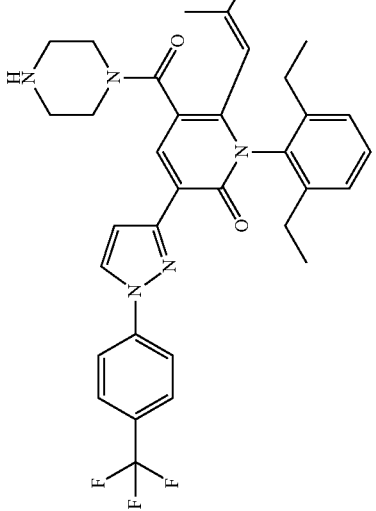 | A | A | 604.2874 | 2.694 | Starting materials: pyrazole 4 (step 2), piperazine (step 5); Methods: V, step 4 with NaOH (xs), no step 6. | TFA salt: 1H NMR (400 MHz, DMSO-d6) δ 8.79 (br s, 1H), 8.67 (m, 2H), 8.37 (s, 1H), 8.21-8.07(m, 2H), 7.96-7.79 (m, 2H), 7.38 (t, J = 7.6 Hz, 1H), 7.32-7.11 (m, 2H), 5.26-5.12 (m, 1H), 3.99 (m, 1H), 3.54 (m, 1H), 3.02 (m, J = 42.9 Hz, 1H), 2.45-2.18 (m, 0H), 2.18-1.96 (m, 2H), 1.54 (t, J = 1.2 Hz, 6H), 1.16-0.87 (m, 6H). |
| 512 | 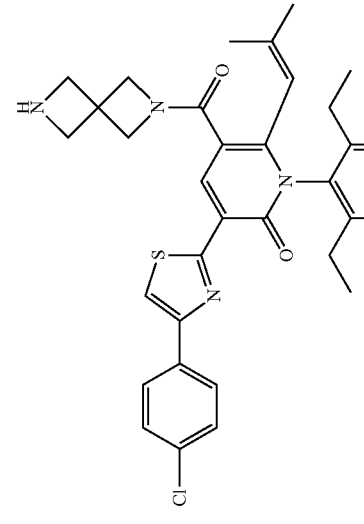 | A | A | 599.225 | 2.749 | Starting materials: 6,6-dimethyldihydro-2H-pyran-2,4(3H)-dione (step 1), Nitrile 1 (step 2), tert-butyl 2,6-diazaspiro[3.3]heptane-2-carboxylate (used in methods V, step 5); Methods: V | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 513 | 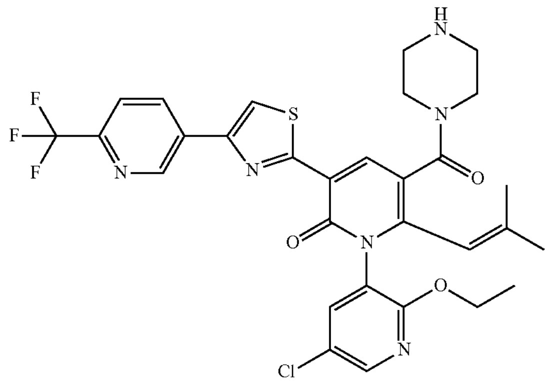 [SMILES: CCOc1ncc(Cl)cc1-n1c(C=C(C)C)c(C(=O)N2CCNCC2)cc(-c2nc(-c3ccc(C(F)(F)F)nc3)cs2)c1=O] | A | B | 645.1662 | 2.635 | Starting materials: pyridyl amine 4 (step 3 of method W); Methods: W, X | TFA salt: 1H NMR (400 MHz, DMSO-d6) δ 9.45 (s, 1H), 8.87-8.62 (m, 2H), 8.58 (s, 1H), 8.38 (d, J = 2.5 Hz, 1H), 8.15 (d, J = 2.5 Hz, 1H), 8.01 (d, J = 8.2 Hz, 1H), 5.60 (s, 1H), 4.30-3.80 (br m, 1H), 3.70-3.35 (br m, 3H), 3.23-2.82 (m, 4H), 1.63 (s, 3H), 1.54 (s, 3H), 1.30-1.00 (br m, 3H). |
| 514 | 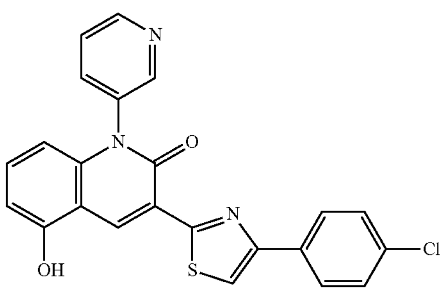 [SMILES: O=c1c(-c2nc(-c3ccc(Cl)cc3)cs2)cc2c(O)cccc2n1-c1cccnc1] | E | C | 432.0585 | 3.036 | Starting material: cyclohexane-1,3-dione (step1 method F); nitrile 1 (step2 method F), Methods: F using microwave irradiation to heat in step 3, then coupling with 3-iodopyridine with Pd2dba3, Xantphos, and Cs2CO3 in DMF at 150° C. followed by HPLC purification | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 515 | 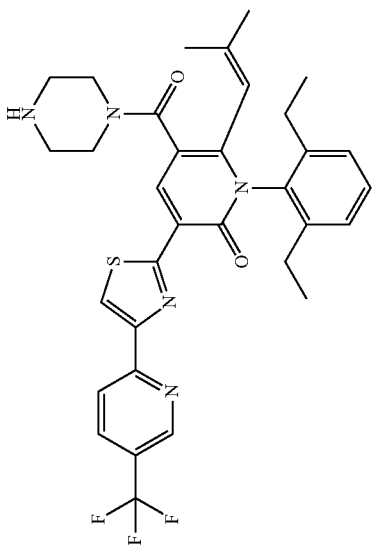 | A | A | 644.2272 | 2.743 | Starting materials: 6,6-dimethyldihydro-2H-pyran-2,4(3H)-dione (step 1), 2-(4-(5-(trifluoromethyl)pyridin-2-yl)thiazol-2-yl)acetonitrile hydrobromide (step 2); Methods: V | TFA salt: 1H NMR(400 MHz, DMSO-d6) δ 9.04 (d, J = 2.3 Hz, 1H), 8.84 (bs, 1H), 8.80 (s, 1H), 8.73 (bs, 1H), 8.54 (s, 1H), 8.44 (d, J = 8.3 Hz, 1H), 8.35 (dd, J = 8.4, 2.4 Hz, 1H), 7.45 (dd, J = 7.7, 7.7 Hz, 1H), 7.34 (d, J = 7.7 Hz, 1H), 7.29 (d, J = 7.7 Hz, 1H), 5.31 (s, 1H), 4.06 (d, J = 14.0 Hz, 1H), 3.61 (d, J = 14.0 Hz, 1H), 3.48-3.28 (m, 5H), 3.24-3.10 (m, 2H), 3.05-2.92 (m, 1H), 2.45-2.24 (m, 1H), 2.19-2.03 (m, 1H), 1.60 (s, 6H), 1.14 (t, J = 7.5 Hz, 3H), 1.01 (t, J = 7.5 Hz, 3H). |
| 517 | 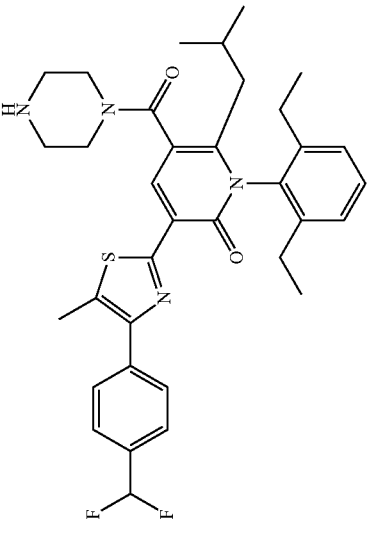 | A | A | 619.2917 | 2.857 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-(difluoromethyl)phenyl) boronic acid (method xix); Methods: S, then ester hydrolyzed with LiOH (4 eq), THF/MeOH/water, 50 C., U, xix, then Boc removal with TFA/DCM rt | 1H NMR (400 MHz, DMSO-d6) δ 8.80 (d, J = 47.8 Hz, 1H), 8.56 (s, 1H), 7.91 (d, J = 8.0 Hz, 2H), 7.66 (d, J = 8.3 Hz, 2H), 7.47 (t, J = 7.7 Hz, 1H), 7.35 (s, 1H), 7.33 (s, 1H), 7.09 (t, J = 56.0 Hz, 1H), 4.02 (s, 1H), 3.75 (s, 1H), 3.55 (s, 2H), 3.17 (dd, J = 14.5, 7.0 Hz, 3H), 3.10-3.03 (m, 1H), 2.58 (s, 3H), 2.29 (s, 3H), 2.12 (dd, J = 14.9, 7.6 Hz, 2H), 2.01-1.94 (m, 1H), 1.30 (dq, J = 13.6, 6.8 Hz, 1H), 1.12-1.02 (m, 6H), 0.60 (d, J = 6.6 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 518 | 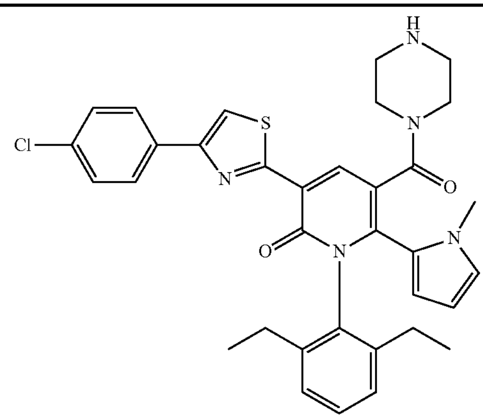 | A | A | 612.2212 | 2.781 | Starting materials: ethyl 3-(1-methyl-1H-pyrrol-2-yl)-3-oxopropanoate (step 1), Nitrile 1 (step 2), piperazine (used in method U); Methods: S, ester hydrolyzed with LiOH, THF/MeOH/water, 60° C.; U | 1H NMR (400 MHz, DMSO-d6) δ 8.79 (s, 1H), 8.26 (s, 1H), 8.18-8.01 (m, 2H), 7.61-7.46 (m, 2H), 7.26 (q, J = 7.9 Hz, 2H), 7.05 (d, J = 7.2 Hz, 1H), 6.79 (s, 1H), 5.85 (dd, J = 3.9, 2.6 Hz, 1H), 5.63 (s, 1H), 3.79-370 (m, 1H), 3.39 (s,3H), 3.16-3.04 (m, 1H), 2.97-2.91 (m, 2H), 2.76-2.67 (m, 1H), 2.63-2.53 (m, 1H), 2.43-2.23 (m, 2H), 2.10-2.00 (m, 2H), 1.24-1.10 (m, 2H), 0.88 (t, J = 7.4 Hz, 6H). |
| 519 | 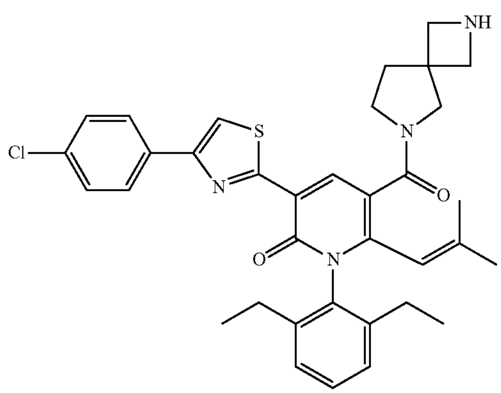 [SMILES: CCc1cccc(CC)c1-n1c(C=C(C)C)c(C(=O)N2CCC3(CNC3)C2)cc(-c2nc(-c3ccc(Cl)cc3)cs2)c1=O] | B | A | 613.2374 | 2.755 | Starting materials: 6,6-dimethyldihydro-2H-pyran-2,4(3H)-dione (step 1), Nitrile 1 (step 2), tert-butyl 2,6-diazaspiro[3.4]octane-2-carboxylate (used in methods V, step 5); Methods: V | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 520 | 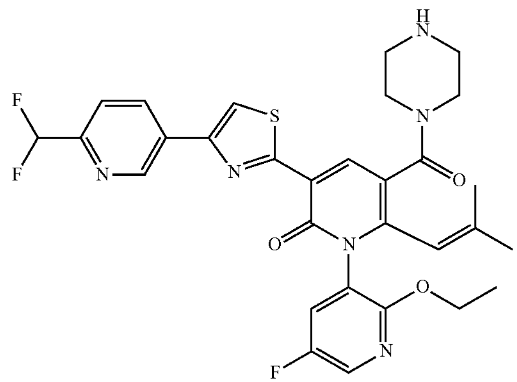 [SMILES: CCOc1ncc(F)cc1-n1c(C=C(C)C)c(C(=O)N2CCNCC2)cc(-c2nc(-c3ccc(C(F)F)nc3)cs2)c1=O] | A | C | 611.2059 | 2.492 | Starting materials: nitrile 25 (step 2 of method W), pyridyl amine 2 (step 3 of method W); Methods: W, X | 1H NMR (400 MHz, DMSO-d6) δ 9.37 (br s, 1H), 8.68-8.56 (m, 2H), 8.48 (S, 1H), 8.33 (s, 1H), 8.09 (br m, 1H), 7.79 (d, J = 8.2 Hz, 1H), 7.00 (t, J = 55.0 Hz, 1H), 5.57 (br m, 1H), 4.45-4.15 (br m, 1H), 3.60-3.35 (br m, 2H), 2.90-2.54 (m, 6H), 1.60 (s, 3H), 1.53 (s, 4H), 1.27-0.97 (m, 3H). |
| 522 | 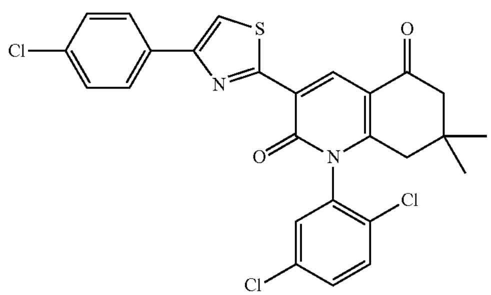 [SMILES: CC1(C)CC(=O)c2cc(-c3nc(-c4ccc(Cl)cc4)cs3)c(=O)n(-c3cc(Cl)ccc3Cl)c2C1] | C | B | 531.029 | 4.037 | Starting material: 5,5-dimethylcyclohexane-1,3-dione (step1 method M); nitrile 1 (step2 method M); 2,5-dichloroaniline (step 3 method M), Methods: M | 1H NMR (400 MHz, CDCl3) δ 9.37 (s, 1H), 7.98 (t, J = 8.5 Hz, 2H), 7.61 (d, J = 10.2 Hz, 2H), 7.54 (dd, J = 8.7, 2.4 Hz, 1H), 7.43 (d, J = 8.5 Hz, 2H), 7.38 (d, J = 2.3 Hz, 1H), 2.56-2.43 (m, 3H), 2.26 (d, J = 17.9 Hz, 1H), 1.11 (d, J = 8.3 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 523 | 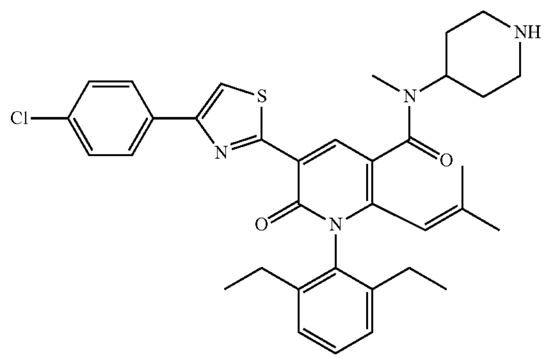 [SMILES: CCc1cccc(CC)c1-n1c(C=C(C)C)c(C(=O)N(C)C2CCNCC2)cc(-c2nc(-c3ccc(Cl)cc3)cs2)c1=O] | A | A | 637.2375 | 2.818 | Starting materials: 6,6-dimethyldihydro-2H-pyran-2,4(3H)-dione (step 1), Nitrile 1 (step 2), tert-butyl 3-(methylamino)piperidine-1-carboxylate (used in methods V, step 5); Methods: V | |
| 524 | 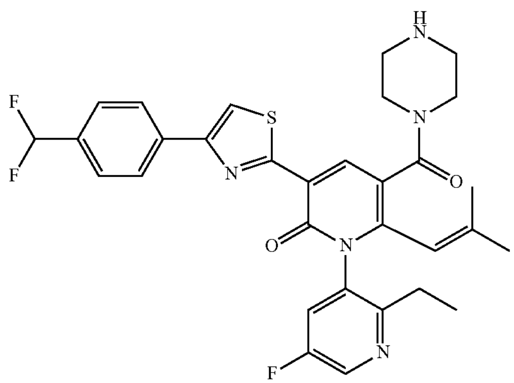 [SMILES: CCc1ncc(F)cc1-n1c(C=C(C)C)c(C(=O)N2CCNCC2)cc(-c2nc(-c3ccc(C(F)F)cc3)cs2)c1=O] | A | A | 594.2151 | 2.553 | Starting materials: nitrile 24 (step 2 method W); pyridyl amine 9 (step 3 method W). Methods: W, then steps 4-6 in method V | 1H NMR (400 MHz, DMSO-d6) δ 8.80-8.67 (m, 3H), 8.32 (s, 1H), 8.20 (d, J = 8.0 Hz, 2H), 8.07-7.80 (m, 1H), 7.66 (d, J = 8.1 Hz, 2H), 7.06 (t, J = 56.0 Hz, 1H), 5.62-5.39 (m, 1H), 4.15-3.85 (m, 1H), 3.81-3.52 (m, 2H), 3.37-3.29 (m, 2H), 3.32 (s, 1H), 2.52 (s, 2H), 2.27 (s, 1H), 1.60 (d, J = 7.1 Hz, 3H), 1.56 (s, 3H), 1.22-1.08 (m, 1H), 1.09-0.97 (m, 3H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 525 | 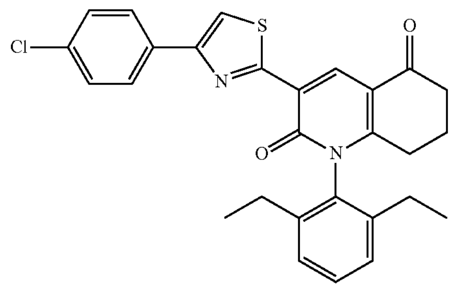 | C | C | 489.141 | 4.085 | Starting material: cyclohexane-1,3-dione (step1 method M); nitrile 1 (step2 method M); 2,6-diethylaniline (step 3 method M), Methods: M | 1H NMR (400 MHz, CD3OD) δ 9.37 (s, 1H), 7.98 (d, J = 8.4 Hz, 2H), 7.56 (s, 1H), 7.46-7.40 (m, 3H), 7.31 (d, J = 8.4 Hz, 2H), 2.61 (t, J = 8.0 Hz, 2H), 2.39 (t, J = 8.0 Hz, 2H), 2.34-2.28 (m, 4H), 2.08-2.05 (m, 2H), 1.15 (t, J = 8.0 Hz, 6H). Aliphatic region complicated significantly by amide rotamers. |
| 526 | 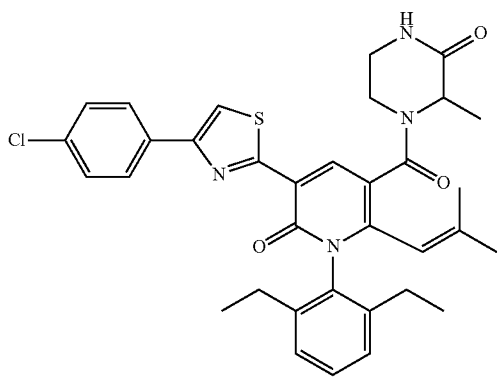 [SMILES: CCc1cccc(CC)c1-n1c(C=C(C)C)c(C(=O)N2CCNC(=O)C2C)cc(-c2nc(-c3ccc(Cl)cc3)cs2)c1=O] | A | A | 615.2187 | 3.678 | Starting materials: 6,6-dimethyldihydro-2H-pyran-2,4(3H)-dione (step 1), Nitrile 1 (step 2), 3-methylpiperazin-2-one (used in methods V, step 5); Methods: V, no step 6. | 1H NMR (400 MHz, DMSO-d6) δ 8.72 (s, 1H), 8.23 (s, 1H), 8.11 (dd, J = 8.6, 2.7 Hz, 2H), 7.59-7.47 (m, 2H), 7.42 (td, J = 7.7, 3.2 Hz, 1H), 7.28 (dd, J = 15.8, 7.6 Hz, 2H), 5.33 (s, 1H), 4.74 (q, J = 7.0 Hz, 1H), 3.62-3.44 (m, 2H), 3.23-3.01 (m, 1H), 2.65 (p, J = 1.9 Hz, 1H), 2.43-2.21 (m, 2H), 2.20-2.04 (m, 2H), 1.61-1.55 (m, 3H), 1.49 (d, J = 1.4 Hz, 3H), 1.32 (d, J = 7.1 Hz, 3H), 1.19 (d, J = 7.1 Hz, 3H), 1.11 (t, J = 7.5 Hz, 3H), 1.01 (t, J = 7.5 Hz, 3H). |
| 527 | 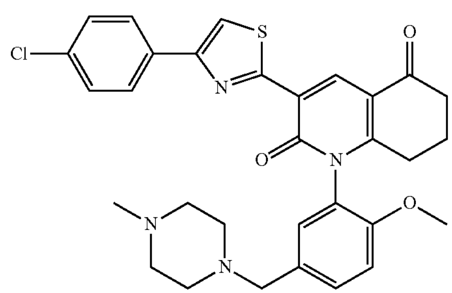 [SMILES: COc1ccc(CN2CCN(C)CC2)cc1-n1c2c(cc(-c3nc(-c4ccc(Cl)cc4)cs3)c1=O)C(=O)CCC2] | E | E | 575.1901 | 2.61 | Starting material: cyclohexane-1,3-dione (step1 method M); nitrile 1 (step2 method M); 2-methoxy-5-((4-methylpiperazin-1-yl)methyl)aniline (step 3 method M), Methods: M | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 528 | 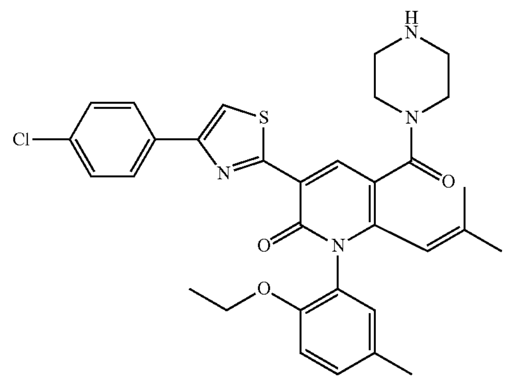 [SMILES: CCOc1ccc(C)cc1-n1c(C=C(C)C)c(C(=O)N2CCNCC2)cc(-c2nc(-c3ccc(Cl)cc3)cs2)c1=O] | A | A | 589.2018 | 2.686 | Starting material: 6,6-dimethyldihydro-2H-pyran-2,4(3H)-dione (step1 method V); nitrile 1 (step2 method V); 2-methoxy-5-methylaniline (step 3 method V), Methods: V | TFA salt: 1H NMR (400 MHz, CD3OD) δ 8.79 (s, 1H), 8.01 (d, J = 8.6 Hz, 2H), 7.91 (s, 1H), 7.43 (d, J = 8.7 Hz, 2H), 7.30-7.25 (m, 1H), 7.16-6.92 (m, 2H), 5.60 (s, 1H), 4.41-3.95 (m, 3H), 3.89-3.74 (m, 1H), 3.71-3.51 (m, 2H), 3.35-3.10 (m, 4H), 2.33 (s, 3H), 1.65-1.59 (m, 6H), 1.30-1.15 (m, 3H). Aliphatic region complicated significantly by amide rotamers. |
| 529 | 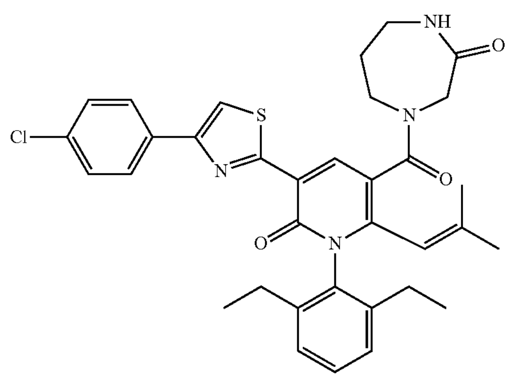 [SMILES: CCc1cccc(CC)c1-n1c(C=C(C)C)c(C(=O)N2CCCNC(=O)C2)cc(-c2nc(-c3ccc(Cl)cc3)cs2)c1=O] | A | A | 615.2209 | 3.666 | Starting materials: 6,6-dimethyldihydro-2H-pyran-2,4(3H)-dione (step 1), Nitrile 1 (step 2), 1,4-diazepan-2-one (used in methods V, step 5); Methods: V, no step 6. | 1H NMR (400 MHz, DMSO-d6) δ 8.66 (s, 1H), 8.22 (d, J = 2.5 Hz, 1H), 8.13-8.06 (m, 2H), 7.62 (dt, J = 21.3, 4.9 Hz, 1H), 7.55-7.48 (m, 2H), 7.41 (td, J = 7.6, 5.7 Hz, 1H), 7.29 (d, J = 15.8 Hz, 1H), 5.22 (s, 1H), 4.03 (dd, J = 76.9,18.4 Hz, 2H), 3.42-3.38 (m, 1H), 3.20-3.12 (m, 1H), 2.42-2.00 (m, 4H), 1.93-1.68 (m, 3H), 1.62-1.45 (m, 7H), 1.05-0.92 (dm, 6H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 530 | (structure) | A | B | 607.1943 | 2.711 | Starting material: 6,6-dimethyldihydro-2H-pyran-2,4(3H)-dione (step1 method V); nitrile 1 (step2 method V); 5-fluoro-2-isopropoxyaniline (step 3 method V), Methods: V | TFA salt: 1H NMR (400 MHz, CD3OD) δ 8.80 (s, 1H), 8.02 (d, J = 8.6 Hz, 2H), 7.91 (s, 1H), 7.43 (d, J = 8.7 Hz, 2H), 7.30-6.93 (m, 3H), 5.70-5.55 (m, 1H), 4.70-4.45 (m, 1H), 4.40-4.10 (m, 1H), 3.90-3.70 (m, 1H), 3.65-3.55 (m, 2H), 3.35-3.10 (m, 4H), 1.70-1.60 (m, 6H), 1.30-1.00 (m, 6H). Aliphatic region complicated significantly by amide rotamers. |
| 531 | (structure) | D | C | 503.1562 | 4.187 | Starting material: cyclohexane-1,3-dione (step1 method M); nitrile 1 (step2 method M); 2,6-diethyl-4-methylaniline (step 3 method M), Methods: M | 1H NMR (400 MHz, CD3OD) δ 9.36 (s, 1H), 7.98 (d, J = 8.4 Hz, 2H), 7.55 (s, 1H), 7.41 (d, J = 8.4 Hz, 2H), 7.10 (s, 2H), 2.62-2.56 (m, 2H), 2.43-2.40 (m, 5H), 2.31-2.23 (m, 4H), 2.08-2.05 (m, 2H), 1.13 (t, J = 8.0 Hz, 6H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 532 | 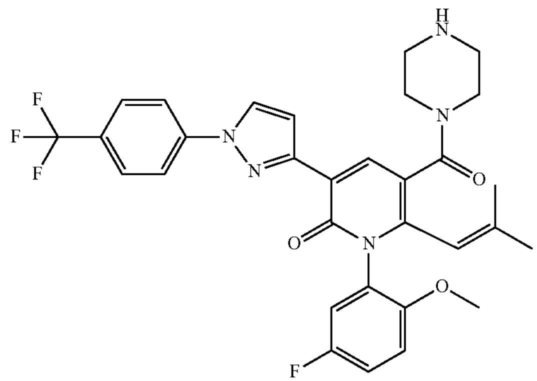 [SMILES: COc1ccc(F)cc1-n1c(C=C(C)C)c(C(=O)N2CCNCC2)cc(-c2ccn(-c3ccc(C(F)(F)F)cc3)n2)c1=O] | B | C | 596.227 | 2.528 | Starting materials: 6,6-dimethyldihydro-2H-pyran-2,4(3H)-dione (step 1), pyrazole 4 (step 2), 5-fluoro-2-methoxyaniline (step 3 of methods V); Methods: V, no step 6. | |
| 533 | 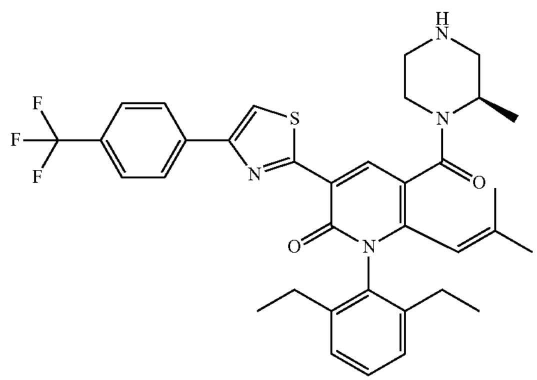 [SMILES: CCc1cccc(CC)c1-n1c(C=C(C)C)c(C(=O)N2CCNC[C@H]2C)cc(-c2nc(-c3ccc(C(F)(F)F)cc3)cs2)c1=O] | A | A | 635.2684 | 2.846 | Starting materials: 6,6-dimethyldihydro-2H-pyran-2,4(3H)-dione (step 1), Nitrile 7 (step 2), (R)-tert-butyl 3-methylpiperazine-1-carboxylate (used in methods V, step 5); Methods: V. | 1H NMR (400 MHz, DMSO-d6) δ 8.72 (s, 1H), 8.40 (s, 1H), 8.29 (d, J = 8.1 Hz, 1H), 7.92-7.77 (m, 2H), 7.46-7.23 (m, 2H), 7.19 (dd, J = 7.5, 3.7 Hz, 2H), 5.29 (s, 1H), 4.35-4.24 (m, 1H), 3.66-3.37 (m, 1H), 3.25-2.95 (m, 2H), 2.71-2.54 (m, 3H), 2.43-2.22 (m, 2H), 2.18-2.00 (m, 2H), 1.67-1.46 (m, 6H), 1.37 (d, J = 1.1 Hz, 6H), 1.03-0.93 (m, 3H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 534 | 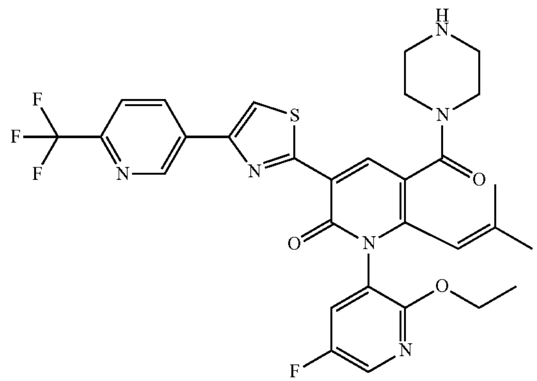 [SMILES: CCOc1ncc(F)cc1-n1c(C=C(C)C)c(C(=O)N2CCNCC2)cc(-c2nc(-c3ccc(C(F)(F)F)nc3)cs2)c1=O] | A | A | 629.1975 | 2.57 | Starting materials: pyridyl amine 2 (step 3 of method W); Methods: W, X | TFA salt: 1H NMR (400 MHz, DMSO-d6) δ 9.46 (s, 1H), 9.03-8.63 (br m, 3H), 8.58 (s, 1H), 8.35 (d, J = 2.9 Hz, 1H), 8.05 (d, J = 7.7 Hz, 1H), 8.01 (d, J = 8.2 Hz, 1H), 5.62 (br m, 1H), 4.48-4.11 (m, 2H), 4.10-3.80 (br m, 1H), 3.75-3.36 (br m, 2H), 3.26-2.77 (br m, 5H), 1.62 (s, 3H), 1.54 (s, 3H), 1.16 (br m, 3H). |
| 535 | 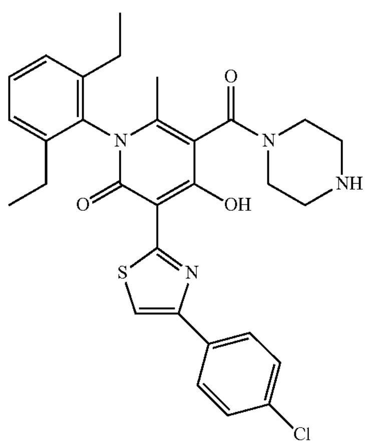 [SMILES: CCc1cccc(CC)c1-n1c(C)c(C(=O)N2CCNCC2)c(O)c(-c2nc(-c3ccc(Cl)cc3)cs2)c1=O] | B | C | 563.1896 | 2.62 | Starting materials: piperazine (method U); Methods: xxiii; ester hydrolyzed with LiOH (xs), THF/MeOH/water, 60° C.; U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 536 | 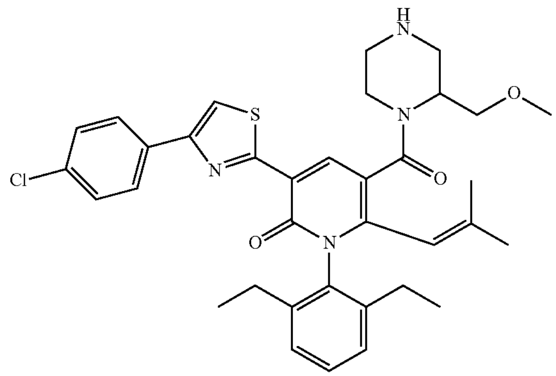 [SMILES: CCc1cccc(CC)c1-n1c(C=C(C)C)c(C(=O)N2CCNCC2COC)cc(-c2nc(-c3ccc(Cl)cc3)cs2)c1=O] | A | A | 631.2492 | 2.846 | Starting materials: 6,6-dimethyldihydro-2H-pyran-2,4(3H)-dione (step 1), Nitrile 1 (step 2), tert-butyl 3-(methoxymethyl)piperazine-1-carboxylate (used in methods V, step 5); Methods: V | 1H NMR (400 MHz, DMSO-d6) δ 8.71 (s, 1H), 8.25 (s, 1H), 8.09 (dd, J = 8.7, 2.7 Hz, 2H), 7.57-7.50 (m, 2H), 7.42 (td, J = 7.6, 2.3 Hz, 2H), 7.35-7.23 (m, 1H), 5.28 (s, 1H), 4.92 (d, J = 5.9 Hz, 1H), 3.76-3.36 (m, 2H), 3.19-2.97 (m, 2H), 2.69-2.53 (m, 1H), 2.43-2.22 (m, 3H), 2.20-2.02 (m, 3H), 1.64-1.50 (m, 9H), 1.37 (d, J = 1.2 Hz, 1H), 1.11 (t, J = 7.5 Hz, 3H), 1.00 (t, J = 7.5 Hz, 3H). |
| 537 | 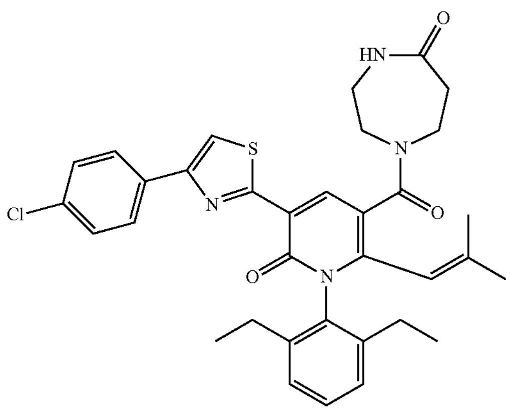 [SMILES: CCc1cccc(CC)c1-n1c(C=C(C)C)c(C(=O)N2CCNC(=O)CC2)cc(-c2nc(-c3ccc(Cl)cc3)cs2)c1=O] | A | A | 615.2168 | 3.621 | Starting materials: 6,6-dimethyldihydro-2H-pyran-2,4(3H)-dione (step 1), Nitrile 1 (step 2), 1,4-diazepan-5-one (used in methods V, step 5); Methods: V, no step 6. | 1H NMR (400 MHz, DMSO-d6) δ 8.69 (s, 1H), 8.23 (s, 1H), 8.15-8.04 (m, 2H), 7.57-7.47 (m, 2H), 7.41 (t, J = 7.7 Hz, 1H), 7.28 (dd, J = 19.2, 7.7 Hz, 2H), 5.25 (s, 1H), 3.81 (dt, J = 37.3, 10.3 Hz, 1H), 3.30-2.99 (m, 2H), 2.72-2.52 (m, 4H), 2.42-2.20 (m, 2H), 2.19-1.99 (m, 2H), 1.56 (dt, J = 8.4, 1.5 Hz, 6H), 1.17-1.04 (m, 3H), 1.04-0.93 (m, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 539 | 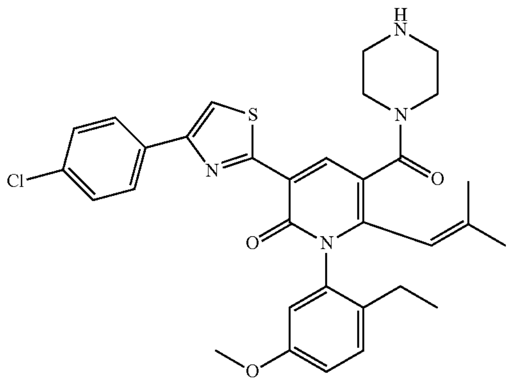 [SMILES: CCc1ccc(OC)cc1-n1c(C=C(C)C)c(C(=O)N2CCNCC2)cc(-c2nc(-c3ccc(Cl)cc3)cs2)c1=O] | A | A | 589.2024 | 2.709 | Starting materials: 6,6-dimethyldihydro-2H-pyran-2,4(3H)-dione (step 1), Nitrile 1 (step 2), 2-ethyl-5-methoxyaniline (step 3); Methods: V | 1H NMR (400 MHz, DMSO-d6) δ 8.69 (s, 1H), 8.24 (s, 1H), 8.10 (d, J = 8.2 Hz, 2H), 7.57-7.50 (m, 3H), 7.04 (d, J = 7.2 Hz, 2H), 5.53 (s, 1H), 3.78 (s, 3H), 3.72-3.67 (m, 2H), 3.45-3.37 (m, 2H), 3.20-3.01 (m, 2H), 2.65 (q, J = 1.9 Hz, 2H), 2.09-2.03 (m, 2H), 1.61-1.52 (m, 6H), 1.15-0.90 (m, 3H). |
| 540 | 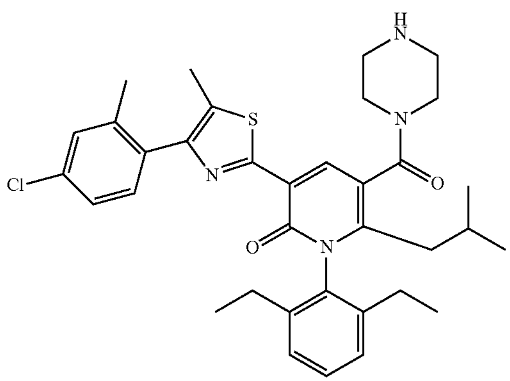 [SMILES: CCc1cccc(CC)c1-n1c(CC(C)C)c(C(=O)N2CCNCC2)cc(-c2nc(-c3ccc(Cl)cc3C)c(C)s2)c1=O] | C | C | 617.2708 | 2.937 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-chloro-2-methylphenyl) boronic acid (method xix); Methods: S, then ester hydrolyzed with LiOH (4 eq), THF/MeOH/water, 50 C., U, xix, then Boc removal with TFA/DCM rt | 1H NMR (400 MHz, DMSO-d6) δ 8.69 (s, 1H), 8.47 (s, 1H), 7.47 (t, J = 7.6 Hz, 1H), 7.42 (d, J = 2.9 Hz, 1H), 7.37-7.29 (m, 3H), 7.26 (d, J = 8.2 Hz, 1H), 4.04-3.95 (m, 1H), 3.77-3.68 (m, 1H), 3.57-3.47 (m, 2H), 3.22-2.90 (m, 4H), 2.27 (s, 3H), 2.19 (s, 3H), 2.17-1.86 (m, 6H), 1.37-1.22 (m, 1H), 1.13-1.03 (m, 6H), 0.59 (d, J = 6.6 Hz, 6H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 541 | (structure) | A | C | 593.2508 | 2.499 | Starting materials: pyrazole 4 (step 2), 2-methoxy-5-methylpyridin-3-amine (step 3); piperazine (step 5); Methods: V, step 4 with NaOH (xs), no step 6. | TFA salt: 1H NMR (400 MHz, DMSO-d6) δ 8.75 (br s, 1H), 8.68 (d, J = 2.6 Hz, 1H), 8.30 (s, 1H), 8.15 (d, J = 8.5 Hz, 3H), 8.07 (dd, J = 2.3, 1.0 Hz, 1H), 7.88 (d, J = 8.6 Hz, 2H), 7.60 (br s, 1H), 7.23 (d, J = 2.6 Hz, 1H), 5.45 (s, 1H), 4.04-3.65 (br m, 4H), 3.65-3.35 (br m, 2H), 3.20-2.85 (br m, 5H), 2.29 (m, 3H), 1.57 (d, J = 1.4 Hz, 3H), 1.51 (d, J = 1.2 Hz, 3H). |
| 542 | (structure) | A | A | 629.2701 | 2.889 | Starting materials: 6,6-dimethyldihydro-2H-pyran-2,4(3H)-dione (step 1), Nitrile 1 (step 2), tert-butyl 2-propylpiperazine-1-carboxylate (used in methods V, step 5); Methods: V | 1H NMR (400 MHz, DMSO-d6) δ 8.75 (s, 1H), 8.25 (s, 1H), 8.16-8.05 (m, 2H), 7.53 (dt, J = 9.7, 2.9 Hz, 2H), 7.49-7.38 (m, 1H), 7.29 (dd, J = 22.4, 7.9 Hz, 2H), 5.28 (s, 1H), 4.66-4.31 (m, 2H), 3.72-3.67 (m, 1H), 3.23-2.94 (m, 2H), 2.89-2.52 (m, 2H), 2.43-2.19 (m, 2H), 2.15-1.99 (m, 2H), 1.65-1.50 (m, 6H), 1.37 (d, J = 1.2 Hz, 1H), 1.16-1.05 (m, 4H), 1.04-0.82 (m, 8H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 543 | 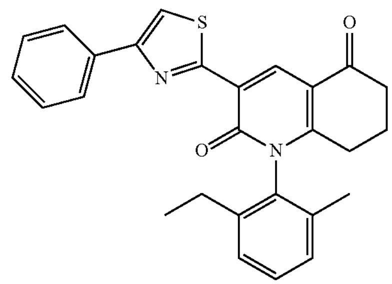 [SMILES: CCc1cccc(C)c1-n1c2c(cc(-c3nc(-c4ccccc4)cs3)c1=O)C(=O)CCC2] | D | C | 441.1648 | 3.852 | Starting material: cyclohexane-1,3-dione (step1 method M); nitrile 2 (step2 method M); 2-ethyl-6-methylaniline (step 3 method M), Methods: M | 1H NMR (400 MHz, CD3OD) δ 9.33 (s, 1H), 8.02-8.00 (m, 2H), 7.76 (s, 1H), 7.43-7.39 (m, 3H), 7.34-7.28 (m, 3H), 2.60-2.58 (m, 2H), 2.50-2.40 (m, 2H), 2.44-2.42 (m, 2H), 2.15-2.05 (m, 2H), 2.04 (s, 3H), 1.13 (t, J = 8.0 Hz, 3H). Aliphatic region complicated significantly by amide rotamers. |
| 544 | 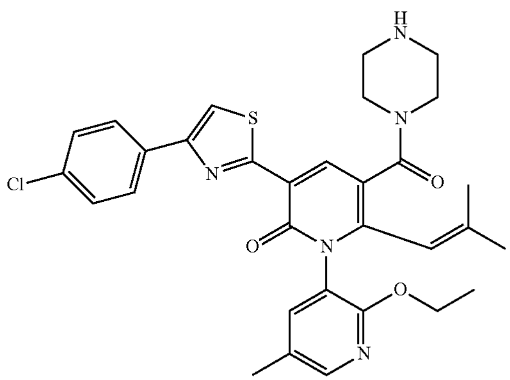 [SMILES: CCOc1ncc(C)cc1-n1c(C=C(C)C)c(C(=O)N2CCNCC2)cc(-c2nc(-c3ccc(Cl)cc3)cs2)c1=O] | A | A | 590.1982 | 2.634 | Starting materials: nitrile 1 (step2 method V); pyridyl amine 6 (step 3 method V); piperidine (step 5 method V), Methods: V, no step 7 | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 545 | (structure) | A | A | 593.1795 | 2.652 | Starting material: 6,6-dimethyldihydro-2H-pyran-2,4(3H)-dione (step1 method V); nitrile 1 (step2 method V); aniline 12 (step 3 method V), Methods: V | TFA salt: 1H NMR (400 MHz, CD3OD) δ 8.85 (s, 1H), 8.05 (d, J = 8.4 Hz, 2H), 7.96 (s, 1H), 7.58-7.41 (m, 3H), 7.09-6.91 (m, 2H), 5.65 (s, 1H), 4.39-3.97 (m, 4H), 3.88-3.48 (m, 3H), 3.24-3.16 (m, 3H), 1.71-1.60 (m, 6H), 1.26 (m, 3H). Aliphatic region complicated significantly by amide rotamers. |
| 546 | (structure) | A | A | 604.2582 | 2.602 | Starting materials: 6,6-dimethyldihydro-2H-pyran-2,4(3H)-dione (step 1), 2-(4-(6-(difluoromethyl)pyridin-3-yl)thiazol-2-yl)acetonitrile (step 2); Methods: W, then V (steps 4-6) | TFA salt: 1H NMR (400 MHz, DMSO-d6) δ 9.40 (d, J = 2.1 Hz, 1H), 8.79 (s, 1H), 8.73 (bs, 2H), 8.63 (dd, J = 8.1, 2.2 Hz, 1H), 8.51 (s, 1H), 7.83 (d, J = 8.2 Hz, 1H), 7.45 (dd, J = 7.7, 7.7 Hz, 1H), 7.33 (d, J = 7.7 Hz, 1H), 7.29 (d, J = 7.4 Hz, 1H), 7.03 (t, J = 55.0 Hz, 1H), 5.31 (s, 1H), 4.06 (d, J = 14.4 Hz, 1H), 3.63 (d, J = 11.1 Hz, 1H), 3.43-2.92 (m, 8H), 2.43-2.26 (m, 1H), 1.59 (s, 6H), 1.13 (t, J = 7.5 Hz, 3H), 1.01 (t, J = 7.5 Hz, 3H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 547 | 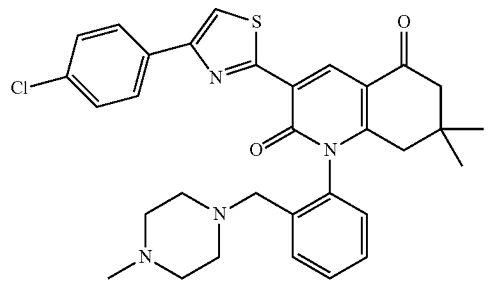 [SMILES: CN1CCN(Cc2ccccc2-n2c3c(cc(-c4nc(-c5ccc(Cl)cc5)cs4)c2=O)C(=O)CC(C)(C)C3)CC1] | D | D | 573.211 | 2.746 | Starting material: 5,5-dimethylcyclohexane-1,3-dione (step1 method M); nitrile 1 (step2 method M); 2-((4-methylpiperazin-1-yl)methyl)aniline (step 3 method M), Methods: M | HCl salt: 1H NMR (400 MHz, dmso-d6) δ 9.10 (s, 1H), 8.26 (s, 1H), 8.14-8.09 (m, 2H), 7.65-7.59 (m, 2H), 7.59-7.54 (m, 2H), 7.50-7.40 (m, 2H), 3.28 (s, 2H), 2.73 (d, J = 42.8 Hz, 7H), 2.57 (dd, J = 40.1, 22.0 Hz, 4H), 2.33 (s, 1H), 2.26 (d, J = 18.0 Hz, 2H), 1.00 (s, 6H). Aliphatic region complicated |
| 548 | 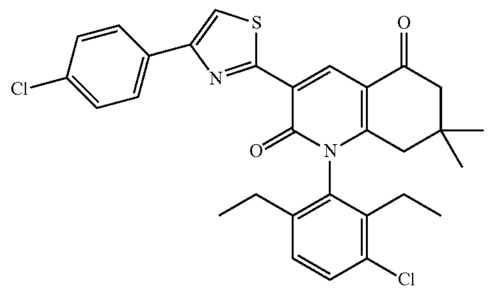 [SMILES: CCc1ccc(Cl)c(CC)c1-n1c2c(cc(-c3nc(-c4ccc(Cl)cc4)cs3)c1=O)C(=O)CC(C)(C)C2] | A | A | 551.1327 | 4.362 | Starting material: 5,5-dimethylcyclohexane-1,3-dione (step1 method M); nitrile 1 (step2 method M); 3-chloro-2,6-diethylaniline (step 3 method M), Methods: M | 1H NMR (400 MHz, CDCl3) δ 9.38 (s, 1H), 7.98 (t, J = 9.4 Hz, 2H), 7.59 (s, 1H), 7.53 (d, J = 8.4 Hz, 1H), 7.43 (d, J = 8.5 Hz, 2H), 7.29 (d, J = 8.4 Hz, 1H), 2.51 (d, J = 6.0 Hz, 2H), 2.31-2.19 (m, 4H), 2.10 (s, 2H), 1.22-1.14 (m, 3H), 1.08 (dd, J = 11.9, 6.4 Hz, 9H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 549 | 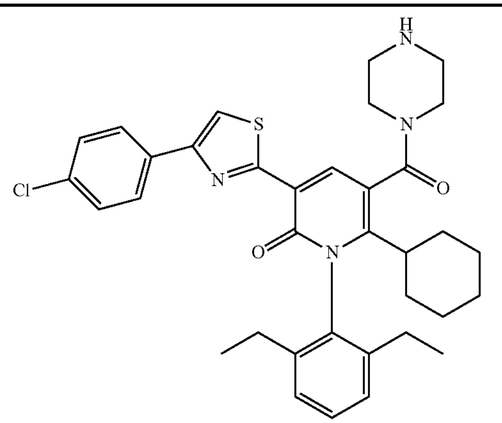 | C | B | 637.2382 | 2.879 | Starting materials: ethyl 3-cyclohexyl-3-oxopropanoate (step 1), piperazine (used in method U); Methods: S, then ester hydrolyzed with LiOH (xs), THF/MeOH/water, 60° C.; U | 1H NMR (400 MHz, DMSO-d6) δ 8.43 (t, J = 2.3 Hz, 1H), 8.18 (d, J = 2.0 Hz, 1H), 8.08 (d, J = 7.8 Hz, 2H), 7.48 (dd, J = 18.7, 8.0 Hz, 3H), 7.35 (d, J = 7.7 Hz, 2H), 3.59 (m, 2H), 3.28 (m, 2H), 2.72 (m, 4H), 2.43-1.94 (m, 5H), 1.90-1.32 (m, 7H), 1.07 (q, J = 7.7 Hz, 6H), 0.99-0.63 (m, 2H), 0.52 (m, 1H). |
| 550 | 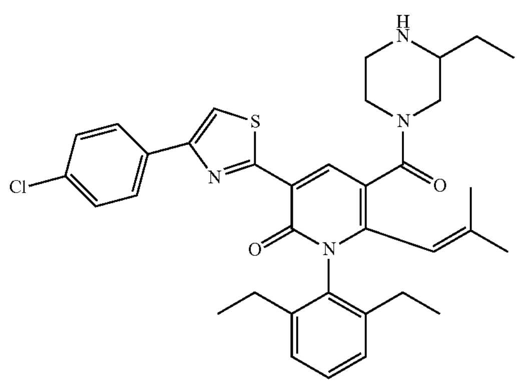 [SMILES: CCc1cccc(CC)c1-n1c(C=C(C)C)c(C(=O)N2CCNC(CC)C2)cc(-c2nc(-c3ccc(Cl)cc3)cs2)c1=O] | A | A | 615.2525 | 2.848 | Starting materials: 6,6-dimethyldihydro-2H-pyran-2,4(3H)-dione (step 1), Nitrile 1 (step 2), tert-butyl 2-ethylpiperazine-1-carboxylate (used in methods V, step 5); Methods: V | 1H NMR (400 MHz, DMSO-d6) δ 8.75 (s, 1H), 8.25 (s, 1H), 8.14-8.05 (m, 2H), 7.57-7.50 (m, 2H), 7.47-7.40 (m, 1H), 7.37-7.22 (m, 2H), 5.29 (s, 1H), 4.67-4.52 (m, 1H), 3.72-3.64 (m, 1H), 3.23-3.05 (m, 2H), 3.01-2.61 (m, 2H), 2.45-2.20 (m, 2H), 2.14-1.99 (m, 2H), 1.66-1.51 (m, 9H), 1.16-1.06 (m, 3H), 1.02-0.94 (m, 3H), 0.87-0.79 (m, 2H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 551 | 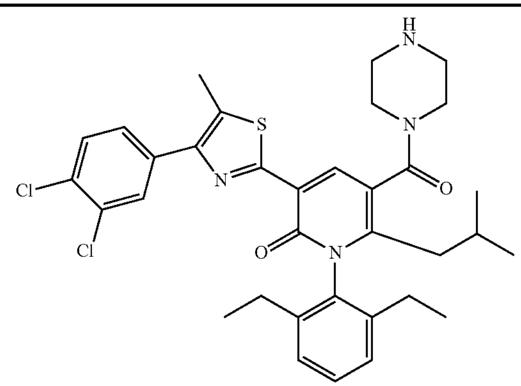 | B | A | 637.2164 | 2.976 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (3,4-dichlorophenyl)boronic acid (method xix); Methods: S, then ester hydrolyzed with LiOH (4 eq), THF/MeOH/water, 50 C., U, xix, then Boc removal with TFA/DCM rt | 1H NMR (400 MHz, DMSO-d6) δ 8.56 (s, 1H), 8.00 (d, J =1.8 Hz, 1H), 7.79-7.68 (m, 3H), 7.47 (t, J = 7.7 Hz, 1H), 7.35 (s, 1H), 7.33 (s, 1H), 4.00-3.85 (m, 1H), 3.76-3.57 (m, 2H), 3.57-3.46 (m, 1H), 3.26-2.89 (m, 4H), 2.57 (s, 3H), 2.24-1.89 (m, 6H), 1.37-1.24 (m, 1H), 1.13-1.02 (m, 6H), 0.60 (d, J = 6.6 Hz, 6H). Aliphatic region complicated significantly by amide rotamers. |
| 552 | 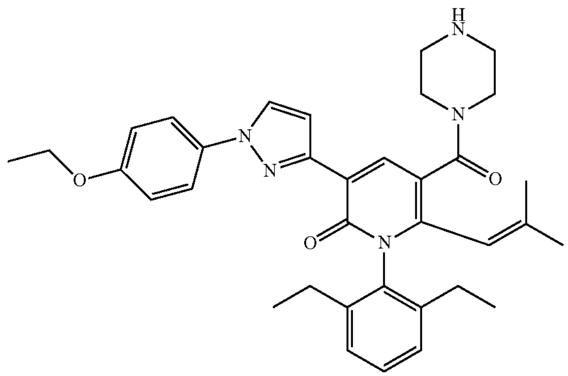 [SMILES: CCOc1ccc(-n2ccc(-c3cc(C(=O)N4CCNCC4)c(C=C(C)C)n(-c4c(CC)cccc4CC)c3=O)n2)cc1] | A | A | 580.3271 | 2.635 | Starting materials: pyrazole 3 (step 2), piperazine (step 5); Methods: V, step 4 with NaOH (xs), no step 6. | TFA salt: 1H NMR (400 MHz, DMSO-d6) δ 8.83 (br s, 1H), 8.75 (br s, 1H), 8.38 (d, J = 2.5 Hz, 1H), 8.31 (s, 1H), 7.84-7.70 (m, 2H), 7.37 (t, J = 7.6 Hz, 1H), 7.24 (dd, J = 17.0, 7.7 Hz, 2H), 7.14 (d, J = 2.4 Hz, 1H), 7.10-6.91 (m, 2H), 5.20 (q, J = 1.4 Hz, 1H), 4.05 (q, J = 7.0 Hz, 2H), 3.99 (m, 1H), 3.47 (m, 4H), 3.21-2.77 (m, 4H), 2.43-2.20 (m, 1H), 2.19-1.97 (m, 2H), 1.53 (dd, J = 2.9, 1.4 Hz, 6H), 1.33 (t, J = 7.0 Hz, 3H), 1.17-0.88 (m, 6H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 553 | 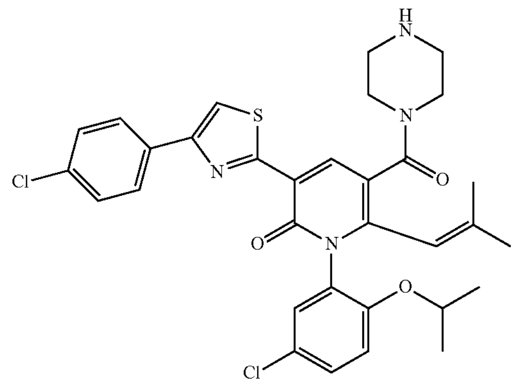 | A | A | 312.0857 | 2.764 | Starting material: 6,6-dimethyldihydro-2H-pyran-2,4(3H)-dione (step1 method V); nitrile 1 (step2 method V); 5-fluoro-6-isopropoxyaniline (step 3 method V). Methods: V | TFA salt: 1H NMR (400 MHz, CD3OD) δ 8.83 (s, 1H), 8.04 (d, J = 8.8 Hz, 2H), 7.94 (s, 1H), 7.49-7.44 (m, 4H), 7.28-7.14 (m, 1H), 5.76-5.59 (m, 1H), 4.74-4.53 (m, 1H), 4.37-4.14 (m, 1H), 3.92-3.49 (m, 4H), 3.27-3.16 (m, 3H), 1.73-1.64 (m, 6H), 1.33-1.06 (m, 6H). Aliphatic region complicated significantly by amide rotamers. |
| 554 | 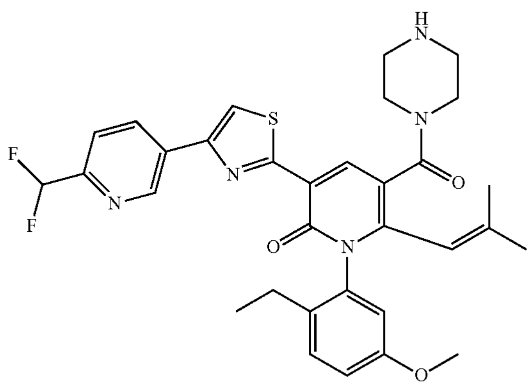 [SMILES: CCc1ccc(OC)cc1-n1c(C=C(C)C)c(C(=O)N2CCNCC2)cc(-c2nc(-c3ccc(C(F)F)nc3)cs2)c1=O] | | | | | | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 555 | 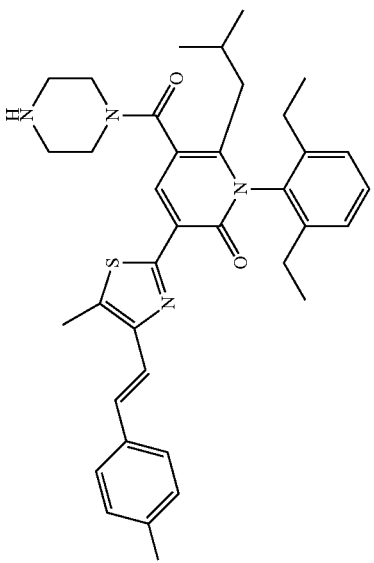 | C | B | 629.2741 | 2.933 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (E)-(4-chlorostyryl)boronic acid (method xix); Methods: S, then ester hydrolyzed with LiOH (4eq), THF/MeOH/water, 50 C., U, xix, then Boc removal with TFA/DCM rt | 1H NMR (400 MHz, DMSO-d6) δ 8.60 (s, 1H), 7.70 (d, J = 8.5 Hz, 2H), 7.58-7.28 (m, 8H), 4.12-4.00 (m, 1H), 3.87-3.75 (m, 1H), 3.69-3.48 (m, 2H), 3.16-2.99 (m, 2H), 2.53 (s,3H), 2.37-2.25 (m, 1H), 2.20-2.03 (m, 6H), 2.02-1.88 (m, 1H), 1.38-1.23 (m, 1H), 1.07 (m, 6H), 0.60 (d, J = 6.4 Hz, 6H). Aliphatic region complicated significantly by amide rotamers. |
| 556 | 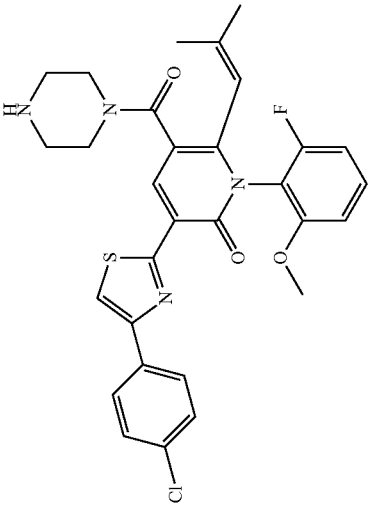 | A | A | 579.1632 | 2.6 | Starting material: 6,6-dimethyldihydro-2H-pyran-2,4(3H)-dione (step1 method V); nitrile 1 (step2 method V); 2-fluoro-6-methoxyaniline (step 3 method V), Methods: V | TFA salt: 1H NMR(400 MHz, CD3OD) δ 8.85 (s, 1H), 8.09-8.00 (m, 2H), 7.95 (s, 1H), 7.54 (td, J = 8.6, 6.6 Hz, 1H), 7.51-7.40 (m, 2H), 6.98 (dd, J = 27.6, 18.6 Hz, 2H), 5.62 (s, 1H), 4.34 (s,2H), 3.87 (dd, J = 25.2,10.8 Hz, 5H), 3.53 (d, J = 35.7 Hz, 2H), 3.30-3.18 (m, 3H), 1.79-1.50 (m, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 557 | 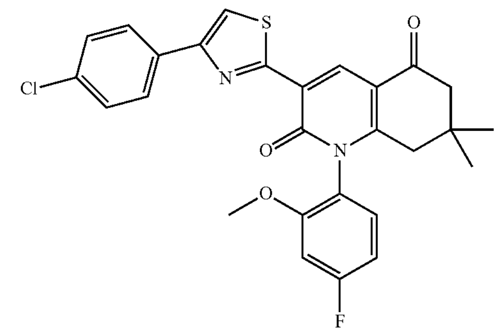 [SMILES: COc1cc(F)ccc1-n1c2c(cc(-c3nc(-c4ccc(Cl)cc4)cs3)c1=O)C(=O)CC(C)(C)C2] | C | C | 509.1072 | 3.859 | Starting material: 5,5-dimethylcyclohexane-1,3-dione (step1 method M); nitrile 1 (step2 method M); 4-fluoro-2-methoxyaniline (step 3 method M), Methods: M | |
| 558 | 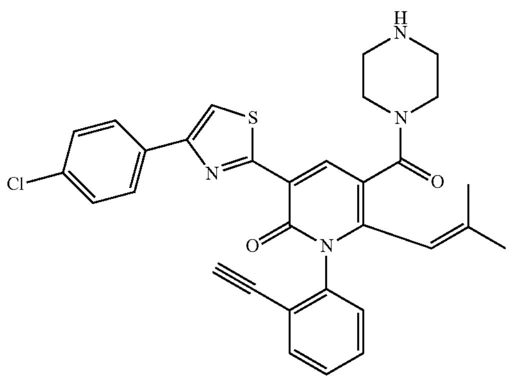 [SMILES: C#Cc1ccccc1-n1c(C=C(C)C)c(C(=O)N2CCNCC2)cc(-c2nc(-c3ccc(Cl)cc3)cs2)c1=O] | A | A | 555.1589 | 2.585 | Starting material: 6,6-dimethyldihydro-2H-pyran-2,4(3H)-dione (step1 method V); nitrile 1 (step2 method V); 2-aminobenzonitrile (step 3 method V), Methods: V | TFA salt: 1H NMR (400 MHz, CD3OD) δ 8.85 (s, 1H), 8.10-8.00 (m, 2H), 7.94 (s, 1H), 7.71 (s, 2H), 7.58 (dt, J = 14.0, 7.8 Hz, 2H), 7.49-7.42 (m, 2H), 5.60 (s, 1H), 4.24 (s, 2H), 3.78 (d, J = 8.9 Hz, 3H), 3.62 (s, 3H), 1.63 (d, J = 17.2 Hz, 6H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 559 | 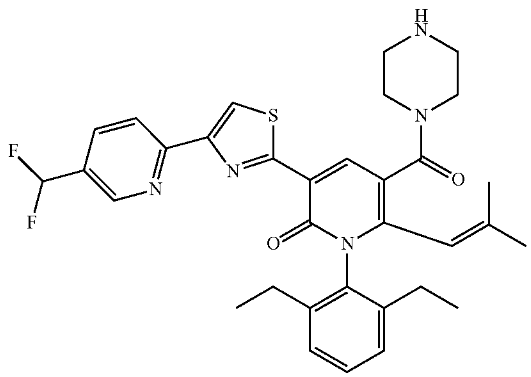 [SMILES: CCc1cccc(CC)c1-n1c(C=C(C)C)c(C(=O)N2CCNCC2)cc(-c2nc(-c3ccc(C(F)F)cn3)cs2)c1=O] | A | A | 604.2568 | 2.608 | Starting materials: nitrile 29 (step 2 method W); Methods: W, then steps 4-6 in method V | 1H NMR (400 MHz, DMSO-d6) δ 8.98-8.67 (m, 3H), 8.47 (s, 1H), 8.39 (dd, J = 8.2, 0.9 Hz, 1H), 8.16 (ddt, J = 8.2, 2.0, 1.0 Hz, 1H), 7.45 (t, J = 7.7 Hz, 1H), 7.37-7.04 (m, 3H), 5.34-5.26 (m, 1H), 4.15-3.97 (m, 1H), 3.53 (s, 5H), 3.13 (s, 2H), 3.00 (s, 1H), 2.46-2.21 (m, 1H), 2.10 (ddt, J = 22.0, 15.0, 7.6 Hz, 2H), 1.59 (d, J = 1.4 Hz, 6H), 1.18-1.08 (m, 3H), 1.01 (t, J = 7.5 Hz, 3H). Aliphatic region complicated significantly by amide rotamers. |
| 561 | 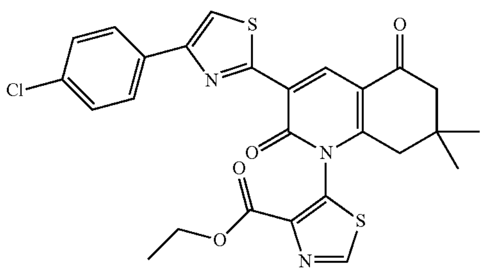 [SMILES: CCOC(=O)c1ncsc1-n1c2c(cc(-c3nc(-c4ccc(Cl)cc4)cs3)c1=O)C(=O)CC(C)(C)C2] | C | C | 540.0822 | 3.7 | Starting material: 5,5-dimethylcyclohexane-1,3-dione (step1 method M); nitrile 1 (step2 method M); ethyl 5-aminothiazole-4-carboxylate (step 3 method M), Methods: M | 1H NMR (400 MHz, CDCl3) δ 9.35 (s, 1H), 9.07 (d, J = 1.7 Hz, 1H), 8.01-7.96 (m, 2H), 7.60 (d, J = 3.0 Hz, 1H), 7.46-7.40 (m, 2H), 4.36-4.20 (m, 2H), 2.62-2.42 (m, 4H), 1.26-1.20 (m, 3H), 1.10 (d, J = 3.8 Hz, 6H), Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 562 | 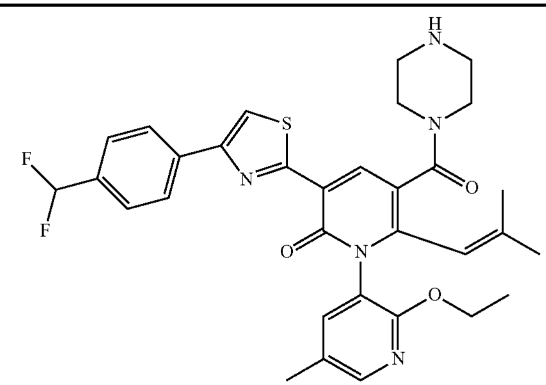 | A | A | 606.2326 | 2.591 | Starting materials: 6,6-dimethyl(dihydro-2H-pyran-2,4(3H)-dione (step 1), Nitrile 24 (step 2), pyridyl amine 6 (step 3 of methods V); Methods: V, no step 6. | 1H NMR (400 MHz, DMSO-d6) δ 8.68 (s, 1H), 8.31 (s, 1H), 8.21 (d, J = 8.0 Hz, 2H), 8.09 (s, 1H), 7.66 (d, J = 8.1 Hz, 3H), 5.53 (s, 1H), 4.37-4.11 (m, 3H), 3.68-3.361 (m, 2H), 3.18-2.89 (m, 2H), 2.68-2.62 (m, 2H), 2.35-2.20 (m, 2H), 1.63-1.49 (m, 7H), 1.35-1.22 (m, 2H), 1.20-1.06 (m, 3H). |
| 563 | 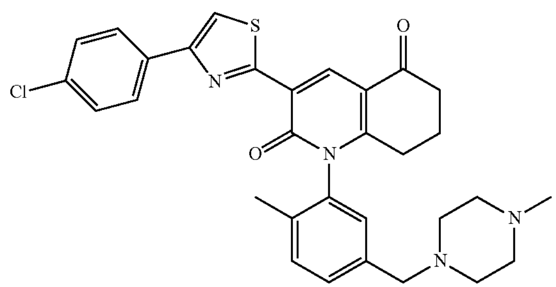 [SMILES: Cc1ccc(CN2CCN(C)CC2)cc1-n1c2c(cc(-c3nc(-c4ccc(Cl)cc4)cs3)c1=O)C(=O)CCC2] | E | E | 559.1941 | 2.699 | Starting material: cyclohexane-1,3-dione (step1 method M); nitrile 1 (step2 method M); 2-methyl-5-((4-methylpiperazin-1-yl)methyl)aniline (step 3 method M), Methods: M | |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 564 | 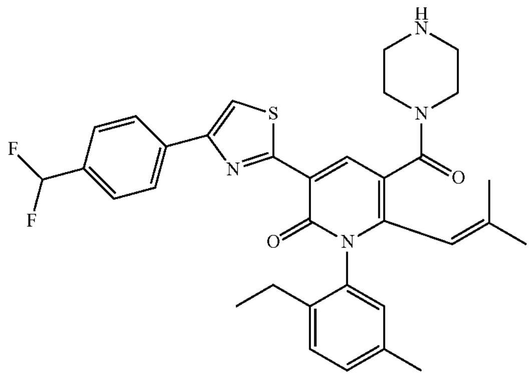 [SMILES: CCc1ccc(C)cc1-n1c(C=C(C)C)c(C(=O)N2CCNCC2)cc(-c2nc(-c3ccc(C(F)F)cc3)cs2)c1=O] | | | | | | |
| 565 | 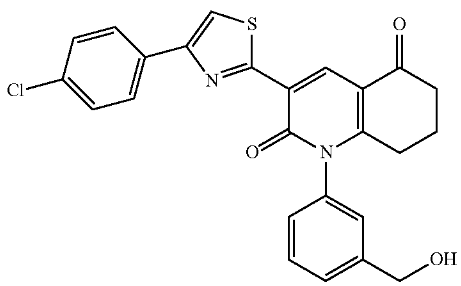 [SMILES: O=C1CCCc2c1cc(-c1nc(-c3ccc(Cl)cc3)cs1)c(=O)n2-c1cccc(CO)c1] | D | D | 463.0876 | 3.451 | Starting material: cyclohexane-1,3-dione (step1 method M); nitrile 1 (step2 method M); (3-aminophenyl)methanol (step 3 method M), Methods: M | 1H NMR (400 MHz, CDCl3) δ 9.37 (s, 1H), 8.03-7.97 (m, 2H), 7.64-7.52 (m, 3H), 7.46-7.40 (m, 2H), 7.34 (s, 1H), 7.21 (d, J = 7.6 Hz, 1H), 5.30 (s, 1H), 4.83 (d, J = 5.8 Hz, 2H), 2.67-2.54 (m, 4H), 2.19-2.03 (m, 2H), 1.89 (t, J = 5.9 Hz, 1H). Aliphatic region complicated significantly by amide rotamers. |
| 567 | 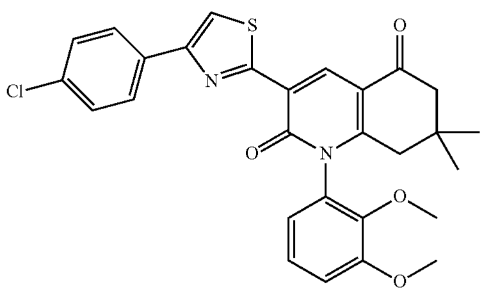 [SMILES: COc1cccc(-n2c3c(cc(-c4nc(-c5ccc(Cl)cc5)cs4)c2=O)C(=O)CC(C)(C)C3)c1OC] | C | C | 521.1304 | 3.935 | Starting material: 5,5-dimethylcyclohexane-1,3-dione (step1 method M); nitrile 1 (step2 method M); 2,3-dimethoxyaniline (step 3 method M), Methods: M | 1H NMR (400 MHz, CDCl3) δ 9.36 (s, 1H), 8.00 (d, J = 7.8 Hz, 2H), 7.57 (d, J = 0.9 Hz, 1H), 7.42 (d, J = 7.7 Hz, 2H), 7.26 (s, 1H), 7.12 (d, J = 8.4 Hz, 1H), 6.81 (d, J = 7.9 Hz, 1H), 3.97 (d, J = 0.6 Hz, 3H), 3.76 (d, J = 0.9 Hz, 3H), 2.53-2.36 (m, 4H), 1.07 (t, J =9.8 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 568 | 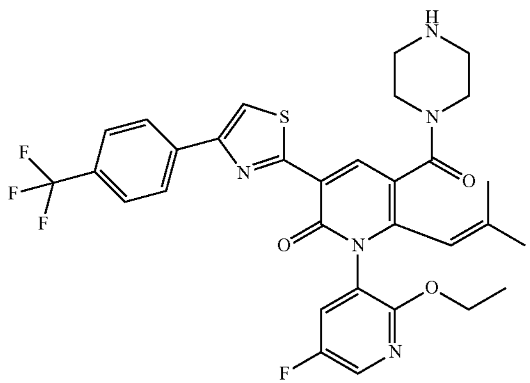 [SMILES: CCOc1ncc(F)cc1-n1c(C=C(C)C)c(C(=O)N2CCNCC2)cc(-c2nc(-c3ccc(C(F)(F)F)cc3)cs2)c1=O] | A | A | 650.184 | 2.708 | Starting materials: 6,6-dimethyldihydro-2H-pyran-2,4(3H)-dione (step 1), 2-(4-(4-(trifluoromethyl)phenyl)thiazol-2-yl)acetonitrile (step 2), 2-ethoxy-5-fluoropyridin-3-amine (step 3); Methods: W, then V (steps 4-6) | TFA salt: 1H NMR(400 MHz, DMSO-d6) δ 8.83 (bs, 2H), 8.73 (s, 1H), 8.44 (s, 1H), 8.36 (d, J = 2.9 Hz, 1H), 8.31 (d, J = 8.1 Hz, 2H), 8.07 (dd, J = 8.1, 3.0 Hz, 1H), 7.85 (d, J = 8.2 Hz, 2H), 5.70-5.51 (m, 1H), 4.54-3.86 (m, 2H), 3.67-2.88 (m, 8H), 1.64 (s, 3H), 1.56 (s, 3H), 1.25-1.10 (m, 3H). |
| 569 | 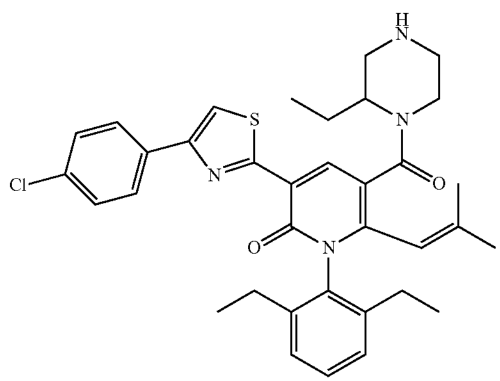 [SMILES: CCc1cccc(CC)c1-n1c(C=C(C)C)c(C(=O)N2CCNCC2CC)cc(-c2nc(-c3ccc(Cl)cc3)cs2)c1=O] | A | A | 615.2534 | 2.871 | Starting materials: 6,6-dimethyldihydro-2H-pyran-2,4(3H)-dione (step 1), Nitrile 1 (step 2), tert-butyl 3-ethylpiperazine-1-carboxylate (used in methods V, step 5); Methods: V | 1H NMR (400 MHz, DMSO-d6) δ 8.73 (s, 1H), 8.25 (s, 1H), 8.14-8.02 (m, 2H), 7.57-7.49 (m, 2H), 7.42 (q, J = 7.5 Hz, 1H), 5.30 (s, 1H), 4.72-4.41 (m, 1H), 3.68-3.51 (m, 1H), 3.27-2.96 (m, 4H), 2.68-2.51 (m, 1H), 2.41-2.19 (m, 2H), 2.10-2.01 (m, 2H), 1.76-1.65 (m, 1H), 1.64-1.35 (m, 7H), 1.11 (qt, J = 7.6, 4.0 Hz, 3H), 1.00 (t, J = 7.5 Hz, 3H), 0.84 (t, J = 7.4 Hz, 3H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 570 | 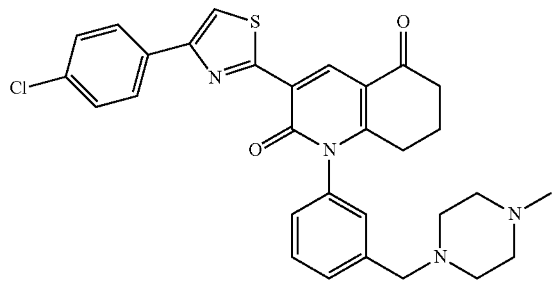 [SMILES: CN1CCN(Cc2cccc(-n3c4c(cc(-c5nc(-c6ccc(Cl)cc6)cs5)c3=O)C(=O)CCC4)c2)CC1] | E | E | 545.1745 | 2.631 | Starting material: cyclohexane-1,3-dione (step1 method M); nitrile 1 (step2 method M); 3-((4-methylpiperazin-1-yl)methyl)aniline (step 3 method M), Methods: M | |
| 571 | 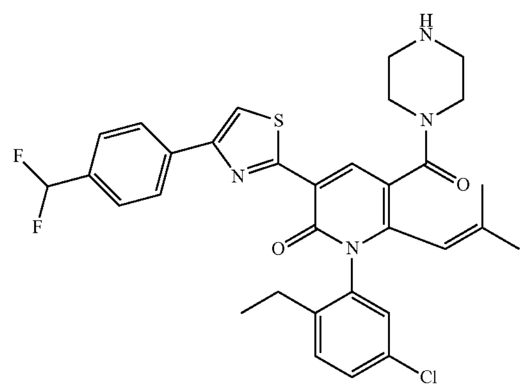 [SMILES: CCc1ccc(Cl)cc1-n1c(C=C(C)C)c(C(=O)N2CCNCC2)cc(-c2nc(-c3ccc(C(F)F)cc3)cs2)c1=O] | A | A | 305.1 | 2.714 | Starting materials: 6,6-dimethyldihydro-2H-pyran-2,4(3H)-dione (step 1), Nitrile 24 (step 2); Methods: V, no step 6. | 1H NMR (400 MHz, DMSO-d6) δ 8.71 (s, 1H), 8.32 (s, 1H), 8.21 (d, J = 8.0 Hz, 3H), 7.75-7.40 (m, 4H), 7.35-6.88 (m, 1H), 5.51 (s, 1H), 4.15-3.54 (m, 2H), 3.22-2.55 (m, 3H), 2.38-1.75 (m, 3H), 1.70-1.46 (m, 7H), 1.41-0.86 (m, 5H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 572 | 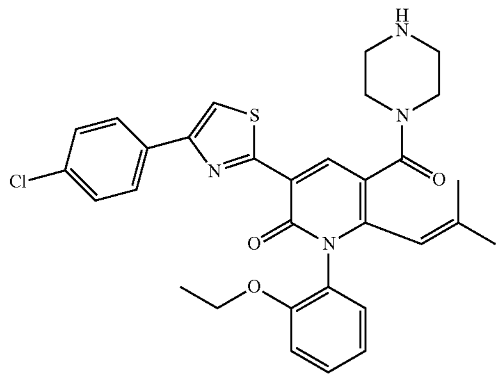 [SMILES: CCOc1ccccc1-n1c(C=C(C)C)c(C(=O)N2CCNCC2)cc(-c2nc(-c3ccc(Cl)cc3)cs2)c1=O] | A | A | 575.1885 | 2.636 | Starting material: 6,6-dimethyldihydro-2H-pyran-2,4(3H)-dione (step1 method V); nitrile 1 (step2 method V); 2-ethoxyaniline (step 3 method V), Methods: V | TFA salt: 1H NMR(400 MHz, CD3OD) δ 8.82 (s, 1H), 8.03 (d, J = 8.7 Hz, 2H), 7.91 (s, 1H), 7.52-7.43 (m, 3H), 7.37-7.07 (m, 3H), 5.61 (s, 1H), 4.40-3.91 (m, 4H), 3.89-3.50 (m, 4H), 3.35-3.10 (m, 2H), 1.65-1.61 (m, 6H), 1.30-1.15 (m, 3H). Aliphatic region complicated significantly by amide rotamers. |
| 573 | 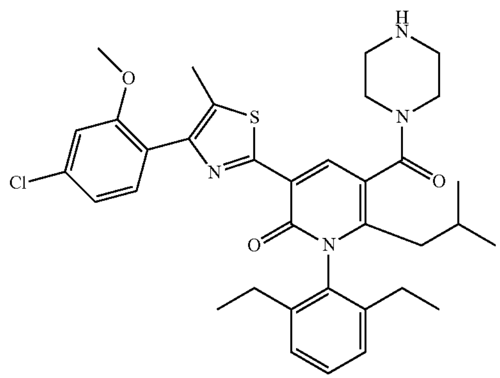 [SMILES: CCc1cccc(CC)c1-n1c(CC(C)C)c(C(=O)N2CCNCC2)cc(-c2nc(-c3ccc(Cl)cc3OC)c(C)s2)c1=O] | B | B | 633.2642 | 2.876 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-chloro-2-methoxyphenyl)boronic acid (method xix); Methods: S, then ester hydrolyzed with LiOH (4 eq), THF/MeOH/water, 50C, U, xix, then Boc removal with TFA/DCM rt | 1H NMR (400 MHz, DMSO-d6) δ 8.73 (s, 1H), 8.44 (s, 1H), 7.47 (t, J = 7.6 Hz, 1H), 7.33 (dd, J = 7.9, 2.4 Hz, 3H), 7.20 (d, J = 2.0 Hz, 1H), 7.09 (dd, J = 8.1, 2.0 Hz, 1H), 4.07-3.87 (m, 1H), 3.78 (s, 3H), 3.69 (s, 1H), 3.51 (dd, J = 25.5, 11.3 Hz, 2H), 3.19-3.06 (m, 2H), 3.07-2.96 (m, 2H), 2.45-2.24 (m, 3H), 2.22 (s, 3H), 2.17-2.03 (m, 2H), 1.97 (dd, J = 16.3, 11.5 Hz, 1H), 1.30 (p, J = 6.8 Hz, 1H), 1.08 (s,6H), 0.59 (d, J = 6.6 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 574 | 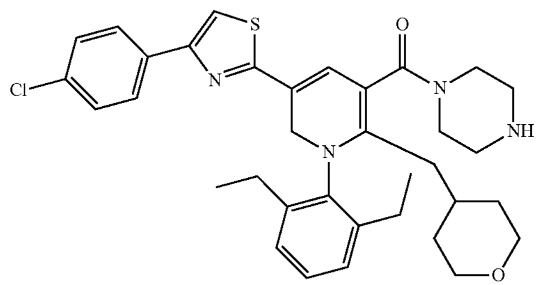 [SMILES: CCc1cccc(CC)c1N1CC(c2nc(-c3ccc(Cl)cc3)cs2)=CC(C(=O)N2CCNCC2)=C1CC1CCOCC1] | C | B | 653.2336 | 2.746 | Starting materials: ethyl 3-oxo-4-(tetrahydro-2H-pyran-4-yl) butanoate (step 1), Nitrile 1 (step 2), piperazine (used in method U); Methods: S, ester hydrolyzed with LiOH (xs), THF/MeOH/water, 60° C.; U | 1H NMR (400 MHz, DMSO-d6) δ 8.67 (s, 1H), 8.19 (s, 1H), 8.08 (d, J = 8.6 Hz, 2H), 7.51-7.41 (m, 3H), 7.33 (d, J = 7.7 Hz, 2H), 4.00 (s, 1H), 3.67-3.60 (m, 3H), 2.95 (td, J = 11.6, 2.4 Hz, 2H), 2.37-2.23 (m, 2H), 2.22-1.98 (m, 4H), 1.22-0.88 (m, 16H). |
| 575 | 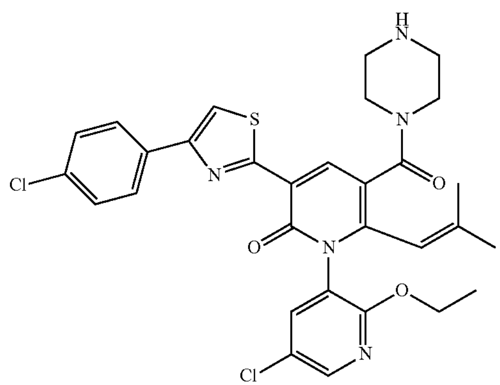 [SMILES: CCOc1ncc(Cl)cc1-n1c(C=C(C)C)c(C(=O)N2CCNCC2)cc(-c2nc(-c3ccc(Cl)cc3)cs2)c1=O] | A | A | 610.1459 | 2.735 | Starting materials: nitrile 1 (step2 method V); pyridyl amine 4 (step 3 method V); piperidine (step 5 method V), Methods: V, no step 7 | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 576 | (structure) | A | A | 627.18 | 2.795 | Starting materials: nitrile 7 (step 2 method W); Aniline 4 (step 3 method W). Methods: W, then steps 4-6 in method V | ¹H NMR (400 MHz, DMSO-d₆) δ 8.83 (s, 1H), 8.74 (s, 1H), 8.43 (s, 1H), 8.31 (d, J = 8.1 Hz, 2H), 7.85 (d, J = 8.3 Hz, 2H), 7.65 (d, J=2.3 Hz, 1H), 7.59-7.45 (m, 2H), 5.53 (s, 1H), 4.07-3.97 (m, 1H), 3.74-3.64 (m, 1H), 3.50-3.42 (m, 1H), 3.20-3.05 (m, 4H), 3.00-2.93 (m, 1H), 2.18-2.08 (m, 2H), 1.62 (s, 3H), 1.58 (s, 3H), 0.99 (t, J = 7.5 Hz, 3H). |
| 577 | (structure) | A | A | 665.2388 | 3.097 | Starting materials: 6,6-dimethyldihydro-2H-pyran-2,4(3H)-dione (step 1), Nitrile 7 (step 2), (S)-1-tert-butyl 2-methyl piperazine-1,2-dicarboxylate (used in methods V, step 5); Methods: V, then ester hydrolyzed with LiOH (xs), THF/MeOH/water, 60° C. | 1H NMR (400 MHz, DMSO-d6) δ 8.72 (s, 1H), 8.41 (s, 1H), 8.29 (d, J = 8.1 Hz, 2H), 7.83 (d, J = 8.1 Hz, 2H), 7.50-7.36 (m, 1H), 7.29 (dt, J = 16.0, 7.1 Hz, 2H), 5.28 (s, 1H), 4.54 (t, J = 13.5 Hz, 1H), 4.13 (d, J = 15.1 Hz, 1H), 3.89-3.54 (m, 2H), 3.14-2.61 (m, 2H), 2.43-2.17 (m, 2H), 2.15-2.00 (m, 2H), 1.65-1.48 (m, 7H), 1.24-1.05 (m, 4H), 1.05-0.92 (m, 3H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 578 | 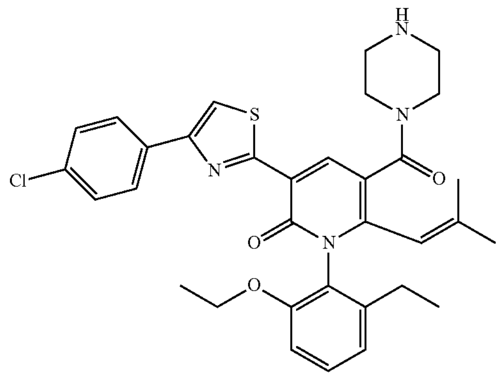 [SMILES: CCOc1cccc(CC)c1-n1c(C=C(C)C)c(C(=O)N2CCNCC2)cc(-c2nc(-c3ccc(Cl)cc3)cs2)c1=O] | A | A | 603.2202 | 2.735 | Starting material: 6,6-dimethyldihydro-2H-pyran-2,4(3H)-dione (step1 method V); nitrile 1 (step2 method V); aniline 7 (step 3 method V), Methods: V | TFA salt: 1H NMR (400 MHz, CD3OD) δ 8.85 (s, 1H), 8.03 (d, J = 8.6 Hz, 2H), 7.92 (s, 1H), 7.45-7.38 (m, 3H), 7.07-6.91 (m, 2H), 5.55-5.35 (m, 1H), 4.40-4.25 (m, 1H), 4.20-3.90 (m, 2H), 3.85-3.65 (m, 1H), 3.60-3.40 (m, 2H), 3.35-3.10 (m, 4H), 2.50-2.20 (m, 2H), 1.68-1.57 (m, 6H), 1.25-1.05 (m, 6H). Aliphatic region complicated significantly by amide rotamers. |
| 579 | 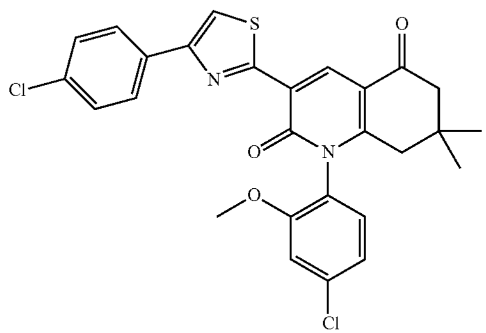 | D | D | 525.0799 | 3.957 | Starting material: 5,5-dimethylcyclohexane-1,3-dione (step1 method M); nitrile 1 (step2 method M); 4-chloro-2-methoxyaniline (step 3 method M), Methods: M | 1H NMR (400 MHz, CDCl3) δ 9.34 (s, 1H), 8.03-7.95 (m, 2H), 7.57 (s, 1H), 7.46-7.39 (m, 2H), 7.20-7.11 (m, 3H), 3.82 (s, 3H), 2.56-2.40 (m, 3H), 2.30 (d, J = 17.7 Hz, 1H), 1.07 (t, J = 6.5 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 580 | 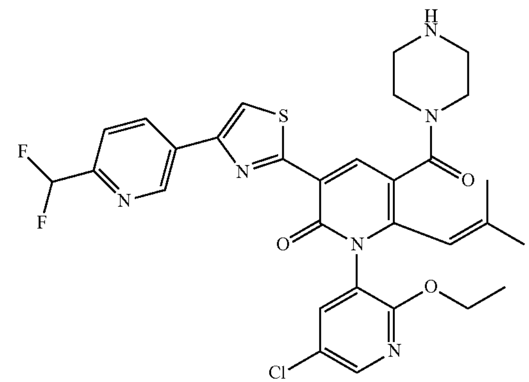 [SMILES: CCOc1ncc(Cl)cc1-n1c(C=C(C)C)c(C(=O)N2CCNCC2)cc(-c2nc(-c3ccc(C(F)F)nc3)cs2)c1=O] | A | B | 627.1772 | 2.548 | Starting materials: nitrile 25 (step 2 of method W), pyridyl amine 4 (step 3 of method W); Methods: W, X | 1H NMR (400 MHz, DMSO-d6) δ 9.46-9.25 (m, 1H), 8.76-8.52 (m, 2H), 8.48 (s, 1H), 8.36 (d, J = 2.4 Hz, 1H), 8.23-8.13 (br m, 1H), 7.79 (d, J = 8.2 Hz, 1H), 7.00 (t, J = 55.0 Hz, 1H), 5.55 (br s, 1H), 4.57-4.02 (m, 2H), 3.60-3.35 (br m, 2H), 2.88-2.52 (m, 4H), 1.61 (s, 3H), 1.53 (s, 3H), 1.26-1.03 (m, 3H). |
| 581 | 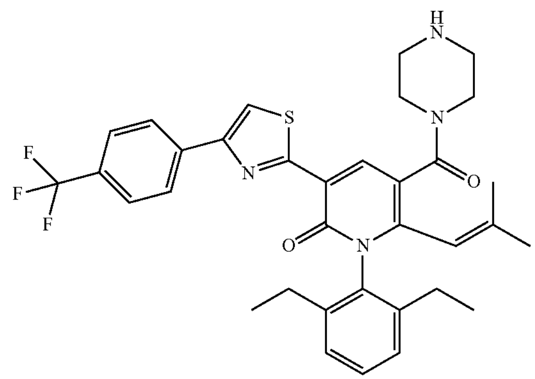 [SMILES: CCc1cccc(CC)c1-n1c(C=C(C)C)c(C(=O)N2CCNCC2)cc(-c2nc(-c3ccc(C(F)(F)F)cc3)cs2)c1=O] | A | A | 621.2502 | 2.82 | Starting materials: 6,6-dimethyldihydro-2H-pyran-2,4(3H)-dione (step 1), Nitrile 7 (step 2); Methods: V | 1H NMR (400 MHz, DMSO-d6) δ 8.67 (s, 1H), 8.38 (s, 1H), 8.33-8.24 (m, 2H), 7.81 (dq, J = 7.3, 0.8 Hz, 2H), 7.41 (t, J = 7.7 Hz, 1H), 7.28 (dd, J = 18.0, 7.6 Hz, 2H), 5.23 (p, J = 1.4 Hz, 1H), 3.61-3.49 (m, 1H), 3.25-3.06 (m, 2H), 2.75-2.52 (m, 4H), 2.28 (dp, J = 22.5, 7.5 Hz, 2H), 2.08 (ddq, J = 16.7,15.0, 7.6 Hz, 2H), 1.55 (dd, J = 7.0,1.4 Hz, 7H), 1.20 (s, 1H), 1.09 (t, J = 7.5 Hz, 3H), 0.98 (t, J = 7.5 Hz, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 582 | 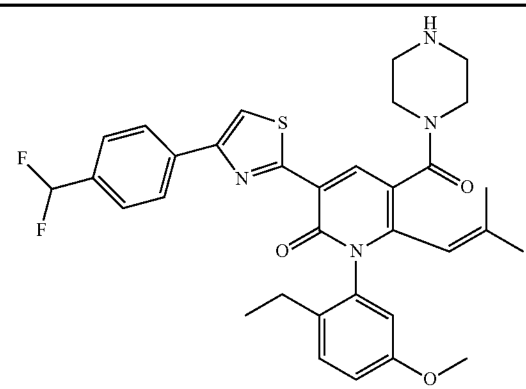 | | | | | | |
| 583 | 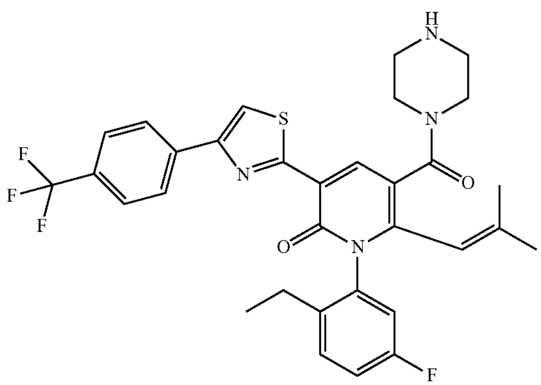 [SMILES: CCc1ccc(F)cc1-n1c(C=C(C)C)c(C(=O)N2CCNCC2)cc(-c2nc(-c3ccc(C(F)(F)F)cc3)cs2)c1=O] | A | A | 611.21 | 2.758 | Starting materials: 6,6-dimethyldihydro-2H-pyran-2,4(3H)-dione (step 1), 2-(4-(4-(trifluoromethyl)phenyl)thiazol-2-yl)acetonitrile (step 2), 2-ethyl-5-fluoroaniline (step 3); Methods: W, then V (steps 4-6) | 1H NMR (400 MHz, DMSO-d6) δ 8.74 (bs, 1H), 8.71 (s, 1H), 8.65 (bs, 1H), 8.40 (s, 1H), 8.28 (d, J = 8.1 Hz, 2H), 7.82 (d, J = 8.2 Hz, 2H), 7.55-7.08 (m, 3H), 5.66-5.27 (m, 1H), 4.09-3.86 (m, 1H), 3.72-3.55 (m, 1H), 3.48-2.88 (m, 6H), 2.15-2.02 (m, 2H), 1.59 (s, 3H), 1.55 (s, 3H), 1.15-0.91 (m, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | $^1$H-NMR |
|---|---|---|---|---|---|---|---|
| 585 | 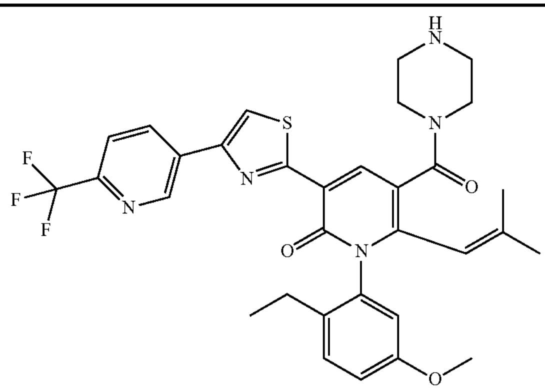 | | | | | | |
| 586 | 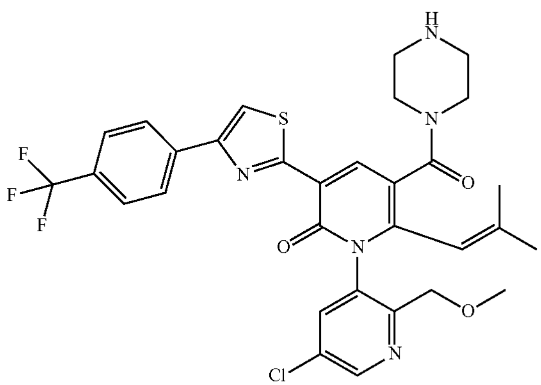 [SMILES: COCc1ncc(Cl)cc1-n1c(C=C(C)C)c(C(=O)N2CCNCC2)cc(-c2nc(-c3ccc(C(F)(F)F)cc3)cs2)c1=O] | A | A | 644.1693 | 2.763 | Starting materials: 6,6-dimethyldihydro-2H-pyran-2,4(3H)-dione (step 1), Nitrile 7 (step 2), pyridyl amine 4 (step 3 of methods V); Methods: V, no step 6. | 1H NMR (400 MHz, DMSO-d6) δ 8.69 (s, 1H), 8.40 (s, 1H), 8.10 (d, J = 2.2 Hz, 1H), 7.83 (d, J = 8.3 Hz, 3H), 5.54 (s, 1H), 4.31-3.89 (m, 2H), 3.67-3.37 (m, 2H), 3.23-2.85 (m, 2H), 2.38-2.20 (m, 4H), 1.65-1.48 (m, 6H), 1.25-1.05 (m, 3H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 587 | 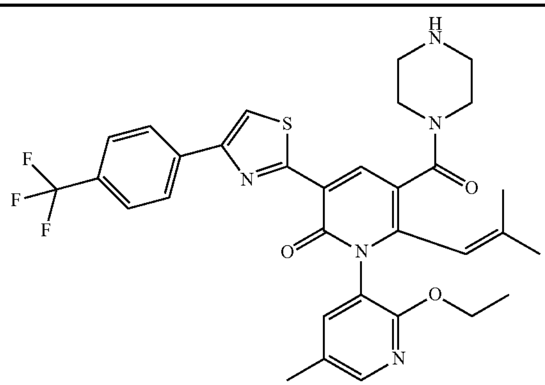 | A | A | 624.225 | 2.689 | Starting materials: 6,6-dimethyldihydro-2H-pyran-2,4(3H)-dione (step 1), Nitrile 7 (step 2), pyridyl amine 8 (step 3 of methods V); Methods: V, no step 6. | 1H NMR (400 MHz, DMSO-d6) δ 8.70 (s, 1H), 8.42 (s, 1H), 8.38 (dd, J = 2.5, 0.7 Hz, 1H), 8.29 (d, J = 8.1 Hz, 2H), 8.14 (d, J = 2.5 Hz, 1H), 7.83 (d, J = 8.2 Hz, 3H), 5.60 (s, 1H), 4.48-4.17 (m, 3H), 3.98-3.83 (m, 1H), 3.69-3.38 (m, 4H), 3.24-2.97 (m, 2H), 2.41-2.04 (m, 2H), 1.75-1.48 (m, 7H), 1.24-1.07 (m, 3H). |
| 589 | 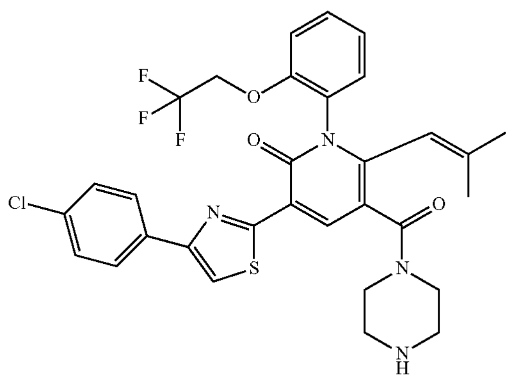 [SMILES: CC(C)=Cc1c(C(=O)N2CCNCC2)cc(-c2nc(-c3ccc(Cl)cc3)cs2)c(=O)n1-c1ccccc1OCC(F)(F)F] | A | A | 629.1595 | 2.639 | Starting material: 6,6-dimethyldihydro-2H-pyran-2,4(3H)-dione (step1 method V); nitrile 1 (step2 method V); 2-(2,2,2-trifluoroethoxy)aniline (step 3 method V), Methods: V | TFA salt: 1H NMR (400 MHz, CD3OD) δ 8.82 (s, 1H), 8.04 (d, J = 8.6 Hz, 2H), 7.93 (s, 1H), 7.56 (t, J = 8.8 Hz, 1H), 7.45 (d, J = 8.6 Hz, 2H), 7.35-7.18 (m, 3H), 5.70-5.50 (m, 1H), 4.21 (s, 2H), 3.90-3.50 (m, 4H), 3.35-3.10 (m, 4H), 1.66-1.59 (m, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 590 | 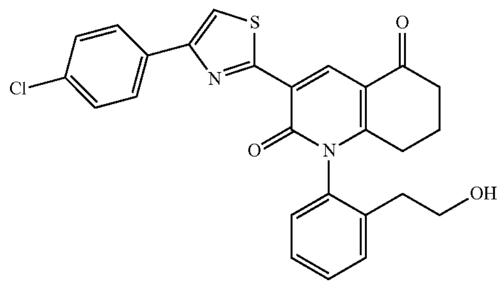 [SMILES: O=C1CCCc2c1cc(-c1nc(-c3ccc(Cl)cc3)cs1)c(=O)n2-c1ccccc1CCO] | D | D | 477.1026 | 3.501 | Starting material: cyclohexane-1,3-dione (step1 method M); nitrile 1 (step2 method M); 2-(2-aminophenyl)ethanol (step 3 method M), Methods: M | 1H NMR (400 MHz, CD3OD) δ 9.28 (s, 1H), 7.93 (d, J = 8.4 Hz, 2H), 7.58 (s, 1H), 7.52-7.49 (m, 2H), 7.42-7.41 (m, 1H), 7.36 (d, J = 8.4 Hz, 2H), 7.15 (d, J = 8.4 Hz, 2H), 4.28 (m, 3H), 3.69 (t, J = 8.4 Hz, 2H), 2.50-2.43 (m, 4H), 2.09-2.00 (m, 2H). Aliphatic region complicated significantly by amide rotamers. |
| 591 | 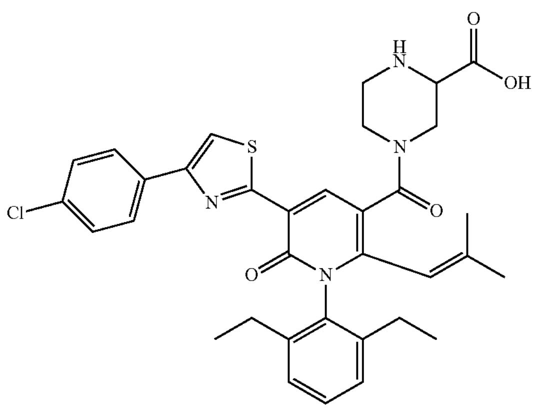 [SMILES: CCc1cccc(CC)c1-n1c(C=C(C)C)c(C(=O)N2CCNC(C(=O)O)C2)cc(-c2nc(-c3ccc(Cl)cc3)cs2)c1=O] | A | A | 631.2151 | 3.038 | Starting materials: 6,6-dimethyldihydro-2H-pyran-2,4(3H)-dione (step 1), Nitrile 1 (step 2), 1-tert-butyl 2-methyl piperazine-1,2-dicarboxylate (used in methods V, step 5); Methods: V, then ester hydrolyzed with LiOH (xs), THF/MeOH/water, 60° C. | 1H NMR (400 MHz, DMSO-d6) δ 8.75 (s, 1H), 8.25 (s, 1H), 8.09 (dd, J = 8.2, 1.3 Hz, 2H), 7.53 (dd, J = 8.6, 2.3 Hz, 2H), 7.43 (td, J = 7.7, 5.6 Hz, 1H), 7.36-7.18 (m, 2H), 5.28 (s, 1H), 4.58-4.48 (m, 1H), 4.20-4.04 (m, 1H), 3.87-3.57 (m, 1H), 3.12-2.62 (m, 2H), 2.44-2.17 (m, 2H), 2.20-1.99 (m, 2H), 1.63-1.49 (m, 6H), 1.24-1.05 (m, 3H), 1.03-0.94 (m, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 592 | 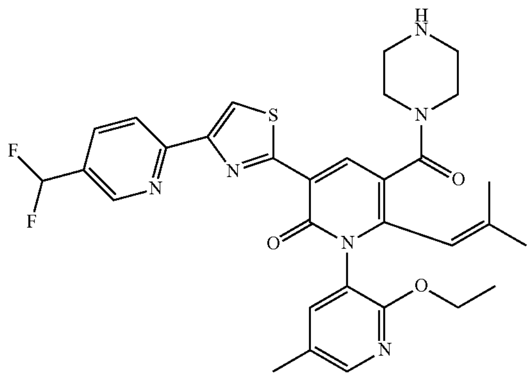 [SMILES: CCOc1ncc(C)cc1-n1c(C=C(C)C)c(C(=O)N2CCNCC2)cc(-c2nc(-c3ccc(C(F)F)cn3)cs2)c1=O] | B | C | 607.2276 | 2.472 | Starting materials: nitrile 29 (step 2 method W); pyridyl amine 6 (step 3 method W), Methods: W, then steps 4-6 in method V | 1H NMR (400 MHz, DMSO-d6) δ 8.85 (dq, J = 2.3,1.2 Hz, 2H), 8.72 (s, 1H), 8.47 (s, 1H), 8.39 (d, J = 8.2 Hz, 1H), 8.16 (ddt, J = 8.3, 2.3, 1.1 Hz, 1H), 8.12 (dd, J = 2.3, 1.0 Hz, 1H), 7.69 (d, J = 35.0 Hz, 1H), 7.22 (t, J = 55.4 Hz, 1H), 5.56 (s, 1H), 4.32-3.91 (m, 2H), 3.57 (d, J=76.9 Hz, 4H), 3.28-2.86 (m, 4H), 2.32 (s, 3H), 1.62 (d, J = 1.4 Hz, 3H), 1.55 (s, 3H), 1.26-1.05 (m, 3H). Aliphatic region complicated significantly by amide rotamers. |
| 593 | 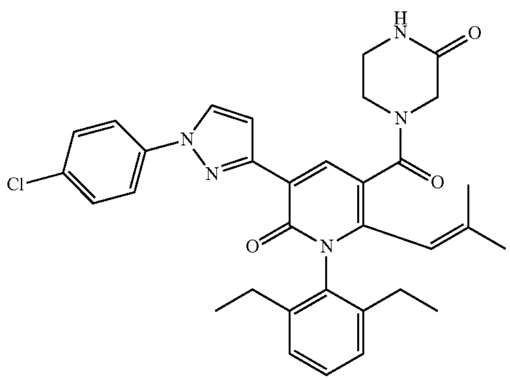 [SMILES: CCc1cccc(CC)c1-n1c(C=C(C)C)c(C(=O)N2CCNC(=O)C2)cc(-c2ccn(-c3ccc(Cl)cc3)n2)c1=O] | A | A | 584.2424 | 3.368 | Starting materials: pyrazole 2 (step 2), piperazine-2-carboxamide (step 5); Methods: V, step 4 with NaOH (xs), no step 6. | |

| Cpd # | Structure | Data for R132H (μM) | Data for R132C (μM) | MZ | RT (min) | Synthesis Method | ¹H-NMR |
|---|---|---|---|---|---|---|---|
| 594 | 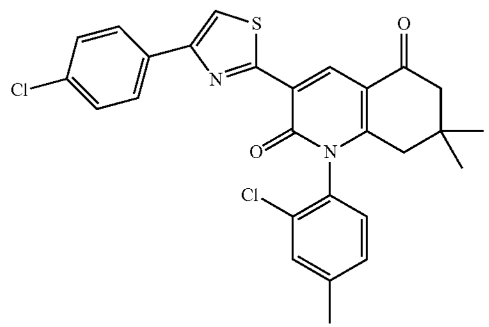 [SMILES: Cc1ccc(-n2c3c(cc(-c4nc(-c5ccc(Cl)cc5)cs4)c2=O)C(=O)CC(C)(C)C3)c(Cl)c1] | E | C | 509.0875 | 4.078 | Starting material: 5,5-dimethylcyclohexane-1,3-dione (step1 method M); nitrile 1 (step2 method M); 2-chloro-4-methylaniline (step 3 method M), Methods: M | 1H NMR (400 MHz, CDCl3) δ 9.36 (s, 1H), 8.03-7.97 (m, 2H), 7.58 (s, 1H), 7.48 (s, 1H), 7.46-7.40 (m, 2H), 7.32 (d, J = 8.0 Hz, 1H), 7.20 (d, J = 8.0 Hz, 1H), 2.55-2.41 (m, 6H), 2.31 (d, J = 17.9 Hz, 1H), 1.07 (d, J = 9.0 Hz, 6H). Aliphatic region complicated significantly by amide rotamers. |
| 595 | 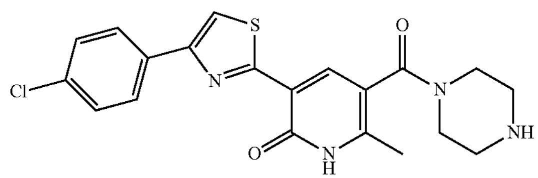 [SMILES: Cc1[nH]c(=O)c(-c2nc(-c3ccc(Cl)cc3)cs2)cc1C(=O)N1CCNCC1] | E | E | 415.0988 | 2.288 | Starting material: methyl 3-oxobutanoate (step1 method F); nitrile 1 (step2 method F); Methods: F (step 1-2), V (step 5-6) | HCl salt: 1H NMR (400 MHz, CD3OD) δ 8.60 (s, 1H), 7.99 (d, J = 8.4 Hz, 2H), 7.88 (s, 1H), 7.42 (d, J = 8.4 Hz, 2H), 3.91-3.87 (m, 4H), 3.29-3.30 (m, 4H), 2.40 (s, 3H). |
| 596 | 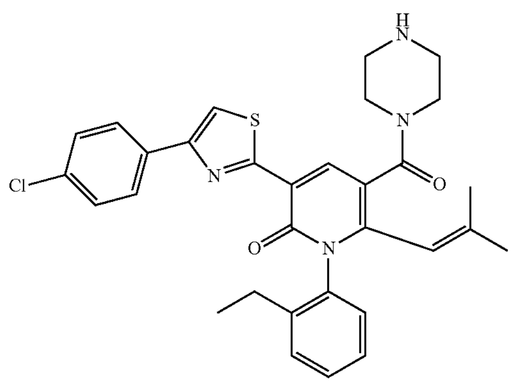 [SMILES: CCc1ccccc1-n1c(C=C(C)C)c(C(=O)N2CCNCC2)cc(-c2nc(-c3ccc(Cl)cc3)cs2)c1=O] | A | A | 559.1937 | 2.675 | Starting material: 6,6-dimethyldihydro-2H-pyran-2,4(3H)-dione (step1 method V); nitrile 1 (step2 method V); 2-ethylaniline (step 3 method V), Methods: V | TFA salt: 1H NMR(400 MHz, CD3OD) δ 8.86 (s, 1H), 8.04 (d, J = 8.7 Hz, 2H), 7.94 (s, 1H), 7.53-7.47 (m, 2H), 7.45 (d, J = 8.6 Hz, 2H), 7.44-7.00 (m, 2H), 5.62-5.42 (m, 1H), 4.35-4.25 (m, 2H), 3.90-3.50 (m, 4H), 3.35-3.10 (m, 2H), 2.50-2.25 (m, 2H), 1.67-1.57 (m, 6H), 1.25-1.05 (m, 3H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 597 | 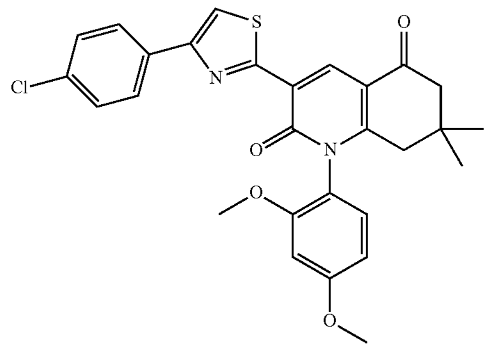 [SMILES: COc1ccc(-n2c3c(cc(-c4nc(-c5ccc(Cl)cc5)cs4)c2=O)C(=O)CC(C)(C)C3)c(OC)c1] | E | E | 521.1308 | 3.882 | Starting material: 5,5-dimethylcyclohexane-1,3-dione (step1 method M); nitrile 1 (step2 method M); 2,4-dimethoxyaniline (step 3 method M), Methods: M | 1H NMR (400 MHz, CDCl3) δ 9.33 (s, 1H), 8.03-7.96 (m, 2H), 7.56 (s, 1H), 7.42 (dd, J = 8.8, 2.2 Hz, 2H), 7.11 (d, J = 9.1 Hz, 1H), 6.70-6.64 (m, 2H), 3.90 (s, 3H), 3.78 (s,3H), 2.55-2.45 (m, 3H), 2.34 (d, J = 17.9 Hz, 1H), 1.06 (d, J = 6.4 Hz, 6H). Aliphatic region complicated significantly by amide rotamers. |
| 598 | 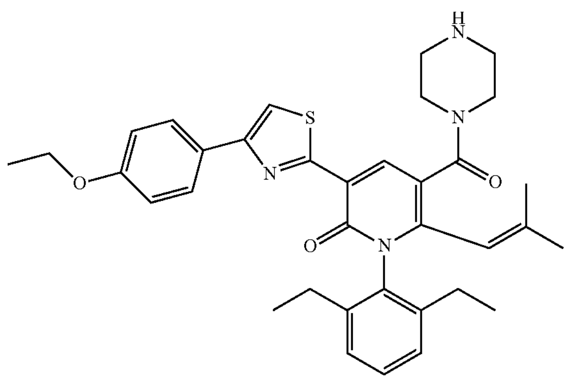 [SMILES: CCOc1ccc(-c2csc(-c3cc(C(=O)N4CCNCC4)c(C=C(C)C)n(-c4c(CC)cccc4CC)c3=O)n2)cc1] | A | A | 597.2907 | 2.745 | Starting materials: 6,6-dimethyldihydro-2H-pyran-2,4(3H)-dione (step 1), Nitrile 28 (step 2); Methods: V | 1H NMR (400 MHz, DMSO-d6) δ 8.71 (s, 1H), 8.02 (s, 1H), 8.00-7.95 (m, 2H), 7.42 (t, J = 7.7 Hz, 1H), 7.29 (dd, J = 19.1, 7.7 Hz, 2H), 7.03-6.97 (m, 2H), 5.31-5.25 (m, 1H), 4.07 (q, J = 7.0 Hz, 2H), 3.62-3.55 (m, 2H), 3.24-2.91 (m, 2H), 2.42-2.20 (m, 4H), 2.16-2.00 (m, 4H), 1.67 (s, 6H), 1.34 (t, J = 7.0 Hz, 2H), 1.11 (t, J = 7.5 Hz, 3H), 0.99 (t, J = 7.6 Hz, 3H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 599 | 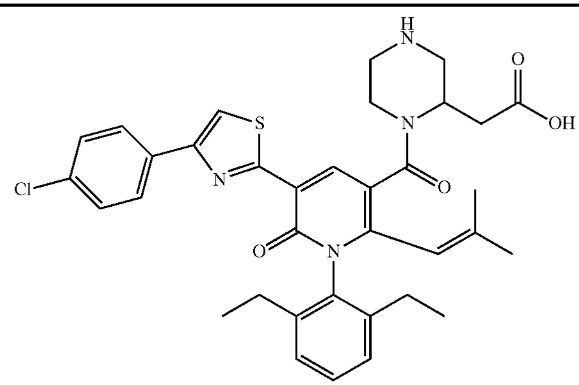 | A | A | 667.2127 | 2.773 | Starting materials: 6,6-dimethyldihydro-2H-pyran-2,4(3H)-dione (step 1), Nitrile 1 (step 2), tert-butyl 3-(2-methoxy-2-oxoethyl)piperazine-1-carboxylate (used in methods V, step 5); Methods: V, then ester hydrolyzed with LiOH (xs), THF/MeOH/water, 60° C. | 1H NMR (400 MHz, DMSO-d6) δ 8.71 (s, 1H), 8.25 (s, 1H), 8.10 (dt, J = 8.1, 2.9 Hz, 1H), 7.59-7.49 (m, 2H), 7.42 (td, J = 7.5, 4.0 Hz, 2H), 7.35-7.21 (m, 2H), 5.28 (s, 1H), 3.71-3.38 (m, 2H), 3.15-2.82 (m, 1H), 2.79-2.52 (m, 2H), 2.45-2.19 (m, 2H), 2.19-1.98 (m, 3H), 1.66-1.49 (m, 8H), 1.24-1.17 (m, 1H), 1.11 (tt, J = 7.3, 3.2 Hz, 3H), 0.98 (dt, J = 8.3, 6.6 Hz, 3H). |
| 600 | 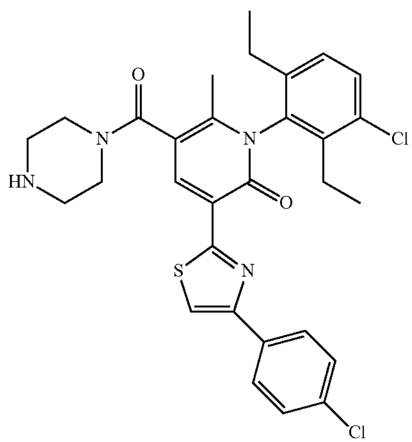 [SMILES: CCc1ccc(Cl)c(CC)c1-n1c(C)c(C(=O)N2CCNCC2)cc(-c2nc(-c3ccc(Cl)cc3)cs2)c1=O] | B | C | 581.1544 | 2.752 | Starting material: methyl 3-oxobutanoate (step1 method M); nitrile 1 (step2 method M); 2,6-diethylaniline (step 3 method M), Methods: M | TFA salt: 1H NMR (400 MHz, CD3OD) δ 8.80 (s, 1H), 8.07-8.02 (m, 2H), 7.94 (s, 1H), 7.60 (d, J = 8.4 Hz, 1H), 7.48-7.43 (m, 2H), 7.42 (d, J = 8.5 Hz, 1H), 4.34-4.04 (m, 1H), 3.87 (s, 3H), 3.45 (d, J = 43.0 Hz, 4H), 2.67 (dt, J = 14.9, 7.4 Hz, 1H), 2.36 (qd, J = 15.1, 7.1 Hz, 3H), 2.02 (s, 3H), 1.18 (t, J = 7.5 Hz, 3H), 1.09 (t, J = 7.5 Hz, 3H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 601 | 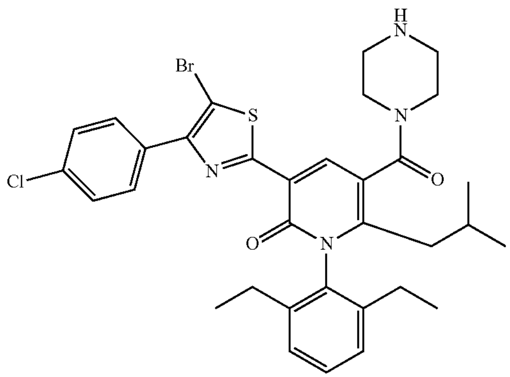 [SMILES: CCc1cccc(CC)c1-n1c(CC(C)C)c(C(=O)N2CCNCC2)cc(-c2nc(-c3ccc(Cl)cc3)c(Br)s2)c1=O] | B | A | 669.1476 | 3.033 | Starting material: methyl 5-methyl-3-oxohexanoate (step1 method V); nitrile 1 (step2 method V); 2,6-diethylaniline (step 3 method V), Methods: V(step1-5), bromination with NBS in DCM, then V (step 6) | TFA salt: 1H NMR(400 MHz, CD3OD) δ 8.67 (s, 1H), 8.02-7.96 (m, 2H), 7.56-7.48 (m, 3H), 7.40 (d, J = 7.7 Hz, 2H), 4.28 (s, 1H), 3.98 (s, 1H), 3.75 (s, 2H), 3.37 (d, J = 16.6 Hz, 3H), 2.69 (s, 2H), 2.42 (dt, J = 22.7, 7.5 Hz, 2H), 2.35-2.18 (m, 3H), 2.14 (s, 2H), 1.55-1.42 (m, 1H), 1.19 (t, J = 7.1 Hz, 6H), 0.71 (d, J = 6.6 Hz, 6H). Aliphatic region complicated significantly by amide rotamers. |
| 602 | 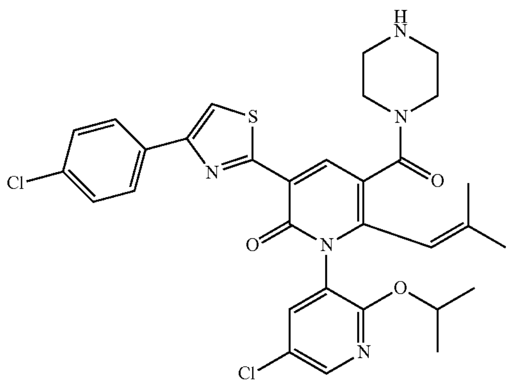 [SMILES: CC(C)=Cc1c(C(=O)N2CCNCC2)cc(-c2nc(-c3ccc(Cl)cc3)cs2)c(=O)n1-c1cc(Cl)cnc1OC(C)C] | A | A | 624.1594 | 2.793 | Starting materials: nitrile 1 (step2 method V); pyridyl amine 5 (step 3 method V); piperidine (step 5 method V), Methods: V, no step 7 | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | $^1$H-NMR |
|---|---|---|---|---|---|---|---|
| 603 | 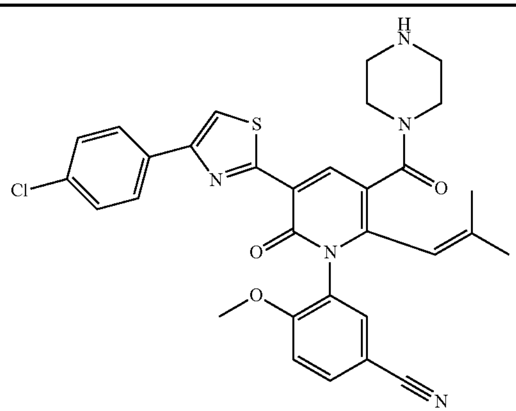 | B | B | 293.5886 | 2.572 | Starting material: 6,6-dimethyldihydro-2H-pyran-2,4(3H)-dione (step1 method V); nitrile 1 (step2 method V); 3-amino-4-methoxybenzonitrile (step 3 method V), Methods: V | TFA salt: 1H NMR(400 MHz, CD3OD) δ 8.83 (s, 1H), 8.03 (t, J = 5.6 Hz, 2H), 7.94 (s, 1H), 7.92 (dd, J = 8.7, 2.1Hz, 1H), 7.48-7.43 (m, 2H), 7.38 (s, 1H), 5.62 (s, 1H), 4.20 (s, 2H), 4.06 (d, J = 8.0 Hz, 1H), 3.90 (t, J = 19.1 Hz, 5H), 3.63 (s, 3H), 3.27 (s, 3H), 1.66 (d, J = 6.6 Hz, 6H). Aliphatic region complicated significantly by amide rotamers. |
| 604 | 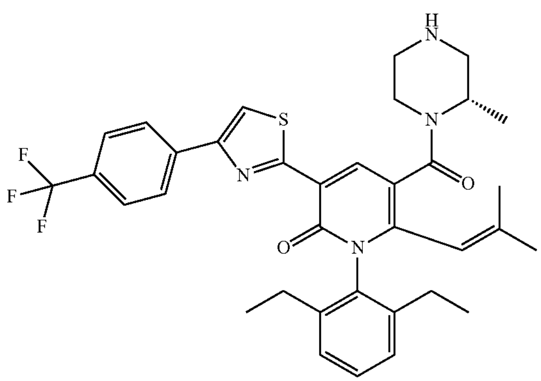 [SMILES: CCc1cccc(CC)c1-n1c(C=C(C)C)c(C(=O)N2CCNC[C@@H]2C)cc(-c2nc(-c3ccc(C(F)(F)F)cc3)cs2)c1=O] | A | A | 635.2673 | 2.849 | Starting materials: 6,6-dimethyldihydro-2H-pyran-2,4(3H)-dione (step 1), Nitrile 7 (step 2), (S)-tert-butyl 3-methylpiperazine-1-carboxylate (used in methods V, step 5); Methods: V. | 1H NMR (400 MHz, DMSO-d6) δ 8.72 (s, 1H), 8.40 (s, 1H), 8.29 (d, J = 8.1 Hz, 2H), 7.83 (d, J = 8.2 Hz, 2H), 7.48-7.23 (m, 3H), 5.29 (s, 1H), 4.34-4.22 (m, 1H), 3.68-3.39 (m, 2H), 2.68-2.56 (m, 2H), 2.43-2.21 (m, 2H), 2.18-2.00 (m, 2H), 1.63-1.47 (m, 7H), 1.06 (dt, J = 48.0, 7.6 Hz, 10H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 605 | 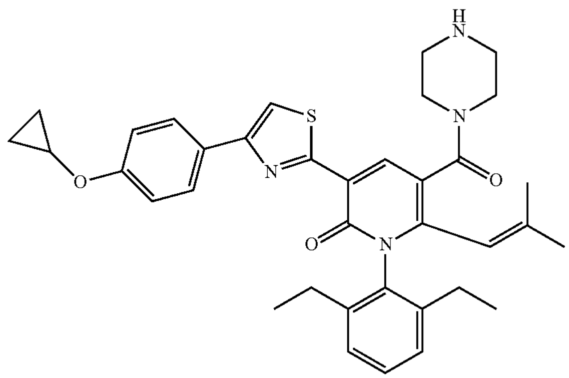 [SMILES: CCc1cccc(CC)c1-n1c(C=C(C)C)c(C(=O)N2CCNCC2)cc(-c2nc(-c3ccc(OC4CC4)cc3)cs2)c1=O] | A | A | 609.2894 | 2.781 | Starting materials: 6,6-dimethyldihydro-2H-pyran-2,4(3H)-dione (step 1), Nitrile 27 (step 2); Methods: V | |
| 606 | 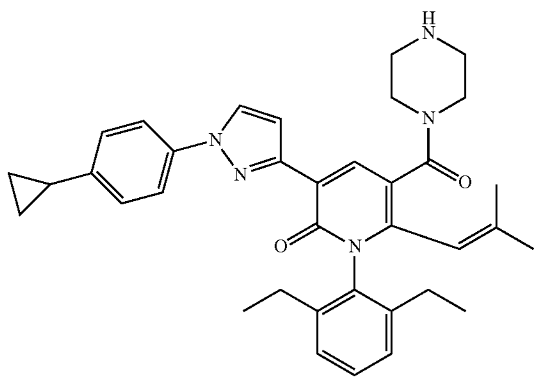 [SMILES: CCc1cccc(CC)c1-n1c(C=C(C)C)c(C(=O)N2CCNCC2)cc(-c2ccn(-c3ccc(C4CC4)cc3)n2)c1=O] | A | A | 598.3139 | 2.697 | Starting materials: pyrazole 7 (step 2), piperazine (step 5); Methods: V, step 4 with NaOH (xs), no step 6. | TFA salt: 1H NMR(400 MHz, DMSO-d6) δ 8.78 (br s, 1H), 8.67 (br s, 1H), 8.44 (d, J = 2.5 Hz, 1H), 8.32 (s, 1H), 7.81-7.68 (m, 2H), 7.37 (t, J = 7.6 Hz, 1H), 7.33-7.08 (m, 4H), 5.28-5.13 (m, 1H), 3.99 (d, J = 13.3 Hz, 1H), 3.54 (m, 1H), 3.10 (m, 3H), 2.42-2.18 (m, 1H), 1.96 (tt, J = 8.4, 5.1 Hz, 1H), 1.53 (t, J = 1.7 Hz, 6H), 1.12 (h, J = 7.2 Hz, 3H), 1.05-0.89 (m, 5H), 0.76-0.56 (m, 2H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | $^1$H-NMR |
|---|---|---|---|---|---|---|---|
| 608 | 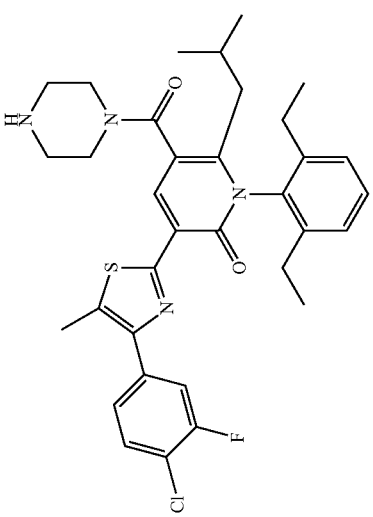 | A | A | 621.2432 | 3.292 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-chloro-3-fluorophenyl) boronic acid (method xix); Methods: S, then ester hydrolyzed LiOH (4 eq), THF/MeOH/water, 50 C., U, xix, with then Boc removal with TFA/DCM rt | 1H NMR (400 MHz, DMSO-d6) δ 8.56 (s, 1H), 7.82 (dd, J = 10.8, 1.9 Hz, 1H), 7.72-7.6 (m, 3H), 7.47 (t, J = 7.7 Hz, 1H), 7.35 (s, 1H), 7.33 (s, 1H), 3.96-3.84 (m, 1H), 3.74-3.55 (m, 2H), 3.55-3.42 (m, 1H), 3.15-2.85 (m, 4H), 2.58 (s, 3H), 2.25-1.90 (m, 6H), 1.38-1.26 (m, 1H), 1.13-1.02 (m, 6H), 0.60 (d, J = 6.6 Hz, 6H). Aliphatic region complicated significantly by amide rotamers. |
| 609 | 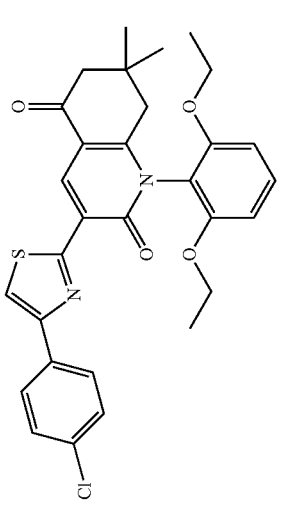 | B | B | 549.161 | 4.023 | Starting material: 5,5-dimethylcyclohexane-1,3-dione (step1 method M); nitrile 1 (step2 method M); 2,6-diethoxyaniline (step 3 method M). Methods: M | 1H NMR (400 MHz, CDCl3) δ 9.34 (s, 1H), 8.03-7.97 (m, 2H), 7.56 (s, 1H), 7.45-7.34 (m, 3H), 6.70 (dd, J = 8.5, 3.8 Hz, 2H), 4.06 (hd, J = 9.8, 7.2 Hz, 4H), 2.49 (s, 2H), 2.40 (s, 2H), 1.22 (t, J = 7.0 Hz, 6H), 1.07 (d, J = 11.2 Hz, 6H). Aliphatic region complicated significantly by amide rotamers. |
| 610 | 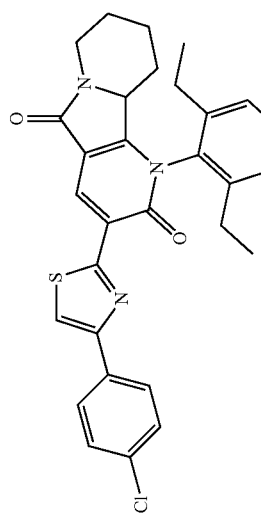 | B | B | 530.1656 | 4.054 | Starting materials: tert-butyl 2-(3-ethoxy-3-oxopropanoyl) piperidine-1-carboxylate (step 1), Nitrile 1 (step 2) piperazine (used in method U); Methods: S, ester hydrolyzed with LiOH (xs), THF/MeOH/water, 60° C.; U | 1H NMR (400 MHz, DMSO-d6) δ 8.86 (s, 1H), 8.22 (s, 1H), 8.13-8.08 (m, 2H) 7.51 (dd, J = 8.3, 1.9 Hz, 3H), 7.38-7.32 (m, 2H), 4.11 (t, J = 4.3 Hz, 1H), 2.43-2.28 (m, 2H), 2.43-2.02 (m, 8H), 1.62-1.53 (m, 2H), 1.10 (t, J = 7.5 Hz, 3H), 1.01 (t, J = 7.5 Hz, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 611 | 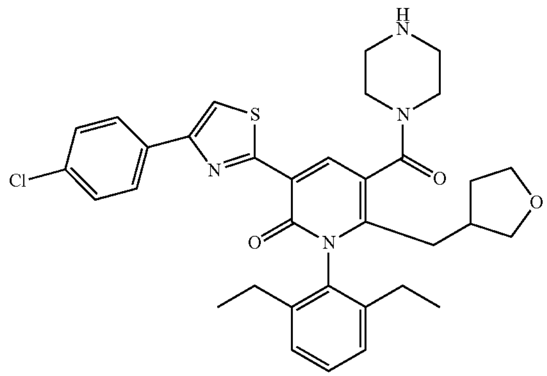 [SMILES: CCc1cccc(CC)c1-n1c(CC2CCOC2)c(C(=O)N2CCNCC2)cc(-c2nc(-c3ccc(Cl)cc3)cs2)c1=O] | A | A | 617.2332 | 2.722 | Starting materials: ethyl 3-oxo-4-(tetrahydrofuran-3-yl)butanoate (step 1), Nitrile 1 (step 2), piperazine (used in method U); Methods: S, ester hydrolyzed with LiOH (xs), THF/MeOH/water, 60° C.; U | 1H NMR (400 MHz, DMSO-d6) δ 8.68 (s, 1H), 8.18 (s, 1H), 8.10-8.05 (m, 2H), 7.48-7.41 (m, 3H), 7.31 (d, J = 7.7 Hz, 2H), 3.98 (s, 1H), 3.72 (s, 2H), 3.46 (d, J = 17.9 Hz, 2H), 3.07-2.95 (m, 6H), 2.57-2.49 (m, 1H), 2.16-1.90 (m, 6H), 1.71 (d, J = 21.7 Hz, 1H), 1.59 (d, J = 10.6 Hz, 2H), 1.38-135 (m, 1H), 1.02 (d, J = 9.1 Hz, 6H). |
| 612 | 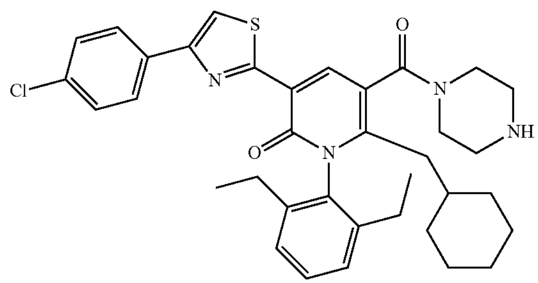 [SMILES: CCc1cccc(CC)c1-n1c(CC2CCCCC2)c(C(=O)N2CCNCC2)cc(-c2nc(-c3ccc(Cl)cc3)cs2)c1=O] | A | A | 629.2699 | 2.97 | Starting materials: ethyl 4-cyclohexyl-3-oxobutanoate (step 1), Nitrile 1 (step 2), piperazine (used in method U); Methods: S, ester hydrolyzed with LiOH (xs), THF/MeOH/water, 60° C.; U | |
| 613 | 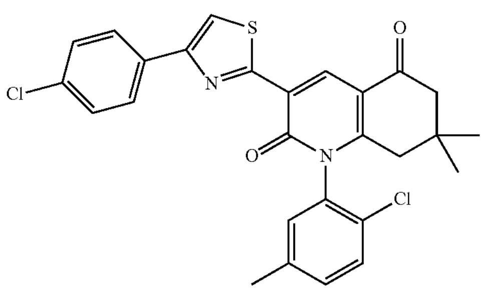 [SMILES: Cc1ccc(Cl)c(-n2c3c(cc(-c4nc(-c5ccc(Cl)cc5)cs4)c2=O)C(=O)CC(C)(C)C3)c1] | B | B | 509.0831 | 4.045 | Starting material: 5,5-dimethylcyclohexane-1,3-dione (step1 method M); nitrile 1 (step2 method M); 2-chloro-5-methylaniline (step 3 method M), Methods: M | 1H NMR (400 MHz, CDCl3) δ 9.37 (s, 1H), 7.99 (dd, J = 8.9, 2.2 Hz, 2H), 7.59 (s, 1H), 7.54 (d, J = 8.3 Hz, 1H), 7.45-7.40 (m, 2H), 7.34 (dd, J = 8.3,1.4 Hz, 1H), 7.14 (d, J = 1.2 Hz, 1H), 2.56-2.47 (m, 2H), 2.47-2.41 (m, 4H), 2.29 (d, J = 17.9 Hz, 1H), 1.09 (d, J = 2.1 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 614 | 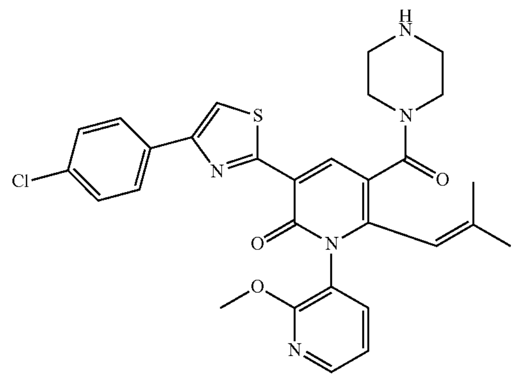 [SMILES: COc1ncccc1-n1c(C=C(C)C)c(C(=O)N2CCNCC2)cc(-c2nc(-c3ccc(Cl)cc3)cs2)c1=O] | A | A | 562.1694 | 2.533 | Starting material: 6,6-dimethyldihydro-2H-pyran-2,4(3H)-dione (step1 method V); nitrile 1 (step2 method V); 2-methoxypyridin-3-amine (step 3 method V), Methods: V | TFA salt: 1H NMR(400 MHz, CD3OD) δ 8.82 (s, 1H), 8.31-8.28 (m, 1H), 8.03 (d, J = 8.6 Hz, 1H), 7.94 (s, 1H), 7.85-7.60 (m, 1H), 7.44 (d, J = 8.6 Hz, 2H), 7.19-7.13 (m, 1H), 5.59 (s, 1H), 4.40-4.15 (m, 1H), 4.00-3.80 (m, 4H), 3.70-3.50 (m, 2H), 3.35-3.10 (m, 4H), 1.68-1.62 (m, 6H). Aliphatic region complicated significantly by amide rotamers. |
| 615 | 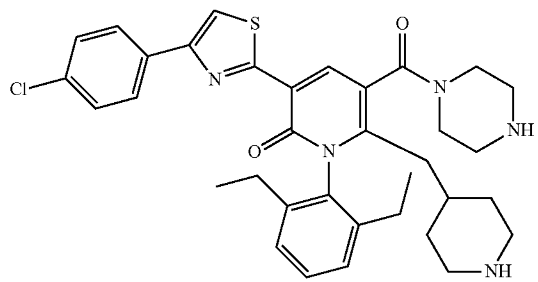 [SMILES: CCc1cccc(CC)c1-n1c(CC2CCNCC2)c(C(=O)N2CCNCC2)cc(-c2nc(-c3ccc(Cl)cc3)cs2)c1=O] | E | E | 315.6377 | 2.327 | Starting materials: tert-butyl 4-(4-ethoxy-2,4-dioxobutyl) piperidine-1-carboxylate(step 1), Nitrile 1 (step 2), tert-butyl piperazine-1-carboxylate (used in method U); Methods: S, ester hydrolyzed with LiOH, THF/MeOH/water, 60° C.; then Boc removal with TFA/DCM rt | 1H NMR (400 MHz, DMSO-d6) δ 8.71 (s, 1H), 8.22 (s, 1H), 8.15-8.05 (m, 2H), 7.55-7.44 (m, 3H), 7.35 (d, J = 7.7 Hz, 2H), 3.73-367 (s, 1H), 3.24-3.17 (m, 4H), 3.10-2.97 (m, 2H), 2.61-2.51 (m, 2H), 2.42-230 (m, 6H), 2.09-1.95 (m, 4H), 1.19-1.11 (m, 6H), 1.09 (t, J = 7.5 Hz, 6H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 616 | 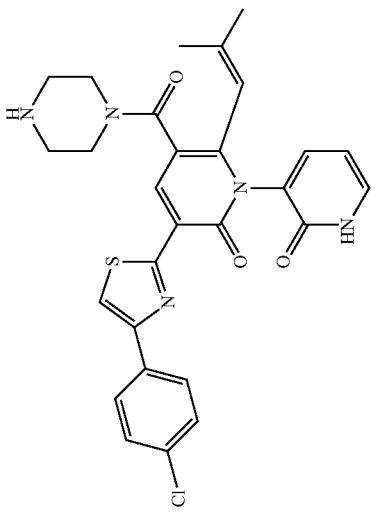 | D | D | 548.1531 | 2.362 | Starting material: 6,6-dimethyldihydro-2H-pyran-2,4(3H)-dione (step1 method V); nitrile 1 (step2 method V); 3-aminopyridin-2(1H)-one (step 3 method V), Methods: V | TFA salt: 1H NMR(400 MHz, CD3OD) δ 8.79 (s, 1H), 8.02 (d, J = 8.6 Hz, 2H), 7.93 (s, 1H), 7.75-7.60 (m, 2H), 7.44 (d, J = 8.6 Hz, 2H), 6.56 (t, J = 6.7 Hz, 1H), 5.72 (s, 1H), 4.30-4.20 (m, 1H), 3.90-3.80 (m, 1H), 3.70-3.50 (m, 2H), 3.35-3.10 (m, 4H), 1.77-1.63 (m, 6H). Aliphatic region complicated significantly by amide rotamers. |
| 617 | 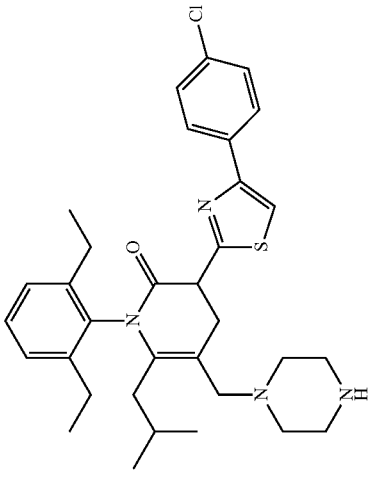 | C | C | 577.2762 | 2.888 | Compound 231 was reduced with DIBAL-H (4.3 eq), THF, 0 deg C. to rt | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 618 | 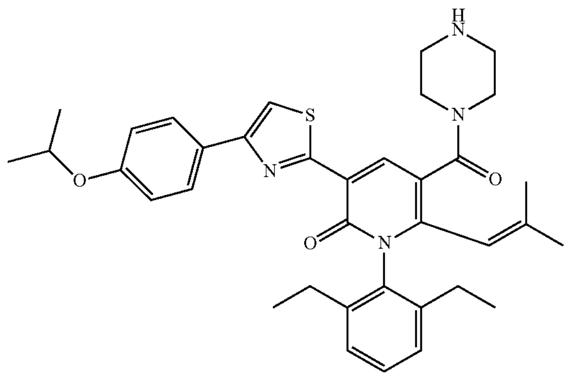 [SMILES: CCc1cccc(CC)c1-n1c(C=C(C)C)c(C(=O)N2CCNCC2)cc(-c2nc(-c3ccc(OC(C)C)cc3)cs2)c1=O] | A | A | 594.3428 | 2.686 | Starting materials: pyrazole 5 (step 2), piperazine (step 5); Methods: V, step 4 with NaOH (xs), no step 6. | TFA salt: 1H NMR(400 MHz, DMSO-d6) δ 8.72 (br s, 2H), 8.38 (d, J = 2.5 Hz, 1H), 8.31 (s, 1H), 7.84-7.66 (m, 2H), 7.37 (t, J = 7.6 Hz, 1H), 7.24 (dd, J = 17.2, 7.6 Hz, 2H), 7.14 (d, J = 2.4 Hz, 1H), 7.10-6.96 (m, 2H), 5.20 (t, J = 1.6 Hz, 1H), 4.64 (hept, J = 6.0 Hz, 1H), 3.99 (br d, J = 14.4 Hz, 1H), 3.54 (m, 1H), 3.39 (m, 1H), 3.22-2.84 (m, 4H), 2.43-2.19 (m, 2H), 2.19-1.96 (m, 2H), 1.53 (dd, J = 2.4, 1.4 Hz, 5H), 1.27 (d, J = 6.0 Hz, 5H), 1.05 (dt, J = 47.8, 7.7 Hz, 6H). |
| 619 | 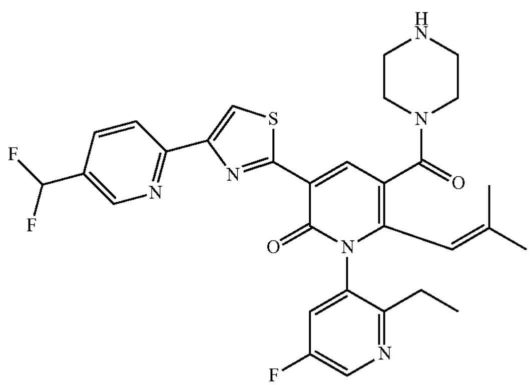 [SMILES: CCc1ncc(F)cc1-n1c(C=C(C)C)c(C(=O)N2CCNCC2)cc(-c2nc(-c3ccc(C(F)F)cn3)cs2)c1=O] | C | C | 595.2115 | 2.442 | Starting materials: nitrile 29 (step 2 method W); pyridyl amine 9 (step 3 method W), Methods: W, then steps 4-6 in method V | 1H NMR (400 MHz, DMSO-d6) δ 8.83 (s, 2H), 8.75 (s, 1H), 8.70 (d, J = 2.7 Hz, 1H), 8.46 (s, 1H), 8.36 (d, J = 8.1 Hz, 1H), 8.13 (d, J = 8.4 Hz, 1H), 8.01 (d, J = 8.7 Hz, 1H), 7.19 (t, J = 55.4 Hz, 1H), 5.57 (s, 1H), 4.00-3.90 (m, 1H), 3.20-3.08 (m, 4H), 3.08-3.00 (m, 2H), 2.96-2.86 (m, 1H), 2.31-2.22 (m, 1H), 1.56 (s, 6H), 1.21-1.10 (m, 1H), 1.04 (t, J = 7.5 Hz, 3H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 620 | 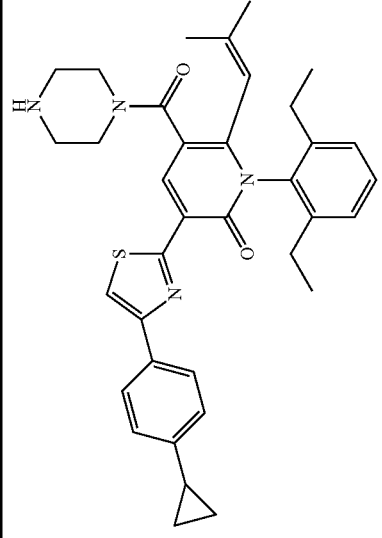 | A | A | 593.293 | 2.82 | Starting materials: 6,6-dimethyldihydro-2H-pyran-2,4(3H)-dione (step 1), Nitrile 32 (step 2); Methods: V | 1H NMR (400 MHz, DMSO-d6) δ 8.70 (s, 1H), 8.25 (d, J = 2.8 Hz, 1H), 8.16-8.05 (m, 3H), 7.58-7.48 (m, 4H), 5.51 (s, 1H), 4.09-3.95 (m, 1H), 3.72-3.65 (m, 1H), 3.22-2.91 (m, 4H), 2.71-2.62 (m, 2H), 2.15-2.05 (m, 4H), 1.63-1.51 (m, 6H), 1.14-1.04 (m, 5H), 0.97 (t, J = 7.7 Hz, 6H). |
| 621 | 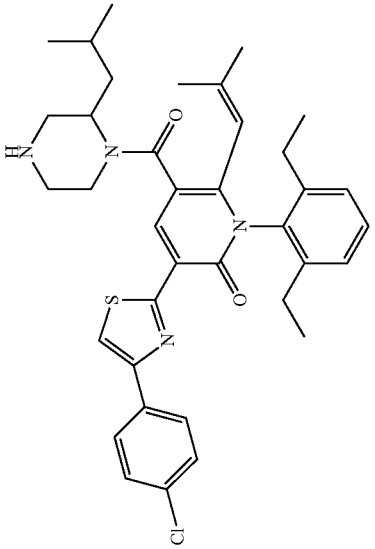 | B | A | 643.2865 | 2.979 | Starting materials: 6,6-dimethyldihydro-2H-pyran-2,4(3H)-dione (step 1), Nitrile 1 (step 2), tert-butyl 3-isobutylpiperazine-1-carboxylate (used in methods V, step 5); Methods: V | 1H NMR (400 MHz, DMSO-d6) δ 8.74 (s, 1H), 8.25 (s, 1H), 8.14-8.04 (m, 2H), 7.53 (dd, J = 8.8, 2.2 Hz, 2H), 7.41 (t, J = 7.7 Hz, 1H), 7.28 (dd, J = 18.2, 7.8 Hz, 2H), 5.30 (s, 1H), 4.90-4.70 (m, 1H), 3.73-3.63 (m, 1H), 3.28-2.86 (m, 4H), 2.43-2.20 (m, 2H), 2.20-1.94 (m, 2H), 1.66-1.44 (m, 6H), 1.43-1.29 (m, 2H), 1.11 (t, J = 7.5 Hz, 3H), 1.04-0.94 (m, 9H), 0.89 (t, J = 6.7 Hz, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 622 | 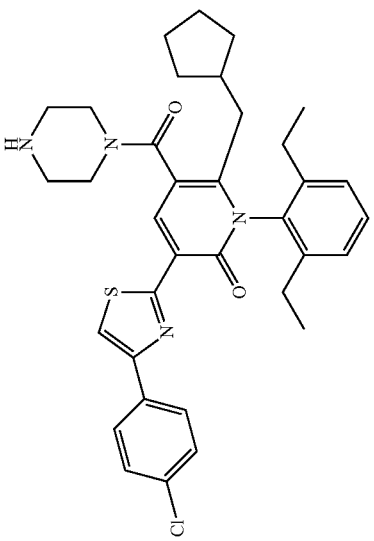 | A | A | 615.2533 | 2.915 | Starting materials: ethyl 4-cyclopentyl-3-oxobutanoate (step 1), Nitrile 1 (step 2), piperazine (used in method U); Methods: S, ester hydrolyzed with LiOH (xs), THF/MeOH/water, 60° C.; U | 1H NMR (400 MHz, DMSO-d6) δ 8.71 (s, 1H), 8.24-8.17 (m, 2H), 8.16-8.08 (m, 1H), 8.02-7.95 (m, 1H), 7.55-7.45 (m, 3H), 7.36-7.31 (m, 2H), 3.65-3.42 (m, 4H), 3.22-2.98 (m, 4H), 2.67-2.54 (m, 4H), 2.30-2.06 (m, 2H), 1.85-1.67 (m, 2H), 1.58-1.25 (m, 8H), 1.13-1.08 (m, 6H). |
| 623 | 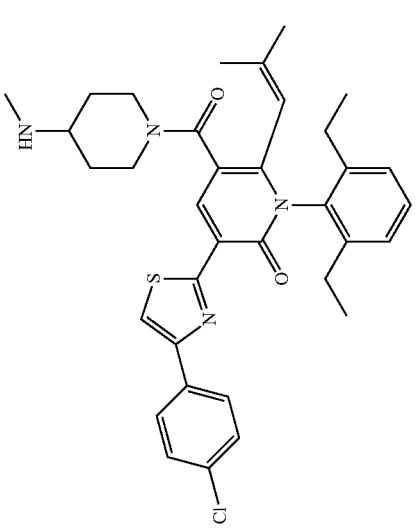 | A | A | 615.2543 | 2.861 | Starting materials: 6,6-dimethyldihydro-2H-pyran-2,4(3H)-dione (step 1), Nitrile 1 (step 2), tert-butylmethyl(piperidin-3-yl)carbamate (used in methods V, step 5); Methods: V | |

TABLE 1-continued
Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 624 | 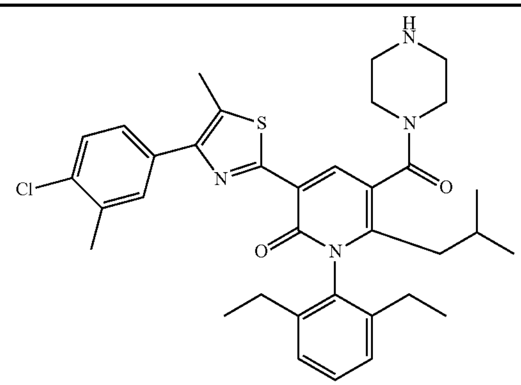 | B | A | 639.2548 | 2.952 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-chloro-3-methylphenyl)boronic acid (method xix); Methods: S, then ester hydrolyzed with LiOH (4 eq), THF/MeOH/water, 50 C., U, xix, then Boc removal with TFA/DCM rt | 1H NMR (400 MHz, DMSO-d6) δ 8.76 (s, 1H), 8.54 (s, 1H), 7.73 (dd, J = 2.2, 0.8 Hz, 1H), 7.59 (dd, J = 8.2, 2.2 Hz, 1H), 7.51-7.43 (m, 2H), 7.35 (s, 1H), 7.33 (s,1H), 4.02 (dd, J = 29.4, 12.1Hz, 1H), 3.80-3.67 (m, 1H), 3.67-3.46 (m, 2H), 3.23-2.98 (m, 4H), 2.54 (s, 3H), 2.40 (s, 3H), 2.23-1.92 (m, 6H), 1.31 (hept, J = 6.8 Hz, 1H), 1.07 (d, J = 7.9 Hz, 6H), 0.60 (d, J = 6.6 Hz, 6H). Aliphatic region complicated significantly by amide rotamers. |
| 625 | 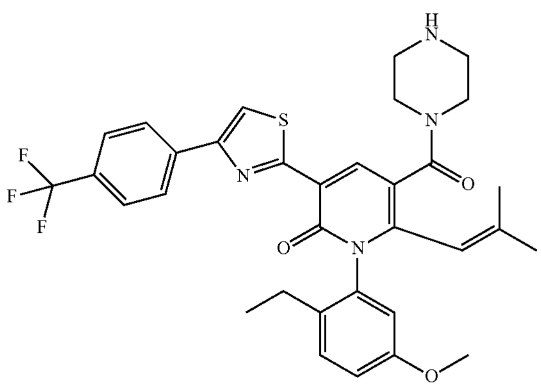 [SMILES: CCc1ccc(OC)cc1-n1c(C=C(C)C)c(C(=O)N2CCNCC2)cc(-c2nc(-c3ccc(C(F)(F)F)cc3)cs2)c1=O] | | | | | | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 626 | 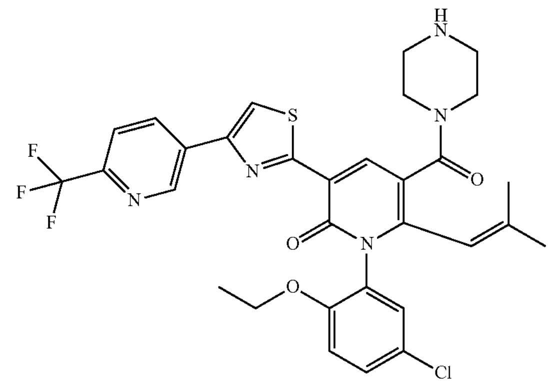 [SMILES: CCOc1ccc(Cl)cc1-n1c(C=C(C)C)c(C(=O)N2CCNCC2)cc(-c2nc(-c3ccc(C(F)(F)F)nc3)cs2)c1=O] | A | B | 322.59 | 2.623 | Starting materials: nitrile 26 (step 2 method W); 5-chloro-2-ethoxyaniline (step 3 method W). Methods: W, then steps 4-6 in method V | 1H NMR (400 MHz, DMSO-d6) δ 9.47 (s, 1H), 8.79 (s, 2H), 8.75-8.67 (m, 2H), 8.58 (s, 1H), 8.03 (d, J = 8.3 Hz, 1H), 7.53 (dd, J = 9.0, 2.6 Hz, 1H), 7.21 (d, J = 9.1 Hz, 1H), 5.56 (s, 1H), 4.12-3.84 (m, 3H), 3.64 (dd, J = 10.3, 5.4 Hz, 1H), 3.51-3.45 (m, 2H), 3.22-3.02 (m, 4H), 1.62 (s, 3H), 1.54 (s, 3H), 1.11 (t, J = 7.2 Hz, 3H). |
| 627 | 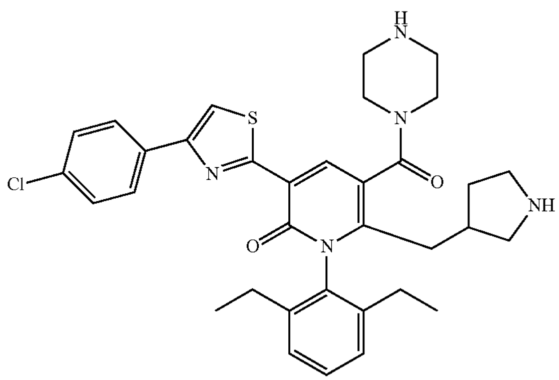 [SMILES: CCc1cccc(CC)c1-n1c(CC2CCNC2)c(C(=O)N2CCNCC2)cc(-c2nc(-c3ccc(Cl)cc3)cs2)c1=O] | D | D | 616.2524 | 2.321 | Starting materials: tert-butyl 3-(4-ethoxy-2,4-dioxobutyl)pyrrolidine-1-carboxylate (step 1), piperazine (used in method U); Methods: S, then ester hydrolyzed with LiOH (xs), THF/MeOH/water, 60° C.; U; Boc removal with TFA (xs)/DCM rt | TFA salt: 1H NMR(400 MHz, DMSO-d6) δ 8.96 (br s, 2H), 8.74 (s, 1H), 8.54 (br s, 2H), 8.24 (s, 1H), 8.16-8.01 (m, 2H), 7.60-7.44 (m, 3H), 7.37 (d, J = 7.7 Hz, 2H), 4.19-2.56 (m, 10H), 2.44-1.94 (m, 5H), 1.63 (dd, J = 101.3, 45.9 Hz, 5H), 1.39-1.15 (m, 1H), 1.10 (t, J = 7.5 Hz, 6H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 628 | 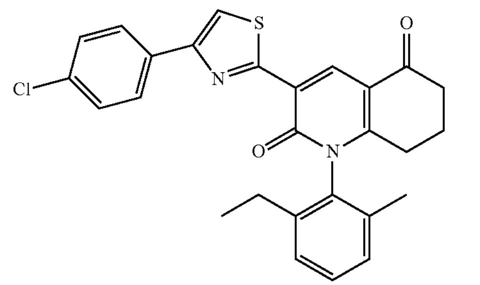 | C | C | 475.1252 | 3.993 | Starting material: cyclohexane-1,3-dione (step1 method M); nitrile 1 (step2 method M); 2-ethyl-6-methylaniline (step 3 method M), Methods: M | 1H NMR (400 MHz, CD3OD) δ 9.37 (s, 1H), 7.98 (d, J = 8.4 Hz, 2H), 7.55 (s, 1H), 7.41-7.36 (m, 3H), 7.30-7.24 (m, 2H), 2.61 (t, J = 8.0 Hz, 2H), 2.40 (t, J = 8.0 Hz, 2H), 2.34-2.28 (m, 2H), 2.08-2.05 (m, 5H), 1.15 (t, J = 8.0 Hz, 3H). Aliphatic region complicated significantly by amide rotamers |
| 629 | 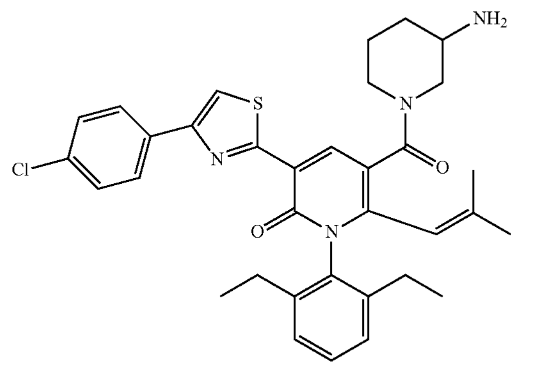 [SMILES: CCc1cccc(CC)c1-n1c(C=C(C)C)c(C(=O)N2CCCC(N)C2)cc(-c2nc(-c3ccc(Cl)cc3)cs2)c1=O] | A | A | 601.2423 | 2.785 | Starting materials: 6,6-dimethyldihydro-2H-pyran-2,4(3H)-dione (step 1), Nitrile 1 (step 2), tert-butyl piperidin-3-ylcarbamate (used in methods V, step 5); Methods: V | 1H NMR (400 MHz, DMSO-d6) δ 8.75 (s, 1H), 8.25 (s, 1H), 8.16-8.04 (m, 2H), 7.54 (dd, J = 8.4, 6.2 Hz, 2H), 7.42 (t, J = 7.7 Hz, 1H), 7.37-7.25 (m, 2H), 5.26 (s, 1H), 4.03-3.33 (m, 2H), 3.24-2.19 (m, 4H), 2.44-2.19 (m, 2H), 2.20-1.98 (m, 2H), 1.96-1.64 (m, 7H), 1.46-1.27 (m, 2H), 1.20-1.06 (m, 3H), 0.99 (t, J = 7.6 Hz, 3H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 630 | 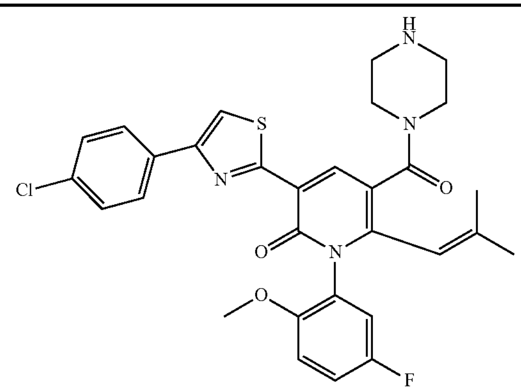 | A | A | 579.1629 | 2.611 | Starting material: 6,6-dimethyldihydro-2H-pyran-2,4(3H)-dione (step method V); nitrile 1 (step2 method V); 5-fluoro-2-methoxyaniline (step 3 method V). Methods: V | TFA salt: 1H NMR(400 MHz, CD3OD) δ 8.82 (s, 1H), 8.09-8.01 (m, 2H), 7.94 (s, 1H), 7.51-7.41 (m, 2H), 7.31-7.13 (m, 3H), 5.63 (s, 1H), 4.25 (s, 2H), 3.91-3.70 (m, 4H), 3.62 (s, 3H), 3.22 (s, 3H), 1.66 (dd, J = 7.7,1.1 Hz, 6H). Aliphatic region complicated significantly by amide rotamers. |
| 631 | 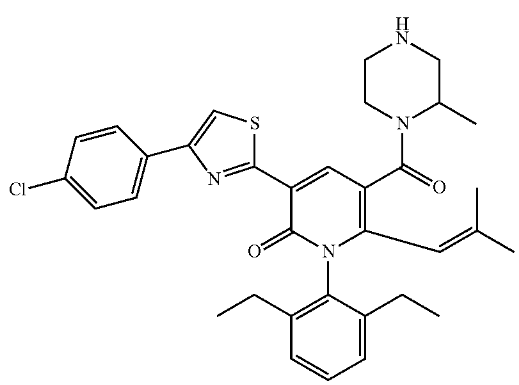 [SMILES: CCc1cccc(CC)c1-n1c(C=C(C)C)c(C(=O)N2CCNCC2C)cc(-c2nc(-c3ccc(Cl)cc3)cs2)c1=O] | A | A | 601.2388 | 2.824 | Starting materials: 6,6-dimethyldihydro-2H-pyran-2,4(3H)-dione (step 1), Nitrile 1 (step 2), tert-butyl 3-methylpiperazine-1-carboxylate (used in methods V, step 5); Methods: V | 1H NMR (400 MHz, DMSO-d6) δ 8.70 (s, 1H), 8.25 (s, 1H), 8.13-8.05 (m, 2H), 7.53 (dd, J = 8.9, 2.3 Hz, 2H), 7.42 (t, J = 7.7 Hz, 1H), 7.35-7.21 (m, 2H), 5.28 (s, 1H), 4.94 (s, 1H), 3.59 (d, J = 14.1 Hz, 1H), 3.27-2.93 (m, 5H), 2.42-2.21 (m, 2H), 2.10 (dp, J = 26.2, 7.5 Hz, 2H), 1.63-1.47 (m, 6H), 1.38-1.19 (m, 1H), 1.17-1.06 (m, 6H), 0.99 (t, J = 7.5 Hz, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 632 | 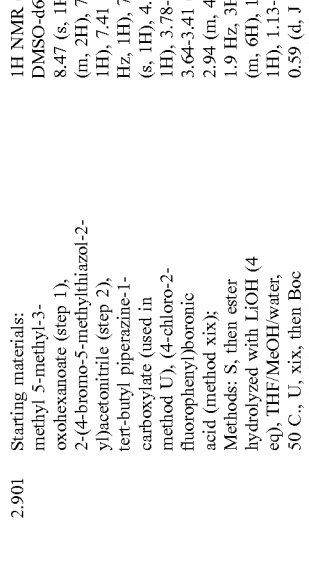 | B | B | 621.245 | 2.901 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-chloro-2-fluorophenyl)boronic acid (method xix); Methods: S, then ester hydrolyzed with LiOH (4 eq), THF/MeOH/water, 50 C., xix, then Boc removal with TFA/DCM rt | 1H NMR (400 MHz, DMSO-d6) δ 8.67 (s, 1H), 8.47 (s, 1H), 7.62-7.53 (m, 2H), 7.47 (t, J = 7.7 Hz, 1H), 7.41 (dd, J = 8.4, 2.0 Hz, 1H), 7.35 (s, 1H), 7.33 (s, 1H), 4.07-3.89 (m, 1H), 3.78-3.64 (m, 1H), 3.64-3.41 (m, 2H), 3.20-2.94 (m, 4H), 2.34 (d, J = 1.9 Hz, 3H), 2.23-1.88 (m, 6H), 1.39-1.22 (m, 1H), 1.13-1.03 (m, 6H), 0.59 (d, J = 6.6 Hz, 6H). Aliphatic region complicated significantly by amide rotamers. |
| 633 | 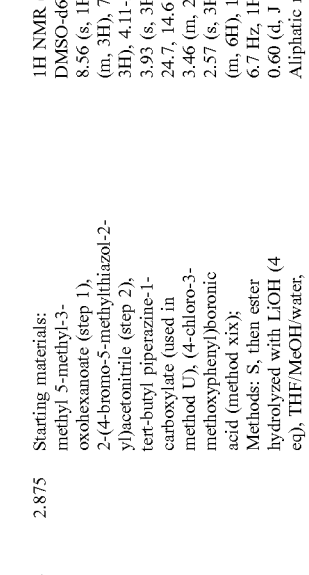 | B | B | 633.2684 | 2.875 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (4-chloro-3-methoxyphenyl)boronic acid (method xix); Methods: S, then ester hydrolyzed with LiOH (4 eq), THF/MeOH/water, 50C, U, xix, then Boc removal with TFA/DCM rt | 1H NMR (400 MHz, DMSO-d6) δ 8.71 (s, 1H), 8.56 (s, 1H), 7.52-7.43 (m, 3H), 7.36-7.30 (m, 3H), 4.11-3.99 (m, 1H), 3.93 (s, 3H), 3.78 (dd, J = 24.7, 14.6 Hz, 1H), 3.62-3.46 (m, 2H), 3.29 (s, 4H), 2.57 (s, 3H), 2.37-1.91 (m, 6H), 1.30 (dq,J = 13.3, 6.7 Hz, 1H), 1.07 (s, 6H), 0.60 (d, J = 6.6 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 634 | 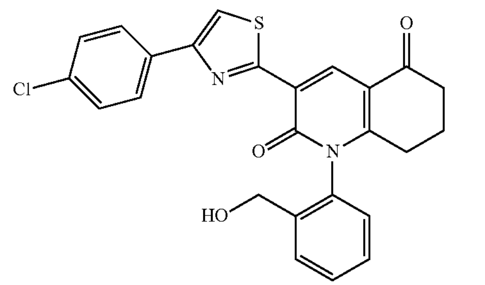 [SMILES: O=C1CCCc2c1cc(-c1nc(-c3ccc(Cl)cc3)cs1)c(=O)n2-c1ccccc1CO] | E | D | 463.0884 | 3.489 | Starting material: cyclohexane-1,3-dione (step1 method M); nitrile 1 (step2 method M); (2-aminophenyl)methanol (step 3 method M), Methods: M | 1H NMR (400 MHz, CDCl3) δ 9.40 (s, 1H), 8.04-7.96 (m, 2H), 7.69 (dd, J = 7.4, 1.7 Hz, 1H), 7.62-7.52 (m, 3H), 7.46-7.40 (m, 2H), 7.20 (dd, J = 7.5, 1.4 Hz, 1H), 5.30 (s, 1H), 4.53-4.43 (m, 2H), 2.73-2.41 (m, 5H), 2.22-2.06 (m, 3H). Aliphatic region complicated significantly by amide rotamers. |
| 635 | 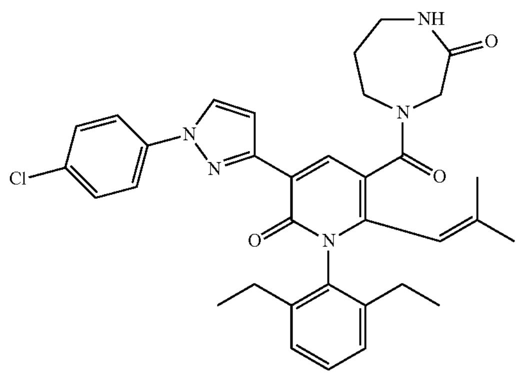 [SMILES: CCc1cccc(CC)c1-n1c(C=C(C)C)c(C(=O)N2CCCNC(=O)C2)cc(-c2ccn(-c3ccc(Cl)cc3)n2)c1=O] | A | A | 598.2576 | 3.432 | Starting materials: pyrazole 2 (step 2), 1,4-diazepan-2-one (step 5); Methods: V, step 4 with NaOH (xs), no step 6. | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 636 | 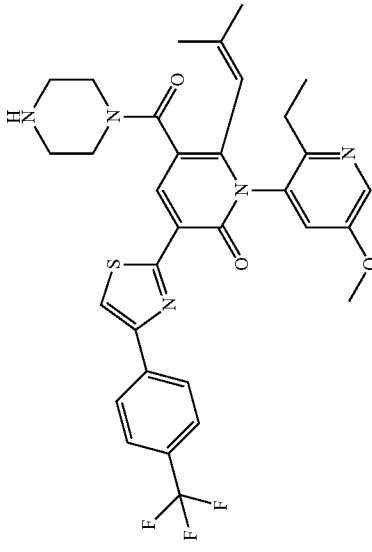 | A | A | 624.224 | 2.609 | Starting materials: nitrile 7 (step 2 method W); pyridyl amine 10 (step 3 method W), Methods: W, then steps 4-6 in method V | |
| 637 | 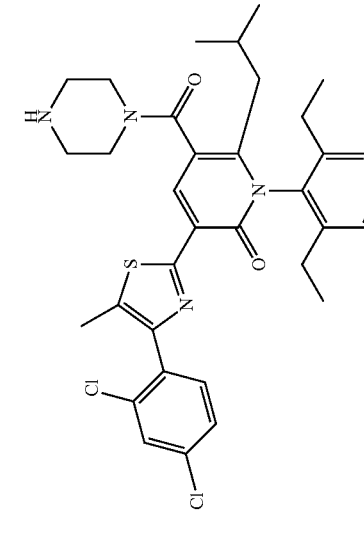 | B | B | 637.2145 | 2.939 | Starting materials: methyl 5-methyl-3-oxohexanoate (step 1), 2-(4-bromo-5-methylthiazol-2-yl)acetonitrile (step 2), tert-butyl piperazine-1-carboxylate (used in method U), (2,4-dichlorophenyl)boronic acid (method xix); Methods: S, then ester hydrolyzed with LiOH (4 eq), THF/MeOH/water, 50C., U, xix, then Boc removal with TFA/DCM rt | 1H NMR (400 MHz, DMSO-d6) δ 8.44 (s, 1H), 7.76 (d, J = 2.1 Hz, 1H), 7.53 (dd, J = 8.3, 2.1Hz, 1H), 7.51-7.42 (m, 3H), 7.35 (s, 1H), 7.33 (s, 1H), 3.98-3.85 (m, 1H), 3.75-3.61 (m, 1H), 3.61-3.4 (m, 2H), 3.16-2.86 (m, 4H), 2.28 (s, 3H), 2.23-1.89 (m, 6H), 1.317-1.25 (m, 1H), 1.08 (d, J = 8.6 Hz, 6H), 0.59 (d, J = 6.6 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 638 | 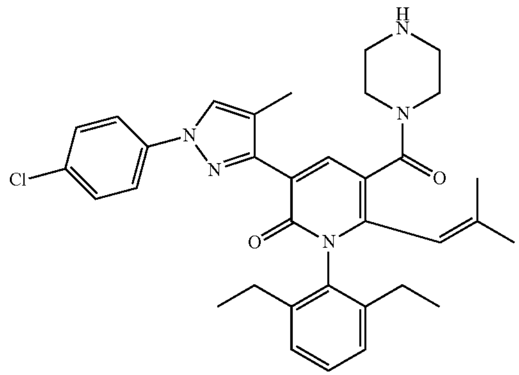 [SMILES: CCc1cccc(CC)c1-n1c(C=C(C)C)c(C(=O)N2CCNCC2)cc(-c2nn(-c3ccc(Cl)cc3)cc2C)c1=O] | A | C | 584.2811 | 2.64 | Starting materials: pyrazole 9 (step 2), piperazine (step 5); Methods: V, step 4 with NaOH (xs), no step 6. | TFA salt: 1H NMR(400 MHz, DMSO-d6) δ 8.72 (br s, 2H), 8.32 (t, J = 0.8 Hz, 1H), 7.90-7.79 (m, 2H), 7.77 (s, 1H), 7.58-7.46 (m, 2H), 7.36 (t, J = 7.6 Hz, 1H), 7.25 (m, 2H), 5.26-5.12 (m, 1H), 3.92 (m, 1H), 3.55 (m, 1H), 3.05 (br m, 5H), 2.43-2.05 (m, 4H), 1.99 (d, J = 0.9 Hz, 3H), 1.53 (dd, J = 4.8,1.4 Hz, 6H), 1.18-0.94 (m, 6H). |
| 639 | 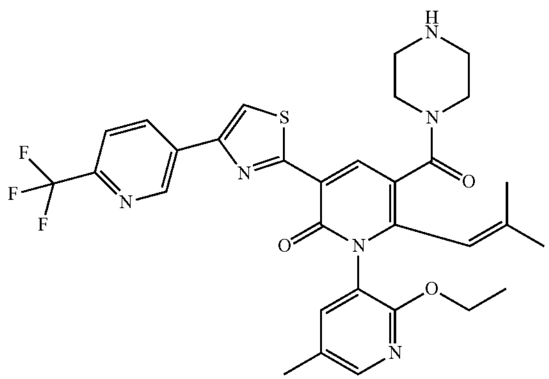 [SMILES: CCOc1ncc(C)cc1-n1c(C=C(C)C)c(C(=O)N2CCNCC2)cc(-c2nc(-c3ccc(C(F)(F)F)nc3)cs2)c1=O] | A | B | 625.2178 | 2.54 | Starting materials: pyridyl amine 6 (step 3 of method W), piperazine (step 5 of method V); Methods: W, then step 4 of method V with NaOH (xs), then step 5 of method V and no step 6. | TFA salt: 1H NMR(400 MHz, DMSO-d6) δ 9.48-9.43 (m, 3H), 8.95-8.60 (m, 3H), 8.56 (s, 1H), 8.10 (dd, J = 2.3, 1.0 Hz, 1H), 8.01 (dd, J = 8.3, 0.8 Hz, 1H), 7.73-7.60 (br m, 1H), 5.54 (s, 1H), 4.52-3.83 (br m, 3H), 3.70-3.40 (br m, 2H), 3.25-2.81 (br m, 5H), 2.36-2.18 (brs, 3H), 1.60 (d, J = 1.5 Hz, 3H), 1.53 (s, 3H), 1.20-1.05 (br m, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 640 | 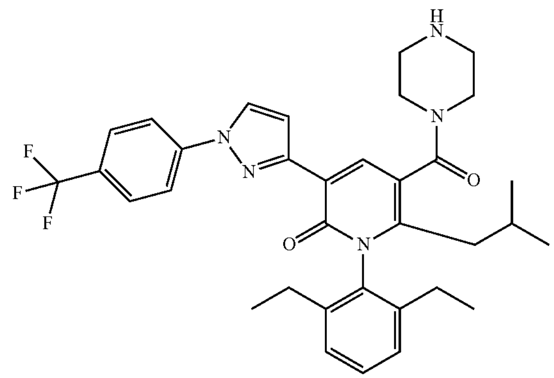 [SMILES: CCc1cccc(CC)c1-n1c(CC(C)C)c(C(=O)N2CCNCC2)cc(-c2ccn(-c3ccc(C(F)(F)F)cc3)n2)c1=O] | A | A | 606.3069 | 2.752 | Starting materials: methyl 5-methyl-3-oxohexanoate (step 1), pyrazole 4 (step 2), piperazine (used in method U). Methods: S, then ester hydrolyzed with LiOH (4 eq), THF/MeOH, 50 C., U. | 1H NMR (400 MHz, DMSO-d6) δ 8.71 (s, 1H), 8.66 (d, J = 2.6 Hz, 1H), 8.30 (s, 1H), 8.16 (d, J = 8.5 Hz, 2H), 7.87 (d, J = 8.6 Hz, 2H), 7.43 (t, J = 7.7 Hz, 1H), 7.32 (s, 1H), 7.30 (s, 1H), 7.21 (d, J = 2.6 Hz, 1H), 4.04-3.89 (m, 1H), 3.81-3.41 (m, 3H), 3.24-3.13 (m, 2H), 2.38-2.23 (m, 3H), 2.15 (d, J = 15.7 Hz, 2H), 1.93 (s, 1H), 1.28 (dt, J = 13.6, 6.8 Hz, 1H), 1.09 (s, 6H), 0.59 (d, J = 6.6 Hz, 6H). Aliphatic region complicated significantly by amide rotamers. |
| 641 | 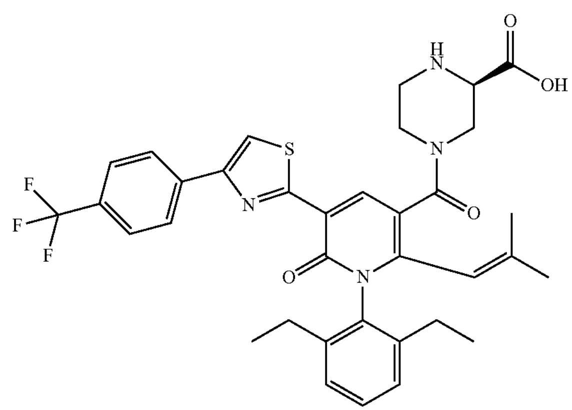 [SMILES: CCc1cccc(CC)c1-n1c(C=C(C)C)c(C(=O)N2CCN[C@@H](C(=O)O)C2)cc(-c2nc(-c3ccc(C(F)(F)F)cc3)cs2)c1=O] | A | A | 665.24 | 3.063 | Starting materials: 6,6-dimethyldihydro-2H-pyran-2,4(3H)-dione (step 1), Nitrile 7 (step 2), (R)-1-tert-butyl 2-methyl piperazine-1,2-dicarboxylate (used in methods V, step 5); Methods: V, then ester hydrolyzed with LiOH (xs), THF/MeOH/water, 60° C. | 1H NMR (400 MHz, DMSO-d6) δ 11.84 (s, 1H), 8.94-8.62 (m, 1H), 8.48-8.18 (m, 3H), 8.01-7.73 (m, 2H), 7.58-7.02 (m, 3H), 5.29 (dd, J = 16.7, 5.6 Hz, 1H), 4.68-3.99 (m, 2H), 3.95-3.54 (m, 2H), 2.68-2.51 (m, 2H), 2.44-2.19 (m, 2H), 2.16-2.00 (m, 2H), 1.63-1.48 (m, 6H), 1.37 (d, J = 1.2 Hz, 2H), 1.18-1.05 (m, 4H), 0.98 (td, J = 7.6, 1.8 Hz, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 642 | 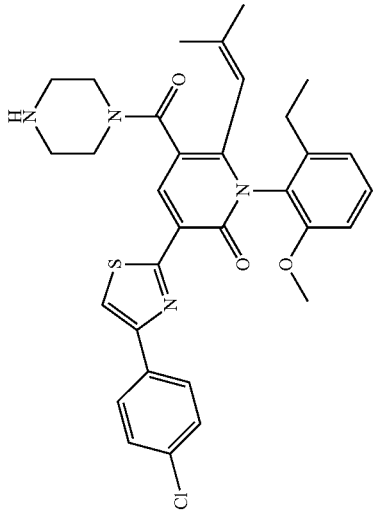 | A | A | 589.2057 | 2.686 | Starting material: 6,6-dimethyldihydro-2H-pyran-2,4(3H)-dione (step1 method V); nitrile 1 (step2 method V); aniline 9 (step 3 method V). Methods: V | TFA salt: 1H NMR (400 MHz, CD3OD) δ 8.84 (s, 1H), 8.02 (d, J = 8.7 Hz, 2H), 7.92 (s, 1H), 7.50-7.40 (m, 3H), 7.10-6.91 (m, 2H), 5.46 (s, 1H), 4.40-4.25 (m, 1H), 3.90-3.65 (m, 4H), 3.85-3.65 (m, 1H), 3.60-3.42 (m, 2H), 3.35-3.10 (m, 4H), 2.50-2.20 (m, 2H), 1.68-1.57 (m, 6H), 1.30-1.05 (m, 3H). Aliphatic region complicated significantly by amide rotamers. |
| 643 | 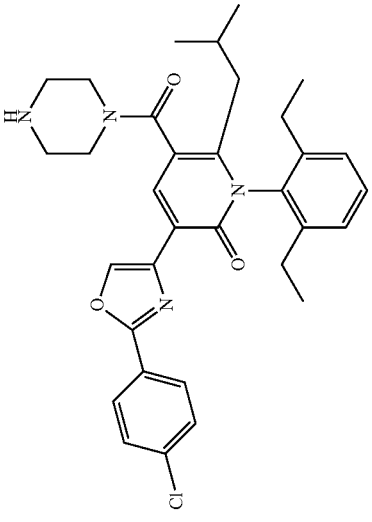 | B | B | 573.2647 | 2.819 | Starting materials: methyl 5-methyl-3-oxohexanoate (step 1), nitrile 35 (step 2), piperazine (used in method U); Methods: S, then ester hydrolyzed with LiOH (xs), THF/MeOH/water, 60° C.; U | TFA salt: 1H NMR(400 MHz, DMS)-d6) δ 8.81 (br m, 2H), 8.61 (s, 1H), 8.23 (d, J = 0.4 Hz, 1H), 8.14-7.99 (m, 2H), 7.74-7.57 (m, 2H), 7.52-7.36 (m, 1H), 7.31 (d, J = 7.7 Hz, 2H), 4.15-3.46 (m, 3H), 3.08 (br m, 1H), 2.36-1.77 (br m, 3H), 1.40-1.18 (m, 1H), 1.07 (m, 6H), 0.59 (d, J = 6.7 Hz, 6H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 644 | 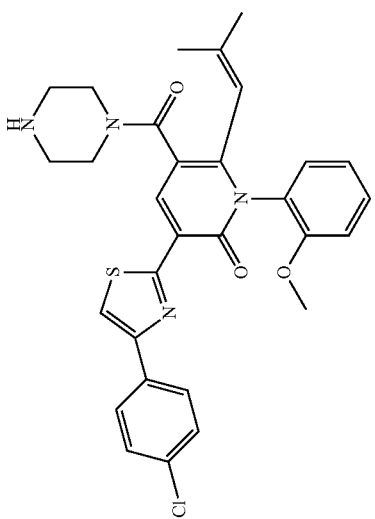 | A | B | 561.171 | 2.574 | Starting material: 6,6-dimethyldihydro-2H-pyran-2,4(3H)-dione (step1 method V); nitrile 1 (step2 method V); 2-methoxyaniline (step 3 method V), Methods: V | TFA salt: 1H NMR(400 MHz, CD3OD) δ 8.83 (s, 1H), 8.07-8.01 (m, 2H), 7.93 (S,1H), 7.55-7.48 (m, 1H), 7.48-7.43 (m, 2H), 7.33 (s, 1H), 7.19 (s, 1H), 7.13 (t, J = 7.5 Hz, 1H), 5.59 (s, 1H), 4.27 (s, 2H), 3.78 (d, J = 23.7 Hz, 5H), 3.59 (s, 2H), 3.28-3.18 (m, 6H), 1.70-1.56 (m, 6H). Aliphatic region complicated significantly by amide rotamers. |
| 645 | 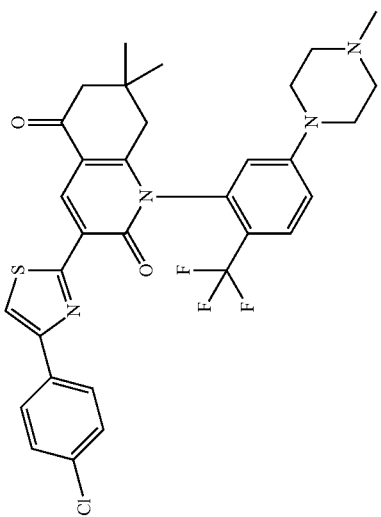 | C | C | 627.1809 | 2.904 | Starting material: 5,5-dimethylcyclohexane-1,3-dione (step1 method M); nitrile 1 (step2 method M); 5-(4-methylpiperazin-1-yl)-2-(trifluoromethyl)aniline (step 3 method M), Methods: M | HCl salt: 1H NMR (400 MHz, dmso-d6) δ 9.08 (s, 1H), 8.26 (s, 1H), 8.13-8.08 (m, 2H), 7.83 (d, J = 9.7 Hz, 1H), 7.59-7.52 (m, 2H), 7.33 (d, J = 7.4 Hz, 2H), 4.10 (t, J = 13.2 Hz, 3H), 3.15 (d, J = 13.1 Hz, 4H), 2.87-2.76 (m, 5H), 2.45 (d, J = 16.5 Hz, 2H), 2.18 (d, J = 17.8 Hz, 2H), 2.02-1.88 (m, 3H), 1.05 (d, J = 8.9 Hz, 3H), 0.93 (s, 3H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 646 | 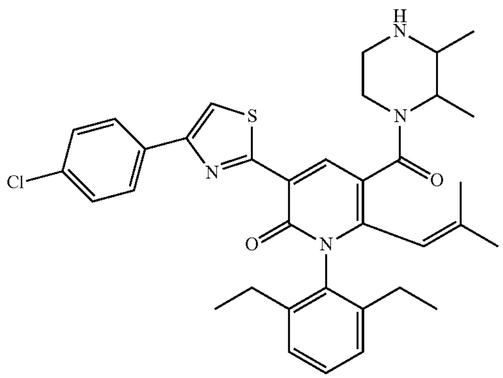 [SMILES: CCc1cccc(CC)c1-n1c(C=C(C)C)c(C(=O)N2CCNC(C)C2C)cc(-c2nc(-c3ccc(Cl)cc3)cs2)c1=O] | A | A | 615.2529 | 2.859 | Starting materials: 6,6-dimethyldihydro-2H-pyran-2,4(3H)-dione (step 1), Nitrile 1 (step 2), 2,3-dimethylpiperazine (used in methods V, step 5); Methods: V, no step 6. | 1H NMR (400 MHz, DMSO-d6) δ 8.70 (s, 1H), 8.25 (s, 1H), 8.14-8.06 (m, 2H), 7.53 (dd, J = 8.9, 2.5 Hz, 2H), 7.42 (t, J = 7.7 Hz, 1H), 7.29 (dd, J = 21.4, 7.7 Hz, 2H), 5.28 (s, 1H), 4.67-4.55 (m, 1H), 3.61-3.43 (m, 2H), 3.11-2.92 (m, 2H), 2.69-2.51 (m, 2H), 2.43-2.20 (m, 2H), 2.19-1.99 (m, 2H), 1.63-1.48 (m, 6H), 1.38-1.30 (m, 3H), 1.16-1.07 (m, 5H), 0.99 (t, J = 7.5 Hz, 3H). |
| 647 | 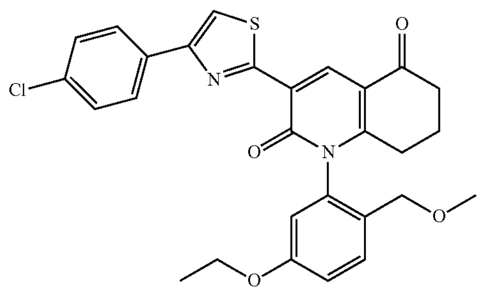 [SMILES: CCOc1ccc(COC)c(-n2c3c(cc(-c4nc(-c5ccc(Cl)cc5)cs4)c2=O)C(=O)CCC3)c1] | B | B | 521.1282 | 3.896 | Starting material: cyclohexane-1,3-dione (step1 method M); nitrile 1 (step2 method M); 2,5-diethoxyaniline (step 3 method M), Methods: M | 1H NMR (400 MHz, CDCl3) δ 9.35 (s, 1H), 8.03-7.96 (m, 2H), 7.57 (s, 1H), 7.45-7.40 (m, 2H), 7.06-6.98 (m, 2H), 6.80 (dd, J = 2.4, 0.8 Hz, 1H), 4.10-3.94 (m, 4H), 2.69-2.52 (m, 4H), 2.11 (dd, J = 12.6, 6.6 Hz, 2H), 1.41 (t, J = 7.0 Hz, 3H), 1.20 (t, J = 7.0 Hz, 3H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 648 | 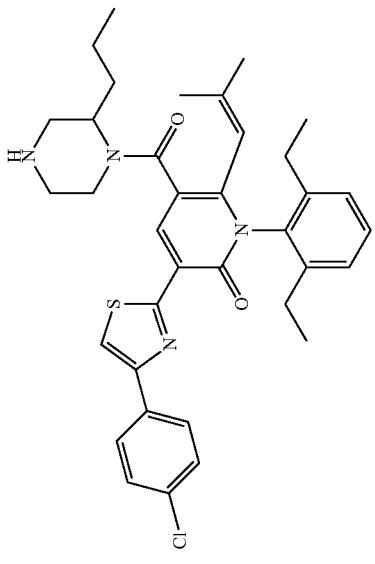 | B | A | 629.2715 | 2.917 | Starting materials: 6,6-dimethyldihydro-2H-pyran-2,4(3H)-dione (step 1), Nitrile 1 (step 2), tert-butyl 3-propylpiperazine-1-carboxylate (used in methods V, step 5); Methods: V | 1H NMR (400 MHz, DMSO-d6) δ 8.73 (s, 1H), 8.25 (d, J = 1.0 Hz, 1H), 8.16-8.03 (m, 2H), 7.53 (dd, J = 8.6,1.5 Hz, 2H), 7.41 (t, J = 7.6 Hz, 1H), 7.35-7.21 (m, 2H), 5.30 (s, 1H), 4.83-4.37 (m, 1H), 3.67-3.38 (m, 2H), 3.27-2.96 (m, 4H), 2.69-2.51 (m, 2H), 2.42-2.20 (m, 2H), 2.20-2.01 (m, 2H), 1.70-1.32 (m, 8H), 1.30-1.16 (m, 2H), 1.16-1.06 (m, 3H), 1.00 (t, J = 7.5 Hz, 3H), 0.88 (t, J = 7.2 Hz, 3H). |
| 649 | 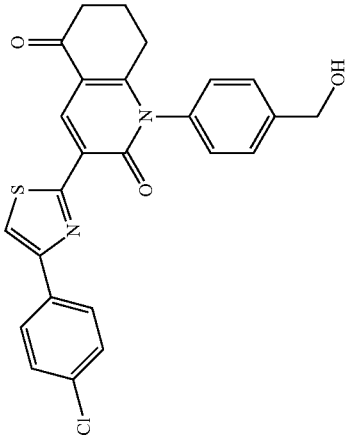 | E | E | 463.088 | 3.434 | Starting material: cyclohexane-1,3-dione (step1 method M); nitrile 1 (step2 method M); (4-aminophenyl)methanol (step 3 method M), Methods: M | 1H NMR (400 MHz, CDCl3) δ 9.37 (s, 1H), 8.03-7.96 (m, 2H), 7.62 (t, J = 6.3 Hz, 2H), 7.58 (s, 1H), 7.45-7.40 (m, 2H), 7.33-7.27 (m, 2H), 4.83 (d, J = 5.7 Hz, 2H), 2.71-2.51 (m, 4H), 2.18-2.06 (m, 2H), 1.83 (t, J = 5.8 Hz, 1H). MS m/z 463.1 Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 650 | 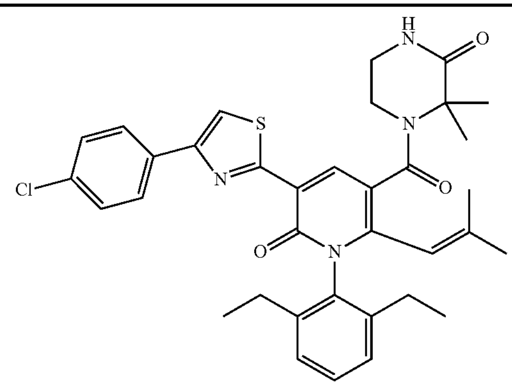 | A | A | 629.2329 | 3.833 | Starting materials: 6,6-dimethyldihydro-2H-pyran-2,4(3H)-dione (step 1), Nitrile 1 (step 2), 3,3-dimethylpiperazin-2-one (used in methods V, step 5); Methods: V, no step 6. | 1H NMR (400 MHz, DMSO-d6) δ 8.60 (s, 1H), 8.23 (s, 1H), 8.13-8.06 (m, 2H), 7.57-7.49 (m, 2H), 7.41 (t, J = 7.7 Hz, 1H), 7.28 (dd, J = 16.0, 7.6 Hz, 2H), 5.32 (s, 1H), 3.58-3.35 (m, 1H), 3.26-3.02 (m, 2H), 2.69-2.61 (m, 1H), 2.40-2.01 (m, 4H), 1.73 (s, 3H), 1.60 (d, J = 1.3 Hz, 3H), 1.52 (d, J = 1.4 Hz, 6H), 1.27-1.19 (m, 1H), 1.10 (t, J = 7.5 Hz, 3H), 1.01 (t, J = 7.5 Hz, 3H). |
| 651 | 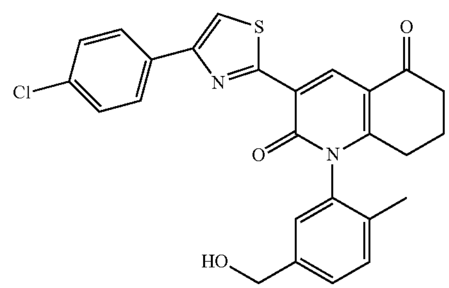 [SMILES: Cc1ccc(CO)cc1-n1c2c(cc(-c3nc(-c4ccc(Cl)cc4)cs3)c1=O)C(=O)CCC2] | C | C | 477.1044 | 3.535 | Starting material: cyclohexane-1,3-dione (step1 method M); nitrile 1 (step2 method M); (3-amino-4-methylphenyl)methanol (step 3 method M), Methods: M | 1H NMR (400 MHz, CDCl3) δ 9.38 (s, 1H), 8.04-7.97 (m, 2H), 7.58 (s, 1H), 7.47-7.40 (m, 4H), 7.22 (s, 1H), 4.77 (d, J = 5.5 Hz, 2H), 2.70-2.56 (m, 3H), 2.41-2.31 (m, 1H), 2.18-2.13 (m, 1H), 2.10 (s, 3H), 2.07 (dd, J = 11.6, 6.3 Hz, 1H), 1.85 (t, J = 5.9 Hz, 1H). Aliphatic region complicated significantly by amide rotamers. |
| 652 | 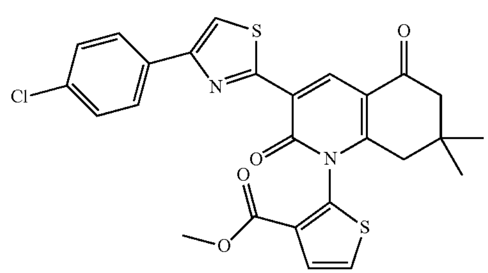 [SMILES: COC(=O)c1ccsc1-n1c2c(cc(-c3nc(-c4ccc(Cl)cc4)cs3)c1=O)C(=O)CC(C)(C)C2] | B | B | 525.071 | 3.812 | Starting material: 5,5-dimethylcyclohexane-1,3-dione (step1 method M); nitrile 1 (step2 method M); methyl 2-aminothiophene-3-carboxylate (step 3 method M), Methods: M | 1H NMR (400 MHz, CDCl3) δ 9.34 (s, 1H), 8.02-7.95 (m, 2H), 7.61 (d, J = 5.7 Hz, 1H), 7.58 (s, 1H), 7.50 (t, J = 6.0 Hz, 1H), 7.45-7.39 (m, 2H), 3.71 (s,3H), 2.61-2.45 (m, 4H), 1.08 (d, J = 9.4 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 653 | 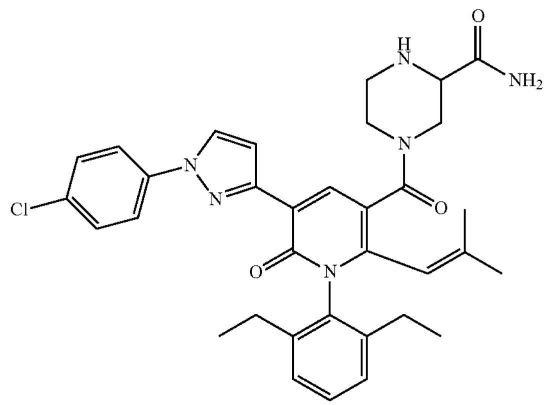 [SMILES: CCc1cccc(CC)c1-n1c(C=C(C)C)c(C(=O)N2CCNC(C(N)=O)C2)cc(-c2ccn(-c3ccc(Cl)cc3)n2)c1=O] | A | A | 613.2667 | 2.615 | Starting materials: pyrazole 2 (step 2), piperazin-2-one (step 5); Methods: V, step 4 with NaOH (xs), no step 6. | |
| 654 | 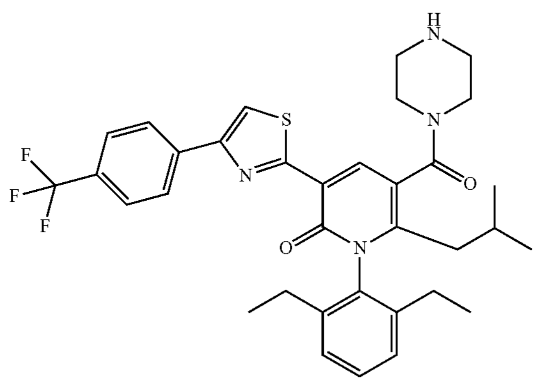 [SMILES: CCc1cccc(CC)c1-n1c(CC(C)C)c(C(=O)N2CCNCC2)cc(-c2nc(-c3ccc(C(F)(F)F)cc3)cs2)c1=O] | A | A | 623.2649 | 2.874 | Starting materials: methyl 5-methyl-3-oxohexanoate (step 1), 2-(4-(trifluoromethyl)phenyl)thiazol-2-yl)acetonitrile (step 2), tert-butylpiperazine-1-carboxylate (used in method U), Methods: S, then ester hydrolyzed with LiOH (4 eq), THF/MeOH, 50 C., U, then Boc removal with TFA/DCM rt | 1H NMR (400 MHz, DMSO-d6) δ 8.86 (d, J = 58.6 Hz, 1H), 8.72 (s, 1H), 8.38 (s, 1H), 8.31 (d, J = 8.1 Hz, 2H), 7.80 (d, J = 8.3 Hz, 2H), 7.48 (t, J = 7.7 Hz, 1H), 7.35 (s, 1H), 7.33 (s, 1H), 4.11-4.01 (m, 1H), 3.90-3.74 (m, 1H), 3.71-3.36 (m, 2H), 3.29-3.11 (m, 3H), 3.12-3.00 (m, 1H), 2.49-2.20 (m, 3H), 2.23-1.91 (m, 3H), 1.31 (dq, J = 13.6, 6.8 Hz, 1H), 1.08 (d, J = 7.3 Hz, 6H), 0.61 (d, J = 6.6 Hz, 6H). Aliphatic region complicated significantly by amide rotamers. |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 655 | (structure) | A | A | 599.1663 | 2.705 | Starting material: 6,6-dimethyldihydro-2H-pyran-2,4(3H)-dione (step1 method V); nitrile 1 (step2 method V); 2-fluoro-6-ethylaniline (step 3 method V), Methods: V | TFA salt: 1H NMR(400 MHz, CD3OD) δ 8.86 (s, 1H), 8.03 (d, J = 8.6 Hz, 2H), 7.94 (s, 1H), 7.55-7.47 (m, 1H), 7.43 (d, J = 8.6 Hz, 2H), 7.35-7.27 (m, 1H), 7.25-7.10 (m, 1H), 5.62-5.44 (m, 1H), 4.40-4.23 (m, 1H), 3.85-3.70 (m, 1H), 3.60-3.45 (m, 2H), 3.35-3.10 (m, 4H), 2.60-2.25 (m, 2H), 1.72-1.62 (m, 6H), 1.30-1.05 (m, 3H). Aliphatic region complicated significantly by amide rotamers. |
| 656 | (structure) | A | A | 573.2082 | 2.735 | Starting material: 6,6-dimethyldihydro-2H-pyran-2,4(3H)-dione (step1 method V); nitrile 1 (step2 method V); aniline 1 (step 3 method V), Methods: V | TFA salt: 1H NMR(400 MHz, CD3OD) δ 8.86 (s, 1H), 8.04 (d, J = 8.4 Hz, 2H), 7.94 (s, 1H), 7.45 (d, J = 8.8 Hz, 2H), 7.37-7.27 (m, 2H), 7.17-7.03 (m, 1H), 5.66-5.41 (m, 1H), 4.42-4.20 (m, 1H), 3.91-3.74 (m, 1H), 3.65-3.49 (m, 2H), 3.25-3.13 (m, 3H), 2.50-2.18 (m, 6H), 1.71-1.61 (m, 6H), 1.23-1.05 (m, 3H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 657 | 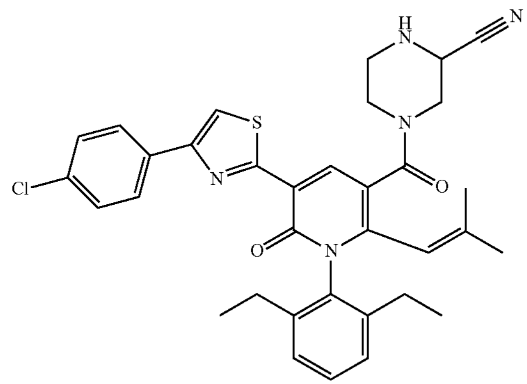 [SMILES: CCc1cccc(CC)c1-n1c(C=C(C)C)c(C(=O)N2CCNC(C#N)C2)cc(-c2nc(-c3ccc(Cl)cc3)cs2)c1=O] | A | A | 612.22 | 3.776 | Starting materials: 6,6-dimethyldihydro-2H-pyran-2,4(3H)-dione (step 1), Nitrile 1 (step 2), tert-butyl 2-cyanopiperazine-1-carboxylate (used in methods V, step 5); Methods: V | 1H NMR (400 MHz, DMSO-d6) δ 8.67 (d, J = 8.6 Hz, 1H), 8.24 (s, 1H), 8.09 (dd, J = 8.3,1.7 Hz, 2H), 7.58-7.48 (m, 2H), 7.42 (t, J = 7.6 Hz, 1H), 7.29 (dd, J = 17.7, 7.3 Hz, 2H), 5.24 (d, J = 8.0 Hz, 1H), 4.45-4.12 (m, 1H), 3.23-2.97 (m, 2H), 2.93-2.63 (m, 4H), 2.44-2.20 (m, 2H), 2.20-2.01 (m, 2H), 1.67-1.50 (m, 6H), 1.11 (t, J = 12.8, 7.4, Hz, 3H), 1.00 (t, J = 7.4 Hz, 3H). |
| 658 | 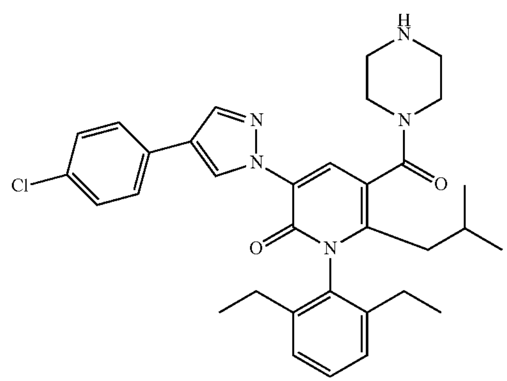 [SMILES: CCc1cccc(CC)c1-n1c(CC(C)C)c(C(=O)N2CCNCC2)cc(-n2cc(-c3ccc(Cl)cc3)cn2)c1=O] | D | D | 572.2805 | 2.834 | Storting materials: methyl 5-methyl-3-oxohexanoate (step 1), 2-(4-phenyl-1H-pyrazol-1-yl)acetonitrile (step 2), piperazine (used in method U); Methods: S, then ester hydrolyzed with LiOH (xs), THF/MeOH/water, 60° C.; U | 1H NMR (400 MHz, DMSO-d6) δ 9.06 (d, J = 0.8 Hz, 1H), 8.28 (d, J = 0.8 Hz, 1H), 8.20 (s, 1H), 7.74-7.59 (m, 2H), 7.54-7.25 (m, 5H), 4.03-3.96 (m, 1H), 3.77-3.65 (m, 2H), 3.52-3.40 (s,5H), 3.25-3.12 (m, 1H), 3.06-2.96 (s, 1H), 2.38-2.15 (m, 2H), 1.90 (d, J = 19.6 Hz, 1H), 1.35-1.15 (m, 1H), 1.10-.89 (m, 8H), 0.59 (d, J = 6.5 Hz, 6H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | 1H-NMR |
|---|---|---|---|---|---|---|---|
| 659 | 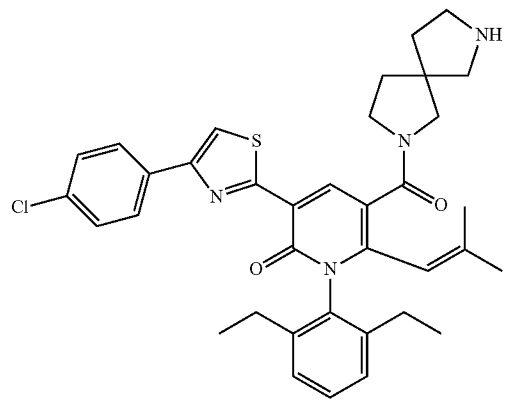 [SMILES: CCc1cccc(CC)c1-n1c(C=C(C)C)c(C(=O)N2CCC3(CCNC3)C2)cc(-c2nc(-c3ccc(Cl)cc3)cs2)c1=O] | B | A | 627.258 | 2.822 | Starting materials: 6,6-dimethyldihydro-2H-pyran-2,4(3H)-dione (step 1), Nitrile 1 (step 2), tert-butyl 2,7-diazaspiro[4.4]nonane-2-carboxylate (used in methods V, step 5); Methods: V | |
| 660 | 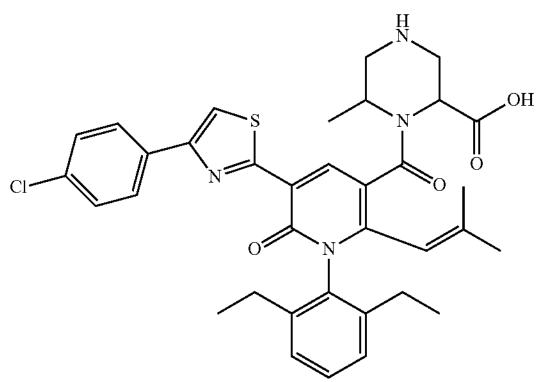 [SMILES: CCc1cccc(CC)c1-n1c(C=C(C)C)c(C(=O)N2C(C)CNCC2C(=O)O)cc(-c2nc(-c3ccc(Cl)cc3)cs2)c1=O] | A | A | 645.2284 | 3.058 | Starting materials: 6,6-dimethyldihydro-2H-pyran-2,4(3H)-dione (step 1), Nitrile 1 (step 2), 1-tert-butyl 3-methyl 5-methylpiperazine-1,3-dicarboxylate (used in methods V, step 5); Methods: V, then ester hydrolyzed with LiOH (xs), THF/MeOH/water, 60° C. | 1H NMR (400 MHz, DMSO-d6) δ 8.72 (s, 1H), 8.25 (s, 1H), 8.14-8.04 (m, 2H), 7.53 (dt, J = 8.3, 2.2 Hz, 2H), 7.49-7.38 (m, 1H), 7.39-7.22 (m, 2H), 5.31 (s, 1H), 4.94-4.75 (m, 1H), 3.87-3.77 (m, 1H), 3.11-2.63 (m, 2H), 2.42-2.18 (m, 2H), 2.18-2.00 (m, 2H), 1.62-1.47 (m, 7H), 1.32-1.19 (m, 2H), 1.16-1.03 (m, 3H), 1.03-0.95 (m, 3H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 661 | 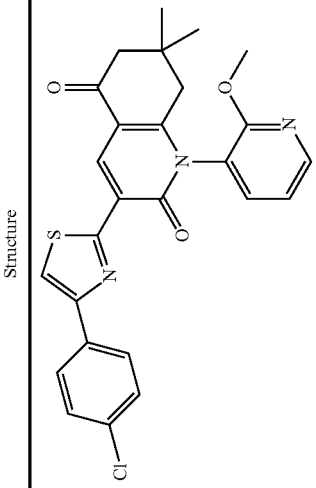 | C | B | 492.116 | 3.836 | Starting material: 5,5-dimethylcyclohexane-1,3-dione (step1 method M); nitrile 1 (step2 method M); 2-methoxypyridin-3-amine (step 3 method M), Methods: M | HCl salt: 1H NMR (400 MHz, CD3OD) δ 9.04 (s, 1H), 8.39-8.38 (m, 1H), 8.22 (s, 1H), 8.07 (d, J = 8.4 Hz, 1H), 7.91-7.89 (m, 1H), 7.52 (d, J = 8.4 Hz, 2H), 7.27 (d, J = 8.4 Hz, 2H), 3.86 (s, 3H), 3.66-3.53 (m, 1H), 3.47-3.32 (m, 1H), 2.57 (d, J = 20 Hz, 1H), 2.23 (d, J = 20 Hz, 1H), 1.19-0.94 (m, 6H). Aliphatic region complicated significantly by amide rotamers. |
| 662 | 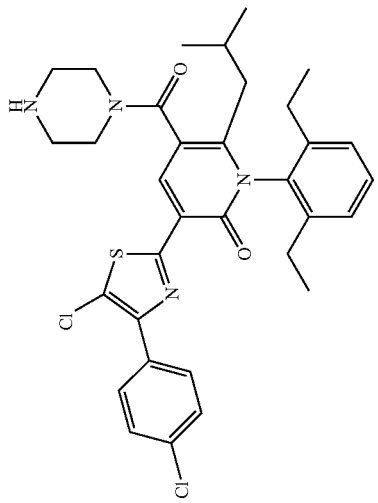 | B | A | 623.2014 | 3.036 | Starting material: methyl 5-methyl-3-oxohexanoate (step1 method V); nitrile 1 (step2 method V); 2,6-diethylaniline (step 3 method V), Methods: V (step1-5), chloronation with NCS in DCM, then V (step 6) | TFA salt: 1H NMR(400 MHz, CD3OD) δ 8.67 (s, 1H), 8.05-7.99 (m, 2H), 7.56-7.48 (m, 3H), 7.40 (d, J = 7.7 Hz, 2H), 4.29 (s, 1H), 3.98 (s, 1H), 3.76 (s, 2H), 3.37 (d, J = 19.7 Hz, 4H), 2.69 (s, 2H), 2.42 (dt, J = 22.5, 7.6 Hz, 2H), 2.28 (s, 2H), 2.14 (s, 2H), 1.54-1.40 (m, 1H), 1.19 (t, J = 7.3 Hz, 6H), 0.71 (d, J = 6.6 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 663 | 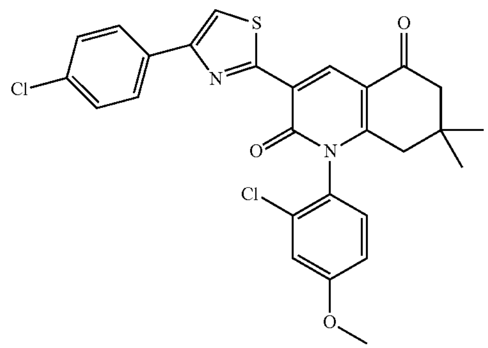 [SMILES: COc1ccc(-n2c3c(cc(-c4nc(-c5ccc(Cl)cc5)cs4)c2=O)C(=O)CC(C)(C)C3)c(Cl)c1] | E | C | 525.0812 | 3.991 | Starting material: 5,5-dimethylcyclohexane-1,3-dione (step1 method M); nitrile 1 (step2 method M); 2-chloro-4-methoxyaniline (step 3 method M), Methods: M | 1H NMR (400 MHz, CDCl3) δ 9.35 (s, 1H), 8.03-7.96 (m, 2H), 7.58 (s, 1H), 7.45-7.39 (m, 2H), 7.22 (d, J = 8.7 Hz, 1H), 7.18 (d, J = 2.7 Hz, 1H), 7.03 (dd, J = 8.7, 2.7 Hz, 1H), 3.90 (s, 3H), 2.57-2.41 (m, 3H), 2.32 (d, J = 17.9 Hz, 1H), 1.09 (s, 6H). Aliphatic region complicated significantly by amide rotamers. |
| 664 | 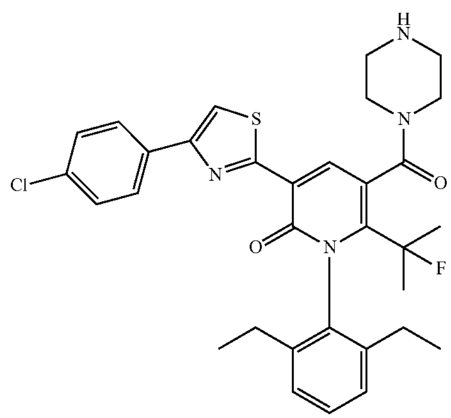 [SMILES: CCc1cccc(CC)c1-n1c(C(C)(C)F)c(C(=O)N2CCNCC2)cc(-c2nc(-c3ccc(Cl)cc3)cs2)c1=O] | B | B | 593.2156 | 2.743 | Starting materials: ethyl 4-fluoro-4-methyl-3-oxopentanoate (step 1), Nitrile 1 (step 2), piperazine (used in method U); Methods: S, ester hydrolyzed with LiOH (xs), THF/MeOH/water, 60° C.; U | |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | 1H-NMR |
|---|---|---|---|---|---|---|---|
| 665 | 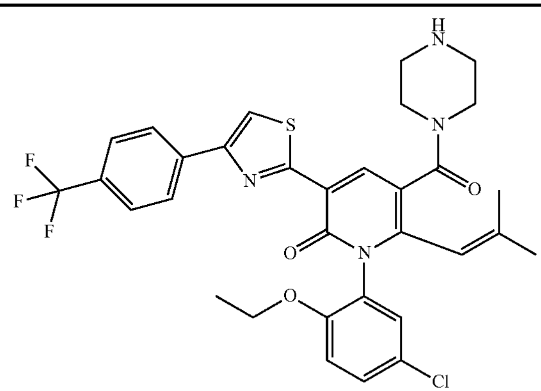 | A | A | 643.18 | 2.754 | Starting materials: nitrile 7 (step 2 method W); 5-chloro-2-ethoxyaniline (step 3 method W), Methods: W, then steps 4-6 in method V | 1H NMR (400MHz, DMSO-d6) δ 8.79 (s, 1H), 8.70 (s, 1H), 8.42 (s, 1H), 8.31(d, J = 8.2 Hz, 2H), 7.85 (d, J = 8.2 Hz, 2H), 7.61 (s, 1H), 7.53 (dd, J = 8.9, 2.6 Hz, 1H), 7.20 (d, J = 9.0 Hz, 1H), 5.56 (s, 1H), 3.98 (dd, J = 60.0, 15.6 Hz, 3H), 3.64 (s, 1H), 3.53-3.32 (m, 2H), 3.09 (s, 3H), 2.98-2.93 (m, 1H), 1.62 (d, J = 1.5 Hz, 3H), 1.54 (d, J = 1.2 Hz, 3H), 1.11 (d, J = 6.9 Hz, 3H). |
| 666 | 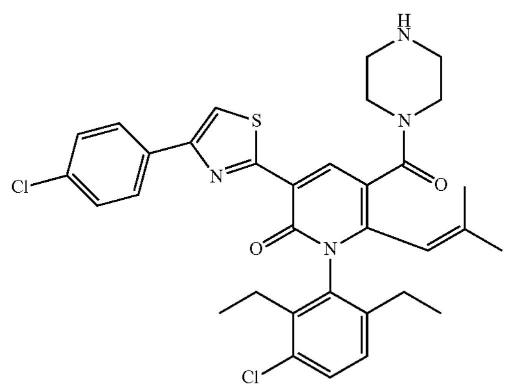 [SMILES: CCc1ccc(Cl)c(CC)c1-n1c(C=C(C)C)c(C(=O)N2CCNCC2)cc(-c2nc(-c3ccc(Cl)cc3)cs2)c1=O] | A | A | 621.1876 | 2.872 | Starting material: 6,6-dimethyldihydro-2H-pyran-2,4(3H)-dione (step1 method V); nitrile 1 (step2 method V); 2-chloro-2,6-ditheylaniline (step 3 method V), Methods: V | TFA salt: 1H NMR (400 MHz, CD3OD) δ 8.89 (s, 1H), 8.03 (d, J = 8.7 Hz, 2H), 7.94 (s, 1H), 7.52 (d, J = 8.4 Hz, 1H), 7.44 (d, J = 8.7 Hz, 2H), 7.38-7.25 (m, 1H), 5.37 (s, 1H), 4.40-4.20 (m, 1H), 3.85-3.70 (m, 1H), 3.60-3.45 (m, 2H), 3.35-3.10 (m, 4H), 2.50-2.25 (m, 4H), 1.71-1.60 (m, 6H), 1.25-0.96 (m, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 667 | 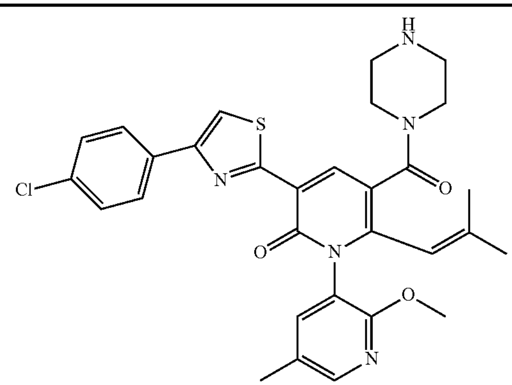 | A | A | 576.1838 | 2.584 | Starting matericals: nitrile 1 (step2 method V); pyridyl amine 11 (step 3 method W); piperidine (step 5 method V), Methods: V, no step 7 | |
| 668 | 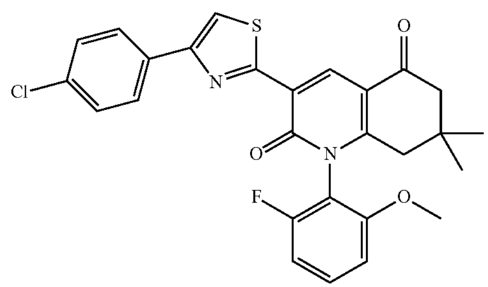 [SMILES: COc1cccc(F)c1-n1c2c(cc(-c3nc(-c4ccc(Cl)cc4)cs3)c1=O)C(=O)CC(C)(C)C2] | C | C | 509.1087 | 3.936 | Starting material: 5,5-dimethylcyclohexane-1,3-dione (step1 method M); nitrile 1 (step2 method M); 6-fluoro-2-methoxyaniline (step 3 method M), Methods: M | 1H NMR (400 MHz, CDCl3) δ 9.34 (d, J = 5.4 Hz, 1H), 8.03-7.95 (m, 2H), 7.57 (d, J = 4.1 Hz, 1H), 7.57-7.47 (m, 1H), 7.45-7.39 (m, 2H), 6.96 (ddd, J = 18.1, 7.6, 6.7 Hz, 2H), 3.83 (d, J = 10.1 Hz, 3H), 2.51 (s, 2H), 2.50-2.34 (m, 2H), 1.07 (t, J = 6.7 Hz, 6H). Aliphatic region complicated significantly by amide rotamers. |
| 669 | 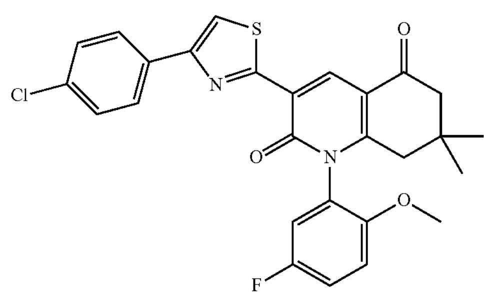 [SMILES: COc1ccc(F)cc1-n1c2c(cc(-c3nc(-c4ccc(Cl)cc4)cs3)c1=O)C(=O)CC(C)(C)C2] | B | B | 509.1102 | 3.858 | Starting material: 5,5-dimethylcyclohexane-1,3-dione (step1 method M); nitrile 1 (step2 method M); 5-fluoro-2-methoxyaniline (step 3 method M), Methods: M | 1H NMR (400 MHz, CDCl3) δ 9.34 (s, 1H), 8.03-7.96 (m, 2H), 7.58 (s, 1H), 7.45-7.39 (m, 2H), 7.26 (s, 1H), 7.08 (dd, J = 9.2, 4.5 Hz, 1H), 7.01 (dd, J = 7.7, 3.0 Hz, 1H), 3.80 (s,3H), 2.47 (dd, J = 18.9, 4.8 Hz, 3H), 2.31 (d, J = 17.8 Hz, 1H), 1.07 (d, J = 9.4 Hz, 6H). Aliphatic region complicated significantly by amide rotamers. |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 670 | 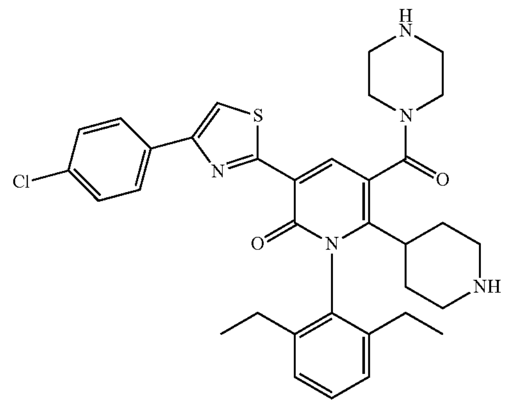 [SMILES: CCc1cccc(CC)c1-n1c(C2CCNCC2)c(C(=O)N2CCNCC2)cc(-c2nc(-c3ccc(Cl)cc3)cs2)c1=O] | D | E | 308.629 | 2.344 | Starting materials: tert-butyl 4-(3-ethoxy-3-oxopropanoyl)piperidine-1-carboxylate (step 1), piperazine (used in method U); Methods: S, then ester hydrolyzed with LiOH (xs), THF/MeOH/water, 60° C.; U; Boc removal with TFA (xs)/DCM rt | TFA salt: 1H NMR(400 MHz, DMSO-d6) δ 8.97 (br s, 2H), 8.68 (s, 1H), 8.40 (br m, 2H), 8.24 (s, 1H), 8.18-8.06 (m, 2H), 7.58-7.44 (m, 3H), 7.38 (dd, J = 9.1, 7.5 Hz, 2H), 4.06-3.89 (m, 1H), 3.89-3.66 (m, 2H), 3.66-3.37 (m, 3H), 3.26-2.95 (m, 6H), 2.45-2.10 (m, 4H), 2.02 (dq, J = 15.0, 7.6 Hz, 1H), 1.92-1.65 (m, 2H), 1.51 (d, J = 9.6 Hz, 1H), 1.44 (s, 1H), 1.08 (dt, J = 24.7, 7.5 Hz, 6H). |
| 685 | 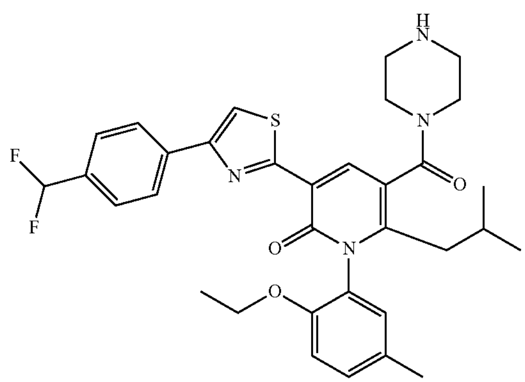 [SMILES: CCOc1ccc(C)cc1-n1c(CC(C)C)c(C(=O)N2CCNCC2)cc(-c2nc(-c3ccc(C(F)F)cc3)cs2)c1=O] | A | A | 607.2537 | 2.694 | Starting materials: methyl 5-methyl-3-oxohexanoate (step 1), nitrile 24 (step 2), 2-ethoxy-5-methylaniline (step 3), piperazine (used in method U); Methods: S, then ester hydrolyzed with LiOH (8 eq), THF/MeOH, 50 C, U, U, | ¹H NMR (400MHz, DMSO-d₆) δ 8.91 (s, 1H), 8.67 (d, J = 16.7 Hz, 1H), 8.31 (s, 1H), 8.24 (d, J = 8.2 Hz, 2H), 7.67 (d, J = 8.1 Hz, 2H), 7.63-7.47 (m, 1H), 7.42 (d, J = 8.7, 3.1Hz, 1H), 7.29 (dd, J = 9.3, 4.8 Hz, 1H), 7.09 (t, J = 55.9 Hz, 1H), 4.18-3.96 (m, 2H), 3.85-3.01 (m, 3H), 3.26-3.01 (m, 4H), 2.50 (p, J = 2.0 Hz, 2H), 2.39-2.23 (m, 3H), 2.18-1.98 (m, 1H), 1.63-1.44 (m, 1H), 1.12 (q, J = 5.5, 3.9 Hz, 3H), 0.67 (dq, J = 25.1, 8.3, 7.1 Hz, 6H). |

TABLE 1-continued

Characterization and Enzymatic Inhibition Data for Selected Compounds

| Cpd # | Structure | Data for R132H (µM) | Data for R132C (µM) | MZ | RT (min) | Synthesis Method | ¹H-NMR |
|---|---|---|---|---|---|---|---|
| 686 | 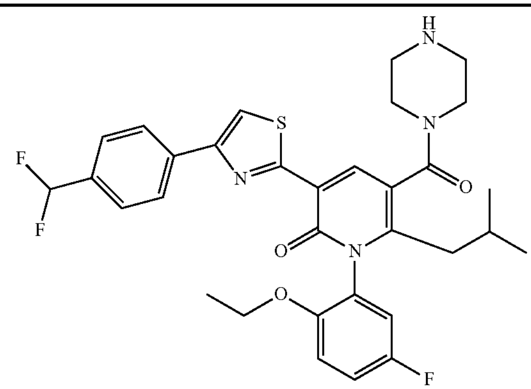 | B | B | 611.2296 | 2.656 | Starting materials: methyl 5-methyl-3-oxohexanoate (step 1), nitrile 24 (step 2), 2-ethoxy-5-fluoroaniline (step 3), piperazinee (used in method U), Methods: S, then ester hydrolyzed with LiOH (8 eq), THF/MeOH, 50 C, U. | ¹H NMR (400 MHz, DMSO-d6) δ 8.93 (s, 1H), 8.65 (d, J = 13.3 Hz, 1H), 8.30 (s, 1H), 8.24 (d, J = 8.1 Hz, 2H), 7.67 (d, J = 8.1 Hz, 2H), 7.33 (dd, J = 8.5, 2.1 Hz, 1H), 7.25 (s, 1H), 7.15 (d, J = 8.5 Hz, 1H), 7.09 (t, J = 55.9 Hz, 1H), 4.09-3.99 (m, 2H), 3.88-3.42 (m, 4H), 3.27-3.16 (m, 4H), 2.41-2.20 (m, 1H), 2.13-1.99 (m, 1H), 1.65-1.47 (m, 1H), 1.12 (t, J = 7.0 Hz, 3H), 0.73-0.57 (m, 6H). |
| 687 | 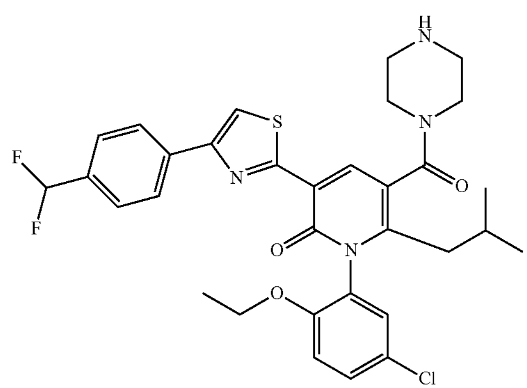 [SMILES: CCOc1ccc(Cl)cc1-n1c(CC(C)C)c(C(=O)N2CCNCC2)cc(-c2nc(-c3ccc(C(F)F)cc3)cs2)c1=O] | B | B | 627.1983 | 2.717 | Starting materials: methyl 5-methyl-3-oxohexanoate (step 1), nitrile 24 (step 2), 5-chloro-2-ethoxyaniline (step 3), piperazinee (used in method U), Methods: S, then ester hydrolyzed with LiOH (8 eq), THF/MeOH, 50 C, U. | ¹H NMR (400 MHz, DMSO-d6) δ 8.94 (s, 1H), 8.66 (d, J = 16.5 Hz, 1H), 8.31 (s, 1H), 8.24 (d, J = 8.1 Hz, 2H), 7.77-7.70 (m, 1H), 7.67 (d, J = 8.3 Hz, 2H), 7.60 (dd, J = 8.9, 2.7 Hz, 1H), 7.31 (d, J = 9.0 Hz, 1H), 7.09 (t, J = 56.0 Hz, 1H), 4.14-4.03 (m, 3H), 3.70 (d, J = 60.4 Hz, 3H), 3.23-3.01 (m, 3H), 2.66-2.56 (m, 1H), 2.32-2.25 (m, 1H), 2.15-2.03 (m, 1H), 1.63-1.43 (m, 1H), 1.13 (t, J = 6.8 Hz, 3H), 0.68 (dq, J = 26.9, 8.5, 7.3 Hz, 6H). |

TABLE 1-continued

Characterization and Enzymatic Inhibition Data for Selected Compounds

| Cpd # | Structure | Data for R132H (μM) | Data for R132C (μM) | MZ | RT (min) | Synthesis Method | ¹H-NMR |
|---|---|---|---|---|---|---|---|
| 690 | 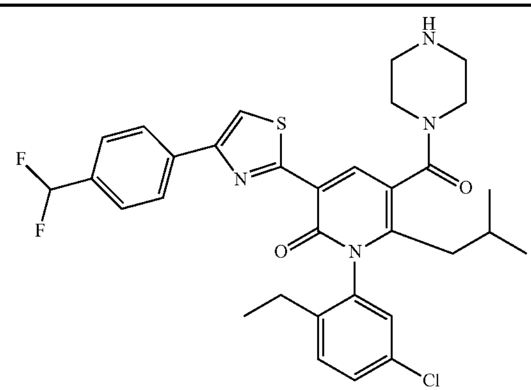 | | | | | | |
| 828 | 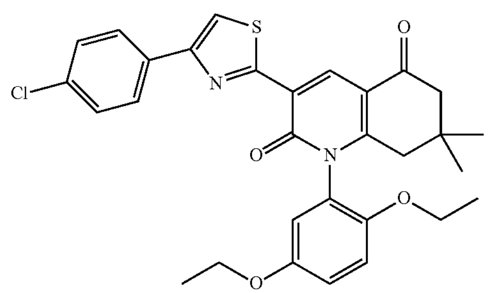 [SMILES: CCOc1ccc(OCC)c(-n2c3c(cc(-c4nc(-c5ccc(Cl)cc5)cs4)c2=O)C(=O)CC(C)(C)C3)c1] | B | A | 549.1603 | 4.027 | Starting materials: methyl 5-methyl-3-oxohexanoate (step 1), nitrile 24 (step 2), Aniline 4 (step 3), piperazinee (used in method U), Methods: S, then ester hydrolyzed with LiOH (8 eq), THF/MeOH, 50 C., U, | |

TABLE 2
Structures and Compound Numbers of Additional Compounds
671
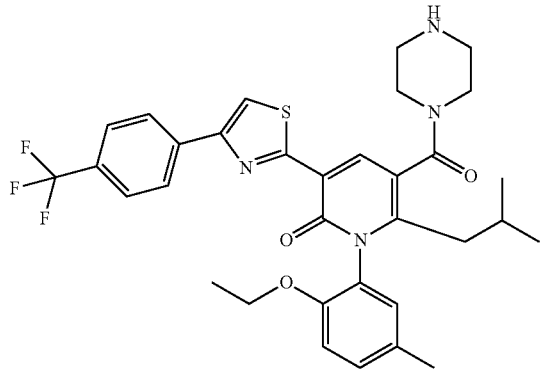 [SMILES: CCOc1ccc(C)cc1-n1c(CC(C)C)c(C(=O)N2CCNCC2)cc(-c2nc(-c3ccc(C(F)(F)F)cc3)cs2)c1=O]
672
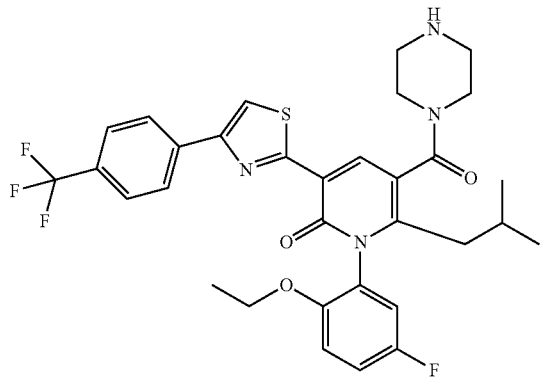 [SMILES: CCOc1ccc(F)cc1-n1c(CC(C)C)c(C(=O)N2CCNCC2)cc(-c2nc(-c3ccc(C(F)(F)F)cc3)cs2)c1=O]
673
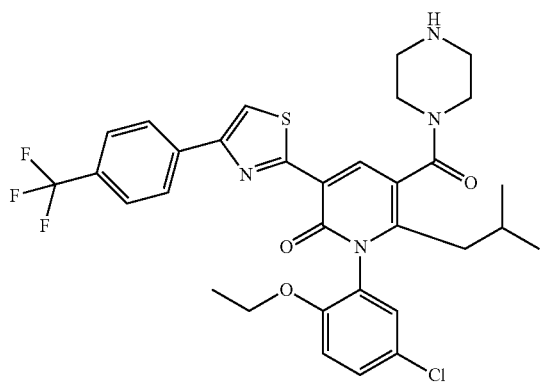 [SMILES: CCOc1ccc(Cl)cc1-n1c(CC(C)C)c(C(=O)N2CCNCC2)cc(-c2nc(-c3ccc(C(F)(F)F)cc3)cs2)c1=O]
674
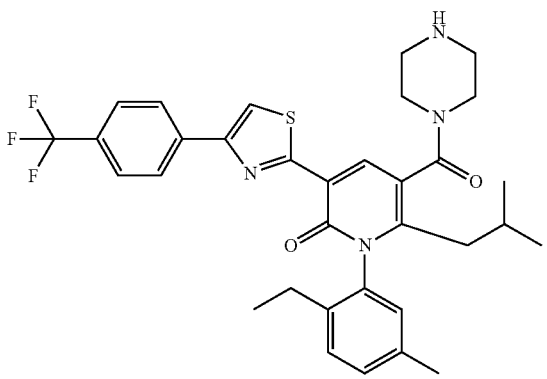 [SMILES: CCc1ccc(C)cc1-n1c(CC(C)C)c(C(=O)N2CCNCC2)cc(-c2nc(-c3ccc(C(F)(F)F)cc3)cs2)c1=O]

TABLE 2-continued
Structures and Compound Numbers of Additional Compounds
675 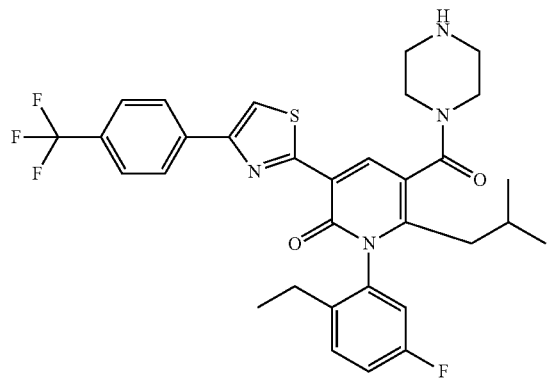
676 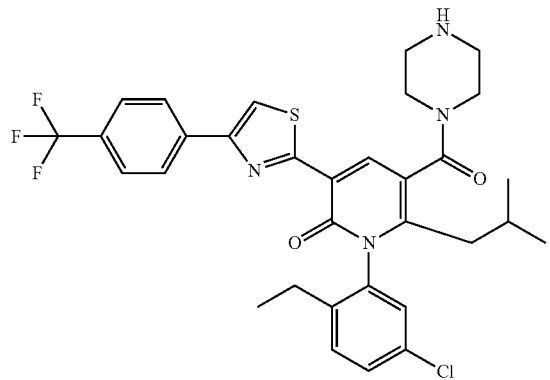
677 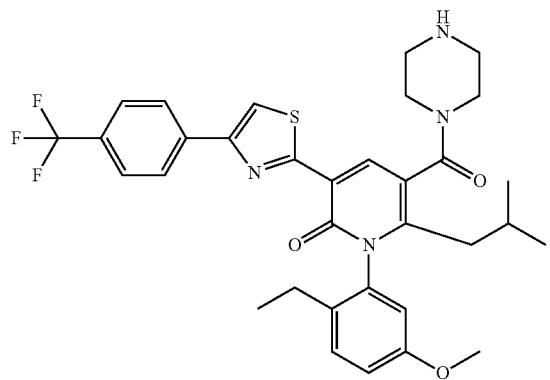
678 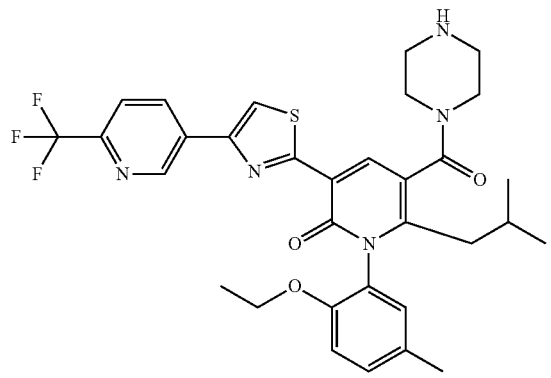 [SMILES: CCOc1ccc(C)cc1-n1c(CC(C)C)c(C(=O)N2CCNCC2)cc(-c2nc(-c3ccc(C(F)(F)F)nc3)cs2)c1=O]

TABLE 2-continued
Structures and Compound Numbers of Additional Compounds
679
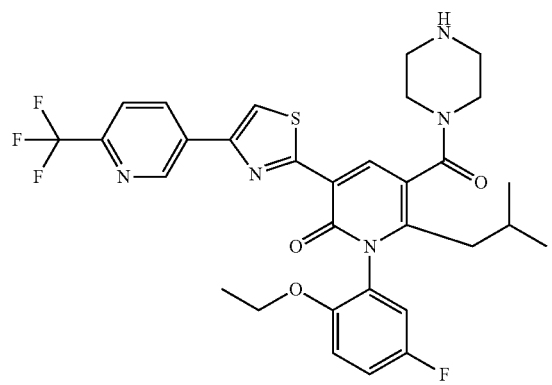
680
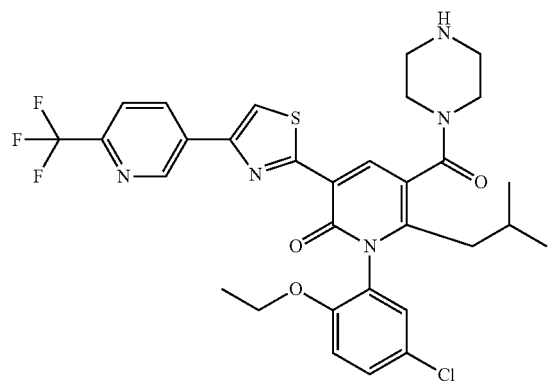 [SMILES: CCOc1ccc(Cl)cc1-n1c(CC(C)C)c(C(=O)N2CCNCC2)cc(-c2nc(-c3ccc(C(F)(F)F)nc3)cs2)c1=O]
681
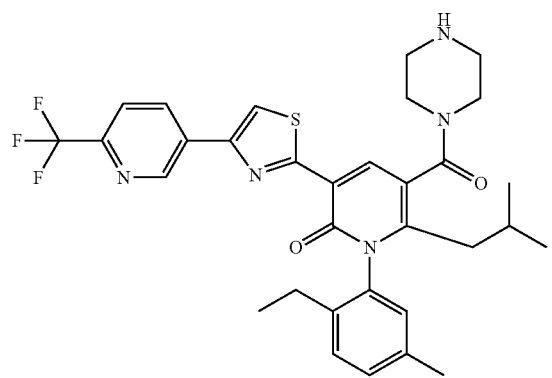
682
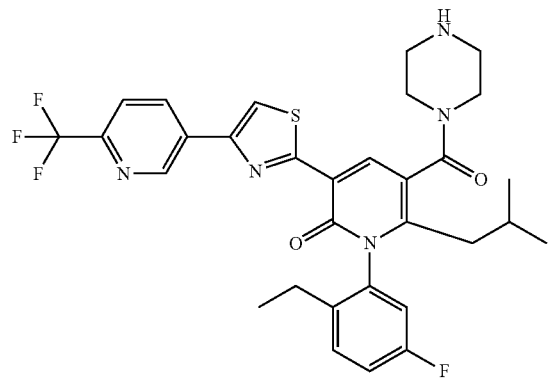 [SMILES: CCc1ccc(F)cc1-n1c(CC(C)C)c(C(=O)N2CCNCC2)cc(-c2nc(-c3ccc(C(F)(F)F)nc3)cs2)c1=O]

TABLE 2-continued
Structures and Compound Numbers of Additional Compounds
683
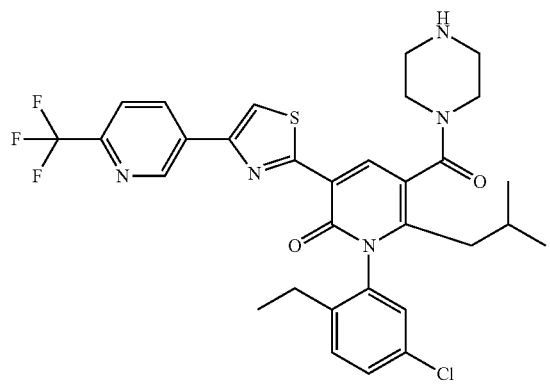
684
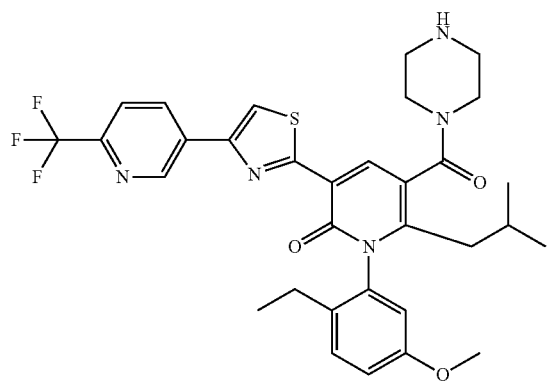 [SMILES: CCc1ccc(OC)cc1-n1c(CC(C)C)c(C(=O)N2CCNCC2)cc(-c2nc(-c3ccc(C(F)(F)F)nc3)cs2)c1=O]
688
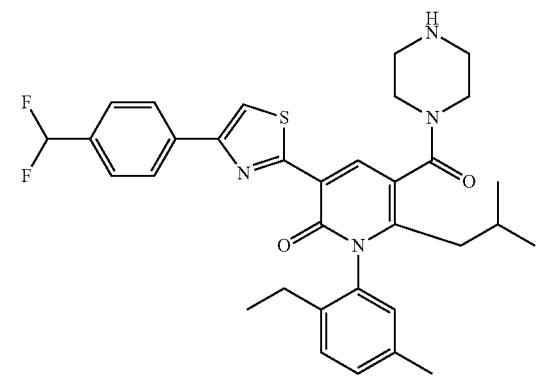 [SMILES: CCc1ccc(C)cc1-n1c(CC(C)C)c(C(=O)N2CCNCC2)cc(-c2nc(-c3ccc(C(F)F)cc3)cs2)c1=O]
689
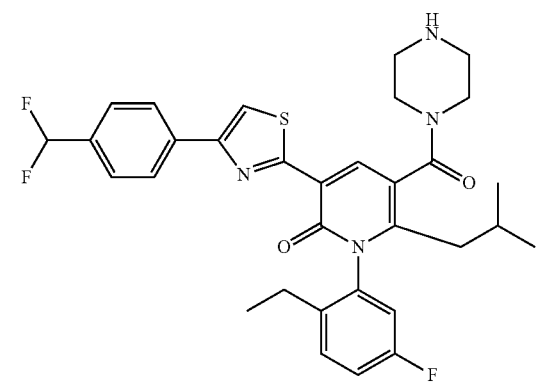 [SMILES: CCc1ccc(F)cc1-n1c(CC(C)C)c(C(=O)N2CCNCC2)cc(-c2nc(-c3ccc(C(F)F)cc3)cs2)c1=O]

TABLE 2-continued
Structures and Compound Numbers of Additional Compounds
691
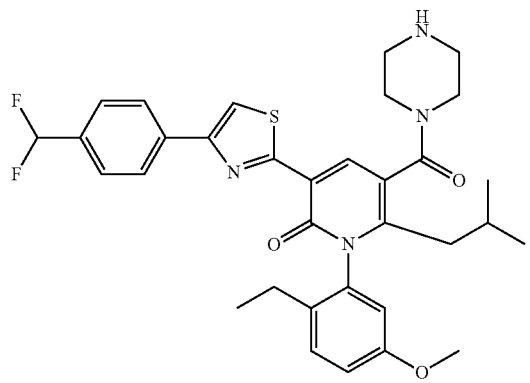
692
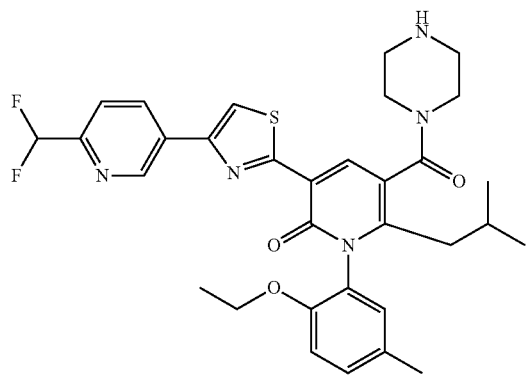 [SMILES: CCOc1ccc(C)cc1-n1c(CC(C)C)c(C(=O)N2CCNCC2)cc(-c2nc(-c3ccc(C(F)F)nc3)cs2)c1=O]
693
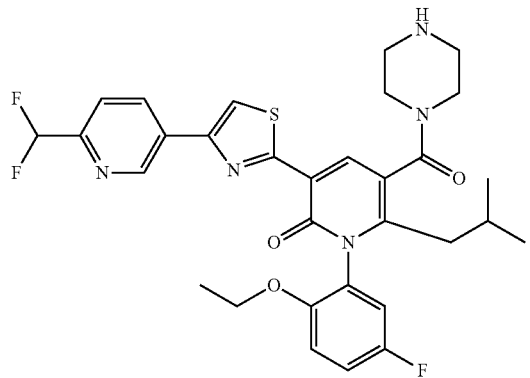 [SMILES: CCOc1ccc(F)cc1-n1c(CC(C)C)c(C(=O)N2CCNCC2)cc(-c2nc(-c3ccc(C(F)F)nc3)cs2)c1=O]
694
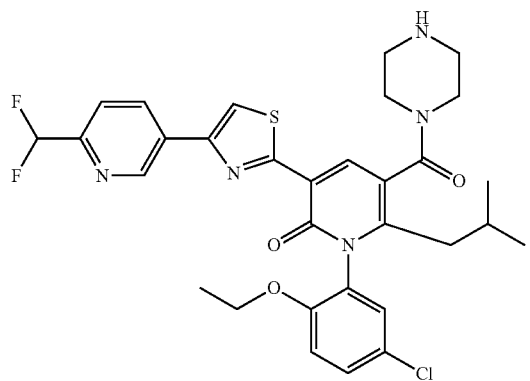 [SMILES: CCOc1ccc(Cl)cc1-n1c(CC(C)C)c(C(=O)N2CCNCC2)cc(-c2nc(-c3ccc(C(F)F)nc3)cs2)c1=O]

TABLE 2-continued
Structures and Compound Numbers of Additional Compounds
695
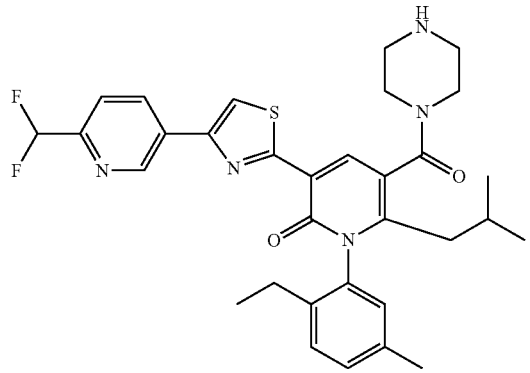 [SMILES: CCc1ccc(C)cc1-n1c(CC(C)C)c(C(=O)N2CCNCC2)cc(-c2nc(-c3ccc(C(F)F)nc3)cs2)c1=O]
696
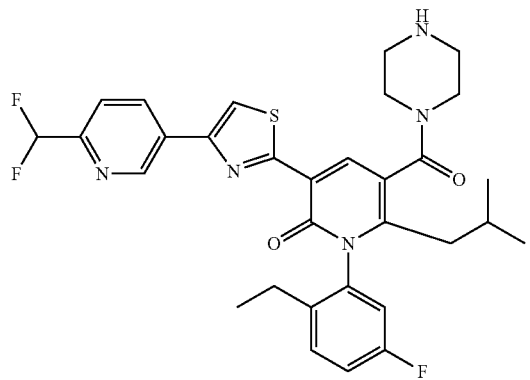 [SMILES: CCc1ccc(F)cc1-n1c(CC(C)C)c(C(=O)N2CCNCC2)cc(-c2nc(-c3ccc(C(F)F)nc3)cs2)c1=O]
697
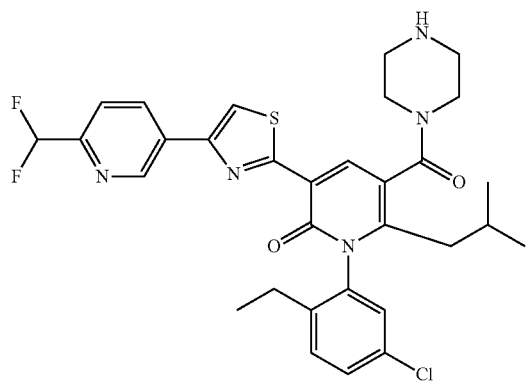 [SMILES: CCc1ccc(Cl)cc1-n1c(CC(C)C)c(C(=O)N2CCNCC2)cc(-c2nc(-c3ccc(C(F)F)nc3)cs2)c1=O]
698
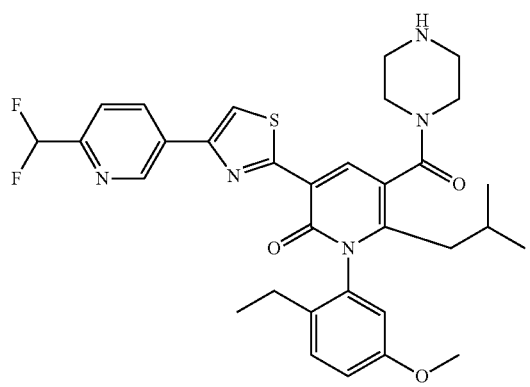 [SMILES: CCc1ccc(OC)cc1-n1c(CC(C)C)c(C(=O)N2CCNCC2)cc(-c2nc(-c3ccc(C(F)F)nc3)cs2)c1=O]

TABLE 2-continued
Structures and Compound Numbers of Additional Compounds
699 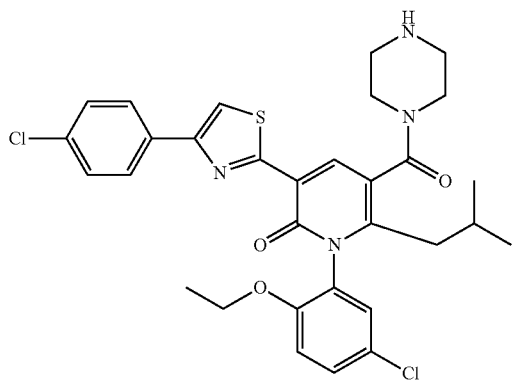 [SMILES: CCOc1ccc(Cl)cc1-n1c(CC(C)C)c(C(=O)N2CCNCC2)cc(-c2nc(-c3ccc(Cl)cc3)cs2)c1=O]
700 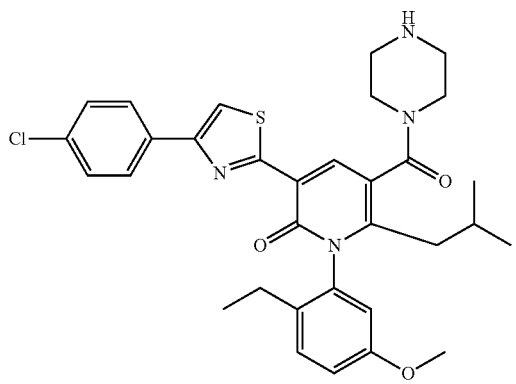 [SMILES: CCc1ccc(OC)cc1-n1c(CC(C)C)c(C(=O)N2CCNCC2)cc(-c2nc(-c3ccc(Cl)cc3)cs2)c1=O]
701 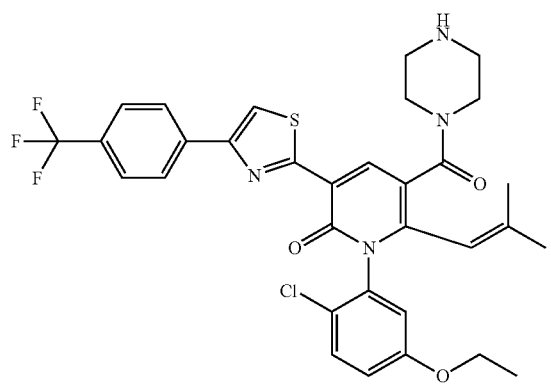
702 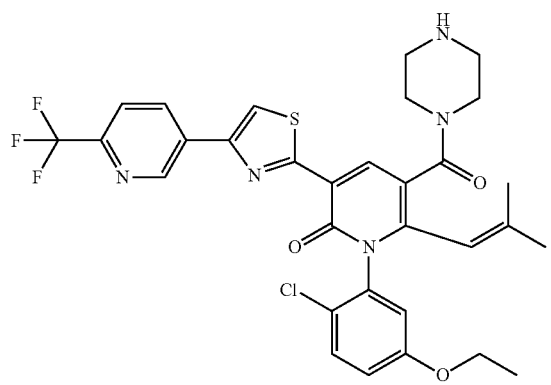 [SMILES: CCOc1ccc(Cl)c(-n2c(C=C(C)C)c(C(=O)N3CCNCC3)cc(-c3nc(-c4ccc(C(F)(F)F)nc4)cs3)c2=O)c1]

TABLE 2-continued
Structures and Compound Numbers of Additional Compounds
703 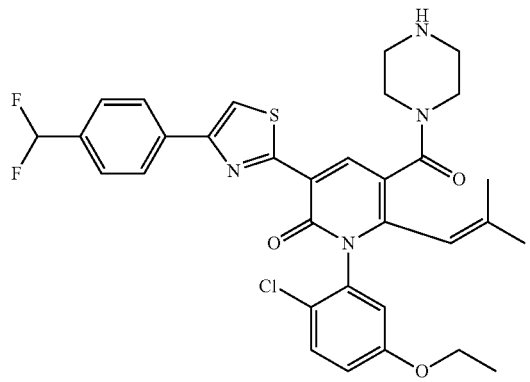 [SMILES: CCOc1ccc(Cl)c(-n2c(C=C(C)C)c(C(=O)N3CCNCC3)cc(-c3nc(-c4ccc(C(F)F)cc4)cs3)c2=O)c1]
704 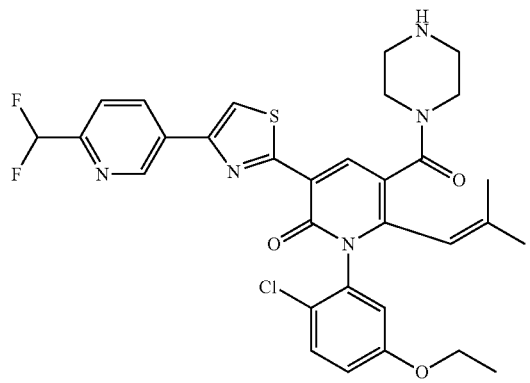 [SMILES: CCOc1ccc(Cl)c(-n2c(C=C(C)C)c(C(=O)N3CCNCC3)cc(-c3nc(-c4ccc(C(F)F)nc4)cs3)c2=O)c1]
705 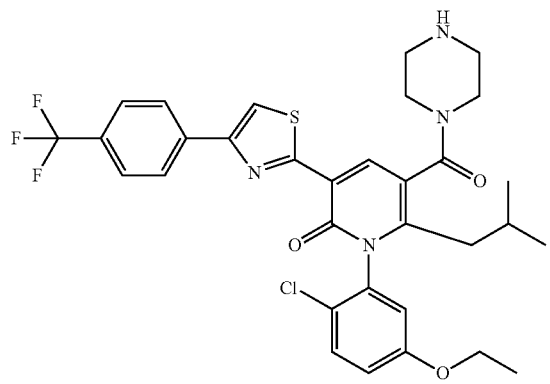 [SMILES: CCOc1ccc(Cl)c(-n2c(CC(C)C)c(C(=O)N3CCNCC3)cc(-c3nc(-c4ccc(C(F)(F)F)cc4)cs3)c2=O)c1]
706 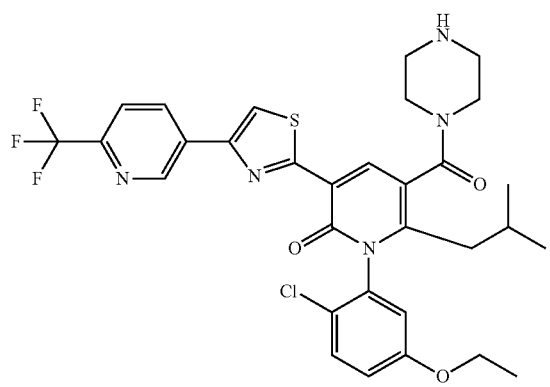 [SMILES: CCOc1ccc(Cl)c(-n2c(CC(C)C)c(C(=O)N3CCNCC3)cc(-c3nc(-c4ccc(C(F)(F)F)nc4)cs3)c2=O)c1]

TABLE 2-continued
Structures and Compound Numbers of Additional Compounds
707
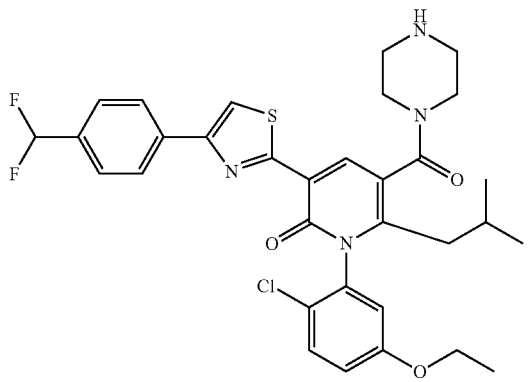 [SMILES: CCOc1ccc(Cl)c(-n2c(CC(C)C)c(C(=O)N3CCNCC3)cc(-c3nc(-c4ccc(C(F)F)nc4)cs3)c2=O)c1]
708
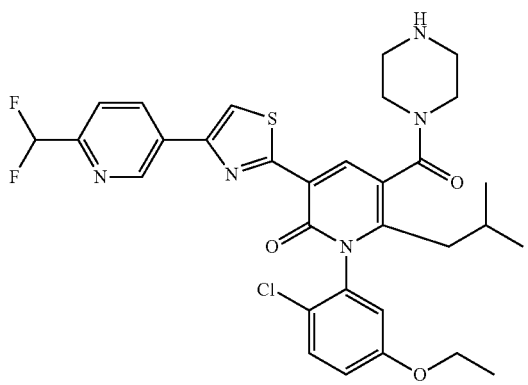
709
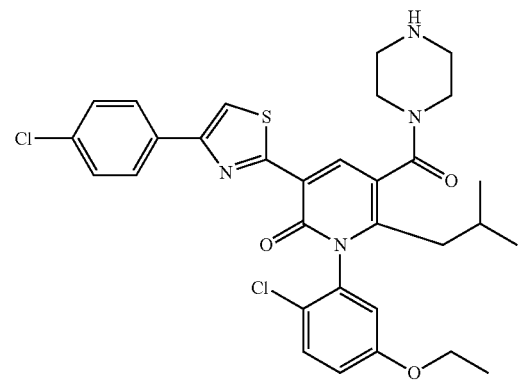 [SMILES: CCOc1ccc(Cl)c(-n2c(CC(C)C)c(C(=O)N3CCNCC3)cc(-c3nc(-c4ccc(Cl)cc4)cs3)c2=O)c1]
710
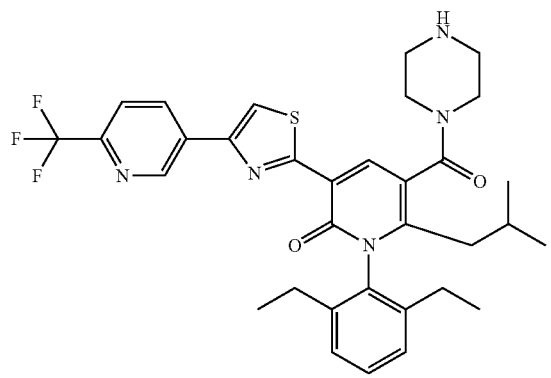 [SMILES: CCc1cccc(CC)c1-n1c(CC(C)C)c(C(=O)N2CCNCC2)cc(-c2nc(-c3ccc(C(F)(F)F)nc3)cs2)c1=O]

TABLE 2-continued
Structures and Compound Numbers of Additional Compounds
711
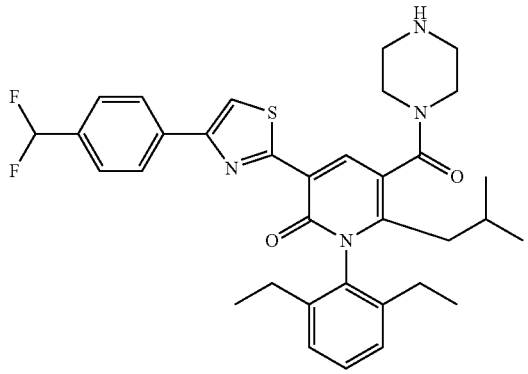 [SMILES: CCc1cccc(CC)c1-n1c(CC(C)C)c(C(=O)N2CCNCC2)cc(-c2nc(-c3ccc(C(F)F)cc3)cs2)c1=O]
712
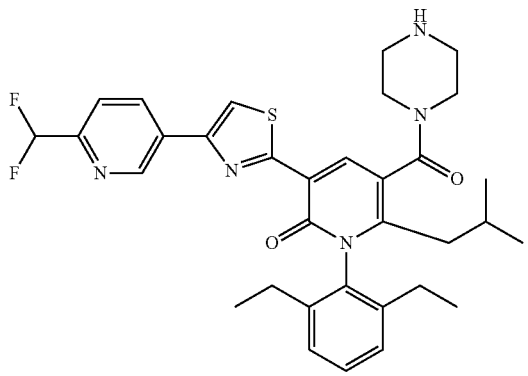 [SMILES: CCc1cccc(CC)c1-n1c(CC(C)C)c(C(=O)N2CCNCC2)cc(-c2nc(-c3ccc(C(F)F)nc3)cs2)c1=O]
713
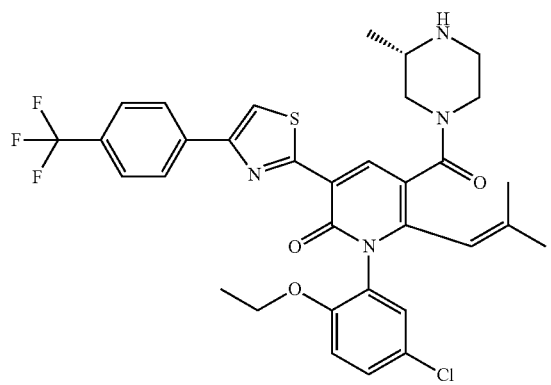
714
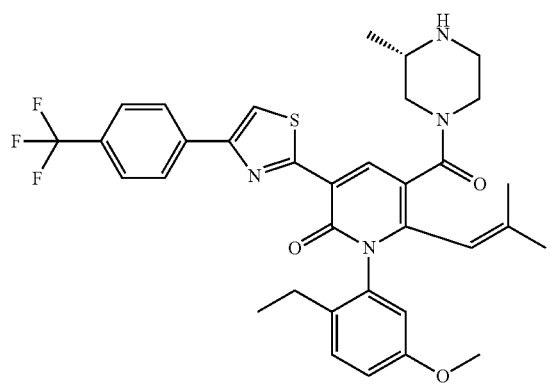 [SMILES: CCc1ccc(OC)cc1-n1c(C=C(C)C)c(C(=O)N2CCN[C@@H](C)C2)cc(-c2nc(-c3ccc(C(F)(F)F)cc3)cs2)c1=O]

TABLE 2-continued
Structures and Compound Numbers of Additional Compounds
715 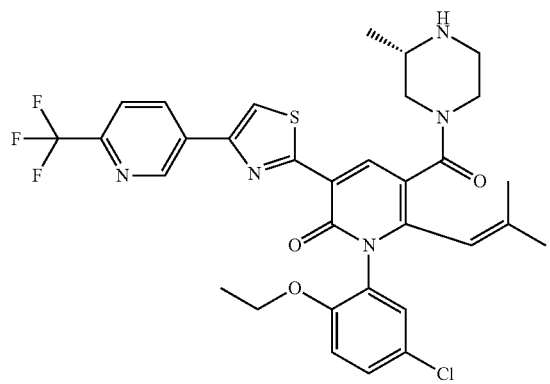 [SMILES: CCOc1ccc(Cl)cc1-n1c(C=C(C)C)c(C(=O)N2CCN[C@@H](C)C2)cc(-c2nc(-c3ccc(C(F)(F)F)nc3)cs2)c1=O]
716 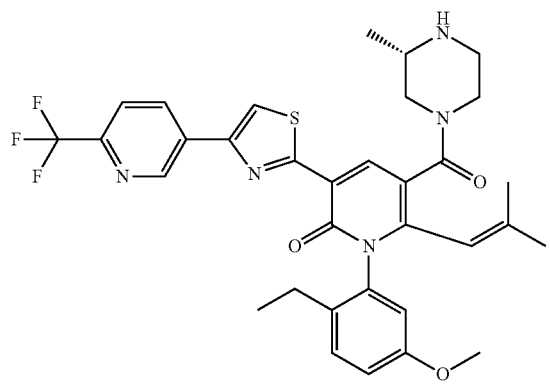 [SMILES: CCc1ccc(OC)cc1-n1c(C=C(C)C)c(C(=O)N2CCN[C@@H](C)C2)cc(-c2nc(-c3ccc(C(F)(F)F)nc3)cs2)c1=O]
717 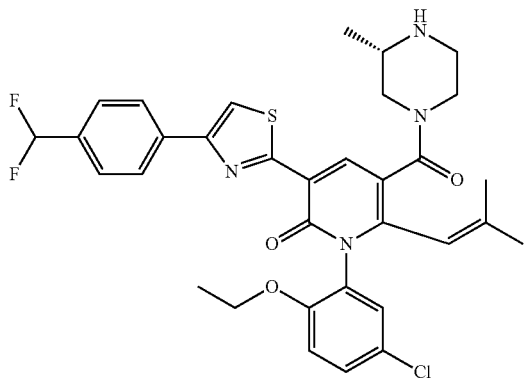 [SMILES: CCOc1ccc(Cl)cc1-n1c(C=C(C)C)c(C(=O)N2CCN[C@@H](C)C2)cc(-c2nc(-c3ccc(C(F)F)cc3)cs2)c1=O]
718 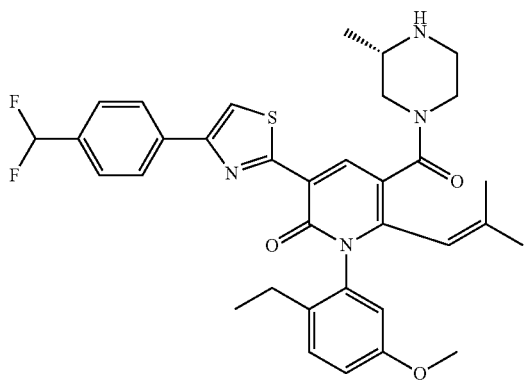 [SMILES: CCc1ccc(OC)cc1-n1c(C=C(C)C)c(C(=O)N2CCN[C@@H](C)C2)cc(-c2nc(-c3ccc(C(F)F)cc3)cs2)c1=O]

TABLE 2-continued
Structures and Compound Numbers of Additional Compounds
719
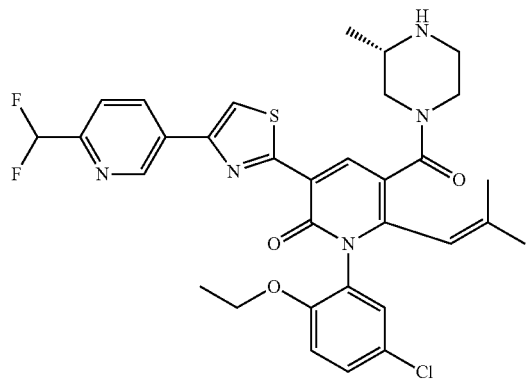
720
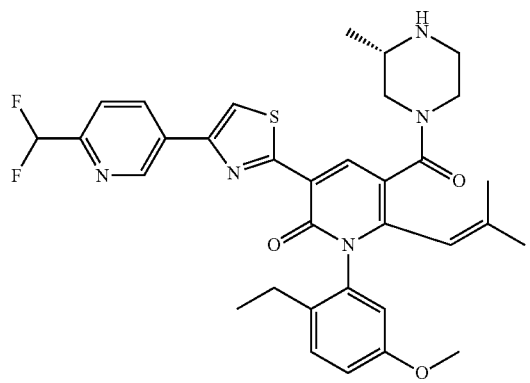 [SMILES: CCc1ccc(OC)cc1-n1c(C=C(C)C)c(C(=O)N2CCN[C@@H](C)C2)cc(-c2nc(-c3ccc(C(F)F)nc3)cs2)c1=O]
721
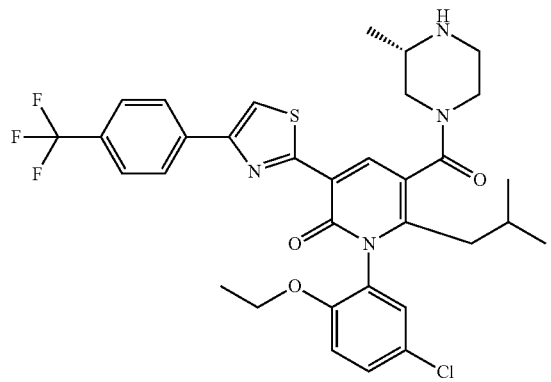 [SMILES: CCOc1ccc(Cl)cc1-n1c(CC(C)C)c(C(=O)N2CCN[C@@H](C)C2)cc(-c2nc(-c3ccc(C(F)(F)F)nc3)cs2)c1=O]
722
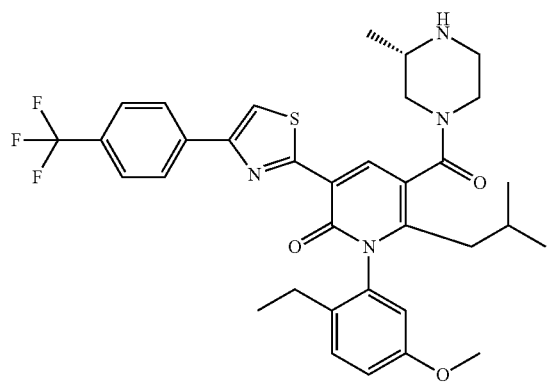

TABLE 2-continued
Structures and Compound Numbers of Additional Compounds
723
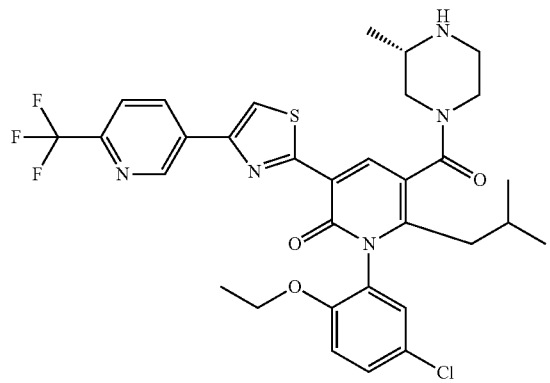
724
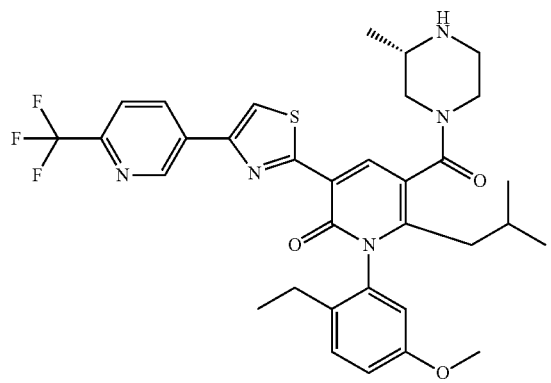
725
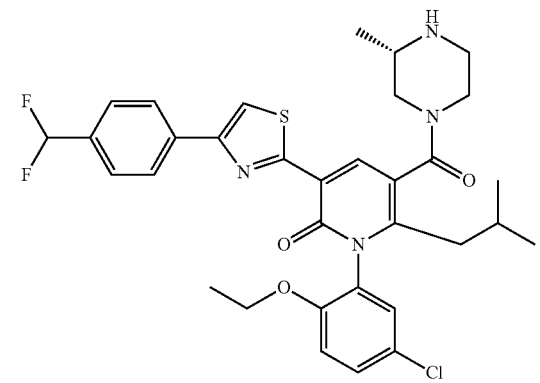
726
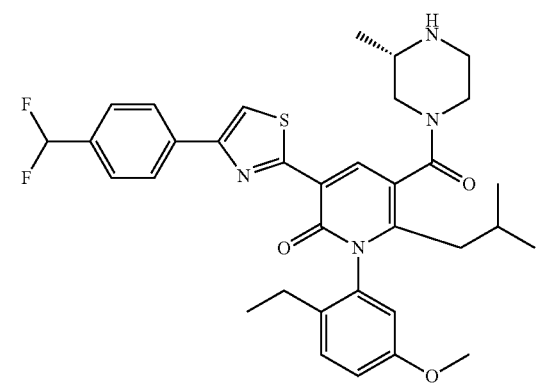

TABLE 2-continued
Structures and Compound Numbers of Additional Compounds
727
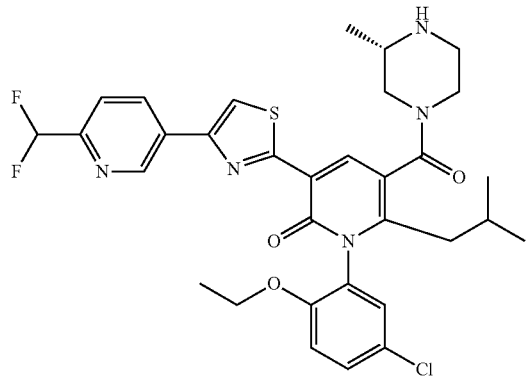 [SMILES: CCOc1ccc(Cl)cc1-n1c(CC(C)C)c(C(=O)N2CCN[C@@H](C)C2)cc(-c2nc(-c3ccc(C(F)F)nc3)cs2)c1=O]
728
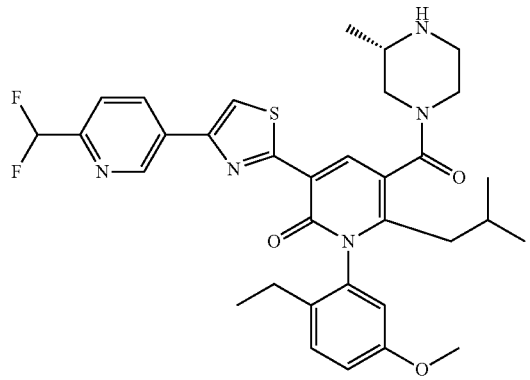 [SMILES: CCc1ccc(OC)cc1-n1c(CC(C)C)c(C(=O)N2CCN[C@@H](C)C2)cc(-c2nc(-c3ccc(C(F)F)nc3)cs2)c1=O]
729
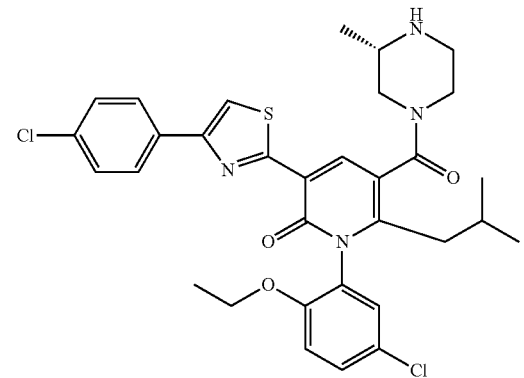
730
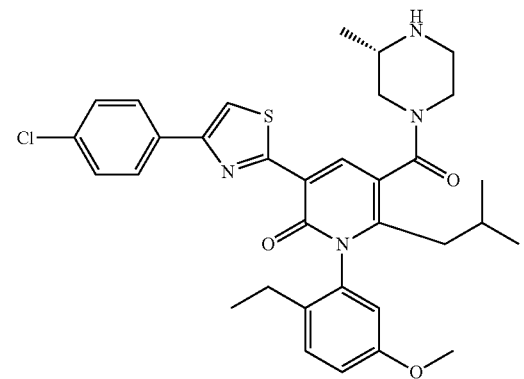

TABLE 2-continued
Structures and Compound Numbers of Additional Compounds
731
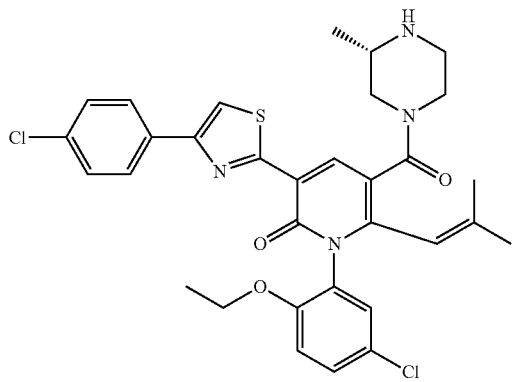 [SMILES: CCOc1ccc(Cl)cc1-n1c(C=C(C)C)c(C(=O)N2CCN[C@@H](C)C2)cc(-c2nc(-c3ccc(Cl)cc3)cs2)c1=O]
732
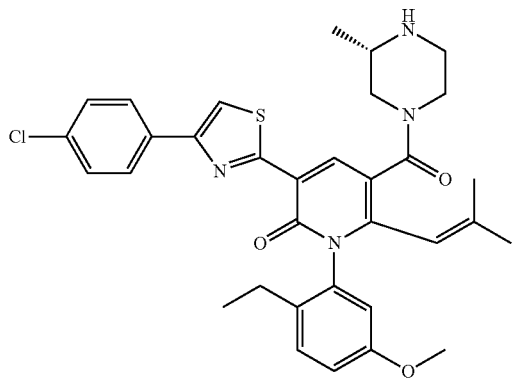 [SMILES: CCc1ccc(OC)cc1-n1c(C=C(C)C)c(C(=O)N2CCN[C@@H](C)C2)cc(-c2nc(-c3ccc(Cl)cc3)cs2)c1=O]
733
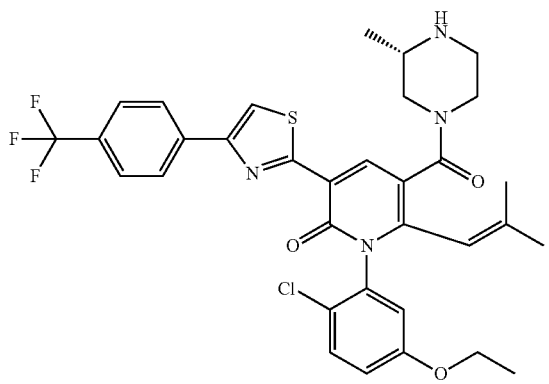 [SMILES: CCOc1ccc(Cl)c(-n2c(C=C(C)C)c(C(=O)N3CCN[C@@H](C)C3)cc(-c3nc(-c4ccc(C(F)(F)F)cc4)cs3)c2=O)c1]
734
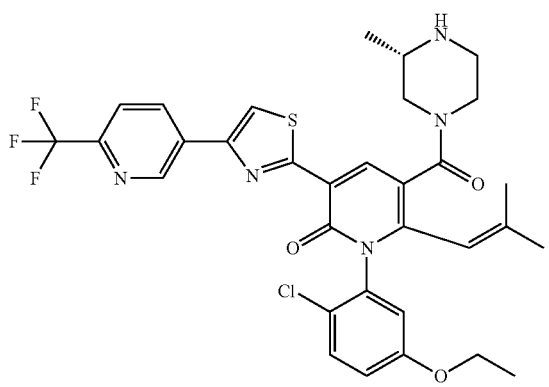 [SMILES: CCOc1ccc(Cl)c(-n2c(C=C(C)C)c(C(=O)N3CCN[C@@H](C)C3)cc(-c3nc(-c4ccc(C(F)(F)F)nc4)cs3)c2=O)c1]

TABLE 2-continued
Structures and Compound Numbers of Additional Compounds
735 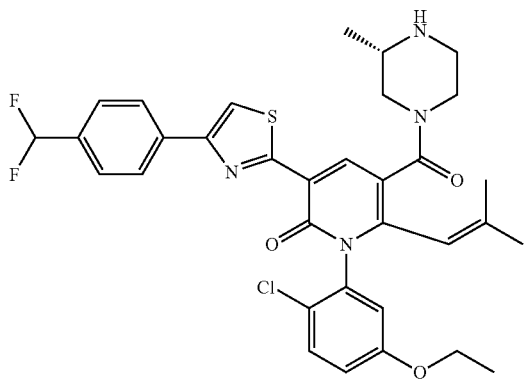 [SMILES: CCOc1ccc(Cl)c(-n2c(C=C(C)C)c(C(=O)N3CCN[C@@H](C)C3)cc(-c3nc(-c4ccc(C(F)F)cc4)cs3)c2=O)c1]
736 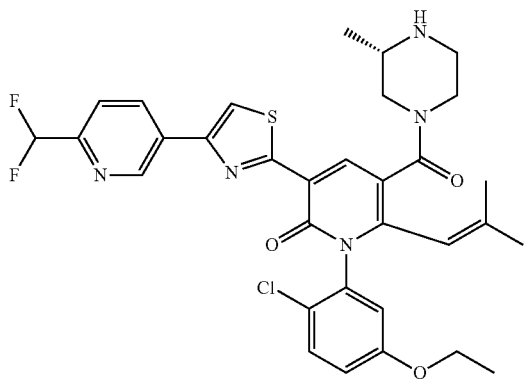 [SMILES: CCOc1ccc(Cl)c(-n2c(C=C(C)C)c(C(=O)N3CCN[C@@H](C)C3)cc(-c3nc(-c4ccc(C(F)F)nc4)cs3)c2=O)c1]
737 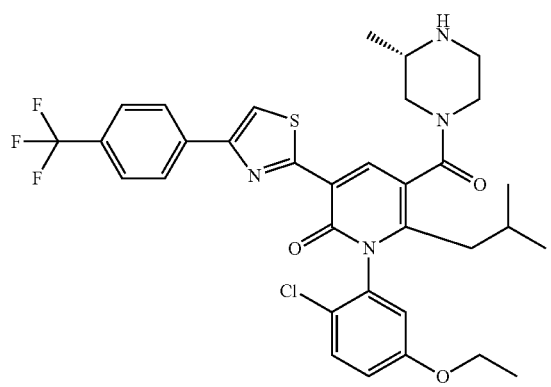
738 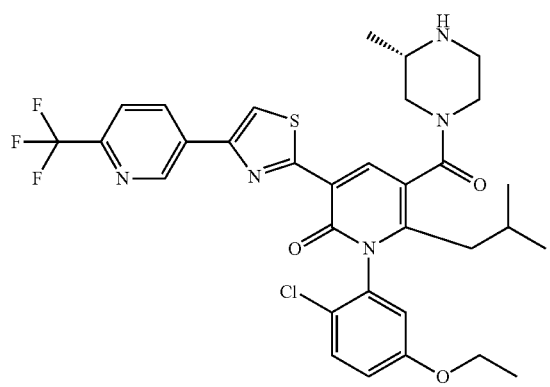 [SMILES: CCOc1ccc(Cl)c(-n2c(CC(C)C)c(C(=O)N3CCN[C@@H](C)C3)cc(-c3nc(-c4ccc(C(F)(F)F)cc4)cs3)c2=O)c1]

TABLE 2-continued
Structures and Compound Numbers of Additional Compounds
739
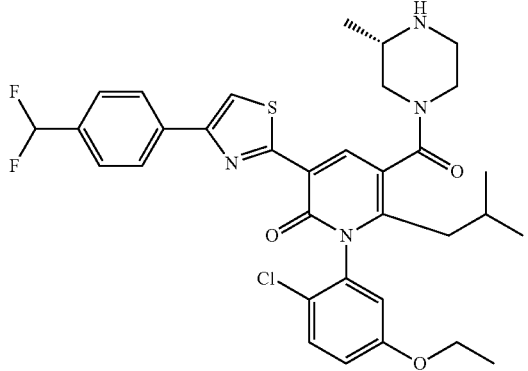 [SMILES: CCOc1ccc(Cl)c(-n2c(CC(C)C)c(C(=O)N3CCN[C@@H](C)C3)cc(-c3nc(-c4ccc(C(F)F)cc4)cs3)c2=O)c1]
740
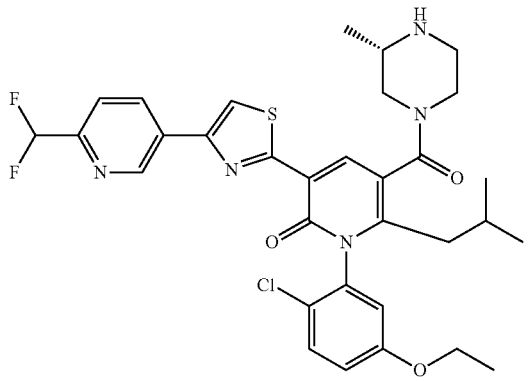 [SMILES: CCOc1ccc(Cl)c(-n2c(CC(C)C)c(C(=O)N3CCN[C@@H](C)C3)cc(-c3nc(-c4ccc(C(F)F)nc4)cs3)c2=O)c1]
741
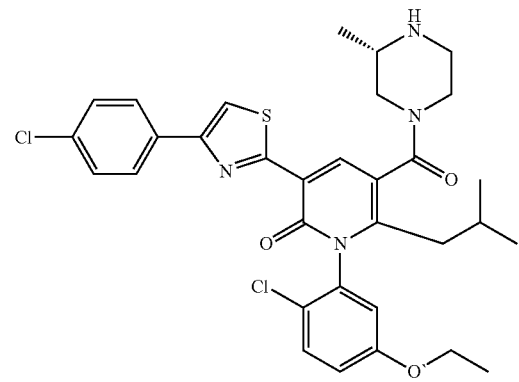
742
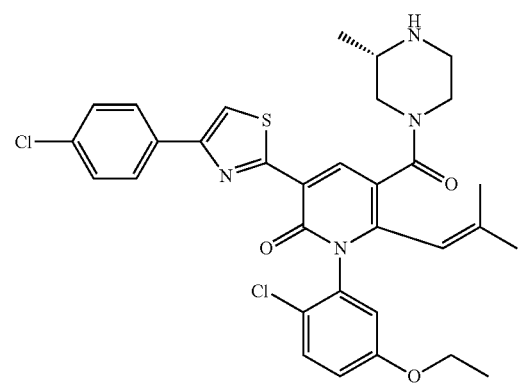 [SMILES: CCOc1ccc(Cl)c(-n2c(C=C(C)C)c(C(=O)N3CCN[C@@H](C)C3)cc(-c3nc(-c4ccc(Cl)cc4)cs3)c2=O)c1]

TABLE 2-continued
Structures and Compound Numbers of Additional Compounds
743
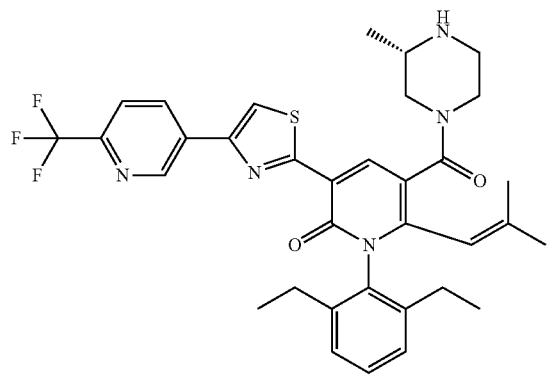 [SMILES: CCc1cccc(CC)c1-n1c(C=C(C)C)c(C(=O)N2CCN[C@@H](C)C2)cc(-c2nc(-c3ccc(C(F)(F)F)nc3)cs2)c1=O]
744
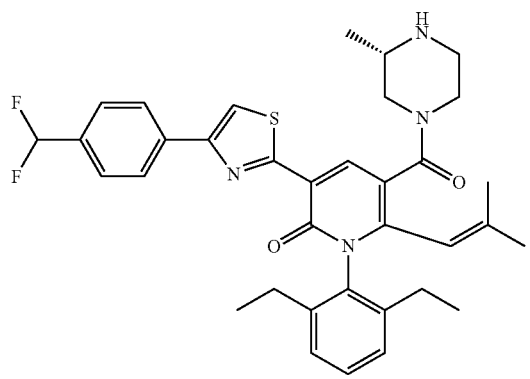
745
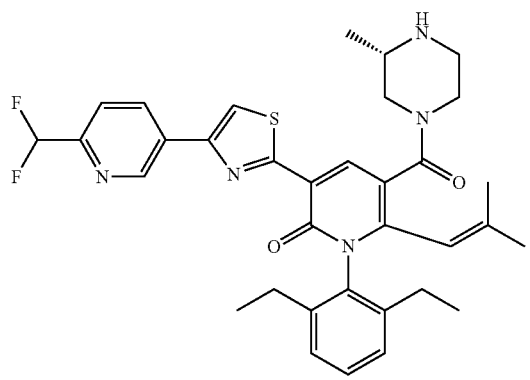 [SMILES: CCc1cccc(CC)c1-n1c(C=C(C)C)c(C(=O)N2CCN[C@@H](C)C2)cc(-c2nc(-c3ccc(C(F)F)cc3)cs2)c1=O]
746
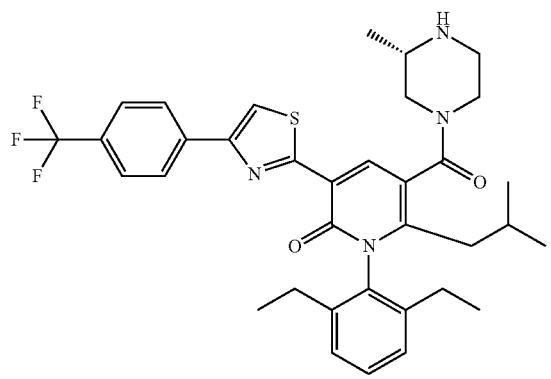 [SMILES: CCc1cccc(CC)c1-n1c(CC(C)C)c(C(=O)N2CCN[C@@H](C)C2)cc(-c2nc(-c3ccc(C(F)(F)F)cc3)cs2)c1=O]

TABLE 2-continued
Structures and Compound Numbers of Additional Compounds
747
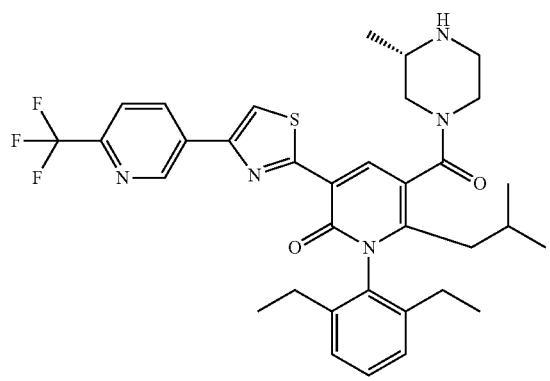
748
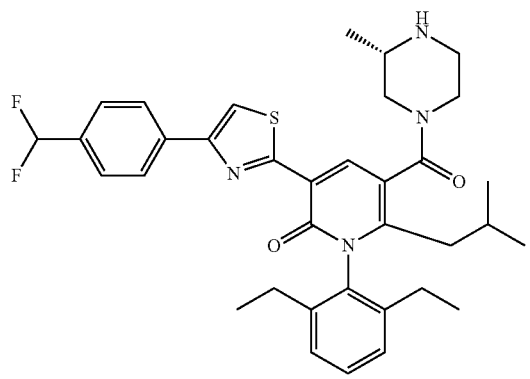 [SMILES: CCc1cccc(CC)c1-n1c(CC(C)C)c(C(=O)N2CCN[C@@H](C)C2)cc(-c2nc(-c3ccc(C(F)F)cc3)cs2)c1=O]
749
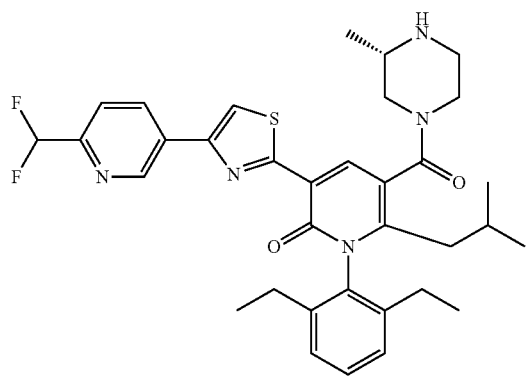
750
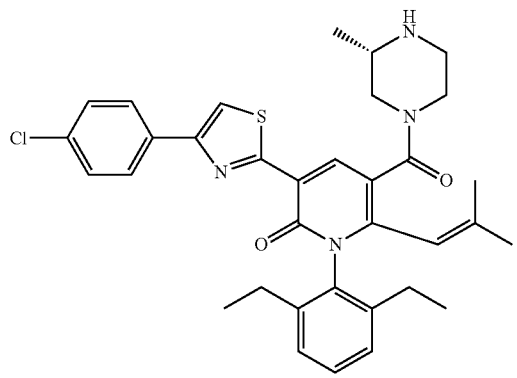 [SMILES: CCc1cccc(CC)c1-n1c(C=C(C)C)c(C(=O)N2CCN[C@@H](C)C2)cc(-c2nc(-c3ccc(Cl)cc3)cs2)c1=O]

TABLE 2-continued
Structures and Compound Numbers of Additional Compounds
751 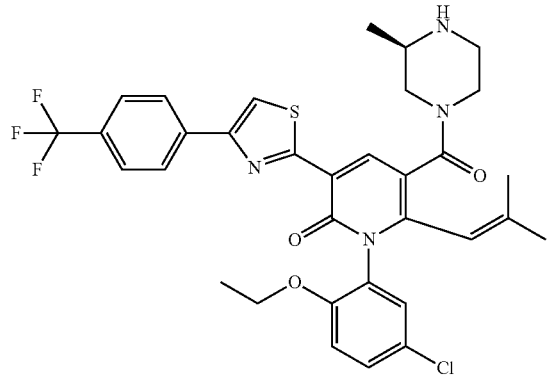
752 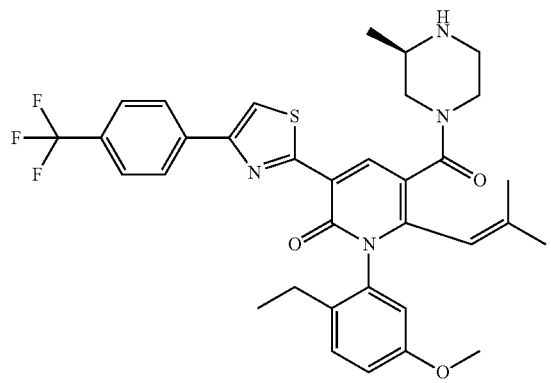
753 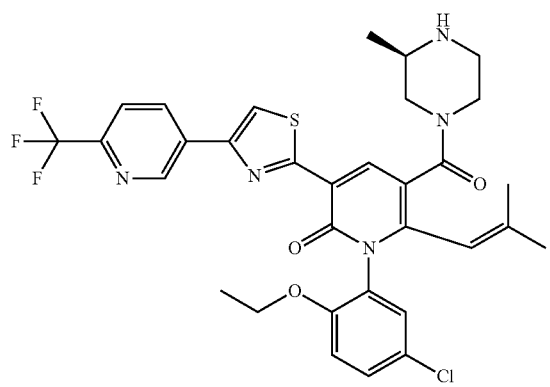 [SMILES: CCOc1ccc(Cl)cc1-n1c(C=C(C)C)c(C(=O)N2CCN[C@H](C)C2)cc(-c2nc(-c3ccc(C(F)(F)F)nc3)cs2)c1=O]
754 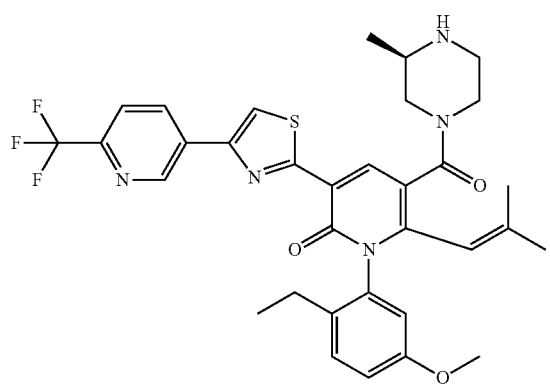 [SMILES: CCc1ccc(OC)cc1-n1c(C=C(C)C)c(C(=O)N2CCN[C@H](C)C2)cc(-c2nc(-c3ccc(C(F)(F)F)nc3)cs2)c1=O]

TABLE 2-continued
Structures and Compound Numbers of Additional Compounds
755
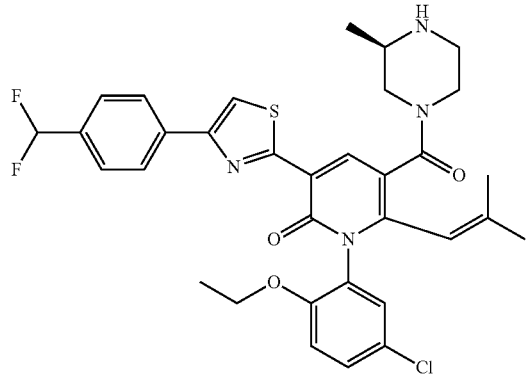 [SMILES: CCOc1ccc(Cl)cc1-n1c(C=C(C)C)c(C(=O)N2CCN[C@H](C)C2)cc(-c2nc(-c3ccc(C(F)F)cc3)cs2)c1=O]
756
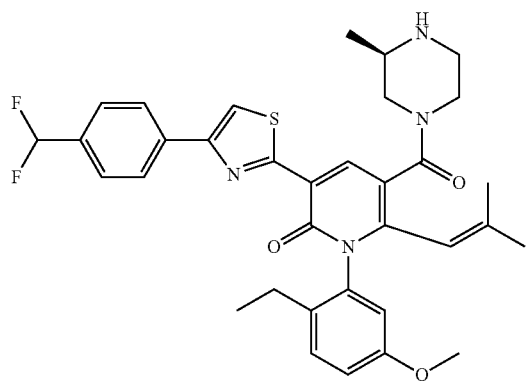 [SMILES: CCc1ccc(OC)cc1-n1c(C=C(C)C)c(C(=O)N2CCN[C@H](C)C2)cc(-c2nc(-c3ccc(C(F)F)cc3)cs2)c1=O]
757
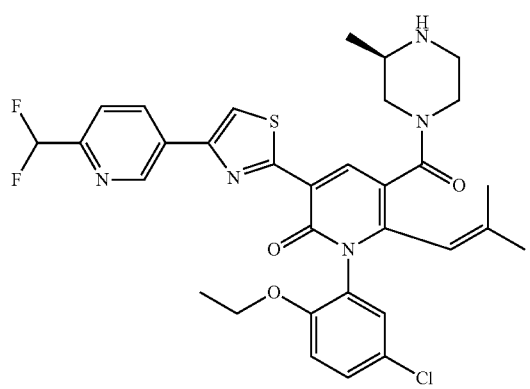
758
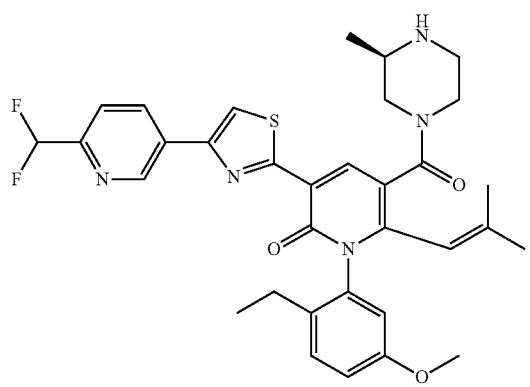

TABLE 2-continued
Structures and Compound Numbers of Additional Compounds
759 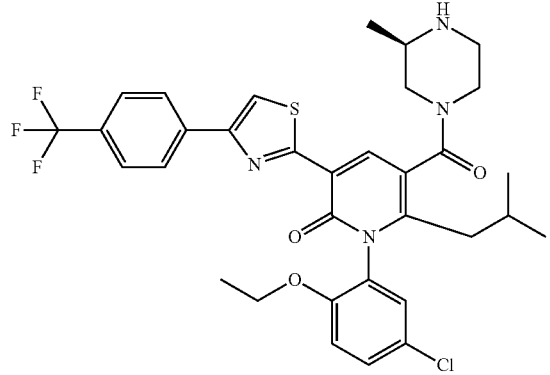
760 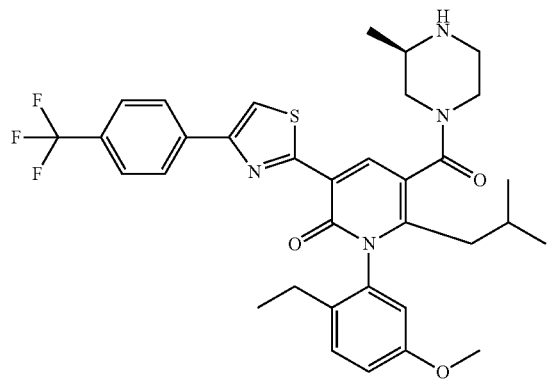 [SMILES: CCc1ccc(OC)cc1-n1c(CC(C)C)c(C(=O)N2CCN[C@H](C)C2)cc(-c2nc(-c3ccc(C(F)(F)F)nc3)cs2)c1=O]
761 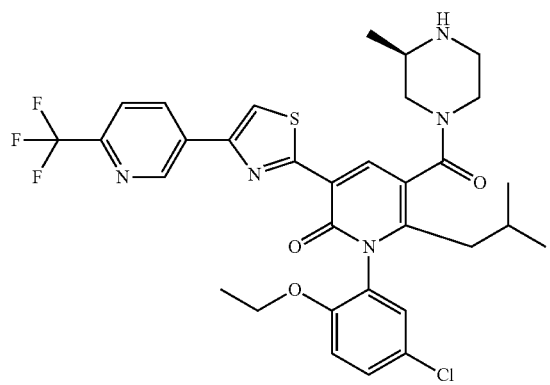
762 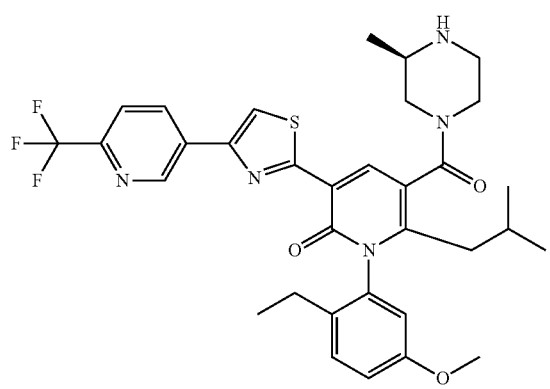

TABLE 2-continued
Structures and Compound Numbers of Additional Compounds
763
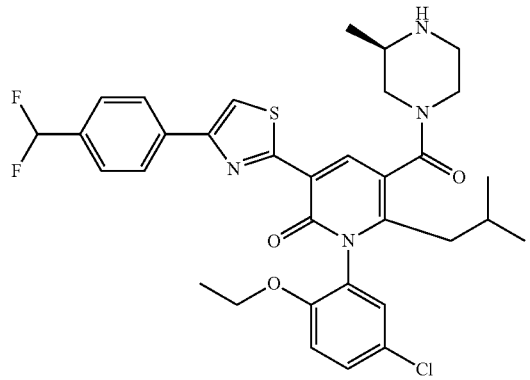 [SMILES: CCOc1ccc(Cl)cc1-n1c(CC(C)C)c(C(=O)N2CCN[C@H](C)C2)cc(-c2nc(-c3ccc(C(F)F)cc3)cs2)c1=O]
764
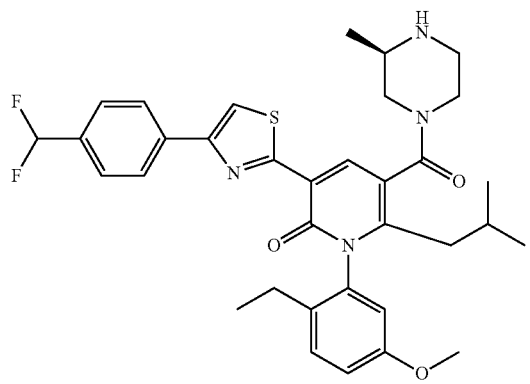 [SMILES: CCc1ccc(OC)cc1-n1c(CC(C)C)c(C(=O)N2CCN[C@H](C)C2)cc(-c2nc(-c3ccc(C(F)F)nc3)cs2)c1=O]
765
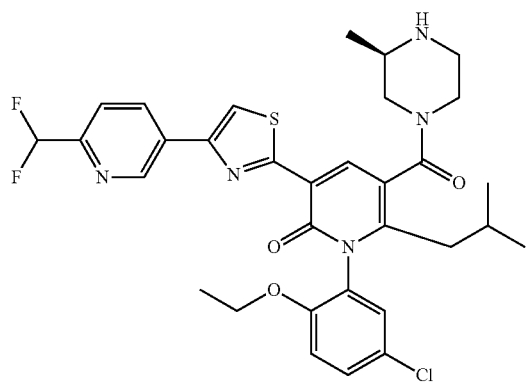
766
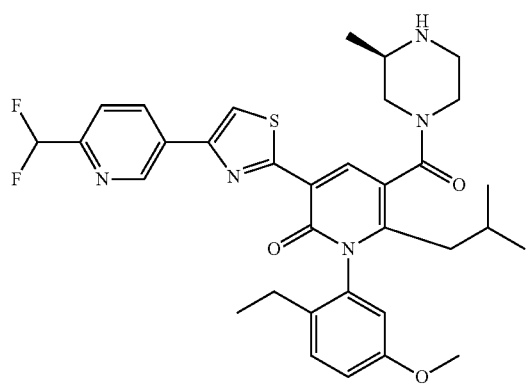

TABLE 2-continued
Structures and Compound Numbers of Additional Compounds
767 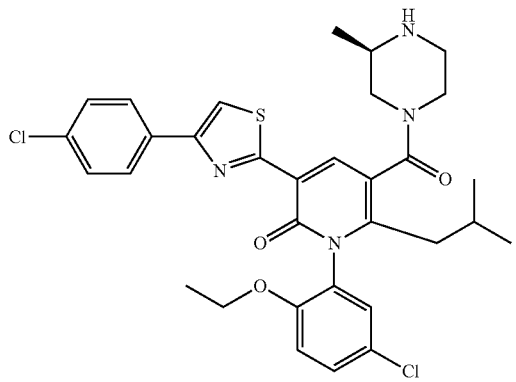 [SMILES: CCOc1ccc(Cl)cc1-n1c(CC(C)C)c(C(=O)N2CCN[C@H](C)C2)cc(-c2nc(-c3ccc(Cl)cc3)cs2)c1=O]
768 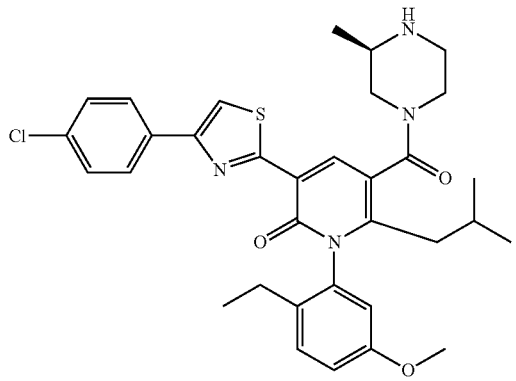 [SMILES: CCc1ccc(OC)cc1-n1c(CC(C)C)c(C(=O)N2CCN[C@H](C)C2)cc(-c2nc(-c3ccc(Cl)cc3)cs2)c1=O]
769 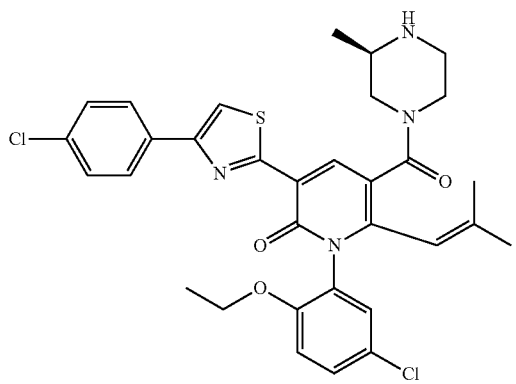 [SMILES: CCOc1ccc(Cl)cc1-n1c(C=C(C)C)c(C(=O)N2CCN[C@H](C)C2)cc(-c2nc(-c3ccc(Cl)cc3)cs2)c1=O]
770 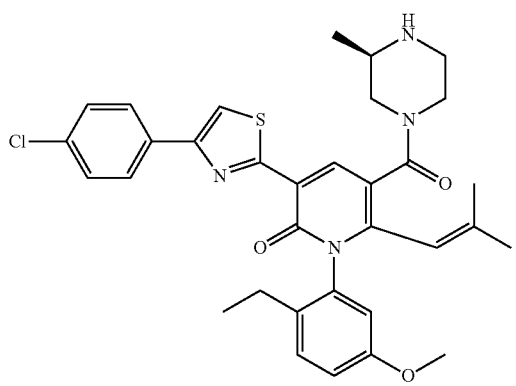 [SMILES: CCc1ccc(OC)cc1-n1c(C=C(C)C)c(C(=O)N2CCN[C@H](C)C2)cc(-c2nc(-c3ccc(Cl)cc3)cs2)c1=O]

TABLE 2-continued
Structures and Compound Numbers of Additional Compounds
771
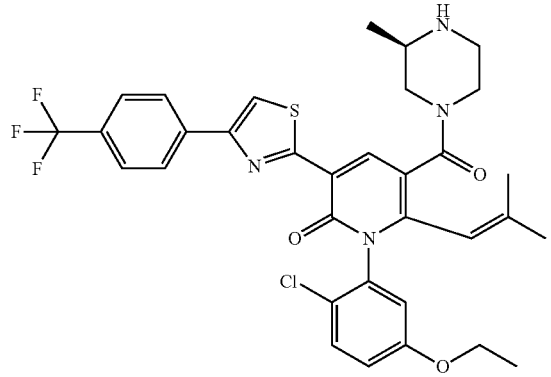 [SMILES: CCOc1ccc(Cl)c(-n2c(C=C(C)C)c(C(=O)N3CCN[C@H](C)C3)cc(-c3nc(-c4ccc(C(F)(F)F)cc4)cs3)c2=O)c1]
772
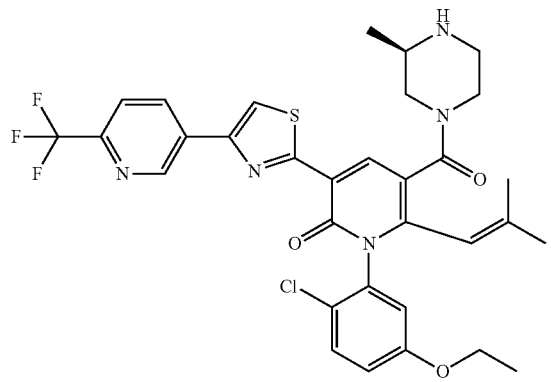 [SMILES: CCOc1ccc(Cl)c(-n2c(C=C(C)C)c(C(=O)N3CCN[C@H](C)C3)cc(-c3nc(-c4ccc(C(F)(F)F)nc4)cs3)c2=O)c1]
773
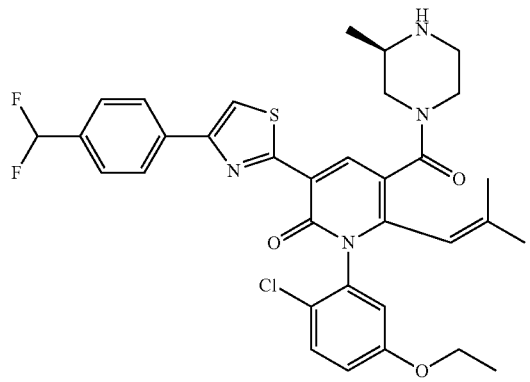 [SMILES: CCOc1ccc(Cl)c(-n2c(C=C(C)C)c(C(=O)N3CCN[C@H](C)C3)cc(-c3nc(-c4ccc(C(F)F)cc4)cs3)c2=O)c1]
774
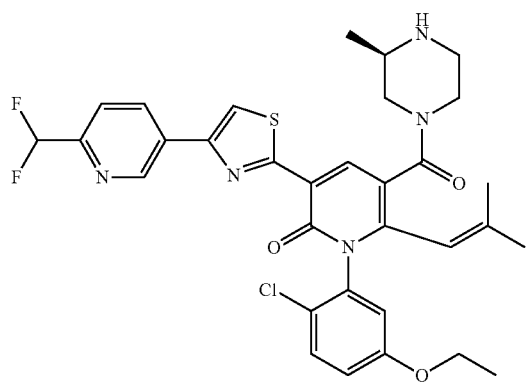 [SMILES: CCOc1ccc(Cl)c(-n2c(C=C(C)C)c(C(=O)N3CCN[C@H](C)C3)cc(-c3nc(-c4ccc(C(F)F)nc4)cs3)c2=O)c1]

TABLE 2-continued
Structures and Compound Numbers of Additional Compounds
775
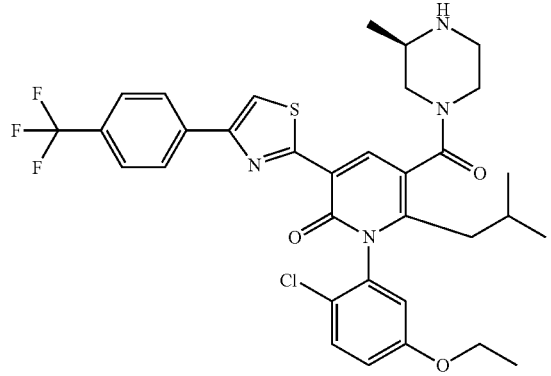
776
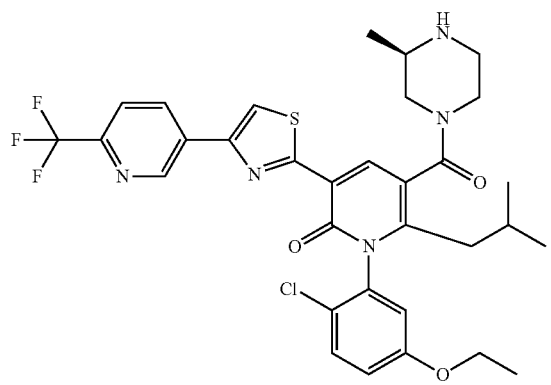 [SMILES: CCOc1ccc(Cl)c(-n2c(CC(C)C)c(C(=O)N3CCN[C@H](C)C3)cc(-c3nc(-c4ccc(C(F)(F)F)nc4)cs3)c2=O)c1]
777
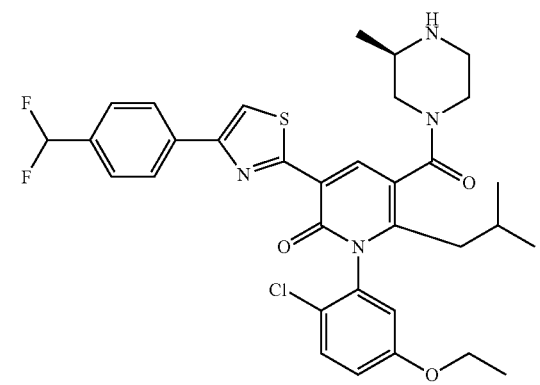 [SMILES: CCOc1ccc(Cl)c(-n2c(CC(C)C)c(C(=O)N3CCN[C@H](C)C3)cc(-c3nc(-c4ccc(C(F)F)cc4)cs3)c2=O)c1]
778
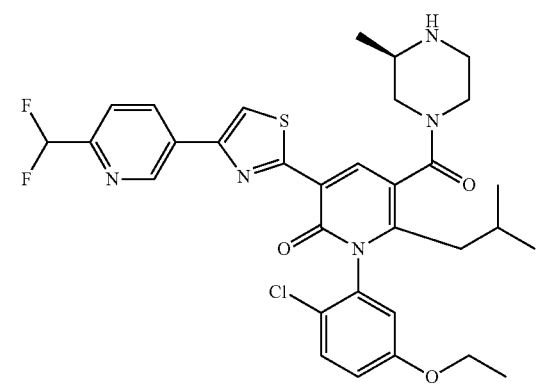

TABLE 2-continued
Structures and Compound Numbers of Additional Compounds
779
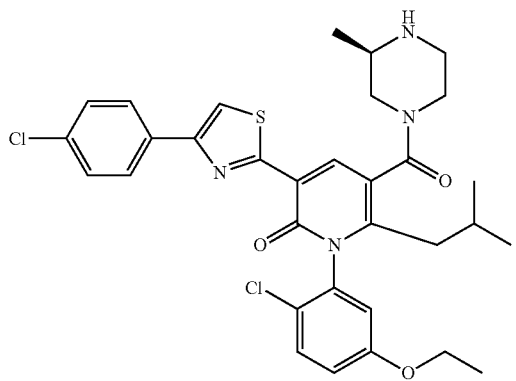 [SMILES: CCOc1ccc(Cl)c(-n2c(CC(C)C)c(C(=O)N3CCN[C@H](C)C3)cc(-c3nc(-c4ccc(Cl)cc4)cs3)c2=O)c1]
780
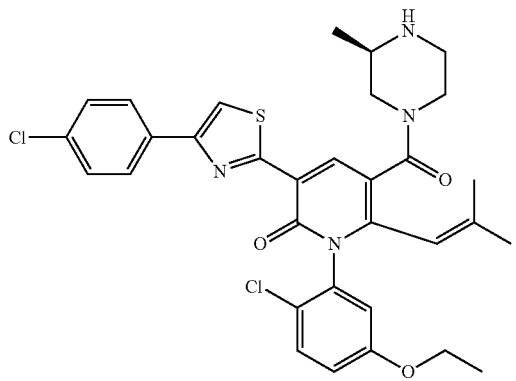 [SMILES: CCOc1ccc(Cl)c(-n2c(C=C(C)C)c(C(=O)N3CCN[C@H](C)C3)cc(-c3nc(-c4ccc(Cl)cc4)cs3)c2=O)c1]
781
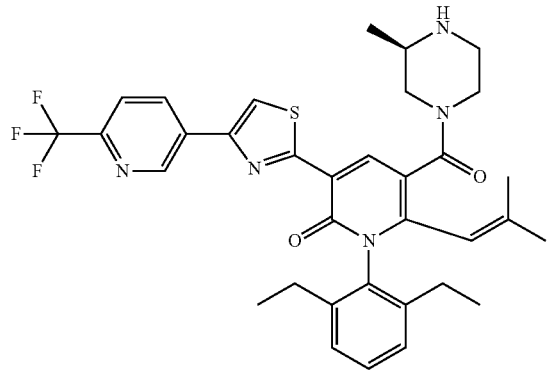 [SMILES: CCc1cccc(CC)c1-n1c(C=C(C)C)c(C(=O)N2CCN[C@H](C)C2)cc(-c2nc(-c3ccc(C(F)(F)F)nc3)cs2)c1=O]
782
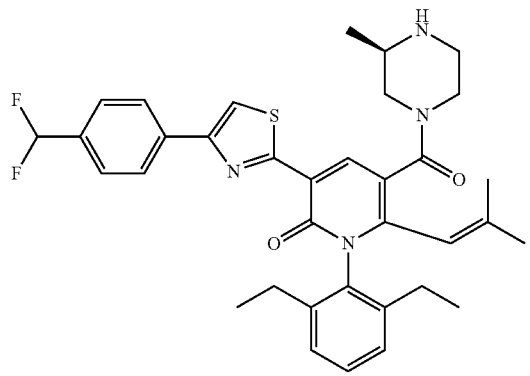 [SMILES: CCc1cccc(CC)c1-n1c(C=C(C)C)c(C(=O)N2CCN[C@H](C)C2)cc(-c2nc(-c3ccc(C(F)F)cc3)cs2)c1=O]

TABLE 2-continued
Structures and Compound Numbers of Additional Compounds
783 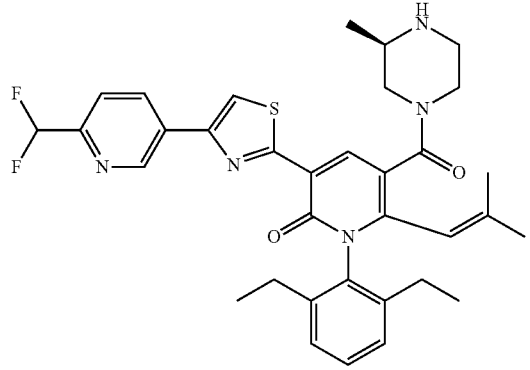 [SMILES: CCc1cccc(CC)c1-n1c(C=C(C)C)c(C(=O)N2CCN[C@H](C)C2)cc(-c2nc(-c3ccc(C(F)F)nc3)cs2)c1=O]
784 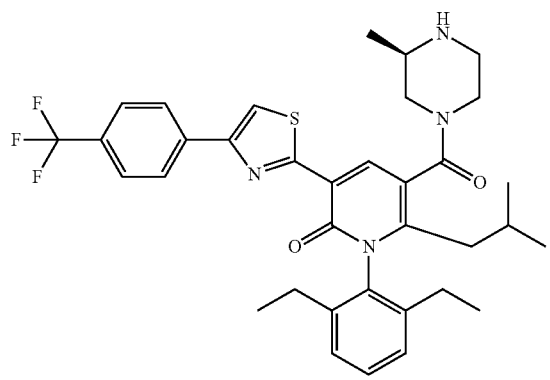 [SMILES: CCc1cccc(CC)c1-n1c(CC(C)C)c(C(=O)N2CCN[C@H](C)C2)cc(-c2nc(-c3ccc(C(F)(F)F)nc3)cs2)c1=O]
785 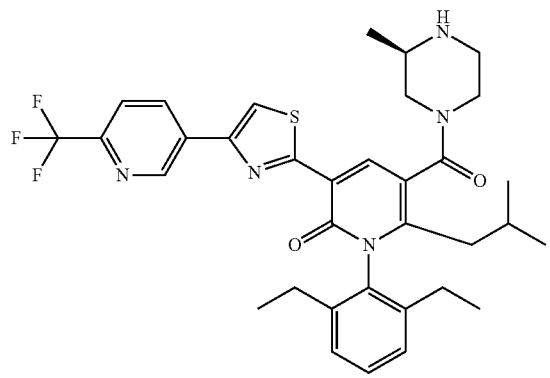
786 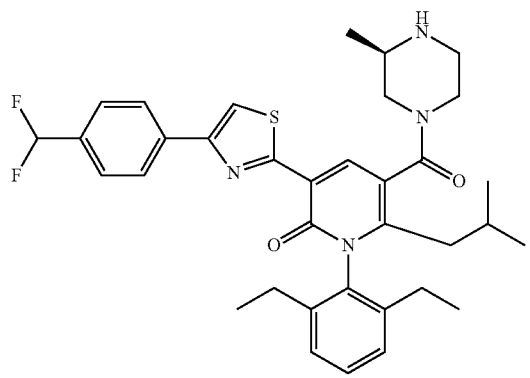 [SMILES: CCc1cccc(CC)c1-n1c(CC(C)C)c(C(=O)N2CCN[C@H](C)C2)cc(-c2nc(-c3ccc(C(F)F)cc3)cs2)c1=O]

TABLE 2-continued
Structures and Compound Numbers of Additional Compounds
787
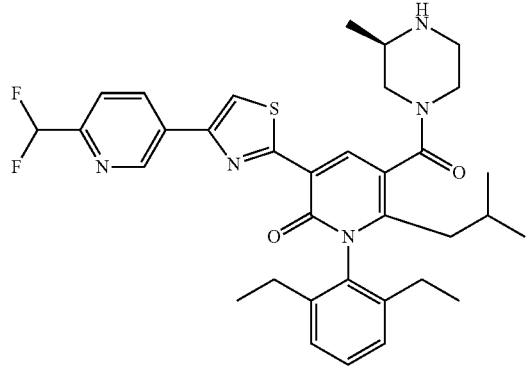 [SMILES: CCc1cccc(CC)c1-n1c(CC(C)C)c(C(=O)N2CCN[C@H](C)C2)cc(-c2nc(-c3ccc(C(F)F)nc3)cs2)c1=O]
788
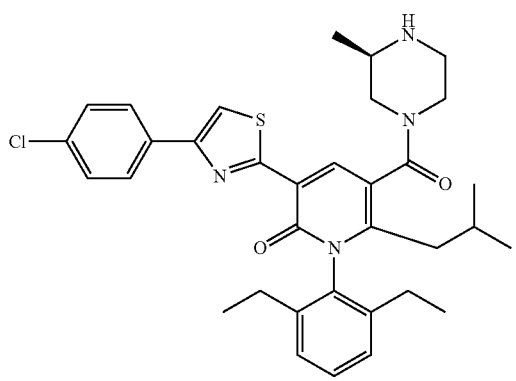 [SMILES: CCc1cccc(CC)c1-n1c(CC(C)C)c(C(=O)N2CCN[C@H](C)C2)cc(-c2nc(-c3ccc(Cl)cc3)cs2)c1=O]
789
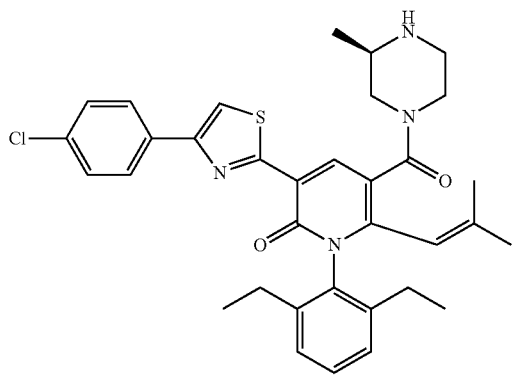 [SMILES: CCc1cccc(CC)c1-n1c(C=C(C)C)c(C(=O)N2CCN[C@H](C)C2)cc(-c2nc(-c3ccc(Cl)cc3)cs2)c1=O]
790
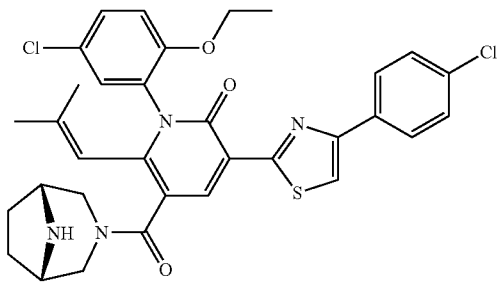 [SMILES: CCOc1ccc(Cl)cc1-n1c(C=C(C)C)c(C(=O)N2C[C@H]3CC[C@@H](C2)N3)cc(-c2nc(-c3ccc(Cl)cc3)cs2)c1=O]

TABLE 2-continued
Structures and Compound Numbers of Additional Compounds
791 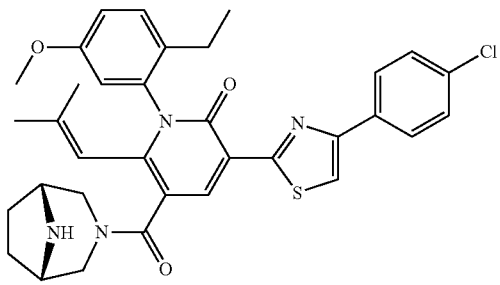
792 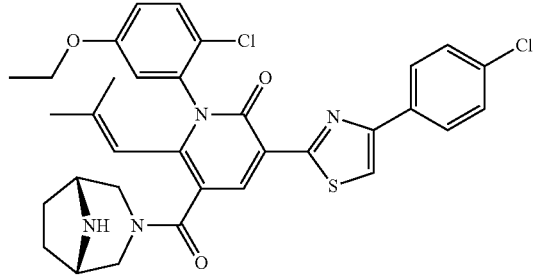 [SMILES: CCOc1ccc(Cl)c(-n2c(C=C(C)C)c(C(=O)N3C[C@H]4CC[C@@H](C3)N4)cc(-c3nc(-c4ccc(Cl)cc4)cs3)c2=O)c1]
793 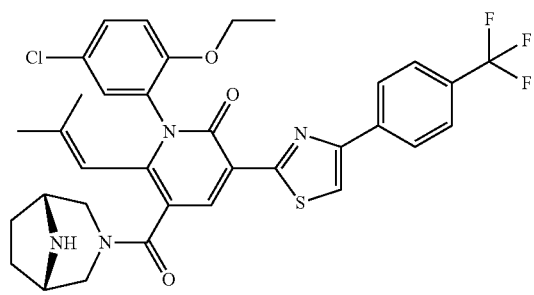 [SMILES: CCOc1ccc(Cl)cc1-n1c(C=C(C)C)c(C(=O)N2C[C@H]3CC[C@@H](C2)N3)cc(-c2nc(-c3ccc(C(F)(F)F)cc3)cs2)c1=O]
794 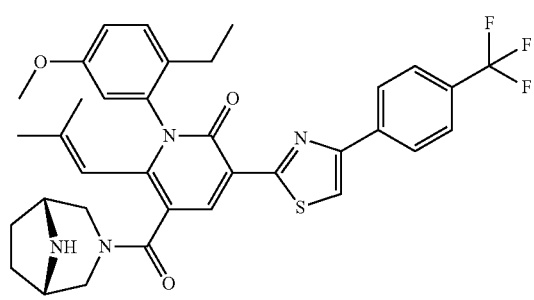 [SMILES: CCc1ccc(OC)cc1-n1c(C=C(C)C)c(C(=O)N2C[C@H]3CC[C@@H](C2)N3)cc(-c2nc(-c3ccc(C(F)(F)F)cc3)cs2)c1=O]
795 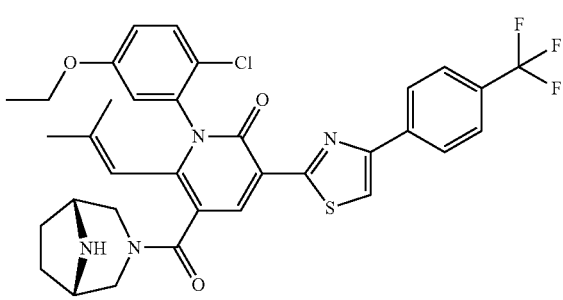 [SMILES: CCOc1ccc(Cl)c(-n2c(C=C(C)C)c(C(=O)N3C[C@H]4CC[C@@H](C3)N4)cc(-c3nc(-c4ccc(C(F)(F)F)cc4)cs3)c2=O)c1]

TABLE 2-continued
Structures and Compound Numbers of Additional Compounds
796
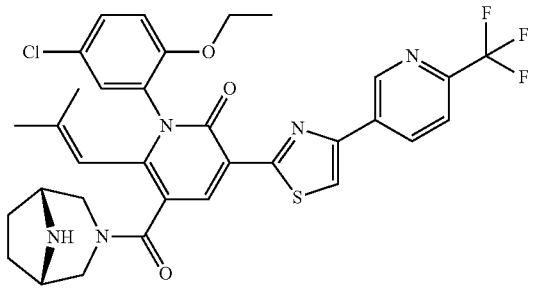
797
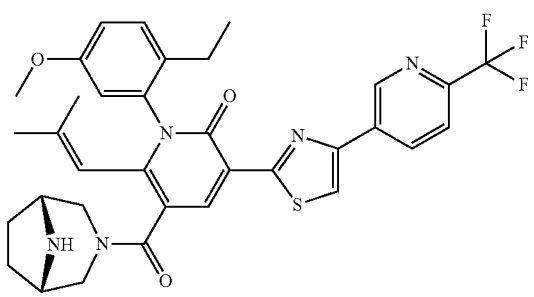
798
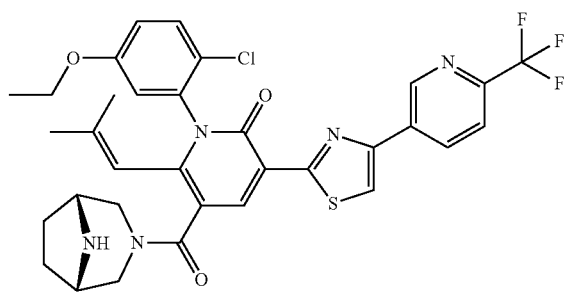 [SMILES: CCOc1ccc(Cl)c(-n2c(C=C(C)C)c(C(=O)N3C[C@H]4CC[C@@H](C3)N4)cc(-c3nc(-c4ccc(C(F)(F)F)nc4)cs3)c2=O)c1]
799
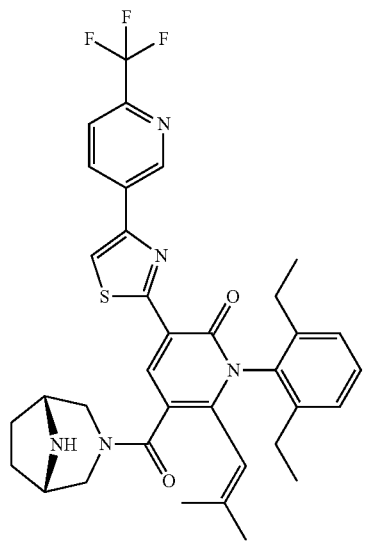 [SMILES: CCc1cccc(CC)c1-n1c(C=C(C)C)c(C(=O)N2C[C@H]3CC[C@@H](C2)N3)cc(-c2nc(-c3ccc(C(F)(F)F)nc3)cs2)c1=O]

TABLE 2-continued
Structures and Compound Numbers of Additional Compounds
800 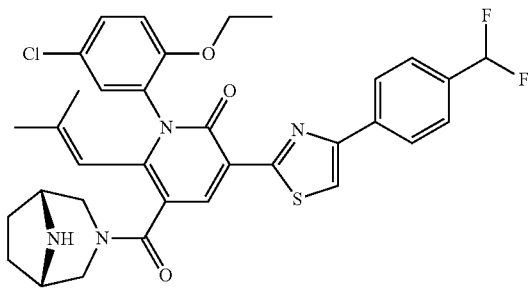
801 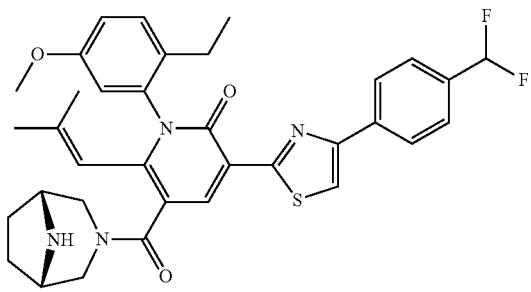 [SMILES: CCc1ccc(OC)cc1-n1c(C=C(C)C)c(C(=O)N2C[C@H]3CC[C@@H](C2)N3)cc(-c2nc(-c3ccc(C(F)F)cc3)cs2)c1=O]
802 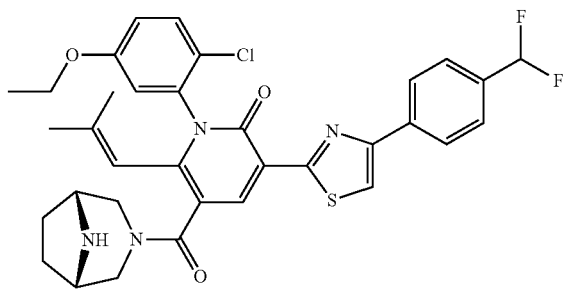 [SMILES: CCOc1ccc(Cl)c(-n2c(C=C(C)C)c(C(=O)N3C[C@H]4CC[C@@H](C3)N4)cc(-c3nc(-c4ccc(C(F)F)cc4)cs3)c2=O)c1]
803 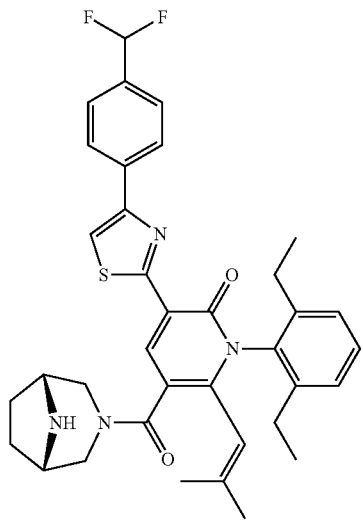 [SMILES: CCc1cccc(CC)c1-n1c(C=C(C)C)c(C(=O)N2C[C@H]3CC[C@@H](C2)N3)cc(-c2nc(-c3ccc(C(F)F)cc3)cs2)c1=O]

TABLE 2-continued
Structures and Compound Numbers of Additional Compounds
804
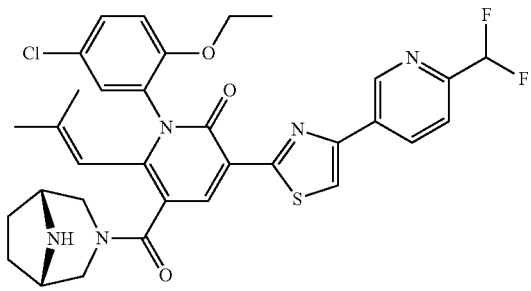 [SMILES: CCOc1ccc(Cl)cc1-n1c(C=C(C)C)c(C(=O)N2C[C@H]3CC[C@@H](C2)N3)cc(-c2nc(-c3ccc(C(F)F)nc3)cs2)c1=O]
805
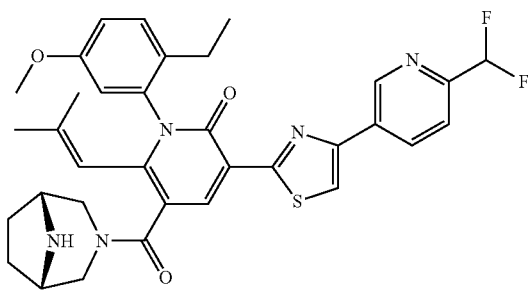 [SMILES: CCc1ccc(OC)cc1-n1c(C=C(C)C)c(C(=O)N2C[C@H]3CC[C@@H](C2)N3)cc(-c2nc(-c3ccc(C(F)F)nc3)cs2)c1=O]
806
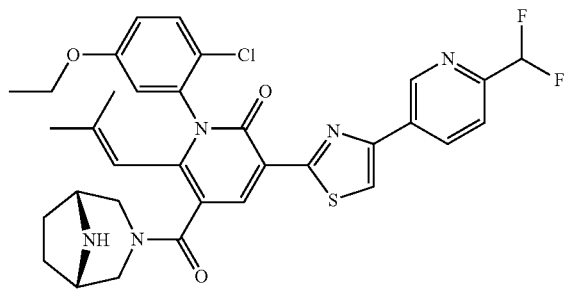
807
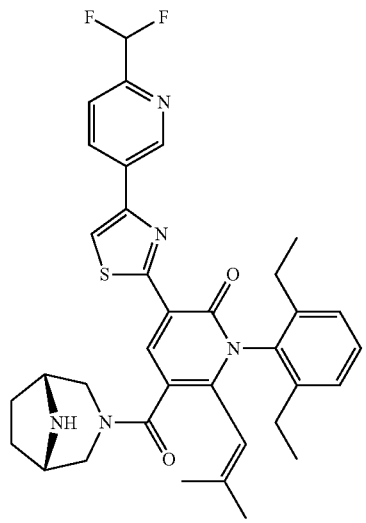 [SMILES: CCc1cccc(CC)c1-n1c(C=C(C)C)c(C(=O)N2C[C@H]3CC[C@@H](C2)N3)cc(-c2nc(-c3ccc(C(F)F)nc3)cs2)c1=O]

TABLE 2-continued
Structures and Compound Numbers of Additional Compounds
808
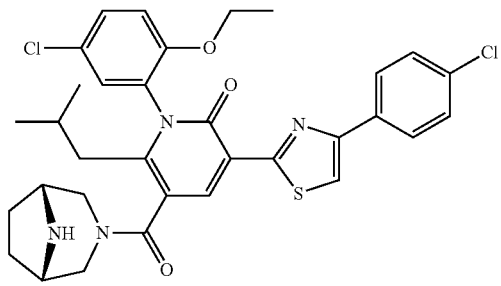 [SMILES: CCOc1ccc(Cl)cc1-n1c(CC(C)C)c(C(=O)N2C[C@H]3CC[C@@H](C2)N3)cc(-c2nc(-c3ccc(Cl)cc3)cs2)c1=O]
809
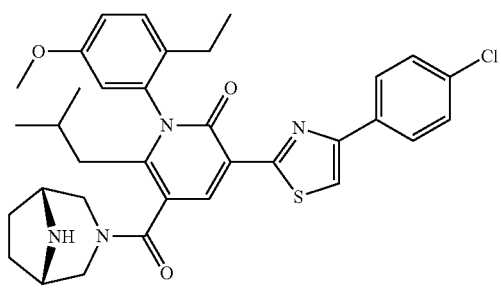 [SMILES: CCc1ccc(OC)cc1-n1c(CC(C)C)c(C(=O)N2C[C@H]3CC[C@@H](C2)N3)cc(-c2nc(-c3ccc(Cl)cc3)cs2)c1=O]
810
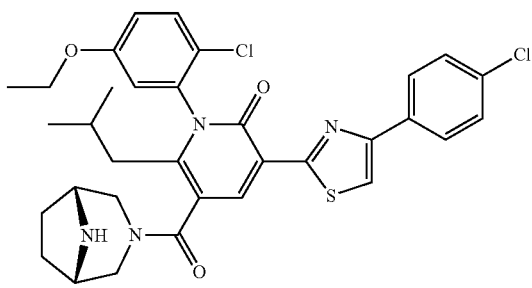
811
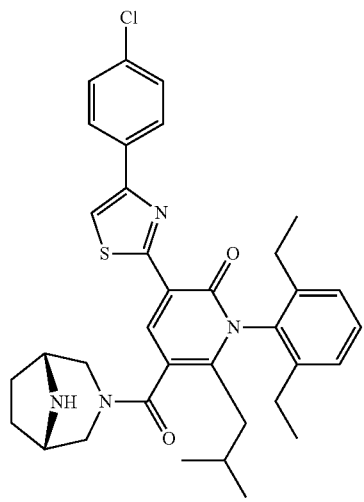 [SMILES: CCc1cccc(CC)c1-n1c(CC(C)C)c(C(=O)N2C[C@H]3CC[C@@H](C2)N3)cc(-c2nc(-c3ccc(Cl)cc3)cs2)c1=O]

TABLE 2-continued
Structures and Compound Numbers of Additional Compounds
812 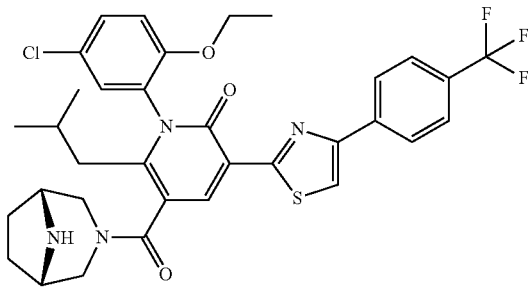 [SMILES: CCOc1ccc(Cl)cc1-n1c(CC(C)C)c(C(=O)N2C[C@H]3CC[C@@H](C2)N3)cc(-c2nc(-c3ccc(C(F)(F)F)cc3)cs2)c1=O]
813 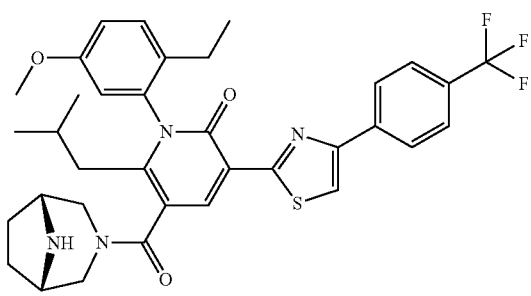 [SMILES: CCc1ccc(OC)cc1-n1c(CC(C)C)c(C(=O)N2C[C@H]3CC[C@@H](C2)N3)cc(-c2nc(-c3ccc(C(F)(F)F)cc3)cs2)c1=O]
814 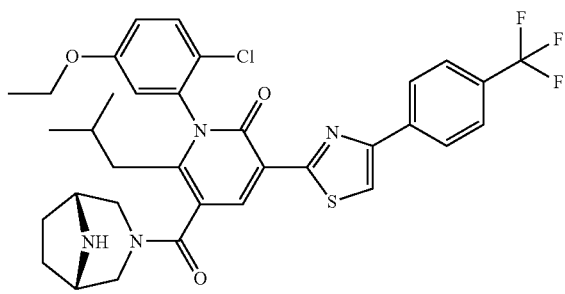 [SMILES: CCOc1ccc(Cl)c(-n2c(CC(C)C)c(C(=O)N3C[C@H]4CC[C@@H](C3)N4)cc(-c3nc(-c4ccc(C(F)(F)F)cc4)cs3)c2=O)c1]
815 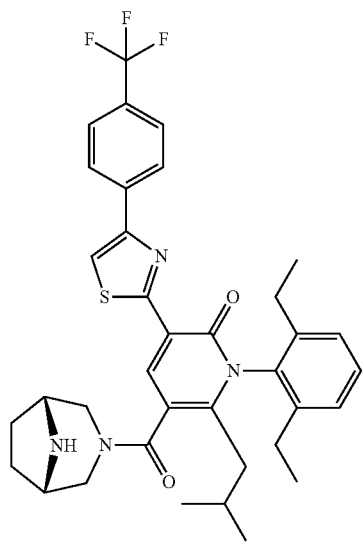 [SMILES: CCc1cccc(CC)c1-n1c(CC(C)C)c(C(=O)N2C[C@H]3CC[C@@H](C2)N3)cc(-c2nc(-c3ccc(C(F)(F)F)cc3)cs2)c1=O]

TABLE 2-continued
Structures and Compound Numbers of Additional Compounds
816
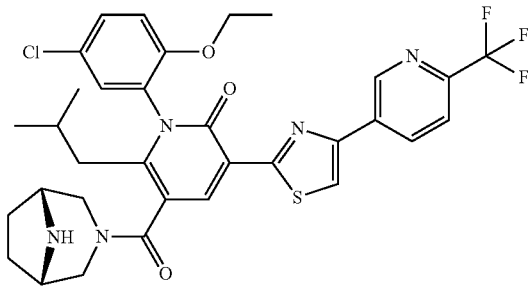
817
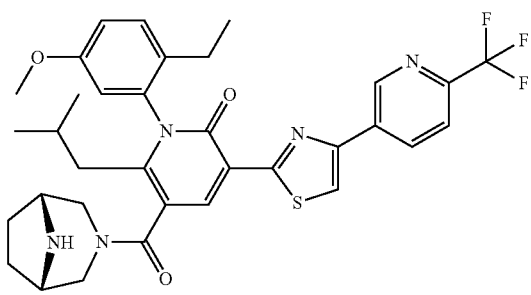 [SMILES: CCc1ccc(OC)cc1-n1c(CC(C)C)c(C(=O)N2C[C@H]3CC[C@@H](C2)N3)cc(-c2nc(-c3ccc(C(F)(F)F)nc3)cs2)c1=O]
818
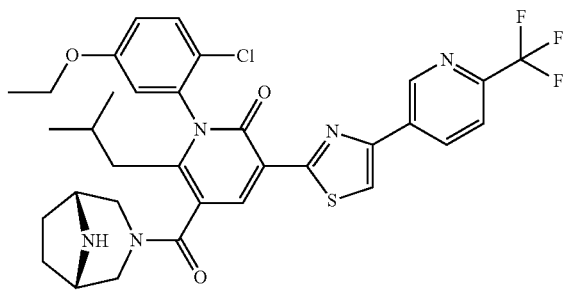 [SMILES: CCOc1ccc(Cl)c(-n2c(CC(C)C)c(C(=O)N3C[C@H]4CC[C@@H](C3)N4)cc(-c3nc(-c4ccc(C(F)(F)F)nc4)cs3)c2=O)c1]
819
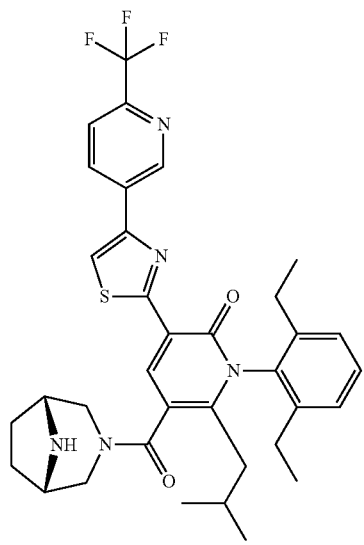 [SMILES: CCc1cccc(CC)c1-n1c(CC(C)C)c(C(=O)N2C[C@H]3CC[C@@H](C2)N3)cc(-c2nc(-c3ccc(C(F)(F)F)nc3)cs2)c1=O]

TABLE 2-continued
Structures and Compound Numbers of Additional Compounds
820 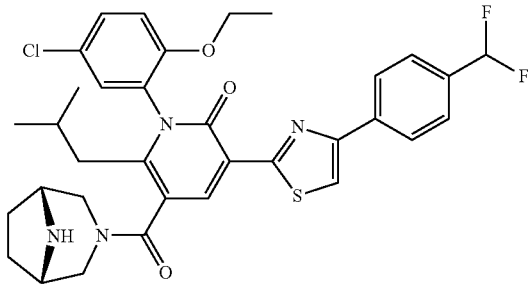 [SMILES: CCOc1ccc(Cl)cc1-n1c(CC(C)C)c(C(=O)N2C[C@H]3CC[C@@H](C2)N3)cc(-c2nc(-c3ccc(C(F)F)cc3)cs2)c1=O]
821 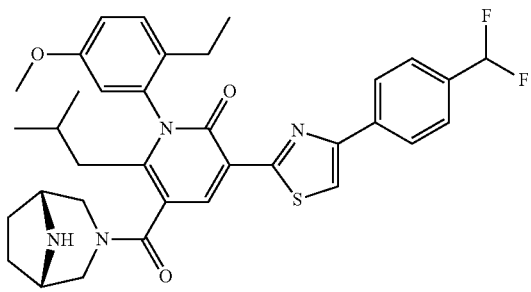
822 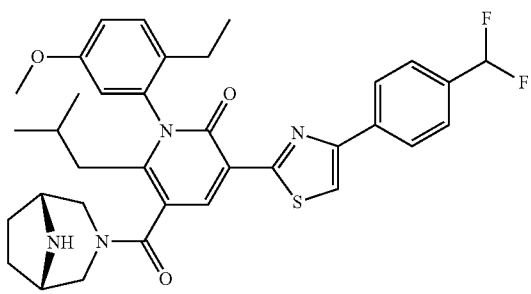
823 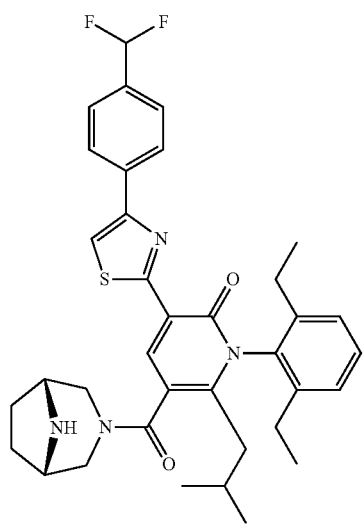

TABLE 2-continued
Structures and Compound Numbers of Additional Compounds
824
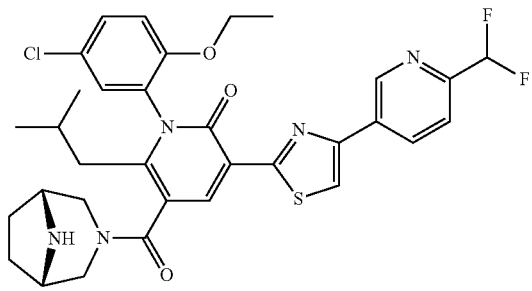 [SMILES: CCOc1ccc(Cl)cc1-n1c(CC(C)C)c(C(=O)N2C[C@H]3CC[C@@H](C2)N3)cc(-c2nc(-c3ccc(C(F)F)nc3)cs2)c1=O]
825
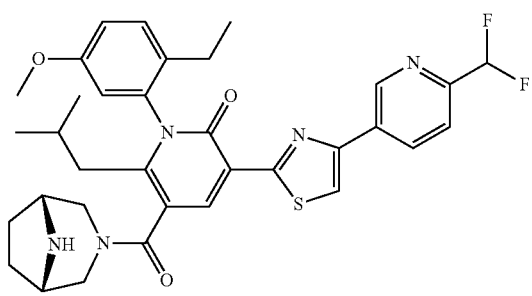
826
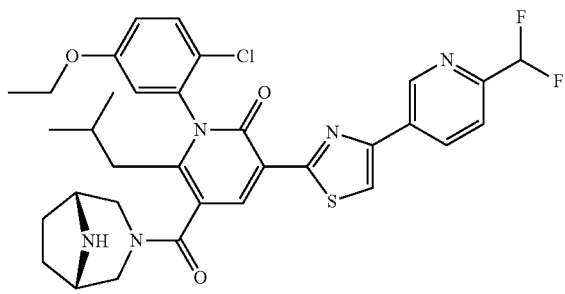 [SMILES: CCOc1ccc(Cl)c(-n2c(CC(C)C)c(C(=O)N3C[C@H]4CC[C@@H](C3)N4)cc(-c3nc(-c4ccc(C(F)F)nc4)cs3)c2=O)c1]
827
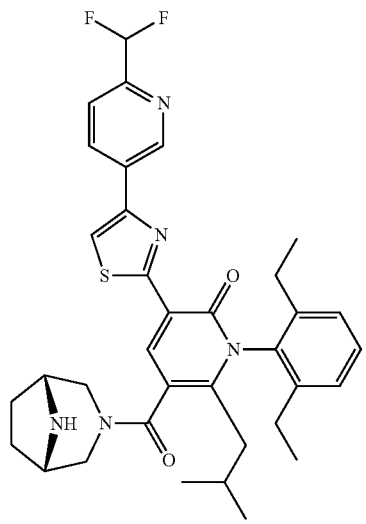 [SMILES: CCc1cccc(CC)c1-n1c(CC(C)C)c(C(=O)N2C[C@H]3CC[C@@H](C2)N3)cc(-c2nc(-c3ccc(C(F)F)nc3)cs2)c1=O]

What is claimed is:

1. A compound of Formula IA:

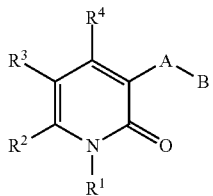

Formula IA or a pharmaceutically acceptable salt thereof, wherein
$R^1$ is $C_1$-$C_6$haloalkyl, —($C_0$-$C_6$alkyl)cycloalkyl, phenyl, or a monocyclic or bicyclic heterocycle of 4 to 10 ring atoms having 1, 2, or 3 ring atoms independently chosen from N, S, and O, where $R^1$ is substituted by 0-3 substituents independently chosen from hydroxyl, halogen, cyano, nitro, oxo, —($C_0$-$C_6$alkyl)phenyl, —O—($C_0$-$C_6$alkyl)phenyl, $C_1$-$C_6$alkyl, $C_2$-$C_6$alkenyl, $C_2$-$C_6$alkynyl, $C_1$-$C_6$alkylthio, $C_1$-$C_6$alkoxy, $C_1$-$C_6$haloalkyl, $C_1$-$C_6$haloalkoxy, —($C_0$-$C_6$alkyl)cycloalkyl, —O—($C_0$-$C_6$alkyl)cycloalkyl, —($C_0$-$C_6$alkyl)$CO_2R^5$, —($C_0$-$C_6$alkyl)C(O)NR$^5$R$^6$, —($C_1$-$C_6$alkyl)OR$^5$, —($C_0$-$C_6$alkyl)NR$^5$R$^6$, —($C_0$-$C_6$alkyl)NR$^5$C(O)R$^6$, and monocyclic heterocycle of 4 to 6 ring atoms having 1, 2, or 3 ring atoms independently chosen from N, O, and S which monocyclic heterocycle of 4 to 6 ring atoms is optionally substituted with one or more substituents independently chosen from halogen, cyano, —$CO_2H$, $C_1$-$C_6$alkyl, $C_1$-$C_6$alkoxy, $C_1$-$C_6$haloalkyl, and $C_1$-$C_6$haloalkoxy;

$R^2$ is hydrogen, halogen, hydroxyl, cyano, —$CO_2H$, $C_1$-$C_6$alkyl, $C_2$-$C_6$alkenyl, $C_2$-$C_6$alkynyl, $C_1$-$C_6$alkoxy, —($C_0$-$C_6$alkyl)cycloalkyl, or phenyl, each of which $R^2$ other than hydrogen, halogen, hydroxyl, cyano, and —$CO_2H$ can have one or more methylenes replaced with O, S, or N(R$^5$), and can have one or more methines replaced by N, or $R^2$ is a monocyclic heteroaryl of 5 ring atoms having 1 to 4 ring atoms independently chosen from N, O, and S, and each of which $R^2$ other than hydrogen, halogen, hydroxyl, cyano, and —$CO_2H$ is optionally substituted with one or more substituents chosen from halogen, hydroxyl, $C_1$-$C_6$alkyl, —OR$^5$, —SR$^5$, NR$_5$R$_6$, $C_1$-$C_6$haloalkyl, phenyl, and $C_1$-$C_6$haloalkoxy;

$R^3$ is cyano, —C(O)$C_1$-$C_6$alkyl, or —C(O)NR$^7$R$^8$;

$R^4$ is hydrogen, hydroxyl, halogen, cyano, —$CO_2H$, $C_1$-$C_6$alkyl, $C_2$-$C_6$alkenyl, $C_2$-$C_6$alkynyl, $C_1$-$C_6$alkoxy, or $C_1$-$C_6$haloalkyl;

A is a phenyl or a monocyclic heteroaryl of 5 or 6 ring atoms having 1 to 4 ring atoms independently chosen from N, O, and S, wherein A is substituted with 0-2 substituents chosen from halogen, cyano, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —O($C_0$-$C_6$alkyl)cycloalkyl, —($C_0$-$C_6$alkyl)$CO_2R^5$, and —($C_0$-$C_6$alkyl)C(O)NR$^5$R$^6$;

B is a phenyl, —($C_1$-$C_6$alkyl)phenyl, —($C_2$-$C_6$alkenyl)phenyl, —($C_2$-$C_6$alkynyl)phenyl, $C_3$-$C_7$cycloalkyl, or a monocyclic heterocycle of 5 or 6 ring atoms having 1, 2, or 3 ring atoms independently chosen from N, O, and S, wherein B is substituted with 0-3 substituents independently chosen from hydroxyl, halogen, cyano, $C_1$-$C_6$alkyl, $C_2$-$C_6$alkenyl, $C_2$-$C_6$alkynyl, $C_1$-$C_6$alkoxy, —$C_0$-$C_2$alkylNR$^5$R$^6$, $C_1$-$C_6$haloalkyl, $C_1$-$C_6$haloalkoxy, —($C_0$-$C_6$alkyl)cycloalkyl, —($C_0$-$C_6$alkyl)phenyl, —O—($C_0$-$C_6$alkyl)phenyl, —($C_0$-$C_6$alkyl)cycloalkyl, —O($C_0$-$C_6$alkyl)cycloalkyl, —($C_0$-$C_6$alkyl)$CO_2R^9$, —($C_0$-$C_6$alkyl)C(O)NR$^9$R$^{10}$, —($C_0$-$C_6$alkyl)NR$^9$R$^{10}$, and —($C_1$-$C_6$alkyl)OR$^9$; or A and B can be taken together to be a bicyclic heteroaryl of 8 to 10 ring atoms, having 1, 2, or 3 ring atoms independently chosen from N, O, and S, wherein the bicyclic heteroaryl is substituted with 0-2 substituents independently chosen from halogen, cyano, $C_1$-$C_6$alkyl, $C_1$-$C_6$alkoxy, $C_1$-$C_6$haloalkyl, and $C_1$-$C_6$haloalkoxy;

$R^5$, $R^6$, $R^7$, $R^9$, and $R^{10}$ are each independently chosen at each occurrence from hydrogen, $C_1$-$C_6$ alkyl, and —($C_0$-$C_6$alkyl)cycloalkyl;

$R^8$ is hydrogen, $C_1$-$C_6$ alkyl, —($C_0$-$C_6$alkyl)cycloalkyl, —($C_0$-$C_6$alkyl)phenyl, or a 4- to 7-membered heterocycloalkyl ring having 1, 2, or 3 ring atoms independently chosen from N, O, and S, where each $R^8$ is substituted with 0-3 substituents independently chosen from hydroxyl, halogen, oxo, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)phenyl, —($C_0$-$C_6$alkyl)$CO_2R^{11}$, —($C_0$-$C_6$alkyl)C(O)NR$^{11}$R$^{12}$, —($C_0$-$C_6$alkyl)NR$^{11}$C(O)R$^{12}$, —($C_1$-$C_6$alkyl)OR$^{11}$, and —($C_0$-$C_6$alkyl)NR$^{11}$R$^{12}$;

any $R^5$ and $R^6$, or $R^7$ and $R^8$, bound to the same nitrogen atom may be taken together to form a 4- to 7-membered monocyclic heterocycloalkyl ring or 6- to 11-membered bridged bicyclic heterocycloalkyl ring, which heterocycloalkyl ring contains 0, 1, or 2 additional heteroatoms chosen from N, O, and S, which heterocycloalkyl ring is optionally substituted at any carbon ring atom with halogen, hydroxyl, cyano, oxo, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)phenyl, —($C_0$-$C_6$alkyl)$CO_2R^{11}$, —($C_0$-$C_6$alkyl)C(O)NR$^{11}$R$^{12}$, —($C_1$-$C_6$alkyl)OR$^{11}$, —($C_0$-$C_6$alkyl)NR$^{11}$R$^{12}$ a spiro fused cycloalkyl ring of 3 to 7 carbons, or a spiro fused heterocycloalkyl ring of 3 to 7 ring atoms with 1 to 3 ring atoms chosen from O, S, and N, the N atoms of said spiro fused heterocycloalkyl ring of 3 to 7 ring atoms are optionally substituted with $C_1$-$C_6$ alkyl, and optionally substituted at any nitrogen ring atom available for substitution with $C_1$-$C_6$ alkyl or ($C_0$-$C_4$alkyl)cycloalkyl;

any $R^9$ and $R^{10}$ bound to the same nitrogen atom may be taken together to form a 4 to 7-membered heterocycloalkyl ring, which heterocycloalkyl ring contains 0, 1, or 2 additional heteroatoms chosen from N, O, and S, which heterocycloalkyl ring is optionally substituted at any carbon ring atom with halogen, hydroxyl, oxo, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, and optionally substituted at any nitrogen ring atom available for substitution by $C_1$-$C_6$ alkyl or ($C_0$-$C_4$alkyl)cycloalkyl; and $R^{11}$ and $R^{12}$ are each independently chosen at each occurrence from hydrogen, $C_1$-$C_6$ alkyl, and —($C_0$-$C_6$alkyl)cycloalkyl.

2. The compound or pharmaceutically acceptable salt thereof of claim 1 wherein
$R^1$ is a phenyl or pyridyl substituted by 0-3 substituents independently chosen from hydroxyl, halogen, cyano, nitro, $C_1$-$C_6$alkyl, $C_1$-$C_6$alkylthio, $C_1$-$C_6$alkoxy, C$_1$-C$_2$haloalkyl, C$_1$-C$_2$haloalkoxy, —(C$_0$-C$_6$alkyl)C$_3$-C$_6$cycloalkyl, —O—(C$_0$-C$_6$alkyl) C$_3$-C$_6$cycloalkyl, —(C$_0$-C$_2$alkyl)phenyl, —O—(C$_0$-C$_2$alkyl)phenyl, —(C$_0$-C$_6$alkyl)CO$_2$R$^5$, —(C$_0$-C$_6$alkyl)C(O)NR$^5$R$^6$, —(C$_1$-C$_6$alkyl)OR$^5$, —(C$_0$-C$_6$alkyl)NR$^5$R$^6$, and —(C$_0$-C$_6$alkyl)NR$^5$C(O)R$^6$;

R$^2$ is C$_1$-C$_6$alkyl, C$_2$-C$_6$alkenyl, C$_2$-C$_6$alkynyl, or —(C$_0$-C$_6$alkyl)cycloalkyl;

R$^3$ is —C(O)NR$^7$R$^8$;

R$^4$ is hydrogen or C$_1$-C$_6$alkyl;

A is a monocyclic heteroaryl of 5 or 6 ring atoms having 1 to 4 ring atoms independently chosen from N, O, and S, wherein A is substituted with 0-2 substituents independently chosen from halogen, cyano, C$_1$-C$_6$alkyl, C$_1$-C$_6$alkoxy, C$_1$-C$_6$haloalkyl, and C$_1$-C$_6$haloalkoxy, —(C$_0$-C$_6$alkyl)cycloalkyl, —O(C$_0$-C$_6$alkyl)cycloalkyl, —(C$_0$-C$_6$alkyl)CO$_2$R$^5$, and —(C$_0$-C$_6$alkyl)C(O)NR$^5$R$^6$; and B is a phenyl or pyridyl substituted with 0-3 substituents independently chosen from hydroxyl, halogen, cyano, C$_1$-C$_6$alkyl, C$_1$-C$_6$alkoxy, C$_1$-C$_6$haloalkyl, C$_1$-C$_6$haloalkoxy, —(C$_0$-C$_6$alkyl)cycloalkyl, —O—(C$_0$-C$_6$alkyl)cycloalkyl, —(C$_0$-C$_6$alkyl)phenyl, —O—(C$_0$-C$_6$alkyl)phenyl, —(C$_0$-C$_6$alkyl)cycloalkyl, —O(C$_0$-C$_6$alkyl)cycloalkyl, —(C$_0$-C$_6$alkyl)CO$_2$R$^9$, —(C$_0$-C$_6$alkyl)C(O)NR$^9$R$^{10}$, C$_6$alkyl)NR$^9$R$^{10}$, and —(C$_1$-C$_6$alkyl)OR$^9$.

3. The compound or pharmaceutically acceptable salt thereof of claim 1 wherein A is one of the following:

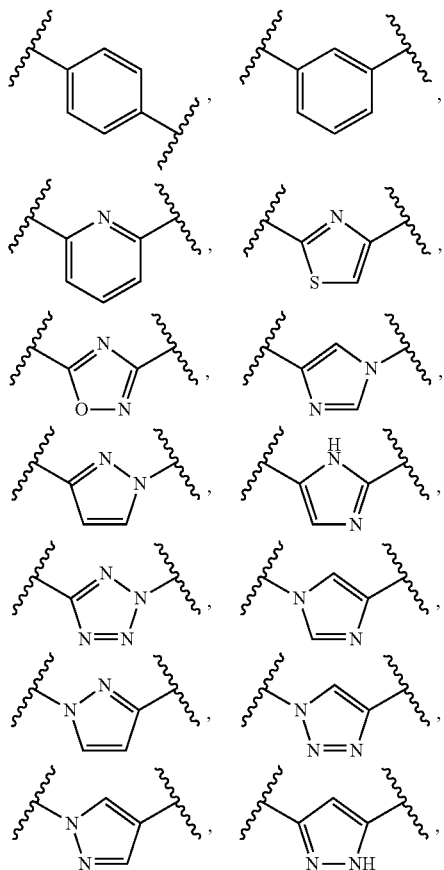

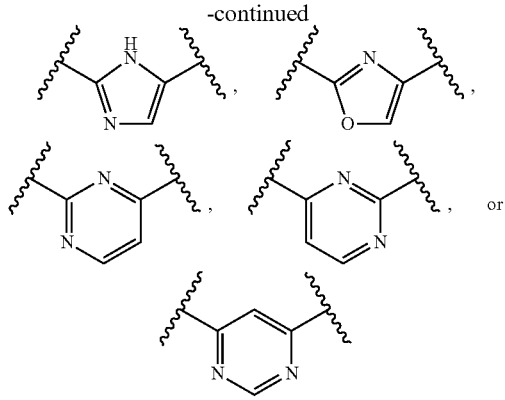

including tautomeric forms, and each which A may be unsubstituted or substituted with a substituent independently chosen from halogen, C$_1$-C$_6$alkyl, C$_1$-C$_6$haloalkyl, —(C$_0$-C$_6$alkyl)cycloalkyl, —O(C$_0$-C$_6$alkyl)cycloalkyl, —(C$_0$-C$_6$alkyl)CO$_2$R$^5$, and —(C$_0$-C$_6$alkyl)C(O)NR$^5$R$^6$.

4. The compound or pharmaceutically acceptable salt thereof of claim 1 wherein R$^1$ is 2,6-diethylphenyl, 2-ethoxy-5-cholorophenyl, 2-chloro-5-ethoxyphenyl, or 2-ethyl-5-methoxyphenyl;

R$^2$ is isobutyl or 2,2-dimethylvinyl;

R$^3$ is

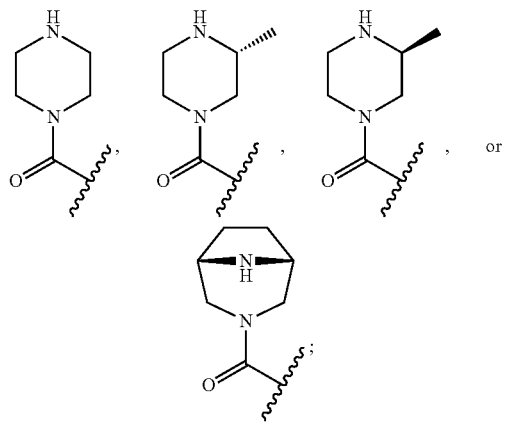

R$^4$ is hydrogen;

A is

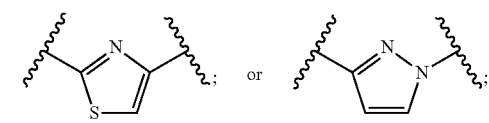 [SMILES: *c1csc(*)n1 ; *c1ccn(*)n1]

and

B is 4-chlorophenyl, 4-(trifluoromethyl)phenyl, 4-(difluoromethyl)phenyl, 6-(trifluoromethyl)-3-pyridyl, or 6-(difluoromethyl)-3-pyridyl.

5. The compound or pharmaceutically acceptable salt thereof of claim 1 wherein R$^1$ is 2,6-diethylphenyl, 2-ethoxy-5-cholorophenyl, 2-chloro-5-ethoxyphenyl, or 2-ethyl-5-methoxyphenyl;

R$^2$ is isobutyl or 2,2-dimethylvinyl; and

R$^4$ is hydrogen.

6. The compound or pharmaceutically acceptable salt thereof of claim 1 wherein A is

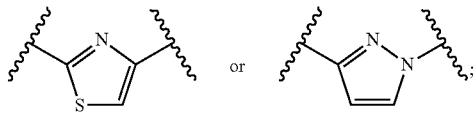 [SMILES: *c1csc(*)n1 ; *c1ccn(*)n1]

and

B is 4-chlorophenyl, 4-(trifluoromethyl)phenyl, 4-(difluoromethyl)phenyl, 6-(trifluoromethyl)-3-pyridyl, or 6-(difluoromethyl)-3-pyridyl.

7. The compound or pharmaceutically acceptable salt thereof of claim 1, wherein $R^1$ is 2,6-diethylphenyl, 5-methyl-2-ethoxypyridin-3-yl, 5-fluoro-2-ethoxypyridin-3-yl, 5-chloro-2-ethoxypyridin-3-yl, 2-chloro-5-methoxyphenyl, 5-Chloro-2-ethoxyphenyl, or 5-chloro-2-isopropoxyphenyl.

8. A pharmaceutical composition comprising a compound or pharmaceutically acceptable salt thereof of claim 1, together with a pharmaceutically acceptable carrier.

9. A method of treating a cancer characterized by the presence of an IDH1 mutation, wherein the IDH1 mutation results in a new ability of IDH1 enzyme to catalyze NADPH-dependent reduction of a-ketoglutarate to R(−)-2-hydroxyglutarate in a patient, comprising a step of administering to a patient in need thereof a therapeutic agent, wherein the therapeutic agent is the compound or pharmaceutically acceptable salt thereof of claim 1.

10. The method of claim 9, wherein the IDH1 mutation is an IDH1 R132H or IDH1 R132C mutation.

11. The method of claim 9, wherein the cancer is selected from glioma, acute myelogenous leukemia, acute myeloid leukemia, myelodysplastic/myeloproliferative neoplasms, sarcoma, chronic myelomonocytic leukemia, non-Hodgkin lymphoma, astrocytoma, melanoma, non-small cell lung cancer, cholangiocarcinomas, chondrosarcoma, or colon cancer.

12. The method of claim 9, further comprising administering to the patient in need thereof at least one additional therapeutic agent.

* * * * *